(12) United States Patent
Castro

(10) Patent No.: US 11,925,651 B2
(45) Date of Patent: *Mar. 12, 2024

(54) TEAD INHIBITORS AND USES THEREOF

(71) Applicant: Ikena Oncology, Inc., Boston, MA (US)

(72) Inventor: Alfredo C. Castro, Somerville, MA (US)

(73) Assignee: Ikena Oncology, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/816,859

(22) Filed: Aug. 2, 2022

(65) Prior Publication Data

US 2023/0148061 A1    May 11, 2023

Related U.S. Application Data

(63) Continuation of application No. 16/887,083, filed on May 29, 2020, now Pat. No. 11,458,149.

(60) Provisional application No. 63/025,336, filed on May 15, 2020, provisional application No. 62/944,567, filed on Dec. 6, 2019, provisional application No. 62/928,931, filed on Oct. 31, 2019, provisional application No. 62/855,082, filed on May 31, 2019.

(51) Int. Cl.
| | | |
|---|---|---|
| *A61K 31/635* | (2006.01) | |
| *A61K 31/09* | (2006.01) | |
| *A61K 31/136* | (2006.01) | |
| *A61K 31/40* | (2006.01) | |
| *A61K 31/4164* | (2006.01) | |
| *A61K 31/42* | (2006.01) | |
| *A61K 31/44* | (2006.01) | |
| *A61K 31/47* | (2006.01) | |
| *A61P 35/00* | (2006.01) | |
| *A61P 35/04* | (2006.01) | |

(52) U.S. Cl.
CPC ............ *A61K 31/635* (2013.01); *A61K 31/09* (2013.01); *A61K 31/136* (2013.01); *A61K 31/40* (2013.01); *A61K 31/4164* (2013.01); *A61K 31/42* (2013.01); *A61K 31/44* (2013.01); *A61K 31/47* (2013.01); *A61P 35/04* (2018.01)

(58) Field of Classification Search
CPC ........ A61P 35/00; A61P 35/04; A61K 31/635; A61K 31/09; A61K 31/136; A61K 31/40; A61K 31/4164; A61K 31/42; A61K 31/44; A61K 31/47; C07D 209/02; C07D 211/58; C07D 215/38; C07D 261/04; C07D 413/04; C07D 413/10
USPC ........................................................ 514/158
See application file for complete search history.

(56) References Cited

U.S. PATENT DOCUMENTS

| | | |
|---|---|---|
| 3,120,564 A | 2/1964 | Milionis et al. |
| 5,256,791 A | 10/1993 | Braish |
| 5,298,629 A | 3/1994 | Braish |
| 5,475,116 A | 12/1995 | Brighty et al. |
| 5,623,078 A | 4/1997 | Urata et al. |
| 5,703,091 A | 12/1997 | Steiner et al. |
| 5,968,929 A | 10/1999 | Blythin et al. |
| 6,051,575 A | 4/2000 | Blythin et al. |
| 6,184,380 B1 | 2/2001 | Chiu et al. |
| 6,590,118 B1 | 7/2003 | Kristiansen et al. |
| 7,019,142 B2 | 3/2006 | Chiu et al. |
| 7,232,835 B2 | 6/2007 | Mehta et al. |
| 7,473,787 B2 | 1/2009 | McHardy et al. |
| 7,488,748 B2 | 2/2009 | Mehta et al. |
| 7,501,443 B2 | 3/2009 | Mehta et al. |
| 7,560,551 B2 | 7/2009 | Cee et al. |
| 7,582,643 B2 | 9/2009 | Blake et al. |
| 7,750,158 B2 | 7/2010 | Shankar et al. |
| 7,902,373 B2 | 3/2011 | Blake et al. |
| 7,932,246 B2 | 4/2011 | Moffat et al. |
| 7,935,725 B2 | 5/2011 | Bembenek et al. |
| 8,022,221 B2 | 9/2011 | Cee et al. |
| 8,067,589 B2 | 11/2011 | Blake et al. |
| 8,124,639 B2 | 2/2012 | McHardy et al. |
| 8,344,008 B2 | 1/2013 | Bacani et al. |
| 8,367,719 B2 | 2/2013 | Bacani et al. |
| 8,686,155 B2 | 4/2014 | Cee et al. |
| 8,772,277 B2 | 7/2014 | Matsumoto et al. |
| 8,895,602 B1 | 11/2014 | Nam et al. |
| 9,079,894 B2 | 7/2015 | Nirogi et al. |
| 9,186,354 B2 | 11/2015 | Morriello et al. |
| 9,216,993 B2 | 12/2015 | Grembecka et al. |
| 9,242,961 B2 | 1/2016 | Cee et al. |
| 9,505,782 B2 | 11/2016 | Grembecka et al. |
| 9,527,830 B2 | 12/2016 | Walsh et al. |
| 9,777,002 B2 | 10/2017 | Walsh et al. |

(Continued)

FOREIGN PATENT DOCUMENTS

| | | |
|---|---|---|
| CN | 1944398 A | 4/2007 |
| EP | 0074768 A2 | 3/1983 |

(Continued)

OTHER PUBLICATIONS

Amidon et al., "Abstract 2474: Potent small molecule TEAD inhibitors targeting the Hippo pathway exhibit antiproliferation in vitro and anti-tumor effect in vivo," Cancer Research. 2020; 80(16):2474.

Bum-Erdene et al., "Small-Molecule Covalent Modification of Conserved Cysteine Leads to Allosteric Inhibition of the TEAD•Yap Protein-Protein Interaction," Cell Chem Biol. Mar. 21, 2019;26(3):378-389.e13.

Chan et al., "Autopalmitoylation of TEAD proteins regulates transcriptional output of the Hippo pathway," Nat Chem Biol. Apr. 2016;12(4):282-9.

(Continued)

*Primary Examiner* — Raymond J Henley, III
(74) *Attorney, Agent, or Firm* — Dechert LLP; Andrea L. C. Reid; Gang Wang

(57) ABSTRACT

The present invention provides compounds, compositions thereof, and methods of using the same.

27 Claims, 7 Drawing Sheets

Specification includes a Sequence Listing.

(56) References Cited

U.S. PATENT DOCUMENTS

| | | |
|---|---|---|
| 9,802,919 B1 | 10/2017 | Sutton et al. |
| 10,023,558 B2 | 7/2018 | Sutton et al. |
| 10,160,769 B2 | 12/2018 | Grembecka et al. |
| 10,314,823 B2 | 6/2019 | Blumstein et al. |
| 11,274,082 B2 | 3/2022 | Castro |
| 11,458,149 B1 | 10/2022 | Castro |
| 11,760,728 B2 | 9/2023 | Castro |
| 2002/0119961 A1 | 8/2002 | Blumberg et al. |
| 2002/0143017 A1 | 10/2002 | Mylari |
| 2004/0034019 A1 | 2/2004 | Tomlinson et al. |
| 2004/0082641 A1 | 4/2004 | Rytved et al. |
| 2005/0054618 A1 | 3/2005 | Rytved et al. |
| 2006/0047114 A1 | 3/2006 | Wlodecki |
| 2008/0300251 A1 | 12/2008 | Sattigeri et al. |
| 2009/0124600 A1 | 5/2009 | Layton |
| 2009/0221664 A1 | 9/2009 | Ray et al. |
| 2010/0016400 A1 | 1/2010 | Kumar et al. |
| 2010/0056496 A1 | 3/2010 | Kumar et al. |
| 2011/0028478 A1 | 2/2011 | Behnke et al. |
| 2016/0039802 A1 | 2/2016 | Cho et al. |
| 2017/0119786 A1 | 5/2017 | Buckley et al. |
| 2017/0158702 A1 | 6/2017 | Vacca et al. |
| 2017/0183328 A1 | 6/2017 | Dowling et al. |
| 2018/0099940 A1 | 4/2018 | Crew et al. |
| 2019/0010136 A1 | 1/2019 | Danjo et al. |
| 2019/0062309 A1 | 2/2019 | Beckwith et al. |
| 2019/0276434 A1 | 9/2019 | Vacca et al. |
| 2020/0095236 A1 | 3/2020 | Teng et al. |
| 2022/0251048 A1* | 8/2022 | Castro .................. C07D 231/12 |

FOREIGN PATENT DOCUMENTS

| | | |
|---|---|---|
| EP | 1184372 A1 | 3/2002 |
| EP | 1717225 A1 | 11/2006 |
| EP | 3479696 A1 | 5/2019 |
| EP | 3712129 A1 | 9/2020 |
| JP | S58179838 A | 10/1983 |
| WO | WO-1997030030 A1 | 8/1997 |
| WO | WO-2001058891 A2 | 8/2001 |
| WO | WO-2004056810 A1 | 7/2004 |
| WO | WO-2006122014 A2 | 11/2006 |
| WO | 2008014291 A2 | 1/2008 |
| WO | WO-2008010061 A2 | 1/2008 |
| WO | WO-2008010238 A2 | 1/2008 |
| WO | WO-2008117229 A1 | 10/2008 |
| WO | WO-2009152027 A1 | 12/2009 |
| WO | WO-2010053732 A1 | 5/2010 |
| WO | 2010116328 A2 | 10/2010 |
| WO | WO-2010135360 A1 | 11/2010 |
| WO | 2013118138 A1 | 8/2013 |
| WO | WO-2013115391 A1 | 8/2013 |
| WO | WO-2014199164 A1 | 12/2014 |
| WO | 2016044792 A1 | 3/2016 |
| WO | 2017027687 A1 | 2/2017 |
| WO | WO-2017053706 A1 | 3/2017 |
| WO | 2017058716 A1 | 4/2017 |
| WO | 2017064277 A1 | 4/2017 |
| WO | WO-2017111076 A1 | 6/2017 |
| WO | 2017210545 A1 | 12/2017 |
| WO | WO-2018039232 A1 | 3/2018 |
| WO | 2018185266 A1 | 10/2018 |
| WO | WO-2018204532 A1 | 11/2018 |
| WO | WO-2018235926 A1 | 12/2018 |
| WO | WO-2019040380 A1 | 2/2019 |
| WO | WO-2019060850 A1 | 3/2019 |
| WO | WO-2019079659 A1 | 4/2019 |
| WO | WO-2019089667 A1 | 5/2019 |
| WO | WO-2019089670 A1 | 5/2019 |
| WO | WO-2019113236 A1 | 6/2019 |
| WO | WO-2019152809 A1 | 8/2019 |
| WO | WO-2019196764 A1 | 10/2019 |
| WO | WO-2019204505 A2 | 10/2019 |
| WO | 2019232216 A1 | 12/2019 |
| WO | WO-2020051099 A1 | 3/2020 |
| WO | WO-2020073031 A1 | 4/2020 |
| WO | WO-2020081450 A1 | 4/2020 |
| WO | WO-2020081572 A1 | 4/2020 |
| WO | WO-2020087063 A1 | 4/2020 |
| WO | 2020121261 A1 | 6/2020 |
| WO | WO-2020165833 A1 | 8/2020 |
| WO | WO-2020190774 A1 | 9/2020 |
| WO | WO-2020206137 A1 | 10/2020 |
| WO | WO-2020219650 A1 | 10/2020 |
| WO | 2020239951 A1 | 12/2020 |
| WO | 2020239999 A1 | 12/2020 |
| WO | 2020254946 A1 | 12/2020 |
| WO | WO-2020243415 A2 | 12/2020 |
| WO | WO-2020243423 A1 | 12/2020 |
| WO | WO-2021097110 A1 | 5/2021 |
| WO | 2021113627 A1 | 6/2021 |
| WO | WO-2021133896 A1 | 7/2021 |
| WO | WO-2021178339 A1 | 9/2021 |
| WO | WO-2021247634 A1 | 12/2021 |
| WO | 2022120354 A1 | 6/2022 |
| WO | WO-2022120353 A1 | 6/2022 |
| WO | WO-2022120355 A1 | 6/2022 |
| WO | WO-2022159986 A1 | 7/2022 |
| WO | 2023060227 A1 | 4/2023 |
| WO | 2023114984 A1 | 6/2023 |

OTHER PUBLICATIONS

Crawford et al., "Hippo pathway inhibition by blocking the YAP/TAZ-TEAD interface: a patent review," Expert Opin Ther Pat. 2018;28(12):867-873.

De Amici et al., "Analogues of the low-efficacy partial GABAA agonist 4-PIOL. Syntheses and in vitro pharmacological studies," Eur J Med Chem. Sep. 1991;26(6):625-31.

Eggenweiler and Wolf, "Preparation of 1,5-diphenylpyrazoles as heat shock protein (HSP90) inhibitors," STN Doc No. 144:254124. Retrived Feb. 23, 2006.

Gibault et al., "Targeting Transcriptional Enhanced Associate Domains (TEADs)," J Med Chem. Jun. 28, 2018;61(12):5057-5072.

Gibault et al., "Toward the Discovery of a Novel Class of YAP-TEAD Interaction Inhibitors by Virtual Screening Approach Targeting YAP-TEAD Protein?Protein Interface," Cancers (Basel). May 8, 2018;10(5):140.

Golub et al., "Molecular classification of cancer: class discovery and class prediction by gene expression monitoring," Science. Oct. 15, 1999;286(5439):531-7.

Holden et al., "Small Molecule Dysregulation of TEAD Lipidation Induces a Dominant-Negative Inhibition of Hippo Pathway Signaling," Cell Rep. 2020;31(12):107809.

Ito et al., "Exploiting ubiquitin ligase cereblon as a target for small-molecule compounds in medicine and chemical biology," Cell Chem Biol. Jul. 15, 2021;28(7):987-999.

Kaneda et al., "Discovery of First in Class TEAD Inhibitor which directly inhibits YAP/TAZ-TEAD protein-protein interaction and shows a potent anti-tumor effect in malignant pleural mesothelioma," AACR Annual Meeting. Apr. 2019;3086.

Kaneda et al., "The novel potent TEAD inhibitor, K-975, inhibits YAP1/TAZ-TEAD protein-protein interactions and exerts an anti-tumor effect on malignant pleural mesothelioma," Am J Cancer Res. 2020;10(12):4399-4415.

Lala and Orucevic, "Role of nitric oxide in tumor progression: lessons from experimental tumors," Cancer Metastasis Rev. Mar. 1998;17(1):91-106.

Lu et al., "Discovery and biological evaluation of vinylsulfonamide derivatives as highly potent, covalent TEAD autopalmitoylation inhibitors," Eur J Med Chem. 2019;184:111767.

MedlinePlus, "Cancer," Health Topics. Updated May 18, 2017; Accessed Dec. 15, 2022: https://medlineplus.gov/cancer.html#.

Noland et al., "Palmitoylation of TEAD Transcription Factors Is Required for Their Stability and Function in Hippo Pathway Signaling," Structure. Jan. 5, 2016;24(1):179-186.

Nouri et al., "Identification of Celastrol as a Novel YAP-TEAD Inhibitor for Cancer Therapy by High Throughput Screening with Ultrasensitive YAP/TAZ-TEAD Biosensors," Cancers (Basel). Oct. 19, 2019;11(10):1596.

(56) References Cited

OTHER PUBLICATIONS

PCT International Search Report and Written Opinion from PCT/US2020/035098, dated Nov. 16, 2020.
PCT International Search Report and Written Opinion from PCT/US2020/035111, dated Sep. 15, 2020.
PCT International Search Report and Written Opinion from PCT/US2021/072683, dated Apr. 7, 2022.
PCT International Search Report and Written Opinion from PCT/US2021/072684, dated May 5, 2022.
PCT International Search Report and Written Opinion from PCT/US2021/072685, dated May 11, 2022.
PCT International Search Report and Written Opinion from PCT/US2022/070330, dated Apr. 5, 2022.
Pobbati and Rubin, "Protein-Protein Interaction Disruptors of the YAP/TAZ-TEAD Transcriptional Complex," Molecules. Dec. 18, 2020;25(24):6001.
Pobbati et al., "Targeting the Central Pocket in Human Transcription Factor TEAD as a Potential Cancer Therapeutic Strategy," Structure. Nov. 3, 2015;23(11):2076-86.
Tang, "Targeting the Hippo-YAP Pathway with novel small molecule inhibitors of the YAP-TEAD transcription activity," AACR Annual Meeting. Apr. 1, 2019.
Teng et al., "Development of CDK2 and CDK5 Dual Degrader TMX-2172," Angew Chem Int Ed Engl. Aug. 10, 2020;59(33):13865-13870.
White et al., "The Complex Entanglement of Hippo-Yap/Taz Signaling in Tumor Immunity," Oncogene. Apr. 2019;38(16):2899-909.
Zambaldo et al., "Selective affinity-based probe for oncogenic kinases suitable for live cell imaging," Chem Sci. Mar. 13, 2013;4:2088-92.
Crosby et al., "YAP vs. TAZ: differences in expression revealed through rigorous validation of target-specific monoclonal antibodies," 2020;43(4):182-195.
Dey et al., "Targeting the Hippo pathway in cancer, fibrosis, wound healing and regenerative medicine," Nat Rev Drug Discov. 2020;19(7):480-494.
Ip et al., "Immunohistochemical validation of overexpressed genes identified by global expression microarrays in adrenocortical carcinoma reveals potential predictive and prognostic biomarkers," 2015;20(3):247-56.
Lodge et al., "Homeostatic and tumourigenic activity of SOX2+ pituitary stem cells is controlled by the LATS/YAP/TAZ cascade," 2019;8:e43996.
PCT International Search Report and Written Opinion from PCT/US2022/077747, dated Jan. 26, 2023.
Eckert et al., "Ruthenium-catalysed synthesis of fluorinated bicyclic amino esters through tandem carbene addition/cyclopropanation of enynes," Chemistry. 2011;17(34):9456-62.
PCT International Search Report and Written Opinion from PCT/US2022/081772, dated May 8, 2023.
U.S. Appl. No. 18/039,781, filed Jun. 1, 2023.
U.S. Appl. No. 18/273,411, filed Jul. 20, 2023.
U.S. Appl. No. 18/336,562, filed Jun. 16, 2023.

* cited by examiner

FIGURE 3

| Cell Line | Oncogene | Cell Line | Oncogene | Cell Line | Oncogene | Cell Line | Oncogene |
|---|---|---|---|---|---|---|---|
| A2058 | STK11/PTEN | DU145 | STK11/NF2 | NCI-H1650 | EGFR | PANC-1 | p53/KRAS |
| A2780 | PIK3CA/PTEN | DU4475 | BRAF | NCI-H1703 | CDKN2A | SK-HEP-1 | BRAF/NF2 |
| A549 | KRAS/STK11 | HCC1143 | p53 | NCIH196 | p53/PTEN | SKOV-3 | p53/PIK3CA/FBXW7 |
| ACHN | EPHA2/NF2 | HCC827 | p53/EGFR | NCI-H1975 | p53/EGFR/PIK3CA/CDKN2A | SNU182 | p53 |
| AM-38 | BRAF | HCT116 | PIK3CA/KRAS/CDKN2A | NCI-H2030 | p53/KRAS | SW1353 | CDKN2A/IDH2 |
| ASPC1 | p53/KRAS/CDK2NA | HT-1080 | IDH1/NRAS | NCIH2052 | NF2 | SW1573 | KRAS/STK11 |
| BxPC-3 | p53 | JHH4 | p53 | NCIH2085 | p53 | SW579 | p53 |
| Caki-1 | NF2 | LN-229 | ERBB2/TEAD2 | NCI-H2228 | p53 | T24 | HRAS |
| CALU1 | KRAS | LOVO | KRAS/FBXW7 | NCI-H226 | NF2 | TE1 | p53/Rb |
| Caov-3 | p53 | MDAMB231 | KRAS/NF2/(atypicalBRAF) | NCIH2452 | EGFR | U251 | p53/PTEN |
| CFPAC1 | p53/KRAS | MDA-MB-468 | p53 | NCI-H28 | VHL | U87MG | PTEN |
| COV362 | EGFR | MKN74 | APC | NCI-H292 | NF2 | YD8 | p53 |
| Daoy | p53 | MSTO211H | LATS1-PSEN | NCIH647 | KRAS | ZR751 | PTEN |
| DETROIT562 | p53/PIK3CA | NCI-H1299 | NRAS | OE33 | p53 | | |
| DMS153 | p53/NOTCH1 | NCIH1563 | STK11 | NCI-H2172 | p53/EGFR/FBXW7 | | |
| DMS53 | p53/STK11 | NCIH1568 | p53 | OVMANA | PIK3CA | | |

[ <0.2uM ]   [ <1uM ]   EC50 for Isomer 2 of compound I-12

TEAD INHIBITORS AND USES THEREOF

CROSS-REFERENCE TO RELATED APPLICATIONS

This application is a continuation application of U.S. patent application Ser. No. 16/887,083, filed May 29, 2020, now U.S. Pat. No. 11,458,149, issued Oct. 4, 2022 which claims the benefit under 35 U.S.C. § 119(e) of U.S. Provisional Patent Application No. 62/855,082, filed May 31, 2019; U.S. Provisional Patent Application No. 62/928,931, filed Oct. 31, 2019; U.S. Provisional Patent Application No. 62/944,567, filed Dec. 6, 2019; and U.S. Provisional Patent Application No. 63/025,336, filed May 15, 2020, the contents of each of which are herein incorporated by reference in their entireties.

SEQUENCE LISTING

The instant application contains a Sequence Listing which has been submitted electronically in XML format and is hereby incorporated by reference in its entirety. Said XML copy, created on Sep. 20, 2022, is named 396661-010USD1_192785_SL.XML and is 10,473 bytes in size.

TECHNICAL FIELD OF THE INVENTION

The present invention relates to compounds and methods useful for inhibition of Transcriptional Enhancer Associate Domain (TEAD). The invention also provides pharmaceutically acceptable compositions comprising compounds of the present invention and methods of using said compositions in the treatment of various diseases, disorders, and conditions as described herein.

BACKGROUND OF THE INVENTION

Yes-associated protein (YAP) and transcriptional co-activator with PDZ-binding motif (TAZ) are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with TEAD transcription factors and coactivate the expression of target genes and promote cell proliferation. Hyperactivation of YAP and TAZ and/or mutations in one or more members of the Hippo pathway network have been implicated in numerous cancers.

SUMMARY OF THE INVENTION

The Hippo signaling cascade is an important pathway for cancer biogenesis and tumor maintenance. The Hippo pathway is heavily mutated across many cancer indications through loss of function mutations in genes such as NF2. These pro-tumor mutations lead to the constitutive activation of the downstream transcriptional coactivators YAP and TAZ that drive the expression of many pro-survival and proliferation genes through the essential interaction with a TEAD protein family member. In addition, this unrestrained transcriptional program drives enhanced immune suppression in the tumor microenvironment. As described herein, to target this oncogenic pathway novel small molecule inhibitors were identified that selectively bind to TEAD and disrupt their interaction with YAP and TAZ, thereby downregulating YAP- and TAZ-dependent transcription. As demonstrated herein, these TEAD inhibitors prevent TEAD palmitoylation, which is critical for the interaction between YAP and TEAD. Furthermore, the TEAD inhibitors described herein inhibit in vitro proliferation of YAP-dependent (i.e., Hippo pathway-deficient cancer cell lines), but not Hippo pathway wild type cancer cell lines. Importantly, as shown herein, the TEAD inhibitor compounds of the present invention did not affect survival of a differentiated mouse podocyte cell line or compromise mouse kidney histology. Subsequent experiments in vivo demonstrate the TEAD inhibitors described herein downregulate YAP-dependent genes in human tumor xenografts after oral dosing. In addition, the TEAD inhibitors described herein exhibit single agent tumor growth inhibition of human tumor xenografts in mice at well tolerated oral doses. The data described herein demonstrate the ability of the small molecule TEAD inhibitors provided herein for targeting the Hippo pathway in cancers.

It has now been found that compounds of the present invention, and pharmaceutically acceptable compositions thereof, are effective as TEAD inhibitors. In one aspect, the present invention provides a compound of Formula I':

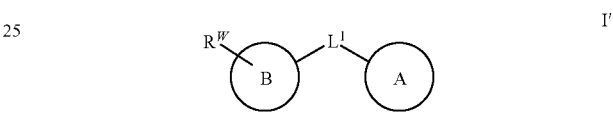

I' or a pharmaceutically acceptable salt thereof, wherein each variable is as defined and described herein. In one aspect, the present invention provides a compound of Formula I:

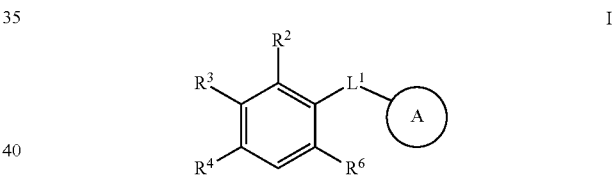

I or a pharmaceutically acceptable salt thereof, wherein each variable is as defined and described herein.

Compounds of the present invention, and pharmaceutically acceptable salts and compositions thereof, are useful for treating a variety of diseases, disorders or conditions associated with TEAD. Such diseases, disorders, or conditions include cellular proliferative disorders (e.g., cancer as described herein).

BRIEF DESCRIPTION OF FIGURES

FIG. 3 shows anti-proliferative effects of isomer 2 of compound I-12 as evaluated in a 3-day Cell TITERGLO™ assay. The cell lines were chosen based on Cancer Dependency score and a sampling of known interacting oncogenes. Cell lines with an EC50<0.2 µM or <1.0 µM are indicated by boxes. EC50 values were calculated from inflection points.

DETAILED DESCRIPTION OF CERTAIN EMBODIMENTS

Figure 1:
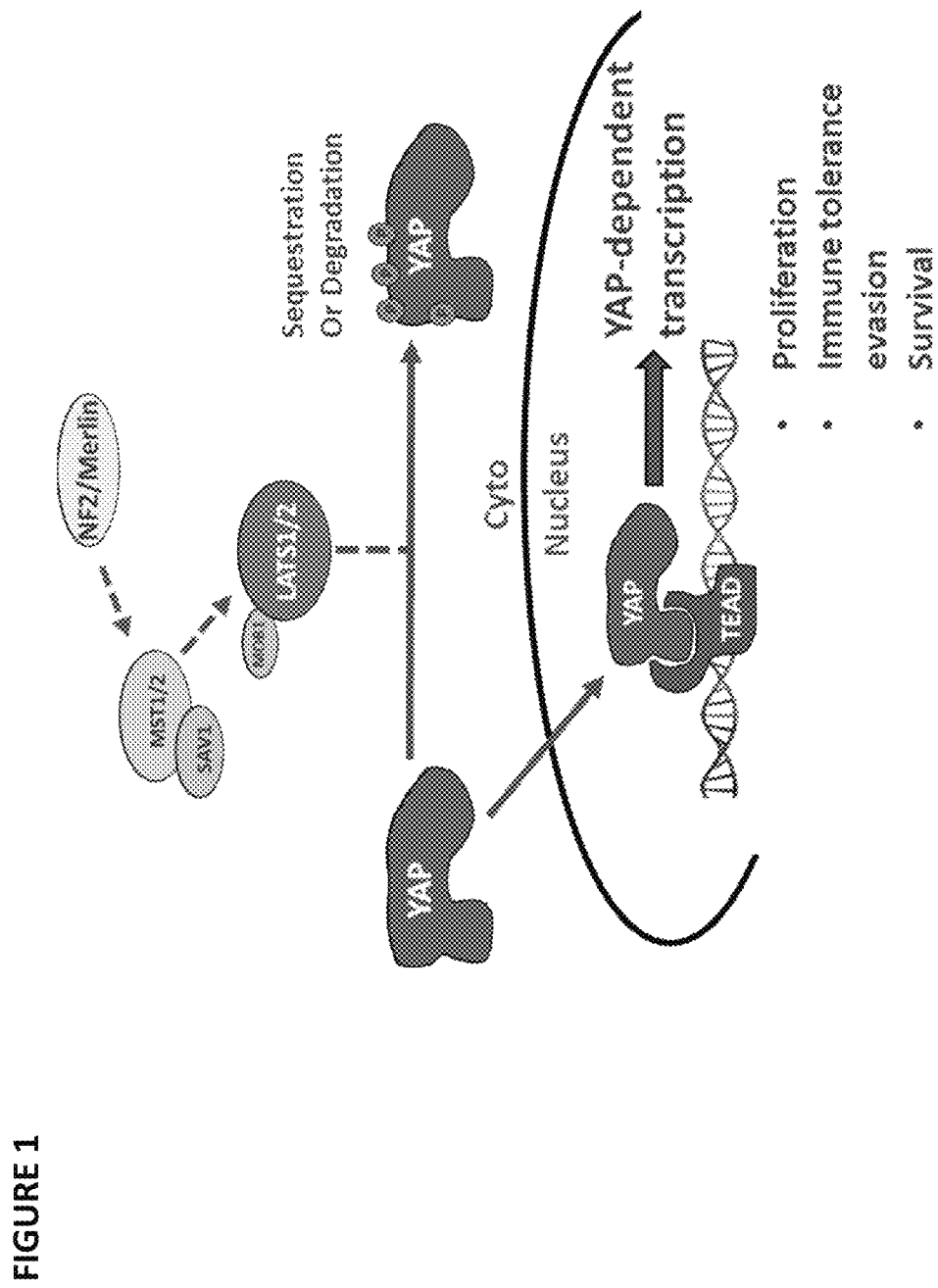
FIG. 1 depicts a schematic of Hippo pathway signaling.

1. General Description of Certain Embodiments of the Invention

Compounds of the present invention, and pharmaceutical salts and compositions thereof, are useful as inhibitors of TEAD. Without wishing to be bound by any particular theory, it is believed that compounds of the present invention, and pharmaceutical compositions thereof, inhibit the activity of TEAD, and thus treat diseases, disorders or conditions associated with TEAD, such as cancer.

In one aspect, the present invention provides a compound of Formula I':

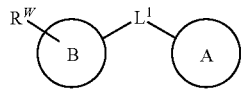

I' or a pharmaceutically acceptable salt thereof, wherein:
$L^1$ is $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, or a 8-10 membered bicyclic heteroaromatic ring having 1-5 heteroatoms independently selected from nitrogen, oxygen, or sulfur;

Ring B is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, a 8-10 membered bicyclic heteroaromatic ring having 1-5 heteroatoms independently selected from nitrogen, oxygen, or sulfur;
$R^w$ is a warhead group; wherein when $R^w$ is a saturated or partially unsaturated monocyclic carbocyclic or heterocyclic ring, it optionally forms a spiro bicyclic ring with Ring B; and
each R is independently —H or optionally substituted —C$_{1-6}$ aliphatic.

In one aspect, the present invention provides a compound of Formula I:

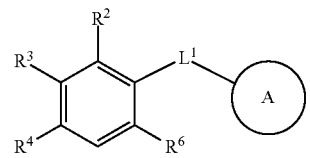

I or a pharmaceutically acceptable salt thereof, wherein:
$L^1$ is $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is a 4-, 5-, or 6-membered saturated or partially unsaturated monocyclic carbocyclic ring, phenyl, a 4-, 5-, or 6-membered saturated or partially unsaturated monocyclic heterocyclic ring having 1-2 heteroatoms independently selected from nitrogen, oxygen, or sulfur, or a 5-6 membered monocyclic heteroaromatic ring having 1, 2, 3, or 4 heteroatoms independently selected from nitrogen, oxygen, or sulfur, wherein Ring A is optionally substituted 1-2 times by -halogen, —CN, —NO$_2$, or —C$_{1-6}$ aliphatic substituted 0-6 times by -halogen, —CN, or —NO$_2$;
$R^2$ is —H, or a warhead group;
$R^3$ is —H or a warhead group;
$R^4$ is —H, halogen, —S(O)$_2$N(R)$_2$, —S(O)N(R)$_2$, —C(O)N(R)$_2$, or a warhead group;
$R^6$ is —H or —C$_{1-6}$ aliphatic substituted 0-6 times by -halogen, —CN, or —NO$_2$; and
each R is independently —H or optionally substituted —C$_{1-6}$ aliphatic.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

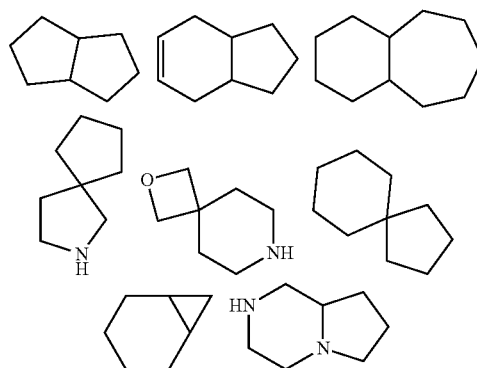

Exemplary bridged bicyclics include:

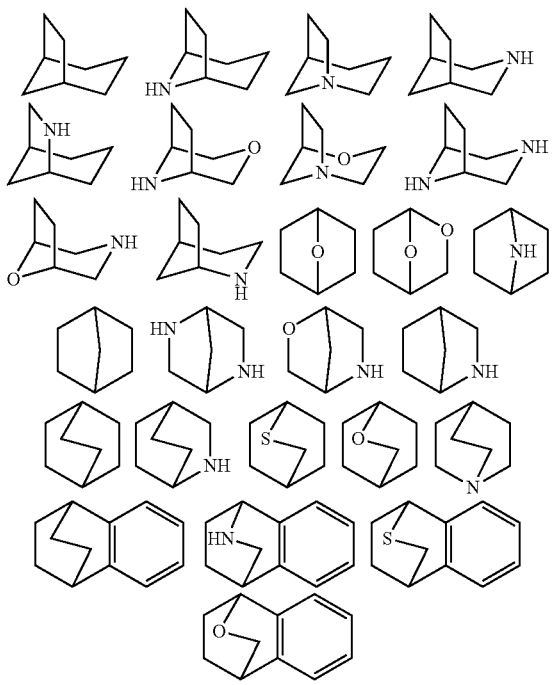

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR[+] (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

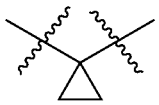

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$;

—(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —S(O)(NR°)R°; —S(O)$_2$N=C(NR°$_2$)$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$.

Each R° is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of R° selected from =O and =S; or each R° is optionally substituted with a monovalent substituent independently selected from halogen, —(CH$_2$)$_{0-2}$R$^{\bullet}$, -(haloR$^{\bullet}$), —(CH$_2$)$_{0-2}$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, OSiR$^{\bullet}$$_3$, —C(O)SR$^{\bullet}$, —(C$_{1-4}$ straight or branched alkylene)C(O)OR$^{\bullet}$, or —SSR$^{\bullet}$.

Each R$^{\bullet}$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens; or wherein an optional substituent on a saturated carbon is a divalent substituent independently selected from =O, =S, =NNR*$_2$, =NNHC(O)R*, =NNHC(O)OR*, =NNHS(O)$_2$ R*, =NR*, =NOR*, —O(C(R*$_2$))$_{2-3}$O—, or —S(C(R*$_2$))$_{2-3}$S—, or a divalent substituent bound to vicinal substitutable carbons of an "optionally substituted" group is —O(CR*$_2$)$_{2-3}$O—, wherein each independent occurrence of R* is selected from hydrogen, C$_{1-6}$ aliphatic or an unsubstituted 5-6-membered saturated, partially unsaturated, or aryl ring having 0-4 heteroatoms independently selected from nitrogen, oxygen, or sulfur.

When R* is C$_{1-6}$ aliphatic, R* is optionally substituted with halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens.

An optional substituent on a substitutable nitrogen is independently —R$^{\dagger}$, —NR$^{\dagger}$$_2$, —C(O)R$^{\dagger}$, —C(O)OR$^{\dagger}$, —C(O)C(O)R$^{\dagger}$, —C(O)CH$_2$C(O)R$^{\dagger}$, —S(O)$_2$R$^{\dagger}$, —S(O)$_2$NR$^{\dagger}$$_2$, —C(S)NR$^{\dagger}$$_2$, —C(NH)NR$^{\dagger}$$_2$, or —N(R$^{\dagger}$)S(O)$_2$R$^{\dagger}$; wherein each R$^{\dagger}$ is independently hydrogen, C$_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R$^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R$^{\dagger}$ is C$_{1-6}$ aliphatic, R$^{\dagger}$ is optionally substituted with halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety of a provided compound comprises one or more deuterium atoms.

As used herein, the terms "inhibitor" or "TEAD inhibitor" or "TEAD antagonist" are defined as a compound that binds to and/or inhibits TEAD with measurable affinity. In some embodiments, inhibition in the presence of the inhibitor is observed in a dose-dependent manner. In some embodiments, the measured signal (e.g., signaling activity or biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% lower than the signal measured with a negative control under comparable conditions. The potency of an inhibitor is usually defined by its $IC_{50}$ value (half maximal inhibitory concentration or concentration required to inhibit 50% of the agonist response). The lower the $IC_{50}$ value the greater the potency of the antagonist and the lower the concentration that is required to inhibit the maximum biological response. In certain embodiments, an inhibitor has an $IC_{50}$ and/or binding constant of less than about 100 µM, less than about 50 µM, less than about 1 µM, less than about 500 nM, less than about 100 nM, less than about 10 nM, or less than about 1 nM.

The terms "measurable affinity" and "measurably inhibit," as used herein, means a measurable change or inhibition in TEAD activity between a sample comprising a compound of the present invention, or composition thereof, and TEAD, and an equivalent sample comprising TEAD, in the absence of said compound, or composition thereof.

3. Description of Exemplary Embodiments

In one aspect, the present invention provides a compound of Formula I':

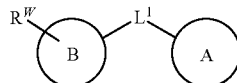

I' or a pharmaceutically acceptable salt thereof, wherein:
$L^1$ is a covalent bond, or a $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, or a 8-10 membered bicyclic heteroaromatic ring having 1-5 heteroatoms independently selected from nitrogen, oxygen, or sulfur;

Ring B is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, a 8-10 membered bicyclic heteroaromatic ring having 1-5 heteroatoms independently selected from nitrogen, oxygen, or sulfur;

$R^w$ is a warhead group; wherein when $R^w$ is a saturated or partially unsaturated monocyclic carbocyclic or heterocyclic ring, it optionally forms a spiro bicyclic ring with Ring B; and each R is independently —H or optionally substituted —$C_{1-6}$ aliphatic.

In one aspect, the present invention provides a compound of Formula I:

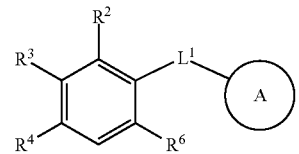

I or a pharmaceutically acceptable salt thereof, wherein:
$L^1$ is $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is a 4-, 5-, or 6-membered saturated or partially unsaturated monocyclic carbocyclic ring, phenyl, a 4-, 5-, or 6-membered saturated or partially unsaturated monocyclic heterocyclic ring having 1-2 heteroatoms independently selected from nitrogen, oxygen, or sulfur, or a 5-6 membered monocyclic heteroaromatic ring having 1, 2, 3, or 4 heteroatoms independently selected from nitrogen, oxygen, or sulfur, wherein Ring A is optionally substituted 1-2 times by halogen, —CN, —NO$_2$, or —C$_{1-6}$ aliphatic substituted 0-6 times by halogen, —CN, or —NO$_2$;

$R^2$ is —H, or a warhead group;
$R^3$ is —H or a warhead group;
$R^4$ is —H, halogen, —S(O)$_2$N(R)$_2$, —S(O)N(R)$_2$, —C(O)N(R)$_2$, or a warhead group;
$R^6$ is —H or —C$_{1-6}$ aliphatic substituted 0-6 times by halogen, —CN, or —NO$_2$; and
each R is independently —H or optionally substituted —C$_{1-6}$ aliphatic.

As defined generally above, $L^1$ is C$_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—.

In some embodiments, $L^1$ is a covalent bond, or a C$_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—.

In some embodiments, $L^1$ is a covalent bond.

In some embodiments, $L^1$ is C$_{1-6}$ bivalent straight or branched hydrocarbon chain wherein 1, 2, or 3 methylene units of the chain are independently and optionally replaced with —O—, —CH(OR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, or —N(R)C(O)N(R)—.

In some embodiments, $L^1$ is C$_{1-6}$ bivalent straight or branched hydrocarbon chain wherein 1, 2, or 3 methylene units of the chain are optionally replaced with —CH(SR)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—.

In some embodiments, $L^1$ is C$_{1-6}$ bivalent straight or branched hydrocarbon chain wherein 1, 2, or 3 methylene units of the chain are independently and optionally replaced with —O—, —S—, or —N(R)—.

In some embodiments, $L^1$ is C$_{1-6}$ bivalent straight or branched hydrocarbon chain wherein 1, 2, or 3 methylene units of the chain are independently and optionally replaced with —CH(OR)—, —CH(SR)—, or —CH(N(R)$_2$)—.

In some embodiments, $L^1$ is C$_{1-6}$ bivalent straight or branched hydrocarbon chain wherein 1, 2, or 3 methylene units of the chain are independently and optionally replaced with —C(O)—, —C(O)O—, —OC(O)—, —SO—, —SO$_2$—, —C(S)—, —C(S)O—, or —OC(S)—.

In some embodiments, $L^1$ is C$_{1-6}$ bivalent straight or branched hydrocarbon chain wherein 1, 2, or 3 methylene units of the chain are independently and optionally replaced with —C(O)N(R)—, —(R)NC(O)—, —OC(O)N(R)—, —(R)NC(O)O—, —N(R)C(O)N(R)—, —SO$_2$N(R)—, —(R)NSO$_2$—, —C(S)N(R)—, —(R)NC(S)—, or —(R)NC(S)N(R)—.

In some embodiments, $L^1$ is —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—.

In some embodiments, $L^1$ is —O—, —CH(OR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, or —N(R)C(O)N(R)—.

In some embodiments, $L^1$ is —CH(SR)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—.

In some embodiments, $L^1$ is —O—, —S—, or —N(R)—. In some embodiments, $L^1$ is —O—. In some embodiments, $L^1$ is —S—. In some embodiments, $L^1$ is —N(R)—. In some embodiments, $L^1$ is —NH—.

In some embodiments, $L^1$ is —CH(OR)—, —CH(SR)—, or —CH(N(R)$_2$)—. In some embodiments, $L^1$ is —CH(OR)—. In some embodiments, $L^1$ is —CH(SR)—. In some embodiments, $L^1$ is —CH(N(R)$_2$)—.

In some embodiments, $L^1$ is —C(O)—, —C(O)O—, —OC(O)—, —SO—, —SO$_2$—, —C(S)—, —C(S)O—, or —OC(S)—. In some embodiments, $L^1$ is —C(O)—. In some embodiments, $L^1$ is —C(O)O—. In some embodiments, $L^1$ is —OC(O)—. In some embodiments, $L^1$ is —SO—. In some embodiments, $L^1$ is —SO$_2$—. In some embodiments, $L^1$ is —C(S)—. In some embodiments, $L^1$ is —C(S)O—. In some embodiments, $L^1$ is —OC(S)—.

In some embodiments, $L^1$ is —C(O)N(R)—, —(R)NC(O)—, —OC(O)N(R)—, —(R)NC(O)O—, —N(R)C(O)N(R)—, —SO$_2$N(R)—, —(R)NSO$_2$—, —C(S)N(R)—, —(R)NC(S)—, or —(R)NC(S)N(R)—. In some embodiments, $L^1$ is —C(O)N(R)—. In some embodiments, $L^1$ is —(R)NC(O)—. In some embodiments, $L^1$ is —OC(O)N(R)—. In some embodiments, $L^1$ is —(R)NC(O)O—. In some embodiments, $L^1$ is —N(R)C(O)N(R)—. In some embodiments, $L^1$ is —SO$_2$N(R)—. In some embodiments, $L^1$ is —(R)NSO$_2$—. In some embodiments, $L^1$ is —C(S)N(R)—. In some embodiments, $L^1$ is —(R)NC(S)—. or In some embodiments, $L^1$ is —(R)NC(S)N(R)—.

In some embodiments, $L^1$ is —CH$_2$—, —CH(CH$_3$)—, —NH—CH$_2$—, —NH—CH(CH$_3$)—, —C(O)—NH—, or —N(CH$_3$)—.

In some embodiments, $L^1$ is

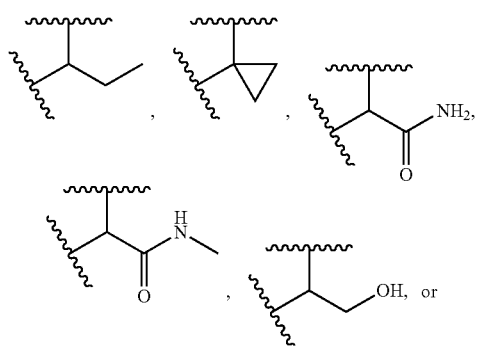

-continued

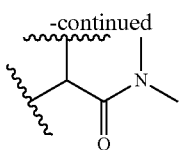

In some embodiments, $L^1$ is selected from the corresponding $L^1$ moieties in those compounds depicted in Table 1, below.

As defined generally above, Ring A is a 4-, 5-, or 6-membered saturated or partially unsaturated monocyclic carbocyclic ring, phenyl, a 4-, 5-, or 6-membered saturated or partially unsaturated monocyclic heterocyclic ring having 1-2 heteroatoms independently selected from nitrogen, oxygen, or sulfur, or a 5-6 membered monocyclic heteroaromatic ring having 1, 2, 3, or 4 heteroatoms independently selected from nitrogen, oxygen, or sulfur, wherein Ring A is optionally substituted 1-2 times by halogen, —CN, —NO$_2$, or —C$_{1-6}$ aliphatic substituted 0-6 times by halogen, —CN, or —NO$_2$.

In some embodiments, Ring A is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, or a 8-10 membered bicyclic heteroaromatic ring having 1-5 heteroatoms independently selected from nitrogen, oxygen, or sulfur.

In some embodiments, Ring A is optionally substituted phenyl. In some embodiments, Ring A is optionally substituted 4-, 5-, or 6-membered saturated or partially unsaturated monocyclic carbocyclic ring. In some embodiments, Ring A is optionally substituted 4-, 5-, or 6-membered saturated or partially unsaturated monocyclic heterocyclic ring having 1-2 heteroatoms independently selected from nitrogen, oxygen, or sulfur. In some embodiments, Ring A is optionally substituted 5-6 membered monocyclic heteroaromatic ring having 1, 2, 3, or 4 heteroatoms independently selected from nitrogen, oxygen, or sulfur. In some embodiments, Ring A is optionally substituted 8-10 membered bicyclic aromatic ring. In some embodiments, Ring A is optionally substituted 8-10 membered bicyclic heteroaromatic ring having 1-5 heteroatoms independently selected from nitrogen, oxygen, or sulfur.

In some embodiments, Ring A is optionally substituted phenyl, a 6-membered monocyclic heteroaromatic ring having 1 or 2 nitrogen, or a 10-membered bicyclic heteroaromatic ring having 1-2 nitrogen.

In some embodiments, Ring A is optionally substituted

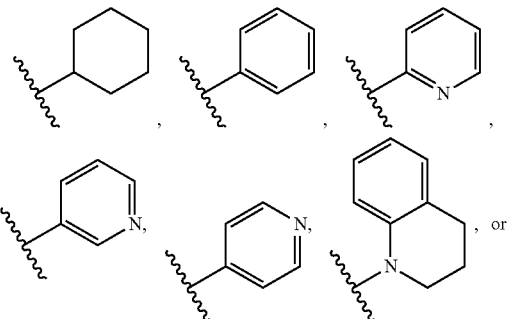

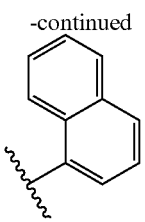

In some embodiments, Ring A is optionally substituted 1-2 times by -halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is independently substituted 0-6 times by -halogen, —CN, or —NO$_2$. In some embodiments, Ring A is optionally substituted 1-2 times by halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is independently substituted 0, 1, 2, 3, 4, 5, or 6 times by halogen, —CN, or —NO$_2$. In some embodiments, Ring A is optionally substituted 1-2 times by halogen, —C$_{1-6}$ aliphatic, or —O—C$_{1-6}$ aliphatic, wherein each of —C$_{1-6}$ aliphatic and —O—C$_{1-6}$ aliphatic is independently substituted 1, 2, 3, 4, 5, or 6 times by halogen.

In some embodiments, Ring A is a 4-, 5-, or 6-membered saturated or partially unsaturated monocyclic carbocyclic ring. In some embodiments, Ring A is cyclohexyl. In some embodiments, Ring A is phenyl. In some embodiments, Ring A is a 4-, 5-, or 6-membered saturated or partially unsaturated monocyclic heterocyclic ring having 1-2 heteroatoms independently selected from nitrogen, oxygen, or sulfur. In some embodiments, Ring A is a 5-6 membered monocyclic heteroaromatic ring having 1, 2, 3, or 4 heteroatoms independently selected from nitrogen, oxygen, or sulfur.

In some embodiments, Ring A is a 8-10 membered bicyclic aromatic ring. In some embodiments, Ring A is a 8-10 membered bicyclic heteroaromatic ring having 1-5 heteroatoms independently selected from nitrogen, oxygen, or sulfur.

In some embodiments, Ring A is optionally substituted 1-2 times by halogen, —CN, —NO$_2$, or —C$_{1-6}$ aliphatic substituted 0, 1, 2, 3, 4, 5, or 6 times by halogen, —CN, or —NO$_2$. In some embodiments, Ring A is optionally substituted 1-2 times by halogen, or —C$_{1-6}$ aliphatic substituted 0, 1, 2, 3, 4, 5, or 6 times by halogen.

In some embodiments, Ring A is selected from

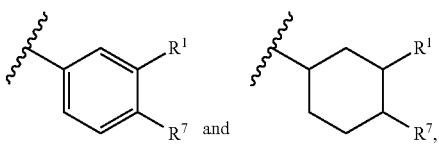

wherein each of $R^1$ and $R^7$ is independently as described herein.

In some embodiments, Ring A is selected from

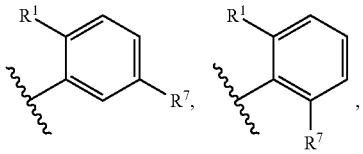

-continued

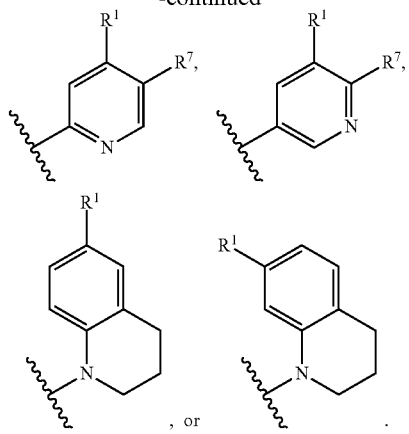

, or .

In some embodiments, $R^1$ is —H, -halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is substituted 0, 1, 2, 3, 4, 5, or 6 times by -halogen, —CN, or —NO$_2$. In some embodiments, $R^1$ is unsubstituted —O—C$_{1-6}$ aliphatic. In some embodiments, $R^1$ is —OCH$_3$. In some embodiments, $R^1$ is —O—C$_{1-6}$ aliphatic substituted 1, 2, 3, 4, 5, or 6 times by -halogen. In some embodiments, $R^1$ is —O—C$_{1-3}$ aliphatic substituted 1, 2, 3, 4, 5, or 6 times by -halogen. In some embodiments, $R^1$ is —O—C$_{1-6}$ aliphatic substituted 1, 2, 3, 4, 5, or 6 times by —F.

In some embodiments, $R^1$ is —H, -halogen, —CN, —NO$_2$, or —C$_{1-6}$ aliphatic substituted 0, 1, 2, 3, 4, 5, or 6 times by -halogen, —CN, or —NO$_2$. In some embodiments, $R^1$ is —H. In some embodiments, $R^1$ is -halogen. In some embodiments, $R^1$ is —F. In some embodiments, $R^1$ is —Cl. In some embodiments, $R^1$ is —Br. In some embodiments, $R^1$ is —CN. In some embodiments, $R^1$ is —NO$_2$. In some embodiments, $R^1$ is unsubstituted —C$_{1-6}$ aliphatic. In some embodiments, $R^1$ is —CH$_3$. In some embodiments, $R^1$ is —C$_{1-6}$ aliphatic substituted 1, 2, 3, 4, 5, or 6 times by -halogen. In some embodiments, $R^1$ is —C$_{1-3}$ aliphatic substituted 1, 2, 3, 4, 5, or 6 times by -halogen. In some embodiments, $R^1$ is —C$_{1-6}$ aliphatic substituted 1, 2, 3, 4, 5, or 6 times by —F. In some embodiments, le is —C$_{1-3}$ aliphatic substituted 1, 2, 3, 4, 5, or 6 times by —F. In some embodiments, $R^1$ is —CF$_3$. In some embodiments, $R^1$ is —C$_{1-6}$ aliphatic substituted 1, 2, 3, 4, 5, or 6 times by —CN. In some embodiments, $R^1$ is —C$_{1-6}$ aliphatic substituted 1, 2, 3, 4, 5, or 6 times by —NO$_2$.

In some embodiments, $R^1$ is phenyl. In some embodiments, $R^1$ is —C(CH$_3$)$_3$. In some embodiments, $R^1$ is —SCF$_3$. In some embodiments, $R^1$ is —S(O)$_2$CF$_3$. In some embodiments, $R^1$ is —N(CH$_3$)$_2$. In some embodiments, $R^1$ is —CHF$_2$. In some embodiments, $R^1$ is cyclopropyl. In some embodiments, $R^1$ is —CF$_2$CF$_3$. In some embodiments, $R^1$ is

.

In some embodiments, $R^7$ is —H, -halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is substituted 0, 1, 2, 3, 4, 5, or 6 times by -halogen, —CN, or —NO$_2$. In some embodiments, $R^7$ is unsubstituted —O—C$_{1-6}$ aliphatic. In some embodiments, $R^7$ is —OCH$_3$. In some embodiments, $R^7$ is —O—C$_{1-6}$ aliphatic substituted 1, 2, 3, 4, 5, or 6 times by -halogen. In some embodiments, $R^7$ is —O—C$_{1-3}$ aliphatic substituted 1, 2, 3, 4, 5, or 6 times by -halogen. In some embodiments, $R^7$ is —O—C$_{1-6}$ aliphatic substituted 1, 2, 3, 4, 5, or 6 times by —F.

In some embodiments, $R^7$ is —H, -halogen, —CN, —NO$_2$, or —C$_{1-6}$ aliphatic substituted 0, 1, 2, 3, 4, 5, or 6 times by -halogen, —CN, or —NO$_2$. In some embodiments, $R^7$ is —H. In some embodiments, $R^7$ is -halogen. In some embodiments, $R^7$ is —F. In some embodiments, $R^7$ is —Cl. In some embodiments, $R^7$ is —Br. In some embodiments, $R^7$ is —CN. In some embodiments, $R^7$ is —NO$_2$. In some embodiments, $R^7$ is unsubstituted —C$_{1-6}$ aliphatic. In some embodiments, $R^1$ is —CH$_3$. In some embodiments, $R^7$ is —C$_{1-6}$ aliphatic substituted 1, 2, 3, 4, 5, or 6 times by -halogen. In some embodiments, $R^7$ is —C$_{1-3}$ aliphatic substituted 1, 2, 3, 4, 5, or 6 times by -halogen. In some embodiments, $R^7$ is —C$_{1-6}$ aliphatic substituted 1, 2, 3, 4, 5, or 6 times by —F. In some embodiments, $R^7$ is —C$_{1-3}$ aliphatic substituted 1, 2, 3, 4, 5, or 6 times by —F. In some embodiments, $R^7$ is —CF$_3$. In some embodiments, $R^7$ is —C$_{1-6}$ aliphatic substituted 1, 2, 3, 4, 5, or 6 times by —CN. In some embodiments, $R^7$ is —C$_{1-6}$ aliphatic substituted 1, 2, 3, 4, 5, or 6 times by —NO$_2$.

In some embodiments, $R^7$ is phenyl. In some embodiments, $R^7$ is —C(CH$_3$)$_3$. In some embodiments, $R^7$ is —SCF$_3$. In some embodiments, $R^7$ is —S(O)$_2$CF$_3$. In some embodiments, $R^7$ is —N(CH$_3$)$_2$. In some embodiments, $R^7$ is —CHF$_2$. In some embodiments, $R^7$ is cyclopropyl. In some embodiments, $R^7$ is —CF$_2$CF$_3$. In some embodiments, $R^7$ is

.

In some embodiments, Ring A is

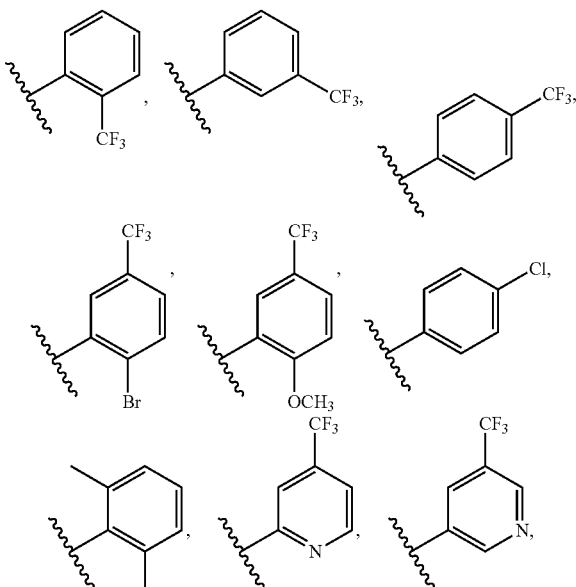

-continued

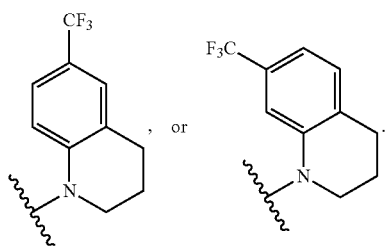

In some embodiments, Ring A is

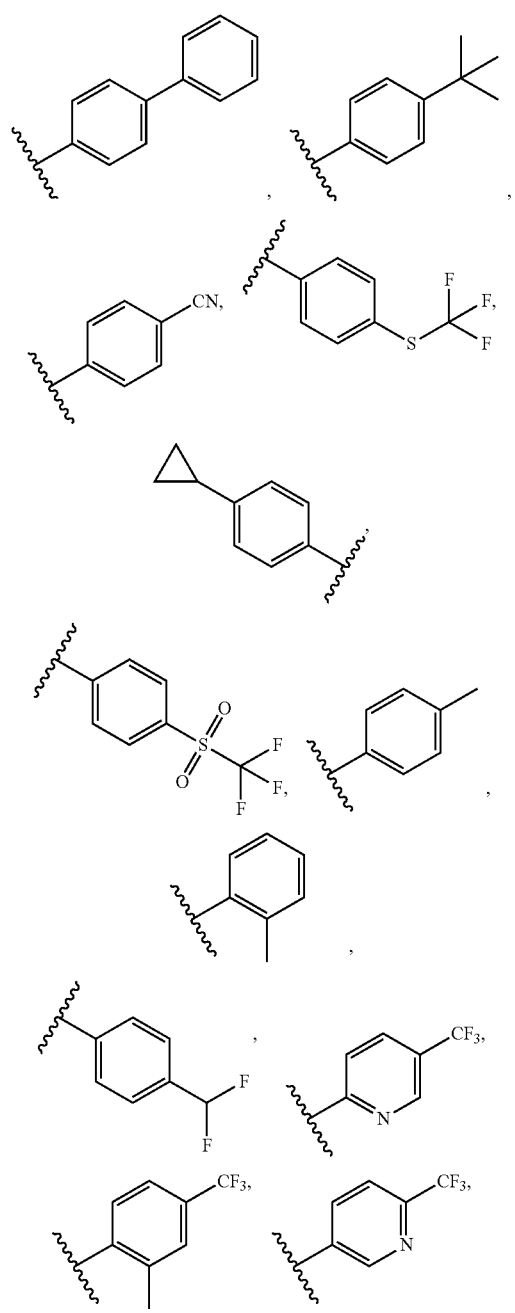

-continued

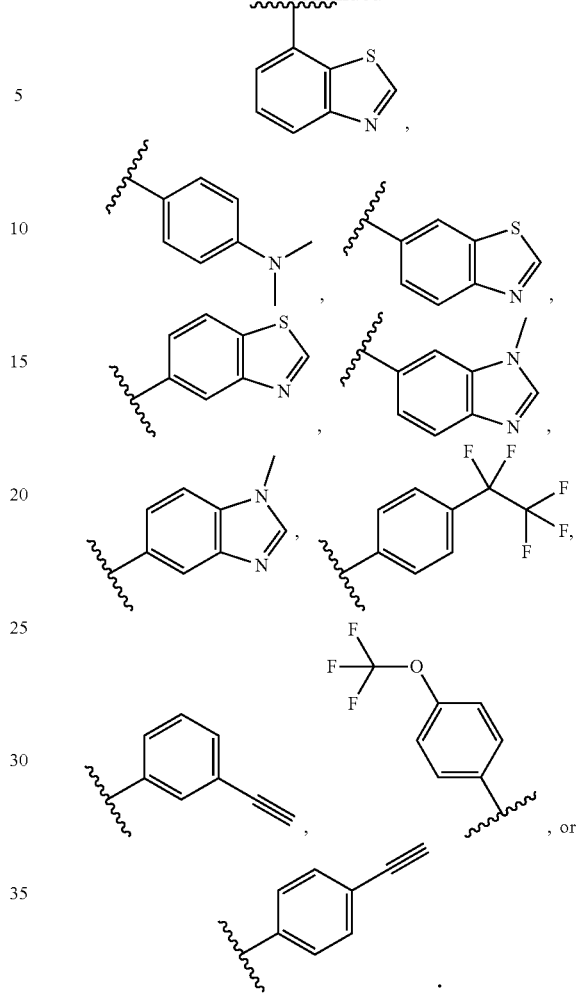

In some embodiments, Ring A is selected from the corresponding Ring A moieties in those compounds depicted in Table 1, below.

As defined generally above, Ring B is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, a 8-10 membered bicyclic heteroaromatic ring having 1-5 heteroatoms independently selected from nitrogen, oxygen, or sulfur.

In some embodiments, Ring B is optionally substituted phenyl. In some embodiments, Ring B is optionally substituted 4-, 5-, or 6-membered saturated or partially unsaturated monocyclic carbocyclic ring. In some embodiments, Ring B is optionally substituted 4-, 5-, or 6-membered saturated or partially unsaturated monocyclic heterocyclic ring having 1-2 heteroatoms independently selected from nitrogen, oxygen, or sulfur. In some embodiments, Ring B is optionally substituted 5-6 membered monocyclic heteroaromatic ring having 1, 2, 3, or 4 heteroatoms independently selected from nitrogen, oxygen, or sulfur. In some embodiments, Ring B is optionally substituted 8-10 membered bicyclic aromatic ring. In some embodiments, Ring B is optionally substituted 8-10 membered bicyclic heteroaromatic ring having 1-5 heteroatoms independently selected from nitrogen, oxygen, or sulfur.

In some embodiments, Ring B is an optionally substituted 6-, 7-, 8-, 9-, or 10-membered bicyclic carbocyclic ring. In some embodiments, Ring B is an optionally substituted 6-, 7-, 8-, 9-, or 10-membered bicyclic heterocyclic ring having 1, 2, 3, 4, or 5 heteroatoms independently selected from nitrogen, oxygen, or sulfur. In some embodiments, Ring B is an optionally substituted 6-membered bicyclic heterocyclic ring having 1 nitrogen.

In some embodiments, Ring B is optionally substituted phenyl or a 6-membered monocyclic heteroaromatic ring having 1 or 2 nitrogen.

In some embodiments, Ring B is optionally substituted

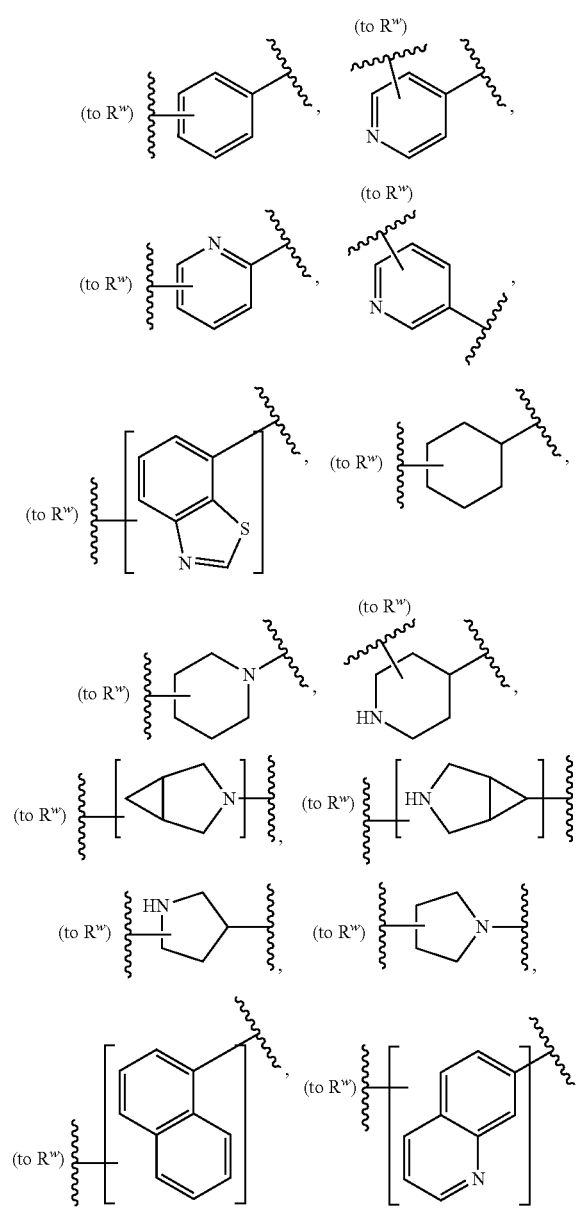

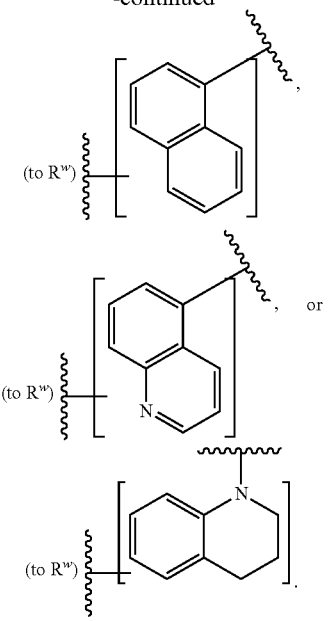

In some embodiments, Ring B is optionally substituted 1-4 times by halogen, —S(O)$_2$N(R)$_2$, —S(O)N(R)$_2$, —C(O)N(R)$_2$, —C(O)OR, —C$_{1-6}$ aliphatic, or —O—C$_{1-6}$ aliphatic, wherein each of —C$_{1-6}$ aliphatic and —O—C$_{1-6}$ aliphatic is independently substituted 0-6 times by halogen, —CN, or —NO$_2$.

In some embodiments, Ring B is optionally substituted 1-4 times by —F, —Cl, —Br—, —S(O)$_2$NHCH$_3$, —S(O)NHCH$_3$, —C(O)N(CH$_3$)$_2$, —C(O)NHCH$_3$, —C(O)OH, —C(O)OCH$_3$, —CH$_3$, —OCH$_3$, or —C(CH$_3$)$_3$.

In some embodiments, Ring B is

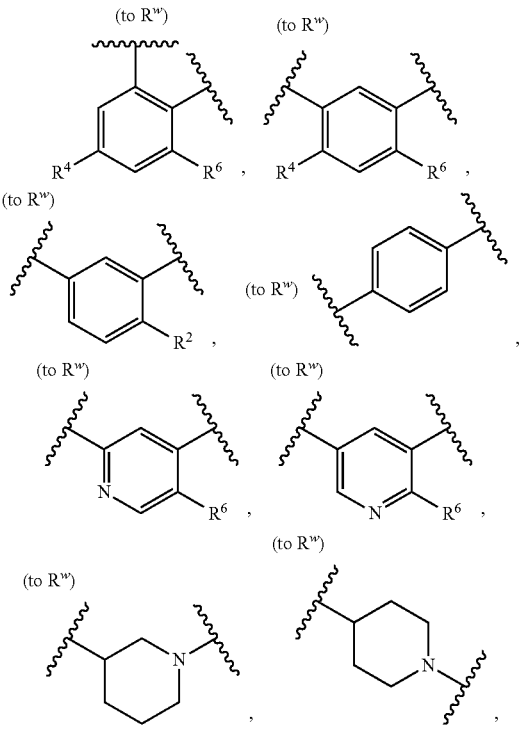

-continued
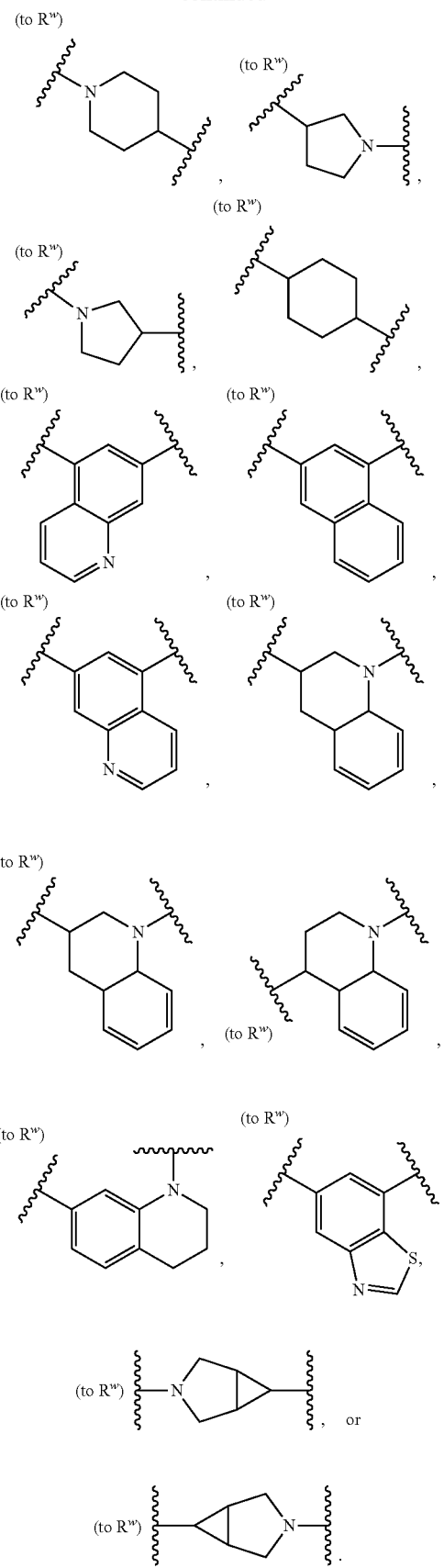
In some embodiments, Ring B is
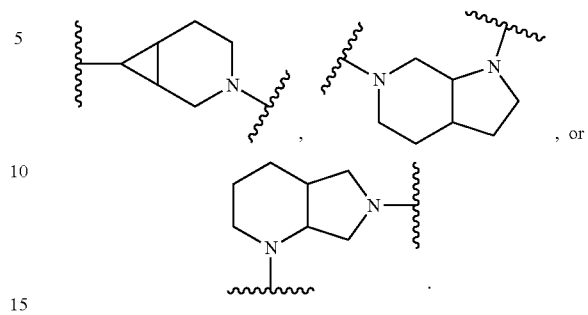
In some embodiments, Ring B is selected from the corresponding Ring B moieties in those compounds depicted in Table 1, below.
As defined generally above, $R^2$ is —H, or a warhead group.
In some embodiments, $R^2$ is —H.
In some embodiments, $R^2$ is a warhead group. In some embodiments, $R^2$ is
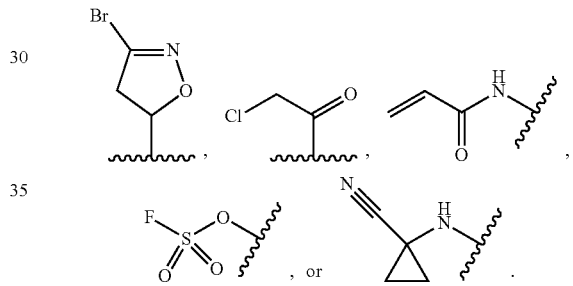
In some embodiments, $R^2$ is
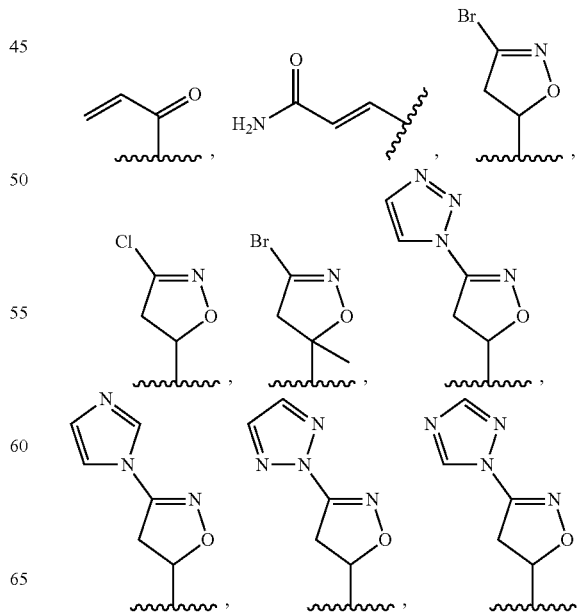

-continued

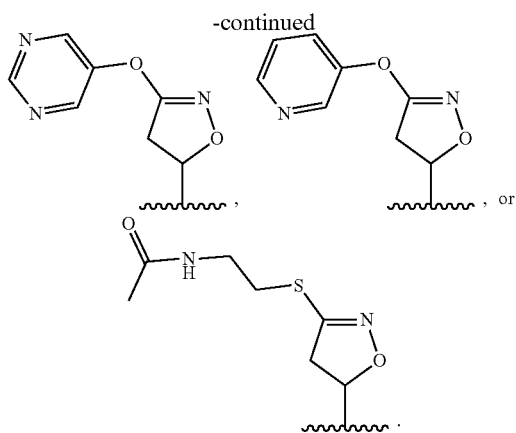

, or

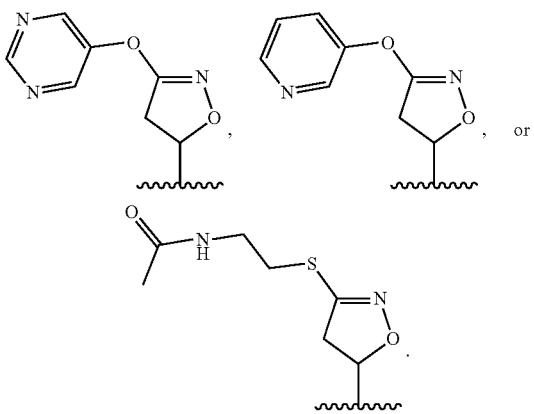

, or

In some embodiments, $R^2$ is selected from the corresponding $R^2$ moieties in those compounds depicted in Table 1, below.

As defined generally above, $R^3$ is —H or a warhead group.

In some embodiments, $R^3$ is —H.

In some embodiments, $R^3$ is a warhead group. In some embodiments, $R^3$ is

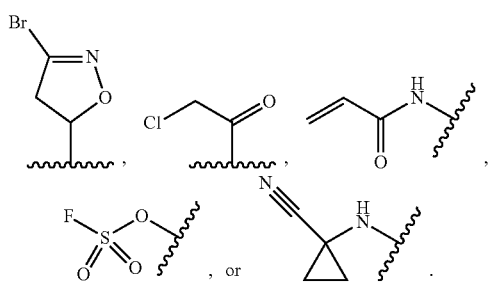

, or

In some embodiments, $R^3$ is

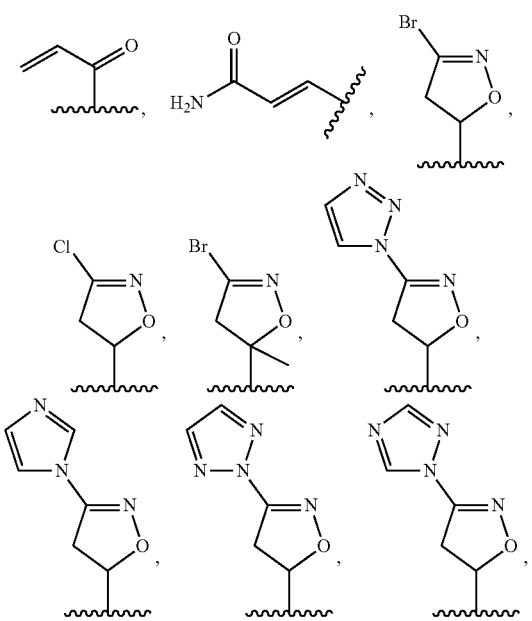

In some embodiments, $R^3$ is selected from the corresponding $R^3$ moieties in those compounds depicted in Table 1, below.

As defined generally above, $R^4$ is —H, halogen, —S(O)$_2$N(R)$_2$, —S(O)N(R)$_2$, —C(O)N(R)$_2$, or a warhead group.

In some embodiments, $R^4$ is —H, halogen, —S(O)$_2$N(R)$_2$, —S(O)N(R)$_2$, —C(O)N(R)$_2$, —C(O)OR, or a warhead group.

In some embodiments, $R^4$ is —H.

In some embodiments, $R^4$ is halogen. In some embodiments, $R^4$ is —F. In some embodiments, $R^4$ is —Cl. In some embodiments, $R^4$ is —Br.

In some embodiments, $R^4$ is —S(O)$_2$N(R)$_2$, —S(O)N(R)$_2$, or —C(O)N(R)$_2$. In some embodiments, $R^4$ is —S(O)$_2$N(R)$_2$. In some embodiments, $R^4$ is —S(O)N(R)$_2$. In some embodiments, $R^4$ is —C(O)N(R)$_2$. In some embodiments, $R^4$ is —S(O)$_2$NHCH$_3$.

In some embodiments, $R^4$ is —S(O)NHCH$_3$, —C(O)N(CH$_3$)$_2$, —C(O)NHCH$_3$, —C(O)OH, or —C(O)OCH$_3$.

In some embodiments, $R^4$ is a warhead group. In some embodiments, $R^4$ is

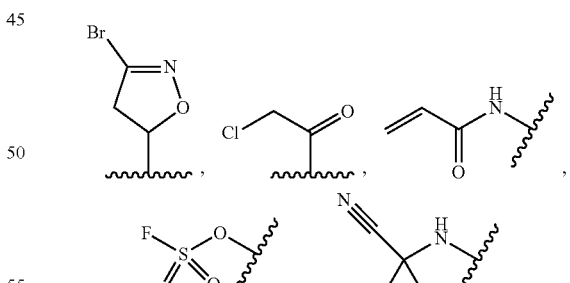

, or

In some embodiments, $R^4$ is

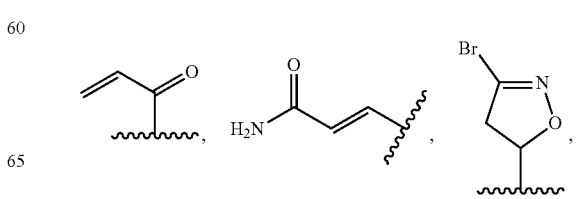

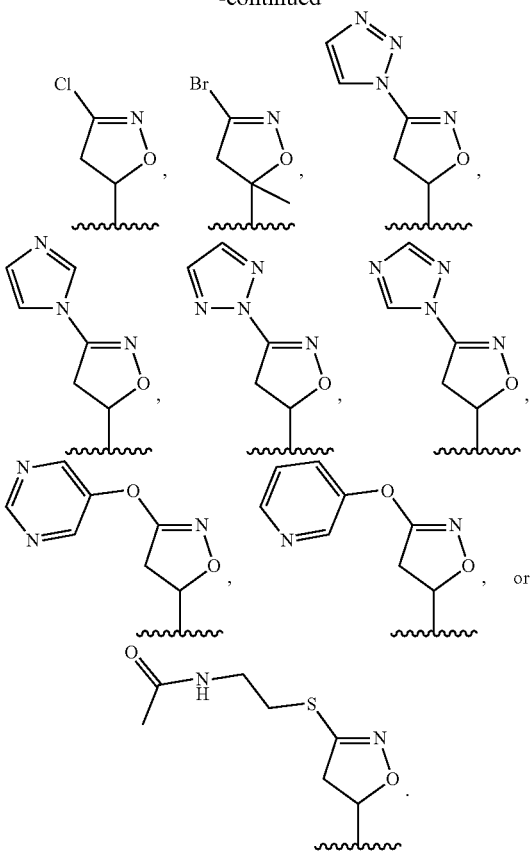

In some embodiments, $R^4$ is selected from the corresponding $R^4$ moieties in those compounds depicted in Table 1, below.

As defined generally above, $R^6$ is —H or —$C_{1-6}$ aliphatic substituted 0, 1, 2, 3, 4, 5, or 6 times by -halogen, —CN, or —$NO_2$.

In some embodiments, $R^6$ is —H, -halogen, —CN, —$NO_2$, —$C_{1-6}$ aliphatic, —$OC_{1-6}$ aliphatic, or a 4-, 5-, or 6-membered ring having 1, 2, 3, or 4 heteroatoms independently selected from nitrogen, oxygen, or sulfur optionally substituted 1-3 times by —$C_{1-6}$ aliphatic or —$OC_{1-6}$ aliphatic, wherein each of —$C_{1-6}$ aliphatic and —$OC_{1-6}$ aliphatic is independently substituted 0, 1, 2, 3, 4, 5, or 6 times by -halogen, —CN, or —$NO_2$.

In some embodiments, $R^6$ is —H. In some embodiments, $R^6$ is —F. In some embodiments, $R^6$ is —Cl. In some embodiments, $R^6$ is —Br. In some embodiments, $R^6$ is —CN. In some embodiments, $R^6$ is —$NO_2$.

In some embodiments, $R^6$ is —$C_{1-6}$ aliphatic, substituted 0, 1, 2, 3, 4, 5, or 6 times by -halogen, —CN, or —$NO_2$. In some embodiments, $R^6$ is unsubstituted —$C_{1-6}$ aliphatic. In some embodiments, $R^6$ is —$CH_3$. In some embodiments, $R^6$ is —$C_{1-6}$ aliphatic substituted 1, 2, 3, 4, 5, or 6 times by -halogen, —CN, or —$NO_2$. In some embodiments, $R^6$ is —$C_{1-6}$ aliphatic substituted 1, 2, 3, 4, 5, or 6 times by —F. In some embodiments, $R^6$ is —$C_{1-3}$ aliphatic substituted 1, 2, 3, 4, 5, or 6 times by —F. In some embodiments, $R^6$ is —$CF_3$.

In some embodiments, $R^6$ is —$OC_{1-6}$ aliphatic, substituted 0, 1, 2, 3, 4, 5, or 6 times by -halogen, —CN, or —$NO_2$. In some embodiments, $R^6$ is unsubstituted —$OC_{1-6}$ aliphatic. In some embodiments, $R^6$ is —$OCH_3$. In some embodiments, $R^6$ is —$OC_{1-6}$ aliphatic substituted 1, 2, 3, 4, 5, or 6 times by -halogen, —CN, or —$NO_2$. In some embodiments, $R^6$ is —$OC_{1-6}$ aliphatic substituted 1, 2, 3, 4, 5, or 6 times by —F. In some embodiments, $R^6$ is —$OC_{1-3}$ aliphatic substituted 1, 2, 3, 4, 5, or 6 times by —F. In some embodiments, $R^6$ is —$OCF_3$.

In some embodiments, $R^6$ is a 4-, 5-, or 6-membered ring having 1, 2, 3, or 4 heteroatoms independently selected from nitrogen, oxygen, or sulfur optionally substituted 1-3 times by —$C_{1-6}$ aliphatic or —$OC_{1-6}$ aliphatic, wherein each of —$C_{1-6}$ aliphatic and —$OC_{1-6}$ aliphatic is independently substituted 0, 1, 2, 3, 4, 5, or 6 times by -halogen, —CN, or —$NO_2$. In some embodiments, $R^6$ is a 5-membered ring having 1, 2, 3, or 4 nitrogen optionally substituted 1-3 times by —$C_{1-6}$ aliphatic. In some embodiments, $R^6$ is

In some embodiments, $R^6$ is selected from the corresponding $R^6$ moieties in those compounds depicted in Table 1, below.

As defined generally above, $R^w$ is a warhead group; wherein when $R^w$ is a saturated or partially unsaturated monocyclic carbocyclic or heterocyclic ring, it optionally forms a spiro bicyclic ring with Ring B.

In some embodiments, $R^w$ is a warhead group.

In some embodiments, $R^w$ is

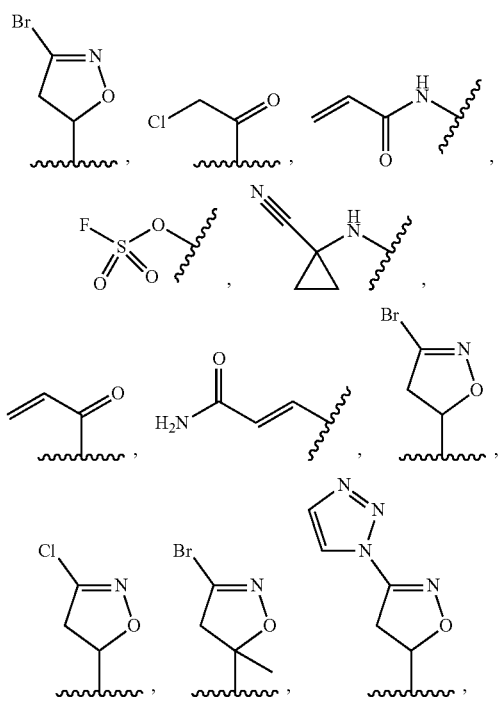

-continued

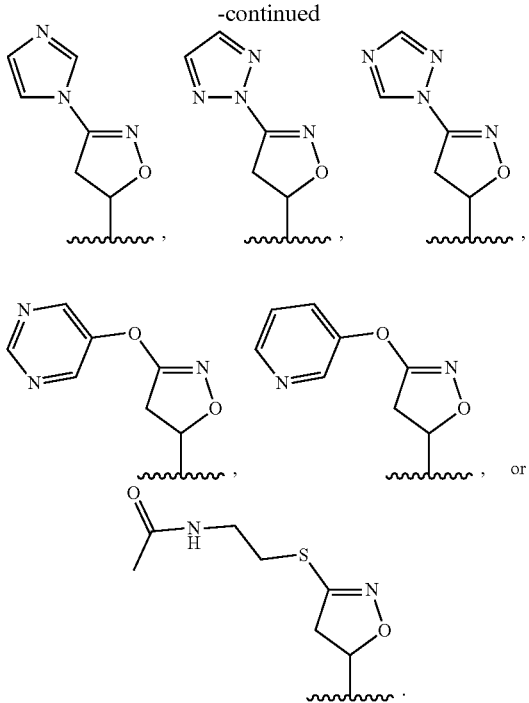

In some embodiments, wherein R$^w$ is a saturated or partially unsaturated monocyclic carbocyclic or heterocyclic ring, R$^w$ forms a spiro bicyclic ring with Ring B. In some embodiments, wherein R$^w$ is a saturated or partially unsaturated 4-, 5-, or 6-membered carbocyclic or heterocyclic ring, R$^w$ forms a spiro bicyclic ring with Ring B. In some embodiments, wherein R$^w$ is optionally substituted

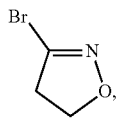

it forms a spiro bicyclic ring with Ring B. In some embodiments, wherein R$^w$ is optionally substituted

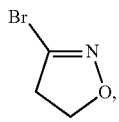

it forms a spiro bicyclic ring with Ring B, for example,

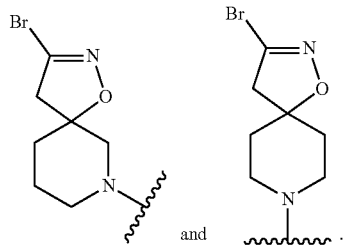 [SMILES: *N1CCCC2(CC(Br)=NO2)C1 ; *N1CCC2(CC1)CC(Br)=NO2]

In some embodiments, R$^w$ is selected from the corresponding R$^w$ moieties in those compounds depicted in Table 1, below.

As defined generally above, R is independently —H or optionally substituted —C$_{1-6}$ aliphatic.

In some embodiments, R is —H.

In some embodiments, R is optionally substituted —C$_{1-6}$ aliphatic. In some embodiments, R is unsubstituted —C$_{1-6}$ aliphatic. In some embodiments, R is —C$_{1-6}$ aliphatic substituted 1, 2, 3, 4, 5, or 6 times by -halogen, —CN, or —NO$_2$. In some embodiments, R is —C$_{1-6}$ aliphatic substituted 1, 2, 3, 4, 5, or 6 times by —F. In some embodiments, R is —C$_{1-3}$ aliphatic substituted 1, 2, 3, 4, 5, or 6 times by —F. In some embodiments, R is —CF$_3$.

In some embodiments, R is —CH$_3$, —C(CH$_3$)$_3$, —CHF$_2$, cyclopropyl, —CF$_2$CF$_3$, or

In some embodiments, R is selected from the corresponding R moieties in those compounds depicted in Table 1, below.

A "warhead group," as used herein, is capable of covalently binding to an amino acid residue (such as cysteine, lysine, histidine, or other residues capable of being covalently modified) present in the binding pocket of a target protein, for example, TEAD, thereby irreversibly inhibiting the protein. In some embodiments, a warhead group is capable of covalently binding to cysteine. In some embodiments, a warhead group is capable of covalently binding to serine. In some embodiments, a warhead group is capable of covalently binding to lysine. In some embodiments, a warhead group is capable of covalently binding to Cys359 of hTEAD1, Cys405 of hTEAD1, Cys380 of hTEAD2, Cys368 of hTEAD3, and/or Cys367 of hTEAD4. In some embodiments, a warhead group is capable of covalently binding to Ser356 of hTEAD1, Ser345 and/or Ser377 of hTEAD2, Ser365 of hTEAD3, and/or Ser364 of hTEAD4. In some embodiments, a warhead group is capable of covalently binding to Lys336 of hTEAD1, Lys357 of hTEAD2, Lys345 of hTEAD3, and/or Lys344 of hTEAD4. Representative reference amino acid sequences of human TEAD1, human TEAD2, human TEAD3, and human TEAD4 include UniProt KB ID P28347-1 (SEQ ID NO: 1), UniProtKB ID Q15562 (SEQ ID NO: 2), UniProtKB ID Q99594 (SEQ ID NO: 3), and UniProtKB ID Q15561 (SEQ ID NO: 4), respectively. Below is the sequence alignments of TEAD coactivator binding domains, which is shown in Table 1 of "Targeting Transcriptional Enhanced Associate Domains (TEAD5)," *J. Med. Chem.* 2018, 61, 5057-5072, the entire content of which is incorporated herein by reference.

| SEQ ID NO: 5 | hTEAD1 | $^{206}$WQGRSIGTTKLRLNEFSAFLEQQRDPDSYNKHLFVHIGHANHSYSDPLLESNDIRQTYDKFPEKKGGLKE$^{275}$ |
|---|---|---|
| SEQ ID NO: 6 | hTEAD2 | $^{218}$WQARGLGTARLQLVEFSAFVEPPDAVDSYQRHLFVHISQHCPSPGAPPLESVDVRQIYDKFPEKKGGLRE$^{287}$ |
| SEQ ID NO: 7 | hTEAD3 | $^{215}$WQDRTIASSRLRLLEYSAFMEVQRDPDTYSKHLFVHIGQTNPAFSDPPLEAVDVRQIYDKFPEKKGGLKE$^{284}$ |
| SEQ ID NO: 8 | hTEAD4 | $^{214}$WQGRSVASSKLWMLEFSAFLEQQQDPDTYNKHLFVHIGQSSPSYSDPYLEAVDIRQIYDKFPEKKGGLKD$^{283}$ |
| SEQ ID NO: 5 | hTEAD1 | $^{276}$LFGKGPQNAFFLVKFWADLNCNIQ-DDAGA--------FYGVTSQYESSENMTVTCSTKVCSFGKQVVEK$^{336}$ |
| SEQ ID NO: 6 | hTEAD2 | $^{288}$LYDRGPPHAFFLVKFWADLNWGPSGEEAGAGGSISSGGFYGVSSQYESLEHMTLTCSSKVCSFGKQVVEK$^{357}$ |
| SEQ ID NO: 7 | hTEAD3 | $^{285}$LYEKGPPNAFFLVKFWADLNSTIQ-EGPGA--------FYGVSSQYSSADSMTISVSTKVCSFGKQVVEK$^{345}$ |
| SEQ ID NO: 8 | hTEAD4 | $^{284}$LFERGPSNAFFLVKFWADLNTNIE-DEGSS--------FYGVSSQYESPENMIITCSTKVCSFGKQVVEK$^{344}$ |
| SEQ ID NO: 5 | hTEAD1 | $^{337}$VETEYARFENGRFVYRINRSPMCEYMINFIFIHKLHLPEKYMMNSVLENFTILLVVTNRDTQETLLCMACV$^{406}$ |
| SEQ ID NO: 6 | hTEAD2 | $^{358}$VETERAQLEDGRFVYRLLRSPMCEYLVNFLHKLRQLPERYMMNSVLENFTILQVVTNRDTQELLLCTAYV$^{427}$ |
| SEQ ID NO: 7 | hTEAD3 | $^{346}$VETEYARLENGRFVYRIHRSPMCEYMINFIHKLKHLPEKYMMNSVLENFTILQVVTSRDSQETLLVIAFV$^{415}$ |
| SEQ ID NO: 8 | hTEAD4 | $^{345}$VETEYARYENGHYSYRIHRSPLCEYMINFIHKLKHLPEKYMMNSVLENFTILQVVTNRDTQETLLCIAYV$^{414}$ |
| SEQ ID NO: 5 | hTEAD1 | $^{407}$FEVSNSEHGAQHHIYRLVKD$^{426}$ |
| SEQ ID NO: 6 | hTEAD2 | $^{428}$FEVSTSERGAQHHIYRLVRD$^{447}$ |
| SEQ ID NO: 7 | hTEAD3 | $^{416}$FEVSTSEHGAQHHVYKLVKD$^{435}$ |
| SEQ ID NO: 8 | hTEAD4 | $^{415}$FEVSASEHGAQHHIYRLVKE$^{434}$ |

In some embodiments, a warhead group is -L-Y, wherein:
L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —C(=S)—, —C(=NR)—, —N=N—, or —C(=N$_2$)—;
Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; and
each R$^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:
Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, NO$_2$, or CN.
In certain embodiments, L is a covalent bond.
In certain embodiments, L is a bivalent $C_{1-8}$ saturated or unsaturated, straight or branched, hydrocarbon chain. In certain embodiments, L is —CH$_2$—.
In certain embodiments, L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—.
In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O).
In certain embodiments, L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.

In some embodiments, L is a bivalent $C_{2-8}$ straight or branched, hydrocarbon chain wherein L has at least one double bond and at least one methylene unit of L is replaced by C(O)—, and one or more additional methylene units of L are optionally and independently replaced by cyclopropylene, —O—, —N(R)—, or —C(O)—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —CH$_2$C(=CH$_2$)CH$_2$—. Thus, in some embodiments, L is a bivalent $C_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent $C_{2-8}$ straight or branched, hydrocarbon chain wherein L has at least one double bond and at least one methylene unit of L is replaced by —C(O)—. In certain embodiments, L is —C(O)CH=CH(CH$_3$)—, —C(O)CH=CHCH$_2$NH(CH$_3$)—, —C(O)CH=CH(CH$_3$)—, —C(O)CH=CH—, —C(O)C(=CH$_2$)CH=CH—, —CH$_2$C(O)CH=CH(CH$_3$)—, —CH$_2$CH$_2$C(O)CH=CH—, —CH$_2$CH$_2$C(O)CH=CHCH$_2$—, —CH$_2$CH$_2$C(O)CH=CHCH$_2$NH(CH$_3$)—, or —CH$_2$CH$_2$C(O)CH=CH(CH$_3$)—, or —CH(CH$_3$)OC(O)CH=CH—.

In certain embodiments, L is a bivalent $C_{2-8}$ straight or branched, hydrocarbon chain wherein L has at least one double bond and at least one methylene unit of L is replaced by —OC(O)—.

In some embodiments, L is a bivalent $C_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—. In some embodiments, L is —CH$_2$OC(O)CH=CHCH$_2$—, —CH$_2$—OC(O)CH=CH—, or —CH(CH=CH$_2$)OC(O)CH=CH—.

In certain embodiments, L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-, wherein each R is independently hydrogen or optionally substituted $C_{1-6}$ aliphatic.

In certain embodiments, L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)C(O)—, —NHC(O)CH=CHCH$_2$N(CH$_3$)—, —NHSO$_2$CH=CH—, —NHSO$_2$CH=CHCH$_2$—, —NHC(O)CH=CHCH$_2$O—, —NHC(O)C(=CH$_2$)CH$_2$—, —CH$_2$NHC(O)—, —CH$_2$NHC(O)CH=CH—, —CH$_2$CH$_2$NHC(O)—, or —CH$_2$NHC(O)cyclopropylene-.

In some embodiments, L is a bivalent $C_{2-8}$ straight or branched, hydrocarbon chain wherein L has at least one triple bond. In certain embodiments, L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, —C≡CCH$_2$N(isopropyl)-, —NHC(O)C≡CCH$_2$CH$_2$—, —CH$_2$—C≡C≡CH$_2$—, —C≡CCH$_2$O—, —CH$_2$C(O)C≡C—, —C(O)C≡C—, or —CH$_2$OC(=O)C≡C—.

In certain embodiments, L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R)—. Exemplary L groups include —NHC(O)-cyclopropylene-SO$_2$— and —NHC(O)-cyclopropylene-.

As defined generally above, Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, NO$_2$, halogen, CN, a suitable leaving group, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and, Z is hydrogen or $C_{1-6}$ aliphatic optionally substituted with oxo, halogen, NO$_2$, or CN.

In certain embodiments, Y is hydrogen.

In certain embodiments, Y is $C_{1-6}$ aliphatic optionally substituted with oxo, halogen, NO$_2$, or CN. In some embodiments, Y is $C_{2-6}$ alkenyl optionally substituted with oxo, halogen, NO$_2$, or CN. In other embodiments, Y is $C_{2-6}$ alkynyl optionally substituted with oxo, halogen, NO$_2$, or CN. In some embodiments, Y is $C_{2-6}$ alkenyl. In other embodiments, Y is $C_{2-4}$ alkynyl.

In other embodiments, Y is $C_{1-6}$ alkyl substituted with oxo, halogen, NO$_2$, or CN. Such Y groups include —CH$_2$F, —CH$_2$Cl, —CH$_2$CN, and —CH$_2$NO$_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each $R^e$ is as defined above and described herein.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above and described herein. Exemplary such rings are epoxide and oxetane rings, wherein each ring is substituted with 1-2 $R^e$ groups, wherein each $R^e$ is as defined above and described herein.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above and described herein. Such rings include piperidine and pyrrolidine, wherein each ring is substituted with 1-4 $R^e$ groups, wherein each $R^e$ is as defined above and described herein. In certain embodiments, Y is

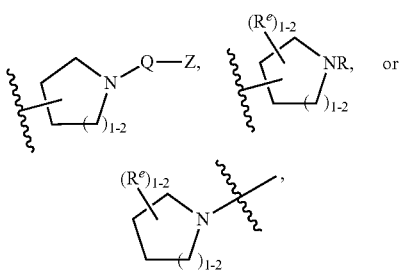

wherein each R, Q, Z, and $R^e$ is as defined above and described herein.

In some embodiments, Y is a saturated 3-6 membered carbocyclic ring, wherein said ring is substituted with 1-4 $R^e$ groups, wherein each $R^e$ is as defined above and described herein. In certain embodiments, Y is cyclopropyl, cyclobutyl, cyclopentyl, or cyclohexyl, wherein each ring is substituted with 1-4 $R^e$ groups, wherein each $R^e$ is as defined above and described herein. In certain embodiments, Y is

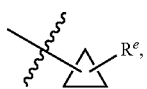

wherein $R^e$ is as defined above and described herein.

In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein.

In some embodiments, Y is a partially unsaturated 3-6 membered carbocyclic ring, wherein said ring is substituted with 1-4 $R^e$ groups, wherein each $R^e$ is as defined above and described herein. In some embodiments, Y is cyclopropenyl, cyclobutenyl, cyclopentenyl, or cyclohexenyl wherein each ring is substituted with 1-4 $R^e$ groups, wherein each $R^e$ is as defined 0-3 above and described herein. In certain embodiments, Y is

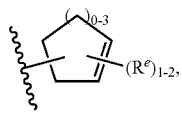

wherein each $R^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

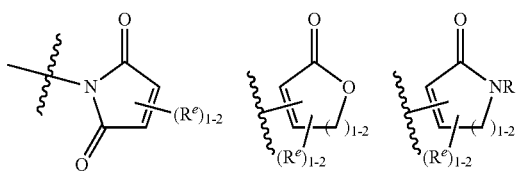

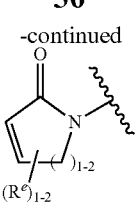

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

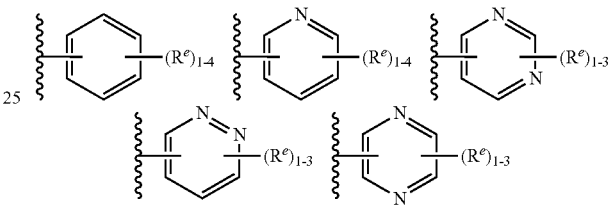

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

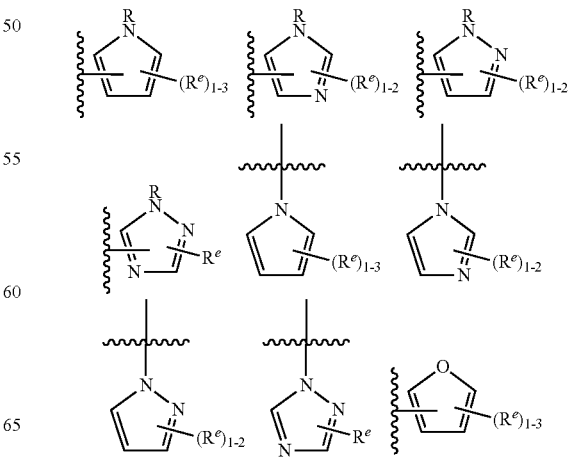

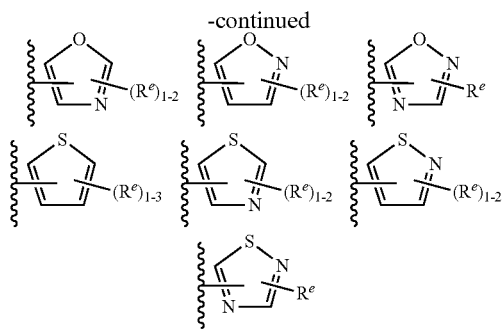

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein Reis as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —SO$_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —SO$_2$—. In certain embodiments, the Z moiety of the $R^e$ group is hydrogen. In some embodiments, -Q-Z is —NHC(O)CH=CH$_2$ or —C(O)CH=CH$_2$.

In certain embodiments, each $R^e$ is independently selected from oxo, $NO_2$, CN, fluoro, chloro, —NHC(O)CH=CH$_2$, —C(O)CH=CH$_2$, —CH$_2$CH=CH$_2$, —C(O)OCH$_2$Cl, —C(O)OCH$_2$F, —C(O)OCH$_2$CN, —C(O)CH$_2$Cl, —C(O)CH$_2$F, —C(O)CH$_2$CN, or —CH$_2$C(O)CH$_3$.

In certain embodiments, $R^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, trifyloxy, nitro-phenylsulfonyloxy (nosyloxy), and bromo-phenylsulfonyloxy (brosyloxy).

In certain embodiments, the following embodiments and combinations of -L-Y apply:

(a) L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or $C_{1-6}$ aliphatic optionally substituted with oxo, halogen, $NO_2$, or CN; or (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (d) L is a bivalent $C_{2-8}$ straight or branched, hydrocarbon chain wherein L has at least one double bond and at least one methylene unit of L is replaced by —C(O)—; and Y is hydrogen or $C_{1-6}$ aliphatic optionally substituted with oxo, halogen, $NO_2$, or CN; or (e) L is a bivalent $C_{2-8}$ straight or branched, hydrocarbon chain wherein L has at least one double bond and at least one methylene unit of L is replaced by —OC(O)—; and Y is hydrogen or $C_{1-6}$ aliphatic optionally substituted with oxo, halogen, $NO_2$, or CN; or (f) L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-; wherein R is H or optionally substituted $C_{1-6}$ aliphatic; and Y is hydrogen or $C_{1-6}$ aliphatic optionally substituted with oxo, halogen, $NO_2$, or CN; or (g) L is —NHC(O)CH=CH—, —NHC(O)CH=CHCH₂N(CH₃)—, —NHC(O)CH=CHCH₂O—, —CH₂NHC(O)CH=CH—, —NHSO₂CH=CH—, —NHSO₂CH=CHCH₂—, —NHC(O)(C=N₂)—, —NHC(O)(C=N₂)C(O)—, —NHC(O)CH=CHCH₂N(CH₃)—, —NHSO₂CH=CH—, —NHSO₂CH=CHCH₂—, —NHC(O) CH=CHCH₂O—, —NHC(O)C(=CH₂)CH₂—, —CH₂NHC(O)—, —CH₂NHC(O)CH=CH—, —CH₂CH₂NHC(O)—, or —CH₂NHC(O)cyclopropylene-; and Y is hydrogen or $C_{1-6}$ aliphatic optionally substituted with oxo, halogen, $NO_2$, or CN; or (h) L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO₂—, —SO₂N(R)—, —S—, —S(O)—, —SO₂—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (i) L is a bivalent $C_{2-8}$ straight or branched, hydrocarbon chain wherein L has at least one triple bond and one or two additional methylene units of L are optionally and independently replaced by —NRC(O)—, —C(O)NR—, —N(R)SO₂—, —SO₂N(R)—, —S—, —S(O)—, —SO₂—, —OC(O)—, or —C(O)O—, and Y is hydrogen or $C_{1-6}$ aliphatic optionally substituted with oxo, halogen, $NO_2$, or CN; or (j) L is —C≡C—, —C≡CCH₂N(isopropyl)-, —NHC(O)C≡CCH₂CH₂—, —CH₂—C≡CCH₂—, —C≡CCH₂O—, —CH₂C(O)C≡C—, —C(O)C≡C—, or —CH₂C(=O)C≡C—; and Y is hydrogen or $C_{1-6}$ aliphatic optionally substituted with oxo, halogen, $NO_2$, or CN; or (k) L is a bivalent $C_{2-8}$ straight or branched, hydrocarbon chain wherein one methylene unit of L is replaced by cyclopropylene and one or two additional methylene units of L are independently replaced by —NRC(O)—, —C(O)NR—, —N(R)SO₂—, —SO₂N(R)—, —S—, —S(O)—, —SO₂—, —OC(O)—, or —C(O)O—; and Y is hydrogen or $C_{1-6}$ aliphatic optionally substituted with oxo, halogen, $NO_2$, or CN; or (l) L is a covalent bond and Y is selected from:
  (i) $C_{1-6}$ alkyl substituted with oxo, halogen, $NO_2$, or CN;
  (ii) $C_{2-6}$alkenyl optionally substituted with oxo, halogen, $NO_2$, or CN; or
  (iii) $C_{2-6}$alkynyl optionally substituted with oxo, halogen, $NO_2$, or CN; or
  (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
  (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi) 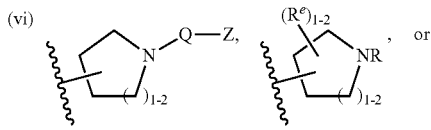

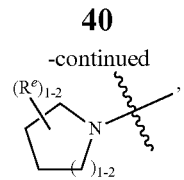

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x) 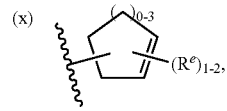

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii) 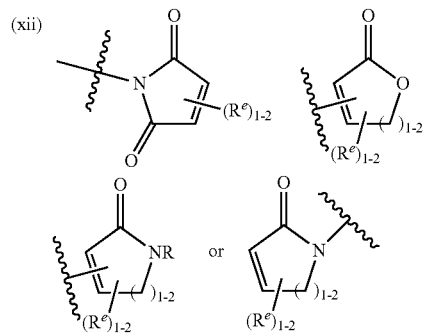

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv) 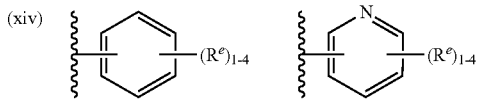

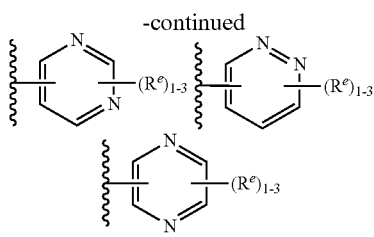

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi) 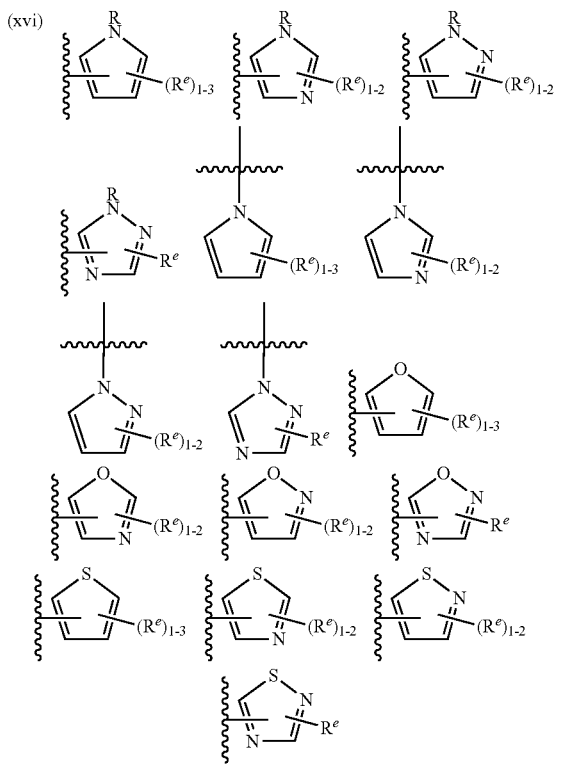

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:
  (i) $C_{1-6}$ alkyl substituted with oxo, halogen, $NO_2$, or CN; or
  (ii) $C_{2-6}$ alkenyl optionally substituted with oxo, halogen, $NO_2$, or CN; or
  (iii) $C_{2-6}$ alkynyl optionally substituted with oxo, halogen, $NO_2$, or CN; or
  (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
  (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi) 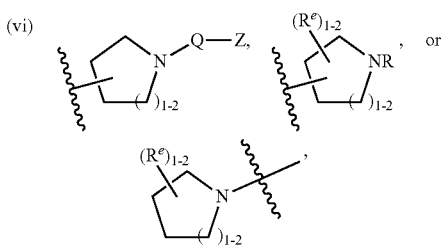

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x) 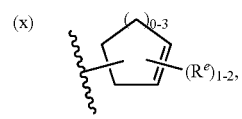

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii) 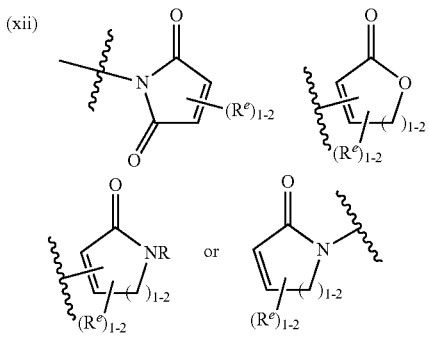

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or

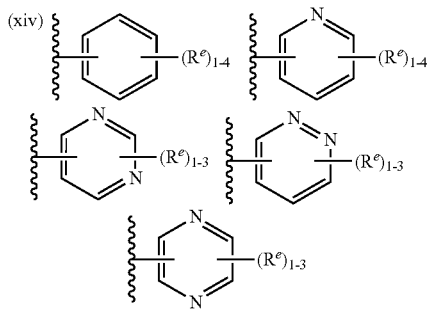

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or

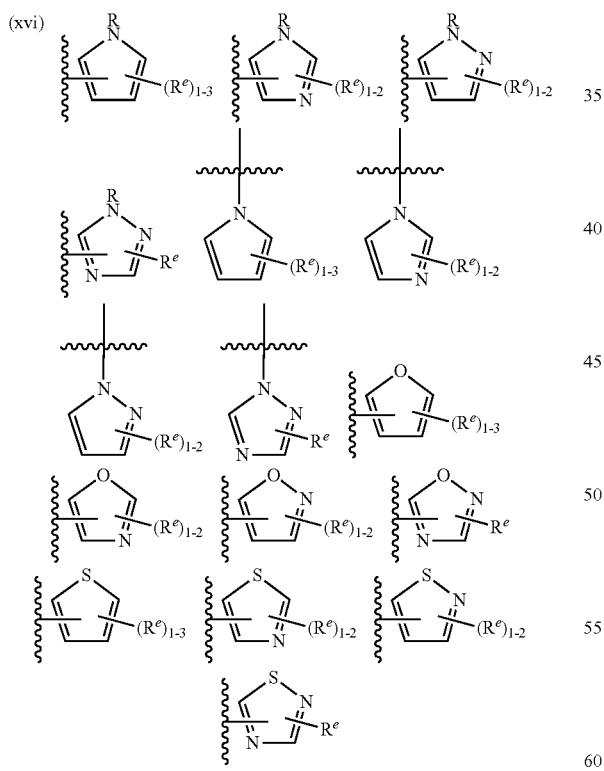

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(n) L is —N(R)C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or

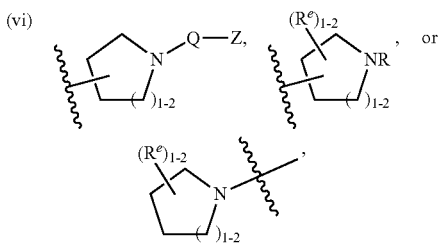

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or

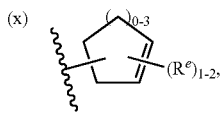

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii) 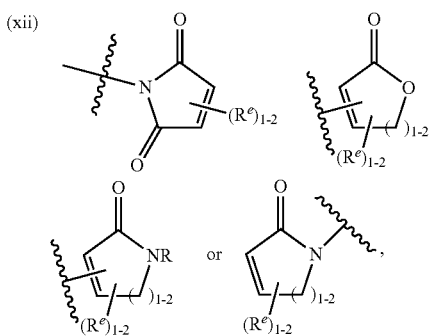

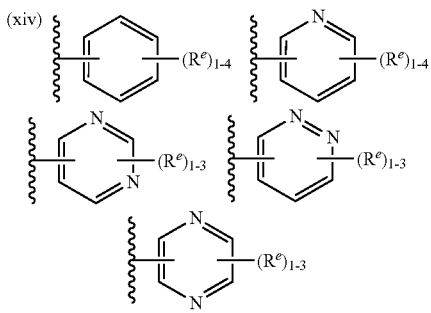

wherein each R and R$^e$ is as defined above and described herein; or (xiii) a 6-membered aromatic ring having 0-2 nitrogens wherein said ring is substituted with 1-4 R$^e$ groups, wherein each R$^e$ group is as defined above and described herein; or (xiv) 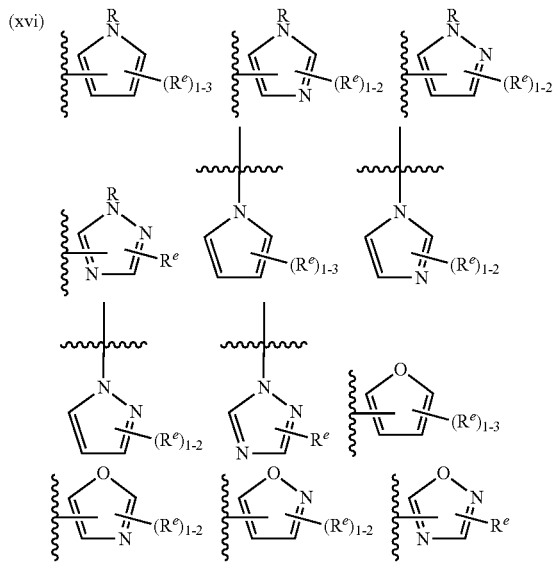

wherein each R$^e$ is as defined above and described herein; or (xv) a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein; or (xvi) 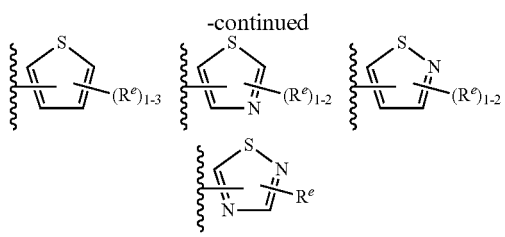

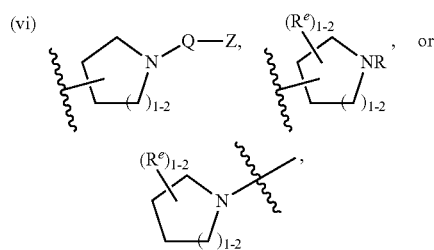

wherein each R and R$^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 R$^e$ groups, wherein R$^e$ is as defined above and described herein;

(o) L is a bivalent C$_{1-8}$ saturated or unsaturated, straight or branched, hydrocarbon chain; and Y is selected from:

(i) C$_{1-6}$ alkyl substituted with oxo, halogen, NO$_2$, or CN;

(ii) C$_{2-6}$alkenyl optionally substituted with oxo, halogen, NO$_2$, or CN; or (iii) C$_{2-6}$alkynyl optionally substituted with oxo, halogen, NO$_2$, or CN; or (iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or (v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or (vi)

wherein each R, Q, Z, and R$^e$ is as defined above and described herein; or (vii) a saturated 3-6 membered carbocyclic ring, wherein said ring is substituted with 1-4 R$^e$ groups, wherein each R$^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or (ix) a partially unsaturated 3-6 membered carbocyclic ring, wherein said ring is substituted with 1-4 R$^e$ groups, wherein each R$^e$ is as defined above and described herein; or

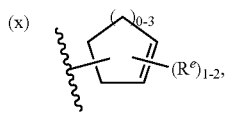

wherein each R$^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 R$^e$ groups, wherein each R$^e$ is as defined above and described herein; or

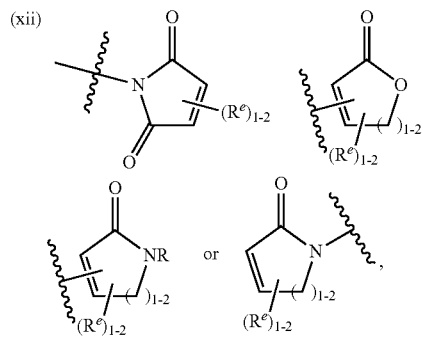

wherein each R and R$^e$ is as defined above and described herein; or (xiii) a 6-membered aromatic ring having 0-2 nitrogens wherein said ring is substituted with 1-4 R$^e$ groups, wherein each R$^e$ group is as defined above and described herein; or

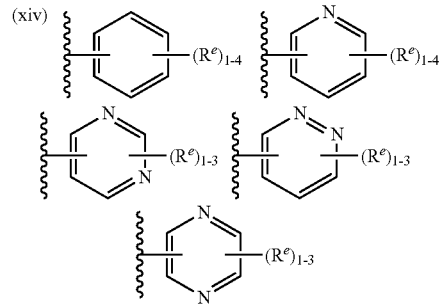

wherein each R$^e$ is as defined above and described herein; or (xv) a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein; or

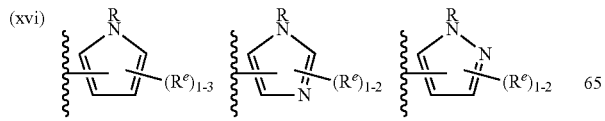

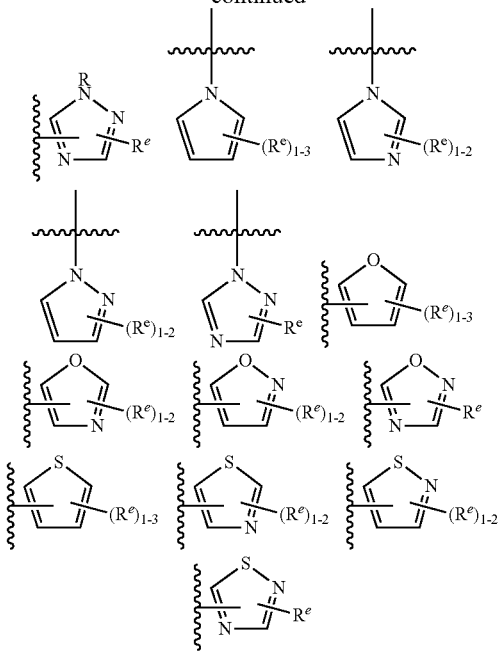

wherein each R and R$^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 R$^e$ groups, wherein R$^e$ is as defined above and described herein;

(p) L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—; and Y is selected from:

(i) C$_{1-6}$ alkyl substituted with oxo, halogen, NO$_2$, or CN; or (ii) C$_{2-6}$alkenyl optionally substituted with oxo, halogen, NO$_2$, or CN; or (iii) C$_{2-6}$alkynyl optionally substituted with oxo, halogen, NO$_2$, or CN; or (iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or (v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or

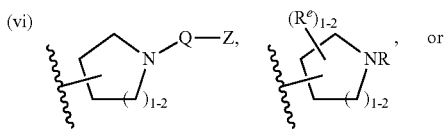

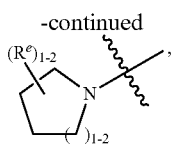

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x) 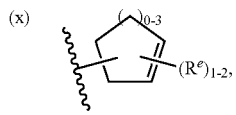

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii) 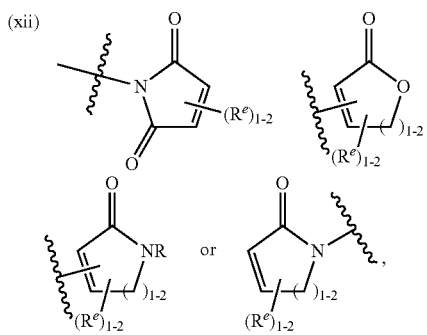

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv) 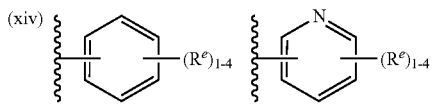

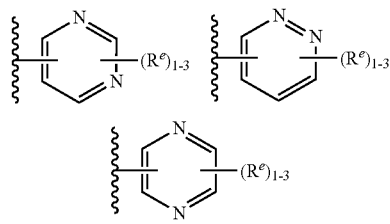

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi) 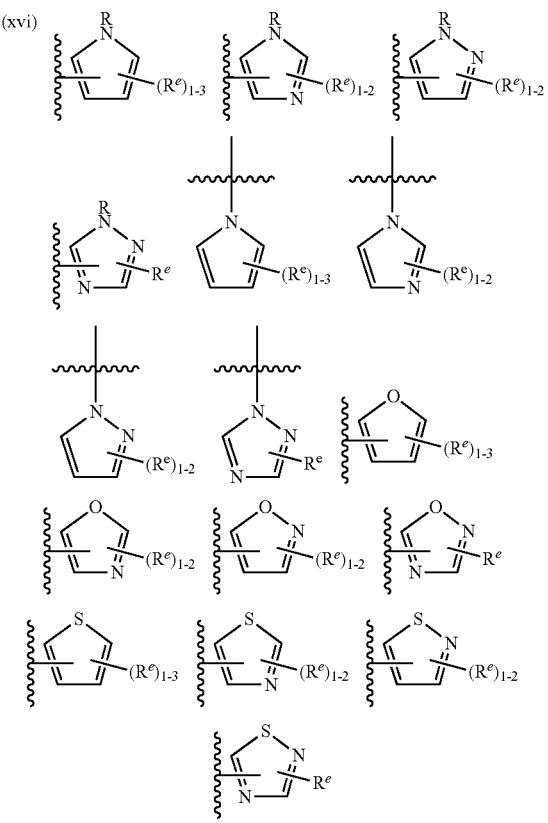

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

In certain embodiments, the Y group is selected from those set forth in Table 1-1 below, wherein each wavy line indicates the point of attachment to the rest of the molecule.

TABLE 1-1

Exemplary Y groups

| | |
|---|---|
| a | maleimide (N-linked) |
| b | 1-acryloylpyrrolidin-2-yl |
| c | 3-methyl-maleimide (N-linked) |
| d | 3-chloro-maleimide (N-linked) |
| e | 3,4-dichloro-maleimide (N-linked) |
| f | 3,4-dimethyl-maleimide (N-linked) |
| g | oxiran-2-yl |
| h | 3-methyloxiran-2-yl |
| i | 3-isopropyloxiran-2-yl |

TABLE 1-1-continued

Exemplary Y groups

| | |
|---|---|
| j | benzo[d]isothiazol-3(2H)-one (N-linked) |
| k | 4-chloropyridin-3-yl |
| l | 6-chloropyridin-3-yl |
| m | 5-methyl-1,3,4-thiadiazol-2-yl |
| n | 2-cyanooxazol-5-yl |
| o | 5-cyano-1,3,4-oxadiazol-2-yl |
| p | 5-cyano-1,2,4-oxadiazol-3-yl |
| q | 1-cyanopyrrolidin-3-yl |
| r | 1-(cyclobut-1-en-1-yl)-1-oxo-butyl |
| s | 2,3,5,6-tetrafluorophenyl |

TABLE 1-1-continued

| Exemplary Y groups | |
|---|---|
| 2-fluoro-3-cyanophenyl (F, CN substituents) | t |
| 4-fluoro-3-nitrophenyl | u |
| 4-fluoro-3-cyanophenyl | v |
| 2-fluoro-3-nitrophenyl | w |
| 4-fluoropyridin-3-yl | x |
| 1-cyanocyclopropyl | y |
| 2-vinylpyridin-3-yl | z |
| 6-vinylpyridin-2-yl | aa |
| 2-vinylpyridin-4-yl | bb |
| 2-vinylpyrimidin-4-yl | cc |
| 6-vinylpyrimidin-4-yl | dd |
| 4-vinylpyrimidin-2-yl | ee |
| 2-ethynylpyridin-3-yl | ff |
| 6-ethynylpyridin-2-yl | gg |
| 2-ethynylpyridin-4-yl | hh |
| 2-ethynylpyrimidin-4-yl | ii |
| 6-ethynylpyrimidin-4-yl | jj |

TABLE 1-1-continued
Exemplary Y groups
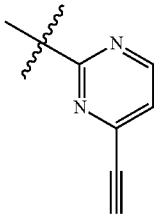 [SMILES: *c1nccc(C#C)n1] kk
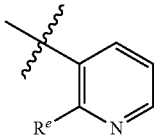 ll
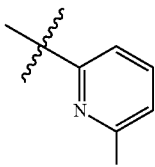 mm
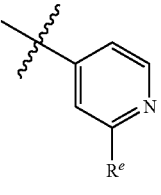 nn
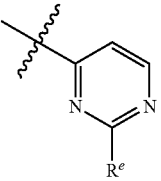 oo
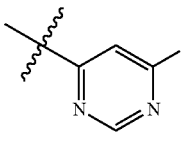 pp
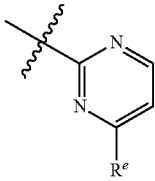 qq
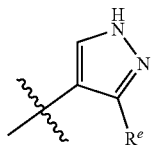 rr
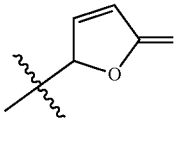 ss
TABLE 1-1-continued
Exemplary Y groups
 tt
 uu
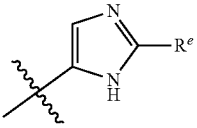 vv
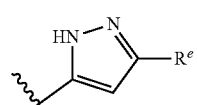 ww
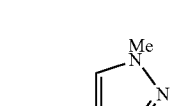 xx
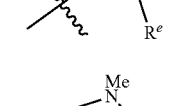 yy
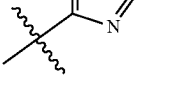 zz
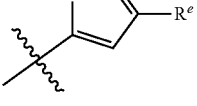 aaa
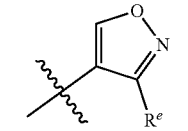 bbb
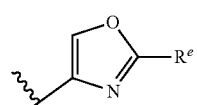 ccc TABLE 1-1-continued Exemplary Y groups

| Structure | Label |
|---|---|
| thiazole with R<sup>e</sup> (ddd-type) | ddd |
| thiazole with R<sup>e</sup> (eee-type) | eee |
| isothiazole with R<sup>e</sup> | fff |
| 1H-pyrazole with vinyl | ggg |
| 1H-imidazole with vinyl | hhh |
| 1H-pyrazole with vinyl | iii |
| N-Me pyrazole with vinyl | jjj |
| N-Me imidazole with vinyl | kkk |
| N-Me imidazole with vinyl | lll |
| N-Me pyrazole with vinyl | mmm |
| isoxazole with vinyl | nnn |
| oxazole with vinyl | ooo |
| oxazole with vinyl | ppp |
| isothiazole with vinyl | qqq |
| thiazole with vinyl | rrr |
| thiazole with vinyl | sss |
| isothiazole with vinyl | ttt |
| isoxazole with vinyl | uuu |
| 1H-pyrazole with ethynyl | vvv |
| dihydropyranone | qqq |

TABLE 1-1-continued

Exemplary Y groups

| Structure | Label |
|---|---|
| imidazole with ethynyl | www |
| N-Me pyrazole with ethynyl | xxx |
| NH-pyrazole with ethynyl | yyy |
| dihydropyridinone | zzz |
| N-Me imidazole with ethynyl | aaaa |
| N-Me pyrazole with ethynyl | bbbb |
| isoxazole with ethynyl | cccc |
| isoxazole with ethynyl | dddd |
| oxazole with ethynyl | eeee |
| oxazole with ethynyl | ffff |
| dihydropyrrolone | gggg |
| isothiazole with ethynyl | hhhh |
| thiazole with ethynyl | iiii |
| N-linked pyrazole with ethynyl | jjjj |
| cyclohexenone | kkkk |
| N-linked imidazole with ethynyl | llll |
| pyrrolidine acrylamide | mmmm |
| isothiazole with ethynyl | nnnn |
| thiazole with ethynyl | oooo |
| N-linked pyrazole with R$^e$ | pppp |

TABLE 1-1-continued

Exemplary Y groups

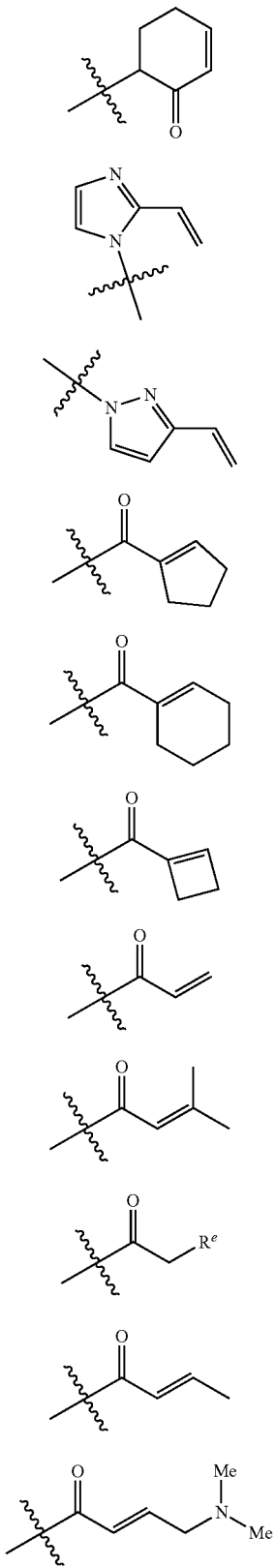

qqqq rrrr ssss tttt uuuu vvvv wwww xxxx yyyy zzzz aaaaa

TABLE 1-1-continued

Exemplary Y groups

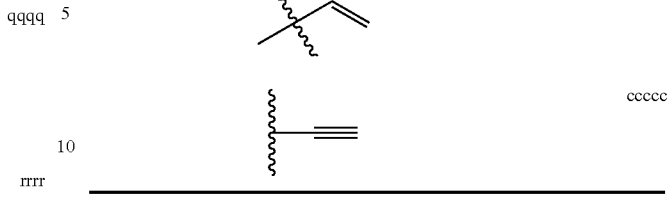

bbbbb ccccc wherein each $R^e$ is independently a suitable leaving group, $NO_2$, CN or oxo.

In certain embodiments, a warhead group is —C≡CH, —C≡CCH$_2$NH(isopropyl), —NHC(O)C≡CCH$_2$CH$_3$, —CH$_2$—C≡C≡CH$_3$, —C≡CCH$_2$OH, —CH$_2$C(O)C≡CH, —C(O)C≡CH, or —CH$_2$C(═O)C≡CH. In some embodiments, $R^1$ is selected from —NHC(O)CH═CH$_2$, —NHC(O)CH═CHCH$_2$N(CH$_3$)$_2$, or —CH$_2$NHC(O)CH═CH$_2$.

In certain embodiments, a warhead group is selected from those set forth in Table 1-2, below, wherein each wavy line indicates the point of attachment to the rest of the molecule.

TABLE 1-2

Exemplary Warhead Groups

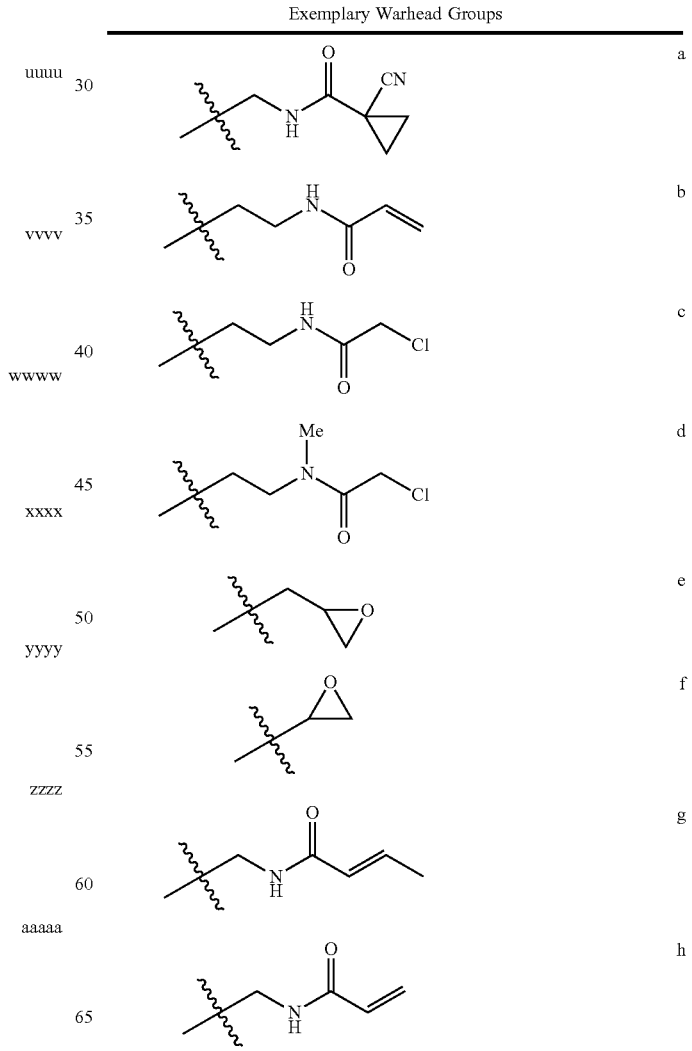

a b c d e f g h

TABLE 1-2-continued
Exemplary Warhead Groups
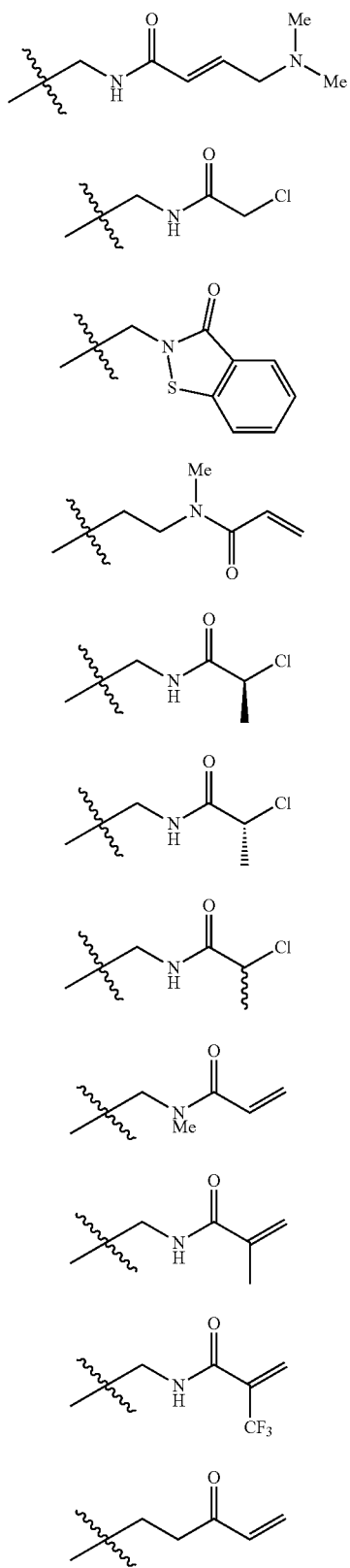
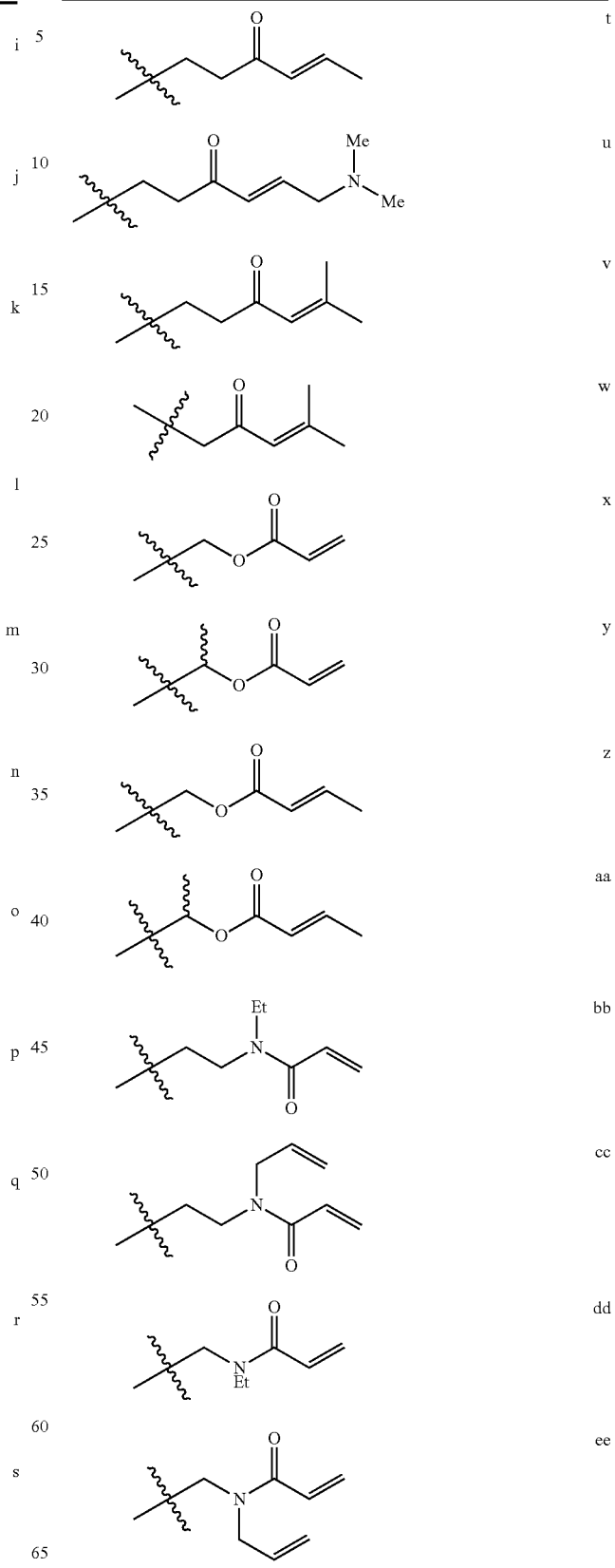

TABLE 1-2-continued
Exemplary Warhead Groups
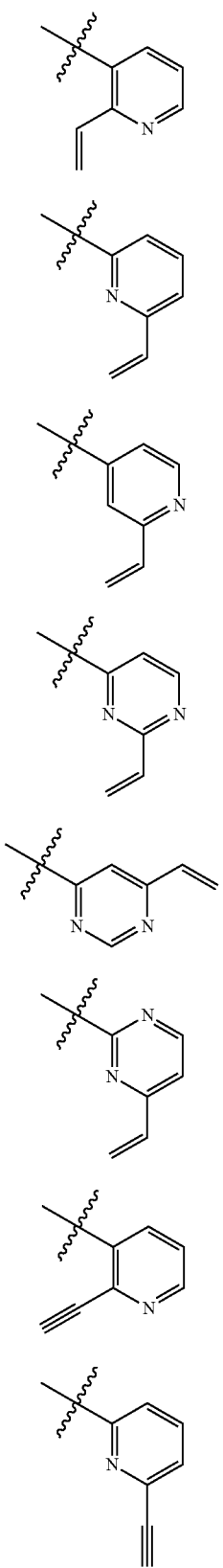
ff
gg
hh
ii
jj
kk
ll
mm
TABLE 1-2-continued
Exemplary Warhead Groups
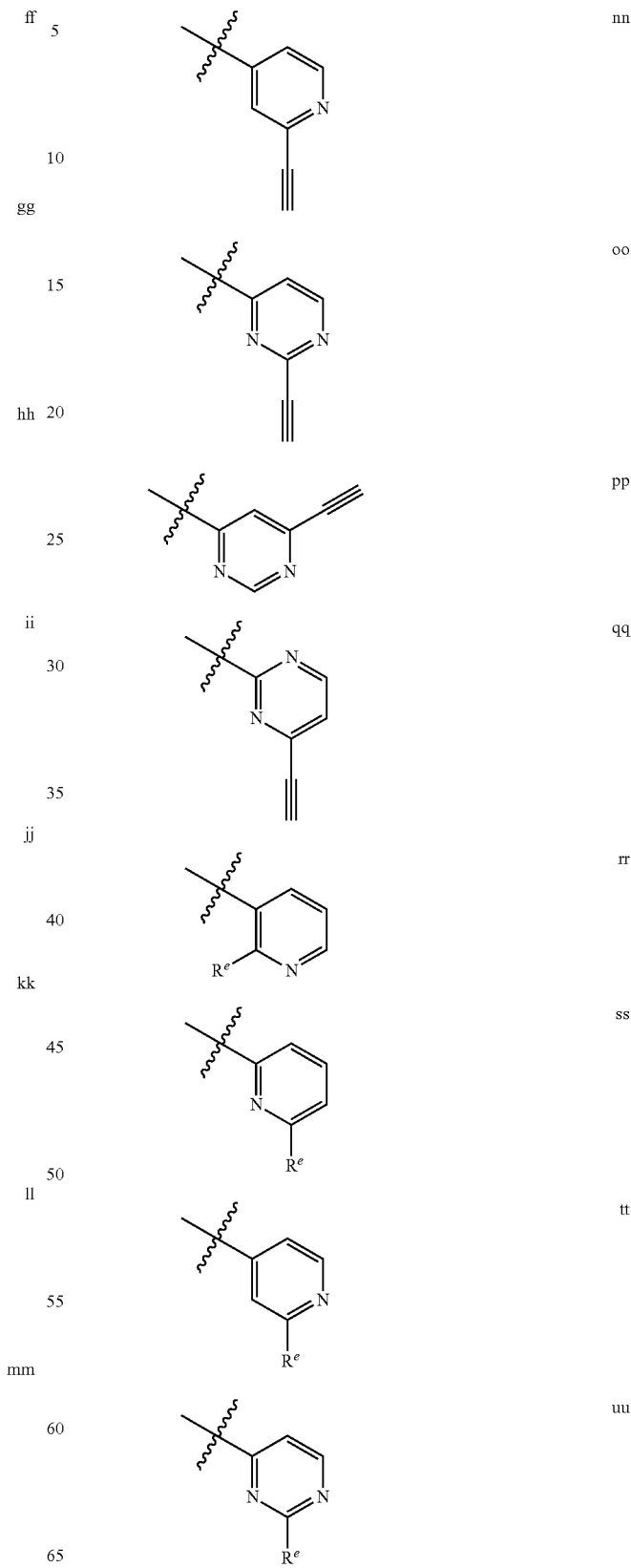
nn
oo
pp
qq
rr
ss
tt
uu TABLE 1-2-continued
Exemplary Warhead Groups
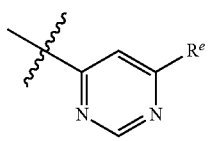 vv
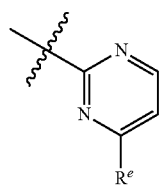 ww
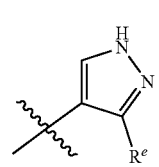 xx
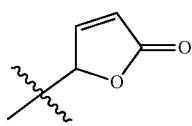 [SMILES: *C1C=CC(=O)O1] yy
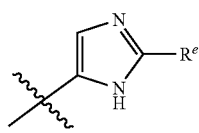 zz
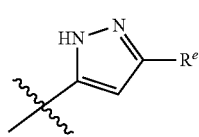 aaa
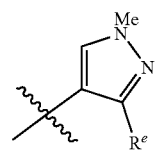 bbb
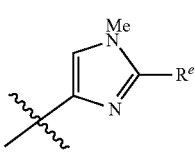 ccc
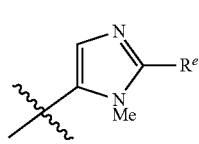 ddd
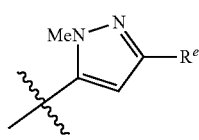 eee
TABLE 1-2-continued
Exemplary Warhead Groups
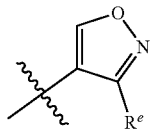 fff
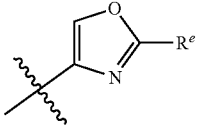 ggg
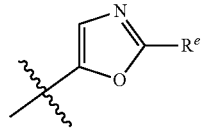 hhh
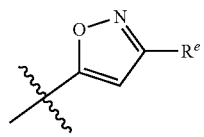 iii
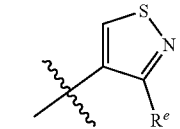 jjj
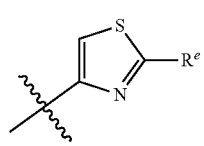 kkk
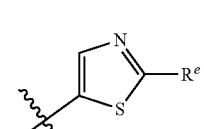 lll
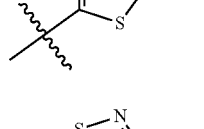 mmm
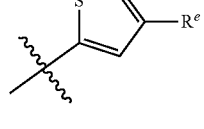 nnn
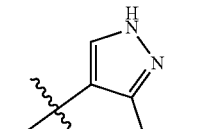 ooo
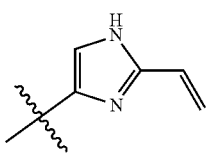 [SMILES: *c1c[nH]c(C=C)n1]

TABLE 1-2-continued
Exemplary Warhead Groups
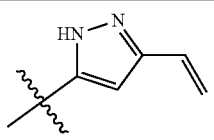 [SMILES: *c1cc(C=C)n[nH]1] ppp
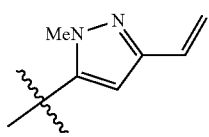 [SMILES: *c1cc(C=C)nn1C] qqq
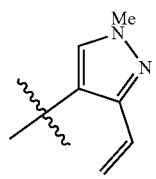 [SMILES: *c1cn(C)nc1C=C] rrr
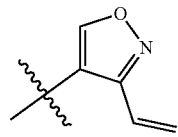 [SMILES: *c1conc1C=C] sss
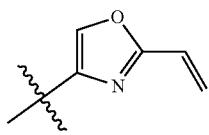 [SMILES: *c1coc(C=C)n1] ttt
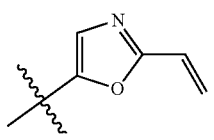 [SMILES: *c1cnc(C=C)o1] uuu
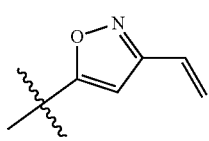 [SMILES: *c1cc(C=C)no1] vvv
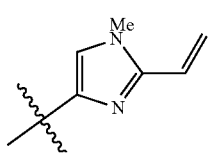 [SMILES: *c1cn(C)c(C=C)n1] www
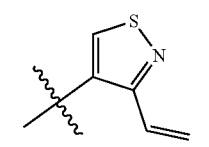 [SMILES: *c1csnc1C=C] xxx
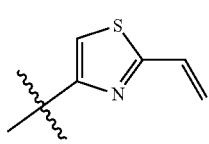 [SMILES: *c1csc(C=C)n1]
TABLE 1-2-continued
Exemplary Warhead Groups
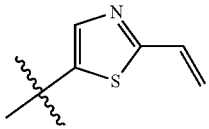 [SMILES: *c1cnc(C=C)s1] yyy
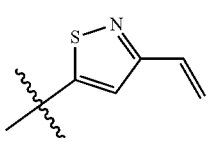 [SMILES: *c1cc(C=C)ns1] zzz
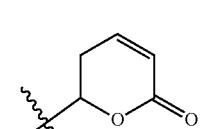 aaaa
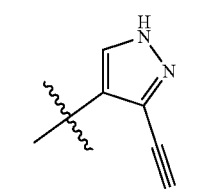 [SMILES: *c1c[nH]nc1C#C] bbbb
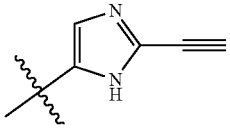 [SMILES: *c1cnc(C#C)[nH]1] cccc
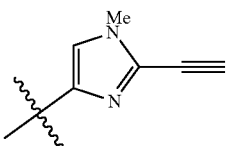 [SMILES: *c1cn(C)c(C#C)n1] dddd
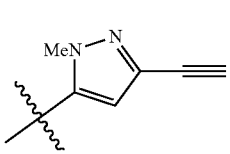 [SMILES: *c1cc(C#C)nn1C] eeee
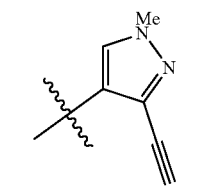 [SMILES: *c1cn(C)nc1C#C] ffff
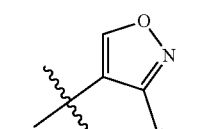 gggg
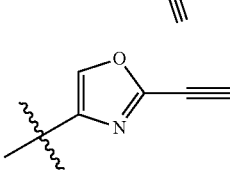 hhhh TABLE 1-2-continued
Exemplary Warhead Groups
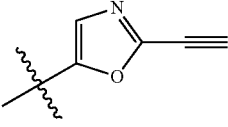 iiii
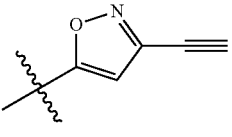 [SMILES: *c1cc(C#C)no1] jjjj
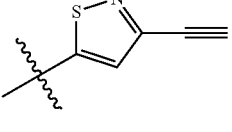 kkkk
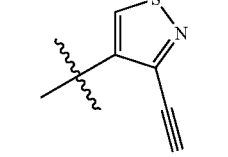 llll
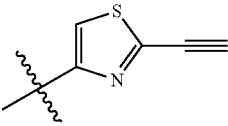 mmmm
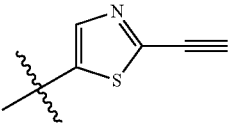 [SMILES: *c1cnc(C#C)s1] nnnn
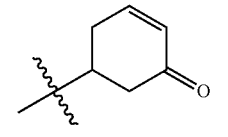 [SMILES: *C1CC=CC(=O)C1] oooo
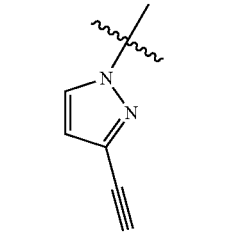 [SMILES: *n1ccc(C#C)n1] pppp
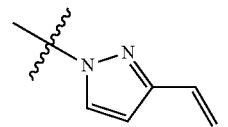 [SMILES: *n1ccc(C=C)n1] qqqq
TABLE 1-2-continued
Exemplary Warhead Groups
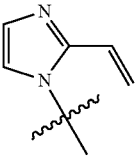 [SMILES: *n1ccnc1C=C] rrrr
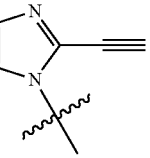 ssss
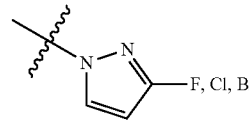 tttt
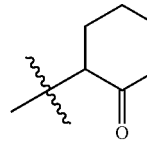 uuuu
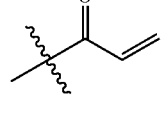 vvvv
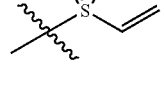 wwww
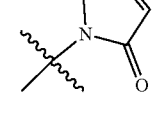 xxxx
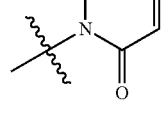 yyyy
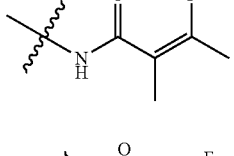 zzzz
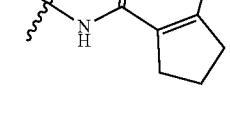 aaaaa TABLE 1-2-continued Exemplary Warhead Groups

| Structure | Label |
|---|---|
| (cyclohexenyl amide with F) | bbbbb |
| (cyclopropane diester ketone) | ccccc |
| (propynyl ketone) | ddddd |
| (propynyl amide) | eeeee |
| (propynyl ester) | fffff |
| (cyclopropane cyano ketone) | ggggg |
| (acrylate ester) | hhhhh |
| (pyrrolidine acrylamide) | iiiii |
| (N-methyl dimethylamino crotonamide) | jjjjj |
| (N-ethyl dimethylamino crotonamide) | kkkkk |
| (N-allyl dimethylamino crotonamide) | lllll |
| (cyclobutenyl ketone) | mmmmm |
| (cyclopentenyl ketone) | nnnnn |
| (cyclohexenyl ketone) | ooooo |
| (tert-butyl acrylate) | ppppp |
| (tert-butyl crotonate) | qqqqq |
| (dimethylamino enone) | rrrrr |
| (tert-butyl dimethylamino crotonate) | sssss |
| (acrylamide) | ttttt |
| (dimethylamino crotonamide) | uuuuu |
| (vinyl ketone) | vvvvv |
| (vinyl sulfonyl) | wwwww |
| (chloroacetyl) | xxxxx |

TABLE 1-2-continued
Exemplary Warhead Groups
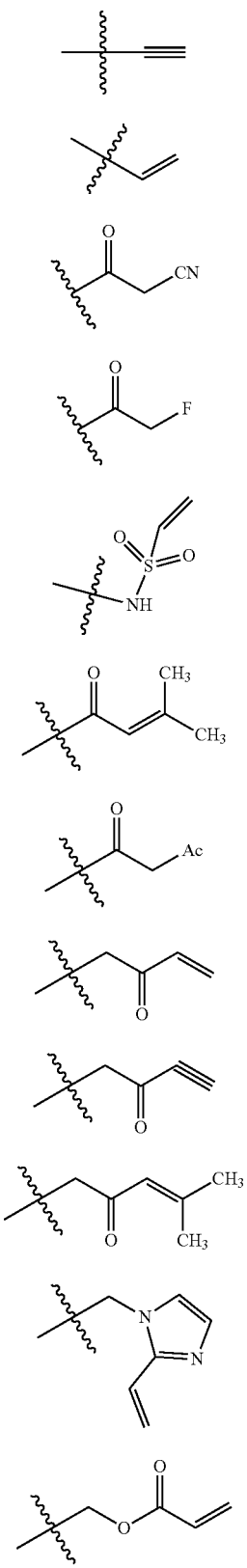
yyyyy
zzzzz
aaaaaa
bbbbbb
cccccc
dddddd
eeeeee
ffffff
gggggg
hhhhhh
iiiiii
jjjjjj
TABLE 1-2-continued
Exemplary Warhead Groups
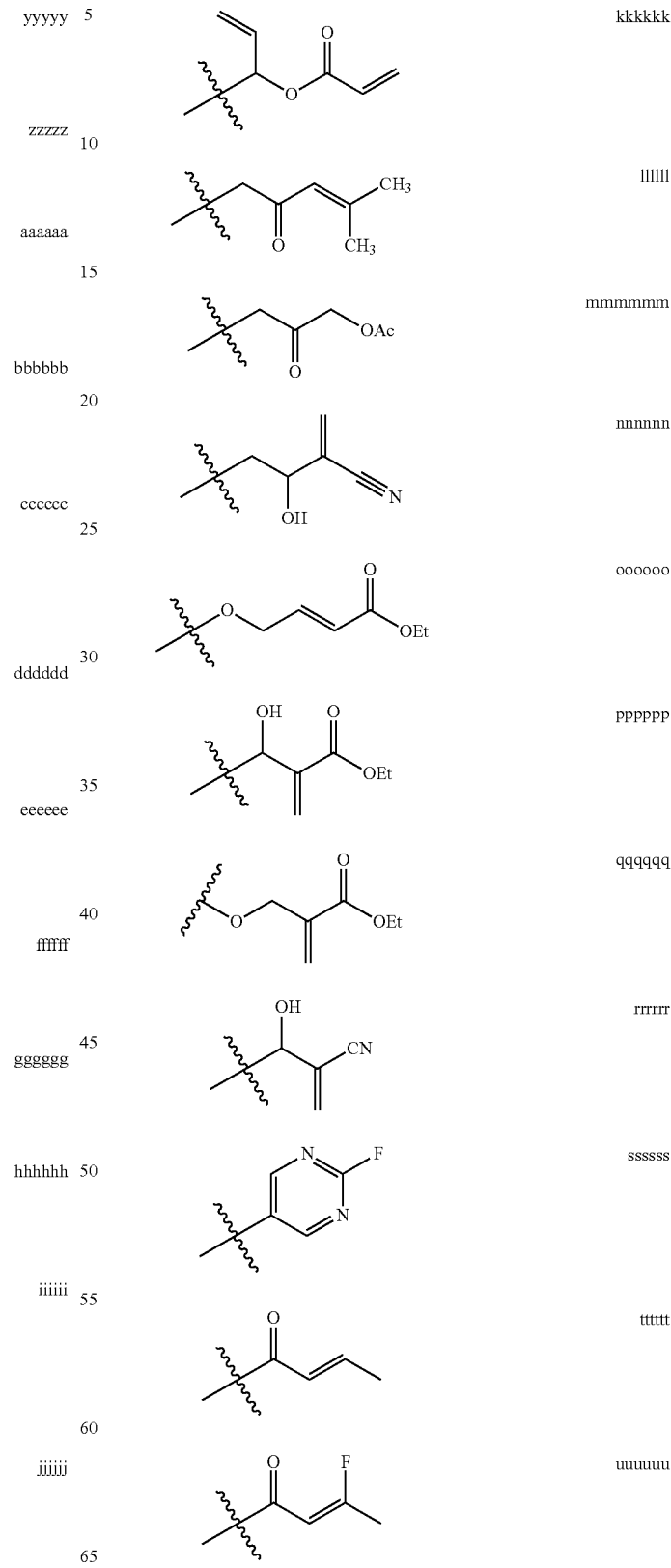
kkkkkk
llllll
mmmmmm
nnnnnn
oooooo
pppppp
qqqqqq
rrrrrr
ssssss
tttttt
uuuuuu TABLE 1-2-continued Exemplary Warhead Groups wherein each $R^e$ is independently a suitable leaving group, $NO_2$, CN, or oxo.

In some embodiments, Y of a warhead group is an isoxazoline compound or derivative capable of covalently binding to serine. In some embodiments, Y of a warhead group is an isoxazoline compound or derivative described in WO 2010135360, the entire content of which is incorporated herein by reference. As understood by one skilled in the art, an isoxazoline compound or derivative described in WO 2010135360, as Y of a warhead group, can covalently connect to L of the warhead group at any reasonable position of the isoxazoline compound or derivative. In some embodiments, Y of a warhead group is:

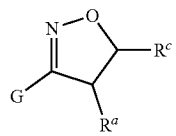

wherein G, $R^a$, and $R^c$ are:

| G | $R^a$ | $R^c$ |
|---|---|---|
| —Br | —H | —H |
| —Cl | —H | —H |
| phenyl-O- | —H | —H |
| 4-F-phenyl-O- | —H | —H |
| 3-F-phenyl-O- | —H | —H |
| 3-CF₃-phenyl-O- | —H | —H |
| 4-CN-phenyl-O- | —H | —H |
| 2-CN-phenyl-O- | —H | —H |
| 4-NO₂-phenyl-O- | —H | —H |
| 4-(MeSO₂)-phenyl-O- | —H | —H |
| 4-Me-3-F-phenyl-O- | —H | —H |
| phenyl-NH- | —H | —H |
| 2-oxo-pyridin-1-yl | —H | —H |
| 1,2,4-triazol-1-yl | —H | —H |
| pyrazol-1-yl | —H | —H |
| pyridin-4-yl-O- | —H | —H |

| G | R$^a$ | R$^c$ |
|---|---|---|
| 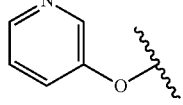 | —H | —H |
| 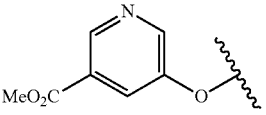 [SMILES: *Oc1cncc(C(=O)OC)c1] | —H | —H |
| 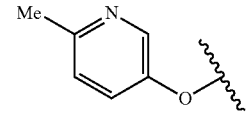 [SMILES: *Oc1ccc(C)nc1] | —H | —H |
| 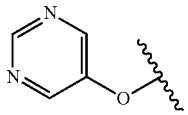 [SMILES: *Oc1cncnc1] | —H | —H |
| 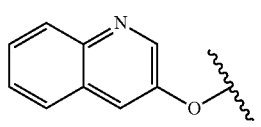 [SMILES: *Oc1cnc2ccccc2c1] | —H | —H |
| 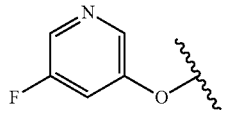 | —H | —H |
| 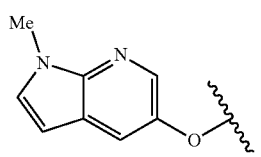 [SMILES: *Oc1cnc2c(ccn2C)c1] | —H | —H |
| —OMe | —H | —H |
| 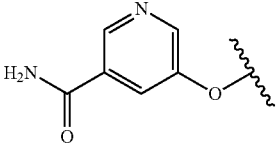 [SMILES: *Oc1cncc(C(N)=O)c1] | —H | —H |
| 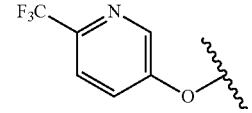 | —H | —H |
| 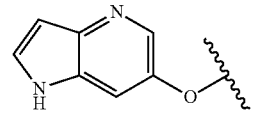 [SMILES: *Oc1cnc2cc[nH]c2c1] | —H | —H |
| 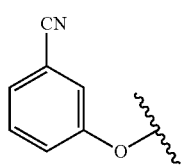 [SMILES: *Oc1cccc(C#N)c1] | —H | —H |
| G | R$^a$ | R$^c$ |
|---|---|---|
| 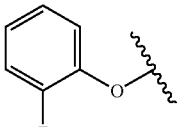 | —H | —H |
| 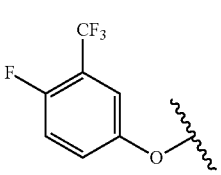 [SMILES: *Oc1ccc(F)c(C(F)(F)F)c1] | —H | —H |
| 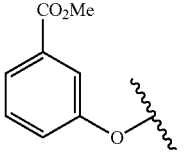 [SMILES: *Oc1cccc(C(=O)OC)c1] | —H | —H |
| 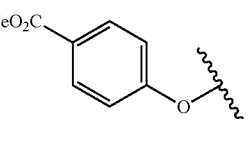 | —H | —H |
| 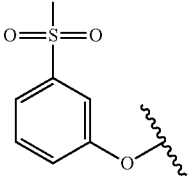 | —H | —H |
| 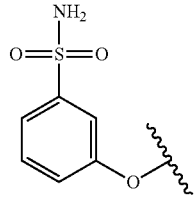 [SMILES: *Oc1cccc(S(N)(=O)=O)c1] | —H | —H |
| 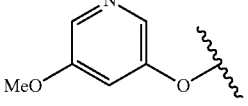 | —H | —H |
| 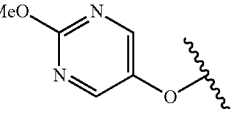 | —H | —H |
| 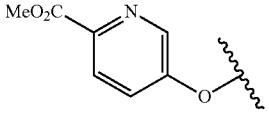 | —H | —H |
| 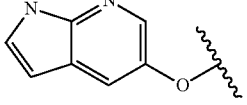 | —H | —H |

-continued
| G | $R^a$ | $R^c$ |
|---|---|---|
| 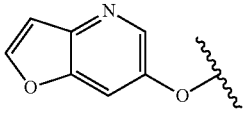 [SMILES: *Oc1cnc2ccoc2c1] | —H | —H |
| 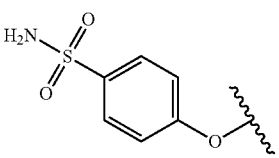 [SMILES: *Oc1ccc(S(N)(=O)=O)cc1] | —H | —H |
| 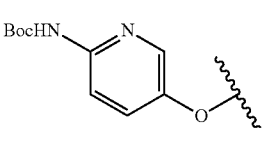 [SMILES: *Oc1ccc(NC(=O)OC(C)(C)C)nc1] | —H | —H |
| 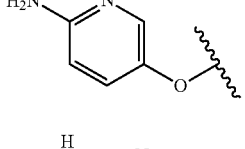 | —H | —H |
| 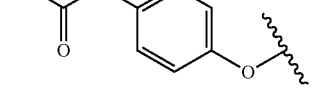 | —H | —H |
| 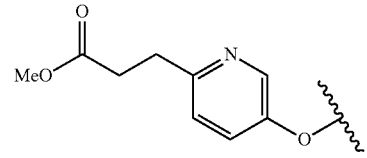 [SMILES: *Oc1ccc(CCC(=O)OC)nc1] | —H | —H |
| 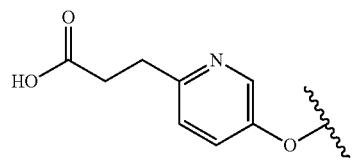 [SMILES: *Oc1ccc(CCC(=O)O)nc1] | —H | —H |
| 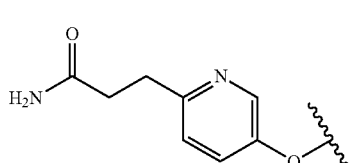 | —H | —H |
| 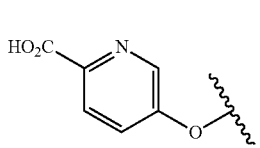 [SMILES: *Oc1ccc(C(=O)O)nc1] | —H | —H |
| 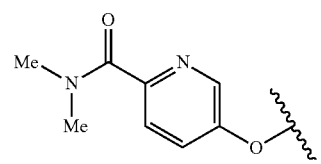 [SMILES: *Oc1ccc(C(=O)N(C)C)nc1] | —H | —H |
-continued
| G | $R^a$ | $R^c$ |
|---|---|---|
| 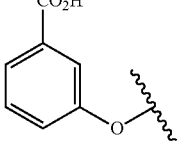 | —H | —H |
| 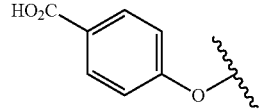 [SMILES: *Oc1ccc(C(=O)O)cc1] | —H | —H |
| 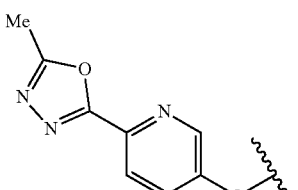 | —H | —H |
| 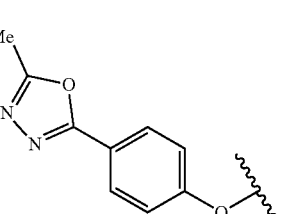 | —H | —H |
| 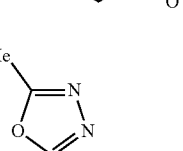 | —H | —H |
| 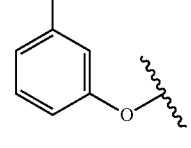 | —H | —H |
| 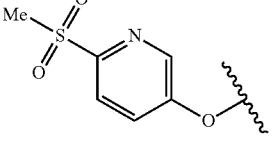 | —H | —H |
| 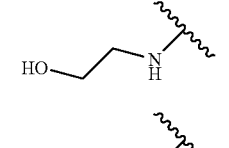 | —H | —H |
| 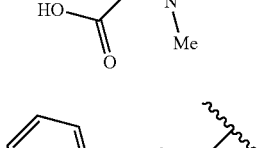 | —H | —H |
| 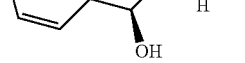 | —H | —H |

83
-continued

| G | $R^a$ | $R^c$ |
|---|---|---|
| pyrrolidine-N | —H | —H |
| 1-methyl-3-(trifluoromethyl)pyrazol-5-yloxy | —H | —H |
| acetoxy (MeC(O)O—) | —H | —H |
| —Br | —CH$_3$ | —H |
| —Br | —CH$_3$ | —H |
| pyridin-3-yloxy | —CH$_3$ | —H |
| —Br | —H | —CH$_3$ |
| pyridin-3-yloxy | —H | —CH$_3$ |
| —Br | —H | —CF$_3$ |
| pyrimidin-5-yloxy | —H | —CF$_3$ |
| —Br | —H | —CH$_2$CH$_3$ |

In some embodiments, the present invention provides a compound of Formula (II):

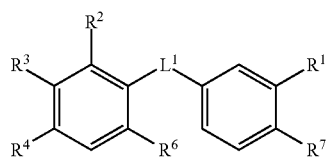

(II)

or a pharmaceutically acceptable salt thereof, wherein the variables are as described herein.

In some embodiments, the present invention provides a compound of Formula (II), or a pharmaceutically acceptable salt thereof, wherein:
$L^1$ is —NH—;
$R^1$ is —C$_{1-6}$ aliphatic substituted 1, 2, 3, 4, 5, or 6 times by halogen;
$R^2$ is a warhead group;
$R^3$ is —H;
$R^4$ is —H, —S(O)$_2$N(R)$_2$; —S(O)N(R)$_2$, or —C(O)N(R)$_2$, each R independently is selected from —H and optionally substituted —C$_{1-6}$ aliphatic;
$R^6$ is —H or —C$_{1-6}$ aliphatic; and
$R^7$ is —H,
with the proviso that the compound is not

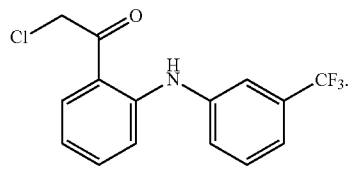 [SMILES: O=C(CCl)c1ccccc1Nc1cccc(C(F)(F)F)c1]

In some embodiments, the present invention provides a compound of Formula (II), or a pharmaceutically acceptable salt thereof, wherein:
$L^1$ is —NH—;
$R^1$ is —C$_{1-6}$ aliphatic substituted 1, 2, 3, 4, 5, or 6 times by halogen;
$R^2$ is an optionally substituted 5-membered aromatic ring having 1, 2, 3, or 4 nitrogen;
$R^3$ is —H;
$R^4$ is a warhead group;
$R^6$ is —H or —C$_{1-6}$ aliphatic; and
$R^7$ is —H.

In some embodiments, the present invention provides a compound of Formula (II), or a pharmaceutically acceptable salt thereof, wherein:
$L^1$ is —O—;
$R^1$ is —H, or —C$_{1-6}$ aliphatic substituted 1, 2, 3, 4, 5, or 6 times by halogen;
$R^2$ is —H;
$R^3$ is a warhead group;
$R^4$ is —H;
$R^6$ is —H or —C$_{1-6}$ aliphatic;
$R^7$ is —H.

In some embodiments, the present invention provides a compound of Formula (II), or a pharmaceutically acceptable salt thereof, wherein:
$L^1$ is —O—;
$R^1$ is —H, or —C$_{1-6}$ aliphatic substituted 1, 2, 3, 4, 5, or 6 times by halogen;
$R^2$ is —H;
$R^3$ is a warhead group;
$R^4$ is —H;
$R^6$ is —H;
$R^7$ is —H or halogen.

In some embodiments, the present invention provides a compound of Formula (II), or a pharmaceutically acceptable salt thereof, wherein:
$L^1$ is —O—;
$R^1$ is —H, or —C$_{1-6}$ aliphatic substituted 1, 2, 3, 4, 5, or 6 times by halogen;
$R^2$ is —H;
$R^3$ is a warhead group;
$R^4$ is —H;
$R^6$ is —H or —C$_{1-6}$ aliphatic; and
$R^7$ is —H or halogen,
with the proviso that the compound is not

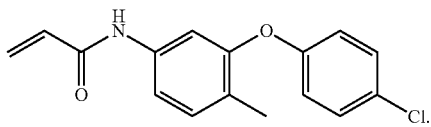 [SMILES: C=CC(=O)Nc1ccc(C)c(Oc2ccc(Cl)cc2)c1]

In some embodiments, the present invention provides a compound of Formula (II), or a pharmaceutically acceptable salt thereof, wherein:
- $L^1$ is —NH—;
- $R^1$ is —H, or —$C_{1-6}$ aliphatic substituted 1, 2, 3, 4, 5, or 6 times by halogen;
- $R^2$ is —H;
- $R^3$ is a warhead group;
- $R^4$ is —H;
- $R^6$ is —H or —$C_{1-6}$ aliphatic;
- $R^7$ is —H or halogen.

In some embodiments, the present invention provides a compound of Formula (II), or a pharmaceutically acceptable salt thereof, wherein:
- $L^1$ is —NH—;
- $R^1$ is —$C_{1-6}$ aliphatic substituted 1, 2, 3, 4, 5, or 6 times by halogen;
- each of $R^2$ and $R^4$ independently is a warhead group;
- $R^3$ is —H;
- $R^6$ is —H or —$C_{1-6}$ aliphatic; and
- $R^7$ is —H or halogen.

In some embodiments, the present invention provides a compound of Formula III:

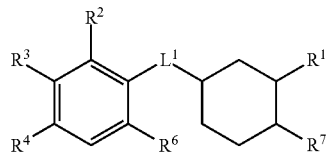

III or a pharmaceutically acceptable salt thereof, wherein the variables are as described herein.

In some embodiments, the present invention provides a compound of Formula (III), or a pharmaceutically acceptable salt thereof, wherein:
- $L^1$ is —NH—;
- $R^1$ is —$C_{1-6}$ aliphatic substituted 1, 2, 3, 4, 5, or 6 times by halogen;
- $R^2$ is a warhead group;
- $R^3$ is —H;
- $R^4$ is —S(O)$_2$N(R)$_2$, —S(O)N(R)$_2$, or —C(O)N(R)$_2$, each R independently is selected from —H and optionally substituted —$C_{1-6}$ aliphatic;
- $R^6$ is —H or —$C_{1-6}$ aliphatic; and
- $R^7$ is —H or halogen,
with the proviso that the compound is not

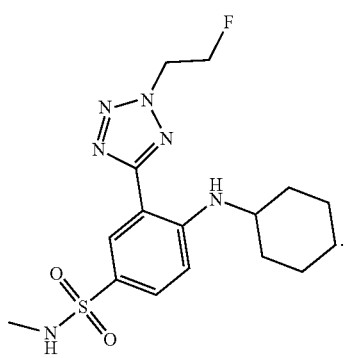 [SMILES: CNS(=O)(=O)c1ccc(NC2CCCCC2)c(-c2nnn(CCF)n2)c1]

In some embodiments, the present invention provides a compound of Formula (IV):

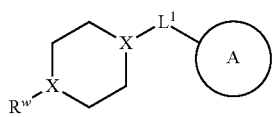

IV or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (IVa) or (IVb):

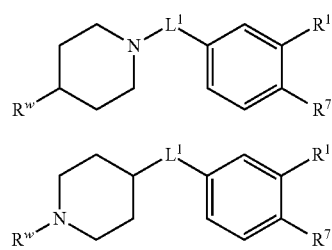

IVa

IVb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (V):

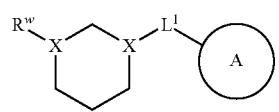

V or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (Va) or (Vb):

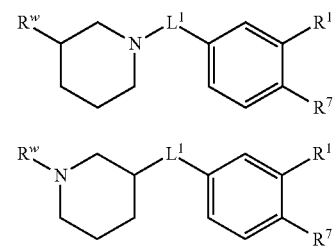

Va

Vb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (VI):

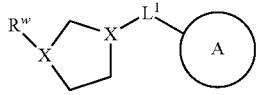

VI or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (VIa) or (VIb):

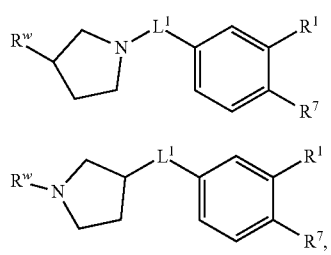

VIa

VIb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (VII):

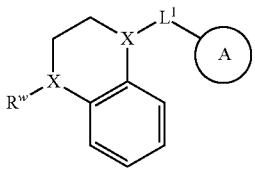

VII or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (VIIa) or (VIIb):

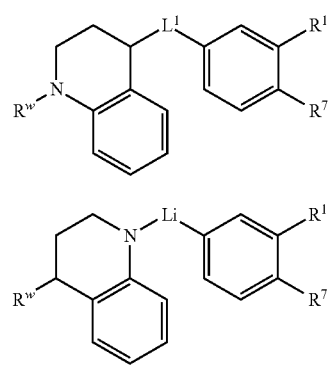

VIIa

VIIb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (VIII):

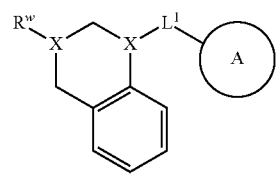

VIII or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (VIIIa) or (VIIIb)

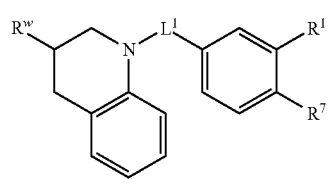

VIIIa

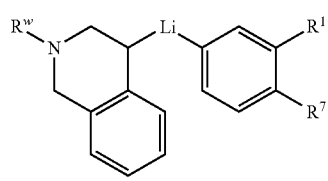

VIIIb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formulas (IV), (IVa), (IVb), (V), (Va), (Vb), (VI), (VIa), (VIb), (VII), (VIIa), (VIIb), (VIII), (VIIIa), or (VIIIb), or a pharmaceutically acceptable salt thereof, wherein $L^1$ is —$CH_2$—, —O—, —$CH(CH_3)$—, —NH—, —C(O)—, or —NH—$CH_2$—; $R^1$ is —H or —$C_{1-6}$ aliphatic substituted 1, 2, 3, 4, 5, or 6 times by halogen; $R^w$ is a warhead group; and $R^7$ is —H or —$C_{1-6}$ aliphatic substituted 1, 2, 3, 4, 5, or 6 times by halogen.

In some embodiments, the present invention provides a compound of Formula (I'), or a pharmaceutically acceptable salt thereof, wherein Ring A is phenyl, a 6-membered monocyclic heteroaromatic ring having 1 or 2 nitrogen, or a 10-membered bicyclic heteroaromatic ring having 1-2 nitrogen; Ring B is phenyl or a 6-membered monocyclic heteroaromatic ring having 1 or 2 nitrogen; and each of $R^w$ and $L^1$ is as defined above and described in embodiments herein, both singly and in combination.

In some embodiments, the present invention provides a compound of Formula (IX):

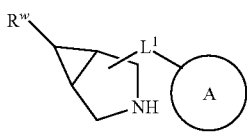

IX or a pharmaceutically acceptable salt thereof, wherein each of Ring A, $R^w$, and $L^1$ is as defined above and described in embodiments herein, both singly and in combination.

In some embodiments, the present invention provides a compound of Formula (IXa) or (IXb):

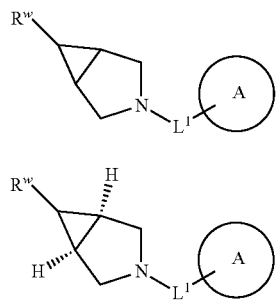

IXa

IXb or a pharmaceutically acceptable salt thereof, wherein each of Ring A, $R^w$, and $L^1$ is as defined above and described in embodiments herein, both singly and in combination.

In some embodiments, the present invention provides a compound of Formula (X):

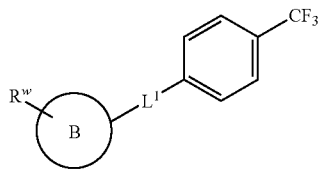

Xa or a pharmaceutically acceptable salt thereof, wherein each of Ring B, $R^w$, and $L^1$ is as defined above and described in embodiments herein, both singly and in combination, with the proviso that $L^1$ is not —NH—C(O)— or —O—CH$_2$—.

In some embodiments, the present invention provides a compound of Formula (Xa):

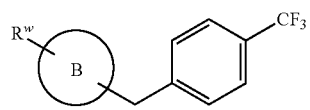

Xa or a pharmaceutically acceptable salt thereof, wherein each of Ring B and $R^w$ is as defined above and described in embodiments herein, both singly and in combination.

In some embodiments, the present invention provides a compound of Formula (XI):

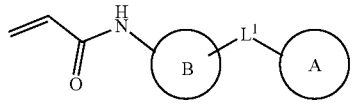

XI or a pharmaceutically acceptable salt thereof, wherein each of Ring A, Ring B, and $L^1$ is as defined above and described in embodiments herein, both singly and in combination, with the proviso that Ring B is not

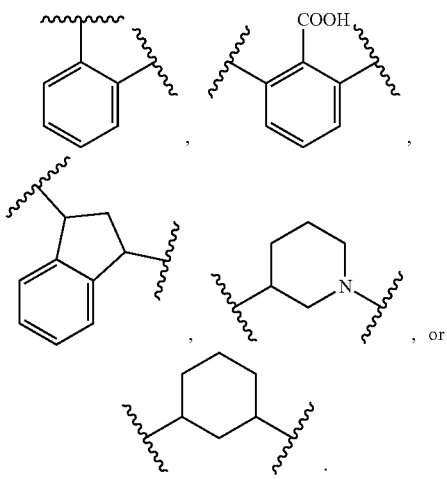

, or

In some embodiments, Ring B is an optionally substituted 6-, 7-, 8-, 9-, or 10-membered bicyclic heterocyclic ring having 1, 2, 3, 4, or 5 heteroatoms independently selected from nitrogen, oxygen, or sulfur. In some embodiments, Ring B is an optionally substituted 6-membered bicyclic heterocyclic ring having 1 nitrogen.

In some embodiments, the present invention provides a compound of Formula (XII):

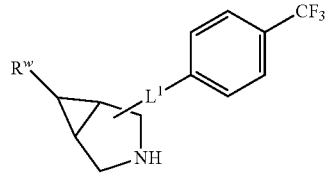

XII or a pharmaceutically acceptable salt thereof, wherein each of $R^w$ and $L^1$ is as defined above and described in embodiments herein, both singly and in combination.

In some embodiments, the present invention provides a compound of Formula (XIIa) or (XIIb):

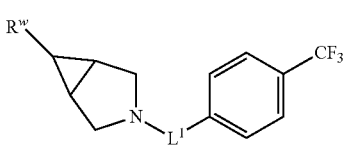

XIIa

-continued

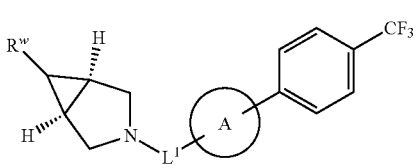

XIIb

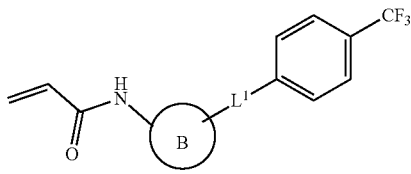

XIV or a pharmaceutically acceptable salt thereof, wherein each of $R^w$ and $L^1$ is as defined above and described in embodiments herein, both singly and in combination.

In some embodiments, the present invention provides a compound of Formula (XIII):

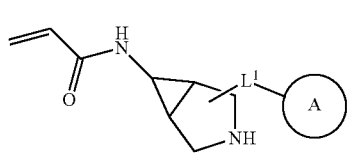

XIII or a pharmaceutically acceptable salt thereof, wherein each of Ring A and $L^1$ is as defined above and described in embodiments herein, both singly and in combination.

In some embodiments, the present invention provides a compound of Formula (XIIIa) or (XIIIb)

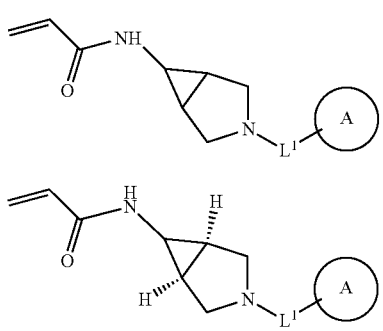

XIIIa

XIIIb or a pharmaceutically acceptable salt thereof, wherein each of Ring A and $L^1$ is as defined above and described in embodiments herein, both singly and in combination.

In some embodiments, the present invention provides a compound of Formula (XIV):

or a pharmaceutically acceptable salt thereof, wherein each of Ring B and $L^1$ is as defined above and described in embodiments herein, both singly and in combination. In some embodiments, $L^1$ is —$CH_2$—.

In some embodiments, the present invention provides a compound of Formula (XV):

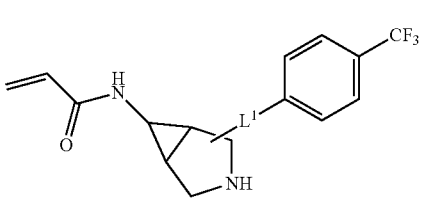

XV or a pharmaceutically acceptable salt thereof, wherein $L^1$ is as defined above and described in embodiments herein.

In some embodiments, the present invention provides a compound of Formula (XVa) or (XVb):

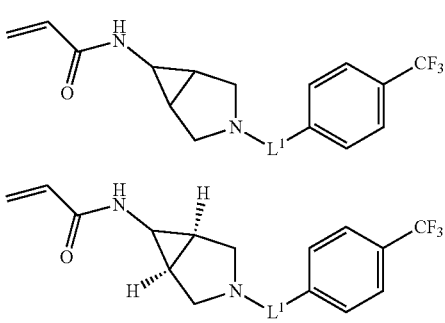

XVa

XVb or a pharmaceutically acceptable salt thereof, wherein $L^1$ is as defined above and described in embodiments herein.

Exemplary compounds of the invention are set forth in Table 1, below.

TABLE 1

Exemplary Compounds

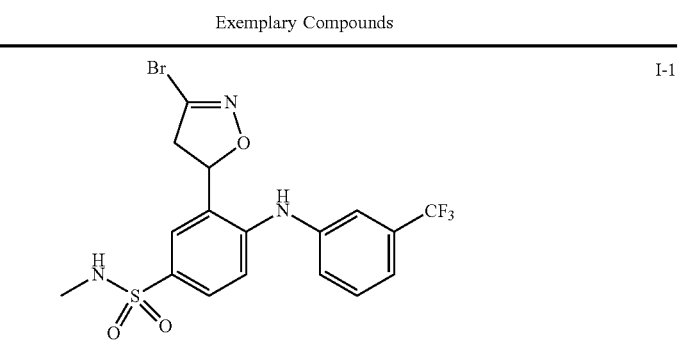

I-1

TABLE 1-continued

| Exemplary Compounds | |
|---|---|
| [structure] | I-2 |
| [structure] | I-3 |
| [structure] | I-4 |
| [structure] | I-5 |
| [structure] | I-6 |
| [structure] | I-7 |
| [structure] | I-8 |
| [structure] | I-9 |
| [structure] | I-10 |

TABLE 1-continued
| Exemplary Compounds | |
|---|---|
| 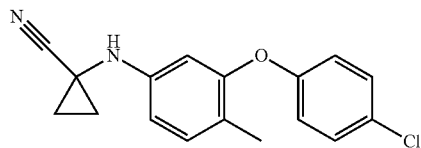 [SMILES: Cc1ccc(NC2(C#N)CC2)cc1Oc1ccc(Cl)cc1] | I-11 |
| 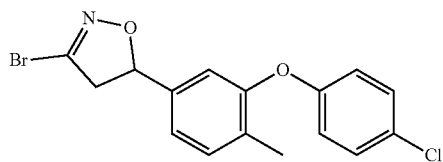 [SMILES: Cc1ccc(C2CC(Br)=NO2)cc1Oc1ccc(Cl)cc1] | I-12 |
| 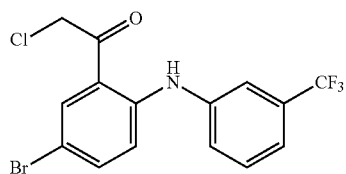 [SMILES: O=C(CCl)c1cc(Br)ccc1Nc1cccc(C(F)(F)F)c1] | I-13 |
| 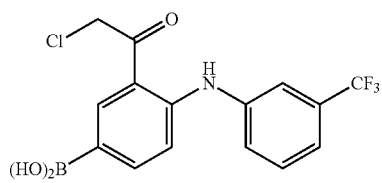 [SMILES: O=C(CCl)c1cc(B(O)O)ccc1Nc1cccc(C(F)(F)F)c1] | I-14 |
| 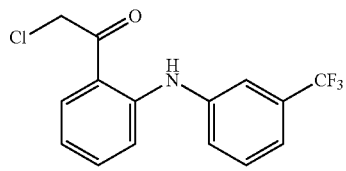 [SMILES: O=C(CCl)c1ccccc1Nc1cccc(C(F)(F)F)c1] | I-15 |
| 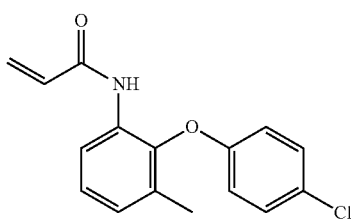 [SMILES: C=CC(=O)Nc1cccc(C)c1Oc1ccc(Cl)cc1] | I-16 |
| 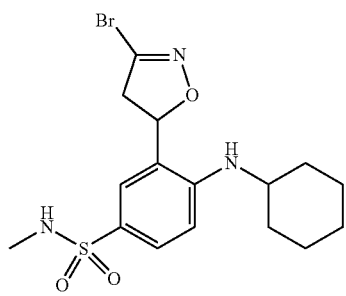 [SMILES: CNS(=O)(=O)c1ccc(NC2CCCCC2)c(C2CC(Br)=NO2)c1] | I-17 |

TABLE 1-continued
Exemplary Compounds
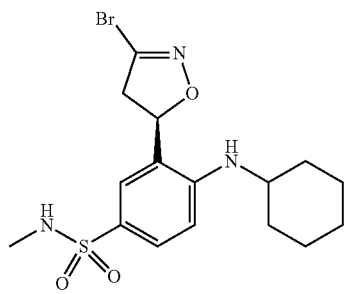
I-18
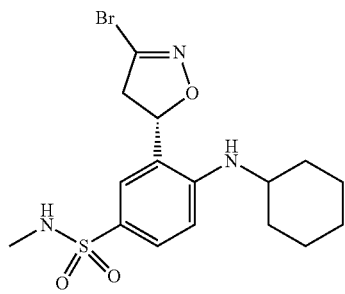 [SMILES: CNS(=O)(=O)c1ccc(NC2CCCCC2)c([C@@H]2CC(Br)=NO2)c1]
I-19
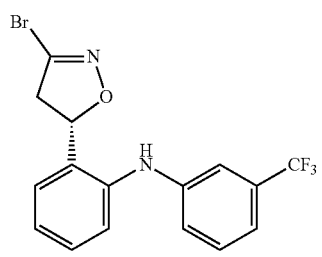 [SMILES: FC(F)(F)c1cccc(Nc2ccccc2[C@@H]2CC(Br)=NO2)c1]
I-20
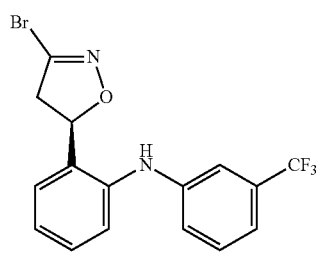 [SMILES: FC(F)(F)c1cccc(Nc2ccccc2[C@H]2CC(Br)=NO2)c1]
I-21
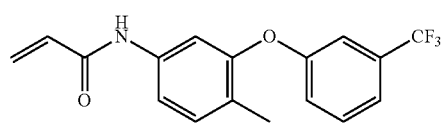 [SMILES: C=CC(=O)Nc1ccc(C)c(Oc2cccc(C(F)(F)F)c2)c1]
I-22
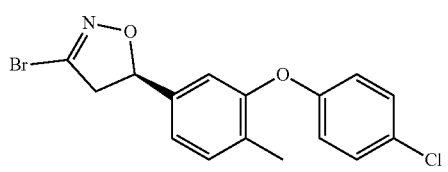 [SMILES: Cc1ccc([C@H]2CC(Br)=NO2)cc1Oc1ccc(Cl)cc1]
I-23
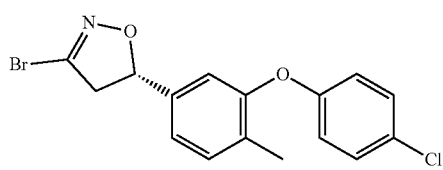
I-24

TABLE 1-continued
Exemplary Compounds
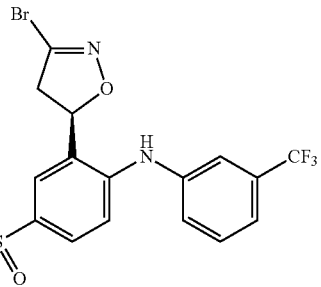 I-25
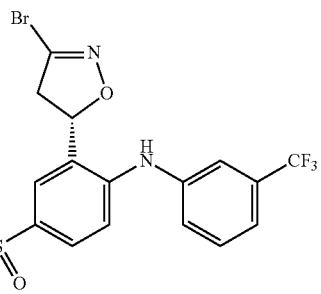 I-26
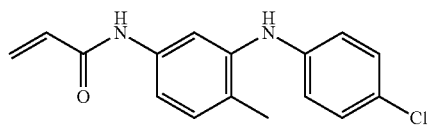 [SMILES: C=CC(=O)Nc1ccc(C)c(Nc2ccc(Cl)cc2)c1] I-27
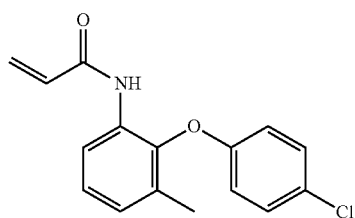 [SMILES: C=CC(=O)Nc1cccc(C)c1Oc1ccc(Cl)cc1] I-28
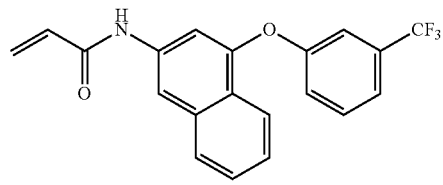 [SMILES: C=CC(=O)Nc1cc(Oc2cccc(C(F)(F)F)c2)c2ccccc2c1] I-29
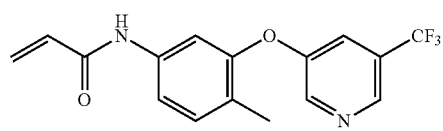 [SMILES: C=CC(=O)Nc1ccc(C)c(Oc2cncc(C(F)(F)F)c2)c1] I-30
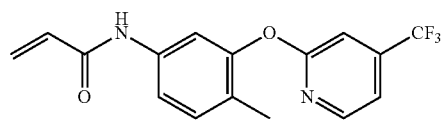 [SMILES: C=CC(=O)Nc1ccc(C)c(Oc2cc(C(F)(F)F)ccn2)c1] I-31

TABLE 1-continued
Exemplary Compounds
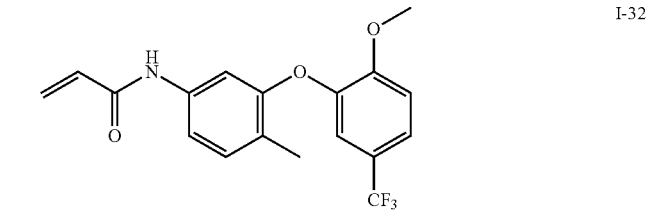
I-32
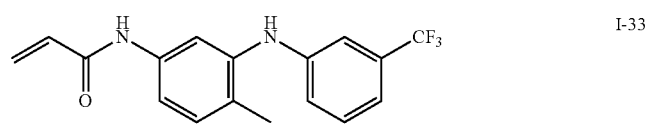
I-33
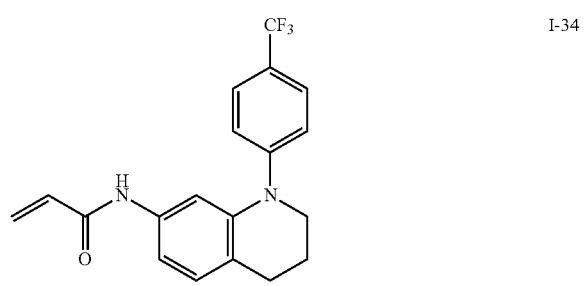
I-34
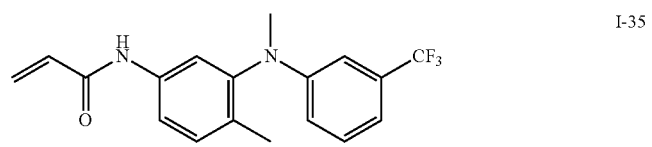
I-35
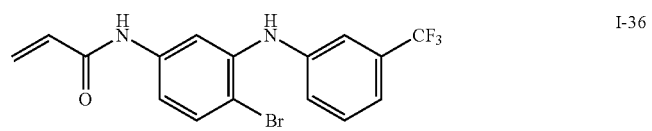
I-36
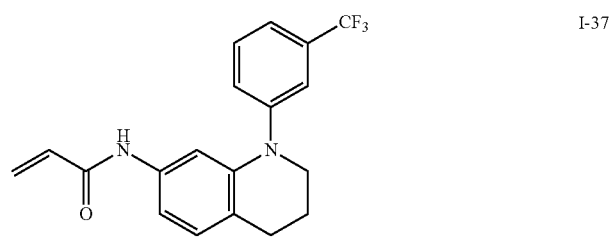
I-37
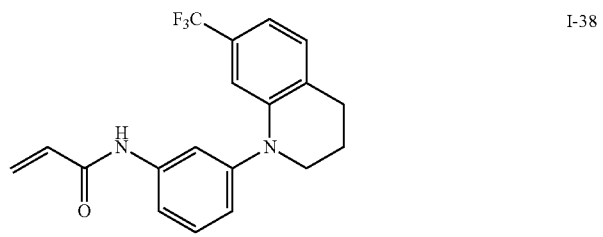
I-38

TABLE 1-continued
Exemplary Compounds
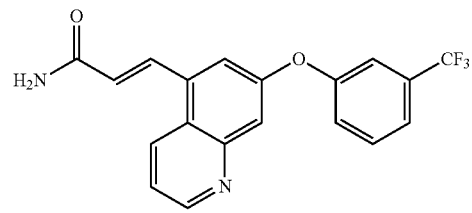 [SMILES: NC(=O)/C=C/c1cc(Oc2cccc(C(F)(F)F)c2)cc2ncccc12]
I-39
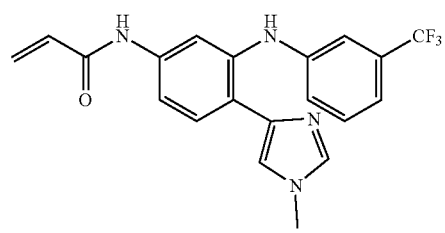 [SMILES: C=CC(=O)Nc1ccc(-c2cn(C)cn2)c(Nc2cccc(C(F)(F)F)c2)c1]
I-40
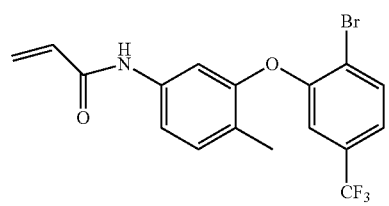 [SMILES: C=CC(=O)Nc1ccc(C)c(Oc2cc(C(F)(F)F)ccc2Br)c1]
I-41
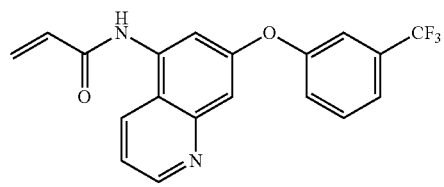 [SMILES: C=CC(=O)Nc1cc(Oc2cccc(C(F)(F)F)c2)cc2ncccc12]
I-42
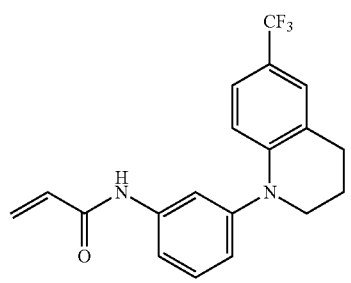 [SMILES: C=CC(=O)Nc1cccc(N2CCCc3cc(C(F)(F)F)ccc32)c1]
I-43
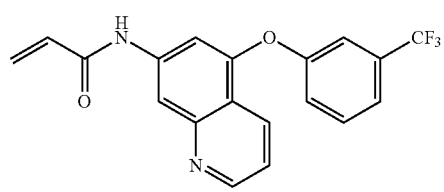
I-44
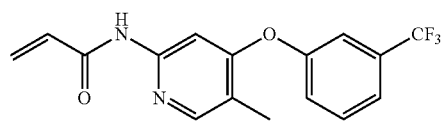 [SMILES: C=CC(=O)Nc1cc(Oc2cccc(C(F)(F)F)c2)c(C)cn1]
I-45
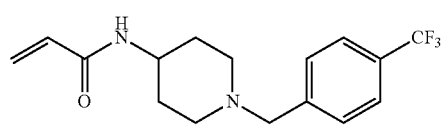 [SMILES: C=CC(=O)NC1CCN(Cc2ccc(C(F)(F)F)cc2)CC1]
I-46

TABLE 1-continued

Exemplary Compounds

I-47, I-48, I-49, I-50, I-51, I-52, I-53, I-54, I-55

TABLE 1-continued

Exemplary Compounds

| Structure | ID |
|---|---|
| (acryloylamino-cyclohexyl)-NH-(4-trifluoromethylphenyl) | I-56 |
| (S)-acryloylamino-pyrrolidine-N-(4-trifluoromethylbenzyl) | I-57 |
| (acryloylamino-cyclohexyl)-NH-(4-trifluoromethylphenyl) | I-58 |
| 1-acryloyl-piperidin-4-yl-NH-(4-trifluoromethylphenyl) | I-59 |
| (S)-acryloylamino-tetrahydroquinoline-N-(3-trifluoromethylbenzyl) | I-60 |
| 1-acryloyl-piperidin-4-yl-NH-(3-trifluoromethylbenzyl) | I-61 |
| acryloylamino-piperidine-N-(R)-1-(4-trifluoromethylphenyl)ethyl | I-62 |
| acryloylamino-piperidine-N-(S)-1-(4-trifluoromethylphenyl)ethyl | I-63 |
| (S)-1-acryloyl-pyrrolidin-3-yl-NH-(4-trifluoromethylbenzyl) | I-64 |

TABLE 1-continued
Exemplary Compounds
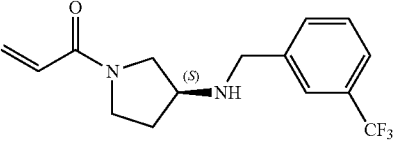 I-65
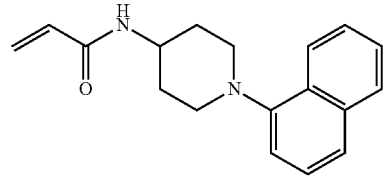 [SMILES: C=CC(=O)NC1CCN(c2cccc3ccccc23)CC1] I-66
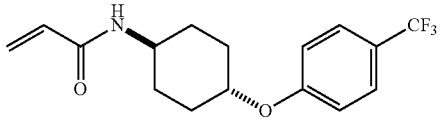 I-67
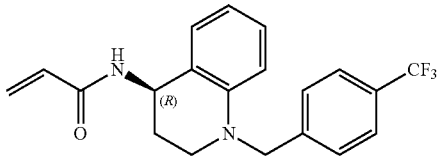 I-68
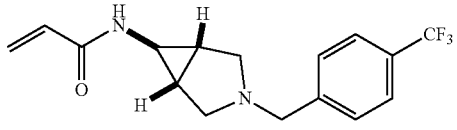 I-69
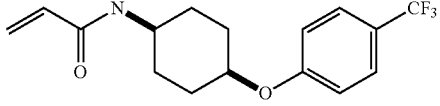 I-70
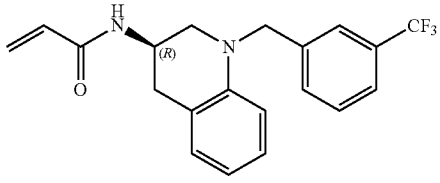 I-71
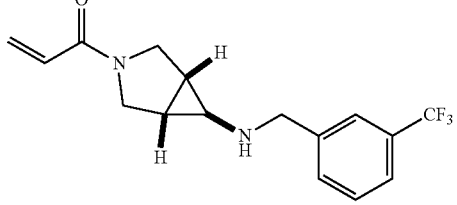 I-72
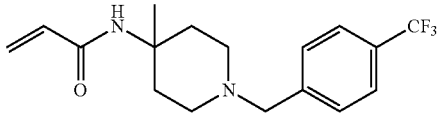 [SMILES: C=CC(=O)NC1(C)CCN(Cc2ccc(C(F)(F)F)cc2)CC1] I-73

TABLE 1-continued
Exemplary Compounds
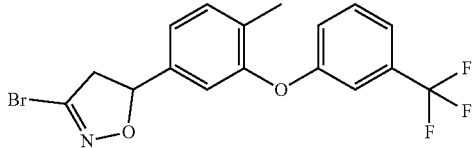 I-74
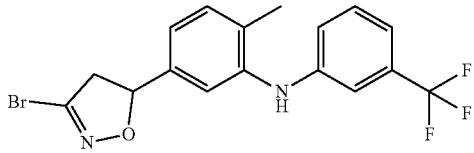 [SMILES: Cc1ccc(C2CC(Br)=NO2)cc1Nc1cccc(C(F)(F)F)c1] I-75
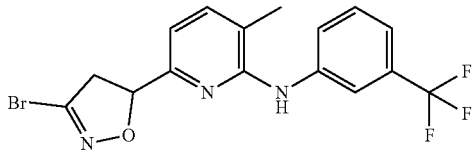 [SMILES: Cc1ccc(C2CC(Br)=NO2)nc1Nc1cccc(C(F)(F)F)c1] I-76
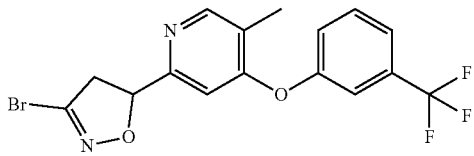 [SMILES: Cc1cnc(C2CC(Br)=NO2)cc1Oc1cccc(C(F)(F)F)c1] I-77
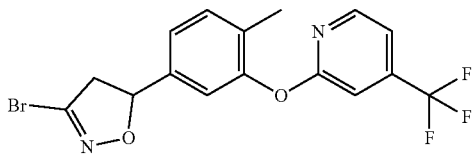 [SMILES: Cc1ccc(C2CC(Br)=NO2)cc1Oc1cc(C(F)(F)F)ccn1] I-78
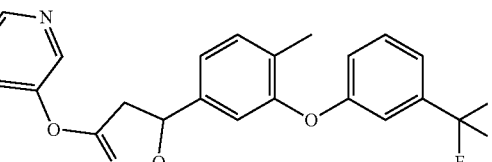 I-79
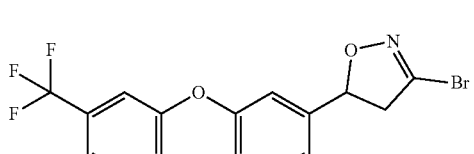 I-80
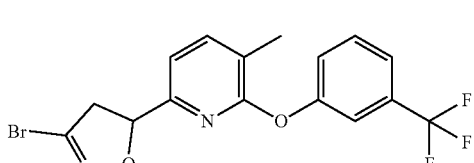 I-81
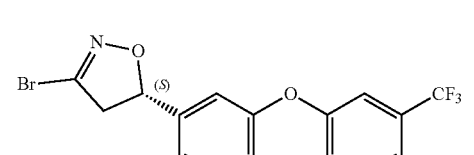 I-82

TABLE 1-continued
| Exemplary Compounds | |
|---|---|
| 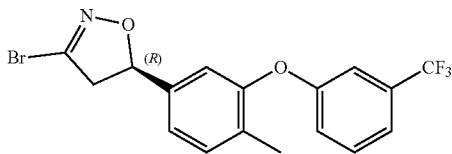 | I-83 |
| 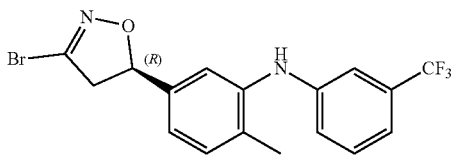 | I-84 |
| 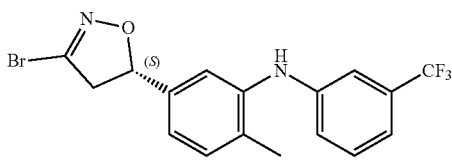 | I-85 |
| 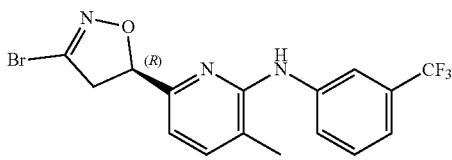 | I-86 |
| 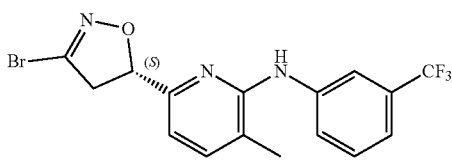 | I-87 |
| 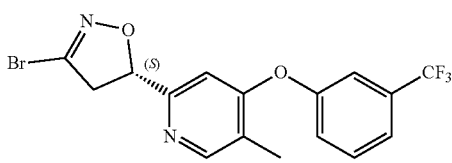 | I-88 |
| 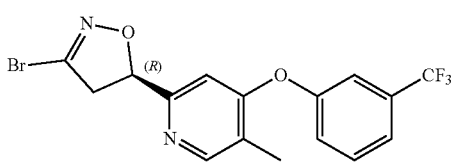 | I-89 |
| 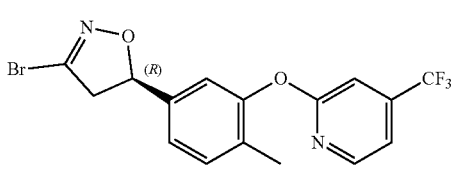 | I-90 |
| 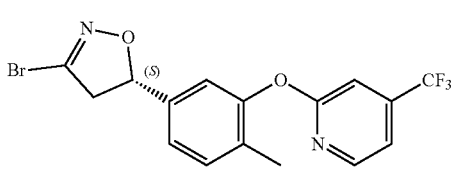 | I-91 |

TABLE 1-continued
Exemplary Compounds
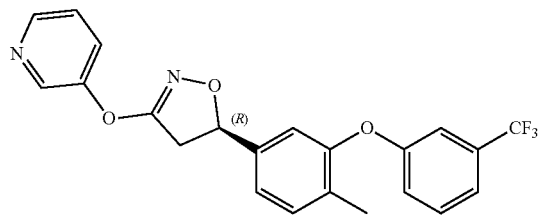
I-92
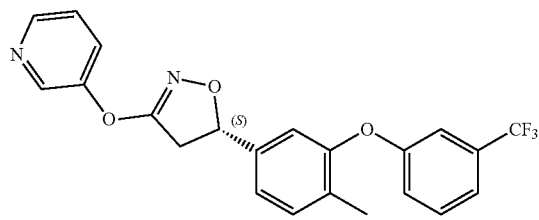
I-93
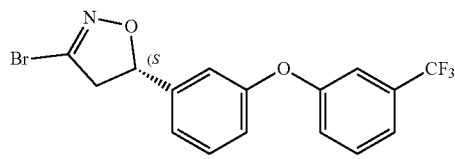
I-94
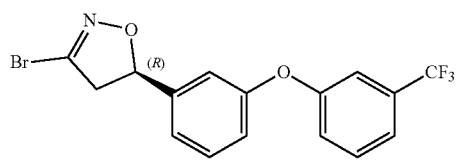
I-95
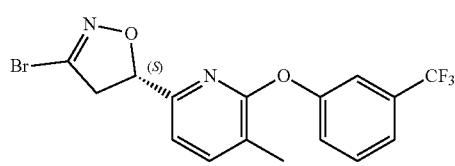
I-96
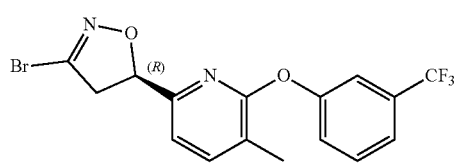
I-97
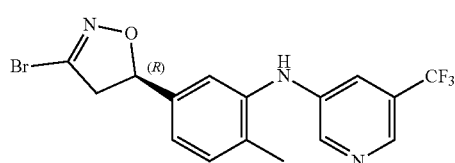
I-98
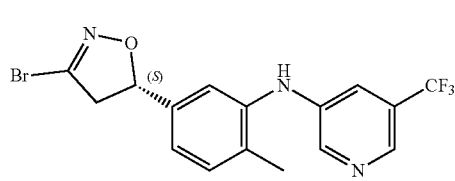
I-99

TABLE 1-continued

Exemplary Compounds

| Compound | ID |
|---|---|
| 3-bromo-4,5-dihydroisoxazol-5-yl (R) attached to quinoline with 7-(3-trifluoromethylphenoxy) substituent | I-100 |
| 3-bromo-4,5-dihydroisoxazol-5-yl (S) attached to quinoline with 7-(3-trifluoromethylphenoxy) substituent | I-101 |
| 3-chloro-4,5-dihydroisoxazol-5-yl (S) attached to 4-methyl-3-(3-trifluoromethylphenoxy)phenyl | I-102 |
| 3-bromo-4,5-dihydroisoxazol-5-yl attached to 4-methylphenyl with NH-linked 5-(trifluoromethyl)pyridin-3-yl | I-103 |
| 3-chloro-4,5-dihydroisoxazol-5-yl (R) attached to 4-methyl-3-(3-trifluoromethylphenoxy)phenyl | I-104 |
| 3-bromo-4,5-dihydroisoxazol-5-yl (S) attached to 2-fluoro-4-methyl-5-(3-trifluoromethylphenoxy)phenyl | I-105 |
| 3-bromo-4,5-dihydroisoxazol-5-yl (R) attached to 5-fluoro-2-methyl-3-(3-trifluoromethylphenoxy)phenyl | I-106 |
| 3-(1H-imidazol-1-yl)-4,5-dihydroisoxazol-5-yl (S) attached to 4-methyl-3-(3-trifluoromethylphenoxy)phenyl | I-107 |
| 3-(1H-imidazol-1-yl)-4,5-dihydroisoxazol-5-yl (R) attached to 4-methyl-3-(3-trifluoromethylphenoxy)phenyl | I-108 |

TABLE 1-continued
| Exemplary Compounds | |
|---|---|
| 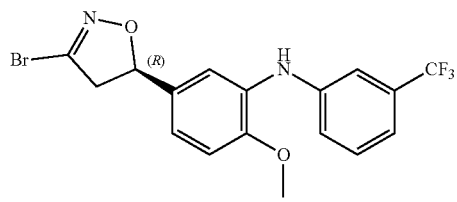 | I-109 |
| 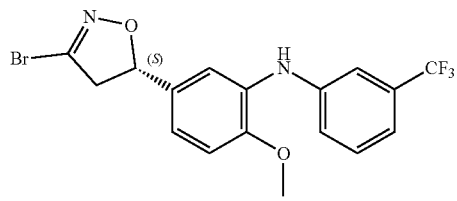 | I-110 |
| 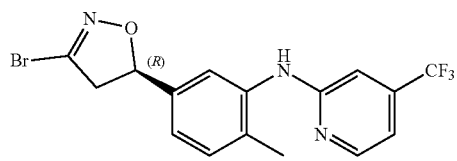 | I-111 |
| 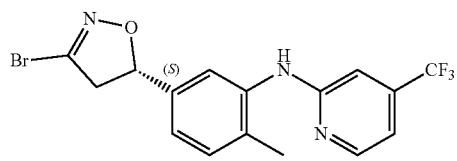 | I-112 |
| 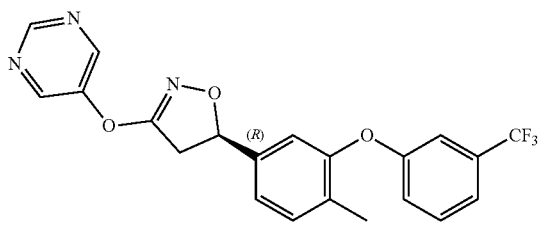 | I-113 |
| 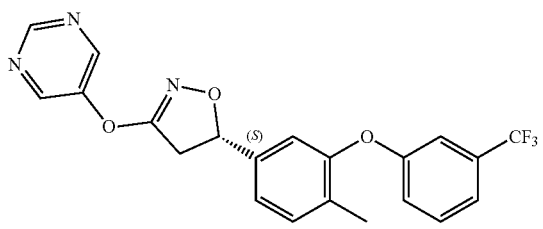 | I-114 |
| 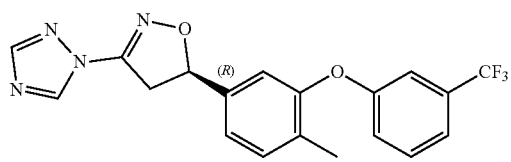 | I-115 |
| 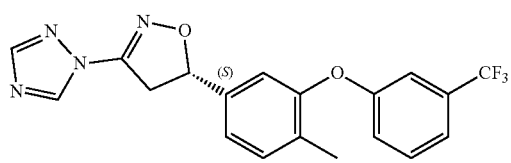 | I-116 |

TABLE 1-continued
Exemplary Compounds
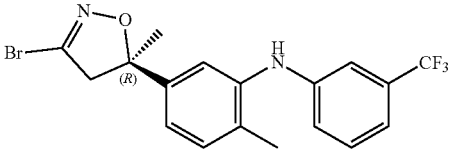 I-117
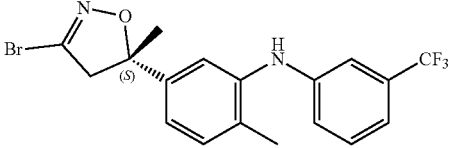 I-118
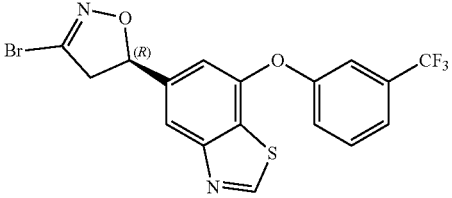 I-119
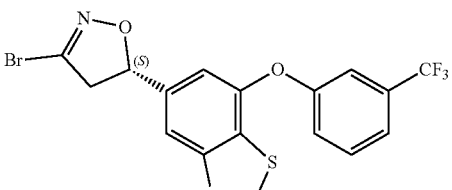 I-120
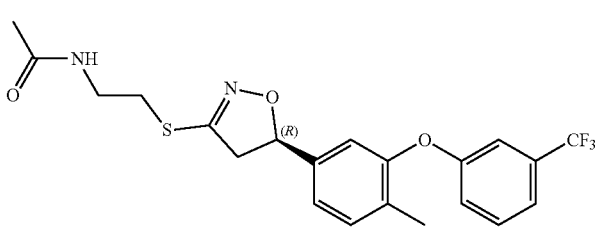 I-121
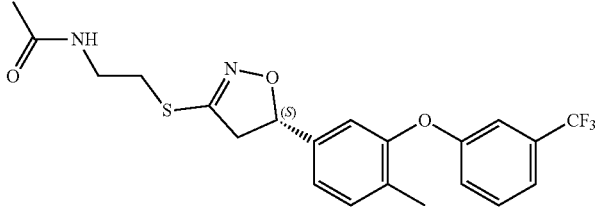 I-122
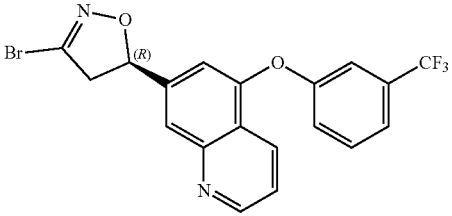 I-123

TABLE 1-continued
| Exemplary Compounds | |
|---|---|
| 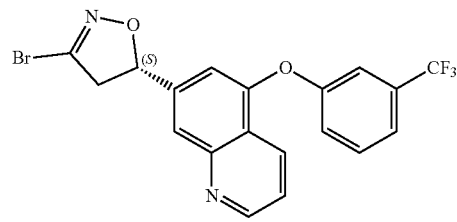 | I-124 |
| 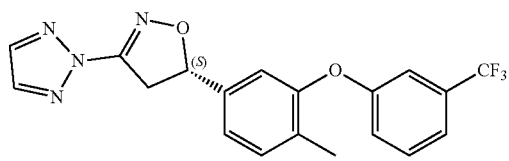 | I-125 |
| 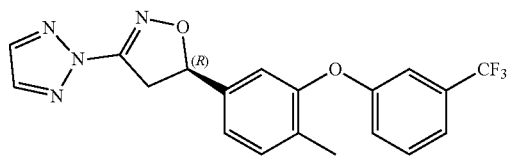 | I-126 |
| 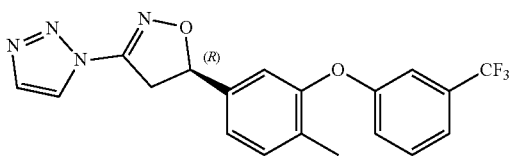 | I-127 |
| 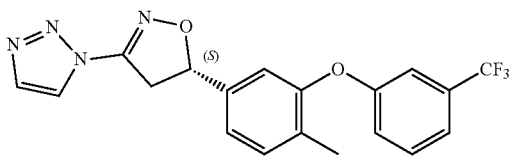 | I-128 |
| 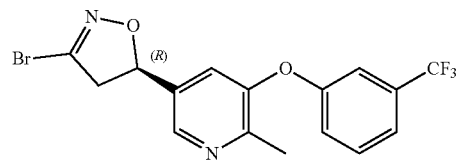 | I-129 |
| 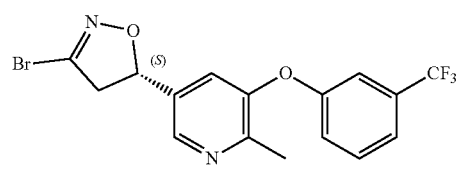 | I-130 |
| 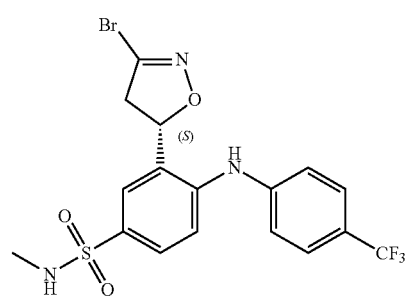 | I-131 |

TABLE 1-continued
| Exemplary Compounds | |
|---|---|
| 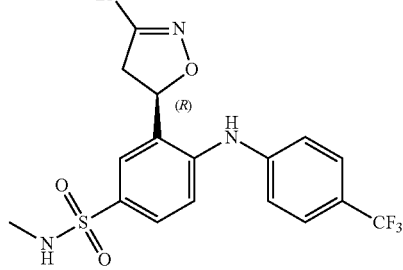 | I-132 |
| 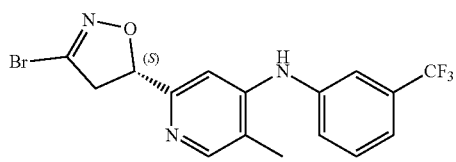 | I-133 |
| 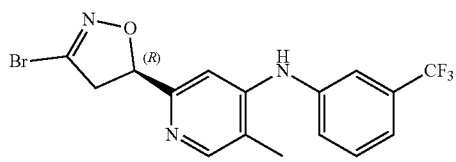 | I-134 |
| 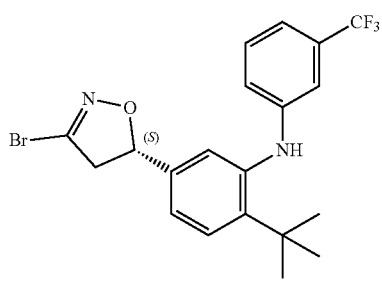 | I-135 |
| 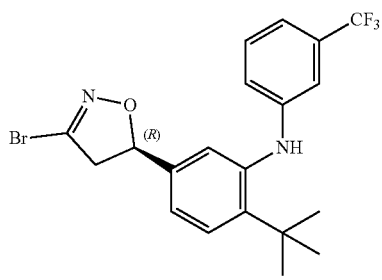 | I-136 |
| 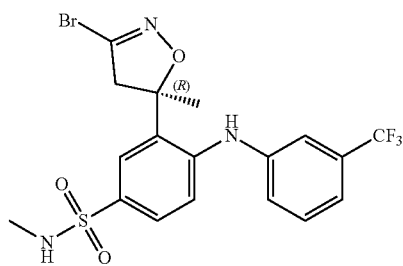 | I-137 |

TABLE 1-continued
Exemplary Compounds
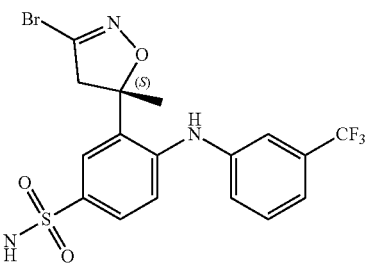
I-138
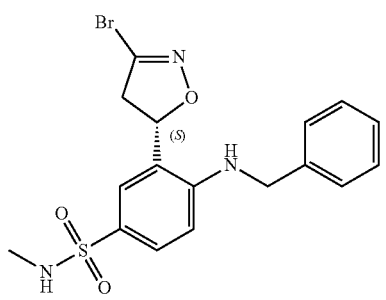
I-139
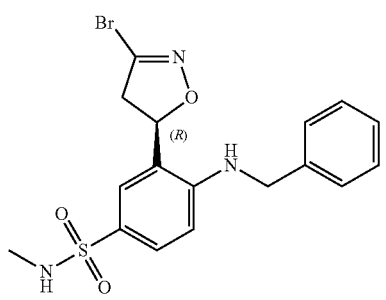
I-140
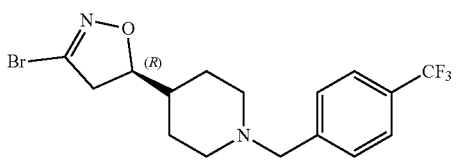
I-141
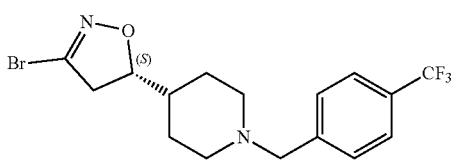
I-142
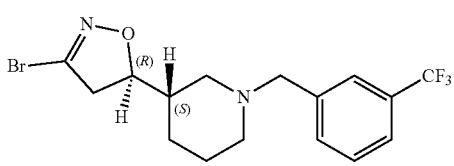
I-143
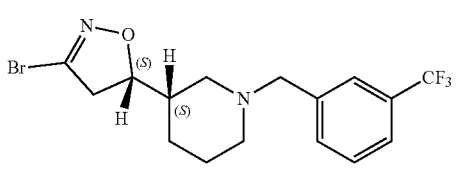
I-144

TABLE 1-continued

Exemplary Compounds

I-145, I-146, I-147, I-148, I-149, I-150, I-151, I-152, I-153

TABLE 1-continued
Exemplary Compounds
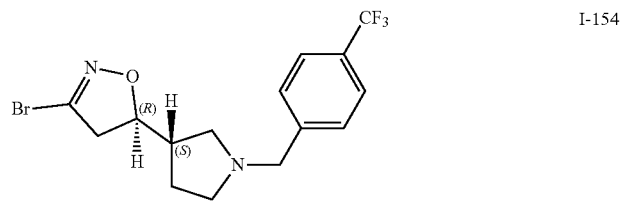  I-154
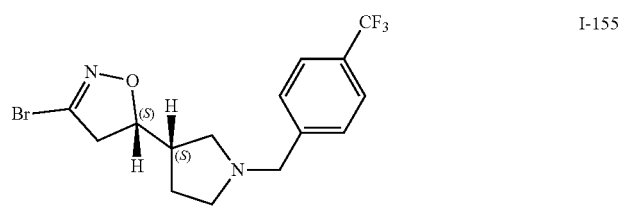  I-155
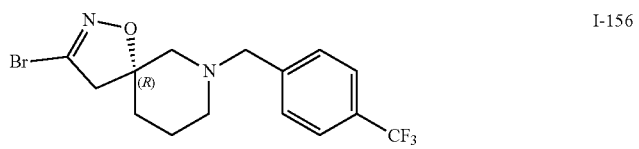  I-156
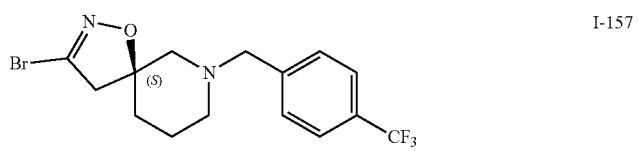  I-157
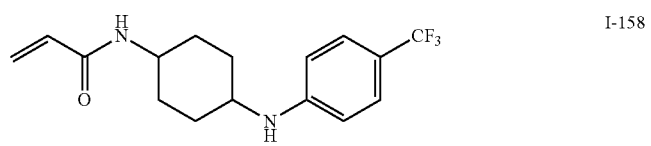  I-158
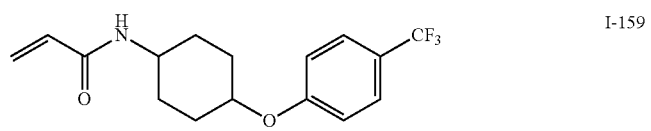  I-159
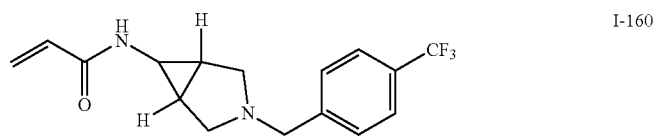  I-160
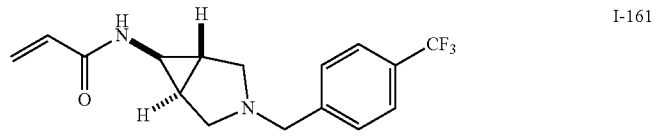  I-161
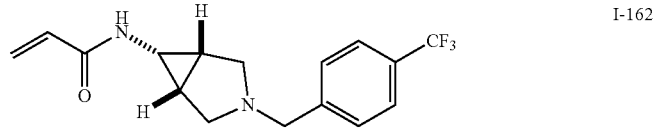  I-162

TABLE 1-continued
Exemplary Compounds
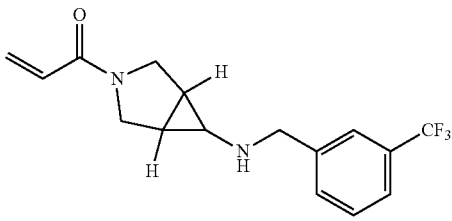 [SMILES: C=CC(=O)N1CC2C(C1)C2NCc1cccc(C(F)(F)F)c1]
I-163
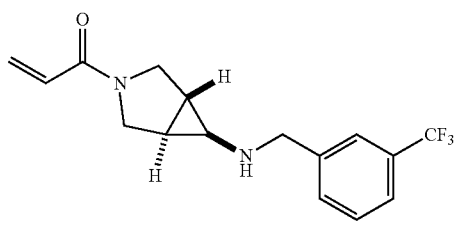
I-164
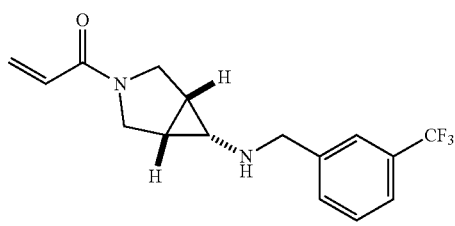 [SMILES: C=CC(=O)N1C[C@@H]2[C@H](C1)[C@@H]2NCc1cccc(C(F)(F)F)c1]
I-165
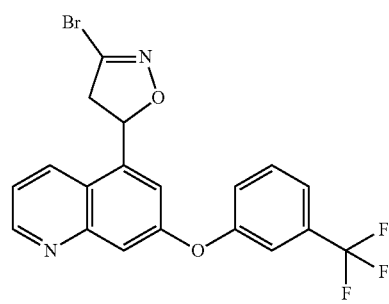 [SMILES: FC(F)(F)c1cccc(Oc2cc(C3CC(Br)=NO3)c3cccnc3c2)c1]
I-166
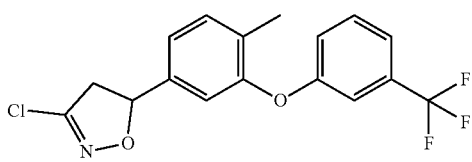 [SMILES: Cc1ccc(C2CC(Cl)=NO2)cc1Oc1cccc(C(F)(F)F)c1]
I-167
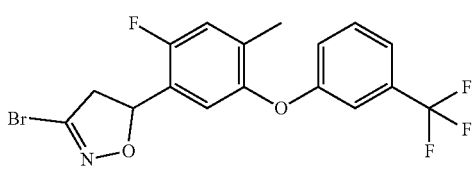 [SMILES: Cc1cc(F)c(C2CC(Br)=NO2)cc1Oc1cccc(C(F)(F)F)c1]
I-168
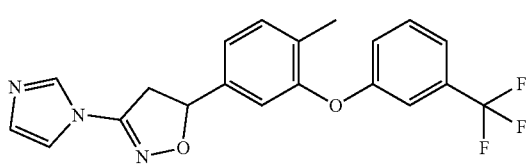 [SMILES: Cc1ccc(C2CC(n3ccnc3)=NO2)cc1Oc1cccc(C(F)(F)F)c1]
I-169

TABLE 1-continued
Exemplary Compounds
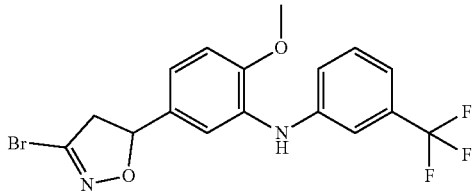 [SMILES: COc1ccc(C2CC(Br)=NO2)cc1Nc1cccc(C(F)(F)F)c1]
I-170
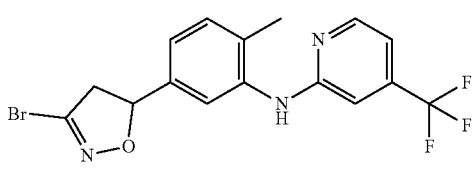 [SMILES: Cc1ccc(C2CC(Br)=NO2)cc1Nc1cc(C(F)(F)F)ccn1]
I-171
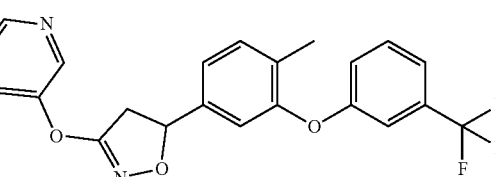
I-172
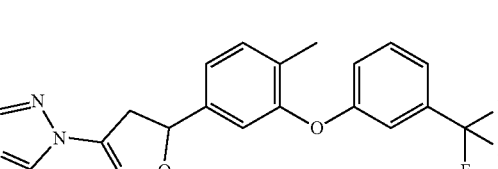
I-173
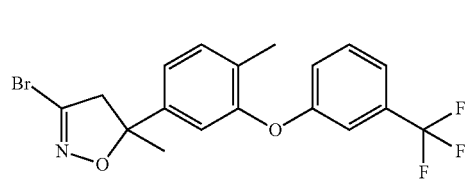 [SMILES: Cc1ccc(C2(C)CC(Br)=NO2)cc1Oc1cccc(C(F)(F)F)c1]
I-174
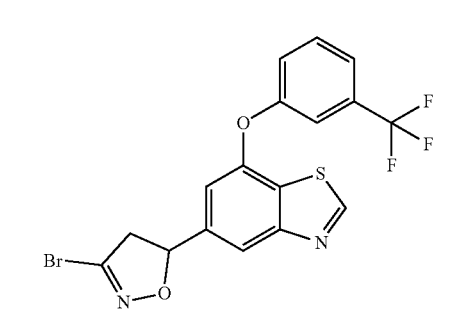 [SMILES: FC(F)(F)c1cccc(Oc2cc(C3CC(Br)=NO3)cc3ncsc23)c1]
I-175
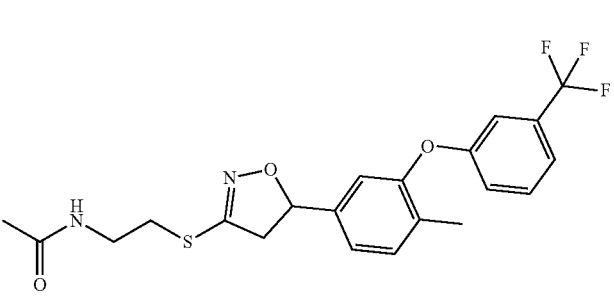 [SMILES: CC(=O)NCCSC1=NOC(c2ccc(C)c(Oc3cccc(C(F)(F)F)c3)c2)C1]
I-176

TABLE 1-continued
Exemplary Compounds
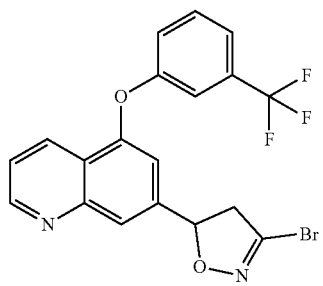 [SMILES: FC(F)(F)c1cccc(Oc2cc(C3CC(Br)=NO3)cc3ncccc23)c1]
I-177
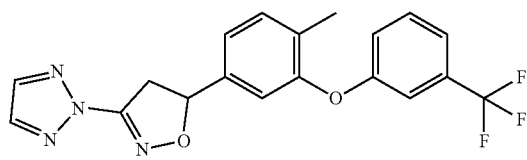
I-178
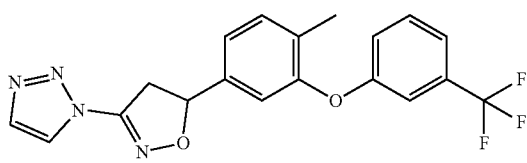 [SMILES: Cc1ccc(C2CC(n3ccnn3)=NO2)cc1Oc1cccc(C(F)(F)F)c1]
I-179
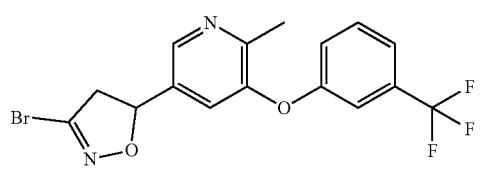 [SMILES: Cc1ncc(C2CC(Br)=NO2)cc1Oc1cccc(C(F)(F)F)c1]
I-180
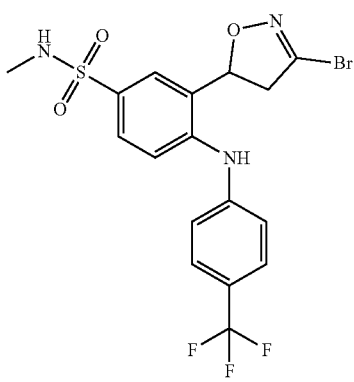 [SMILES: CNS(=O)(=O)c1ccc(Nc2ccc(C(F)(F)F)cc2)c(C2CC(Br)=NO2)c1]
I-181
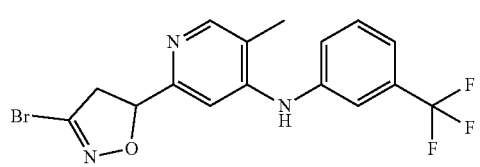 [SMILES: Cc1cnc(C2CC(Br)=NO2)cc1Nc1cccc(C(F)(F)F)c1]
I-182

TABLE 1-continued
Exemplary Compounds
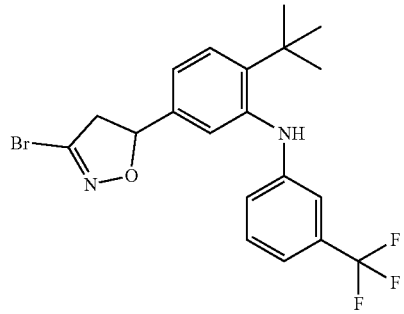 [SMILES: CC(C)(C)c1ccc(C2CC(Br)=NO2)cc1Nc1cccc(C(F)(F)F)c1]
I-183
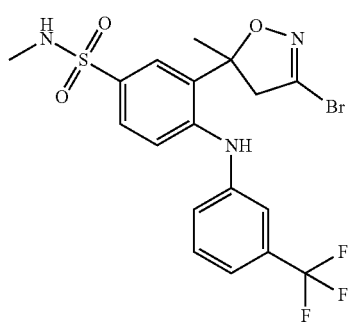 [SMILES: CNS(=O)(=O)c1ccc(Nc2cccc(C(F)(F)F)c2)c(C2(C)CC(Br)=NO2)c1]
I-184
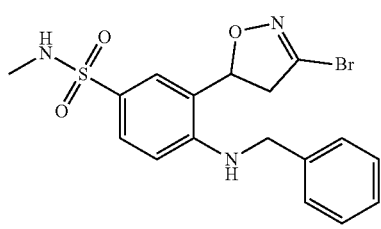 [SMILES: CNS(=O)(=O)c1ccc(NCc2ccccc2)c(C2CC(Br)=NO2)c1]
I-185
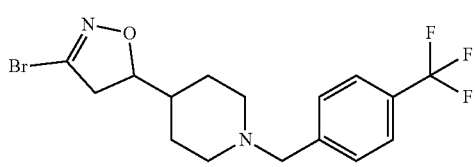 [SMILES: FC(F)(F)c1ccc(CN2CCC(C3CC(Br)=NO3)CC2)cc1]
I-186
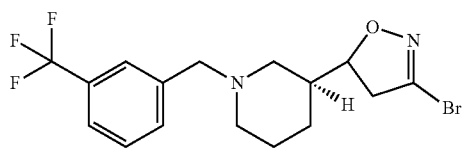 [SMILES: FC(F)(F)c1cccc(CN2CCC[C@H](C3CC(Br)=NO3)C2)c1]
I-187
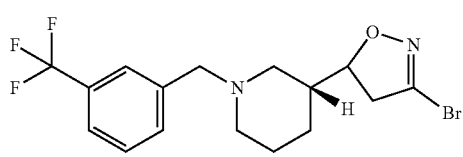 [SMILES: FC(F)(F)c1cccc(CN2CCC[C@@H](C3CC(Br)=NO3)C2)c1]
I-188
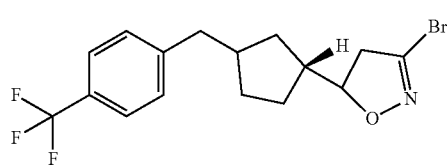 [SMILES: FC(F)(F)c1ccc(CC2CC[C@@H](C3CC(Br)=NO3)C2)cc1]
I-189

TABLE 1-continued
Exemplary Compounds
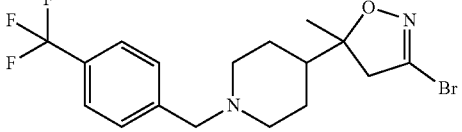 I-190
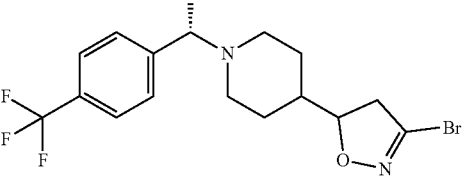 I-191
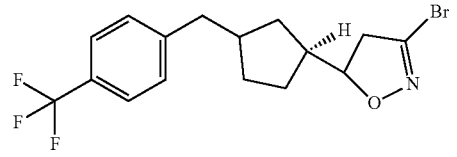 [SMILES: FC(F)(F)c1ccc(CC2CC[C@H](C3CC(Br)=NO3)C2)cc1] I-192
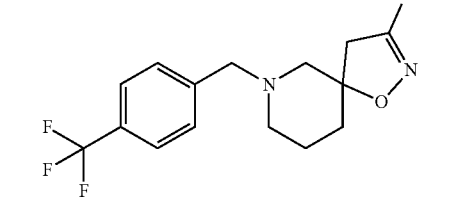 I-193
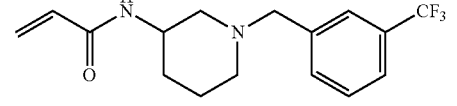 I-194
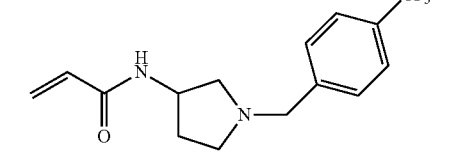 I-195
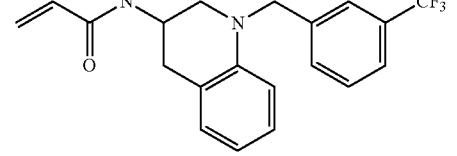 I-196
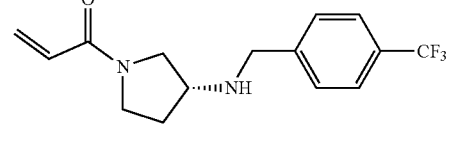 I-197
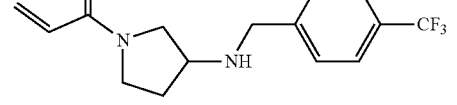 I-198

TABLE 1-continued
Exemplary Compounds
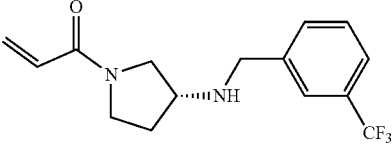
I-199
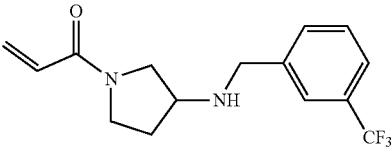 [SMILES: C=CC(=O)N1CC[C@@H](NCc2cccc(C(F)(F)F)c2)C1]
I-200
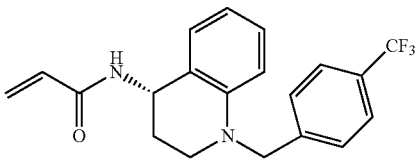 [SMILES: C=CC(=O)N[C@H]1CCN(Cc2ccc(C(F)(F)F)cc2)c2ccccc21]
I-201
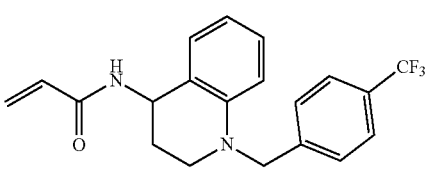 [SMILES: C=CC(=O)NC1CCN(Cc2ccc(C(F)(F)F)cc2)c2ccccc21]
I-202
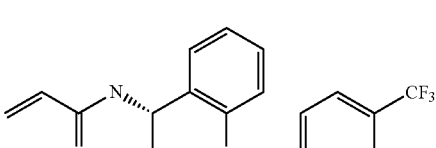
I-203
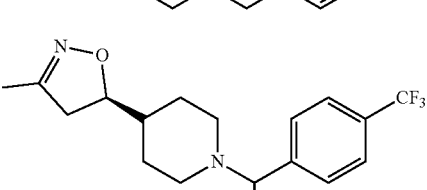
I-204
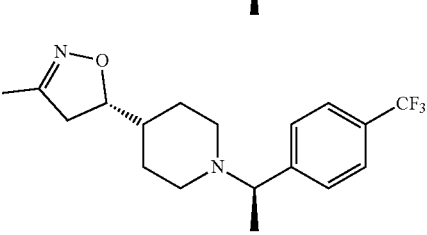
I-205
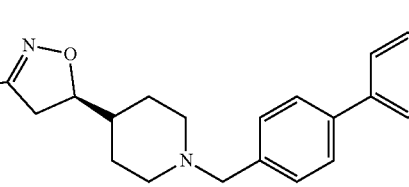
I-206
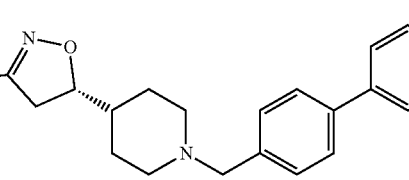
I-207

TABLE 1-continued
Exemplary Compounds
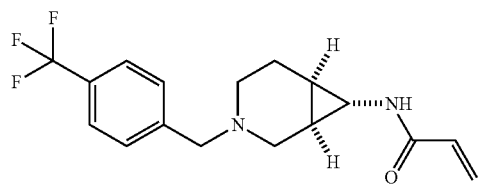 [SMILES: C=CC(=O)N[C@H]1[C@@H]2CCN(Cc3ccc(C(F)(F)F)cc3)C[C@@H]21]
I-208
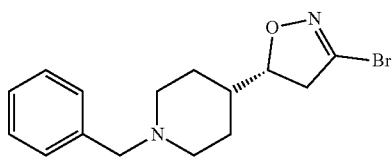
I-209
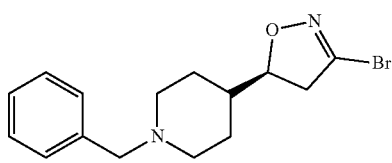 [SMILES: BrC1=NO[C@H](C2CCN(Cc3ccccc3)CC2)C1]
I-210
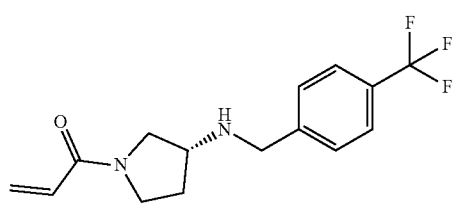 [SMILES: C=CC(=O)N1CC[C@@H](NCc2ccc(C(F)(F)F)cc2)C1]
I-211
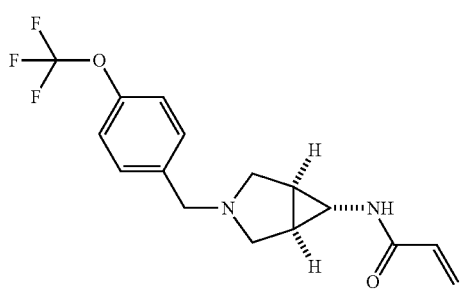
I-212
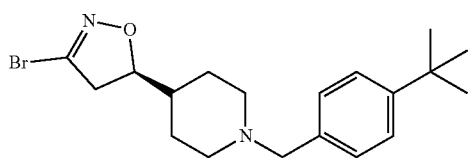 [SMILES: CC(C)(C)c1ccc(CN2CCC([C@H]3CC(Br)=NO3)CC2)cc1]
I-213
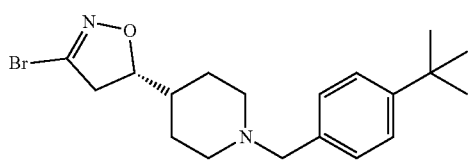
I-214
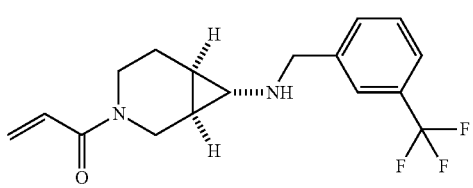
I-217

TABLE 1-continued
Exemplary Compounds
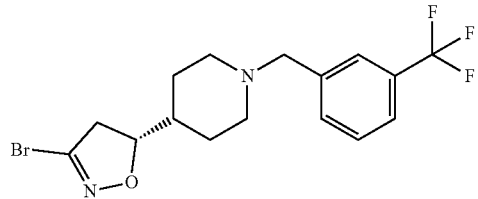 I-218
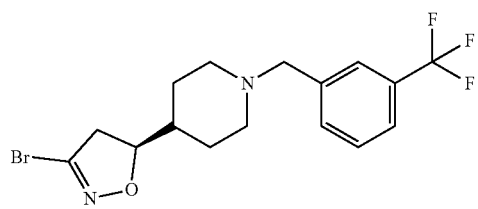 [SMILES: FC(F)(F)c1cccc(CN2CCC([C@@H]3CC(Br)=NO3)CC2)c1] I-219
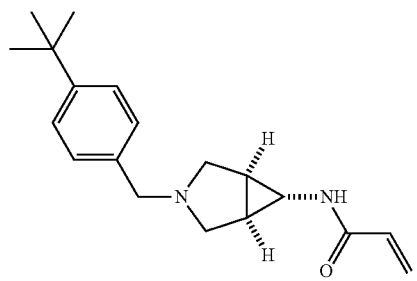 [SMILES: C=CC(=O)N[C@H]1[C@@H]2CN(Cc3ccc(C(C)(C)C)cc3)C[C@@H]21] I-220
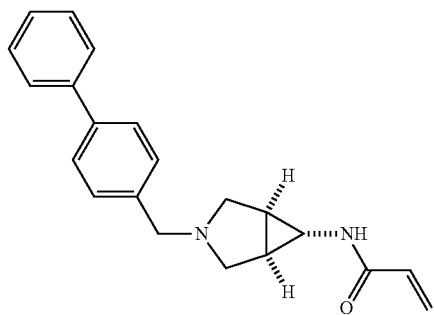 I-221
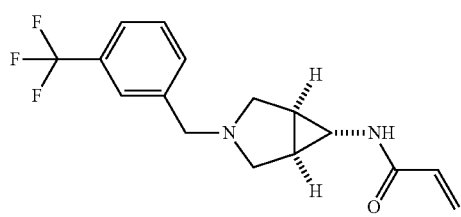 [SMILES: C=CC(=O)N[C@H]1[C@@H]2CN(Cc3cccc(C(F)(F)F)c3)C[C@@H]21] I-222
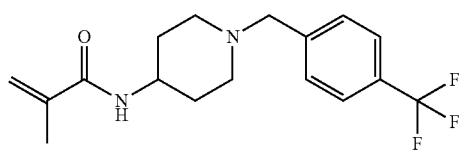 [SMILES: C=C(C)C(=O)NC1CCN(Cc2ccc(C(F)(F)F)cc2)CC1] I-223

TABLE 1-continued
Exemplary Compounds
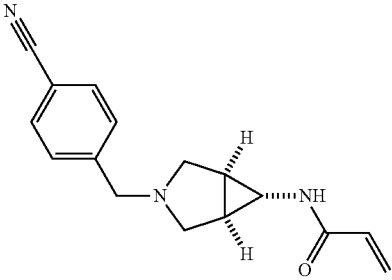 [SMILES: C=CC(=O)N[C@H]1[C@@H]2CN(Cc3ccc(C#N)cc3)C[C@@H]21] I-224
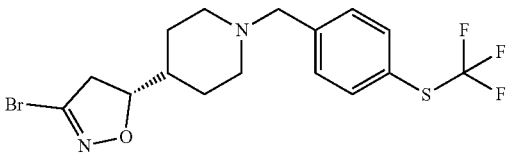 I-225
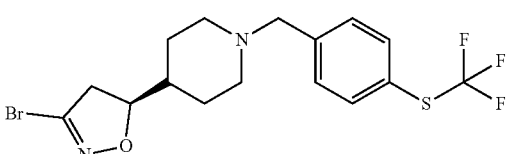 I-226
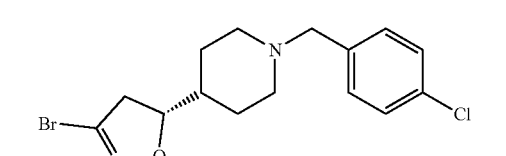 I-227
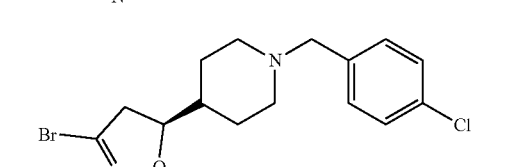 I-228
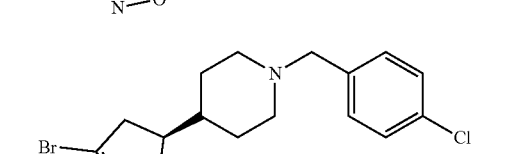 I-229
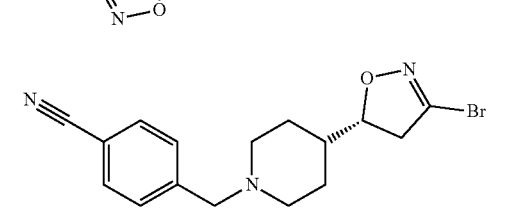 I-230
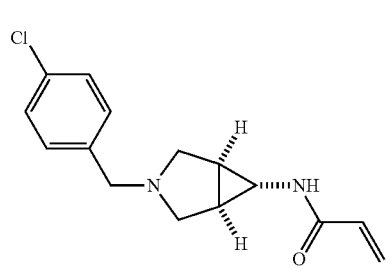 [SMILES: C=CC(=O)N[C@H]1[C@@H]2CN(Cc3ccc(Cl)cc3)C[C@@H]21] I-231

TABLE 1-continued
Exemplary Compounds
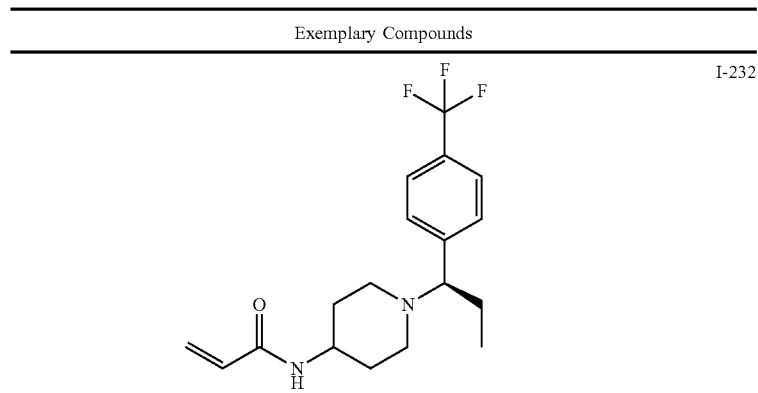
I-232
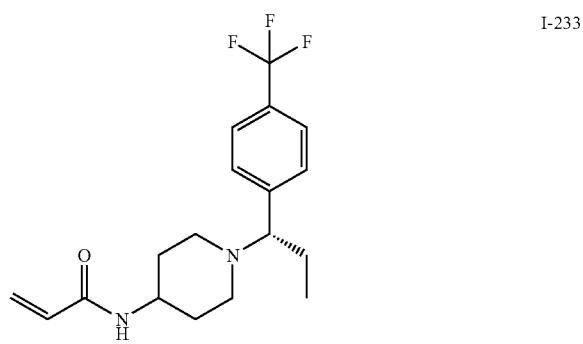
I-233
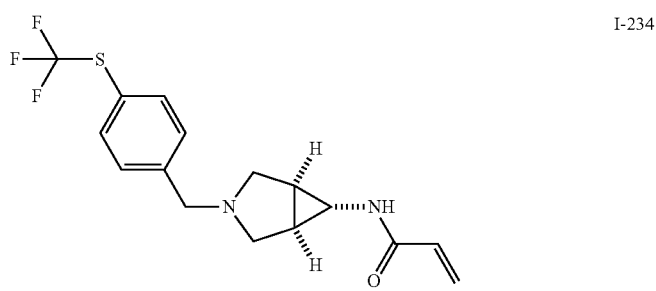
I-234
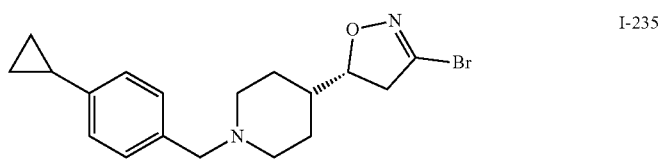
I-235
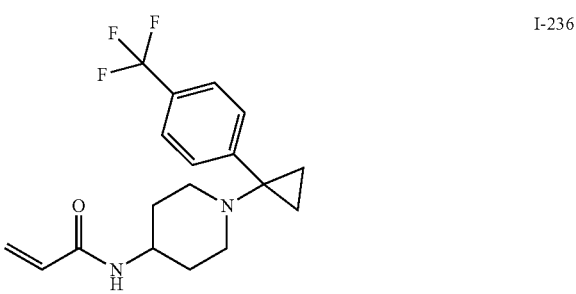
I-236
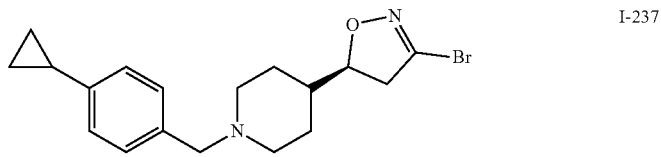
I-237

TABLE 1-continued
Exemplary Compounds
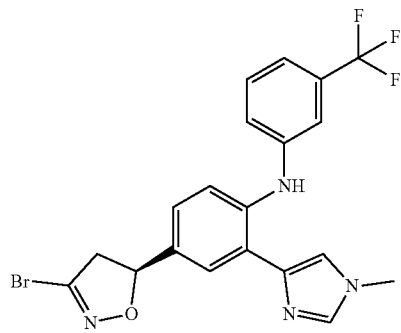 [SMILES: Cn1cnc(-c2cc([C@@H]3CC(Br)=NO3)ccc2Nc2cccc(C(F)(F)F)c2)c1]
I-238
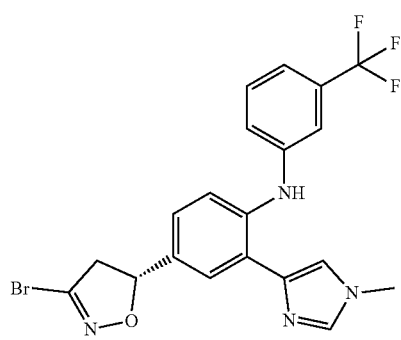 [SMILES: Cn1cnc(-c2cc([C@H]3CC(Br)=NO3)ccc2Nc2cccc(C(F)(F)F)c2)c1]
I-239
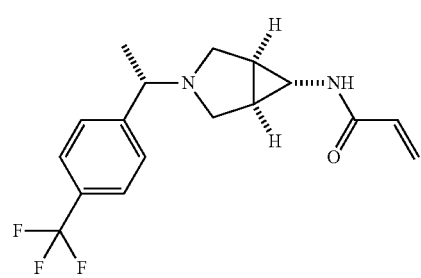
I-240
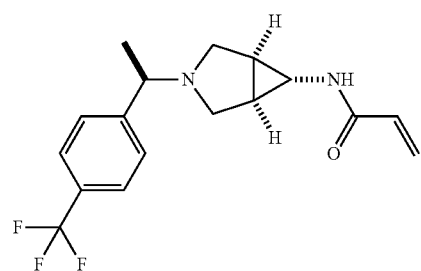
I-241
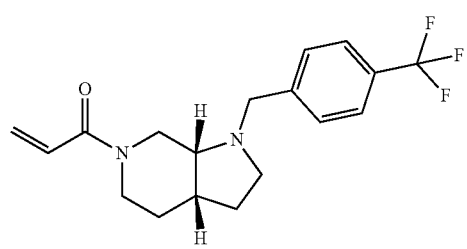 [SMILES: C=CC(=O)N1CC[C@H]2CCN(Cc3ccc(C(F)(F)F)cc3)[C@H]2C1]
I-242

TABLE 1-continued
Exemplary Compounds
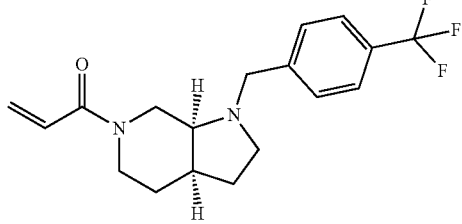 I-243
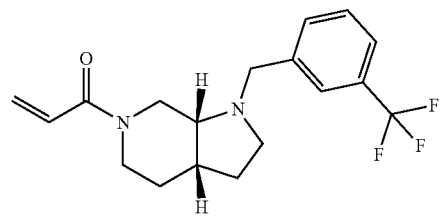 [SMILES: C=CC(=O)N1CC[C@H]2CCN(Cc3cccc(C(F)(F)F)c3)[C@H]2C1] I-244
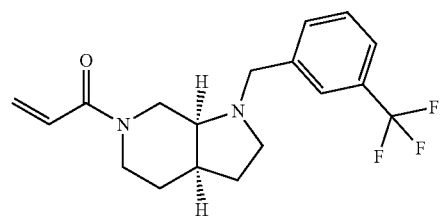 [SMILES: C=CC(=O)N1CC[C@@H]2CCN(Cc3cccc(C(F)(F)F)c3)[C@@H]2C1] I-245
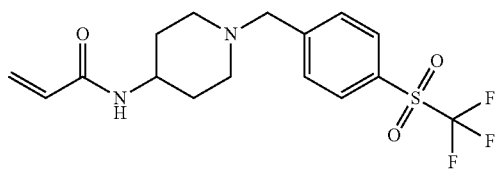 [SMILES: C=CC(=O)NC1CCN(Cc2ccc(S(=O)(=O)C(F)(F)F)cc2)CC1] I-246
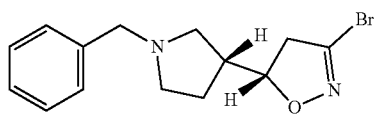 [SMILES: BrC1=NO[C@H]([C@@H]2CCN(Cc3ccccc3)C2)C1] I-247
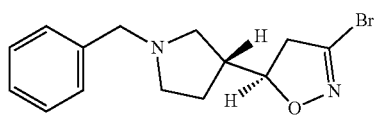 [SMILES: BrC1=NO[C@@H]([C@@H]2CCN(Cc3ccccc3)C2)C1] I-248
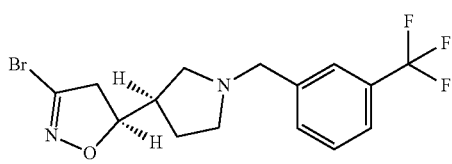 [SMILES: FC(F)(F)c1cccc(CN2CC[C@@H]([C@@H]3CC(Br)=NO3)C2)c1] I-249
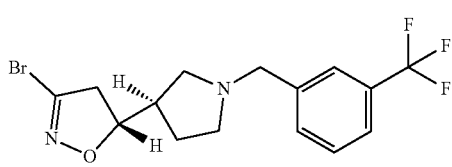 [SMILES: FC(F)(F)c1cccc(CN2CC[C@@H]([C@H]3CC(Br)=NO3)C2)c1] I-250
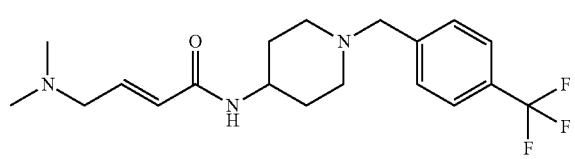 [SMILES: CN(C)C/C=C/C(=O)NC1CCN(Cc2ccc(C(F)(F)F)cc2)CC1] I-251

TABLE 1-continued
Exemplary Compounds
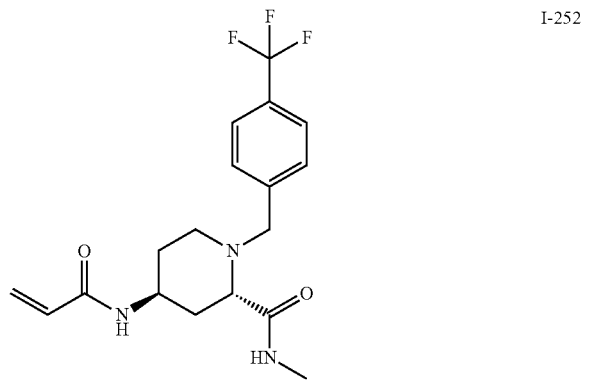
I-252
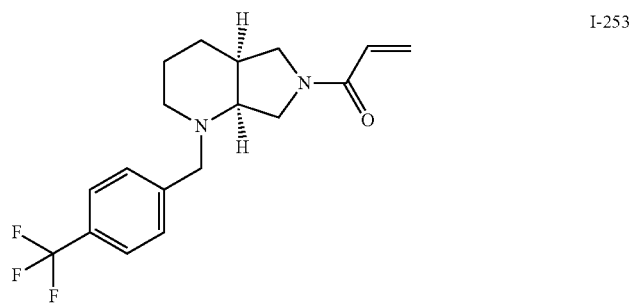
I-253
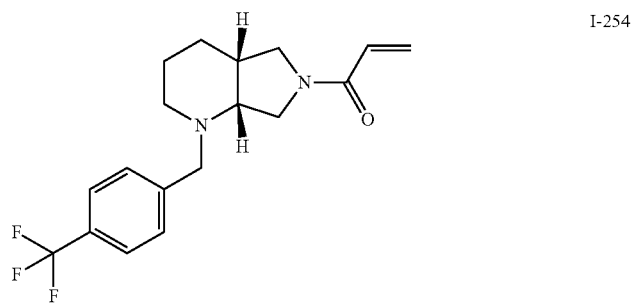
I-254
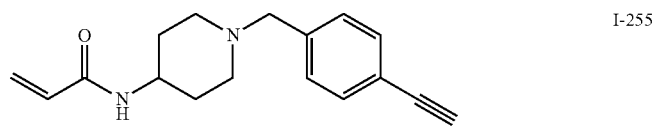
I-255
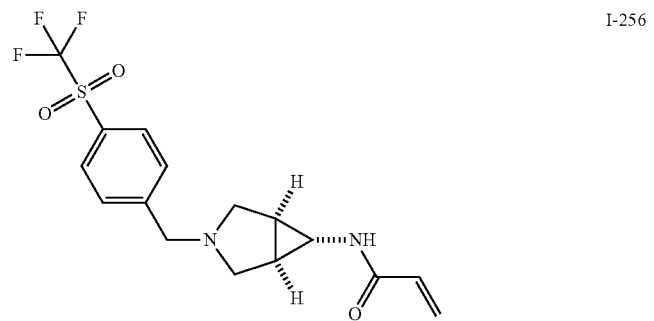
I-256

TABLE 1-continued
Exemplary Compounds
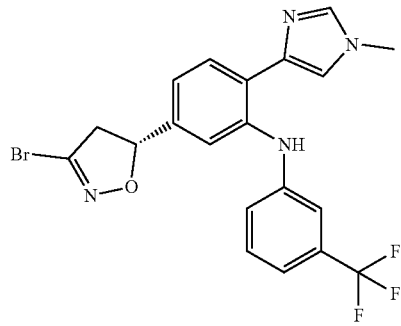 [SMILES: Cn1cnc(-c2ccc([C@H]3CC(Br)=NO3)cc2Nc2cccc(C(F)(F)F)c2)c1]
I-257
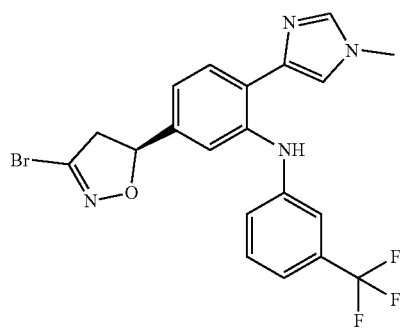 [SMILES: Cn1cnc(-c2ccc([C@@H]3CC(Br)=NO3)cc2Nc2cccc(C(F)(F)F)c2)c1]
I-258
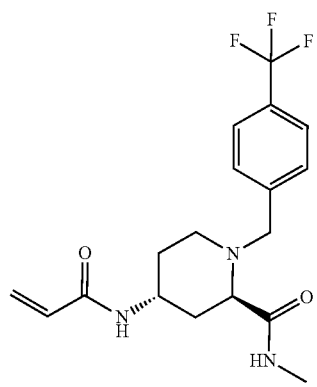 [SMILES: C=CC(=O)N[C@@H]1CCN(Cc2ccc(C(F)(F)F)cc2)[C@@H](C(=O)NC)C1]
I-259
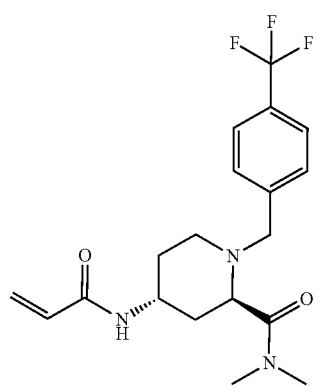 [SMILES: C=CC(=O)N[C@@H]1CCN(Cc2ccc(C(F)(F)F)cc2)[C@@H](C(=O)N(C)C)C1]
I-260

TABLE 1-continued
Exemplary Compounds
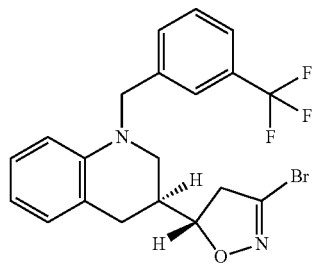 [SMILES: FC(F)(F)c1cccc(CN2C[C@@H]([C@@H]3CC(Br)=NO3)Cc3ccccc32)c1]
I-261
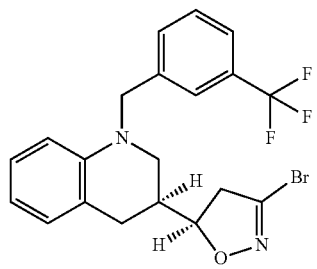
I-262
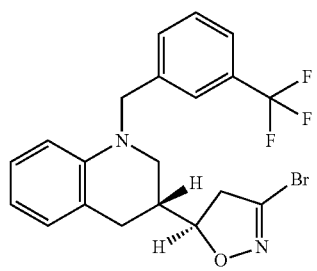 [SMILES: FC(F)(F)c1cccc(CN2C[C@H]([C@H]3CC(Br)=NO3)Cc3ccccc32)c1]
I-263
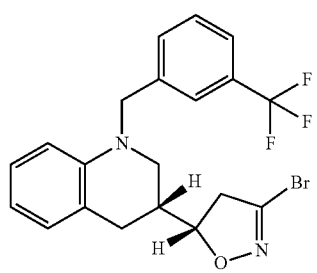 [SMILES: FC(F)(F)c1cccc(CN2C[C@H]([C@@H]3CC(Br)=NO3)Cc3ccccc32)c1]
I-264
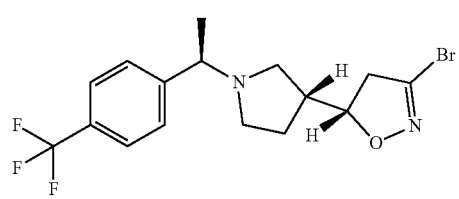 [SMILES: C[C@H](c1ccc(C(F)(F)F)cc1)N1CC[C@@H]([C@@H]2CC(Br)=NO2)C1]
I-265
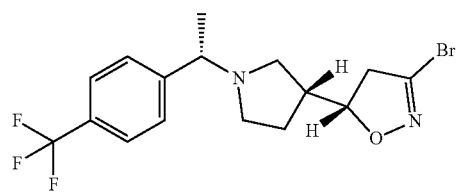 [SMILES: C[C@@H](c1ccc(C(F)(F)F)cc1)N1CC[C@@H]([C@@H]2CC(Br)=NO2)C1]
I-266

163
TABLE 1-continued
Exemplary Compounds
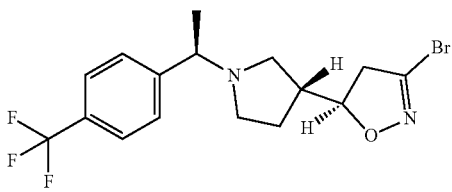 [SMILES: C[C@H](c1ccc(C(F)(F)F)cc1)N1CC[C@@H]([C@H]2CC(Br)=NO2)C1] I-267
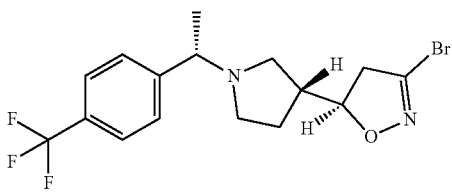 [SMILES: C[C@@H](c1ccc(C(F)(F)F)cc1)N1CC[C@@H]([C@H]2CC(Br)=NO2)C1] I-268
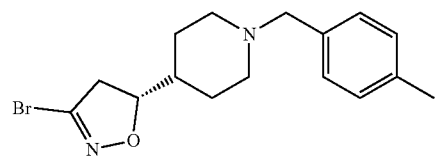 [SMILES: Cc1ccc(CN2CCC([C@H]3CC(Br)=NO3)CC2)cc1] I-269
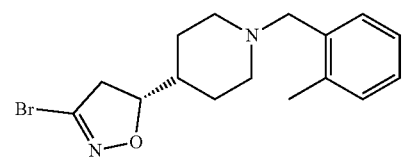 I-270
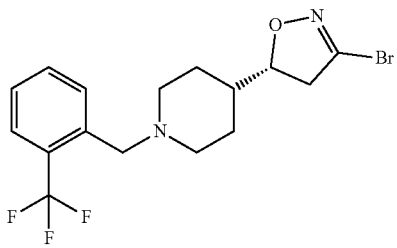 I-271
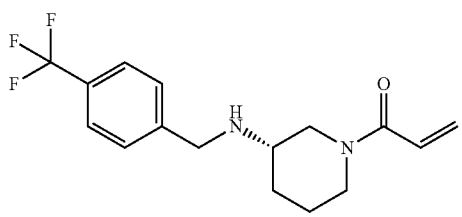 [SMILES: C=CC(=O)N1CCC[C@H](NCc2ccc(C(F)(F)F)cc2)C1] I-272
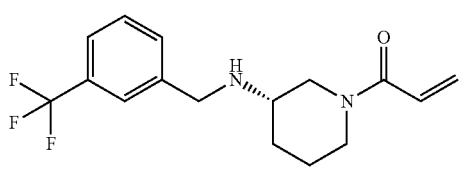 [SMILES: C=CC(=O)N1CCC[C@H](NCc2cccc(C(F)(F)F)c2)C1] I-273
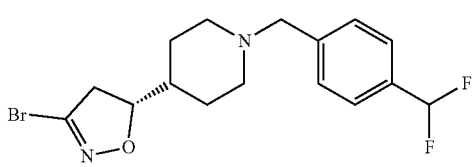 [SMILES: FC(F)c1ccc(CN2CCC([C@H]3CC(Br)=NO3)CC2)cc1] I-274

165
166
TABLE 1-continued
Exemplary Compounds
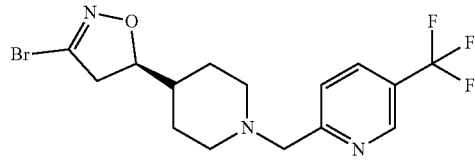 [SMILES: FC(F)(F)c1ccc(CN2CCC([C@H]3CC(Br)=NO3)CC2)nc1] I-275
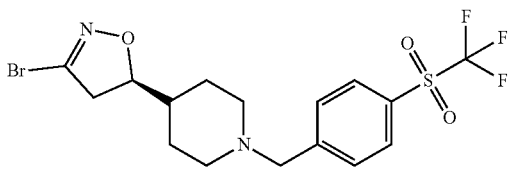 [SMILES: O=S(=O)(c1ccc(CN2CCC([C@H]3CC(Br)=NO3)CC2)cc1)C(F)(F)F] I-276
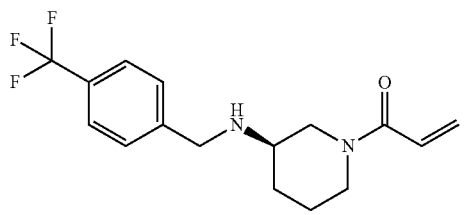 [SMILES: C=CC(=O)N1CCC[C@@H](NCc2ccc(C(F)(F)F)cc2)C1] I-277
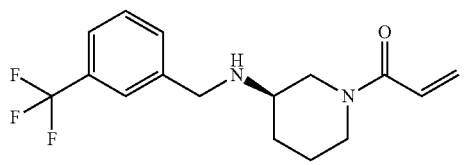 [SMILES: C=CC(=O)N1CCC[C@@H](NCc2cccc(C(F)(F)F)c2)C1] I-278
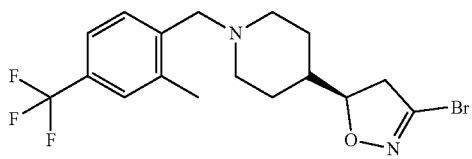 [SMILES: Cc1cc(C(F)(F)F)ccc1CN1CCC([C@H]2CC(Br)=NO2)CC1] I-279
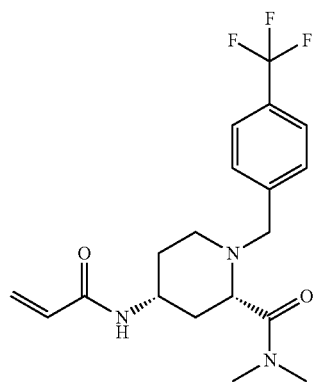 I-280

TABLE 1-continued
Exemplary Compounds
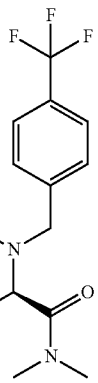
I-281
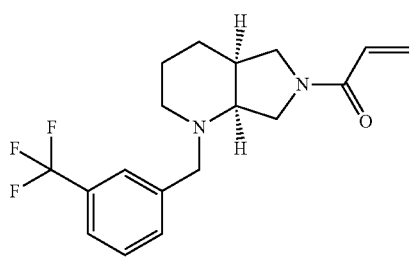 [SMILES: C=CC(=O)N1C[C@@H]2CCCN(Cc3cccc(C(F)(F)F)c3)[C@@H]2C1]
I-282
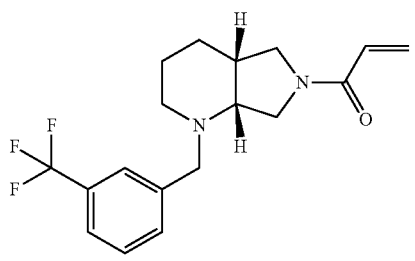 [SMILES: C=CC(=O)N1C[C@H]2CCCN(Cc3cccc(C(F)(F)F)c3)[C@H]2C1]
I-283
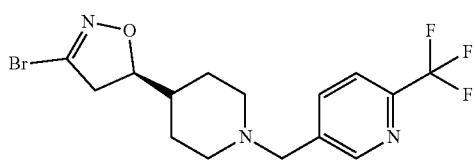 [SMILES: FC(F)(F)c1ccc(CN2CCC([C@H]3CC(Br)=NO3)CC2)cn1]
I-284
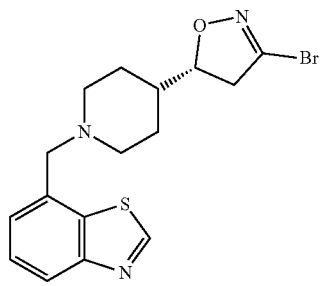 [SMILES: BrC1=NO[C@@H](C2CCN(Cc3cccc4ncsc34)CC2)C1]
I-285
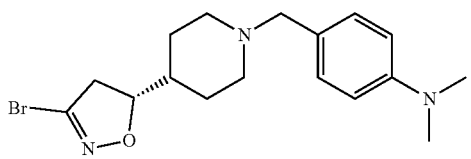 [SMILES: CN(C)c1ccc(CN2CCC([C@H]3CC(Br)=NO3)CC2)cc1]
I-286

TABLE 1-continued
Exemplary Compounds
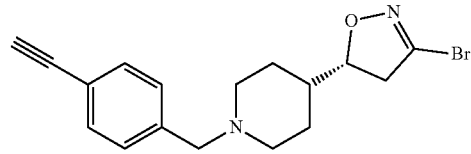
I-287
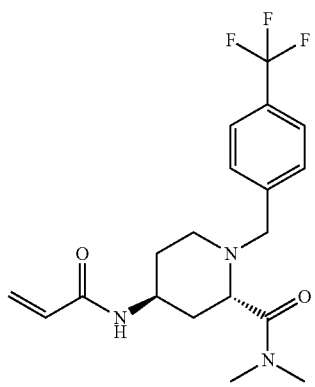
I-288
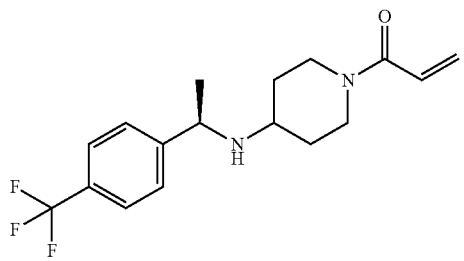 [SMILES: C=CC(=O)N1CCC(N[C@H](C)c2ccc(C(F)(F)F)cc2)CC1]
I-289
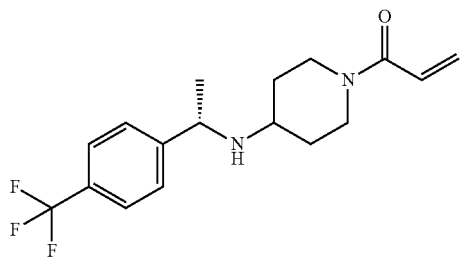
I-290
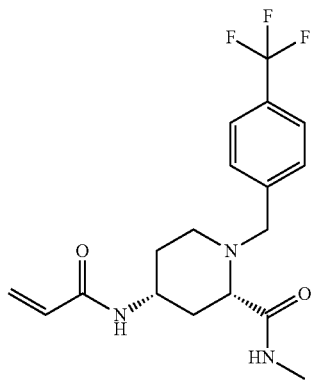
I-291

TABLE 1-continued
Exemplary Compounds
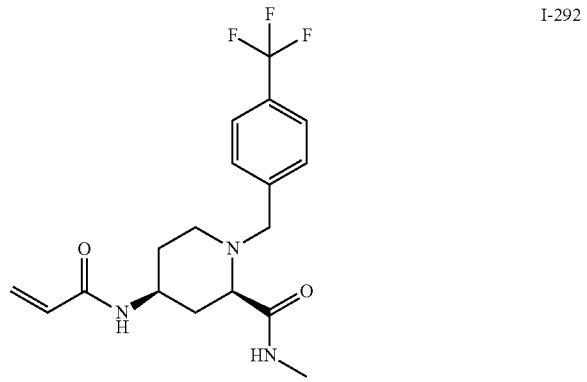
I-292
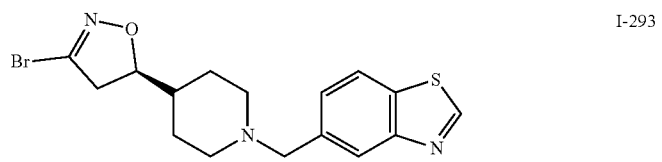
I-293
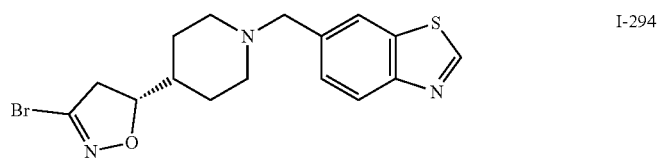
I-294
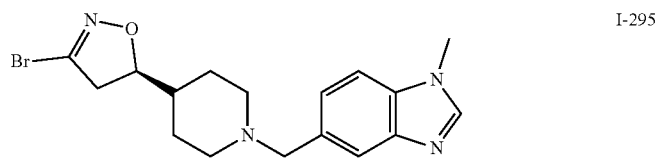
I-295
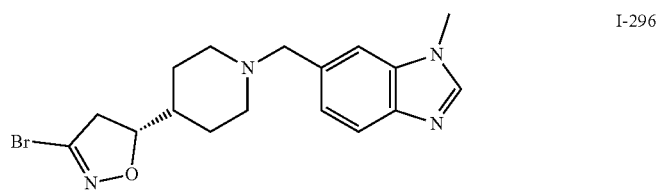
I-296
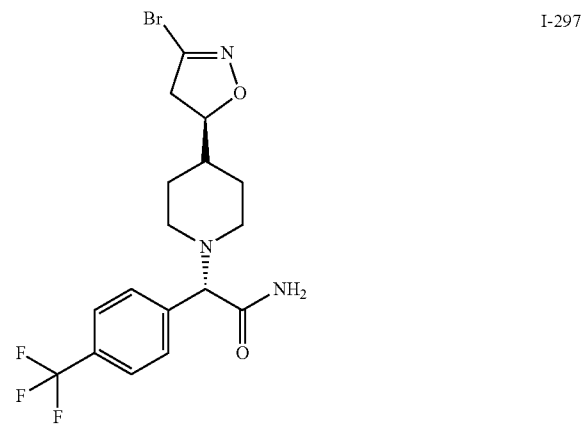
I-297

TABLE 1-continued
Exemplary Compounds
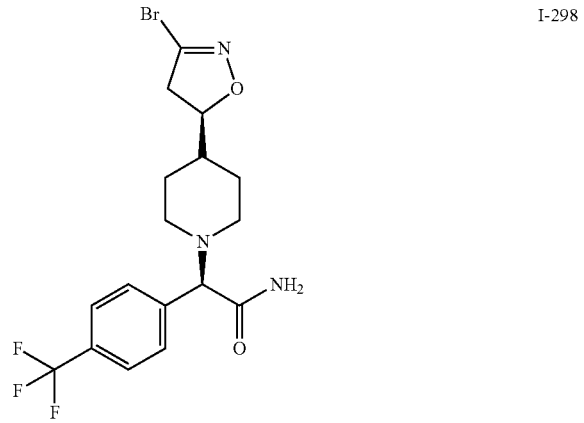
I-298
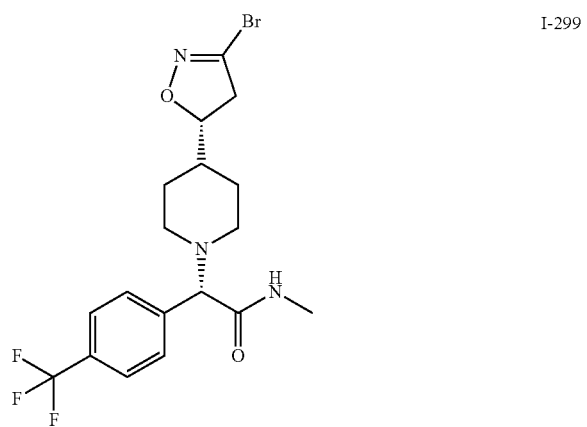
I-299
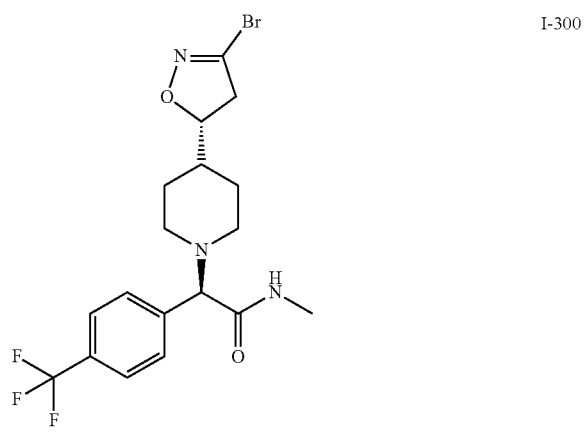
I-300

TABLE 1-continued
| Exemplary Compounds | |
|---|---|
| 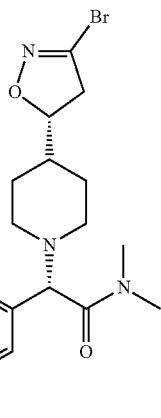 | I-301 |
| 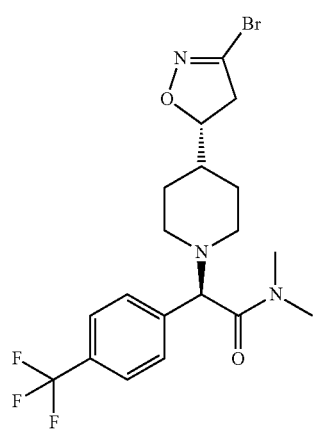 [SMILES: CN(C)C(=O)[C@@H](c1ccc(C(F)(F)F)cc1)N1CCC([C@H]2CC(Br)=NO2)CC1] | I-302 |
| 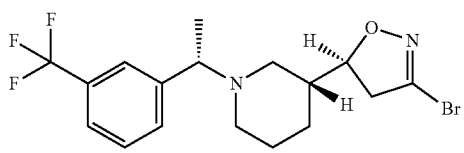 [SMILES: C[C@@H](c1cccc(C(F)(F)F)c1)N1CCC[C@@H]([C@@H]2CC(Br)=NO2)C1] | I-303 |
| 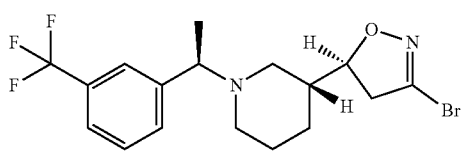 [SMILES: C[C@H](c1cccc(C(F)(F)F)c1)N1CCC[C@@H]([C@@H]2CC(Br)=NO2)C1] | I-304 |
| 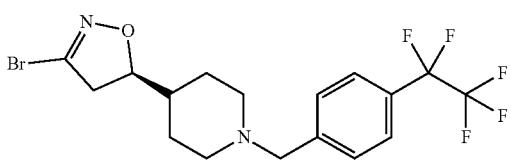 [SMILES: FC(F)(F)C(F)(F)c1ccc(CN2CCC([C@H]3CC(Br)=NO3)CC2)cc1] | I-305 |
| 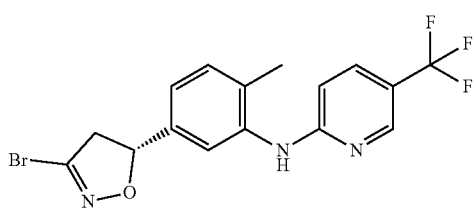 [SMILES: Cc1ccc([C@H]2CC(Br)=NO2)cc1Nc1ccc(C(F)(F)F)cn1] | I-306 |

TABLE 1-continued
Exemplary Compounds
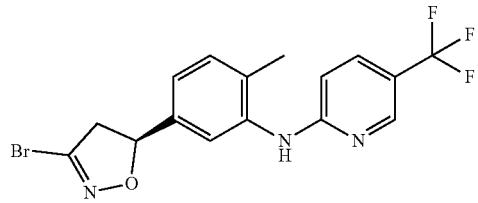 [SMILES: Cc1ccc([C@@H]2CC(Br)=NO2)cc1Nc1ccc(C(F)(F)F)cn1] I-307
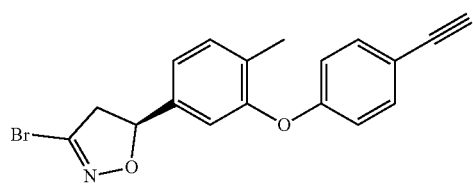 [SMILES: C#Cc1ccc(Oc2cc([C@@H]3CC(Br)=NO3)ccc2C)cc1] I-308
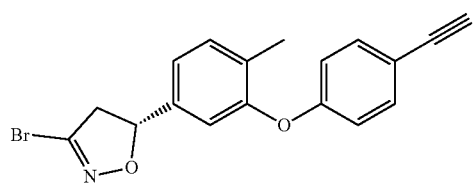 [SMILES: C#Cc1ccc(Oc2cc([C@H]3CC(Br)=NO3)ccc2C)cc1] I-309
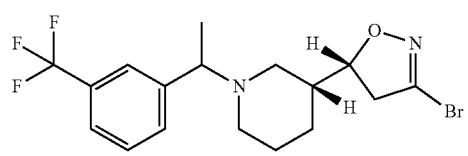 [SMILES: CC(c1cccc(C(F)(F)F)c1)N1CCC[C@@H]([C@H]2CC(Br)=NO2)C1] I-310
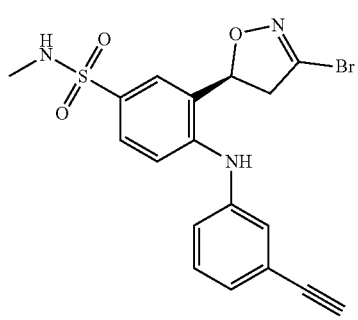 [SMILES: C#Cc1cccc(Nc2ccc(S(=O)(=O)NC)cc2[C@@H]2CC(Br)=NO2)c1] I-311
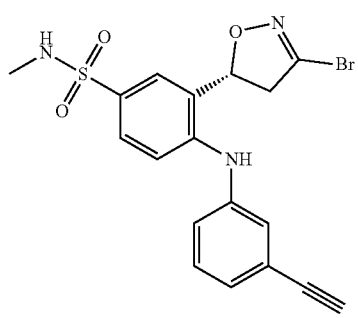 [SMILES: C#Cc1cccc(Nc2ccc(S(=O)(=O)NC)cc2[C@H]2CC(Br)=NO2)c1] I-312

TABLE 1-continued
Exemplary Compounds
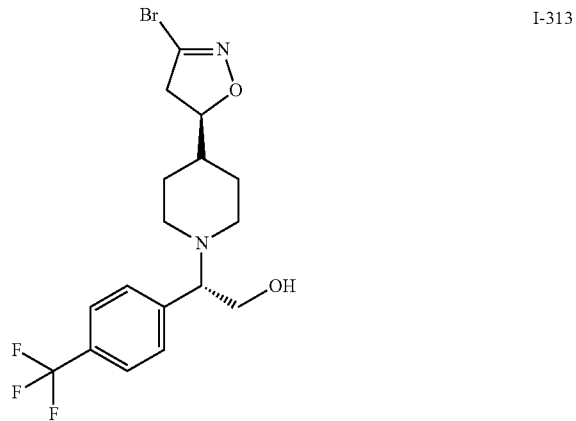
I-313
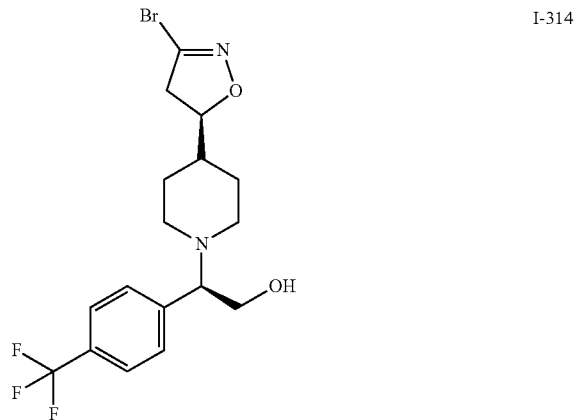
I-314
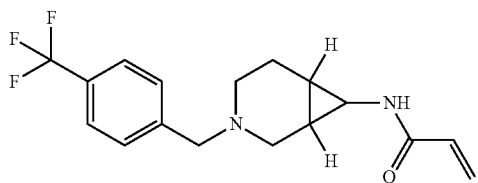 [SMILES: C=CC(=O)NC1C2CCN(Cc3ccc(C(F)(F)F)cc3)CC21]
I-315
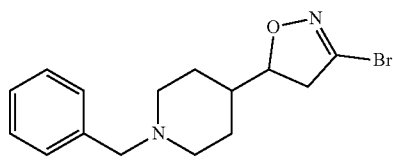 [SMILES: BrC1=NOC(C2CCN(Cc3ccccc3)CC2)C1]
I-316
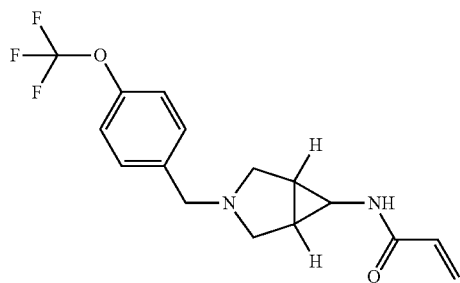 [SMILES: C=CC(=O)NC1C2CN(Cc3ccc(OC(F)(F)F)cc3)CC21]
I-317

TABLE 1-continued
Exemplary Compounds
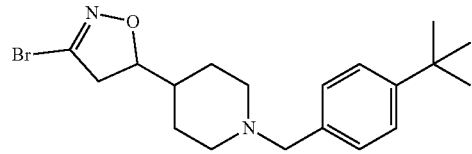 [SMILES: CC(C)(C)c1ccc(CN2CCC(C3CC(Br)=NO3)CC2)cc1] I-318
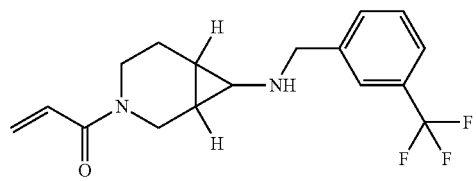 I-320
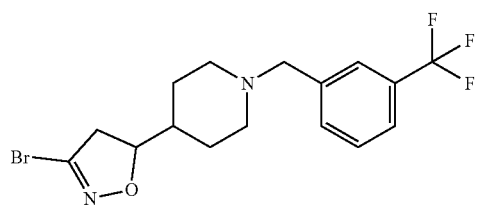 I-321
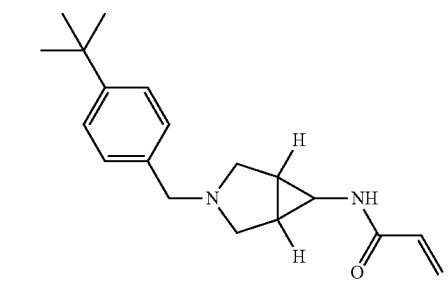 I-322
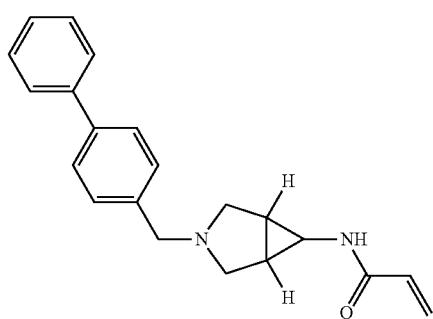 [SMILES: C=CC(=O)NC1C2CN(Cc3ccc(-c4ccccc4)cc3)CC21] I-323
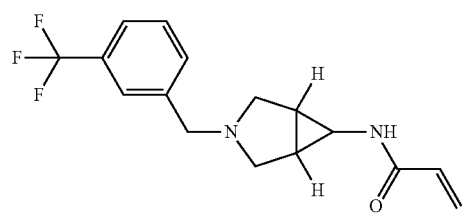 I-324

TABLE 1-continued
Exemplary Compounds
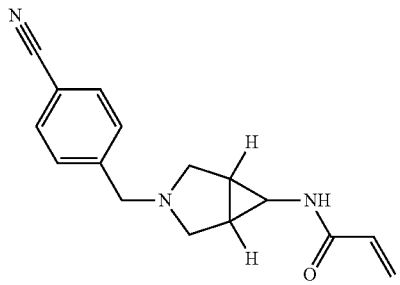 [SMILES: C=CC(=O)NC1C2CN(Cc3ccc(C#N)cc3)CC21] I-325
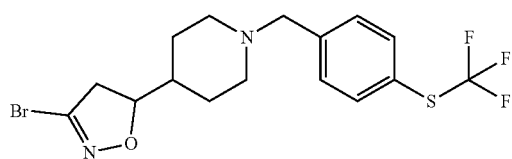 I-326
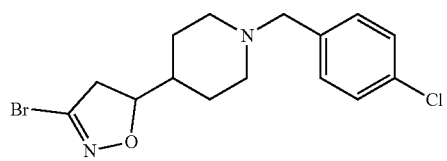 [SMILES: Clc1ccc(CN2CCC(C3CC(Br)=NO3)CC2)cc1] I-327
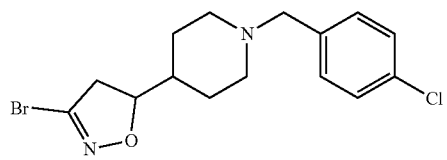 [SMILES: Clc1ccc(CN2CCC(C3CC(Br)=NO3)CC2)cc1] I-328
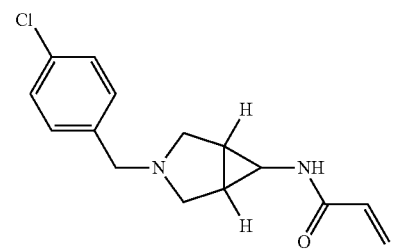 [SMILES: C=CC(=O)NC1C2CN(Cc3ccc(Cl)cc3)CC21] I-329
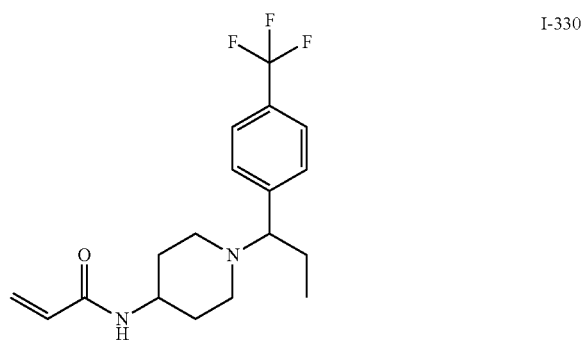 I-330

TABLE 1-continued
Exemplary Compounds
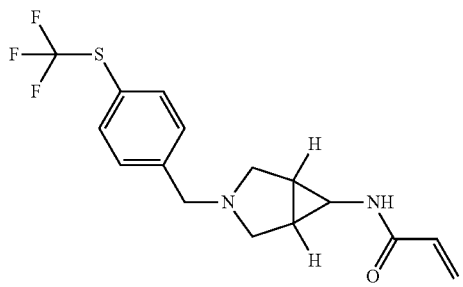 I-331
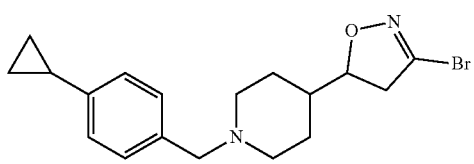 [SMILES: BrC1=NOC(C2CCN(Cc3ccc(C4CC4)cc3)CC2)C1] I-332
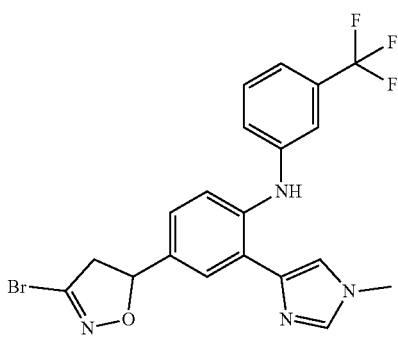 [SMILES: Cn1cnc(-c2cc(C3CC(Br)=NO3)ccc2Nc2cccc(C(F)(F)F)c2)c1] I-333
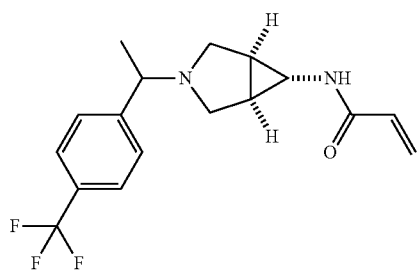 [SMILES: C=CC(=O)N[C@H]1[C@@H]2CN(C(C)c3ccc(C(F)(F)F)cc3)C[C@@H]21] I-334
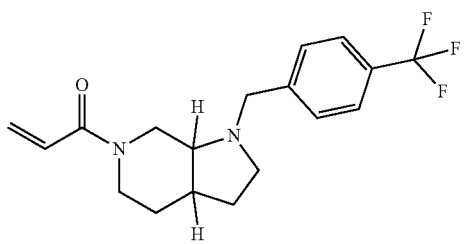 [SMILES: C=CC(=O)N1CCC2CCN(Cc3ccc(C(F)(F)F)cc3)C2C1] I-335
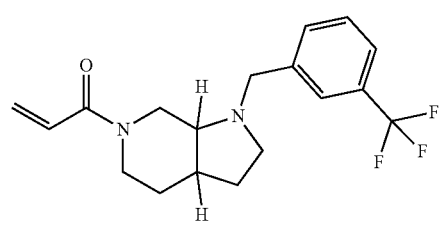 [SMILES: C=CC(=O)N1CCC2CCN(Cc3cccc(C(F)(F)F)c3)C2C1] I-336

TABLE 1-continued
Exemplary Compounds
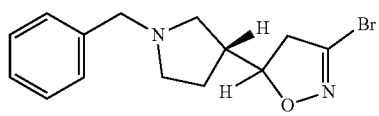 [SMILES: BrC1=NOC([C@@H]2CCN(Cc3ccccc3)C2)C1]
I-337
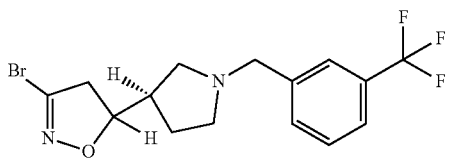
I-338
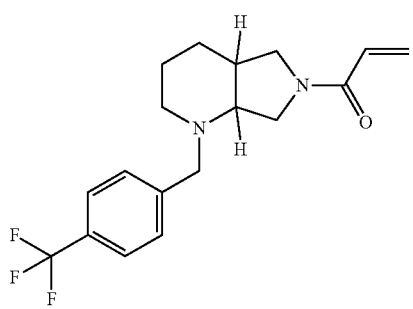
I-339
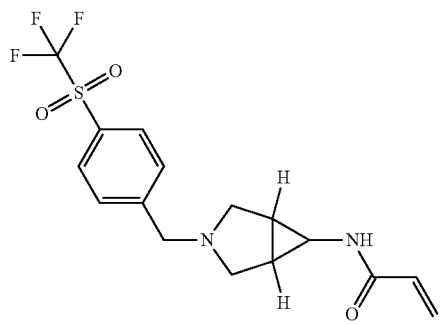 [SMILES: C=CC(=O)NC1C2CN(Cc3ccc(S(=O)(=O)C(F)(F)F)cc3)CC21]
I-340
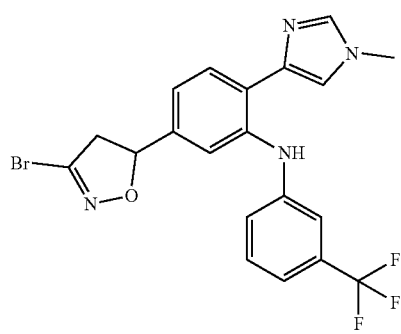
I-341
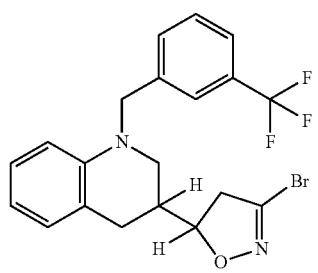 [SMILES: FC(F)(F)c1cccc(CN2CC(C3CC(Br)=NO3)Cc3ccccc32)c1]
I-342

TABLE 1-continued
Exemplary Compounds
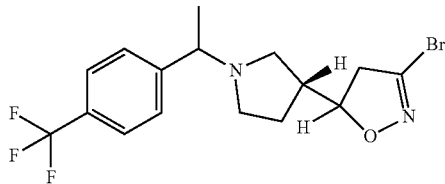 [SMILES: CC(c1ccc(C(F)(F)F)cc1)N1CC[C@@H](C2CC(Br)=NO2)C1]
I-343
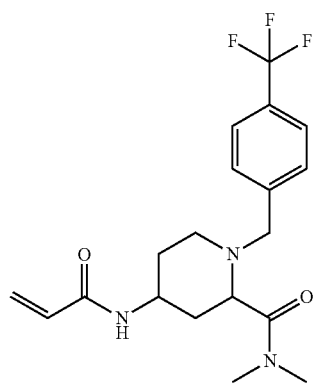 [SMILES: C=CC(=O)NC1CCN(Cc2ccc(C(F)(F)F)cc2)C(C(=O)N(C)C)C1]
I-344
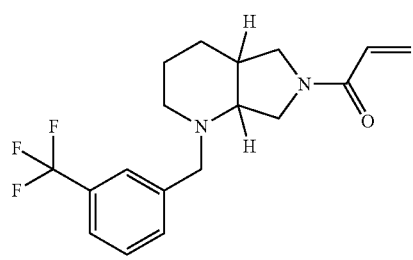 [SMILES: C=CC(=O)N1CC2CCCN(Cc3cccc(C(F)(F)F)c3)C2C1]
I-345
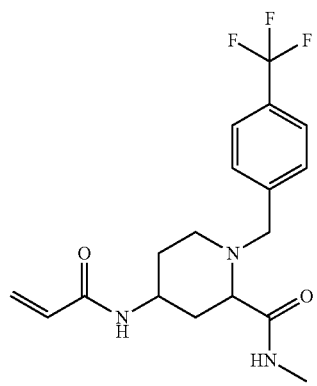 [SMILES: C=CC(=O)NC1CCN(Cc2ccc(C(F)(F)F)cc2)C(C(=O)NC)C1]
I-346

TABLE 1-continued
Exemplary Compounds
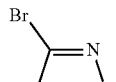
I-347
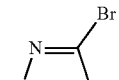
I-348

I-349
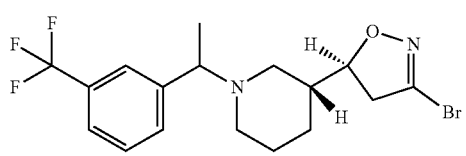 [SMILES: CC(c1cccc(C(F)(F)F)c1)N1CCC[C@@H]([C@@H]2CC(Br)=NO2)C1]
I-350

TABLE 1-continued
Exemplary Compounds
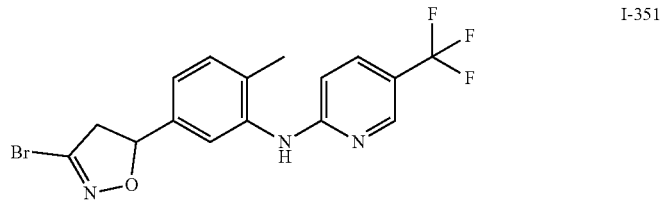
I-351
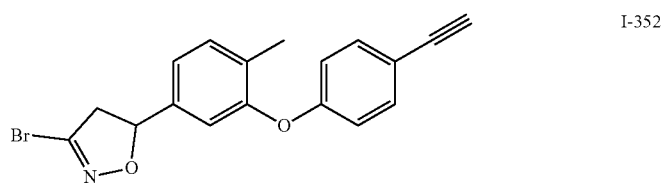
I-352
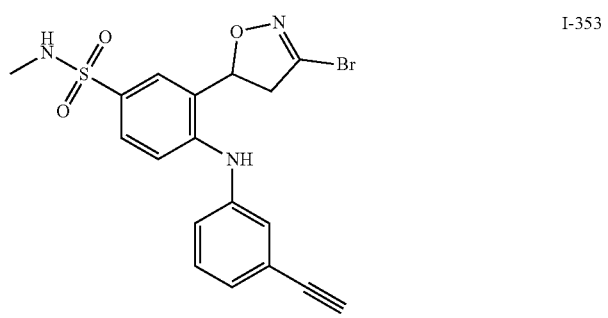
I-353
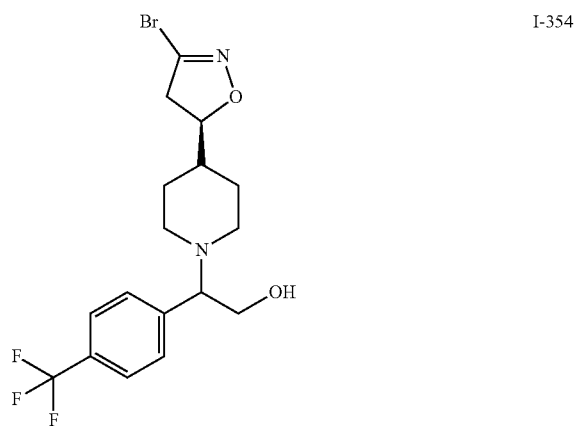
I-354
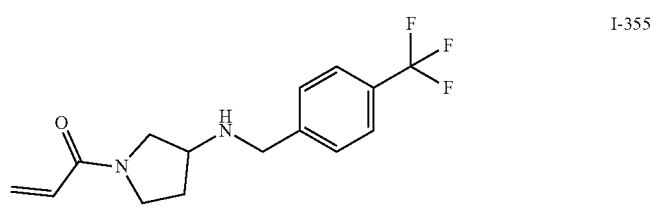
I-355

TABLE 1-continued
Exemplary Compounds
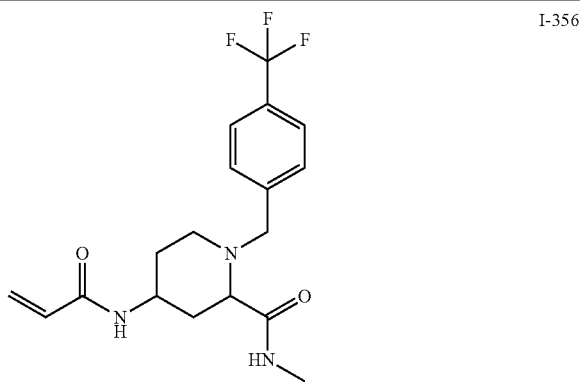
I-356
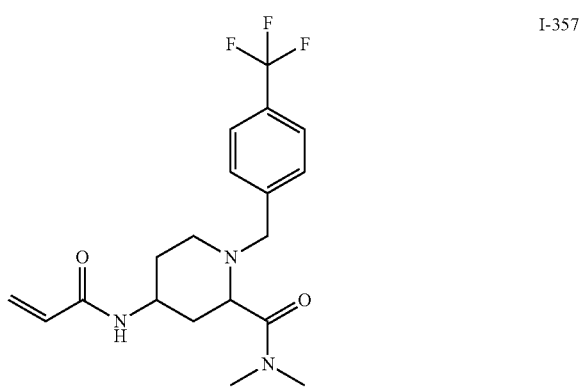
I-357
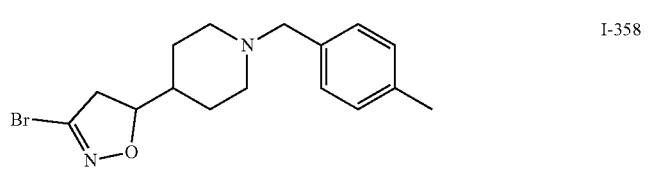
I-358
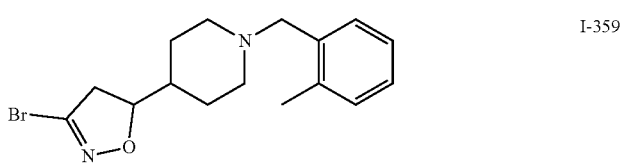
I-359
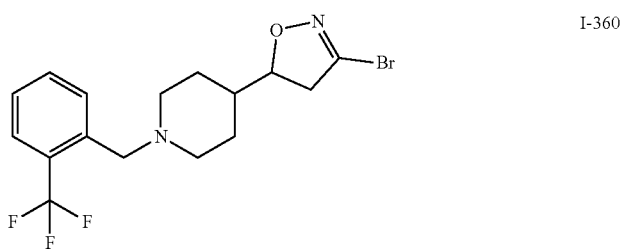
I-360
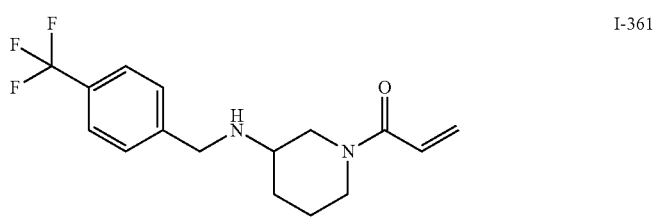
I-361

TABLE 1-continued
| Exemplary Compounds | |
|---|---|
| 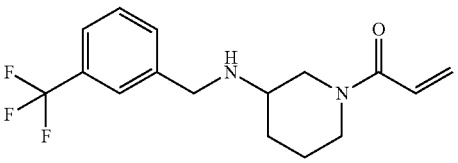 [SMILES: C=CC(=O)N1CCCC(NCc2cccc(C(F)(F)F)c2)C1] | I-362 |
| 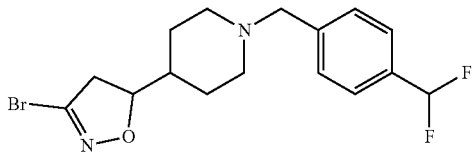 [SMILES: FC(F)c1ccc(CN2CCC(C3CC(Br)=NO3)CC2)cc1] | I-363 |
| 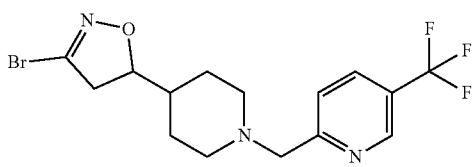 [SMILES: FC(F)(F)c1ccc(CN2CCC(C3CC(Br)=NO3)CC2)nc1] | I-364 |
| 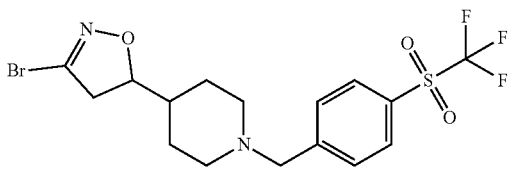 [SMILES: O=S(=O)(c1ccc(CN2CCC(C3CC(Br)=NO3)CC2)cc1)C(F)(F)F] | I-365 |
| 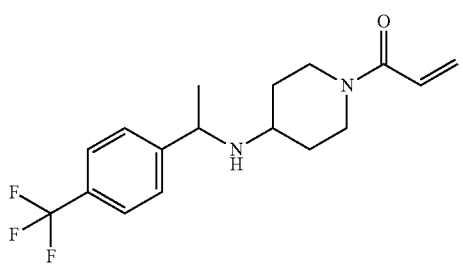 [SMILES: C=CC(=O)N1CCC(NC(C)c2ccc(C(F)(F)F)cc2)CC1] | I-366 |
| 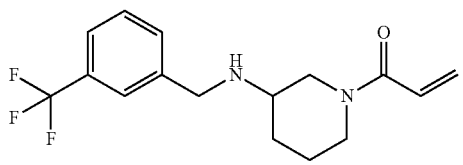 [SMILES: C=CC(=O)N1CCCC(NCc2cccc(C(F)(F)F)c2)C1] | I-367 |
| 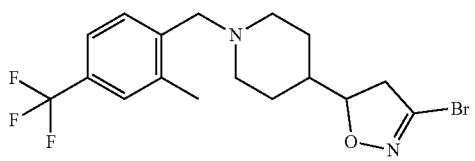 [SMILES: Cc1cc(C(F)(F)F)ccc1CN1CCC(C2CC(Br)=NO2)CC1] | I-368 |
| 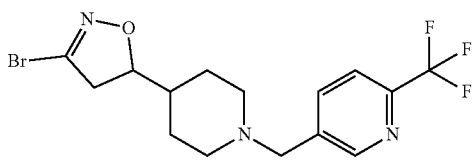 [SMILES: FC(F)(F)c1ccc(CN2CCC(C3CC(Br)=NO3)CC2)cn1] | I-369 |

TABLE 1-continued
Exemplary Compounds
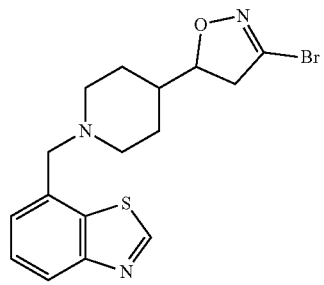 [SMILES: BrC1=NOC(C2CCN(Cc3cccc4ncsc34)CC2)C1] I-370
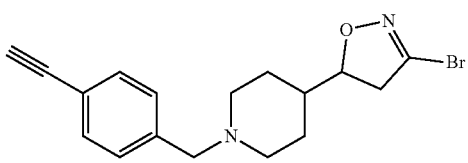 [SMILES: C#Cc1ccc(CN2CCC(C3CC(Br)=NO3)CC2)cc1] I-371
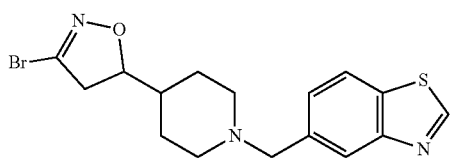 [SMILES: BrC1=NOC(C2CCN(Cc3ccc4scnc4c3)CC2)C1] I-372
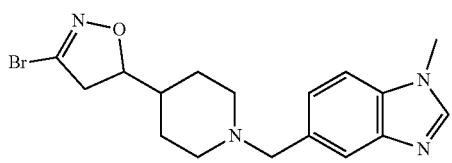 [SMILES: Cn1cnc2cc(CN3CCC(C4CC(Br)=NO4)CC3)ccc21] I-373
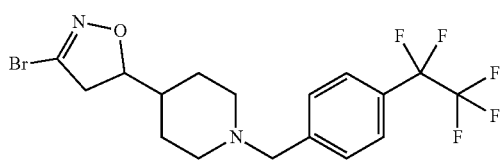 [SMILES: FC(F)(F)C(F)(F)c1ccc(CN2CCC(C3CC(Br)=NO3)CC2)cc1] I-374
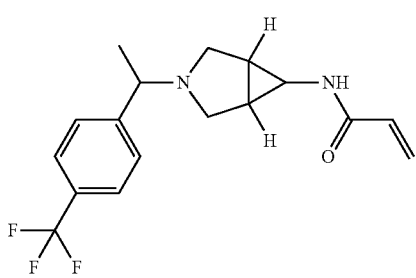 I-375
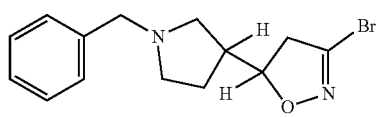 [SMILES: BrC1=NOC(C2CCN(Cc3ccccc3)C2)C1] I-376
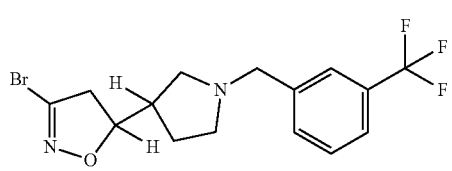 [SMILES: FC(F)(F)c1cccc(CN2CCC(C3CC(Br)=NO3)C2)c1] I-377

TABLE 1-continued
Exemplary Compounds
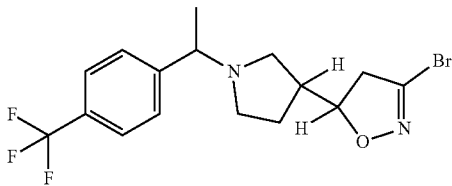 [SMILES: CC(c1ccc(C(F)(F)F)cc1)N1CCC(C2CC(Br)=NO2)C1] I-378
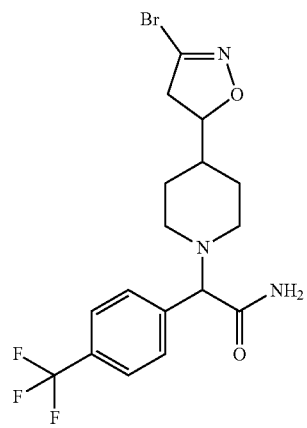 [SMILES: NC(=O)C(c1ccc(C(F)(F)F)cc1)N1CCC(C2CC(Br)=NO2)CC1] I-379
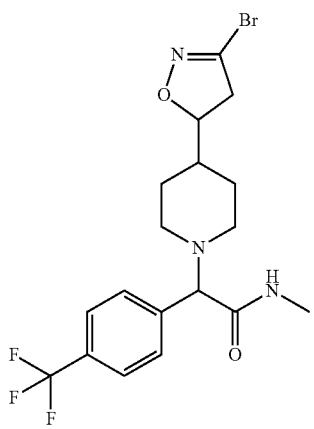 I-380
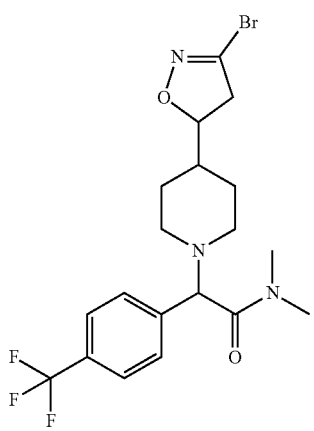 I-381

TABLE 1-continued
Exemplary Compounds
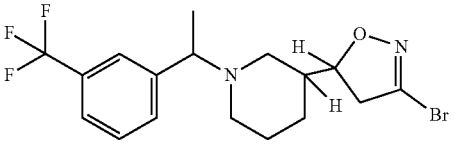 I-382
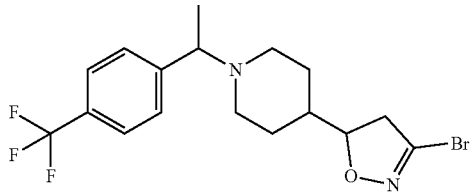 [SMILES: CC(c1ccc(C(F)(F)F)cc1)N1CCC(C2CC(Br)=NO2)CC1] I-385
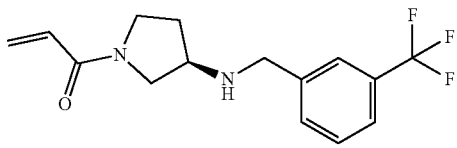 [SMILES: C=CC(=O)N1CC[C@@H](NCc2cccc(C(F)(F)F)c2)C1] I-386
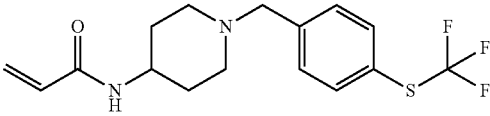 [SMILES: C=CC(=O)NC1CCN(Cc2ccc(SC(F)(F)F)cc2)CC1] I-387
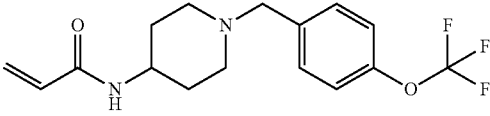 [SMILES: C=CC(=O)NC1CCN(Cc2ccc(OC(F)(F)F)cc2)CC1] I-388
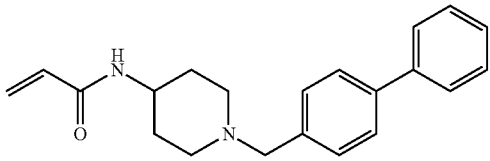 [SMILES: C=CC(=O)NC1CCN(Cc2ccc(-c3ccccc3)cc2)CC1] I-389
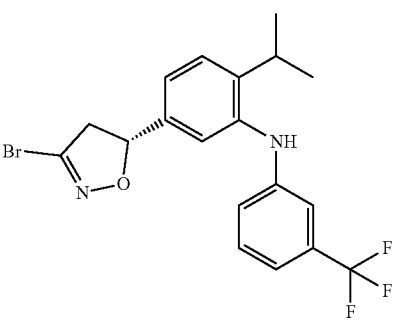 [SMILES: CC(C)c1ccc([C@H]2CC(Br)=NO2)cc1Nc1cccc(C(F)(F)F)c1] I-391
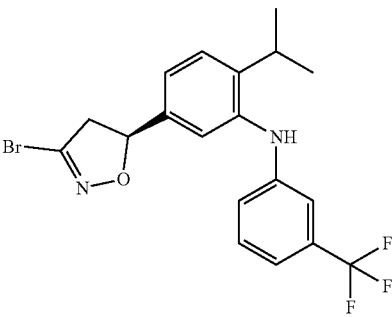 [SMILES: CC(C)c1ccc([C@@H]2CC(Br)=NO2)cc1Nc1cccc(C(F)(F)F)c1] I-392

TABLE 1-continued

Exemplary Compounds

| | |
|---|---|
| [structure] | I-393 |
| [structure] | I-394 |
| [structure] | I-395 |
| [structure] | I-397 |
| [structure] | I-398 |
| [structure] | I-399 |
| [structure] | I-400 |
| [structure] | I-402 |
| [structure] | I-403 |

TABLE 1-continued
Exemplary Compounds
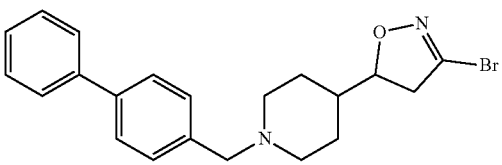 [SMILES: BrC1=NOC(C2CCN(Cc3ccc(-c4ccccc4)cc3)CC2)C1]
I-404
In some embodiments, the present invention provides a compound set forth in Table 1, above, or a pharmaceutically acceptable salt thereof.
In some embodiments, a compound of the present invention is not a compound selected from:
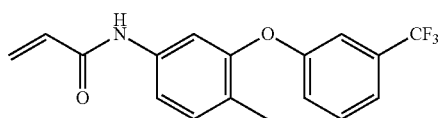
P-1
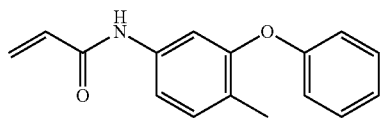
P-2
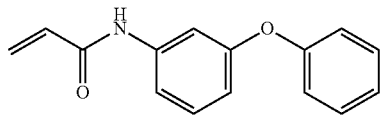
P-3
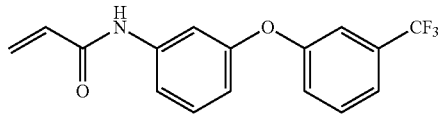
P-4
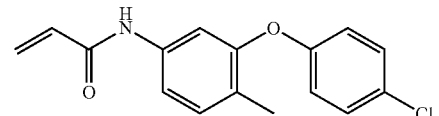
P-5
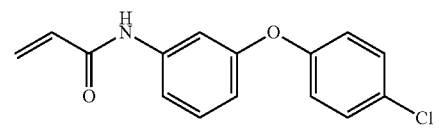
P-6
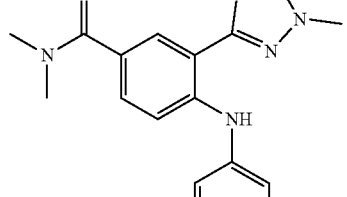
P-7
-continued
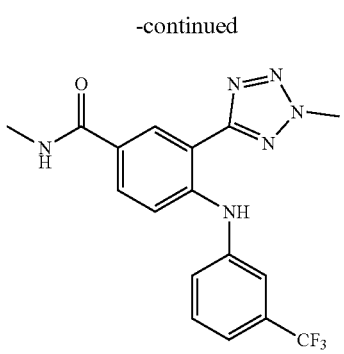
P-8
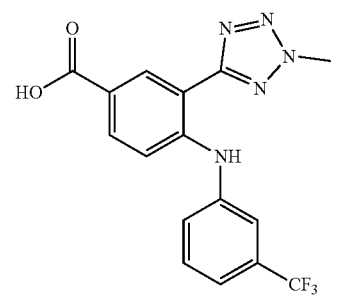
P-9
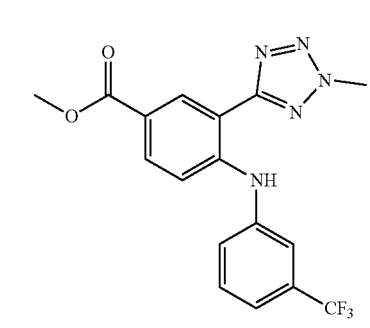
P-10
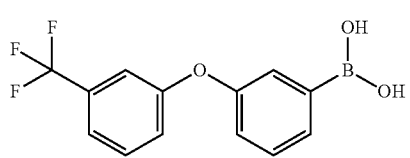
P-11

-continued

P-12 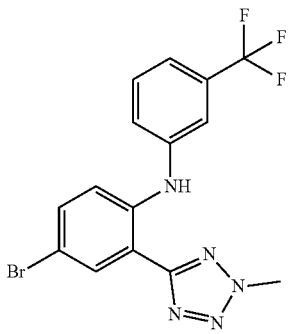

P-13 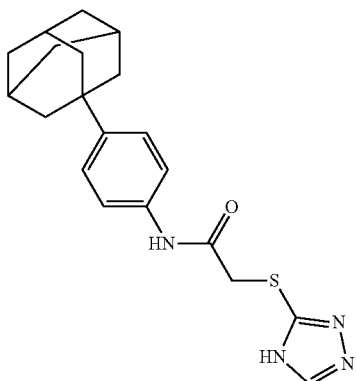

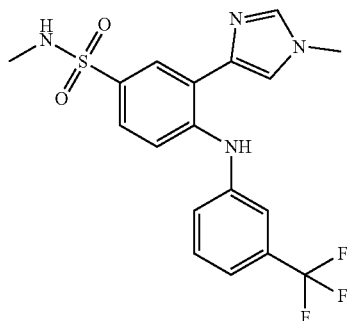

P-14 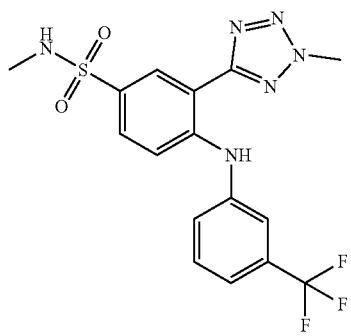

P-15 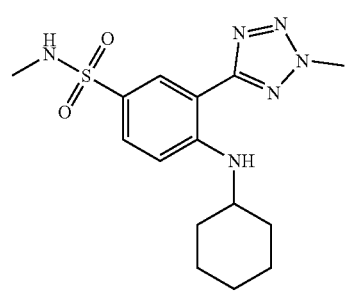

P-16 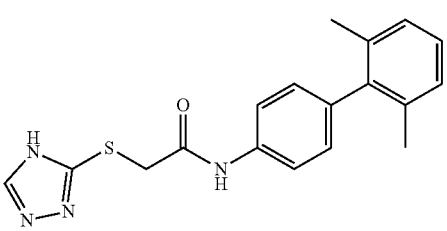

P-17

The compounds of this invention can be prepared or isolated in general by synthetic and/or semi-synthetic methods known to those skilled in the art for analogous compounds and by methods described in detail in the Examples, herein. In some embodiments, the present invention provides an intermediate compound described in the Examples, or a salt thereof.

4. Uses, Formulation and Administration

Pharmaceutically Acceptable Compositions

According to another embodiment, the invention provides a pharmaceutical composition comprising a compound of this invention or a pharmaceutically acceptable derivative thereof and a pharmaceutically acceptable carrier, adjuvant, or vehicle. The amount of compound in compositions of this invention is such that is effective to measurably inhibit TEAD, or a variant or mutant thereof, in a biological sample or in a patient. In certain embodiments, the amount of compound in compositions of this invention is such that is effective to measurably inhibit TEAD, or a variant or mutant thereof, in a biological sample or in a patient. In certain embodiments, a composition of this invention is formulated for administration to a patient in need of such composition. In some embodiments, a composition of this invention is formulated for oral administration to a patient.

The terms "patient" or "subject" as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of TEAD, or a variant or mutant thereof.

Compositions of the present invention can be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention cancan be aqueous or oleaginous suspension. These suspensions cancan be formulated according to techniques known in the art using suitable dispersing or wetting agents and suspending agents. The sterile injectable preparation cancan also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium.

For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms can also be used for the purposes of formulation.

Pharmaceutically acceptable compositions of this invention can be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Alternatively, pharmaceutically acceptable compositions of this invention can be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For topical applications, provided pharmaceutically acceptable compositions can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations can be administered with or without food. In some embodiments, pharmaceutically acceptable compositions of this invention are administered without food. In other embodiments, pharmaceutically acceptable compositions of this invention are administered with food.

The amount of compounds of the present invention that can be combined with the carrier materials to produce a composition in a single dosage form varies depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient depends upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition also depends upon the particular compound in the composition.

Uses of Compounds and Pharmaceutically Acceptable Compositions

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional co-activator with PDZ-binding motif (TAZ; also known as WWTR1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST1/2 (homologues of Hippo/Hpo in *Drosophila*), Lats1/2 (homologues of Warts/Wts), and their adaptor proteins Sav1 (homologue of Salvador/Sav) and Mob (MOBKL1A and MOBKL1B; homologues of Mats), respectively. In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] consensus motifs. YAP comprises five [HXRXXS] consensus motifs, wherein X denotes any amino acid residue. In some instances, Lats1/2 phosphorylates YAP at one or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ primes both proteins for further phosphorylation events by CK1δ/ε in the degradation motif, which then signals for interaction with the β-TRCP E3 ubiquitin ligase, leading to polyubiquitination and degradation of YAP.

In some instances, Lats1/2 phosphorylates TAZ at the [HXRXXS] consensus motifs. TAZ comprises four [HXRXXS] consensus motifs, wherein X denotes any amino acid residues. In some instances, Lats1/2 phosphorylates TAZ at one or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cyto-plasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes $SCF^{\beta-TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g., Cdc4), Skp1, a bridging protein, and RBX1, which contains a small RING Finger domain which interacts with E2-ubiquitin conjugating enzyme. In some cases, the F-box family comprises more than 40 members, in which exemplary members include F-box/WD repeat-containing protein 1A (FBXW1A, βTrCP1, Fbxwl, hsSlimb, plkappaBalpha-E3 receptor subunit) and S-phase kinase-associated proteins 2 (SKP2). In some embodiments, the SCF complex (e.g., $SCF^{\beta TrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, UBA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE20, UBE2Q1, UBE2Q2, UBE2R1, UBE2R2, UBE2S, UBE2T, UBE2U, UBE2V1, UBE2V2, UBE2Z, ATG2, BIRC5, and UFC1. In some embodiments, the ubiquitinated YAP/TAZ further undergoes the degradation process through the 26S proteasome.

In some embodiments, the Hippo pathway is regulated upstream by several different families of regulators. In some instances, the Hippo pathway is regulated by the G-protein and its coupled receptors, the Crumbs complex, regulators upstream of the MST kinases, and the adherens junction.

YAP/TAZ Interaction with TEAD

In some embodiments, un-phosphorylated and/or dephosphorylated YAP/TAZ accumulates in the nucleus. Within the nucleus, YAP/TAZ interacts with the TEAD family of transcription factors (e.g., human TEAD1 (UniProt KB ID P28347-1 (SEQ ID NO: 1)), human TEAD2 (UniProtKB ID Q15562 (SEQ ID NO: 2)), human TEAD3 (UniProtKB ID Q99594 (SEQ ID NO: 3)), and human TEAD4 (UniProtKB ID Q15561 (SEQ ID NO: 4)) to activate genes involved in anti-apoptosis and proliferation, such as, for example, CTFG, Cyr61, and FGF1.

Proteomic and biochemical studies have shown that the TEAD (TEA Domain) transcription factors are palmitoylated at evolutionarily conserved cysteine residues. Three cysteine residues were found that are evolutionarily conserved and mutated to serine in human TEAD1 (C53S, C327S and C359S) to test whether the mutation affects TEAD1 palmitoylation. The C359S mutant showed the greatest loss of palmitoylation, and C327S and C53S also showed decreased palmitoylation. These results suggest that C359 plays a critical role in TEAD1 palmitoylation. Furthermore, combination mutation of all three cysteine residues, C53/327/359S (3CS), completely ablated TEAD1 palmitoylation, indicating that these residues are involved in TEAD1 palmitoylation. It has been found that TEADs undergo PAT-independent autopalmitoylation, under physiological concentrations of palmitoyl-CoA. Furthermore, autopalmitoylation plays critical roles in regulating TEAD-YAP association and their physiological functions in vitro and in vivo. Chan, et al. Nature Chem. Biol. 12, pages 282-289 (2016); Noland, et al. Structure, 24, 1-8 (2016); Gibault et al. J. Med. Chem. 61, 5057-5072 (2018). Therefore, palmitoylation of TEADs play important roles in regulating Hippo pathway transcriptional complexes.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

In some embodiments, the compounds described herein irreversibly inhibit a TEAD transcription factor. In some embodiments, the transcription factor is TEAD1. In some embodiments, the transcription factor is TEAD2. In some embodiments, the transcription factor is TEAD3. In some embodiments, the transcription factor is TEAD4. In some embodiments, the compounds described herein covalently bind to the TEAD transcription factor (e.g., TEAD1, TEAD2, TEAD3, or TEAD4). In some embodiments, the compounds described herein irreversibly inhibit the activity of a TEAD transcription factor (e.g., TEAD1, TEAD2, TEAD3, or TEAD4). In some embodiments, the compounds described herein covalently inhibit the activity of a TEAD transcription factor (e.g., TEAD1, TEAD2, TEAD3, and/or TEAD4).

In some embodiments, the compounds disclosed herein bind to TEAD1 and disrupt or inhibit the interaction between YAP and TEAD1. In some embodiments, the compounds disclosed herein bind to TEAD2 and disrupt or inhibit the interaction between YAP and TEAD2. In some embodiments, the compounds disclosed herein bind to TEAD3 and disrupt or inhibit the interaction between YAP and TEAD3. In some embodiments, the compounds disclosed herein bind to TEAD4 and disrupt or inhibit the interaction between YAP and TEAD4.

In some embodiments, the compounds disclosed herein bind to TEAD1 and disrupt or inhibit the interaction between YAP and TEAD1. In some embodiments, the compounds disclosed herein bind to TEAD1 at C359, and disrupt or inhibit the interaction between YAP and TEAD1. In some embodiments, the compounds disclosed herein bind to TEAD1 at C53, and disrupt or inhibit the interaction between YAP and TEAD1. In some embodiments, the compounds disclosed herein bind to TEAD1 at C327, and disrupt or inhibit the interaction between YAP and TEAD1. In some embodiments, the compounds disclosed herein bind to TEAD1 at C405, and disrupt or inhibit the interaction between YAP and TEAD1. In some embodiments, the compounds disclosed herein bind to TEAD1 at C359 and C327, and disrupt or inhibit the interaction between YAP and TEAD1. In some embodiments, the compounds disclosed herein bind to TEAD1 at C359 and C53, and disrupt or inhibit the interaction between YAP and TEAD1. In some embodiments, the compounds disclosed herein bind to TEAD1 at C53 and C327, and disrupt or inhibit the interaction between YAP and TEAD1. In some embodiments, the compounds disclosed herein bind to TEAD1 at C359 and C405, and disrupt or inhibit the interaction between YAP and TEAD1. In some embodiments, the compounds disclosed herein bind to TEAD1 at C53 and C405, and disrupt or inhibit the interaction between YAP and TEAD1. In some embodiments, the compounds disclosed herein bind to TEAD1 at C327 and C405, and disrupt or inhibit the interaction between YAP and TEAD1. In some embodiments, the compounds disclosed herein bind to TEAD1 at C359, C327, and C53, and disrupt or inhibit the interaction between YAP and TEAD1. In some embodiments, the compounds disclosed herein bind to TEAD1 at C359, C327, and C405, and disrupt or inhibit the interaction between YAP and TEAD1. In some embodiments, the compounds disclosed herein bind to TEAD1 at C359, C353, and C405, and disrupt or inhibit the interaction between YAP and TEAD1. In some embodiments, the compounds disclosed herein bind to TEAD1 at C327, C53, and C405, and disrupt or inhibit the interaction between YAP and TEAD1. In some embodiments, the compounds disclosed herein bind to TEAD1 at C359, C327, C53, and C405, and disrupt or inhibit the interaction between YAP and TEAD1.

In some embodiments, the compounds disclosed herein bind to TEAD, prevent TEAD palmitoylation, and disrupt or inhibit the interaction between YAP and TEAD. In some embodiments, the compounds disclosed herein bind to TEAD1 and prevent TEAD1 palmitoylation. In some embodiments, the compounds disclosed herein bind to TEAD1 and prevent TEAD1 palmitoylation at C359. In some embodiments, the compounds disclosed herein bind to TEAD1 and prevent TEAD1 palmitoylation at C53. In some embodiments, the compounds disclosed herein bind to TEAD1 and prevent TEAD1 palmitoylation at C327. In some embodiments, the compounds disclosed herein bind to TEAD1 and prevent TEAD1 palmitoylation at C405. In some embodiments, the compounds disclosed herein bind to TEAD1 and prevent TEAD1 palmitoylation at C359 and C327. In some embodiments, the compounds disclosed herein bind to TEAD1 and prevent TEAD1 palmitoylation at C359 and C53. In some embodiments, the compounds disclosed herein bind to TEAD1 and prevent TEAD1 palmitoylation at C53 and C327. In some embodiments, the compounds disclosed herein bind to TEAD1 and prevent TEAD1 palmitoylation at C359 and C405. In some embodiments, the compounds disclosed herein bind to TEAD1 and prevent TEAD1 palmitoylation at C53 and C405. In some embodiments, the compounds disclosed herein bind to TEAD1 and prevent TEAD1 palmitoylation at C327 and C405. In some embodiments, the compounds disclosed herein bind to TEAD1 and prevent TEAD1 palmitoylation at C359, C327, and C53. In some embodiments, the compounds disclosed herein bind to TEAD1 and prevent TEAD1 palmitoylation at C359, C327, and C405. In some embodiments, the compounds disclosed herein bind to TEAD1 and prevent TEAD1 palmitoylation at C359, C353, and C405. In some embodiments, the compounds disclosed herein bind to TEAD1 and prevent TEAD1 palmitoylation at C327, C53, and C405. In some embodiments, the compounds disclosed herein bind to TEAD1 and prevent TEAD1 palmitoylation at C359, C327, C53, and C405.

In some embodiments, the compounds disclosed herein bind to TEAD1, prevent TEAD1 palmitoylation, and disrupt or inhibit the interaction between YAP and TEAD1. In some embodiments, the compounds disclosed herein bind to TEAD1 and prevent TEAD1 palmitoylation at C359, and disrupt or inhibit the interaction between YAP and TEAD1. In some embodiments, the compounds disclosed herein bind to TEAD1 and prevent TEAD1 palmitoylation at C53, and disrupt or inhibit the interaction between YAP and TEAD1. In some embodiments, the compounds disclosed herein bind to TEAD1 and prevent TEAD1 palmitoylation at C327, and disrupt or inhibit the interaction between YAP and TEAD1. In some embodiments, the compounds disclosed herein bind to TEAD1 and prevent TEAD1 palmitoylation at C405, and disrupt or inhibit the interaction between YAP and TEAD1. In some embodiments, the compounds disclosed herein bind to TEAD1 and prevent TEAD1 palmitoylation at C359 and C327, and disrupt or inhibit the interaction between YAP and TEAD1. In some embodiments, the compounds disclosed herein bind to TEAD1 and prevent TEAD1 palmitoylation at C359 and C53, and disrupt or inhibit the interaction between YAP and TEAD1. In some embodiments, the compounds disclosed herein bind to TEAD1 and prevent TEAD1 palmitoylation at C53 and C327, and disrupt or inhibit the interaction between YAP and TEAD1. In some embodiments, the compounds disclosed herein bind to TEAD1 and prevent TEAD1 palmitoylation at C359 and C405, and disrupt or inhibit the interaction between YAP and TEAD1. In some embodiments, the compounds disclosed herein bind to TEAD1 and prevent TEAD1 palmitoylation at C53 and C405, and disrupt or inhibit the interaction between YAP and TEAD1. In some embodiments, the compounds disclosed herein bind to TEAD1 and prevent TEAD1 palmitoylation at C327 and C405, and disrupt or inhibit the interaction between YAP and TEAD1. In some embodiments, the compounds disclosed herein bind to TEAD1 and prevent TEAD1 palmitoylation at C359, C327, and C53, and disrupt or inhibit the interaction between YAP and TEAD1. In some embodiments, the compounds disclosed herein bind to TEAD1 and prevent TEAD1 palmitoylation at C359, C327, and C405, and disrupt or inhibit the interaction between YAP and TEAD1. In some embodiments, the compounds disclosed herein bind to TEAD1 and prevent TEAD1 palmitoylation at C359, C353, and C405, and disrupt or inhibit the interaction between YAP and TEAD1. In some embodiments, the compounds disclosed herein bind to TEAD1 and prevent TEAD1 palmitoylation at C327, C53, and C405, and disrupt or inhibit the interaction between YAP and TEAD1. In some embodiments, the compounds disclosed herein bind to TEAD1 and prevent TEAD1 palmitoylation at C359, C327, C53, and C405, and disrupt or inhibit the interaction between YAP and TEAD1.

In some embodiments, the compounds disclosed herein bind to TEAD2 at C380, and disrupt or inhibit the interaction between YAP and TEAD2.

In some embodiments, the compounds disclosed herein bind to TEAD2 and prevent TEAD2 palmitoylation. In some embodiments, the compounds disclosed herein bind to TEAD2 and prevent TEAD2 palmitoylation at C380.

In some embodiments, the compounds disclosed herein bind to TEAD2, prevent TEAD2 palmitoylation, and disrupt or inhibit the interaction between YAP and TEAD2. In some embodiments, the compounds disclosed herein bind to TEAD2 and prevent TEAD2 palmitoylation at C380, and disrupt or inhibit the interaction between YAP and TEAD2.

In some embodiments, the compounds disclosed herein bind to TEAD3 at C371, and disrupt or inhibit the interaction between YAP and TEAD3. In some embodiments, the compounds disclosed herein bind to TEAD3 at C368, and disrupt or inhibit the interaction between YAP and TEAD3. In some embodiments, the compounds disclosed herein bind to TEAD3 at C371 and C368, and disrupt or inhibit the interaction between YAP and TEAD3.

In some embodiments, the compounds disclosed herein bind to TEAD3 and prevent TEAD3 palmitoylation. In some embodiments, the compounds disclosed herein bind to TEAD3 and prevent TEAD3 palmitoylation at C371. In some embodiments, the compounds disclosed herein bind to TEAD3 and prevent TEAD3 palmitoylation at C368. In some embodiments, the compounds disclosed herein bind to TEAD3 and prevent TEAD3 palmitoylation at C368 and C371.

In some embodiments, the compounds disclosed herein bind to TEAD3, prevent TEAD3 palmitoylation, and disrupt or inhibit the interaction between YAP and TEAD3. In some embodiments, the compounds disclosed herein bind to TEAD3 and prevent TEAD3 palmitoylation at C371, and disrupt or inhibit the interaction between YAP and TEAD3. In some embodiments, the compounds disclosed herein bind to TEAD3 and prevent TEAD3 palmitoylation at C368, and disrupt or inhibit the interaction between YAP and TEAD3. In some embodiments, the compounds disclosed herein bind to TEAD3 and prevent TEAD3 palmitoylation at C371 and C368, and disrupt or inhibit the interaction between YAP and TEAD3.

In some embodiments, the compounds disclosed herein bind to TEAD4 at C367, and disrupt or inhibit the interaction between YAP and TEAD4.

In some embodiments, the compounds disclosed herein bind to TEAD4 and prevent TEAD4 palmitoylation. In some embodiments, the compounds disclosed herein bind to TEAD4 and prevent TEAD4 palmitoylation at C367.

In some embodiments, the compounds disclosed herein bind to TEAD4, prevent TEAD4 palmitoylation, and disrupt or inhibit the interaction between YAP and TEAD4. In some embodiments, the compounds disclosed herein bind to TEAD4 and prevent TEAD4 palmitoylation at C367, and disrupt or inhibit the interaction between YAP and TEAD4.

YAP/TAZ Regulation Mediated by G-Proteins/GPCRs

In some embodiments, the Hippo pathway is regulated by the G protein-coupled receptor (GPCR) and G protein (also known as guanine nucleotide-binding proteins) family of proteins. G proteins are molecular switches that transmit extracellular stimuli into the cell through GPCRs. In some instances, there are two classes of G proteins: monomeric small GTPases and heterotrimeric G protein complexes. In some instances, the latter class of complexes comprise of alpha ($G_\alpha$), beta ($G_\beta$), and gamma ($G_\gamma$) subunits. In some cases, there are several classes of $G_\alpha$ subunits: $G_{q/11}\alpha$, $G_{12/13}\alpha$, $G_{i/o}\alpha$ (G inhibitory, G other), and $G_s\alpha$ (G stimulatory).

In some instances, $Gi\alpha$ (G inhibitory), $G_o\alpha$ (G other), $G_q/11\alpha$, and $G12/13\alpha$ coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s\alpha$, in some embodiments, induces Lats1/2 activity, thereby promoting YAP/TAZ degradation.

$G_q$ Family $G_q\alpha$ (also known as $G_{q/11}$ protein), participates in the inositol trisphosphate ($IP_3$) signal transduction pathway and calcium ($Ca^{2+}$) release from intracellular storage through the activation of phospholipase C (PLC). The activated PLC hydrolyzes phosphatidylinositol 4,5-bisphosphate ($PIP_2$) to diacyl glycerol (DAG) and $IP_3$. In some instances, $IP_3$ then diffuses through the cytoplasm into the ER or the sarcoplasmic reticulum (SR) in the case of muscle cells, and then binds to inositol trisphosphate receptor (InsP3R), which is a $Ca^{2+}$ channel. In some cases, the binding triggers the opening of the $Ca^{2+}$ channel, and thereby increases the release of $Ca^{2+}$ into the cytoplasm.

In some embodiments, the GPCRs that interact with $G_q\alpha$ include, but are not limited to, 5-hydroxytryptamine receptor (5-HT receptor) types $5-HT_2$ and $5-HT_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors $M_1$, $M_3$, and $M_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q\alpha$ genes have been associated with cancer. Indeed, studies have shown that mutations in $G_q\alpha$ promote uveal melanoma (UM) tumorigenesis. In some instances, about 80% of UM cases have been detected to contain a mutation in GNAQ and/or GNA11.

In some instances, mutations or modifications of the $G_q\alpha$ genes have been associated with congenital diseases. In some instances, mutations of $G_q\alpha$ have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

G12/13 Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g., Rho family such as Cdc42), which is involved in cell differentiation, proliferation, cytoskeletal organization, vesicle trafficking, and nuclear transport.

In some embodiments, the GPCRs that interact with $G_{12/13}\alpha$ include, but are not limited to, purinergic receptors (e.g., $P2Y_1$, $P2Y_2$, $P2Y_4$, $P2Y_6$); muscarinic acetylcholine receptors M1 and M3; receptors for thrombin [protease-activated receptor (PAR)-1, PAR-2]; thromboxane (TXA2); sphingosine 1-phosphate (e.g., $S1P_2$, $S1P_3$, $S1P_4$ and $S1P_5$); lysophosphatidic acid (e.g., $LPA_1$, $LPA_2$, $LPA_3$); angiotensin II (AT1); serotonin ($5-HT_{2c}$ and $5-HT_4$); somatostatin ($sst_5$); endothelin ($ET_A$ and $ET_B$); cholecystokinin ($CCK_1$); $V_{1a}$ vasopressin receptors; $D_5$ dopamine receptors; fMLP formyl peptide receptors; $GAL_2$ galanin receptors; $EP_3$ prostanoid receptors; $A_1$ adenosine receptors; $\alpha_1$ adrenergic receptors; $BB_2$ bombesin receptors; $B_2$ bradykinin receptors; calcium-sensing receptors; KSHV-ORF74 chemokine receptors; $NK_1$ tachykinin receptors; and thyroid-stimulating hormone (TSH) receptors.

In some instances, $G_{12/13}\alpha$ is further subdivided into $G_{12}$ and $G_{13}$ types which are encoded by GNA12 and GNA13, respectively.

$G_{i/O}$ Family $G_{i/O}\alpha$ (G inhibitory, G other) (also known as $G_i/G_o$ or $G_i$ protein) suppresses the production of 3', 5'-cyclic AMP (cAMP) from adenosine triphosphate (ATP) through an inhibition of adenylate cyclase activity, which converts ATP to cAMP.

In some embodiments, the GPCRs that interact with $G_{i\alpha}$ include, but are not limited to, 5-hydroxytryptamine receptor (5-HT receptor) types $5-HT_1$ and $5-HT_5$; muscarinic acetylcholine receptors such as $M_2$ and $M_4$; adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as δ, κ, μ, and nociceptin receptors; prostaglandin receptors such as prostaglandin E receptor 1 ($EP_1$), prostaglandin E receptor 3 ($EP_3$), prostaglandin F receptor (FP), and thromboxane receptor (TP); somatostatin receptors $sst_1$, $sst_2$, $sst_3$, $sst_4$, and $sst_5$; and trace amine-associated receptor 8.

In some instances, there are several types of $G_i\alpha$: $G_i\alpha 1$, $G_i\alpha 2$, $G_i\alpha 3$, $G_i\alpha 4$, $G_o\alpha$, $G_t$, $G_{gust}$, and $G_z$. $G_i\alpha 1$ is encoded by GNAI1. $G_i\alpha 2$ is encoded by GNAI2. $G_i\alpha 3$ is encoded by GNAI3. $G_o\alpha$, the $\alpha_o$ subunit, is encoded by GNAO1. $G_t$ is encoded by GNAT1 and GNAT2. $G_{gust}$ is encoded by GNAT3. $G_z$ is encoded by GNAZ.

$G_s$ Family $G_s\alpha$ (also known as G stimulatory, $G_s$ alpha subunit, or $G_s$ protein) activates the cAMP-dependent pathway through the activation of adenylate cyclase, which convers adenosine triphosphate (ATP) to 3',5'-cyclic AMP (cAMP) and pyrophosphate. In some embodiments, the GPCRs that interact with $G_s\alpha$ include, but are not limited to, 5-hydroxytryptamine receptor (5-HT receptor) types $5-HT_4$, $5-HT_6$, and $5-HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $\beta_1$, $\beta_2$, and $\beta_3$; calcitonin receptor; calcitonin gene-related peptide receptor; corticotropin-releasing hormone receptor; dopamine receptor D1-like family receptors such as $D_1$ and $D_5$; follicle-stimulating hormone receptor (FSH-receptor); gastric inhibitory polypeptide receptor; glucagon receptor; histamine $H_2$ receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein a-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dig), KIBRA, PTPN14, NPHP3, LKB1, Ajuba, and ZO1/2.

In some embodiments, the compounds described herein are inhibitors of transcriptional coactivator with PDZ binding motif/Yes-associated protein transcriptional coactivator (TAZ/YAP). In some embodiments, the compounds described herein increase the phosphorylation of transcriptional coactivator with PDZ binding motif/Yes-associated protein transcriptional coactivator (TAZ/YAP) or decrease the dephosphorylation of transcriptional coactivator with PDZ binding motif/Yes-associated protein transcriptional coactivator (TAZ/YAP). In some embodiments, the compounds increase the ubiquitination of transcriptional coactivator with PDZ binding motif/Yes-associated protein transcriptional coactivator (TAZ/YAP) or decrease the deubiquitination of transcriptional coactivator with PDZ binding motif/Yes-associated protein transcriptional coactivator (TAZ/YAP).

In some embodiments, the compounds disclosed herein are inhibitors of one or more of the proteins encompassed by, or related to, the Hippo pathway. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha1$, $G_i\alpha2$, $G_i\alpha3$, $G_i\alpha4$, $G_o\alpha$, $G_t$, $G_{gust}$, and $G_z$. In some embodiments, an inhibitor of the Hippo pathway is an inhibitor of $G_q$. In some embodiments, an inhibitor of the Hippo pathway is an inhibitor of $G_{q/11}$. In some embodiments, an inhibitor of the Hippo pathway is an inhibitor of $G_{q/14}$. In some embodiments, an inhibitor of the Hippo pathway is an inhibitor of $G_{q/15}$. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha1$. In some embodiments, an inhibitor of the Hippo pathway is an inhibitor of $G_i\alpha2$. In some embodiments, an inhibitor of the Hippo pathway is an inhibitor of $G_i\alpha3$. In some embodiments, an inhibitor of the Hippo pathway is an inhibitor of $G_i\alpha4$. In some embodiments, an inhibitor of the Hippo pathway is an inhibitor of $G_o\alpha$. In some embodiments, an inhibitor of the Hippo pathway is an inhibitor of $G_t$. In some embodiments, an inhibitor of the Hippo pathway is an inhibitor of $G_{gust}$. In some embodiments, an inhibitor of the Hippo pathway is an inhibitor of $G_z$.

In some embodiments, an inhibitor of the Hippo pathway is an inhibitor of a core protein of the Hippo pathway. In some embodiments, an inhibitor of the Hippo pathway is an inhibitor of Sav1. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g., 26S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

In some embodiments, the present invention provides a use of a compound, or a pharmaceutical salt or composition thereof, for treating one or more disorders, diseases, and/or conditions wherein the disorder, disease, or condition includes, but is not limited to, a cellular proliferative disorder.

The activity of a compound utilized in this invention as an inhibitor of TEAD (e.g., TEAD1, TEAD2, TEAD3, and/or TEAD4), or a variant or mutant thereof, can be assayed in vitro, in vivo or in a cell line. In vitro assays include assays that determine inhibition of TEAD (e.g., TEAD1, TEAD2, TEAD3, and/or TEAD4), or a variant or mutant thereof. Alternate in vitro assays quantitate the ability of the inhibitor to bind to TEAD (e.g., TEAD1, TEAD2, TEAD3, and/or TEAD4) or a variant or mutant thereof. Detailed conditions for assaying a compound utilized in this invention as an inhibitor of TEAD (e.g., TEAD1, TEAD2, TEAD3, and/or TEAD4), or a variant or mutant thereof, are set forth in the Examples below. See, for example, Examples 2 and 5.

As used herein, the terms "treatment," "treat," and "treating" refer to reversing, alleviating, delaying the onset of, or inhibiting the progress of a disease or disorder, or one or more symptoms thereof, as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example, to prevent or delay their recurrence.

The provided compounds are inhibitors of TEAD (e.g., TEAD1, TEAD2, TEAD3, and/or TEAD4) and are therefore useful for treating one or more disorders associated with activity of TEAD (e.g., TEAD1, TEAD2, TEAD3, and/or TEAD4). Thus, in certain aspects and embodiments, the present invention provides a method for treating a TEAD-mediated disorder comprising the step of administering to a patient in need thereof a therapeutically effective compound of the present invention, or pharmaceutically acceptable composition thereof.

As used herein, the term "TEAD-mediated" disorders, diseases, and/or conditions as used herein means any disease or other deleterious condition in which TEAD (e.g., TEAD1, TEAD2, TEAD3, and/or TEAD4), or a variant or mutant thereof, is known to play a role. Accordingly, another aspect or embodiment of the present invention relates to treating or lessening the severity of one or more diseases in which TEAD (e.g., TEAD1, TEAD2, TEAD3, and/or TEAD4), or a variant or mutant thereof, are known to play a role.

As used herein, the term "a therapeutically effective amount of" refers to the amount of a TEAD inhibitor or a pharmaceutically acceptable salt thereof, which is effective to reduce or attenuate the biological activity of TEAD (e.g., TEAD1, TEAD2, TEAD3, and/or TEAD4) or a variant or mutant thereof, provide a therapeutic benefit in the treatment of a condition, or to delay or minimize one or more symptoms associated with the condition in a biological sample or in a patient. In some embodiments, "a therapeutically effective amount of" refers to the amount of a TEAD inhibitor or a pharmaceutically acceptable salt thereof that measurably decreases the binding or signaling activity of TEAD (e.g., TEAD1, TEAD2, TEAD3, and/or TEAD4), or a variant or mutant thereof or any TEAD-mediated activity. The term "therapeutically effective amount" can encompass, in some embodiments, an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibition of a TEAD transcription factor. In certain embodiments, a therapeutically effective amount is an amount sufficient for treating a proliferative disease.

In some aspects and embodiments, provided herein are methods of treating, reducing the severity of, delaying the onset of, or inhibiting the progress of a disease or disorder, or one or more symptoms thereof of a disease or disorder characterized by or associated with increased TEAD (e.g., TEAD1, TEAD2, TEAD3, and/or TEAD4) expression and/or increased TEAD (e.g., TEAD1, TEAD2, TEAD3, and/or TEAD4) activity comprising the step of administering to a patient in need thereof a therapeutically effective compound of the present invention, or pharmaceutically acceptable composition thereof. In some aspects and embodiments, provided herein are methods of treating, reducing the severity of, delaying the onset of, or inhibiting the progress of a disease or disorder, or one or more symptoms thereof of a disease or disorder in which inhibition or antagonizing of TEAD (e.g., TEAD1, TEAD2, TEAD3, and/or TEAD4) activity is beneficial comprising the step of administering to a patient in need thereof a therapeutically effective compound of the present invention, or pharmaceutically acceptable composition thereof. In some aspects and embodiments, provided herein are methods of treating, reducing the severity of, delaying the onset of, or inhibiting the progress of a disease or disorder, or one or more symptoms thereof of a disease or disorder in which inhibition or antagonizing of the Hippo pathway is beneficial comprising the step of administering to a patient in need thereof a therapeutically effective compound of the present invention, or pharmaceutically acceptable composition thereof.

In some aspects and embodiments, the present invention provides a method for treating one or more disorders, diseases, and/or conditions wherein the disorder, disease, or condition includes, but is not limited to, a cellular proliferative disorder, comprising administering to a patient in need thereof, a TEAD inhibitor compound as described herein, or a pharmaceutical salt or composition thereof. In some embodiments, a cellular proliferative disorder is cancer. In some embodiments, the cancer is characterized by increased TEAD (e.g., TEAD1, TEAD2, TEAD3, and/or TEAD4) expression and/or increased TEAD (e.g., TEAD1, TEAD2, TEAD3, and/or TEAD4) activity.

As used herein, the terms "increased," "elevated," or "enhanced," are used interchangeably and encompass any measurable increase in a biological function and/or biological activity and/or a concentration. For example, an increase can be by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 2-fold, about 3-fold, about 4-fold, about 5-fold, about 6-fold, about 7-fold, about 8-fold, about 9-fold, about 10-fold, about 20-fold, about 25-fold, about 50-fold, about 100-fold, or higher, relative to a control or baseline amount of a function, or activity, or concentration.

As used herein, the terms "increased expression" and/or "increased activity" of a substance, such as TEAD, in a sample or cancer or patient refers to an increase in the amount of the substance, such as TEAD, of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 2-fold, about 3-fold, about 4-fold, about 5-fold, about 6-fold, about 7-fold, about 8-fold, about 9-fold, about 10-fold, about 20-fold, about 25-fold, about 50-fold, about 100-fold, or higher, relative to the amount of the substance, such as TEAD, in a control sample or control samples, such as an individual or group of individuals who are not suffering from the disease or disorder (e.g., cancer) or an internal control, as determined by techniques known in the art. A subject can also be determined to have an "increased expression" or "increased activity" of TEAD if the expression and/or activity of TEAD is increased by one standard deviation, two standard deviations, three standard deviations, four standard deviations, five standard deviations, or more, relative to the mean (average) or median amount of TEAD in a control group of samples or a baseline group of samples or a retrospective analysis of patient samples. As practiced in the art, such control or baseline expression levels can be previously determined, or measured prior to the measurement in the sample or cancer or subject, or can be obtained from a database of such control samples.

As used herein, a "proliferative disease" refers to a disease that occurs due to abnormal growth or extension by the multiplication of cells (Walker, Cambridge Dictionary of Biology, Cambridge University Press: Cambridge, UK, 1990). A proliferative disease can be associated with: 1) the pathological proliferation of normally quiescent cells; 2) the pathological migration of cells from their normal location (e.g., metastasis of neoplastic cells); 3) the pathological expression of proteolytic enzymes, such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

Cancer

The cancer or proliferative disorder or tumor to be treated using the compounds and methods and uses described herein include, but are not limited to, a hematological cancer, a lymphoma, a myeloma, a leukemia, a neurological cancer, skin cancer, breast cancer, a prostate cancer, a colorectal cancer, lung cancer, head and neck cancer, a gastrointestinal cancer, a liver cancer, a pancreatic cancer, a genitourinary cancer, a bone cancer, renal cancer, and a vascular cancer.

In some embodiments of the methods and uses described herein, a cancer is mediated by activation of transcriptional coactivator with PDZ binding motif/Yes-associated protein transcription coactivator (TAZ/YAP). In some embodiments of the methods and uses described herein, a cancer is mediated by modulation of the interaction of YAP/TAZ with TEAD (e.g., TEAD1, TEAD2, TEAD3, and/or TEAD4). In some embodiments of the methods and uses described herein, the cancer is characterized by or associated with increased TEAD (e.g., TEAD1, TEAD2, TEAD3, and/or TEAD4) expression and/or increased TEAD (e.g., TEAD1, TEAD2, TEAD3, and/or TEAD4) activity. In some embodiments of the methods and uses described herein, the cancer is a cancer in which YAP is localized in the nucleus of the cancer cells.

In some embodiments, a cancer is characterized by a mutant Gα-protein. In some embodiments, a mutant Gα-protein is selected from G12, G13, Gq, G11, Gi, Go, and Gs. In some embodiments, a mutant Gα-protein is G12. In some embodiments, a mutant Gα-protein is G13. In some embodiments, a mutant Gα-protein is Gq. In some embodiments, a mutant Gα-protein is G11. In some embodiments, a mutant Gα-protein is Gi. In some embodiments, a mutant Gα-protein is Go. In some embodiments, a mutant Gα-protein is Gs.

In some embodiments of the methods and uses described herein, a cancer is treated by inhibiting or reducing or decreasing or arresting further growth or spread of the cancer or tumor. In some embodiments of the methods and uses described herein, a cancer is treated by inhibiting or reducing the size (e.g., volume or mass) of the cancer or tumor by at least 5%, at least 10%, at least 25%, at least 50%, at least 75%, at least 90% or at least 99% relative to the size of the cancer or tumor prior to treatment. In some embodiments of the methods and uses described herein, a cancer is treated by reducing the quantity of the cancers or tumors in the patient by at least 5%, at least 10%, at least 25%, at least 50%, at least 75%, at least 90% or at least 99% relative to the quantity of the cancers or tumors prior to treatment.

In some embodiments of the methods and uses described herein, the cancer is lung cancer, thyroid cancer, ovarian cancer, colorectal cancer, prostate cancer, cancer of the pancreas, cancer of the esophagus, liver cancer, breast cancer, skin cancer, or mesothelioma. In some embodiments, the cancer is mesothelioma, such as malignant mesothelioma. In some embodiments, cancer includes, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g., Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (WA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC);

prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, a cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, a cancer is a viral-associated cancer, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See clinicaltrials.gov, study NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See clinicaltrials.gov, studies NCT02488759, NCT0240886, and NCT02426892)

In some embodiments, a cancer is melanoma cancer. In some embodiments, a cancer is breast cancer. In some embodiments, a cancer is lung cancer. In some embodiments, a cancer is small cell lung cancer (SCLC). In some embodiments, a cancer is non-small cell lung cancer (NSCLC).

The compounds and compositions, according to the methods of the present invention, can be administered using any amount and any route of administration effective for treating or lessening the severity of a cancer or tumor. The exact amount required varies from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention is decided by the attending physician within the scope of sound medical judgment. The specific effective dose level for any particular patient or organism depends upon a variety of factors, including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The terms "patient" or "subject", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention can be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Co-Administration with One or More Other Therapeutic Agent(s)

Depending upon the particular condition, or disease, to be treated, additional therapeutic agents that are normally administered to treat that condition, can also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention can also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides, or in addition, be administered especially for tumor therapy in combination with chemotherapy, radiotherapy, immunotherapy, phototherapy, surgical intervention, or a combination of these. Long-term therapy is equally possible, as is adjuvant therapy in the context of other treatment strategies, as described above. Other possible treatments are therapy to maintain the patient's status after tumor regression, or even chemopreventive therapy, for example in patients at risk.

One or more other therapeutic agent(s) may be administered separately from a compound or composition of the invention, as part of a multiple dosage regimen. Alternatively, one or more other therapeutic agents agents(s) be part of a single dosage form, mixed together with a compound of this invention in a single composition. If administered as a multiple dosage regime, one or more other therapeutic agent(s) and a compound or composition of the invention can be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent(s) and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention can be administered with one or more other therapeutic agent(s) simultaneously or sequentially in separate unit dosage forms or together in a single unit dosage form. Accordingly, the present invention provides a single unit dosage form comprising a compound of the current invention, one or more other therapeutic agent(s), and a pharmaceutically acceptable carrier, adjuvant, or vehicle.

The amount of a compound of the invention and one or more other therapeutic agent(s) (in those compositions which comprise an additional therapeutic agent as described above) that may be combined with the carrier materials to produce a single dosage form will vary depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent(s), the one or more other therapeutic agent(s) and a compound of the invention may act synergistically. Therefore, the amount of the one or more other therapeutic agent(s) in such compositions may be less than that required in a monotherapy utilizing only that therapeutic agent. In such compositions a dosage of between 0.01-1,000 µg/kg body weight/day of the one or more other therapeutic agent(s) can be administered.

The amount of one or more other therapeutic agent present in the compositions of this invention may be no more than the amount that would normally be administered in a composition comprising that therapeutic agent as the only active agent. Preferably the amount of one or more other therapeutic agent(s) in the presently disclosed compositions will range from about 50% to 100% of the amount normally present in a composition comprising that agent as the only therapeutically active agent. In some embodiments, one or more other therapeutic agent(s) is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approvided for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Other Therapeutic Agents

In some embodiments, one or more other therapeutic agent is a Poly ADP ribose polymerase (PARP) inhibitor. In some embodiments, a PARP inhibitor is selected from olaparib (LYNPARZA®, AstraZeneca); rucaparib (RUBRACA®, Clovis Oncology); niraparib (ZEJULA®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (ZOLINZA®, Merck); romidepsin (ISTODAX®, Celgene); panobinostat (FARYDAK®, Novartis); belinostat (BELEODAQ®, Spectrum Pharmaceuticals); entinostat (SNDX-275, Syndax Pharmaceuticals) (NCT00866333); and chidamide (EPIDAZA®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (IBRANCE®, Pfizer); ribociclib (KISQALI®, Novartis); abemaciclib (Ly2835219, Eli Lilly); and trilaciclib (G1T28, G1 Therapeutics).

In some embodiments, one or more other therapeutic agent is a phosphatidylinositol 3 kinase (PI3K) inhibitor. In some embodiments, a PI3K inhibitor is selected from idelalisib (ZYDELIG®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells.

In some embodiments, a platinum-based therapeutic is selected from cisplatin (PLATINOL®, Bristol-Myers Squibb); carboplatin (PARAPLATIN®, Bristol-Myers Squibb; also, Teva; Pfizer); oxaliplatin (ELOXITIN® Sanofi-Aventis); nedaplatin (AQUPLA®, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (TAXOL®, Bristol-Myers Squibb), docetaxel (TAXOTERE®, Sanofi-Aventis; DOCEFREZ®, Sun Pharmaceutical), albumin-bound paclitaxel (ABRAXANE®; Abraxis/Celgene), cabazitaxel (JEVTANA®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, YONDELIS®, Janssen Oncology), mechlorethamine (alkylating agent, VALCHLOR®, Aktelion Pharmaceuticals); vincristine (ONCOVIN®, Eli Lilly; VINCASAR®, Teva Pharmaceuticals; MARQIBO®, Talon Therapeutics); temozolomide (prodrug to alkylating agent 5-(3-methyltriazen-1-yl)-imidazole-4-carboxamide (MTIC) TEMODAR®, Merck); cytarabine injection (ara-C, antimetabolic cytidine analog, Pfizer); lomustine (alkylating agent, CEENU®, Bristol-Myers Squibb; GLEOSTINE®, NextSource Biotechnology); azacitidine (pyrimidine nucleoside analog of cytidine, VIDAZA®, Celgene); omacetaxine mepesuccinate (cephalotaxine ester) (protein synthesis inhibitor, SYNRIBO®; Teva Pharmaceuticals); asparaginase Erwinia chrysanthemi (enzyme for depletion of asparagine, ELSPAR®, Lundbeck; ERWINAZE®, EUSA Pharma); eribulin mesylate (microtubule inhibitor, tubulin-based antimitotic, HALAVEN®, Eisai); cabazitaxel (microtubule inhibitor, tubulin-based antimitotic, JEVTANA®, Sanofi-Aventis); capacetrine (thymidylate synthase inhibitor, XELODA®, Genentech); bendamustine (bifunctional mechlorethamine derivative, believed to form interstrand DNA cross-links, TREANDA®, Cephalon/Teva); ixabepilone (semi-synthetic analog of epothilone B, microtubule inhibitor, tubulin-based antimitotic, IXEMPRA®, Bristol-Myers Squibb); nelarabine (prodrug of deoxyguanosine analog, nucleoside metabolic inhibitor, ARRANON®, Novartis); clorafabine (prodrug of ribonucleotide reductase inhibitor, competitive inhibitor of deoxycytidine, CLOLAR®, Sanofi-Aventis); and trifluridine and tipiracil (thymidine-based nucleoside analog and thymidine phosphorylase inhibitor, LONSURF®, Taiho Oncology).

In some embodiments, one or more other therapeutic agent is a kinase inhibitor or VEGF-R antagonist. Approved VEGF inhibitors and kinase inhibitors useful in the present invention include: bevacizumab (AVASTIN®, Genentech/Roche) an anti-VEGF monoclonal antibody; ramucirumab (CYRAMZA®, Eli Lilly), an anti-VEGFR-2 antibody and ziv-aflibercept, also known as VEGF Trap (ZALTRAP®; Regeneron/Sanofi). VEGFR inhibitors, such as regorafenib (STIVARGA®, Bayer); vandetanib (CAPRELSA®, AstraZeneca); axitinib (INLYTA®, Pfizer); and lenvatinib (LENVIMA®, Eisai); Raf inhibitors, such as sorafenib (NEXAVAR®, Bayer AG and Onyx); dabrafenib (TAFINLAR®, Novartis); and vemurafenib (ZELBORAF®, Genentech/Roche); MEK inhibitors, such as cobimetanib (COTELLIC®, Exelexis/Genentech/Roche); trametinib (MEKINIST®, Novartis); Bcr-Abl tyrosine kinase inhibitors, such as imatinib (GLEEVEC®, Novartis); nilotinib (TASIGNA®, Novartis); dasatinib (SPRYCEL®, BristolMyersSquibb); bosutinib (BOSULIF®, Pfizer); and ponatinib (INCLUSIG®, Ariad Pharmaceuticals); Her2 and EGFR inhibitors, such as gefitinib ORES SA®, AstraZeneca); erlotinib (TARCEEVA®, Genentech/Roche/Astellas); lapatinib (TYKERB®, Novartis); afatinib (GILOTRIF®, Boehringer Ingelheim); osimertinib (targeting activated EGFR, TAGRISSO®, AstraZeneca); and brigatinib (ALUNBRIG®, Ariad Pharmaceuticals); c-Met and VEGFR2 inhibitors, such as cabozanitib (COMETRIQ®, Exelexis); and multikinase inhibitors, such as sunitinib (SUTENT®, Pfizer); pazopanib (VOTRIENT®, Novartis); ALK inhibitors, such as crizotinib (XALKORI®, Pfizer); ceritinib (ZYKADIA®, Novartis); and alectinib (ALECENZa®, Genentech/Roche); Bruton's tyrosine kinase inhibitors, such as ibrutinib (IMBRUVICA®, Pharmacyclics/Janssen); and Flt3 receptor inhibitors, such as midostaurin (RYDAPT®, Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (SUPECT®, IY5511, Il-Yang Pharmaceuticals, S. Korea); ruxolitinib (JAKAFI®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In some embodiments, one or more other therapeutic agent is an mTOR inhibitor, which inhibits cell proliferation, angiogenesis and glucose uptake. In some embodiments, an mTOR inhibitor is everolimus (AFINITOR®, Novartis); temsirolimus (TORISEL®, Pfizer); and sirolimus (RAPAMUNE®, Pfizer).

In some embodiments, one or more other therapeutic agent is a proteasome inhibitor. Approved proteasome inhibitors useful in the present invention include bortezomib (VELCADE®, Takeda); carfilzomib (KYPROLIS®, Amgen); and ixazomib (NINLARO®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (LARTRUVO®; Eli Lilly). Approved EGFR antagonists which may be used in the present invention include cetuximab (ERBITUX®, Eli Lilly); necitumumab (PORTRAZZA®, Eli Lilly), panitumumab (VECTIBIX®, Amgen); and osimertinib (targeting activated EGFR, TAGRISSO®, AstraZeneca).

In some embodiments, one or more other therapeutic agent is an aromatase inhibitor. In some embodiments, an aromatase inhibitor is selected from exemestane (AROMASIN®, Pfizer); anastazole (ARIMIDEX®, AstraZeneca) and letrozole (FEMARA®, Novartis).

In some embodiments, one or more other therapeutic agent is an antagonist of the hedgehog pathway. Approved hedgehog pathway inhibitors which may be used in the present invention include sonidegib (ODOMZO®, Sun Pharmaceuticals); and vismodegib (ERIVEDGE®, Genentech), both for treatment of basal cell carcinoma.

In some embodiments, one or more other therapeutic agent is a folic acid inhibitor. Approved folic acid inhibitors useful in the present invention include pemetrexed (ALIMTA®, Eli Lilly).

In some embodiments, one or more other therapeutic agent is a CC chemokine receptor 4 (CCR4) inhibitor. CCR4 inhibitors being studied that may be useful in the present invention include mogamulizumab (POTELIGEO®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (RITUXAN®, Genentech/BiogenIdec); ofatumumab (anti-CD20, ARZERRA®, GlaxoSmithKline); obinutuzumab (anti-CD20, GAZYVA®, Genentech), ibritumomab (anti-CD20 and Yttrium-90, ZEVALIN®, Spectrum Pharmaceuticals); daratumumab (anti-CD38, DARZALEX®, Janssen Biotech), dinutuximab (anti-glycolipid GD2, UNITUXIN®, United Therapeutics); trastuzumab (anti-HER2, HERCEPTIN®, Genentech); ado-trastuzumab emtansine (anti-HER2, fused to emtansine, KADCYLA®, Genentech); and pertuzumab (anti-HER2, PERJETA®, Genentech); and brentuximab vedotin (anti-CD30-drug conjugate, ADCETRIS®, Seattle Genetics).

In some embodiments, one or more other therapeutic agent is a topoisomerase inhibitor. Approved topoisomerase inhibitors useful in the present invention include irinotecan (ONIVYDE®, Merrimack Pharmaceuticals); topotecan (HYCAMTIN®, GlaxoSmithKline). Topoisomerase inhibitors being studied which may be used in the present invention include pixantrone (PIXUVRI®, CTI Biopharma).

In some embodiments, one or more other therapeutic agent is an inhibitor of anti-apoptotic proteins, such as BCL-2. Approved anti-apoptotics which may be used in the present invention include venetoclax (VENCLEXTA®, AbbVie/Genentech); and blinatumomab (BLINCYTO®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (XTANDI®, Astellas/Medivation); approved inhibitors of androgen synthesis include abiraterone (ZYTIGA®, Centocor/Ortho); approved antagonist of gonadotropin-releasing hormone (GnRH) receptor (degaralix, FIRMAGON®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (EVISTA®, Eli Lilly).

In some embodiments, one or more other therapeutic agent is an inhibitor of bone resorption. An approved therapeutic which inhibits bone resorption is Denosumab (XGEVA®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (ZOMETA®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agents is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd$_6$244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name AROMASIN™. Formestane is marketed under the trade name LENTARON™. Fadrozole is marketed under the trade name AFEMA™. Anastrozole is marketed under the trade name ARIMIDEX™. Letrozole is marketed under the trade names FEMARA™ or FEMAr™. Aminoglutethimide is marketed under the trade name ORIMETEN™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name NOLVADEX™. Raloxifene hydrochloride is marketed under the trade name EVISTA™. Fulvestrant can be administered under the trade name FASLODEX™ Fulvestrant can be administered under the trade name Faslodex™. A combination of the invention comprising a chemotherapeutic agent which is an anti estrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (CASODEX™). The term "gonadorelin agonist" as used herein includes, but is not limited to abarelix, goserelin, and goserelin acetate. Goserelin can be administered under the trade name ZOLADEX™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g., under the trademark CAMPTOSAR™. Topotecan is marketed under the trade name HYCAMPTIN™.

The term "topoisomerase II inhibitor" as used herein includes, but is not limited to the anthracyclines such as doxorubicin (including liposomal formulation, such as CAELYX™) daunorubicin, epirubicin, idarubicin and nemorubicin, the anthraquinones mitoxantrone and losoxantrone, and the podophillotoxines etoposide and teniposide. Etoposide is marketed under the trade name ETOPOPHOS™. Teniposide is marketed under the trade name VM 26-Bristol Doxorubicin is marketed under the trade name ACRIBLASTIN™ or ADRIAMYCIN™. Epirubicin is marketed under the trade name FARMORUBICIN™. Idarubicin is marketed. under the trade name ZAVEDOS™. Mitoxantrone is marketed under the trade name NOVANTRON™.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name TAXOL™. Docetaxel is marketed under the trade name TAXOTERE™. Vinblastine sulfate is marketed under the trade name VINBLASTIN R.P™. Vincristine sulfate is marketed under the trade name FARMISTIN™.

The term "alkylating agent" as used herein includes, but is not limited to, cyclophosphamide, ifosfamide, melphalan or nitrosourea (BCNU or Gliadel). Cyclophosphamide is marketed under the trade name CYCLOSTIN™. Ifosfamide is marketed under the trade name HOLOXAN™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name XELODA™. Gemcitabine is marketed under the trade name GEMZAR™.

The term "platin compound" as used herein includes, but is not limited to, carboplatin, cis-platin, cisplatinum and oxaliplatin. Carboplatin can be administered, e.g., in the form as it is marketed, e.g., under the trademark CARBOPLAT™. Oxaliplatin can be administered, e.g., in the form as it is marketed, e.g. under the trademark ELOXATIN™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (HERCEPTIN™), cetuximab (ERBITUX™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g., unrelated to protein or lipid kinase inhibition e.g., thalidomide (THALOMID™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g., inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name DIDRONEL™. Clodronic acid is marketed under the trade name BONEFOS™. Tiludronic acid is marketed under the trade name Skelid™. Pamidronic acid is marketed under the trade name AREDIA™. Alendronic acid is marketed under the trade name FOSAMAX™. Ibandronic acid is marketed under the trade name BONDRANAT™. Risedronic acid is marketed under the trade name ACTONEL™. Zoledronic acid is marketed under the trade name ZOMETA™. The term "mTOR inhibitors" relates to compounds which inhibit the mammalian target of rapamycin (mTOR) and which possess antiproliferative activity such as sirolimus (RAPAMUNE®), everolimus (CERTICAN™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (ZARNESTRA™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (VELCADE™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (HERCEPTIN™), Trastuzumab-DM1, erbitux, bevacizumab (AVASTIN™), rituximab (RITUXAN®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; ANGIOSTATIN™; ENDOSTATIN™; anthranilic acid amides; ZD4190; Zd$_6$474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (AVASTIN™).

Photodynamic therapy as used herein refers to therapy which uses certain chemicals known as photosensitizing compounds to treat or prevent cancers. Examples of photodynamic therapy include treatment with compounds, such as VISUDYNE™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGUTL1A, TRAMP/DR3, EDAR, EDA1, XEDAR, EDA2, TNFR1, Lymphotoxin α/TNFβ, TNFR2, TNFα, LTβR, Lymphotoxin al f32, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase— (TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8$^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications.

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/ SIRPa inhibitors that are being studied in clinical trials include ALX-148 (Alexo Therapeutics), an antagonistic variant of (SIRPa) that binds to CD47 and prevents CD47/ SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Example 1: Synthesis of Exemplary Compounds

Certain exemplary compounds are prepared following the following schemes.

Synthesis of I-5

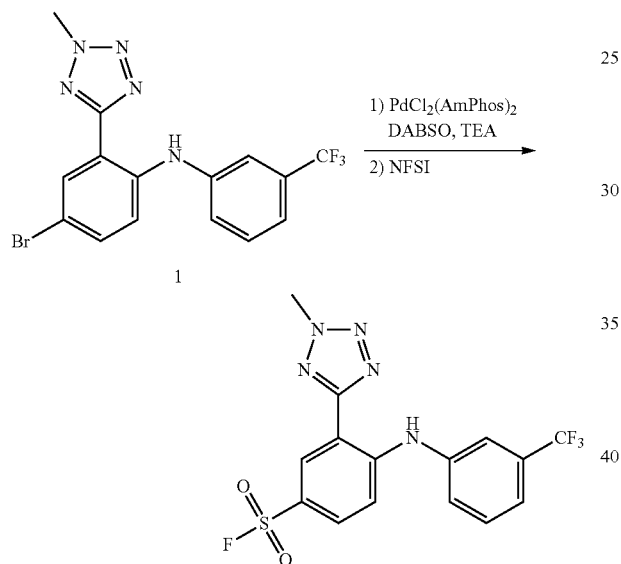

Synthesis of I-11

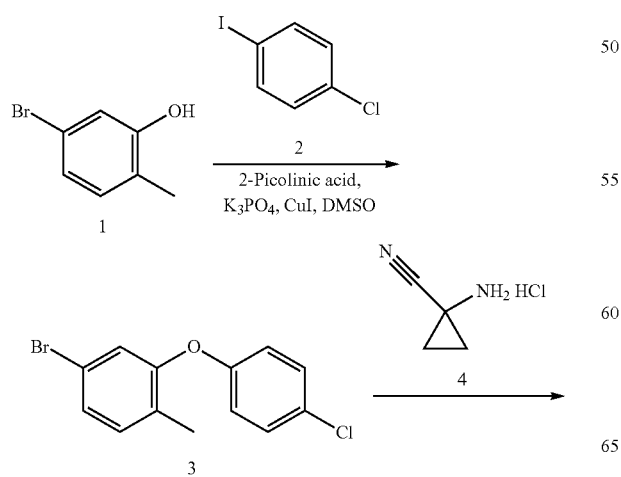

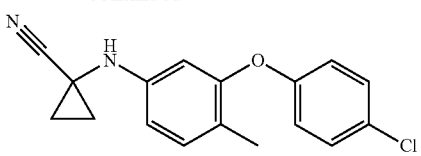

Synthesis of I-3

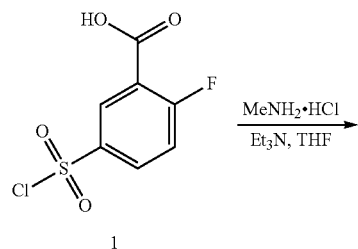

1

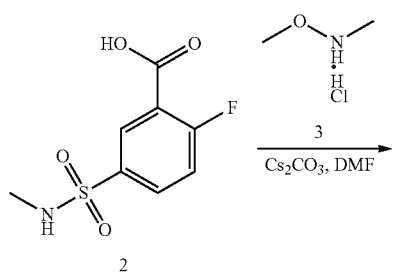

2

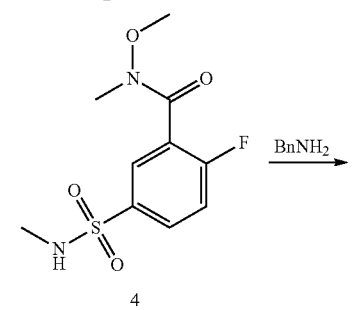

4

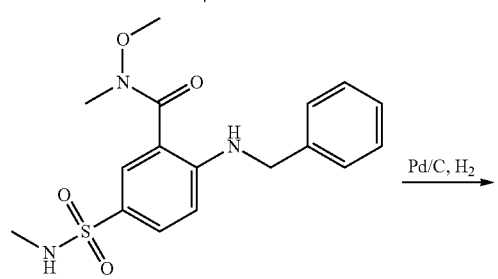

5

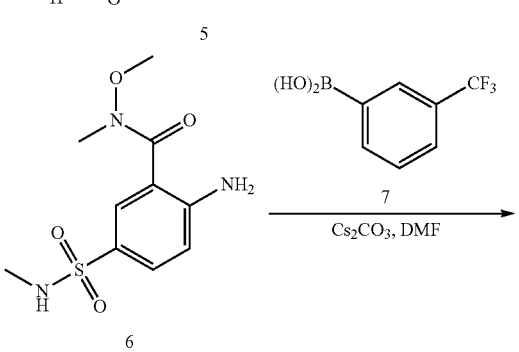

6

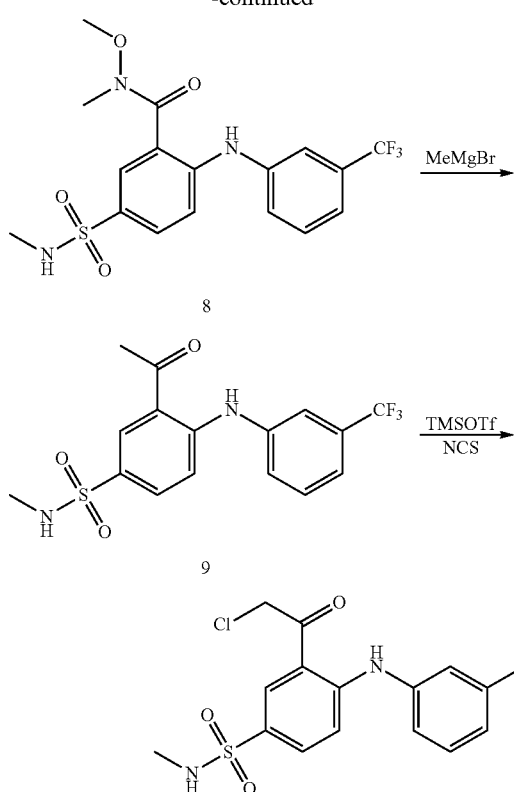
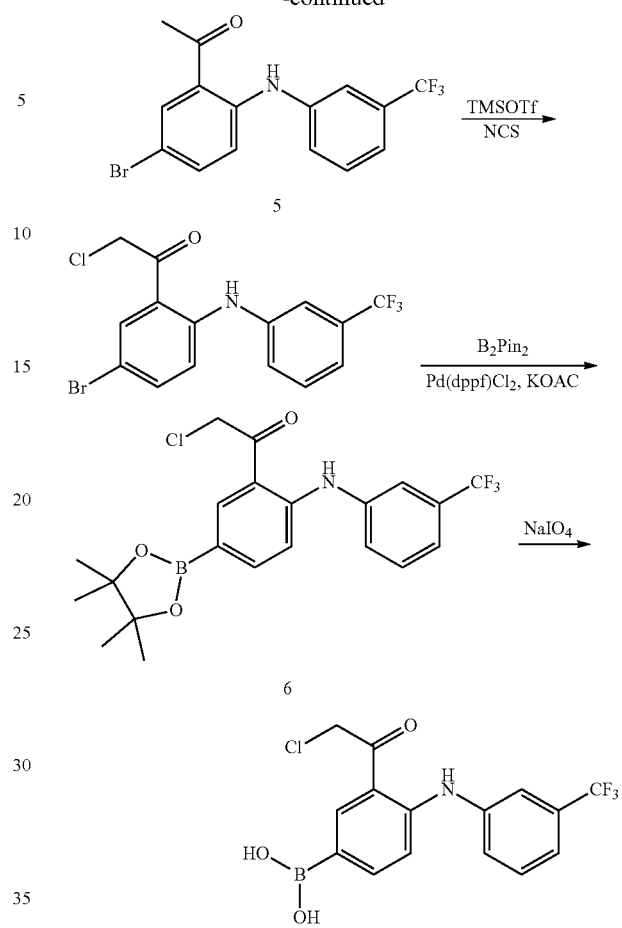
Synthesis of I-13 & I-14
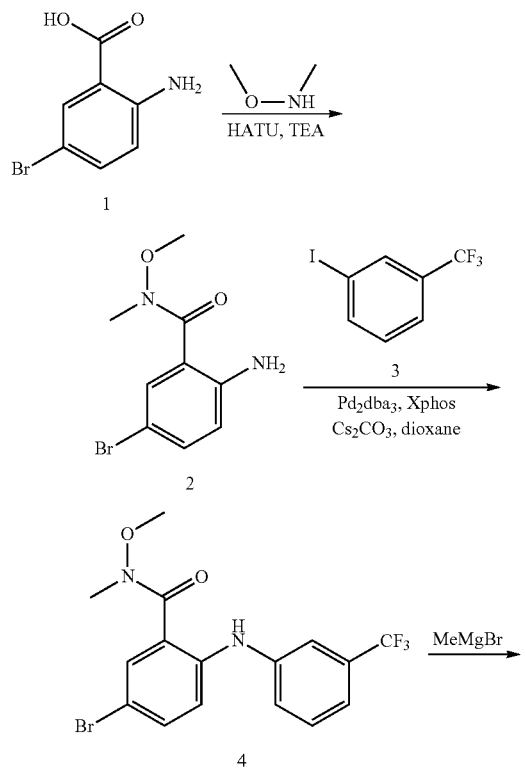
Synthesis of I-15
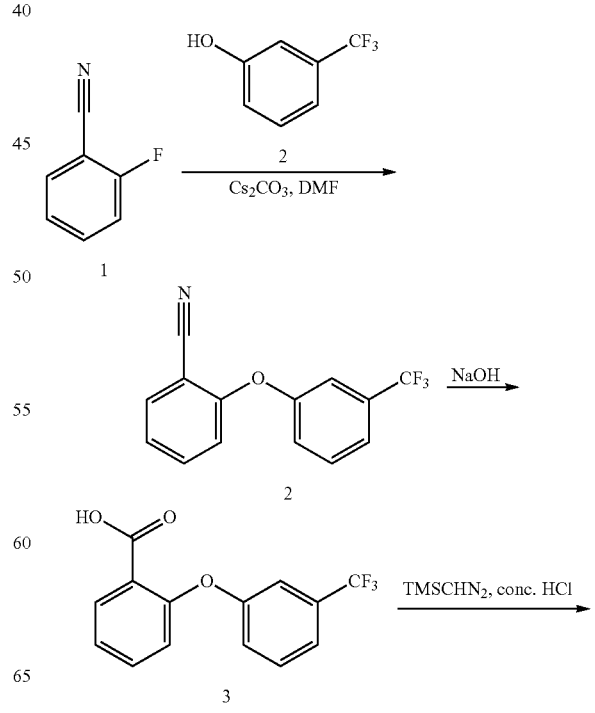

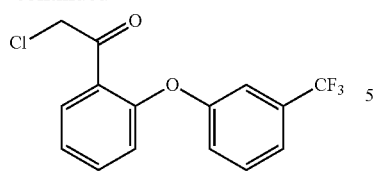
Synthesis of I-1, I-25, & I-26
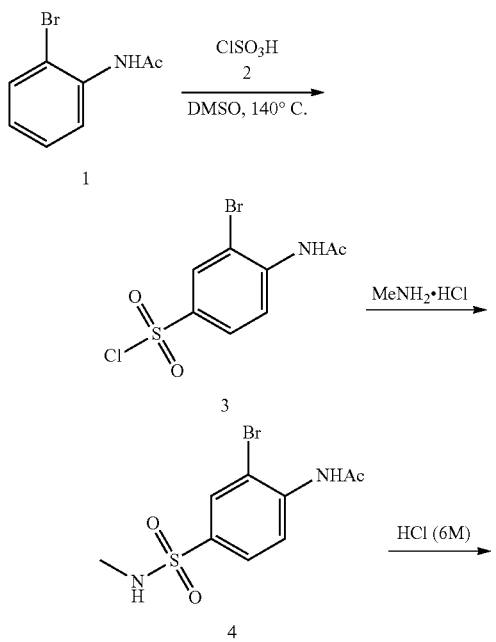
Synthesis of I-12, I-23, & I-24
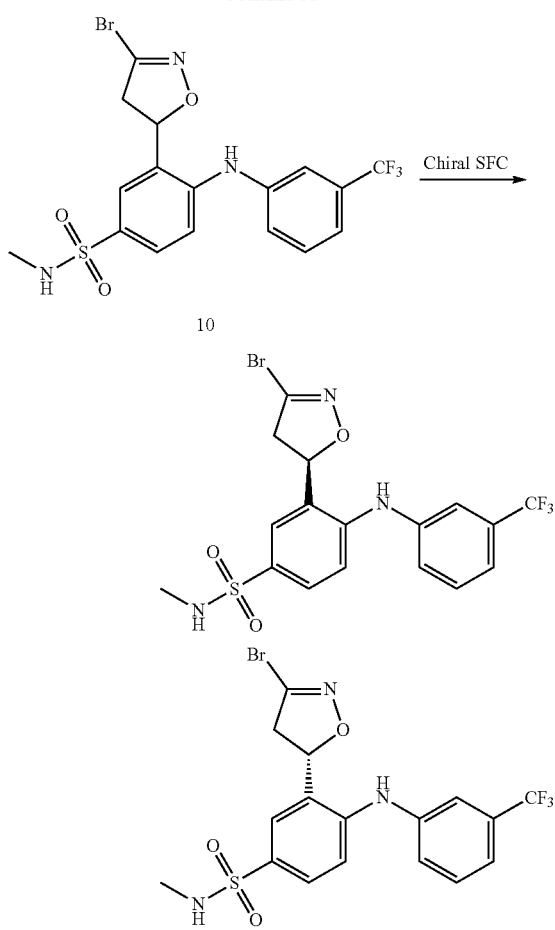
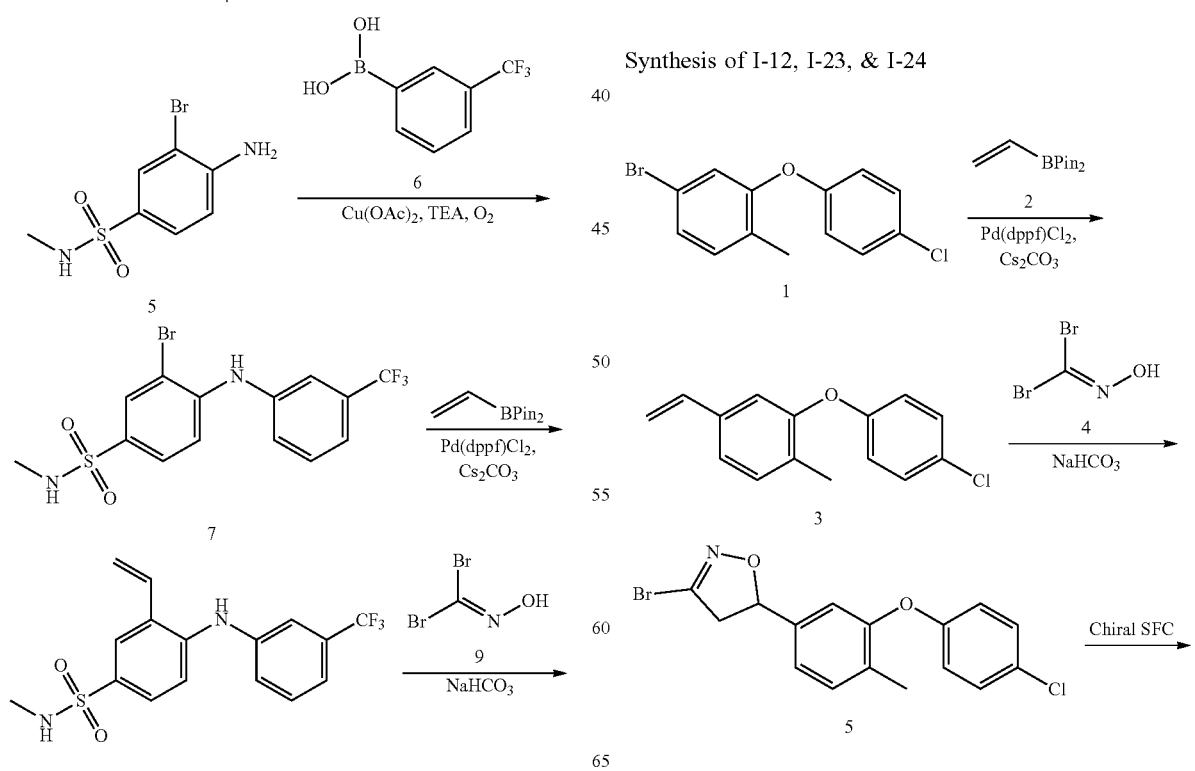

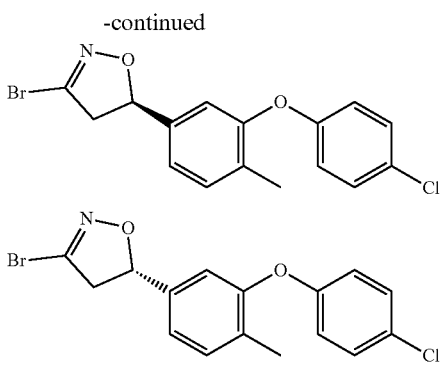
Synthesis of I-22
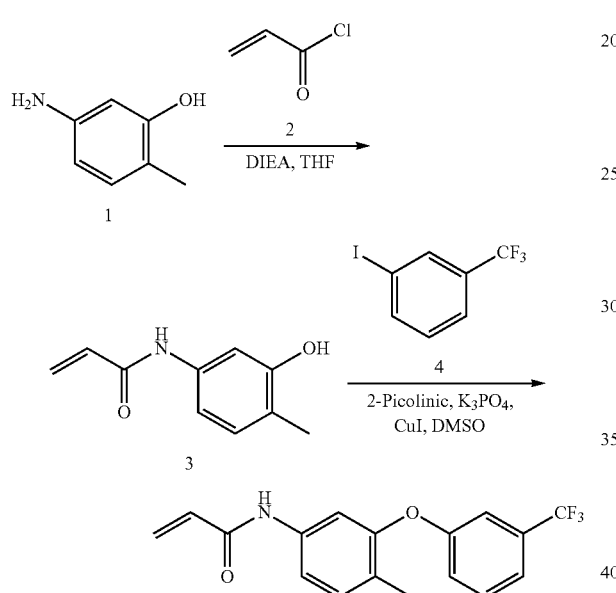
Synthesis of I-18 & I-19
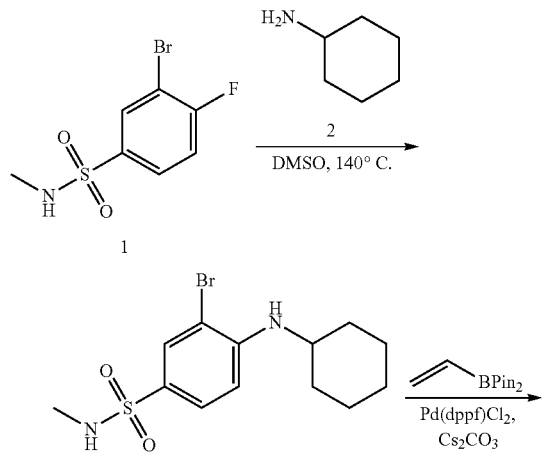
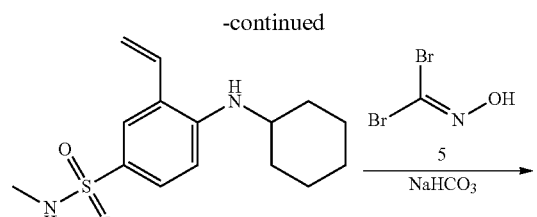
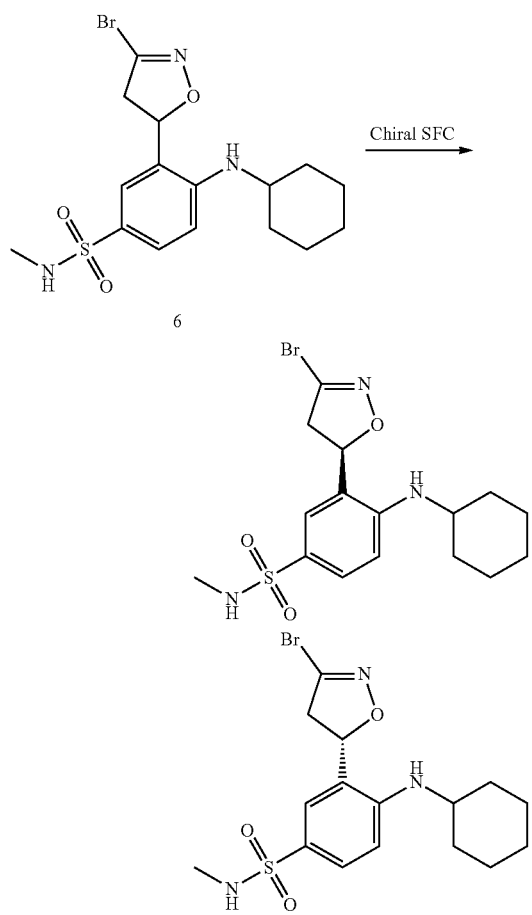
Synthesis of I-20 & I-21
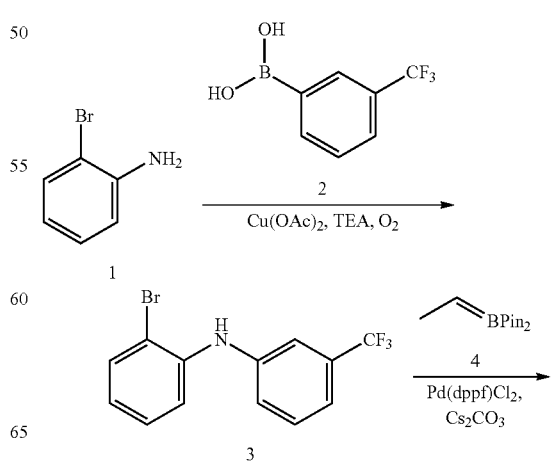

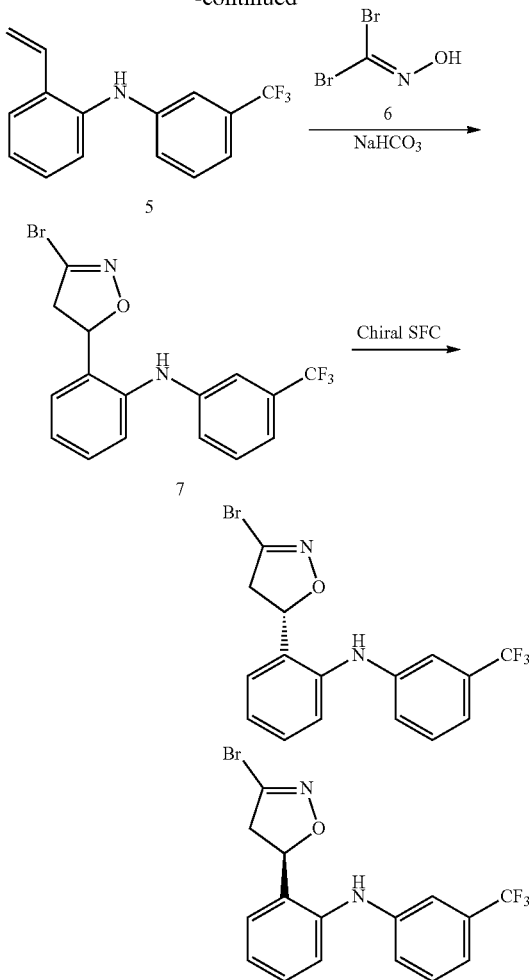

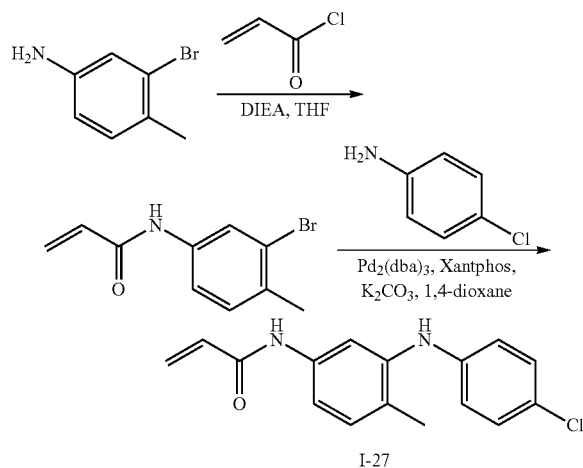

Step 1:
N-(3-Bromo-4-methyl-phenyl)prop-2-enamide

To a solution of 3-bromo-4-methyl-aniline (1 g, 5.37 mmol, 1 eq) and DIEA (2.08 g, 16.12 mmol, 2.81 mL, 3 eq) in THF (20 mL) was added prop-2-enoyl chloride (600 mg, 6.63 mmol, 540.54 μL, 1.23 eq) dropwise at 20° C. The mixture was stirred at 20° C. for 1 h. TLC (PE/EtOAc=1/1, $R_f$=0.30) showed the starting material was consumed completely. The reaction mixture was diluted with $H_2O$ (50 mL) and extracted with EtOAc (50 mL×3). The organic layer was dried over $Na_2SO_4$, filtered and concentrated under reduced pressure to yield N-(3-bromo-4-methyl-phenyl)prop-2-enamide (1.1 g, 4.42 mmol, 82.2% yield, 96.4% purity) as a yellow solid, which was used in the next step without further purification. $^1$H NMR (400 MHz, $CDCl_3$) δ ppm 7.84 (br s, 1H), 7.43 (d, J=7.8 Hz, 1H), 7.38 (s, 1H), 7.18 (d, J=8.1 Hz, 1H), 6.48-6.40 (m, 1H), 6.29-6.19 (m, 1H), 5.78 (dd, J=1.2, 10.3 Hz, 1H), 2.36 (s, 3H); ES-LCMS m/z 239.9, 241.9 $[M+H]^+$.

Step 2: N-[3-(4-Chloroanilino)-4-methyl-phenyl]prop-2-enamide

A mixture of N-(3-bromo-4-methyl-phenyl)prop-2-enamide (500 mg, 2.01 mmol, 1 eq), 4-chloroaniline (300 mg, 2.35 mmol, 1.17 eq), $K_2CO_3$ (280 mg, 2.03 mmol, 1.01 eq), $Pd_2(dba)_3$ (190 mg, 207.49 μmol, 1.03e-1 eq) and Xantphos (190 mg, 328.37 μmol, 1.64e-1 eq) in 1,4-dioxane (10 mL) was bubbled with $N_2$ for 2 minutes and sealed. The mixture was irradiated under microwave at 110° C. for 30 minutes. TLC (PE/EtOAc=1/1, $R_f$=0.24) showed the starting material was almost consumed. The reaction mixture was diluted with $H_2O$ (20 mL) and extracted with EtOAc (20 mL×3). The organic layer was dried over $Na_2SO_4$, filtered and concentrated under reduced pressure to yield a residue which was purified by flash silica gel chromatography (from PE/EtOAc=100/1 to 8/1, TLC: PE/EtOAc=1/1, $R_f$=0.24) to yield N-[3-(4-chloroanilino)-4-methyl-phenyl]prop-2-enamide (61.35 mg, 208.78 μmol, 10.4% yield, 97.6% purity) as a yellow solid. $^1$H NMR (500 MHz, $CDCl_3$) δ ppm 7.48 (s, 1H), 7.26-7.18 (m, 3H), 7.16-7.08 (m, 2H), 6.95-6.91 (m, 2H), 6.40 (d, J=16.9 Hz, 1H), 6.20 (dd, J=10.3, 16.9 Hz, 1H), 5.74 (d, J=10.2 Hz, 1H), 5.39 (s, 1H), 2.21 (s, 3H); ES-LCMS m/z 287.0 $[M+H]^+$. I-28

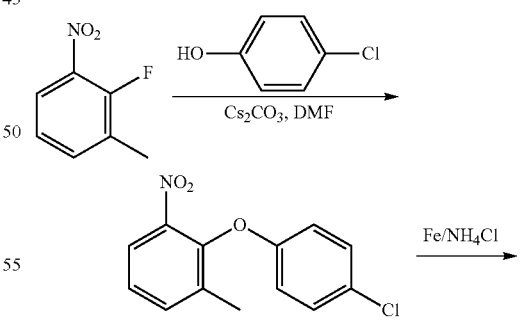

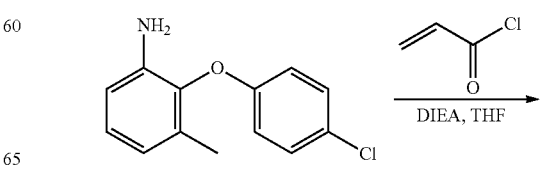

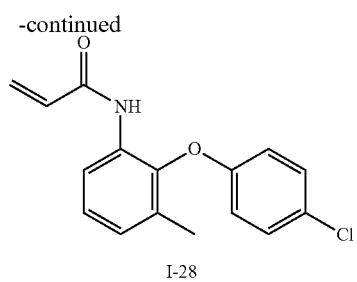

I-28

Step 1: 2-(4-Chlorophenoxy)-1-methyl-3-nitro-benzene

To a solution of 2-fluoro-1-methyl-3-nitro-benzene (500 mg, 3.22 mmol, 1 eq) in DMF (20 mL) was added $Cs_2CO_3$ (3.15 g, 9.67 mmol, 3 eq) and 4-chlorophenol (414.36 mg, 3.22 mmol, 316.31 μL, 1 eq). The mixture was stirred at 120° C. for 12 h. To the mixture was added water (30 mL) and extracted with ethyl acetate (30 mL×3). The combined organic phase was washed with brine (20 mL), dried with anhydrous $Na_2SO_4$, filtered and concentrated to yield a residue which was purified by flash silica gel chromatography (from PE/EtOAc=1/0, TLC: PE/EtOAc=100/1, $R_f$=0.32) to yield 2-(4-chlorophenoxy)-1-methyl-3-nitrobenzene (820 mg, 2.95 mmol, 91.7% yield, 95.0% purity) as yellow oil. $^1$H NMR (500 MHz, $CD_3OD$) δ ppm 7.83 (dd, J=1.1, 8.1 Hz, 1H), 7.64 (dd, J=0.7, 7.7 Hz, 1H), 7.43-7.36 (m, 1H), 7.32-7.28 (m, 2H), 6.82-6.76 (m, 2H), 2.19 (s, 3H).

Step 2: 2-(4-Chlorophenoxy)-3-methyl-aniline

To a solution of 2-(4-chlorophenoxy)-1-methyl-3-nitrobenzene (770 mg, 2.77 mmol, 1 eq) in EtOH (15 mL) and $H_2O$ (7.5 mL) was added Fe (774.64 mg, 13.87 mmol, 5 eq) and $NH_4Cl$ (1.48 g, 27.74 mmol, 10 eq). The mixture was stirred at 90° C. for 3 h. The reaction mixture was filtered and concentrated under reduced pressure to yield a residue. To the residue was added water (30 mL) and extracted with ethyl acetate (30 mL×3). The combined organic phase was washed with brine (20 mL), dried with anhydrous $Na_2SO_4$, filtered and concentrated to yield a residue which was purified by flash silica gel chromatography (from PE/EtOAc=200/1 to 5/1, TLC: PE/EtOAc=5/1, $R_f$=0.50) to yield 2-(4-chlorophenoxy)-3-methyl-aniline (640 mg, 2.73 mmol, 98.4% yield, 99.7% purity) as colorless oil. $^1$H NMR (500 MHz, $CD_3OD$) δ ppm 7.27-7.21 (m, 2H), 6.92 (t, J=7.8 Hz, 1H), 6.83-6.78 (m, 2H), 6.72 (dd, J=1.1, 7.9 Hz, 1H), 6.59 (dd, J=0.7, 7.6 Hz, 1H), 2.02 (s, 3H); ES-LCMS m/z 234.0, 236.0 [M+H]$^+$.

Step 3: N-[2-(4-Chlorophenoxy)-3-methyl-phenyl]prop-2-enamide

To a solution of 2-(4-chlorophenoxy)-3-methyl-aniline (300 mg, 1.28 mmol, 1 eq) in THF (10 mL) was added DIEA (497.74 mg, 3.85 mmol, 670.81 μL, 3 eq) and prop-2-enoyl chloride (232.38 mg, 2.57 mmol, 209.35 μL, 2 eq). The mixture was stirred at 25° C. for 1 h. The reaction mixture was concentrated under reduced pressure to yield a residue which was purified by preparative HPLC (column: Agela DuraShell C18 150*25 mm*5 μm; mobile phase: [water (0.04% $NH_3·H_2O$+10 mM $NH_4HCO_3$)-ACN]; B %: 50%-65%, 14 min), followed by lyophilization to yield N-[2-(4-chlorophenoxy)-3-methyl-phenyl]prop-2-enamide (95.34 mg, 331.34 μmol, 25.8% yield, 100% purity) as a white solid. $^1$H NMR (400 MHz, $CD_3OD$) δ ppm 7.79 (d, J=7.8 Hz, 1H), 7.28-7.13 (m, 4H), 6.79-6.74 (m, 2H), 6.37-6.20 (m, 2H), 5.67 (dd, J=2.0, 9.8 Hz, 1H), 2.13 (s, 3H); ES-LCMS m/z 288.0, 290.0 [M+H]$^+$.

P-16

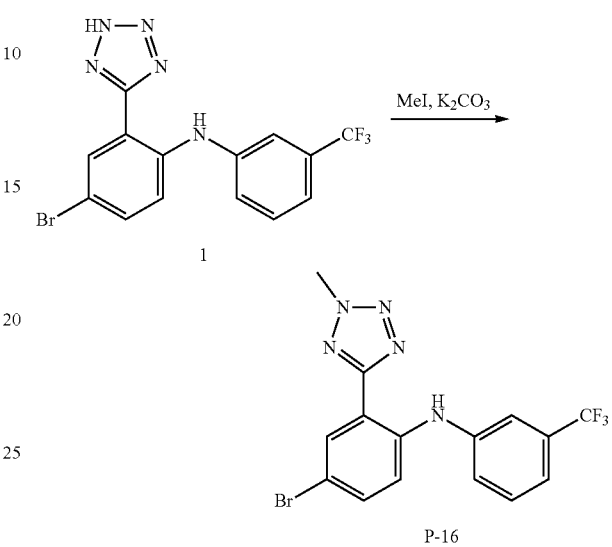

P-16

Step 1: 4-Bromo-2-(2-methyltetrazol-5-yl)-N-[3-(trifluoromethyl)phenyl]aniline To a solution of 4-bromo-2-(2H-tetrazol-5-yl)-N-[3-(trifluoromethyl)phenyl]aniline (450 mg, 1.05 mmol, 1 eq) in ACN (10 mL) was added $K_2CO_3$ (291.41 mg, 2.11 mmol, 2 eq) and MeI (224.46 mg, 1.58 mmol, 98.45 μL, 1.5 eq). The mixture was stirred at 20° C. for 2 h. TLC (PE/EtOAc=3/1, $R_f$=0.45) showed starting material was consumed and one major new spot was detected. The reaction mixture was concentrated to yield a residue which was added $H_2O$ (20 mL) and extracted with EtOAc (20 mL×3). The combine organic layers were washed with brine (20 mL), dried over anhydrous $Na_2SO_4$, filtered and concentrated to yield a residue which was purified by flash silica gel chromatography (from pure PE to PE/EtOAc=3/1, TLC: PE/EtOAc=3/1, $R_f$=0.45) to yield 4-bromo-2-(2-methyltetrazol-5-yl)-N-[3-(trifluoromethyl)phenyl]aniline (230 mg, 573.79 μmol, 54.4% yield, 99.3% purity) as a white solid. $^1$H NMR (500 MHz, DMSO-$d_6$) δ ppm 8.69 (br s, 1H), 8.10 (br s, 1H), 7.59 (d, J=8.9 Hz, 1H), 7.54-7.48 (m, 1H), 7.47-7.41 (m, 2H), 7.36 (d, J=8.7 Hz, 1H), 7.28 (d, J=7.3 Hz, 1H), 4.45 (s, 3H); ES-LCMS m/z 399.4 [M+H]$^+$.

I-9

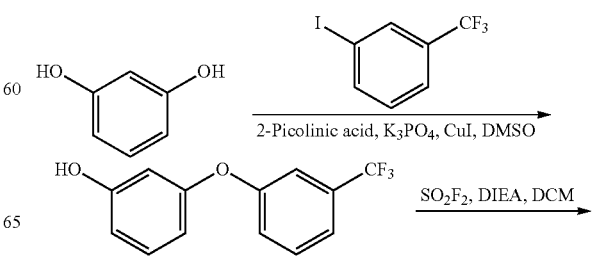

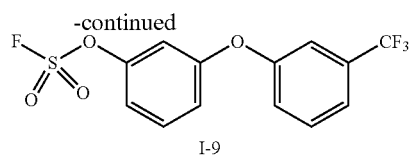

I-9

Step 1: 3-(3-(Trifluoromethyl)phenoxy)phenol

To a solution of 1-iodo-3-(trifluoromethyl)benzene (0.8 g, 2.94 mmol, 423.28 μL, 1 eq) in DMSO (20 mL) was added $K_3PO_4$ (1.25 g, 5.88 mmol, 2.0 eq) and benzene-1,3-diol (340.04 mg, 3.09 mmol, 515.21 μL, 1.05 eq), CuI (28.01 mg, 147.06 μmol, 0.05 eq) and 2-picolinic acid (36.21 mg, 294.11 μmol, 0.1 eq). The mixture was stirred at 120° C. for 16 h. TLC (PE/EtOAc=10/1, $R_f$=0.2) showed the reaction was completed. Water (20 mL) was added, the mixture was extracted with EtOAc (30 mL×3). The combined organic layers were washed with brine (50 mL), dried over $Na_2SO_4$, filtered and concentrated to yield a crude material which was purified by flash silica gel chromatography (from PE/EtOAc=100/1 to 5/1, TLC: PE/EtOAc=10/1, $R_f$=0.2) to yield 3-[3-(trifluoromethyl)phenoxy]phenol (500 mg, 1.77 mmol, 60.2% yield, 90.0% purity) as yellow oil. $^1$H NMR (400 MHz, $CDCl_3$) δ ppm 7.42 (t, J=8.0 Hz, 1H), 7.33 (d, J=8.0 Hz, 1H), 7.24-7.15 (m, 3H), 6.62-6.56 (m, 2H), 6.52 (s, 1H), 4.99 (s, 1H); ES-LCMS m/z 296.1 $[M+MeCN+H]^+$.

Step 2: 1-(3-Fluorosulfonyloxyphenoxy)-3-(trifluoromethyl)benzene

To a solution of 3-[3-(trifluoromethyl)phenoxy]phenol (300 mg, 1.06 mmol, 1 eq) in DCM (10 mL) was added DIEA (273.99 mg, 2.12 mmol, 369.26 μL, 2.0 eq). The mixture was stirred under sulfuryl fluoride (30 psi) at 20° C. for 16 h. TLC (PE/EtOAc=100/1, $R_f$=0.3) showed the reaction was completed. The mixture was concentrated and then water (10 mL) was added. The mixture was extracted with EtOAc (10 mL×3). The combined organic layers were washed with brine (10 mL), dried over $Na_2SO_4$, filtered and concentrated to yield a crude material which was purified by flash silica gel chromatography (from pure PE to PE/EtOAc 100/1, TLC: PE/EtOAc=100/1, $R_f$=0.3) to yield 1-(3-fluorosulfonyloxyphenoxy)-3-(trifluoromethyl)benzene (79.86 mg, 236.31 μmol, 22.3% yield, 99.5% purity) as yellow oil. $^1$H NMR (400 MHz, $CDCl_3$) δ ppm 7.54-7.45 (m, 3H), 7.32 (s, 1H), 7.25-7.23 (m, 1H), 7.15-7.13 (m, 1H), 7.07-7.02 (m, 2H); ES-LCMS m/z 334.87 $[M-H]^-$.

I-18 & I-19

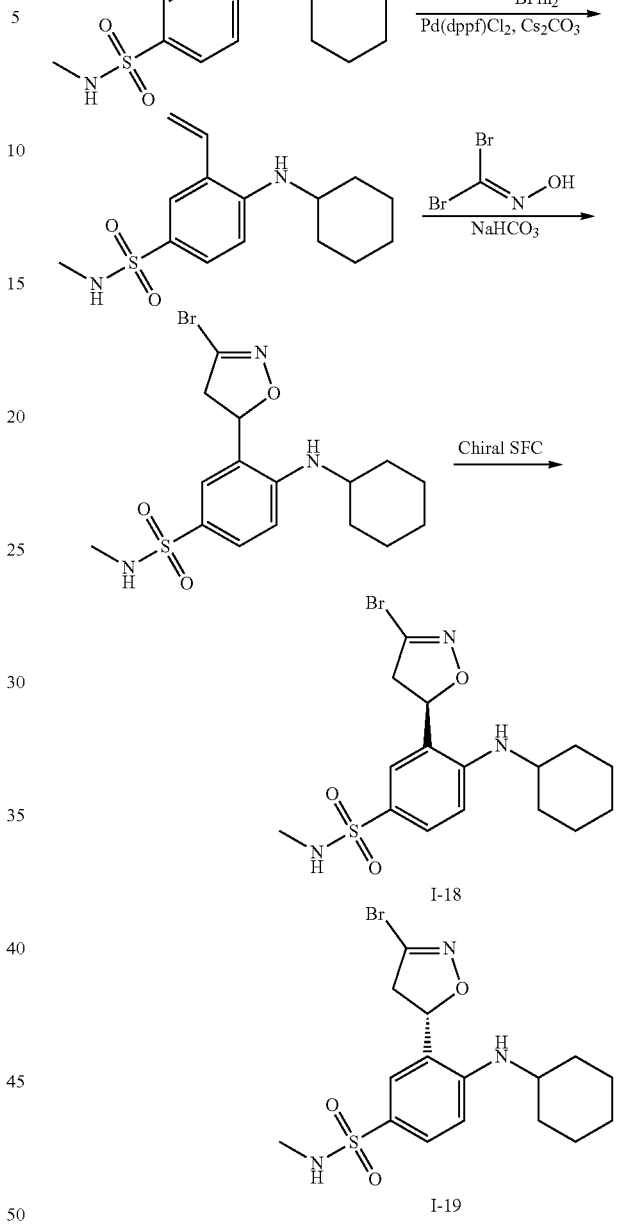

I-18

I-19

Step 1: 3-Bromo-4-fluoro-N-methyl-benzenesulfonamide

To a stirred solution of 3-bromo-4-fluoro-benzenesulfonyl chloride (1.5 g, 5.48 mmol, 1 eq) in THF (20 mL) was added methanamine/EtOH (1.03 g, 10.97 mmol, 1.5 mL, 33% purity, 2 eq). The reaction mixture was stirred at 25° C. for 5 min. TLC (PE/EtOAc=3/1, $R_f$=0.35) showed starting material was remained and one new spot was detected. The reaction mixture was concentrated to yield a residue which was purified by flash silica gel chromatography (from PE/EtOAc=100/1 to 3/1, TLC: PE/EtOAc=3/1, $R_f$=0.35) to yield 3-bromo-4-fluoro-N-methyl-benzenesulfonamide (1.3 g, 4.61 mmol, 84.0% yield, 95.0% purity) as colorless oil. $^1$H NMR (500 MHz, $CDCl_3$) δ ppm 8.10 (dd, J=2.3, 6.3 Hz, 1H), 7.83-7.80 (m, 8.7 Hz, 1H), 7.29-7.25 (m, 1H), 4.48 (d, J=4.6 Hz, 1H), 2.70 (d, J=5.3 Hz, 3H).

Step 2: 3-Bromo-4-(cyclohexylamino)-N-methyl-benzenesulfonamide

To a stirred solution of 3-bromo-4-fluoro-N-methyl-benzenesulfonamide (500 mg, 1.77 mmol, 1 eq) in DMSO (15 mL) was added cyclohexanamine (439.27 mg, 4.43 mmol, 506.94 µL, 2.5 eq). The reaction mixture was stirred at 140° C. for 2 h. The reaction mixture was diluted with water (100 mL), extracted with EtOAc (50 mL×3). The combined organic layers were dried over $Na_2SO_4$, filtered and the filtrate was concentrated to yield a residue which was purified by flash silica gel chromatography (from PE/EtOAc=100/1 to 3/1, TLC: PE/EtOAc=3/1, $R_f$=0.45) to yield 3-bromo-4-(cyclohexylamino)-N-methyl-benzenesulfonamide (600 mg, 1.64 mmol, 92.6% yield, 95.0% purity) as yellow oil. $^1$H NMR (500 MHz, $CDCl_3$) δ ppm 7.90 (d, J=2.3 Hz, 1H), 7.62 (dd, J=2.0, 8.7 Hz, 1H), 6.64 (d, J=8.9 Hz, 1H), 4.77 (d, J=7.5 Hz, 1H), 4.18 (q, J=5.5 Hz, 1H), 3.44-3.33 (m, 1H), 2.65 (d, J=5.5 Hz, 3H), 2.07-2.04 (m, 2H), 1.80 (td, J=3.9, 13.3 Hz, 2H), 1.68 (td, J=3.8, 12.7 Hz, 1H), 1.46-1.38 (m, 2H), 1.36-1.28 (m, 3H); ES-LCMS m/z 347.0, 348.9 [M+H]$^+$.

Step 3: 4-(Cyclohexylamino)-N-methyl-3-vinyl-benzenesulfonamide

To a stirred solution of 3-bromo-4-(cyclohexylamino)-N-methyl-benzenesulfonamide (550 mg, 1.50 mmol, 1 eq) and 4,4,5,5-tetramethyl-2-vinyl-1,3,2-dioxaborolane (278.07 mg, 1.81 mmol, 306.25 µL, 1.2 eq) in water (3 mL) and 1,4-dioxane (9 mL) was added $Cs_2CO_3$ (1.47 g, 4.51 mmol, 3 eq) and Pd(dppf)$Cl_2$ (110.09 mg, 150.46 µmol, 0.1 eq). The reaction mixture was bubbled with $N_2$ for 3 min then stirred at 100° C. for 30 min under microwave. The reaction mixture was filtered through a pad of celite and the filtrate was concentrated to yield a residue which was purified by flash silica gel chromatography (from PE/EtOAc=100/1 to 3/1, TLC: PE/EtOAc=3/1, $R_f$=0.40) to yield 4-(cyclohexylamino)-N-methyl-3-vinyl-benzenesulfonamide (450 mg, 1.50 mmol, 99.5% yield, 97.9% purity) as yellow oil. $^1$H NMR (400 MHz, $CDCl_3$) δ ppm 7.66 (t, J=2.6 Hz, 1H), 7.63-7.58 (m, 1H), 6.67-6.59 (m, 2H), 5.71-5.63 (m, 1H), 5.46-5.40 (m, 1H), 4.27-4.15 (m, 2H), 3.37 (d, J=3.4 Hz, 1H), 2.64 (dd, J=3.3, 5.5 Hz, 3H), 2.09-2.05 (m, 2H), 1.78 (dd, J=3.3, 13.3 Hz, 2H), 1.68 (dd, J=3.5, 9.2 Hz, 1H), 1.45-1.36 (m, 2H), 1.29-1.26 (m, 3H); ES-LCMS m/z 295.0 [M+H]$^+$.

Step 4: 3-[(5S)-3-bromo-4,5-dihydroisoxazol-5-yl]-4-(cyclohexylamino)-N-methyl-benzenesulfonamide & 3-[(5R)-3-bromo-4,5-dihydroisoxazol-5-yl]-4-(cyclohexylamino)-N-methyl-benzenesulfonamide To a stirred solution of 4-(cyclohexylamino)-N-methyl-3-vinyl-benzenesulfonamide (440 mg, 1.46 mmol, 1 eq) and dibromomethanone oxime (445.15 mg, 2.19 mmol, 1.5 eq) in EtOAc (30 mL) was added NaHCO$_3$ (1.23 g, 14.63 mmol, 10 eq). The reaction mixture was stirred at 25° C. for 2 h. The reaction mixture was washed with water (30 mL×2). The organic layer was concentrated to yield a residue which was purified by flash silica gel chromatography (from PE/EtOAc=100/1 to 3/1, TLC: PE/EtOAc=3/1, $R_f$=0.50) to yield a residue which was separated by SFC (column: DAICEL CHIRALPAK IC (250 mm*30 mm, 5 um); mobile phase: [0.1% $NH_3H_2O$ EtOH]; B %: 40%-40%, min), followed by lyophilization to yield 3-[(5S)-3-bromo-4,5-dihydroisoxazol-5-yl]-4-(cyclohexylamino)-N-methyl-benzenesulfonamide (104.74 mg, 246.04 µmol, 16.8% yield, 97.8% purity, SFC: $R_t$=5.614 min, ee=99.9%, $[α]^{24.0}_D$=+63.6, MeOH, c=0.107 g/100 mL) as white solid; $^1$H NMR (400 MHz, $CDCl_3$) δ ppm 7.70 (dd, J=2.0, 8.8 Hz, 1H), 7.55 (d, J=2.2 Hz, 1H), 6.76 (d, J=8.6 Hz, 1H), 5.67 (t, J=11.2 Hz, 1H), 4.66 (d, J=6.8 Hz, 1H), 4.20 (q, J=5.1 Hz, 1H), 3.61-3.34 (m, 3H), 2.64 (d, J=5.4 Hz, 3H), 2.01 (s, 2H), 1.75 (dd, J=4.3, 8.9 Hz, 2H), 1.69-1.60 (m, 1H), 1.49-1.38 (m, 2H), 1.36-1.26 (m, 3H); ES-LCMS m/z 416.0, 418.0 [M+H]$^P$ and 3-[(5R)-3-bromo-4,5-dihydroisoxazol-5-yl]-4-(cyclohexylamino)-N-methyl-benzenesulfonamide (99.78 mg, 236.55 µmol, 16.2% yield, 98.7% purity, SFC: $R_t$=5.904 min, ee=98.1%, $[α]^{24.0}_D$=−69.4, MeOH, c=0.098 g/100 mL) as white solid; $^1$H NMR (400 MHz, $CDCl_3$) δ ppm 7.70 (dd, J=2.1, 8.7 Hz, 1H), 7.55 (d, J=2.2 Hz, 1H), 6.76 (d, J=8.8 Hz, 1H), 5.67 (t, J=11.2 Hz, 1H), 4.66 (d, J=7.1 Hz, 1H), 4.19 (q, J=5.4 Hz, 1H), 3.57-3.38 (m, 3H), 2.64 (d, J=5.6 Hz, 3H), 2.01 (s, 2H), 1.75 (dd, J=4.2, 8.8 Hz, 2H), 1.68-1.61 (m, 1H), 1.48-1.38 (m, 2H), 1.37-1.26 (m, 3H); ES-LCMS m/z 416.0, 417.9 [M+H]$^+$.

I-20 & I-21

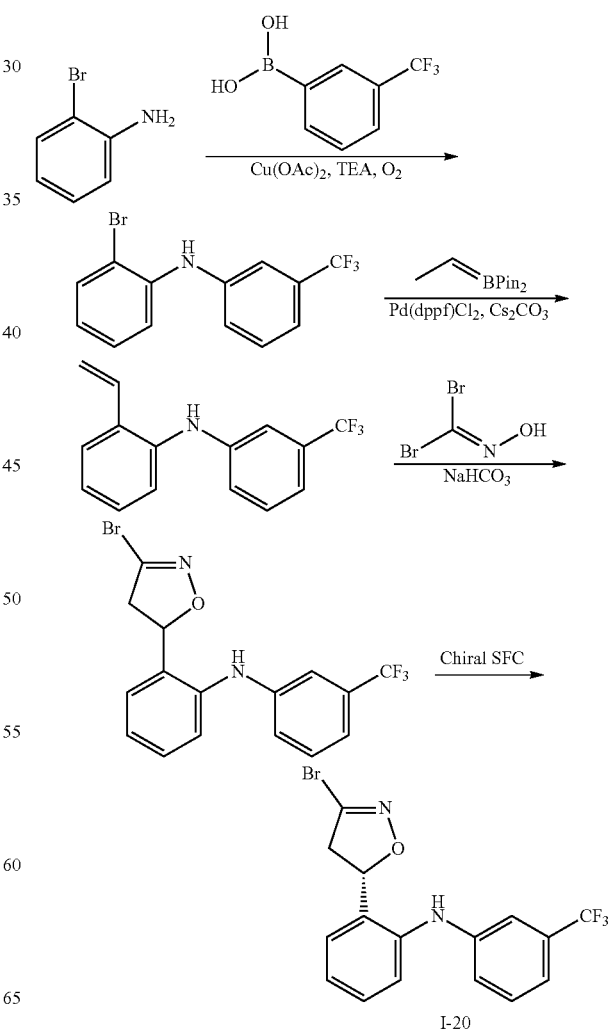

I-20

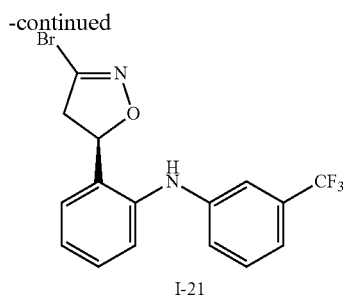

I-21

Step 1: 2-Bromo-N-[3-(trifluoromethyl)phenyl]aniline

To a mixture of 2-bromoaniline (2 g, 11.63 mmol, 1 eq), [3-(trifluoromethyl)phenyl]boronic acid (2.21 g, 11.63 mmol, 1 eq) and Cu(OAc)$_2$ (2.11 g, 11.63 mmol, 1 eq) in DCM (20 mL) was added DIEA (2.25 g, 17.44 mmol, 3.04 mL, 1.5 eq). The mixture was stirred under O$_2$ atmosphere at 20° C. for 17 h. TLC (PE/EA=3/1, R$_f$=0.5) showed starting material disappeared. The reaction mixture was filtered and the filtrate was concentrated under reduced pressure to yield a residue which was purified by flash silica gel chromatography (from pure PE to PE/EtOAc=3/1) to yield 2-bromo-N-[3-(trifluoromethyl)phenyl]aniline (2.4 g, 6.07 mmol, 52.2% yield, 80.0% purity) as light yellow oil. $^1$H NMR (400 MHz, CDCl$_3$) δ ppm 7.55 (dd, J=1.5, 7.8 Hz, 1H), 7.42-7.36 (m, 1H), 7.34 (s, 1H), 7.29-7.21 (m, 4H), 6.86-6.78 (m, 1H), 6.13 (br s, 1H); ES-LCMS m/z 316.0, 318.0 [M+H]$^+$.

Step 2: N-[3-(Trifluoromethyl)phenyl]-2-vinyl-aniline

To a mixture of 2-bromo-N-[3-(trifluoromethyl)phenyl]aniline (2.2 g, 5.57 mmol, 1 eq), 4,4,5,5-tetramethyl-2-vinyl-1,3,2-dioxaborolane (1.29 g, 8.35 mmol, 1.42 mL, 1.5 eq) and Pd(dppf)Cl$_2$ (203.69 mg, 278.38 µmol, 0.05 eq) in 1,4-dioxane (8 mL) was added Cs$_2$CO$_3$ (2 M, 5.57 mL, 2 eq). The mixture was stirred under N$_2$ atmosphere at 100° C. for 0.5 h in microwave. TLC (PE/EA=10/1, R$_f$=0.6) showed starting material disappeared. The reaction mixture was concentrated under reduced pressure to remove solvent. The residue was diluted with H$_2$O (20 mL) and extracted with EtOAc (20 mL×2). The combined organic layers were washed with brine (30 mL), dried over Na$_2$SO$_4$, filtered and concentrated under reduced pressure to yield a residue which was purified by flash silica gel chromatography (pure PE) to yield N-[3-(trifluoromethyl)phenyl]-2-vinyl-aniline (570 mg, 1.95 mmol, 35.0% yield, 90.0% purity) as light yellow oil. $^1$H NMR (400 MHz, CDCl$_3$) δ ppm 7.54 (d, J=7.8 Hz, 1H), 7.34-7.28 (m, 1H), 7.27-7.22 (m, 2H), 7.16-7.07 (m, 3H), 7.02 (d, J=7.0 Hz, 1H), 6.86 (dd, J=11.0, 17.6 Hz, 1H), 5.72 (dd, J=1.4, 17.4 Hz, 1H), 5.64 (br s, 1H), 5.33 (dd, J=1.4, 11.2 Hz, 1H); ES-LCMS m/z 264.0 [M+H]$^+$.

Step 3: 2-[(5R)-3-Bromo-4,5-dihydroisoxazol-5-yl]-N-[3-(trifluoromethyl)phenyl]aniline and 2-[(5S)-3-bromo-4,5-dihydroisoxazol-5-yl]-N-[3-(trifluoromethyl)phenyl]aniline To a mixture of N-[3-(trifluoromethyl)phenyl]-2-vinyl-aniline (500.19 mg, 1.71 mmol, 1 eq) in EtOAc (10 mL) was added dibromomethanone oxime (416.21 mg, 2.05 mmol, 1.2 eq) and NaHCO$_3$ (287.19 mg, 3.42 mmol, 2.0 eq). The mixture was stirred at 20° C. for 4 h. TLC (PE/EtOAc=3/1, R$_f$=0.5) indicated Reactant 1 was consumed completely and one new spot formed. The reaction mixture was diluted with water (10 mL) and extracted with EtOAc (10 mL×3). The combined organic layers were washed with brine (20 mL), dried over Na$_2$SO$_4$, filtered and concentrated under reduced pressure to yield a crude material which was purified on silica gel column chromatography (from PE/EtOAc=100/1 to 3/1, TLC (PE/EtOAc=3/1, R$_f$=0.5). The desired fraction was concentrated under reduced pressure to yield a reside which was separated by chiral SFC (column: DAICEL CHIRALPAK AS (250 mm*30 mm, 10 um); mobile phase: [0.1% NH$_3$·H$_2$O/EtOH]; B %: 20%-20%) to yield peak 1 and peak 2. Peak 1 was concentrated under reduced pressure to yield a residue which was lyophilized to yield 2-[(5R)-3-bromo-4,5-dihydroisoxazol-5-yl]-N-[3-(trifluoromethyl)phenyl]aniline (28.52 mg, 74.04 µmol, 4.3% yield, 100.0% purity, SFC: R$_t$=2.28, ee=99.9%, [α]$^{24.2}_D$=−19.2 (EtOH, c=0.104 g/100 mL) as a white solid. $^1$H NMR (400 MHz, CD$_3$OD) δ ppm 7.48 (d, J=12.0 Hz, 1H), 7.45-7.18 (m, 4H), 7.00-6.95 (m, 3H), 5.88-5.83 (m, 1H), 3.63 (q, J=10.8 Hz, 1H), 3.06 (q, J=8.8 Hz, 1H); ES-LCMS m/z 384.9, 386.9 [M+H]$^+$. Peak 2 was concentrated under reduced pressure to yield a residue which was lyophilized to yield 2-[(5S)-3-bromo-4,5-dihydroisoxazol-5-yl]-N-[3-(trifluoromethyl)phenyl]aniline (26.28 mg, 68.23 µmol, 4.0% yield, 100.0% purity, SFC: R$_t$=2.579, ee=99.5% and [α]$^{24.2}_D$=−9.3 (EtOH, c=0.108 g/100 mL)) as a white solid. $^1$H NMR (400 MHz, CD$_3$OD) δ ppm 7.46 (d, J=16.0 Hz, 1H), 7.32-7.18 (m, 4H), 7.00-6.95 (m, 3H), 5.88-5.83 (m, 1H), 3.65 (q, J=12.0 Hz, 1H), 3.08 (q, J=12.0 Hz, 1H); ES-LCMS m/z 384.9, 386.9 [M+H]$^+$.

I-13

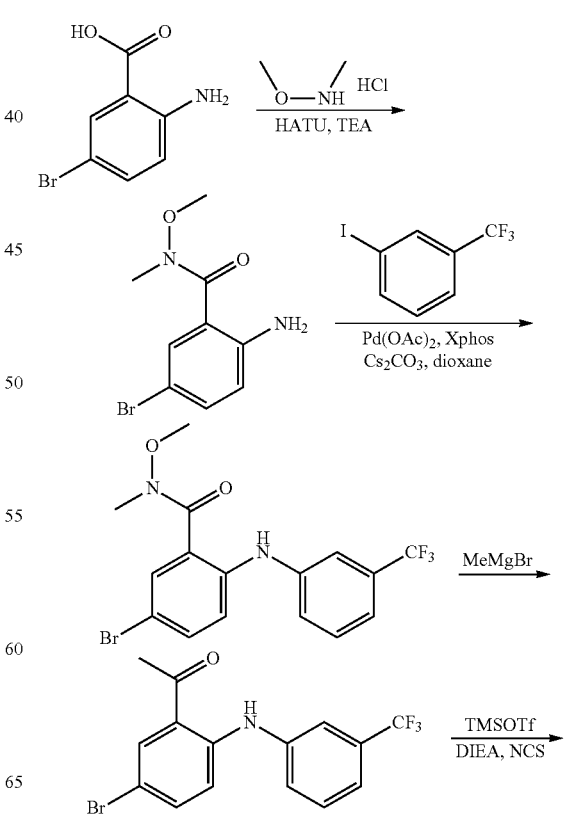

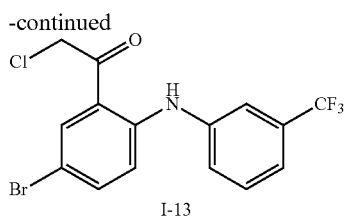

I-13

Step 1:
2-Amino-5-bromo-N-methoxy-N-methyl-benzamide

To a solution of 2-amino-5-bromo-benzoic acid (3.5 g, 16.20 mmol, 1 eq) in DMF (50 mL) was added N-methoxymethanamine (4.74 g, 48.60 mmol, 3 eq, HCl), HATU (7.39 g, 19.44 mmol, 1.2 eq) and TEA (4.92 g, 48.60 mmol, 6.77 mL, 3 eq). The mixture was stirred at 15° C. for 12 h. TLC (PE/EtOAc=1/1, $R_f$=0.39) indicated the starting material was consumed completely and one new spot formed. The reaction mixture was quenched by addition of water (200 mL) and extracted with EtOAc (200 mL×3). The combined organic layers were washed with brine (200 mL), dried over $Na_2SO_4$, concentrated under reduced pressure to yield a residue which was purified by flash silica gel chromatography (from pure PE to PE/EtOAc=2/1) to yield 2-amino-5-bromo-N-methoxy-N-methyl-benzamide (3.5 g, 12.89 mmol, 79.5% yield, 95.4% purity) as a yellow solid. $^1$H NMR (400 MHz, $CD_3OD$) δ ppm 7.37 (d, J=2.3 Hz, 1H), 7.26 (dd, J=2.3, 9.0 Hz, 1H), 6.71 (d, J=8.6 Hz, 1H), 3.60 (s, 3H), 3.32 (s, 3H); ES-LCMS m/z 258.9, 260.9 [M+H]$^+$.

Step 2: 5-Bromo-N-methoxy-N-methyl-2-[3-(trifluoromethyl)anilino]benzamide

A mixture of 2-amino-5-bromo-N-methoxy-N-methyl-benzamide (3.5 g, 12.89 mmol, 1 eq), 1-iodo-3-(trifluoromethyl)benzene (5.26 g, 19.33 mmol, 2.78 mL, 1.5 eq), $Cs_2CO_3$ (8.40 g, 25.77 mmol, 2 eq), XPhos (614.35 mg, 1.29 mmol, 0.1 eq) and Pd(OAc)$_2$ (144.66 mg, 644.35 μmol, 0.05 eq) in 1,4-dioxane (200 mL) was degassed and purged with $N_2$ for 3 times and the mixture was stirred under $N_2$ atmosphere at 90° C. for 12 h. The reaction mixture was quenched by addition of water (300 mL) and extracted with EtOAc (300 mL×3). The combined organic layers were washed with brine (100 mL), dried over $Na_2SO_4$, filtered and concentrated under reduced pressure to yield a residue which was purified by flash silica gel chromatography (from PE/EtOAc=1/0 to 5/1, TLC:PE/EtOAc=3/1, $R_f$=0.60) to yield 5-bromo-N-methoxy-N-methyl-2-[3-(trifluoromethyl)anilino]benzamide (1 g, 2.29 mmol, 17.8% yield, 92.3% purity) as a yellow oil. $^1$H NMR (400 MHz, DMSO-d$_6$) δ ppm 8.13 (s, 1H), 7.57-7.52 (m, 2H), 7.43-7.37 (m, 1H), 7.27-7.20 (m, 3H), 7.12 (d, J=7.7 Hz, 1H), 3.47 (s, 3H), 3.19-3.14 (m, 3H); ES-LCMS m/z 402.9, 404.9 [M+H]$^+$.

Step 3: 1-[5-Bromo-2-[3-(trifluoromethyl)anilino]phenyl]ethanone

To a solution of 5-bromo-N-methoxy-N-methyl-2-[3-(trifluoromethyl)anilino]benzamide (700 mg, 1.60 mmol, 1 eq) in THF (10 mL) was added MeMgBr (3 M, 4.27 mL, 8 eq) at −70° C. under $N_2$ atmosphere. After being stirred for 1 h, the mixture was stirred at 0° C. for 1 h. TLC (PE/EtOAc=10/1, $R_f$=0.85) indicated starting material was consumed completely and one new spot formed. The reaction mixture was quenched by addition of water (50 mL) and extracted with EtOAc (50 mL×3). The combined organic layers were washed with brine (40 mL), dried over $Na_2SO_4$, filtered and concentrated under reduced pressure to yield a residue which was purified by flash silica gel chromatography (from PE/EtOAc=1/0 to 20/1, TLC: PE/EtOAc=10/1, $R_f$=0.85) to yield 1-[5-bromo-2-[3-(trifluoromethyl)anilino]phenyl]ethanone (450 mg, 1.26 mmol, 78.4% yield, 100.0% purity) as a yellow solid. $^1$H NMR (400 MHz, $CD_3OD$) δ ppm 8.06 (d, J=2.3 Hz, 1H), 7.57-7.45 (m, 4H), 7.38 (d, J=7.8 Hz, 1H), 7.20 (d, J=9.0 Hz, 1H), 2.63 (s, 3H); ES-LCMS m/z 357.9, 359.9 [M+H]$^+$.

Step 4: 1-[5-Bromo-2-[3-(trifluoromethyl)anilino]phenyl]-2-chloro-ethanone

To a solution of 1-[5-bromo-2-[3-(trifluoromethyl)anilino]phenyl]ethanone (300 mg, 837.63 μmol, 1 eq) in DCM (10 mL) was added dropwise DIEA (324.77 mg, 2.51 mmol, 437.70 μL, 3 eq) and TMSOTf (558.52 mg, 2.51 mmol, 454.08 μL, 3 eq) at 0° C. After addition, the mixture was stirred at 25° C. for 2 h and then NCS (167.77 mg, 1.26 mmol, 1.5 eq) was added. The resulting mixture was stirred at 25° C. for 2 h. TLC (PE/EtOAc=10/1, $R_f$=0.78) indicated starting material was consumed completely and one new spot formed. The reaction mixture was quenched by addition of water (50 mL) and extracted with EtOAc (50 mL×3). The combined organic layers were washed with brine (30 mL), dried over $Na_2SO_4$, filtered and concentrated under reduced pressure to yield a residue which was purified by flash silica gel chromatography (from pure PE to PE/EtOAc=25/1, TLC: PE/EtOAc=10/1, $R_f$=0.78) to yield 1-[5-bromo-2-[3-(trifluoromethyl)anilino]phenyl]-2-chloro-ethanone (180 mg, 443.78 μmol, 52.9% yield, 96.8% purity) as a yellow solid. $^1$H NMR (400 MHz, $CD_3OD$) δ ppm 8.05 (d, J=2.3 Hz, 1H), 7.62-7.47 (m, 4H), 7.42 (d, J=7.0 Hz, 1H), 7.21 (d, J=9.0 Hz, 1H), 4.90 (s, 2H); ES-LCMS m/z 391.9, 393.9, 395.9 [M+H]$^+$.

I-23 & I-24

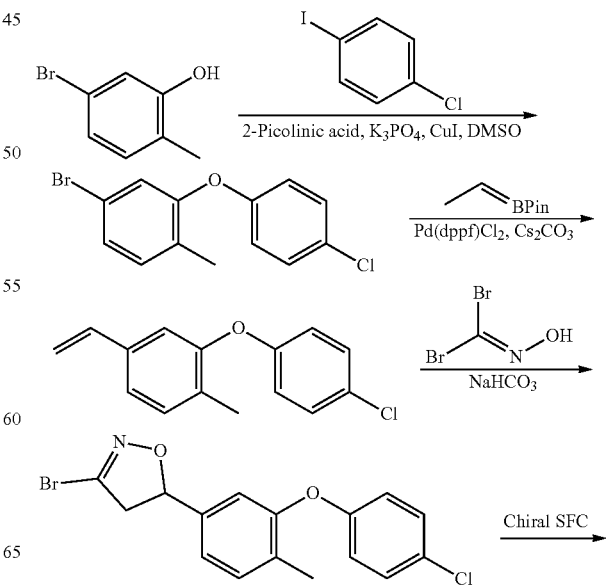

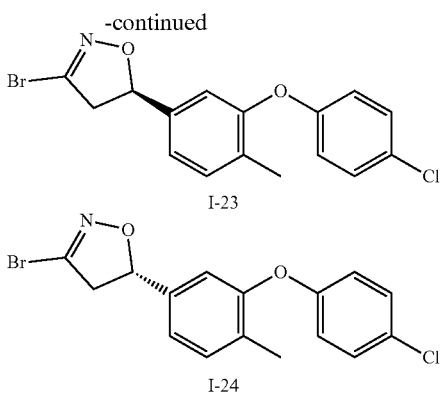

Step 1:
4-Bromo-2-(4-chlorophenoxy)-1-methylbenzene

To a solution of 1-chloro-4-iodo-benzene (6 g, 25.16 mmol, 1 eq) in DMSO (100 mL) was added $K_3PO_4$ (10.68 g, 50.32 mmol, 2.0 eq) and 5-bromo-2-methyl-phenol (5.18 g, 27.68 mmol, 1.1 eq), CuI (239.61 mg, 1.26 mmol, 0.05 eq) and 2-Picolinic acid (309.77 mg, 2.52 mmol, 0.1 eq). The mixture was stirred at 120° C. for 16 h. TLC (PE/EtOAc=100/1, $R_f$=0.5) showed the reaction was completed. To the mixture was added water (100 mL). The mixture was extracted with EtOAc (100 mL×3). The combined organic layers were washed with brine (100 mL), dried over $Na_2SO_4$, filtered and concentrated to yield a crude material which was purified by flash silica gel chromatography (from PE/EtOAc=1/0 to 100/1, TLC: PE/EtOAc=100/1, $R_f$=0.6) to yield 4-bromo-2-(4-chlorophenoxy)-1-methyl-benzene (7 g, 21.17 mmol, 84.1% yield, 90.0% purity) as yellow oil. $^1$H NMR (400 MHz, $CDCl_3$) δ ppm 7.29-7.28 (m, 2H), 7.27 (s, 1H), 7.26-7.25 (m, 1H), 7.21-6.98 (m, 1H), 6.99-6.88 (m, 2H), 2.18 (s, 3H).

Step 2:
2-(4-Chlorophenoxy)-1-methyl-4-vinylbenzene

To a mixture of 4-bromo-2-(4-chlorophenoxy)-1-methylbenzene (3 g, 9.07 mmol, 1 eq) in DMF (20 mL) was added 4,4,5,5-tetramethyl-2-vinyl-1,3,2-dioxaborolane (1.68 g, 10.89 mmol, 1.85 mL, 1.2 eq), cyclopentyl(diphenyl)phosphane;dichloropalladium;iron (663.90 mg, 907.34 μmol, 0.1 eq) and $Cs_2CO_3$ (5.91 g, 18.15 mmol, 2.0 eq). The mixture was stirred under $N_2$ atmosphere at 100° C. for 4 h. TLC (PE/EtOAc=3/1, $R_f$=0.5) showed the reaction was completed. The reaction mixture was concentrated under reduced pressure to remove solvent. The residue was diluted with $H_2O$ (20 mL) and extracted with EtOAc (20 mL×2). The combined organic layers were washed with brine (30 mL), dried over $Na_2SO_4$, filtered and concentrated under reduced pressure to yield a residue which was purified by flash silica gel chromatography (from pure PE to PE/EtOAc=3/1, TLC: PE/EtOAc=3/1, $R_f$=0.5) to yield 2-(4-chlorophenoxy)-1-methyl-4-vinyl-benzene (1.5 g, 5.52 mmol, 60.8% yield, 90.0% purity) as yellow oil. $^1$H NMR (400 MHz, $CD_3OD$) δ ppm 7.31-7.24 (m, 3H), 7.20-7.19 (m, 1H), 6.97-6.88 (m, 1H), 6.86-6.84 (m, 2H), 6.64 (s, 1H), 5.67 (d, J=8.0 Hz, 1H), 5.17 (d, J=8.0 Hz, 1H), 2.17 (s, 3H).

Step 3: (R)-3-Bromo-5-(3-(4-chlorophenoxy)-4-methylphenyl)-4,5-dihydroisoxazole and (S)-3-bromo-5-(3-(4-chlorophenoxy)-4-methylphenyl)-4,5-dihydroisoxazole To a mixture of 2-(4-chlorophenoxy)-1-methyl-4-vinylbenzene (500 mg, 1.84 mmol, 1 eq) in EtOAc (10 mL) was added $NaHCO_3$ (1.54 g, 18.40 mmol, 10 eq) and dibromomethanone oxime (447.86 mg, 2.21 mmol, 1.2 eq). The mixture was stirred at 20° C. for 4 h. TLC (PE/EtOAc=3/1, $R_f$=0.5) indicated Reactant 1 was consumed completely and one new spot formed. The reaction mixture was diluted with water (10 mL) and extracted with EtOAc (10 mL×3). The combined organic layers were washed with brine (20 mL), dried over $Na_2SO_4$, filtered and concentrated under reduced pressure to yield a crude material which was purified by flash silica gel chromatography (from PE/EtOAc=100/1 to 3/1, TLC PE/EtOAc=3/1, $R_f$=0.5). The desired fraction was concentrated under reduced pressure to yield a reside which was separated by chiral SFC (column: DAICEL CHIRALPAK AS-H (250 mm*30 mm, 5 um); mobile phase: [0.1% $NH_3·H_2O$/EtOH]; B %: 25%-25%) to yield peak 1 and peak 2. Peak 1 was concentrated under reduced pressure to yield a residue which was lyophilized to yield (5R)-3-bromo-5-[3-(4-chlorophenoxy)-4-methyl-phenyl]-4,5-dihydroisoxazole (25.1 mg, 65.79 μmol, 3.6% yield, 96.1% purity, SFC: $R_t$=2.674, ee=98.0%, $[α]^{24.2}_D$=145 (MeOH, c=0.04 g/100 mL) as a white solid. $^1$H NMR (400 MHz, $CD_3OD$) δ ppm 7.34-7.32 (m, 3H), 7.25-7.23 (m, 1H), 6.90-6.85 (m, 3H), 5.65-5.60 (m, 1H), 3.63 (q, J=11.8 Hz, 1H), 3.17 (q, J=9.8 Hz, 1H), 2.20 (s, 3H); ES-LCMS m/z 365.9, 367.9 [M+H]$^+$. Peak 2 was concentrated under reduced pressure to yield a residue which was lyophilized to yield (5S)-3-bromo-5-[3-(4-chlorophenoxy)-4-methyl-phenyl]-4,5-dihydroisoxazole (23.28 mg, 62.35 μmol, 3.4% yield, 98.2% purity, SFC: $R_t$=2.674, ee=98.6%, $[α]^{24.2}_D$=−185 (MeOH, c=0.04 g/100 mL) as a white solid. $^1$H NMR (400 MHz, $CD_3OD$) δ ppm 7.32-7.29 (m, 3H), 7.25-7.24 (m, 1H), 6.89-6.84 (m, 3H), 5.64-5.59 (m, 1H), 3.62 (q, J=11.8 Hz, 1H), 3.16 (q, J=9.8 Hz, 1H), 2.19 (s, 3H); ES-LCMS m/z 365.9, 367.9 [M+H]$^+$.

I-5

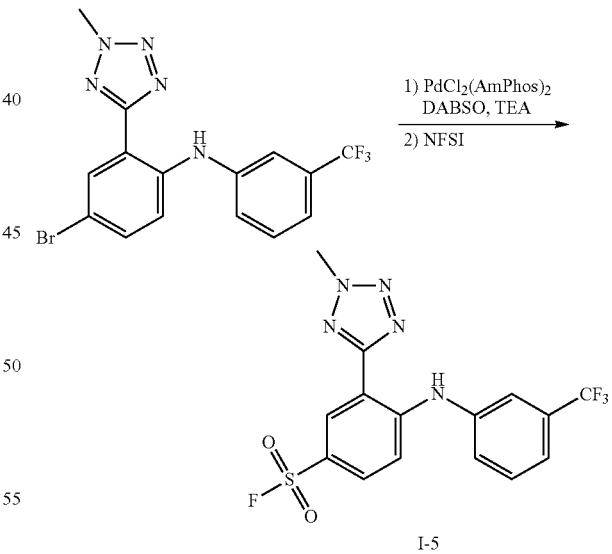

Step 1: 3-(2-Methyltetrazol-5-yl)-4-[3-(trifluoromethyl)anilino]benzenesulfonyl Fluoride To a solution of 4-bromo-2-(2-methyltetrazol-5-yl)-N-[3-(trifluoromethyl)phenyl]aniline (60 mg, 135.62 μmol, 1 eq) in i-PrOH (4 mL) was added 1,4-diazoniabicyclo[2.2.2]octane-1,4-disulfinate (97.77 mg, 406.85 μmol, 3 eq), 4-di-tert-butylphosphanyl-N,N-dimethyl-aniline;dichloropalladium (28.81 mg, 40.69 μmol, 28.81 μL, 0.3 eq), N-cyclohexyl-N-methyl-cyclohexanamine (158.95 mg, 813.70 μmol, 172.59 μL, 6 eq) and stirred at 110° C. in microwave (5 bar) for 1 h under N₂ atmosphere. To the mixture was added NFSI (256.59 mg, 813.70 μmol, 6.00 eq) and stirred at 25° C. for 11 h. The reaction was carried out for 4 times in parallel. TLC (PE/EtOAc=4:1, R$_f$=0.35) showed starting material was consumed completely and two major new spots were detected. The reaction mixture was concentrated, diluted with H₂O (15 mL) and extracted with EtOAc (10 mL×2). The combine organic layers were dried over anhydrous Na₂SO₄, filtered and concentrated to yield a residue which was purified by preparative TLC (PE/EtOAc=4/1, TLC: PE/EtOAc=4/1, R$_f$=0.35) and then by flash silica gel chromatography (from pure PE to PE/EtOAc=8/1, TLC: PE/EtOAc=4/1, R$_f$=0.35) to yield 3-(2-methyltetrazol-5-yl)-4-[3-(trifluoromethyl)anilino] benzenesulfonyl fluoride (48.29 mg, 120.32 μmol, 22.2% yield, 100.0% purity) as a white solid. ¹H NMR (500 MHz, DMSO-d₆) δ ppm 9.53 (s, 1H), 8.56 (d, J=2.4 Hz, 1H), 8.01 (dd, J=2.4, 9.1 Hz, 1H), 7.76-7.71 (m, 2H), 7.71-7.67 (m, 1H), 7.60 (d, J=7.5 Hz, 1H), 7.41 (d, J=9.0 Hz, 1H), 4.51 (s, 3H); ES-LCMS m/z 402.0 [M+H]⁺, 443.1 [M+ACN+H]⁺.

I-29

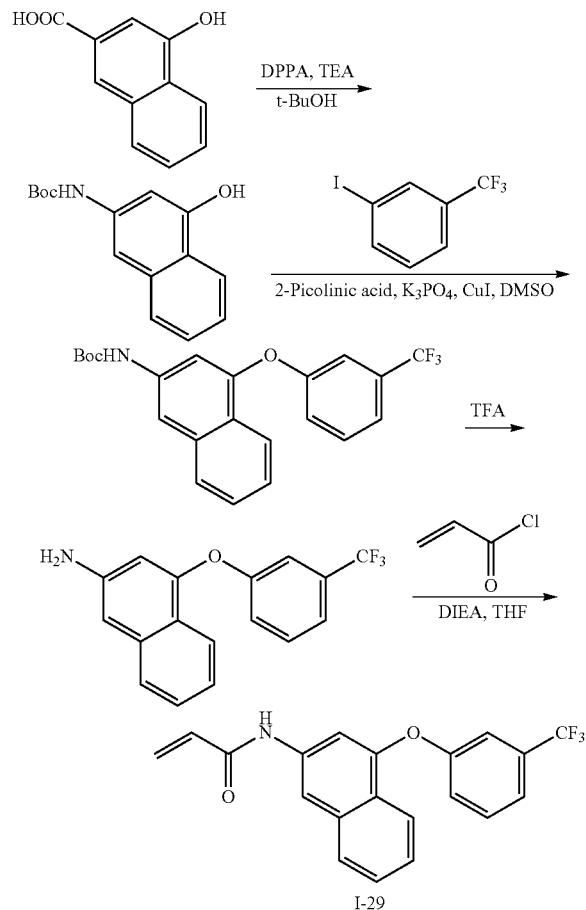

I-29

Step 1: tert-Butyl N-(4-hydroxy-2-naphthyl)carbamate

To a solution of 4-hydroxynaphthalene-2-carboxylic acid (2 g, 10.63 mmol, 1 eq) in toluene (20 mL) was added DPPA (3.51 g, 12.75 mmol, 2.76 mL, 1.2 eq), t-BuOH (3.94 g, 53.14 mmol, 5.08 mL, 5 eq) and TEA (2.15 g, 21.26 mmol, 2.96 mL, 2 eq) under N₂. The mixture was stirred at 90° C. for 12 h. The reaction mixture was quenched by addition of sat. aq. NaHCO₃ (100 mL), extracted with EtOAc (100 mL×3). The combined organic layers were washed with brine (10 mL), dried over Na₂SO₄, filtered and concentrated under reduced pressure to yield a residue which was purified by flash silica gel chromatography (from PE/EtOAc=1/0 to 5/1, TLC: PE/EtOAc=5/1, R$_f$=0.72) to yield tert-butyl N-(4-hydroxy-2-naphthyl)carbamate (1.0 g, 2.31 mmol, 21.7% yield, 60.0% purity) as a brown solid. ¹H NMR (400 MHz, CDCl₃) δ ppm 8.07 (d, J=8.2 Hz, 1H), 7.67 (d, J=8.2 Hz, 1H), 7.45-7.40 (m, 1H), 7.33 (d, J=7.0 Hz, 2H), 7.26-7.21 (m, 1H), 7.09 (s, 1H), 6.59 (br s, 1H), 1.55 (s, 9H); ES-LCMS m/z 260.0 [M+H]⁺.

Step 2: tert-Butyl N-[4-[3-(trifluoromethyl)phenoxy]-2-naphthyl]carbamate

A mixture of tert-butyl N-(4-hydroxy-2-naphthyl)carbamate (700 mg, 1.62 mmol, 1 eq), 1-iodo-3-(trifluoromethyl)benzene (352.46 mg, 1.30 mmol, 186.49 μL, 0.8 eq), 2-Picolinic acid (19.94 mg, 161.97 μmol, 0.1 eq), K₃PO₄ (687.65 mg, 3.24 mmol, 2 eq) and CuI (15.42 mg, 80.99 μmol, 0.05 eq) in DMSO (30 mL) was degassed and purged with N₂ for 3 times, and then the mixture was stirred at 120° C. for 12 h under N₂ atmosphere. The reaction mixture was quenched by addition of water (100 mL), extracted with EtOAc (100 mL×3). The combined organic layers were washed with brine (30 mL), dried over Na₂SO₄, filtered and concentrated under reduced pressure to yield a residue which was purified by flash silica gel chromatography (from PE/EtOAc=1/0 to 10/1, TLC: PE/EtOAc=5/1, R$_f$=0.72) to yield tert-butyl N-[4-[3-(trifluoromethyl)phenoxy]-2-naphthyl]carbamate (150 mg, 167.33 μmol, 10.3% yield, 45.0% purity) as brown oil. ES-LCMS m/z 404.0 [M+H]⁺.

Step 3: 4-[3-(Trifluoromethyl)phenoxy]naphthalen-2-amine

To a solution of tert-butyl N-[4-[3-(trifluoromethyl)phenoxy]-2-naphthyl]carbamate (150 mg, 173.28 μmol, 1 eq) in DCM (5 mL) was added TFA (2.31 g, 20.26 mmol, 1.5 mL, 116.92 eq). The mixture was stirred at 20° C. for 2 h. The reaction mixture was concentrated to yield 4-[3-(trifluoromethyl)phenoxy]naphthalen-2-amine (78 mg, 117.76 μmol, 67.9% yield, 63.0% purity, TFA) as brown oil, which was used in the next step without further purification, ES-LCMS m/z 304.0 [M+H]⁺.

Step 4: N-[4-[3-(Trifluoromethyl)phenoxy]-2-naphthyl]prop-2-enamide

To a solution of 4-[3-(trifluoromethyl)phenoxy]naphthalen-2-amine (78 mg, 117.76 μmol, 1 eq, TFA) and TEA (119.16 mg, 1.18 mmol, 163.90 μL, 10 eq) in THF (5 mL) was added prop-2-enoyl chloride (21.32 mg, 235.51 μmol, 19.20 μL, 2 eq). The mixture was stirred at 20° C. for 2 h. The reaction mixture was concentrated to yield a residue which was purified by preparative HPLC (column: Welch Xtimate C18 150*25 mm*5 μm; mobile phase: [water (10 mM NH₄HCO₃)-ACN]; B %: 53%-83%, 10 min), followed by lyophilization to yield N-[4-[3-(trifluoromethyl)phenoxy]-2-naphthyl]prop-2-enamide (19.39 mg, 54.26 μmol, 46.0% yield, 100% purity) as a white solid. ¹H NMR (400 MHz, DMSO-d₆) δ ppm 10.34 (s, 1H), 8.25 (s, 1H), 8.01 (d, J=8.3 Hz, 1H), 7.92 (d, J=8.3 Hz, 1H), 7.71-7.64 (m, 1H), 7.60-7.54 (m, 2H), 7.53-7.43 (m, 2H), 7.39 (d, J=8.1 Hz, 1H), 7.25 (d, J=1.7 Hz, 1H), 6.47-6.36 (m, 1H), 6.32-6.23 (m, 1H), 5.83-5.73 (m, 1H); ES-LCMS m/z 358.0 [M+H]⁺.

I-25 & I-26

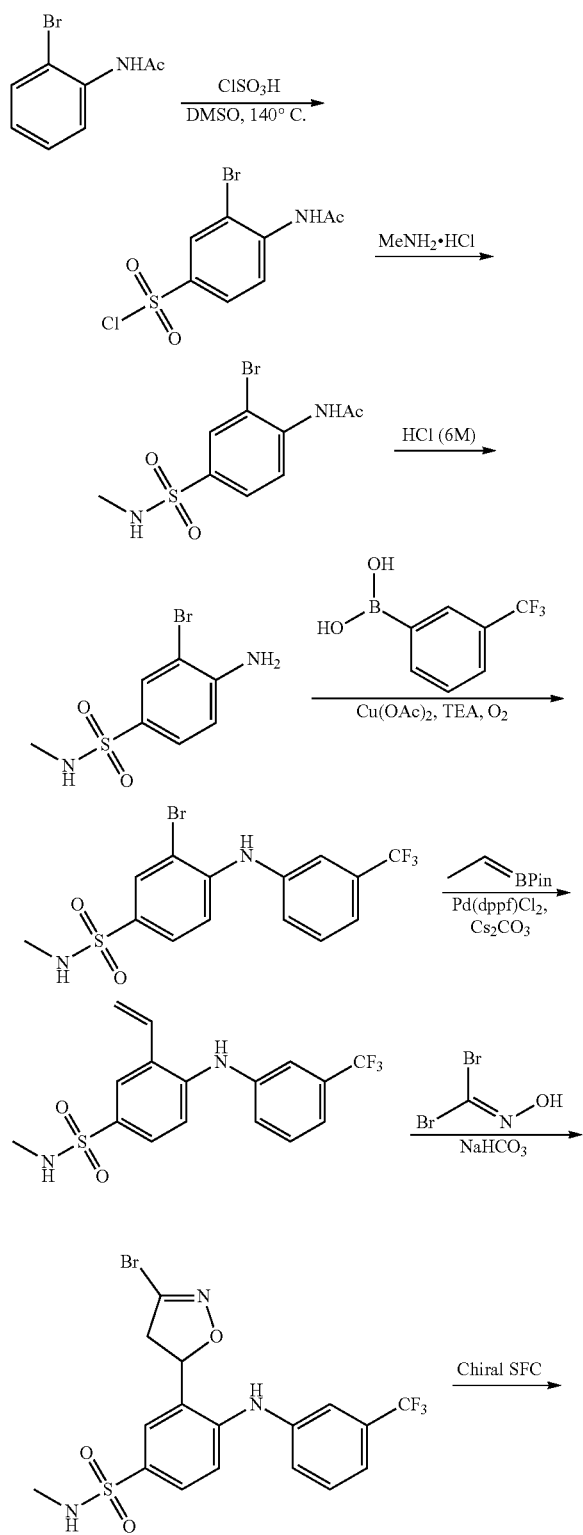

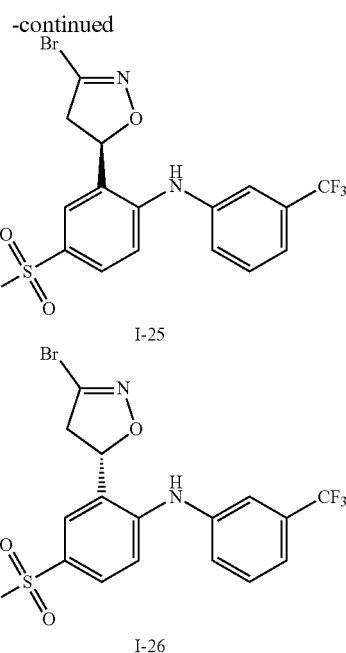

Step 1: 4-Acetamido-3-bromobenzenesulfonyl Chloride

Chlorosulfonic acid (13.470 g, 115.60 mmol, 7.70 mL, 4.95 eq) was added into N-(2-bromophenyl)acetamide (5. g, 23.36 mmol, 1 eq) at 0° C. The mixture was stirred at 80° C. for 4 h. TLC (PE/EtOAc=3/1, $R_f$=0.5) indicated starting material was consumed completely and one new spot formed. The reaction mixture was quenched by addition ice water (50 mL) at 0° C., then diluted with $H_2O$ (20 mL) and extracted with EtOAc (20 mL×3). The combined organic layers were washed with brine (20 mL), dried over $Na_2SO_4$, filtered and concentrated under reduced pressure to yield 4-acetamido-3-bromo-benzenesulfonyl chloride (4.5 g, crude) as yellow oil, which was used in the next step without further purification.

Step 2: N-(2-Bromo-4-(N-methylsulfamoyl)phenyl)acetamide

To a solution of 4-acetamido-3-bromo-benzenesulfonyl chloride (4.5 g, 14.40 mmol, 1 eq) in DCM (40 mL) was added $MeNH_2$/EtOH (2.71 g, 28.79 mmol, 14.40 mL, 33% purity, 2.0 eq) at 0° C. The mixture was stirred at 20° C. for 4 h. TLC (PE/EtOAc=3:1, $R_f$=0.1) showed the reaction was completed. The mixture was concentrated and then water (20 mL) was added. The mixture was extracted with EtOAc (20 mL×3). The combined organic layers were washed with brine (50 mL), dried over $Na_2SO_4$, filtered and concentrated to yield N-[2-bromo-4-(methylsulfamoyl)phenyl]acetamide (3.3 g, 9.67 mmol, 67.2% yield, 90.0% purity) as a yellow solid, which was used in the next step without further purification. ¹H NMR (400 MHz, DMSO-$d_6$) δ ppm 9.66 (s, 1H), 7.99-7.93 (m, 2H), 7.75 (dd, J=2.0, 8.5 Hz, 1H), 7.55 (q, J=4.9 Hz, 1H), 2.44 (d, J=4.9 Hz, 3H), 2.15 (s, 3H).

Step 3: 4-Amino-3-bromo-N-methylbenzenesulfonamide

To a solution of N-[2-bromo-4-(methylsulfamoyl)phenyl] acetamide (3.0 g, 8.79 mmol, 1 eq) in HCl (20 mL) was added H₂O (20 mL). The mixture was stirred at 100° C. for 16 h. TLC (PE/EtOAc=3:1, $R_f$=0.1) showed the reaction was completed. The mixture was concentrated and then water (20 mL) was added. The mixture was extracted with EtOAc (20 mL×3). The combined organic layers were washed with brine (50 mL), dried over Na₂SO₄, filtered and concentrated to yield 4-amino-3-bromo-N-methyl-benzenesulfonamide (2.5 g, 8.49 mmol, 96.6% yield, 90.0% purity) as yellow solid, which was used in the next step without further purification. ¹H NMR (400 MHz, DMSO-d₆) δ ppm 7.68 (d, J=4.9 Hz, 1H), 7.43 (dd, J=1.8, 8.5 Hz, 1H), 7.12 (q, J=4.9 Hz, 1H), 6.86 (q, J=8.5 Hz, 1H), 6.15 (s, 2H), 2.36 (d, J=5.0 Hz, 3H).

Step 4: 3-Bromo-N-methyl-44(3-(trifluoromethyl) phenyl)amino)benzenesulfonamide

To a mixture of 4-amino-3-bromo-N-methyl-benzenesulfonamide (2.5 g, 8.49 mmol, 1 eq) in DCM (20 mL) was added [3-(trifluoromethyl)phenyl]boronic acid (2.42 g, 12.73 mmol, 1.5 eq) and Cu(OAc)₂ (1.85 g, 10.18 mmol, 1.2 eq), DIEA (3.29 g, 25.46 mmol, 4.43 mL, 3.0 eq). The mixture was stirred under O₂ (30 psi) at 20° C. for 16 h. TLC (PE/EtOAc=3/1, $R_f$=0.3) showed the reaction was completed. The mixture was concentrated and diluted with water (20 mL). The mixture was extracted with DCM (20 mL×3). The combined organic layers were washed with brine (50 mL), dried over Na₂SO₄, filtered and concentrated to yield the residue to yield a residue which was purified by flash silica gel chromatography (from PE/EtOAc=20/1 to 3/1, TLC: PE/EtOAc=3/1, $R_f$=0.3) to yield 3-bromo-N-methyl-4-[3-(trifluoromethyl)anilino]benzenesulfonamide (1.5 g, 3.30 mmol, 38.9% yield, 90.0% purity) as yellow oil. ¹H NMR (400 MHz, CD₃OD) δ ppm 7.96 (d, J=2.0 Hz, 1H), 7.62-7.60 (m, 2H), 7.24-7.22 (m, 1H), 7.13-7.12 (m, 1H), 6.77-6.75 (m, 1H), 2.52 (q, J=10.8 Hz, 1H), 2.51 (q, J=2.4 Hz, 3H); ES-LCMS m/z 408.9, 410.9 [M+H]⁺.

Step 4: N-Methyl-4-((3-(trifluoromethyl)phenyl) amino)-3-vinylbenzenesulfonamide To a solution of 3-bromo-N-methyl-4-[3-(trifluoromethyl)anilino]benzenesulfonamide (400 mg, 918.82 μmol, 1 eq) in DMF (20 mL) was added Cs₂CO₃ (598.74 mg, 1.84 mmol, 2.0 eq), Pd(dppf)Cl₂ (67.23 mg, 91.88 μmol, 0.1 eq), 4,4,5,5-tetramethyl-2-vinyl-1,3,2-dioxaborolane (141.51 mg, 918.82 μmol, 155.85 μL, 1 eq). The mixture was stirred under N₂ at 100° C. for 4 h. TLC (PE/EtOAc=10/1, $R_f$=0.5) showed the reaction was completed. The mixture was added water (20 mL), extracted with EtOAc (40 mL×3). The combined organic layers were washed with brine (50 mL), dried over Na₂SO₄, filtered and concentrated to yield a residue which was purified by flash silica gel chromatography (from PE/EtOAc=100/1 to 5/1, TLC: PE/EtOAc=5/1, $R_f$=0.5) to yield N-methyl-4-[3-(trifluoromethyl)anilino]-3-vinyl-benzenesulfonamide (300 mg, 673.47 μmol, 73.3% yield, 80.0% purity) as yellow oil. ¹H NMR (400 MHz, CDCl₃) δ ppm 7.61-7.43 (m, 6H), 7.20-7.19 (m, 1H), 6.72-6.70 (m, 1H), 5.80 (d, J=20.0 Hz, 1H), 5.53 (d, J=12.0 Hz, 1H), 3.16 (q, J=4.0 Hz, 3H); ES-LCMS m/z 357.0 [M+H]⁺.

Step 5: (R)-3-(3-Bromo-4,5-dihydroisoxazol-5-yl)-N-methyl-4-((3-(trifluoromethyl)phenyl)amino)benzenesulfonamide and (S)-3-(3-bromo-4,5-dihydroisoxazol-5-yl)-N-methyl-4-((3-(trifluoromethyl) phenyl)amino)benzenesulfonamide To a mixture of N-methyl-4-[3-(trifluoromethyl)anilino]-3-vinyl-benzenesulfonamide (250 mg, 631.38 μmol, 1 eq) in EtOAc (10 mL) was added NaHCO₃ (530.42 mg, 6.31 mmol, 10 eq) and dibromomethanone oxime (153.68 mg, 757.66 μmol, 1.2 eq). The mixture was stirred at 20° C. for 4 h. The reaction mixture was diluted with water (10 mL) and extracted with EtOAc (10 mL×3). The combined organic layers were washed with brine (20 mL), dried over Na₂SO₄, filtered and concentrated under reduced pressure to yield a residue which was purified by flash silica gel chromatography (from PE/EtOAc=100/1 to 3/1, TLC (PE/EtOAc=3/1, $R_f$=0.2). The desired fraction was concentrated under reduced pressure to yield a reside which was separated by chiral SFC (column: column: DAICEL CHIRALCEL OJ-H (250 mm*30 mm, 5 um); mobile phase: [0.1% NH₃·H₂O EtOH]; B %: 40%-40%) to yield peak 1 and peak 2. Peak 1 was concentrated under reduced pressure to yield a residue which was lyophilized to yield 3-[(5R)-3-bromo-4,5-dihydroisoxazol-5-yl]-N-methyl-4-[3-(trifluoromethyl) anilino]benzenesulfonamide (13.15 mg, 27.49 μmol, 4.4% yield, 100.0% purity, SFC: $R_t$=3.304, ee=100%, [α]²⁴·²_D=+10 (MeOH, c=0.02 g/100 mL)) as a white solid. ¹H NMR (400 MHz, CD₃OD) δ ppm 7.87 (d, J=4.0 Hz, 1H), 7.71 (d, J=8.0 Hz, 1H), 7.50-7.47 (m, 1H), 7.38-7.31 (m, 3H), 7.30 (d, J=1.6 Hz, 1H), 6.00 (q, J=8.0 Hz, 1H), 3.75 (q, J=4.0 Hz, 1H), 3.23-3.17 (m, 1H), 2.53 (d, J=4.2 Hz, 3H); ES-LCMS m/z 478.0, 480.0 [M+H]⁺. Peak 2 was concentrated under reduced pressure to yield a residue which was lyophilized to yield 3-[(5S)-3-bromo-4,5-dihydroisoxazol-5-yl]-N-methyl-4-[3-(trifluoromethyl)anilino]benzenesulfonamide (14.20 mg, 29.69 μmol, 4.7% yield, 100.0% purity, SFC: $R_t$=3.553, ee=100%, [α]²⁴·²_D=−50 (MeOH, c=0.02 g/100 mL) as a white solid. ¹H NMR (400 MHz, CD₃OD) δ ppm 7.88 (d, J=4.0 Hz, 1H), 7.72 (d, J=8.0 Hz, 1H), 7.51-7.48 (m, 1H), 7.38-7.31 (m, 3H), 7.30 (d, J=1.6 Hz, 1H), 6.01 (q, J=8.0 Hz, 1H), 3.77 (q, J=4.0 Hz, 1H), 3.24-3.17 (m, 1H), 2.54 (d, J=4.2 Hz, 3H); ES-LCMS m/z 478.0, 480.0 [M+H]⁺.

I-15

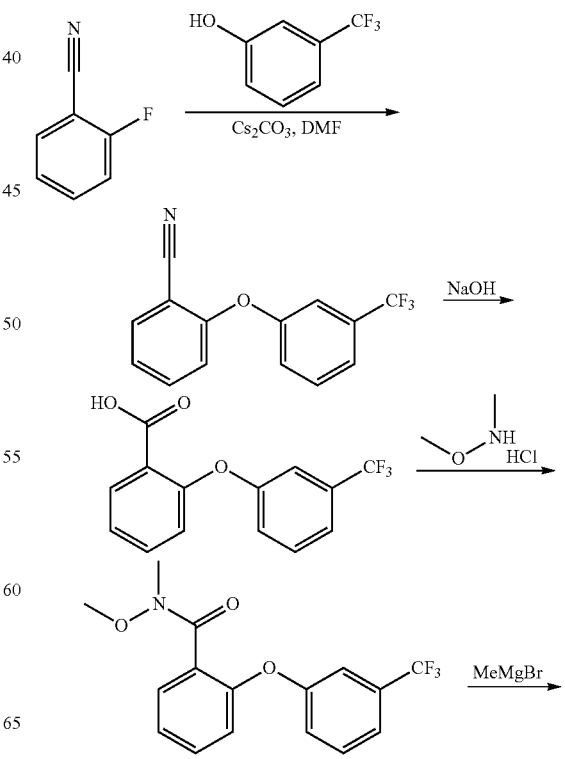

283

-continued

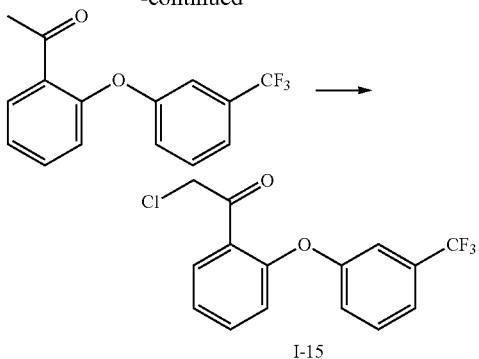

I-15

Step 1: 2-(3-(Trifluoromethyl)phenoxy)benzonitrile

To a solution of 2-fluorobenzonitrile (1 g, 8.26 mmol, 877.19 µL, 1 eq) in DMF (20 mL) was added $K_2CO_3$ (2.28 g, 16.51 mmol, 2 eq) and 3-(trifluoromethyl)phenol (1.61 g, 9.91 mmol, 1.19 mL, 1.2 eq). The mixture was stirred at 100° C. for 4 h. TLC (PE/EtOAc=100/1, $R_f$=0.2) showed the reaction was completed. Water (20 mL) was added. The mixture was extracted with EtOAc (30 mL×3). The combined organic layers were washed with brine (50 mL), dried over $Na_2SO_4$, filtered and concentrated to yield a residue which was purified by flash silica gel chromatography (from pure PE to PE/EtOAc=100/1, TLC: PE/EtOAc=10/1, $R_f$=0.2) to yield 2-[3-(trifluoromethyl)phenoxy]benzonitrile (1 g, 3.42 mmol, 41.4% yield, 90.0% purity) as yellow oil. $^1$H NMR (400 MHz, $CDCl_3$) δ ppm 7.81-7.79 (m, 1H), 7.66-7.64 (m, 2H), 7.55 (s, 1H), 7.38-7.32 (m, 3H), 7.05-7.03 (m, 1H).

Step 2: 2-(3-(Trifluoromethyl)phenoxy)benzoic Acid

To a solution of 2-[3-(trifluoromethyl)phenoxy]benzonitrile (1 g, 3.42 mmol, 1 eq) in EtOH (5 mL) was added NaOH (1.03 g, 25.64 mmol, 7.5 eq) and $H_2O$ (5 mL). The mixture was stirred at 100° C. for 16 h. TLC (PE/EtOAc=100/1, $R_f$=0.1) showed the reaction was completed. The reaction mixture was concentrated under reduced pressure to remove solvent. The residue was diluted with $H_2O$ (20 mL) and extracted with EtOAc (20 mL×2). The combined organic layers were washed with brine (30 mL), dried over $Na_2SO_4$, filtered and concentrated under reduced pressure to yield 2-[3-(trifluoromethyl)phenoxy]benzoic acid (1 g, 3.19 mmol, 93.3% yield, 90.0% purity) as a white solid. $^1$H NMR (400 MHz, $CD_3OD$) δ ppm 10.05 (s, 1H), 8.17-8.14 (m, 1H), 7.56-7.43 (m, 5H), 7.28-7.17 (m, 1H), 6.98-6.95 (m, 1H); ES-LCMS m/z 283.1 [M+H]$^+$.

Step 3: N-Methoxy-N-methyl-2-(3-(trifluoromethyl)phenoxy)benzamide

To a solution of 2-[3-(trifluoromethyl)phenoxy]benzoic acid (500 mg, 1.59 mmol, 1 eq) in DCM (10 mL) was added HATU (727.55 mg, 1.91 mmol, 1.2 eq) and N-methoxymethanamine;hydrochloride (186.64 mg, 1.91 mmol, 1.2 eq), DIEA (618.25 mg, 4.78 mmol, 833.22 µL, 3.0 eq). The mixture was stirred at 20° C. for 16 h. TLC (PE/EtOAc=5/1, $R_f$=0.3) showed the reaction was completed. The mixture was concentrated and then water (10 mL) was added. The mixture was extracted with EtOAc (10

284 mL×3). The combined organic layers were washed with brine (10 mL), dried over $Na_2SO_4$, filtered and concentrated to yield a residue which was purified by flash silica gel chromatography (from PE/EtOAc=100/1 to 5/1, TLC (PE/EtOAc=5/1, $R_f$=0.3) to yield N-methoxy-N-methyl-2-[3-(trifluoromethyl)phenoxy]benzamide (250 mg, 691.71 µmol, 43.4% yield, 90.0% purity) as yellow oil. $^1$H NMR (400 MHz, $CDCl_3$) δ ppm 7.43-7.38 (m, 4H), 7.34-7.23 (m, 3H), 6.92 (s, 1H), 3.51 (s, 3H), 3.26 (s, 3H); ES-LCMS m/z 326.0 [M+H]$^+$.

Step 4: 1-(2-(3-(Trifluoromethyl)phenoxy)phenyl)ethan-1-one

To a mixture of N-methoxy-N-methyl-2-[3-(trifluoromethyl)phenoxy]benzamide (200 mg, 553.37 µmol, 1 eq) in THF (10 mL) was added MeMgBr (3 M, 1.84 mL, 10 eq) at 0° C. The mixture was stirred under $N_2$ atmosphere at 0° C. for 2 h. TLC (PE/EtOAc=5/1, $R_f$=0.4) showed the reaction was completed. The reaction mixture was quenched by the addition of saturated aqueous $NH_4Cl$ solution (20 mL) at 0° C. The mixture was concentrated, diluted with water (10 mL) and extracted with EtOAc (10 mL×3). The combined organic layers were washed with brine (10 mL), dried over $Na_2SO_4$, filtered and concentrated to yield a residue which was purified by flash silica gel chromatography (from PE/EtOAc=100/1 to 5/1, TLC (PE/EtOAc=5/1, $R_f$=0.4) to yield 1-[2-[3-(trifluoromethyl)phenoxy]phenyl]ethanone (90 mg, 289.04 µmol, 52.2% yield, 90.0% purity) as yellow oil. $^1$H NMR (400 MHz, $CDCl_3$) δ ppm 7.85-7.83 (m, 1H), 7.46-7.40 (m, 2H), 7.39-7.35 (m, 1H), 7.30-7.25 (m, 2H), 7.23 (d, J=4.0 Hz, 1H), 6.91 (d, J=8.4 Hz, 1H), 2.59 (s, 3H); ES-LCMS m/z 280.9 [M+H]$^+$.

Step 5: 2-Chloro-1-(2-(3-(trifluoromethyl)phenoxy)phenyl)ethan-1-one

To a mixture of 1-[2-[3-(trifluoromethyl)phenoxy]phenyl]ethanone (90 mg, 289.04 µmol, 1 eq) in DCM (2 mL) was added sulphuryl chloride (58.52 mg, 433.55 µmol, 43.35 µL, 1.5 eq). The mixture was stirred under $N_2$ at 0° C. for 2 h. The reaction mixture was quenched by the addition of saturated aqueous $NaHCO_3$ solution (20 mL) at 0° C. The mixture was concentrated, diluted with water (10 mL) and extracted with EtOAc (10 mL×3). The combined organic layers were washed with brine (10 mL), dried over $Na_2SO_4$, filtered and concentrated to yield a residue which was purified preparative HPLC (column: Phenomenex Synergi C18 150*30 mm*4 um; mobile phase: [water (0.05% HCl)-ACN]; B %: 64%-84%, 10 min), followed by lyophilization to yield 2-chloro-1-(2-(3-(trifluoromethyl)phenoxy)phenyl)ethan-1-one (15.56 mg, 51.75 µmol, 17.1% yield, 100.0% purity) as a white solid. $^1$H NMR (400 MHz, $CDCl_3$) δ ppm 7.96 (d, J=24.0 Hz, 1H), 7.54-7.50 (m, 3H), 7.35 (s, 1H), 7.28-7.24 (m, 2H), 6.89-6.88 (m, 1H), 4.77 (s, 2H); ES-LCMS m/z 314.9, 316.9 [M+H]$^+$.

I-30

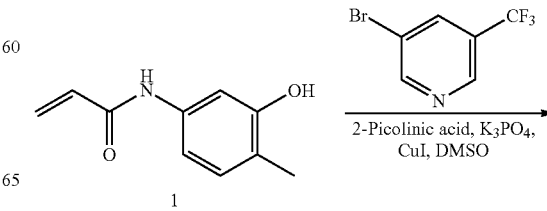

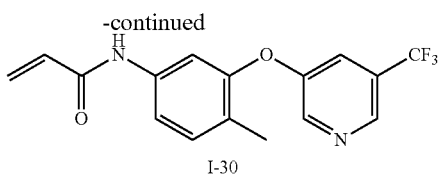

I-30

Step 1: N-[4-Methyl-3-[[5-(trifluoromethyl)-3-pyridyl]oxy]phenyl]prop-2-enamide To a stirred solution of N-(3-hydroxy-4-methyl-phenyl)prop-2-enamide (100 mg, 536.12 µmol, 1 eq) in 1,4-dioxane (3 mL) was added $K_3PO_4$ (227.60 mg, 1.07 mmol, 2 eq), CuI (5.11 mg, 26.81 µmol, 0.05 eq), pyridine-2-carboxylic acid (6.60 mg, 53.61 µmol, 0.1 eq) and 3-bromo-5-(trifluoromethyl)pyridine (109.04 mg, 482.51 µmol, 0.9 eq). The reaction mixture was at 120° C. for 12 h under microwave. The reaction mixture was filtered through a pad of celite and the filtrate was concentrated to yield a residue which was purified by preparative HPLC (column: Agela DuraShell C18 150*25 mm*5um; mobile phase: [water (0.04% $NH_3H_2O$+10 mM $NH_4HCO_3$)-ACN]; B %: 41%-56%, 14 min). The desired fraction was lyophilized to yield N-[4-methyl-3-[[5-(trifluoromethyl)-3-pyridyl]oxy]phenyl]prop-2-enamide (15.97 mg, 49.01 µmol, 9.1% yield, 98.9% purity) as white solid. $^1$H NMR (500 MHz, DMSO-$d_6$) δ ppm 10.22 (s, 1H), 8.75 (s, 1H), 8.61 (d, J=2.6 Hz, 1H), 7.72 (s, 1H), 7.47-7.38 (m, 2H), 7.32 (d, J=8.2 Hz, 1H), 6.41-6.32 (m, 1H), 6.26-6.17 (m, 1H), 5.74 (dd, J=1.9, 10.1 Hz, 1H), 2.15 (s, 3H); ES-LCMS m/z 322.9 [M+H]$^+$.
I-31 mmol, 77.0% yield, 95.0% purity) as a yellow solid. $^1$H NMR (400 MHz, $CD_3OD$) δ ppm 7.26 (d, J=2.0 Hz, 1H), 6.99 (d, J=8.2 Hz, 1H), 6.87 (dd, J=2.2, 8.0 Hz, 1H), 6.46-6.35 (m, 1H), 6.35-6.29 (m, 1H), 5.73 (dd, J=2.0, 9.8 Hz, 1H), 2.14 (s, 3H); ES-LCMS m/z 178.0 [M+H]$^+$.

Step 2: N-[4-methyl-3-[[4-(trifluoromethyl)-2-pyridyl]oxy]phenyl]prop-2-enamide To a stirred solution of N-(3-hydroxy-4-methyl-phenyl)prop-2-enamide (100 mg, 536.12 µmol, 1 eq) in 1,4-dioxane (3 mL) was added 2-bromo-4-(trifluoromethyl)pyridine (109.04 mg, 482.51 µmol, 0.9 eq), $K_3PO_4$ (227.60 mg, 1.07 mmol, 2 eq), pyridine-2-carboxylic acid (6.60 mg, 53.61 µmol, 0.1 eq) and CuI (5.11 mg, 26.81 µmol, 0.05 eq). The reaction mixture was stirred at 120° C. in microwave (3 bar) for 12 h. The reaction mixture was quenched by addition of water (50 mL), extracted with EtOAc (50 mL×3). The combined organic layers were washed with brine (20 mL), dried over $Na_2SO_4$, filtered and concentrated under reduced pressure to yield a residue which was purified by preparative HPLC (column: Welch Xtimate C18 150*25 mm*5 µm; mobile phase: [water (10 mM $NH_4HCO_3$)-ACN]; B %: 43%-73%, 10 min), followed by lyophilization to yield N-[4-methyl-3-[[4-(trifluoromethyl)-2-pyridyl]oxy]phenyl]prop-2-enamide (50 mg, 154.52 µmol, 27.3% yield, 99.6% purity) as a brown solid. $^1$H NMR (400 MHz, DMSO-$d_6$) δ ppm 10.18 (s, 1H), 8.36 (d, J=5.1 Hz, 1H), 7.52 (d, J=2.0 Hz, 1H), 7.49-7.42 (m, 2H), 7.37 (dd, J=2.0, 8.2 Hz, 1H), 7.25 (d, J=8.2 Hz, 1H), 6.44-6.31 (m, 1H), 6.26-6.10 (m, 1H), 5.76-5.66 (m, 1H), 2.01 (s, 3H); ES-LCMS m/z 323.0 [M+H]$^+$.
I-32

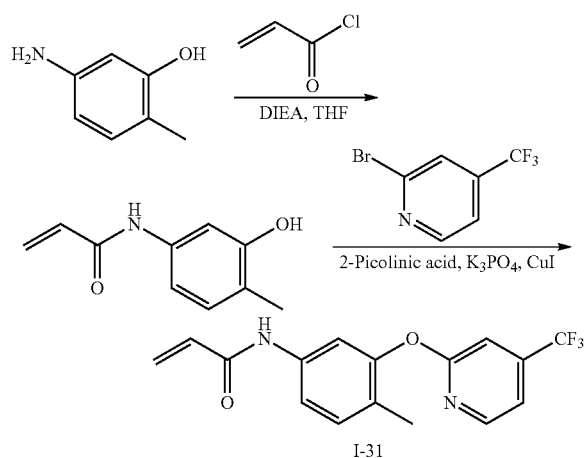

I-31

Step 1: N-(3-Hydroxy-4-methyl-phenyl)prop-2-enamide

To a solution of 5-amino-2-methyl-phenol (480 mg, 3.90 mmol, 1 eq) in THF (10 mL) was added DIEA (1.51 g, 11.69 mmol, 2.04 mL, 3 eq) and prop-2-enoyl chloride (352.77 mg, 3.90 mmol, 317.81 µL, 1 eq). The mixture was stirred at 25° C. for 1 h. The reaction mixture was concentrated under reduced pressure to yield a residue which was purified by flash silica gel chromatography (from PE/EtOAc=200/1 to 1/1, TLC: PE/EtOAc=1/1, $R_f$=0.35) to yield N-(3-hydroxy-4-methyl-phenyl)prop-2-enamide (560 mg, 3.00

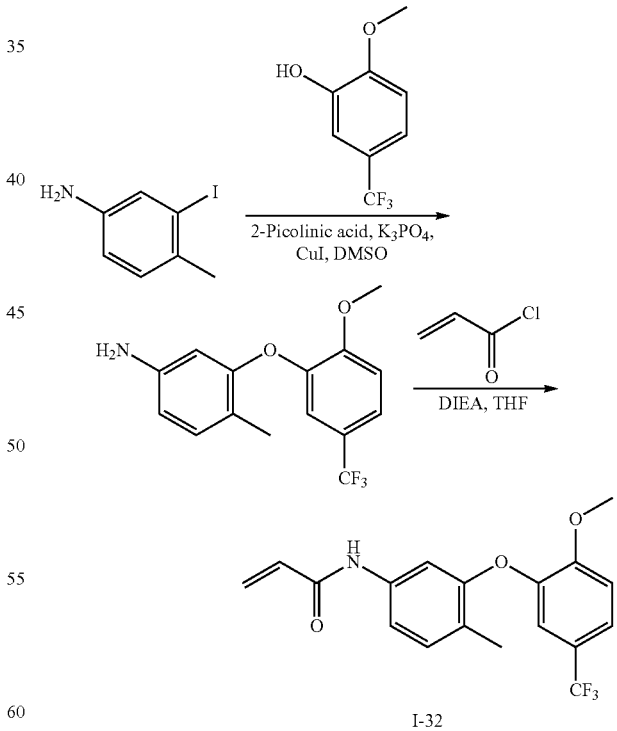

I-32

Step 1: 3-[2-Methoxy-5-(trifluoromethyl)phenoxy]-4-methyl-aniline

To a stirred solution of 3-iodo-4-methyl-aniline (200 mg, 858.19 µmol, 1 eq) in DMSO (5 mL) was added $K_3PO_4$ (364.34 mg, 1.72 mmol, 2 eq), CuI (8.17 mg, 42.91 μmol, 0.05 eq), pyridine-2-carboxylic acid (10.57 mg, 85.82 μmol, 0.1 eq) and 2-methoxy-5-(trifluoromethyl)phenol (164.89 mg, 858.19 μmol, 1 eq). The reaction mixture was at 120° C. for 12 h under $N_2$ atmosphere. The reaction mixture was diluted with EtOAc (50 mL) then washed with saturated NaCl solution (30 mL×2). The aqueous phase was extracted with EtOAc (50 mL×2). The combined organic layers were dried over $Na_2SO_4$, filtered and the filtrate was concentrated to yield a residue which was purified by flash silica gel chromatography (from PE/EtOAc=100/1 to 3/1, TLC: PE/EtOAc=3/1, $R_f$=0.45) to yield 3-[2-methoxy-5-(trifluoromethyl)phenoxy]-4-methyl-aniline (110 mg, 360.41 μmol, 42.0% yield, 97.4% purity) as yellow oil. $^1$H NMR (400 MHz, DMSO-$d_6$) δ ppm 7.47 (d, J=8.6 Hz, 1H), 7.31 (d, J=8.6 Hz, 1H), 6.97 (d, J=1.7 Hz, 1H), 6.91 (d, J=8.1 Hz, 1H), 6.28 (dd, J=2.0, 8.1 Hz, 1H), 5.96 (d, J=2.0 Hz, 1H), 4.99 (s, 2H), 3.87 (s, 3H), 2.04-1.96 (m, 3H); ES-LCMS m/z 298.0 [M+H]$^+$.

Step 2: N-[3-[2-Methoxy-5-(trifluoromethyl)phenoxy]-4-methyl-phenyl]prop-2-enamide To a stirred solution of 3-[2-methoxy-5-(trifluoromethyl)phenoxy]-4-methyl-aniline (110 mg, 360.41 μmol, 1 eq) in THF (3 mL) was added DIEA (139.74 mg, 1.08 mmol, 188.33 μL, 3 eq) and prop-2-enoyl chloride (65.24 mg, 720.82 μmol, 58.78 μL, 2 eq). The reaction mixture was at 25° C. for 1 h under $N_2$ atmosphere. The reaction mixture was concentrated to yield a residue which was purified by preparative HPLC (column: YMC Triart 30*150 mm*7 um; mobile phase: [water (0.05% ammonia hydroxide v/v)-ACN]; B %: 57%-77%, 10 min). The desired fraction was lyophilized to yield N-[3-[2-methoxy-5-(trifluoromethyl)phenoxy]-4-methyl-phenyl]prop-2-enamide (65.11 mg, 185.33 μmol, 51.4% yield, 100.0% purity) as white solid. $^1$H NMR (400 MHz, DMSO-$d_6$) δ ppm 10.06 (s, 1H), 7.60-7.53 (m, 1H), 7.41-7.31 (m, 2H), 7.25-7.17 (m, 2H), 7.04 (d, J=1.7 Hz, 1H), 6.39-6.27 (m, 1H), 6.22-6.14 (m, 1H), 5.74-5.66 (m, 1H), 3.85 (s, 3H), 2.19 (s, 3H); ES-LCMS m/z 352.0 [M+H]$^+$.
I-4

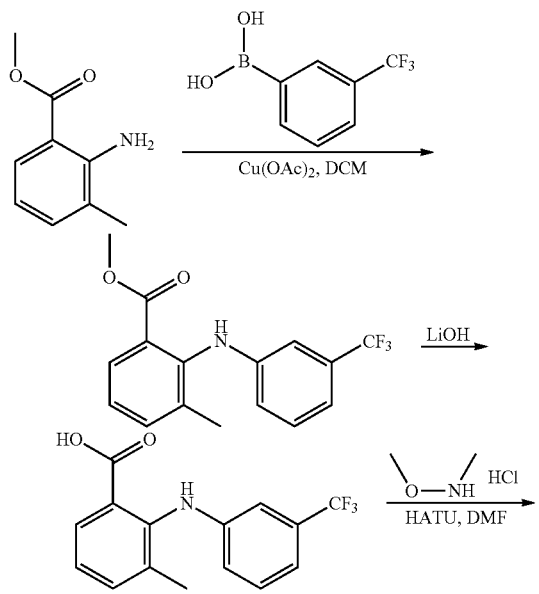

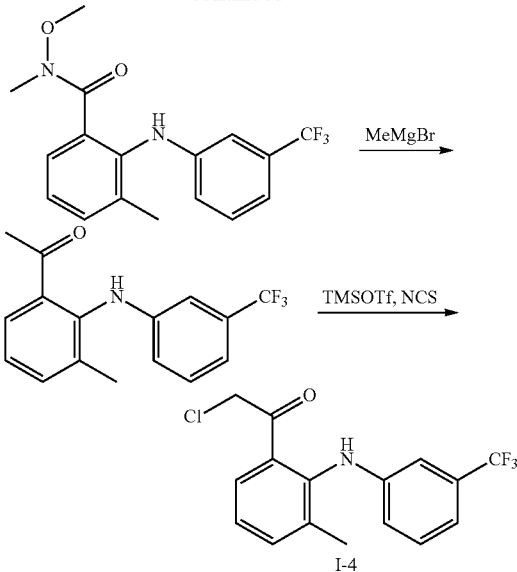

Step 1: Methyl 3-methyl-2-[3-(trifluoromethyl)anilino]benzoate

To a mixture of methyl 2-amino-3-methyl-benzoate (3.91 g, 23.69 mmol, 1.5 eq) and [3-(trifluoromethyl)phenyl]boronic acid (3 g, 15.80 mmol, 1.41 mL, 1 eq) in DCM (50 mL) was added $Cu(OAc)_2$ (3.44 g, 18.95 mmol, 1.2 eq) and DIEA (4.08 g, 31.59 mmol, 5.50 mL, 2 eq). The mixture was stirred under oxygen (15 psi) atmosphere at 25° C. for 12 h. TLC (PE/EtOAc=10/1, $R_f$=0.60) showed starting material was consumed and one major new spot was detected. The mixture was filtered and the filtrate was concentrated to yield a residue which was purified by flash silica gel chromatography (from pure PE to PE/EtOAc=10/1, TLC: PE/EtOAc=10/1, $R_f$=0.60) to yield methyl 3-methyl-2-[3-(trifluoromethyl)anilino]benzoate (1.4 g, 4.07 mmol, 25.8% yield, 90.0% purity) as yellow oil. $^1$H NMR (400 MHz, DMSO-$d_6$) δ ppm 8.27 (s, 1H), 7.66 (dd, J=1.2, 7.8 Hz, 1H), 7.53 (d, J=6.8 Hz, 1H), 7.33 (t, J=7.9 Hz, 1H), 7.23 (t, J=7.7 Hz, 1H), 7.00 (d, J=7.6 Hz, 1H), 6.83 (s, 1H), 6.76 (dd, J=2.0, 8.1 Hz, 1H), 3.64 (s, 3H), 2.13 (s, 3H); ES-LCMS m/z 310.0 [M+H]$^+$.

Step 2: 3-Methyl-2-[3-(trifluoromethyl)anilino]benzoic Acid

To a mixture of methyl 3-methyl-2-[3-(trifluoromethyl)anilino]benzoate (1.4 g, 4.07 mmol, 1 eq) in THF (5 mL), $H_2O$ (5 mL) and ACN (5 mL) was added LiOH (487.82 mg, 20.37 mmol, 5 eq) and stirred at 25° C. for 12 h. TLC (PE/EtOAc=1/1, $R_f$=0.4) showed starting material was consumed, and one major new spot was detected. The reaction mixture was concentrated, diluted with $H_2O$ (20 mL), acidified with 1 N HCl (20 mL, adjust pH to 5) and extracted with EtOAc (20 mL×3). The combine organic layers were dried over anhydrous $Na_2SO_4$, filtered and concentrated to yield 3-methyl-2-[3-(trifluoromethyl)anilino]benzoic acid (1.3 g, 3.96 mmol, 97.3% yield, 90.0% purity) as colorless oil. $^1$H NMR (500 MHz, DMSO-$d_6$) δ ppm 12.96 (br s, 1H), 8.46 (br s, 1H), 7.77-7.68 (m, 1H), 7.50 (d, J=6.7 Hz, 1H), 7.34 (t, J=7.9 Hz, 1H), 7.21 (t, J=7.7 Hz, 1H), 7.02 (d, J=7.6 Hz, 1H), 6.85 (s, 1H), 6.77 (d, J=8.1 Hz, 1H), 2.09 (s, 3H).

Step 3: N-Methoxy-N,3-dimethyl-2-[3-(trifluoromethyl)anilino]benzamide

To a mixture of 3-methyl-2-[3-(trifluoromethyl)anilino]benzoic acid (1.3 g, 3.96 mmol, 1 eq) and N-methoxymethanamine (773.07 mg, 7.93 mmol, 2 eq, HCl) in DCM (20 mL) was added HATU (1.81 g, 4.76 mmol, 1.2 eq) and DIEA (1.54 g, 11.89 mmol, 2.07 mL, 3 eq). The mixture was stirred at 60° C. for 12 h. TLC (PE/EtOAc=5/1, $R_f$=0.5) showed starting material was consumed and one major new spot was detected. The mixture was diluted with $H_2O$ (40 mL) and extracted with EtOAc (50 mL×3). The combine organic layers were dried over anhydrous $Na_2SO_4$, filtered and concentrated to yield a residue which was purified by flash silica gel chromatography (from pure PE to PE/EtOAc=3/1, TLC: PE/EtOAc=5/1, $R_f$=0.5) to yield N-methoxy-N,3-dimethyl-2-[3-(trifluoromethyl)anilino]benzamide (1.4 g, 3.31 mmol, 83.5% yield, 80.0% purity) as colorless oil. $^1$H NMR (400 MHz, DMSO-$d_6$) δ ppm 7.82 (br s, 1H), 7.38 (t, J=4.5 Hz, 1H), 7.29-7.21 (m, 3H), 6.90 (d, J=7.6 Hz, 1H), 6.76 (s, 1H), 6.73-6.67 (m, 1H), 3.37 (s, 3H), 3.04 (br s, 3H), 2.11 (s, 3H).

Step 4: 1-[3-Methyl-2-[3-(trifluoromethyl)anilino]phenyl]ethanone

To a solution of N-methoxy-N,3-dimethyl-2-[3-(trifluoromethyl)anilino]benzamide (1.4 g, 3.31 mmol, 1 eq) in THF (40 mL) was added MeMgBr (3 M, 11.03 mL, 10 eq) under $N_2$ atmosphere at −78° C. and stirred under $N_2$ atmosphere at 25° C. for 12 h. TLC (PE/EtOAc=3:1, $R_f$=0.60) showed starting material was remained and one major new spot was detected. Then to the mixture was added MeMgBr (3 M, 7.72 mL, 7 eq) at 0° C. and stirred at 25° C. for 12 h. TLC (PE/EtOAc=3/1, $R_f$=0.60) showed starting material was consumed and one major new spot was detected. The mixture was added saturated $NH_4Cl$ (300 mL) and extracted with EtOAc (150 mL×3). The combine organic layers were dried over anhydrous $Na_2SO_4$, filtered and concentrated to yield a residue which was purified by flash silica gel chromatography (from pure PE to PE/EtOAc=5/1, TLC: PE/EtOAc=5/1, $R_f$=0.60) to yield 1-[3-methyl-2-[3-(trifluoromethyl)anilino]phenyl]ethanone (450 mg, 1.38 mmol, 41.7% yield, 90.0% purity) as yellow oil. $^1$H NMR (500 MHz, DMSO-$d_6$) δ ppm 8.52 (s, 1H), 7.56 (d, J=7.8 Hz, 1H), 7.50 (d, J=7.2 Hz, 1H), 7.34 (t, J=7.9 Hz, 1H), 7.25 (t, J=7.6 Hz, 1H), 7.00 (d, J=7.6 Hz, 1H), 6.80 (s, 1H), 6.75 (d, J=8.2 Hz, 1H), 2.41 (s, 3H), 2.13-2.08 (m, 1H), 2.11 (s, 3H); ES-LCMS m/z 294.0 [M+H]$^+$.

Step 5: 2-Chloro-1-[3-methyl-2-[3-(trifluoromethyl)anilino]phenyl]ethanone

To a solution of 1-[3-methyl-2-[3-(trifluoromethyl)anilino]phenyl]ethanone (160 mg, 490.99 μmol, 1 eq) in DCM (3 mL) was added DIEA (380.74 mg, 2.95 mmol, 513.13 μL, 6 eq) and TMSOTf (654.76 mg, 2.95 mmol, 532.33 μL, 6 eq) at 0° C. and stirred at 25° C. for 2 h. Then to the mixture was added NCS (131.13 mg, 981.99 μmol, 2 eq) and stirred at 25° C. for 10 h. TLC (PE/EtOAc=3/1, $R_f$=0.60) showed starting material was consumed and one major new spot was detected. The mixture was diluted with $H_2O$ (20 mL) and extracted with EtOAc (20 mL×3). The combine organic layers were dried over anhydrous $Na_2SO_4$, filtered and concentrated to yield a residue which was purified by preparative TLC (PE/EtOAc=3/1, TLC: PE/EtOAc=3/1, $R_f$=0.60) and then by preparative HPLC (column: Welch Xtimate C18 150*25 mm*5 μm; mobile phase: [water (10 mM $NH_4HCO_3$)-ACN]; B %: 56%-86%, 10 min) and lyophilized to yield 2-chloro-1-[3-methyl-2-[3-(trifluoromethyl)anilino]phenyl]ethanone (16.87 mg, 51.48 μmol, 10.5% yield, 100.0% purity) as a yellow solid. $^1$H NMR (500 MHz, CDCl$_3$) δ ppm 9.09 (s, 1H), 7.68 (d, J=7.9 Hz, 1H), 7.45 (d, J=7.5 Hz, 1H), 7.35-7.29 (m, 1H), 7.18-7.11 (m, 2H), 6.91-6.87 (m, 2H), 4.74 (s, 2H), 2.07 (s, 3H); ES-LCMS m/z 328.1, 330.1, 332.1 [M+H]$^+$.

I-3

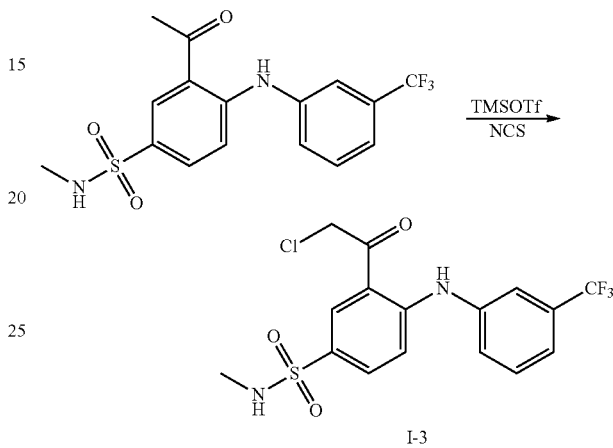

Step 1: 3-(2-Chloroacetyl)-N-methyl-4-[3-(trifluoromethyl)anilino]benzenesulfonamide To a solution of 3-acetyl-N-methyl-4-[3-(trifluoromethyl)anilino]benzenesulfonamide (200 mg, 530.67 μmol, 1 eq) in DCM (3 mL) was added DIEA (205.76 mg, 1.59 mmol, 277.30 μL, 3 eq) and TMSOTf (353.84 mg, 1.59 mmol, 287.67 μL, 3 eq) at 0° C. The mixture was stirred at 25° C. for 2 h. NIS (179.09 mg, 796.00 μmol, 1.5 eq) was added at 25° C. The mixture was stirred at 25° C. for 2 h. The reaction mixture was concentrated under reduced pressure to yield a residue which was purified by flash silica gel chromatography (from PE/EtOAc=100/1 to 8/1, TLC: PE/EtOAc=2/1, $R_f$=0.55). The desired fraction was concentrated under reduced pressure to yield a residue which was purified by preparative HPLC (column: Welch Xtimate C18 150*25 mm*5 um; mobile phase: [water (10 mM $NH_4HCO_3$)-ACN]; B %: 43%-73%, 10 min). The desired fraction was lyophilized to yield 3-(2-chloroacetyl)-N-methyl-4-[3-(trifluoromethyl)anilino]benzenesulfonamide (18.97 mg, 46.63 μmol, 8.8% yield, 100.0% purity) as a yellow solid. $^1$H NMR (400 MHz, CDCl$_3$) δ ppm 10.83 (s, 1H), 8.31 (d, J=2.0 Hz, 1H), 7.78 (dd, J=2.0, 9.0 Hz, 1H), 7.60-7.51 (m, 3H), 7.47 (d, J=7.8 Hz, 1H), 7.23 (d, J=9.4 Hz, 1H), 4.78 (s, 2H), 4.40-4.33 (m, 1H), 2.71 (d, J=5.1 Hz, 3H); ES-LCMS m/z 406.9 [M+H]$^+$.

I-33

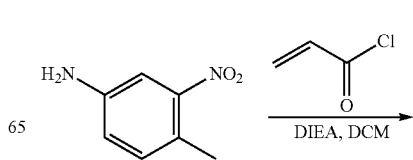

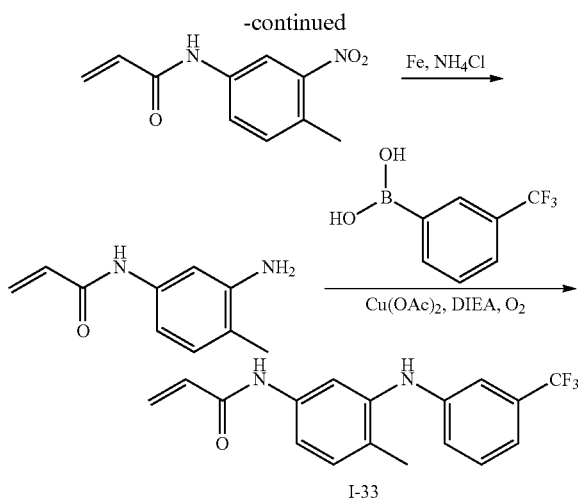

Step 1: N-(4-Methyl-3-nitro-phenyl)prop-2-enamide

To a solution of 4-methyl-3-nitro-aniline (2 g, 13.14 mmol, 1 eq) and DIEA (5.10 g, 39.43 mmol, 6.87 mL, 3 eq) in DCM (20 mL) was added prop-2-enoyl chloride (1.31 g, 14.46 mmol, 1.18 mL, 1.1 eq) dropwise at 25° C. The mixture was stirred at 25° C. for 1 h. TLC (PE/EtOAc=2/1, $R_f$=0.30) showed the starting material was consumed completely. The reaction mixture was quenched with $H_2O$ (50 mL) and extracted with DCM (50 mL×3). The organic layer was dried over $Na_2SO_4$, filtered and concentrated under reduced pressure to yield N-(4-methyl-3-nitro-phenyl)prop-2-enamide (2.68 g, 12.70 mmol, 96.6% yield, 97.7% purity) as a yellow solid, which was used in the next step without further purification. $^1$H NMR (400 MHz, $CDCl_3$) δ ppm 8.21 (d, J=2.0 Hz, 1H), 7.89-7.81 (m, 1H), 7.72 (s, 1H), 7.31 (d, J=8.2 Hz, 1H), 6.52-6.46 (m, 1H), 6.33-6.23 (m, 1H), 5.83 (dd, J=1.0, 10.4 Hz, 1H), 2.57 (s, 3H); ES-LCMS m/z 207.0 [M+H]$^+$.

Step 2: N-(3-Amino-4-methyl-phenyl)prop-2-enamide

A mixture of N-(4-methyl-3-nitro-phenyl)prop-2-enamide (2.68 g, 12.70 mmol, 1 eq), Fe (7.09 g, 126.98 mmol, 10 eq) and $NH_4Cl$ (6.79 g, 126.98 mmol, 10 eq) in THF (20 mL), EtOH (20 mL) and $H_2O$ (20 mL) was stirred at 55° C. for 4 h. TLC (PE/EtOAc=1/1, $R_f$=0.20) showed the starting material was consumed completely. The mixture was filtered. The filtrate was diluted with $H_2O$ (50 mL) and extracted with EtOAc (50 mL×3). The organic layer was dried over $Na_2SO_4$, filtered and concentrated under reduced pressure to yield N-(3-amino-4-methyl-phenyl)prop-2-enamide (2.2 g, 11.86 mmol, 93.4% yield, 95.0% purity) as a brown solid, which was used in the next step without further purification. $^1$H NMR (400 MHz, $CDCl_3$) δ ppm 7.23 (s, 1H), 6.98 (d, J=8.2 Hz, 1H), 6.67 (d, J=7.4 Hz, 1H), 6.48-6.36 (m, 1H), 6.31-6.14 (m, 1H), 5.74 (d, J=10.2 Hz, 1H), 3.66 (s, 2H), 2.13 (s, 3H).

Step 3: N-[4-Methyl-3-[3-(trifluoromethyl)anilino]phenyl]prop-2-enamide

A mixture of N-(3-amino-4-methyl-phenyl)prop-2-enamide (1 g, 5.39 mmol, 1 eq), [3-(trifluoromethyl)phenyl]boronic acid (2.05 g, 10.78 mmol, 2 eq), $Cu(OAc)_2$ (2.15 g, 11.86 mmol, 2.2 eq) and DIEA (2.09 g, 16.17 mmol, 2.82 mL, 3 eq) in DCM (20 mL) was stirred under $O_2$ (15 psi) at 25° C. for 12 h. TLC (PE/EtOAc=1/1, $R_f$=0.52) showed the starting material was consumed completely. The reaction mixture was diluted with $H_2O$ (50 mL) and filtered. The filtrate was extracted with DCM (50 mL×3). The organic layer was dried over $Na_2SO_4$, filtered and concentrated under reduced pressure to yield a residue which was purified by flash silica gel chromatography (from PE/EtOAc=100/1 to 3/1, TLC: PE/EtOAc=1/1, $R_f$=0.52) to yield N-[4-methyl-3-[3-(trifluoromethyl)anilino]phenyl]prop-2-enamide (850 mg, 2.65 mmol, 49.2% yield, 100.0% purity) as a yellow solid. $^1$H NMR (500 MHz, $CDCl_3$) δ ppm 7.52 (s, 1H), 7.37-7.31 (m, 1H), 7.27 (s, 1H), 7.19 (s, 2H), 7.14-7.08 (m, 3H), 6.41 (d, J=16.6 Hz, 1H), 6.22 (dd, J=10.4, 16.8 Hz, 1H), 5.80-5.68 (m, 1H), 5.55 (s, 1H), 2.22 (s, 3H); ES-LCMS m/z 321.0 [M+H]$^+$.

I-34

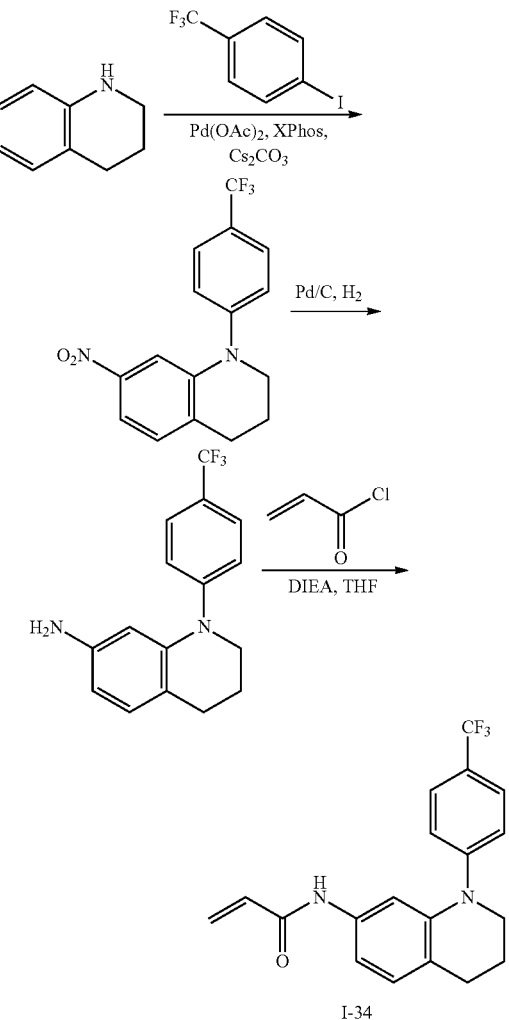

Step 1: 7-Nitro-1-[4-(trifluoromethyl)phenyl]-3,4-dihydro-2H-quinoline

To a solution of 7-nitro-1,2,3,4-tetrahydroquinoline (400 mg, 2.24 mmol, 1 eq) and 1-iodo-4-(trifluoromethyl)benzene (1.22 g, 4.49 mmol, 660.11 μL, 2 eq) in toluene (10 mL) was added Pd(OAc)$_2$ (50.40 mg, 224.48 µmol, 0.1 eq), XPhos (214.03 mg, 448.97 µmol, 0.2 eq) and Cs$_2$CO$_3$ (2.19 g, 6.73 mmol, 3 eq) under N$_2$ atmosphere. The mixture was stirred at 100° C. for 12 h. To the mixture was added water (50 mL) and extracted with ethyl acetate (50 mL×3). The combined organic phase was washed with brine (20 mL), dried with anhydrous Na$_2$SO$_4$, filtered and concentrated in vacuum to yield a residue which was purified by flash silica gel chromatography (from PE/EtOAc=200/1 to 5/1, TLC: PE/EtOAc=5/1, R$_f$=0.40) to yield 7-nitro-1-[4-(trifluoromethyl)phenyl]-3,4-dihydro-2H-quinoline (580 mg, 1.80 mmol, 80.1% yield, 100% purity) as a yellow solid. $^1$H NMR (500 MHz, CD$_3$OD) δ ppm 7.69 (d, J=8.5 Hz, 2H), 7.62 (d, J=2.1 Hz, 1H), 7.58 (dd, J=2.3, 8.2 Hz, 1H), 7.45 (d, J=8.4 Hz, 2H), 7.28 (d, J=8.4 Hz, 1H), 3.76-3.71 (m, 2H), 2.94 (t, J=6.4 Hz, 2H), 2.09 (q, J=6.1 Hz, 2H); ES-LCMS m/z 323.0 [M+H]$^+$.

Step 2: 1-[4-(Trifluoromethyl)phenyl]-3,4-dihydro-2H-quinolin-7-amine

To a solution of 7-nitro-1-[4-(trifluoromethyl)phenyl]-3,4-dihydro-2H-quinoline (200 mg, 620.58 µmol, 1 eq) in MeOH (15 mL) was added Pd/C (200 mg, 10%) under N$_2$. The suspension was degassed under vacuum and purged with H$_2$ several times. The mixture was stirred under H$_2$ (15 psi) at 25° C. for 2 h. The reaction mixture was filtered and concentrated to yield the residue which was purified by flash silica gel chromatography (from PE/EtOAc=200/1 to 3/1, TLC: PE/EtOAc=3/1, R$_f$=0.47) to yield 1-[4-(trifluoromethyl)phenyl]-3,4-dihydro-2H-quinolin-7-amine (120 mg, 348.96 µmol, 56.2% yield, 85.0% purity) as yellow oil. $^1$H NMR (500 MHz, CD$_3$OD) δ ppm 7.52 (d, J=8.7 Hz, 2H), 7.31 (d, J=8.5 Hz, 2H), 6.85 (d, J=7.9 Hz, 1H), 6.42 (d, J=2.0 Hz, 1H), 6.29 (dd, J=2.1, 7.9 Hz, 1H), 3.62 (t, J=6.0 Hz, 2H), 2.67 (t, J=6.4 Hz, 2H), 1.95 (q, J=6.2 Hz, 2H); ES-LCMS m/z 293.0 [M+H]$^+$.

Step 3: N-[1-[4-(Trifluoromethyl)phenyl]-3,4-dihydro-2H-quinolin-7-yl]prop-2-enamide To a solution of 1-[4-(trifluoromethyl)phenyl]-3,4-dihydro-2H-quinolin-7-amine (90 mg, 261.72 µmol, 1 eq) in THF (5 mL) was added prop-2-enoyl chloride (47.38 mg, 523.44 µmol, 42.68 µL, 2 eq) and DIEA (101.47 mg, 785.16 µmol, 136.76 µL, 3 eq). The mixture was stirred at 25° C. for 1 h. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=200/1 to 5/1, TLC: PE/EtOAc=5/1, R$_f$=0.40) to yield a product. The product was purified by preparative HPLC (column: Agela DuraShell C18 150*25 mm*5 µm; mobile phase: [water (0.04% NH$_3$H$_2$O+10 mM NH$_4$HCO$_3$)-ACN]; B %: 52%-82%, 10 min), followed by lyophilization to yield N-[1-[4-(trifluoromethyl)phenyl]-3,4-dihydro-2H-quinolin-7-yl]prop-2-enamide (47.63 mg, 137.52 µmol, 52.6% yield, 100% purity) as a white solid. $^1$H NMR (500 MHz, CD$_3$OD) δ ppm 7.57 (d, J=8.7 Hz, 2H), 7.40-7.33 (m, 3H), 7.09-7.02 (m, 2H), 6.41-6.22 (m, 2H), 5.69 (dd, J=1.8, 9.9 Hz, 1H), 3.72-3.64 (m, 2H), 2.78 (t, J=6.4 Hz, 2H), 2.02 (q, J=6.1 Hz, 2H); ES-LCMS m/z 347.0 [M+H]$^+$.

I-46

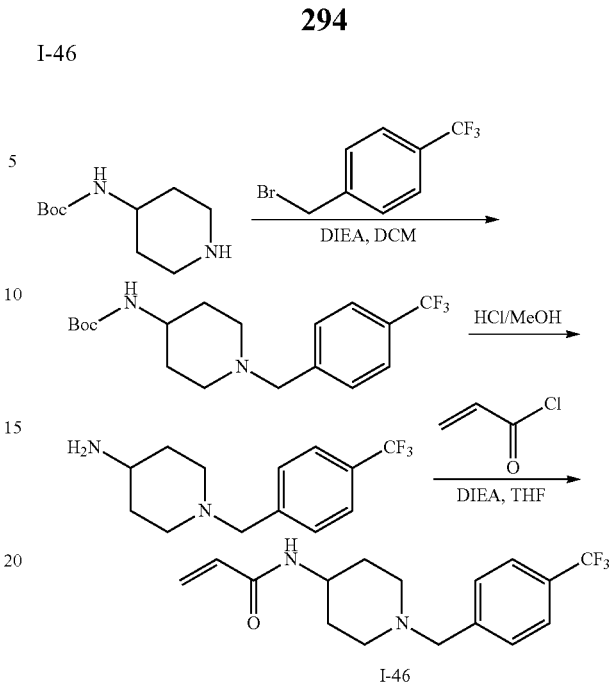

Step 1: Tert-Butyl N-[1-[[4-(trifluoromethyl)phenyl]methyl]-4-piperidyl]carbamate To a solution of tert-butyl N-(4-piperidyl)carbamate (450 mg, 2.25 mmol, 1 eq) and 1-(bromomethyl)-4-(trifluoromethyl)benzene (483.37 mg, 2.02 mmol, 311.85 µL, 0.9 eq) in DCM (10 mL) was added DIEA (435.59 mg, 3.37 mmol, 587.05 µL, 1.5 eq). The mixture was stirred at 25° C. for 1 h. To the mixture was added water (30 mL) and extracted with DCM (30 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=200/1 to 5/1, TLC: PE/EtOAc=3/1, R$_f$=0.32) to yield tert-butyl N-[1-[[4-(trifluoromethyl)phenyl]methyl]-4-piperidyl]carbamate (590 mg, 1.65 mmol, 73.3% yield, 100% purity) as a white solid. $^1$H NMR (500 MHz, CD$_3$OD) δ ppm 7.62 (d, J=8.1 Hz, 2H), 7.53 (d, J=8.1 Hz, 2H), 3.59 (s, 2H), 2.83 (d, J=11.9 Hz, 2H), 2.13 (t, J=11.3 Hz, 2H), 1.84 (d, J=11.6 Hz, 2H), 1.51-1.45 (m, 2H), 1.44-1.41 (m, 9H).

Step 2: 1-[[4-(Trifluoromethyl)phenyl]methyl]piperidin-4-amine

A mixture of tert-butyl N-[1-[[4-(trifluoromethyl)phenyl]methyl]-4-piperidyl]carbamate (550 mg, 1.53 mmol, 1 eq) in HCl/MeOH (10 mL, 4 M) was stirred at 25° C. for 1 h under N$_2$ atmosphere. The reaction mixture was concentrated under reduced pressure to yield a residue which was neutralized by addition of sat. aq. NaHCO$_3$ (5 mL), and to the mixture was added water (30 mL) and extracted with ethyl acetate (30 mL×3). The combined organic phase was washed with brine (20 mL), dried over anhydrous Na$_2$SO$_4$, filtered and concentrated in vacuum to yield 1-[[4-(trifluoromethyl)phenyl]methyl]piperidin-4-amine (350 mg, 1.36 mmol, 88.3% yield, 100% purity) as a yellow solid which was used in the next step without further purification. $^1$H NMR (500 MHz, CD$_3$OD) δ ppm 7.82 (s, 4H), 4.45 (s, 2H), 3.59 (d, J=11.9 Hz, 2H), 3.49 (s, 1H), 3.22 (s, 2H), 2.26 (d, J=13.4 Hz, 2H), 2.12-1.97 (m, 2H); ES-LCMS m/z 259.0 [M+1]$^+$.

Step 3: N-[1-[[4-(Trifluoromethyl)phenyl]methyl]-4-piperidyl]prop-2-enamide

To a solution of 1-[[4-(trifluoromethyl)phenyl]methyl]piperidin-4-amine (300 mg, 1.16 mmol, 1 eq) in THF (5 mL) was added prop-2-enoyl chloride (210.25 mg, 2.32 mmol, 189.42 μL, 2 eq) and DIEA (450.34 mg, 3.48 mmol, 606.93 μL, 3 eq). The mixture was stirred at 25° C. for 1 h. To the mixture was added water (30 mL) and extracted with ethyl acetate (30 mL×3). The combined organic phase was washed with brine (20 mL), dried over anhydrous $Na_2SO_4$, filtered and concentrated in vacuum to yield a residue which was purified by preparative HPLC (column: Agela DuraShell C18 150*25 mm*5 μm; mobile phase: [water (0.04% $NH_3 \cdot H_2O$+10 mM $NH_4HCO_3$)-ACN]; B %: 30%-60%, 10 min), followed by lyophilization to yield N-[1-[[4-(trifluoromethyl)phenyl]methyl]-4-piperidyl]prop-2-enamide (72.71 mg, 232.80 μmol, 20.0% yield, 100% purity) as a white solid. $^1$H NMR (500 MHz, $CD_3OD$) δ ppm 7.63 (d, J=8.1 Hz, 2H), 7.54 (d, J=7.9 Hz, 2H), 6.28-6.17 (m, 2H), 5.63 (dd, J=3.8, 8.2 Hz, 1H), 3.81-3.69 (m, 1H), 3.61 (s, 2H), 2.88 (d, J=12.1 Hz, 2H), 2.17 (t, J=11.1 Hz, 2H), 1.88 (d, J=12.4 Hz, 2H), 1.56 (dq, J=3.6, 11.9 Hz, 2H); ES-LCMS m/z 313.0 [M+H]$^+$.

I-47

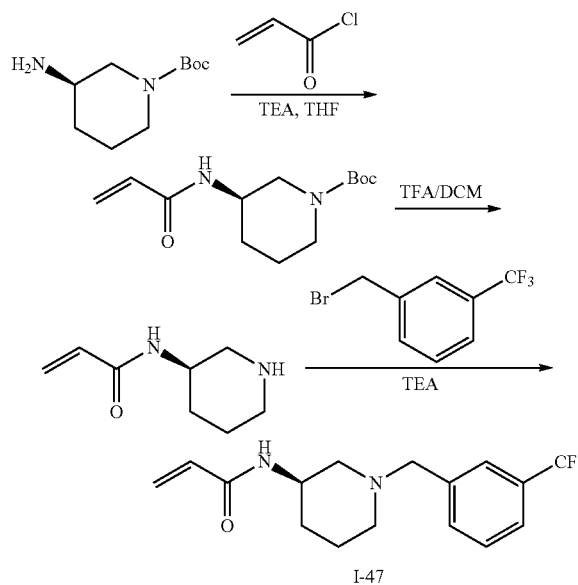

I-47

Step 1: tert-Butyl (3R)-3-(Prop-2-Enoylamino)piperidine-1-Carboxylate

To a solution of tert-butyl (3R)-3-aminopiperidine-1-carboxylate (500 mg, 2.50 mmol, 1 eq) in DCM (15 mL) was added $Et_3N$ (757.87 mg, 7.49 mmol, 1.04 mL, 3 eq) and prop-2-enoyl chloride (271.15 mg, 3.00 mmol, 244.28 μL, 1.2 eq). The mixture was stirred at 25° C. for 2 h. The reaction mixture was quenched by addition of $NH_4Cl$ (aq, 20 mL) and extracted with EtOAc (30 mL×3). The combined organic layers were washed with brine (30 mL), dried over $Na_2SO_4$, filtered and concentrated under reduced pressure to tert-Butyl (3R)-3-(Prop-2-Enoylamino)piperidine-1-Carboxylate (650 mg, 2.43 mmol, 97.3% yield, 95.0% purity) as a colorless oil, which was used in the next step without further purification. $^1$H NMR (500 MHz, $CDCl_3$) δ ppm 6.27 (d, J=17.0 Hz, 1H), 6.06 (dd, J=10.0 Hz, 17.0 Hz, 1H), 5.64 (d, J=10.5 Hz, 1H), 4.06-4.01 (m, 1H), 3.50-3.20 (m, 4H), 1.85-1.50 (m, 5H), 1.45 (s, 9H). ES-LCMS m/z no found.

Step 2: N-[(3R)-3-Piperidyl]prop-2-Enamide

To a solution of tert-butyl (3R)-3-(Prop-2-Enoylamino)piperidine-1-carboxylate (650 mg, 2.43 mmol, 1 eq) in DCM (10 mL) was added TFA (2 mL). The mixture was stirred at 28° C. for 2 h. TLC (PE/EtOAc=2/1, $R_f$=0.1) showed that new point was formed and start material was consumed completely. The mixture was concentrated to give N-[(3R)-3-Piperidyl]prop-2-Enamide (350 mg, 1.82 mmol, 74.8% yield, 80.0% purity) as a white solid, which was used in the next step without further purification. ES-LCMS m/z no found.

Step 3: N-[(3R)-1-[[3-(Trifluoromethyl)phenyl]methyl]-3-Piperidyl]prop-2-Enamide To a solution of N-[(3R)-3-Piperidyl]prop-2-Enamide (350 mg, 1.82 mmol, 1 eq) in DCM (8 mL) was added $Et_3N$ (183.73 mg, 1.82 mmol, 252.73 μL, 1 eq) and 1-(bromomethyl)-3-(trifluoromethyl)benzene (434.01 mg, 1.82 mmol, 276.44 μL, 1 eq). The mixture was stirred at 28° C. for 1 h. The reaction mixture was quenched by addition of aqueous solution of $NH_4Cl$ (20 mL) and extracted with EtOAc (20 mL×3). The combined organic layers were washed with brine (30 mL), dried over $Na_2SO_4$, filtered and concentrated under reduced pressure to give a residue which was purified by preparative HPLC (column: Welch Xtimate C18 150*25 mm*5 um; mobile phase: [water (10 mM $NH_4HCO_3$)-ACN]; B %: 36%-66%, 10 min) to yield N-[(3R)-1-[[3-(Trifluoromethyl)phenyl]methyl]-3-Piperidyl]prop-2-Enamide (19.93 mg, 62.28 μmol, 3.4% yield, 97.6% purity, $R_f$=1.862, ee=99.82%, $[\alpha]^{30.5}_D$=+26 (MeOH, c=0.100 g/100 mL)) as a white solid. $^1$H NMR (500 MHz, DMSO-$d_6$) δ ppm 7.96 (d, J=7.5 Hz, 1H), 7.66-7.59 (m, 3H), 7.58-7.53 (m, 1H), 6.22 (dd, J=10.0, 17.0 Hz, 1H), 6.04 (dd, J=2.0, 17.0 Hz, 1H), 5.55 (dd, J=2.0, 10.0 Hz, 1H), 3.85-3.75 (m, 1H), 3.57 (s, 2H), 2.72 (d, J=8.5 Hz, 1H), 2.64-2.57 (m, 1H), 2.01 (t, J=10.0 Hz, 1H), 1.87 (t, J=10.0 Hz, 1H), 1.78-1.60 (m, 2H), 1.54-1.43 (m, 1H), 1.25-1.13 (m, 1H); ES-LCMS m/z 313.2 [M+H]$^+$.

I-48

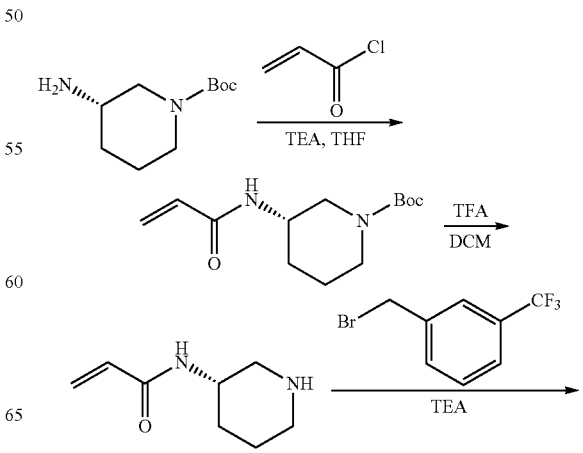

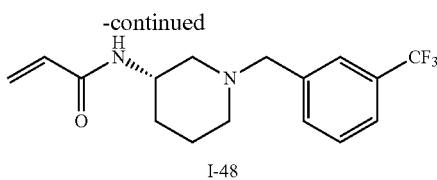

I-48

Step 1: tert-Butyl (3S)-3-(prop-2-enoylamino)piperidine-1-carboxylate

To a solution of tert-butyl (3S)-3-aminopiperidine-1-carboxylate (200 mg, 998.61 μmol, 316.46 μL, 1 eq) in THF (5 mL) was added TEA (202.10 mg, 2.00 mmol, 277.99 μL, 2 eq) and prop-2-enoyl chloride (99.42 mg, 1.10 mmol, 89.57 μL, 1.1 eq) under $N_2$. The mixture was stirred at 25° C. for 1 h. TLC (PE/EtOAc=5/1, $R_f$=0.60) indicated the starting material was consumed completely and one new spot formed. The mixture was concentrated and $NaHCO_3$ (40 mL) was added. The mixture was extracted with EtOAc (40 mL×3), washed with brine (10 mL), dried over $Na_2SO_4$, filtered and concentrated to yield tert-butyl (3S)-3-(prop-2-enoylamino)piperidine-1-carboxylate (100 mg, 382.78 μmol, 38.3% yield, 97.4% purity) as a white solid which was used in the next step directly without further purification. $^1$H NMR (400 MHz, $CDCl_3$) δ ppm 6.28 (d, J=16.8 Hz, 1H), 6.13-5.98 (m, 1H), 5.66 (d, J=11.3 Hz, 1H), 4.06 (s, 1H), 3.49-3.47 (m, 3H), 3.33-3.30 (m, 1H), 1.83-1.81 (m, 4H), 1.46 (s, 9H); ES-LCMS m/z 255.1 [M+H]$^+$.

Step 2: N-[(3S)-3-Piperidyl]prop-2-enamide

To a solution of tert-butyl (3S)-3-(prop-2-enoylamino)piperidine-1-carboxylate (100 mg, 382.78 μmol, 1 eq) in DCM (5 mL) was added TFA (1.34 g, 11.74 mmol, 869.57 μL, 30.68 eq) under $N_2$. The mixture was stirred at 25° C. for 12 h. The reaction mixture was concentrated under reduced pressure to yield N-[(3S)-3-piperidyl]prop-2-enamide (102 mg, 361.25 μmol, 94.4% yield, 95.0% purity, TFA salt) as a light white solid which was used in next step directly without further purification. $^1$H NMR (400 MHz, $CDCl_3$) δ ppm 6.34-6.28 (m, 1H), 6.21-6.13 (m, 1H), 5.76 (d, J=10.2 Hz, 1H), 4.43 (s, 1H), 3.33-3.30 (m, 1H), 3.36-3.27 (m, 1H), 3.16-3.13 (m, 1H), 1.92-1.89 (m, 4H).

Step 3: N-[(3S)-1-[[3-(Trifluoromethyl)phenyl]methyl]-3-piperidyl]prop-2-enamide To a solution of N-[(3S)-3-piperidyl]prop-2-enamide (100 mg, 354.17 μmol, 1 eq, TFA) in DCM (5 mL) were added 1-(bromomethyl)-3-(trifluoromethyl)benzene (84.66 mg, 354.17 μmol, 53.92 μL, 1 eq) and TEA (179.19 mg, 1.77 mmol, 246.48 μL, 5 eq). The mixture was stirred at 25° C. for 1 h under $N_2$. The reaction mixture was concentrated under reduced pressure to yield a residue which was purified by preparative HPLC (column: Agela DuraShell C18 150*25 mm*5 μm; mobile phase: [water (0.04% $NH_3H_2O$+ 10 mM $NH_4HCO_3$)-ACN]; B %: 37%-67%, 10 min), followed by lyophilization to yield N-[(3S)-1-[[3-(trifluoromethyl)phenyl]methyl]-3-piperidyl]prop-2-enamide (51.03 mg, 160.12 μmol, 45.2% yield, 98.0% purity, SFC: $R_t$=2.032, ee=99.28%, $[α]^{30.6}_D$=−33 (MeOH, c=0.1 g/100 mL)) as a white solid. $^1$H NMR (400 MHz, DMSO-$d_6$) δ ppm 7.94 (d, J=8.2 Hz, 1H), 7.64-7.53 (m, 4H), 6.26-6.15 (m, 1H), 6.07-5.99 (m, 1H), 5.54 (dd, J=2.3, 10.2 Hz, 1H), 3.88-3.73 (m, 1H), 3.56 (s, 2H), 2.70 (d, J=10.2 Hz, 1H), 2.59 (d, J=11.0 Hz, 1H), 2.01 (t, J=10.4 Hz, 1H), 1.86 (t, J 9.8 Hz, 1H), 1.74-1.64 (m, 2H), 1.54-1.43 (m, 1H), 1.24-1.13 (m, 1H); ES-LCMS m/z 313.0 [M+H]$^+$.

P-10

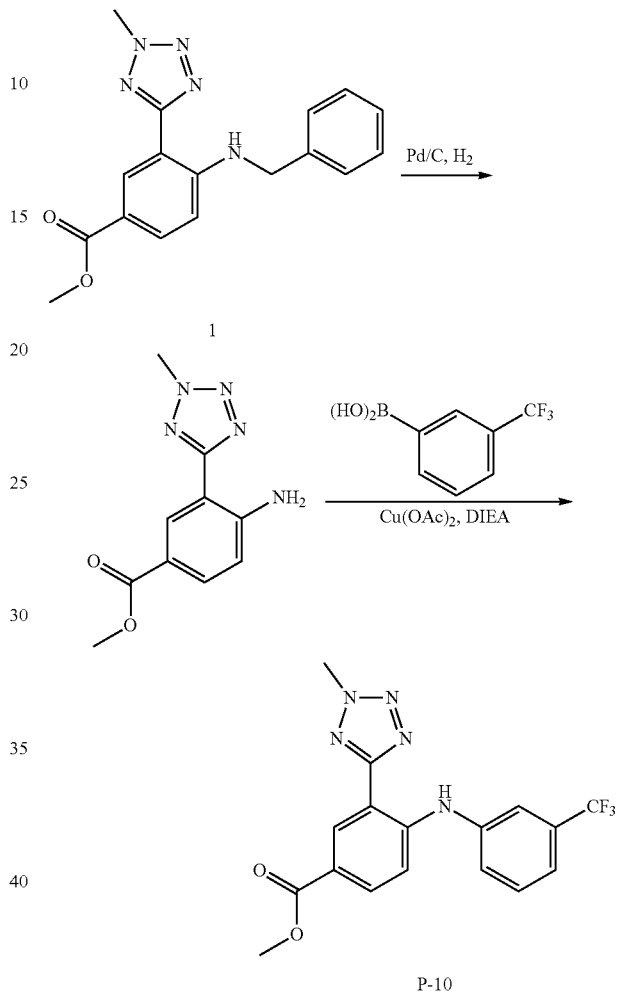

P-10

Step 1: Methyl 4-amino-3-(2-methyltetrazol-5-yl)benzoate

To a stirred solution of methyl 4-(benzylamino)-3-(2-methyltetrazol-5-yl)benzoate (400 mg, 1.24 mmol, 1 eq) in MeOH (50 mL) was added Pd/C (0.4 g, 10% Pd in C in 50% water) slowly. The reaction mixture was stirred at 25° C. for 12 h under $H_2$ atmosphere (45 psi). TLC (PE/EtOAc=1/1, $R_f$=0.30) showed starting material was remained and one new spot was detected. The reaction mixture was filtered through a pad of celite. The filtrate was concentrated under reduced pressure to give a residue which was purified by flash silica gel chromatography (from PE/EtOAc=100/1 to 1/1, TLC: PE/EtOAc=1/1, $R_f$=0.30) to yield methyl 4-amino-3-(2-methyltetrazol-5-yl)benzoate (200 mg, 857.54 μmol, 69.3% yield, 100.0% purity) as white solid. $^1$H NMR (400 MHz, DMSO-$d_6$) δ ppm 8.58 (d, J=2.0 Hz, 1H), 7.76 (dd, J=2.0, 8.6 Hz, 1H), 7.07 (s, 2H), 6.92 (d, J=8.8 Hz, 1H), 4.46 (s, 3H), 3.80 (s, 3H).

Step 2: N-Methyl-3-(4-methyl-1H-imidazol-2-yl)-4-[3-(trifluoromethyl)phenoxy]benzenesulfonamide To a stirred solution of methyl 4-amino-3-(2-methyltetrazol-5-yl)benzoate (180 mg, 771.78 umol, 1 eq) and [3-(trifluoromethyl)phenyl]boronic acid (366.46 mg, 1.93 mmol, 2.5 eq) in DCM (10 mL) was added Cu(OAc)$_2$ (280.36 mg, 1.54 mmol, 2 eq) and DIEA (299.24 mg, 2.32 mmol, 403.29 µL, 3 eq). The reaction mixture was stirred at 25° C. for 48 h under oxygen atmosphere (15 psi). The reaction mixture was diluted with water (50 mL) then extracted with DCM (30 mL×3). The combined organic layers were dried over Na$_2$SO$_4$, filtered and the filtrate was concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 55%-85%, 10 min). The desired fraction was lyophilized to yield methyl 3-(2-methyltetrazol-5-yl)-4-[3-(trifluoromethyl)anilino]benzoate (215.65 mg, 571.53 µmol, 74.1% yield, 100.0% purity) as white solid. $^1$H NMR (400 MHz, DMSO-d$_6$) δ ppm 9.20 (s, 1H), 8.64 (d, J=2.0 Hz, 1H), 7.94 (dd, J=2.0, 8.8 Hz, 1H), 7.66-7.58 (m, 3H), 7.45 (d, J=6.8 Hz, 1H), 7.39 (d, J=8.8 Hz, 1H), 4.49 (s, 3H), 3.85 (s, 3H); ES-LCMS m/z 378.0 [M+H]$^+$.
I-35

Step 1: N-[4-Methyl-3-[N-methyl-3-(trifluoromethyl)anilino]phenyl]prop-2-enamide To a solution of N-[4-methyl-3-[3-(trifluoromethyl)anilino]phenyl]prop-2-enamide (300 mg, 936.60 µmol, 1 eq) in DCM (10 mL) and AcOH (0.5 mL) was added paraformaldehyde (100 mg). The mixture was stirred at 25° C. for 1 h. NaBH$_3$CN (200 mg, 3.18 mmol, 3.40 eq) was added. The mixture was stirred at 25° C. for 11 h. TLC (PE/EtOAc=3/1, R$_f$=0.36) showed about 50% of the starting material was consumed completely. The reaction mixture was diluted with H$_2$O (50 mL) and extracted with DCM (50 mL×3). The organic layer was dried over Na$_2$SO$_4$, filtered and concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 47%-77%, 10 min). The desired fraction was lyophilized to yield a residue which was purified by preparative HPLC (column: Phenomenex Synergi C18 150*30 mm*4 um; mobile phase: [water (0.05% HCl)-ACN]; B %: 60%-80%, 10 min). The desired fraction was basified with saturated aqueous NaHCO$_3$ until pH=8 and extracted with EtOAc (50 mL×3). The organic layer was dried over Na$_2$SO$_4$, filtered and concentrated under reduced pressure to yield a residue which was dissolved in MeCN (10 mL) and water (10 mL) and lyophilized to yield N-[4-methyl-3-[N-methyl-3-(trifluoromethyl)anilino]phenyl]prop-2-enamide (45.32 mg, 135.55 µmol, 14.5% yield, 100.0% purity) as a white solid. $^1$H NMR (500 MHz, CDCl$_3$) δ ppm 7.52-7.38 (m, 2H), 7.28 (s, 1H), 7.27 (s, 1H), 7.23 (t, J=8.0 Hz, 1H), 6.95 (d, J=7.6 Hz, 1H), 6.76 (s, 1H), 6.62 (dd, J=1.8, 8.4 Hz, 1H), 6.42 (d, J=16.9 Hz, 1H), 6.22 (dd, J=10.2, 16.8 Hz, 1H), 5.77 (d, J=10.2 Hz, 1H), 3.25 (s, 3H), 2.09 (s, 3H); ES-LCMS m/z 335.0 [M+H]$^+$.
I-36

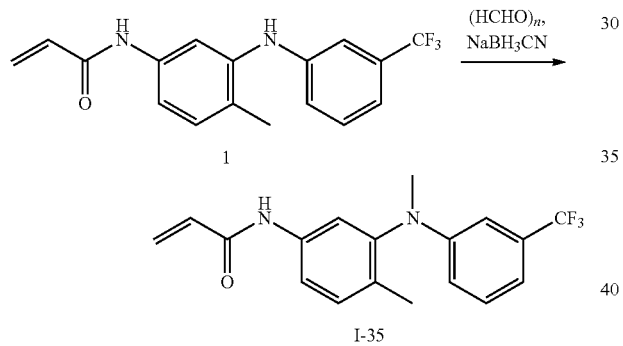

I-36

Step 1: N-(4-Bromo-3-nitro-phenyl)prop-2-enamide

To a mixture of 4-bromo-3-nitro-aniline (3 g, 13.82 mmol, 1 eq) and DIEA (5.36 g, 41.47 mmol, 7.22 mL, 3 eq) in DCM (20 mL) was added prop-2-enoyl chloride (1.50 g, 16.59 mmol, 1.35 mL, 1.2 eq) dropwise at 0° C. The mixture was stirred at 25° C. for 2 h. TLC (PE/EtOAc=1/1, R$_f$=0.35) showed the starting material was consumed completely. The reaction mixture was diluted with H$_2$O (50 mL) and extracted with DCM (50 mL×3). The organic layer was dried over Na$_2$SO$_4$, filtered and concentrated under reduced pressure to yield N-(4-bromo-3-nitro-phenyl)prop-2-enamide (3.7 g, 10.92 mmol, 79.0% yield, 80.0% purity) as a white solid, which was used in the next step without further purification. $^1$H NMR (400 MHz, CDCl$_3$) δ ppm 8.26 (d, J=2.3 Hz, 1H), 8.15 (s, 1H), 7.79 (dd, J=2.5, 8.8 Hz, 1H), 7.66 (d, J=9.0 Hz, 1H), 6.54-6.51 (m, 1H), 6.38-6.28 (m, 1H), 5.84 (dd, J=1.0, 10.0 Hz, 1H); ES-LCMS m/z 270.9, 272.9 [M+H]$^+$.

Step 2:
N-(3-Amino-4-bromo-phenyl)prop-2-enamide

A mixture of N-(4-bromo-3-nitro-phenyl)prop-2-enamide (3.7 g, 10.92 mmol, 1 eq), Fe (3.05 g, 54.60 mmol, 5 eq) and NH$_4$Cl (2.92 g, 54.60 mmol, 5 eq) in THF (15 mL), EtOH (15 mL) and H$_2$O (15 mL) was stirred at 55° C. for 12 h. TLC (PE/EtOAc=1/1, R$_f$=0.28) showed the starting material was consumed completely. The mixture was filtered. The filtrate was diluted with H$_2$O (50 mL) and extracted with EtOAc (50 mL×3). The organic layer was dried over Na$_2$SO$_4$, filtered and concentrated under reduced pressure to yield a residue which was purified by flash silica gel chromatography (from PE/EtOAc=100/1 to 2/1, TLC: PE/EtOAc=1/1, R$_f$=0.28) to yield N-(3-amino-4-bromo-phenyl)prop-2-enamide (2.2 g, 9.13 mmol, 83.6% yield, 100.0% purity) as a white solid. $^1$H NMR (400 MHz, CDCl$_3$) δ ppm 7.43 (s, 1H), 7.33 (d, J=8.6 Hz, 1H), 7.18-7.10 (m, 1H), 6.60-6.55 (m, 1H), 6.45-6.40 (m, 1H), 6.25-6.18 (m, 1H), 5.80-5.77 (m, 1H), 4.15 (s, 2H); ES-LCMS m/z 240.9, 242.9 [M+H]$^+$.

Step 3: N-[4-Bromo-3-[3-(trifluoromethyl)anilino]phenyl]prop-2-enamide

To a solution of N-(3-amino-4-bromo-phenyl)prop-2-enamide (2 g, 8.30 mmol, 1 eq), [3-(trifluoromethyl)phenyl]boronic acid (3.5 g, 18.43 mmol, 2.22 eq), Cu(OAc)$_2$ (3.77 g, 20.74 mmol, 2.5 eq) and DIEA (3.22 g, 24.89 mmol, 4.33 mL, 3 eq) in DCM (40 mL) was stirred under O$_2$ (15 psi) at 25° C. for 12 h. TLC (PE/EtOAc=1/1, R$_f$=0.40) showed about 60% of the starting material was consumed. The reaction mixture was diluted with H$_2$O (50 mL) and filtered. The filtrate was extracted with DCM (50 mL×3). The organic layer was dried over Na$_2$SO$_4$, filtered and concentrated under reduced pressure to yield a residue which was purified by flash silica gel chromatography (from PE/EtOAc=100/1 to 1/1, TLC: PE/EtOAc=1/1, R$_f$=0.40) to yield N-[4-bromo-3-[3-(trifluoromethyl)anilino]phenyl]prop-2-enamide (1.7 g, 3.97 mmol, 47.9% yield, 90% purity) as a white solid. $^1$H NMR (500 MHz, CDCl$_3$) δ ppm 7.61 (s, 1H), 7.49 (d, J=8.5 Hz, 1H), 7.46-7.42 (m, 1H), 7.40-7.35 (m, 2H), 7.31-7.24 (m, 2H), 7.10-6.98 (m, 1H), 6.45-6.37 (m, 1H), 6.25-6.16 (m, 2H), 5.77 (dd, J=0.9, 10.4 Hz, 1H); ES-LCMS m/z 384.9, 386.9 [M+H]t N-[4-Bromo-3-[3-(trifluoromethyl)anilino]phenyl]prop-2-enamide (100 mg, 90% purity) was purified by preparative HPLC (column: Phenomenex Synergi C18 150*30 mm*4 um; mobile phase: [water (0.05% HCl)-ACN]; B %: 60%-80%, 10.5 min). The desired fraction was basified with saturated aqueous NaHCO$_3$ until pH=8 and extracted with EtOAc (50 mL×3). The organic layer was dried over Na$_2$SO$_4$, filtered and concentrated under reduced pressure to yield a residue which was dissolved in MeCN (10 mL) and water (10 mL) and lyophilized to yield N-[4-bromo-3-[3-(trifluoromethyl)anilino]phenyl]prop-2-enamide (29.76 mg, 99.1% purity) as a white solid. $^1$H NMR (500 MHz, DMSO-d$_6$) δ ppm 10.23 (s, 1H), 8.05 (s, 1H), 7.80 (d, J=2.1 Hz, 1H), 7.59 (d, J=8.7 Hz, 1H), 7.49-7.42 (m, 1H), 7.32-7.24 (m, 3H), 7.16 (d, J=7.6 Hz, 1H), 6.44-6.35 (m, 1H), 6.29-6.20 (m, 1H), 5.81-5.72 (m, 1H); ES-LCMS m/z 385.0, 387.0 [M+H]$^+$.
I-82 & I-83

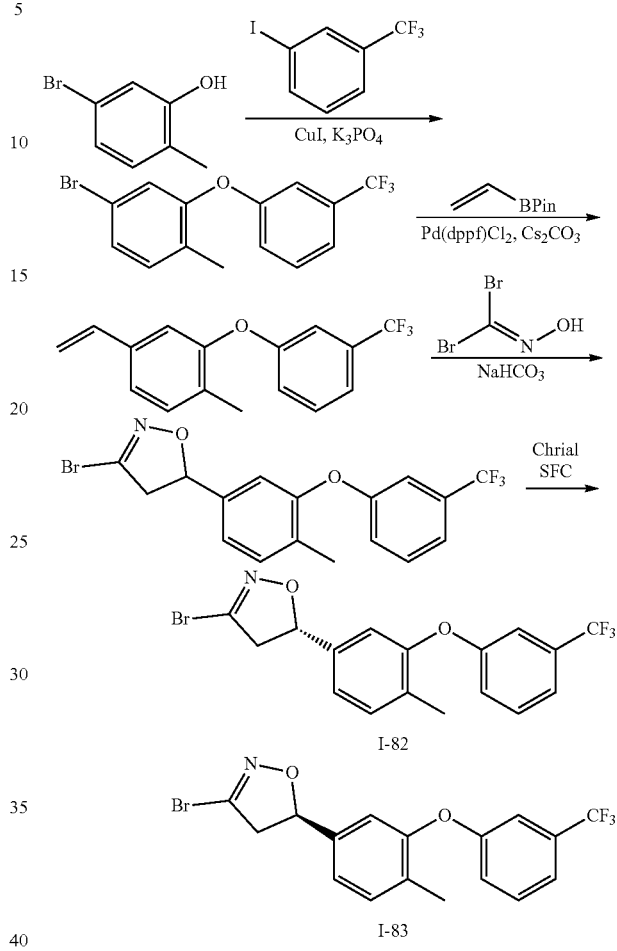

Step 1: 4-Bromo-1-methyl-2-[3-(trifluoromethyl)phenoxy]benzene

To a mixture of 5-bromo-2-methyl-phenol (1 g, 5.35 mmol, 1 eq) and 1-iodo-3-(trifluoromethyl)benzene (1.45 g, 5.35 mmol, 769.48 µL, 1 eq) in DMSO (10 mL) was added CuI (50.91 mg, 267.33 µmol, 0.05 eq), pyridine-2-carboxylic acid (65.82 mg, 534.66 µmol, 0.1 eq) and K$_3$PO$_4$ (1.82 g, 8.55 mmol, 1.6 eq). The mixture was stirred at 120° C. for 12 h. TLC (pure PE, R$_f$=0.80) showed starting material was consumed, and one major new spot was detected. The mixture was filtered and the filtrate was added H$_2$O (40 mL) and extracted with EtOAc (80 mL×3). The combine organic layers were dried over anhydrous Na$_2$SO$_4$, filtered and concentrated to yield a residue which was purified by flash silica gel chromatography (pure PE, TLC: pure PE, R$_f$=0.80) to yield 4-bromo-1-methyl-2-[3-(trifluoromethyl)phenoxy]benzene (800 mg, crude) as colorless oil. $^1$H NMR (500 MHz, DMSO-d$_6$) δ ppm 7.64-7.58 (m, 1H), 7.50-7.45 (m, 1H), 7.45-7.29 (m, 2H), 7.28-7.24 (m, 1H), 7.21-7.14 (m, 2H), 2.15-2.09 (m, 3H).

Step 2: 1-Methyl-2-[3-(trifluoromethyl)phenoxy]-4-vinyl-benzene

To a solution of 4-bromo-1-methyl-2-[3-(trifluoromethyl)phenoxy]benzene (700 mg, 2.11 mmol, 1 eq) in 1,4-dioxane (9 mL) was added Pd(dppf)Cl$_2$ (154.68 mg, 211.40 μmol, 0.1 eq), 4,4,5,5-tetramethyl-2-vinyl-1,3,2-dioxaborolane (390.70 mg, 2.54 mmol, 430.29 μL, 1.2 eq) and Cs$_2$CO$_3$ (2 M, 3.17 mL, 3 eq) under N$_2$ atmosphere. The mixture was stirred at 80° C. for 0.5 h under N$_2$ atmosphere. TLC (pure PE, R$_f$=0.75) showed starting material was consumed, and one major new spot was detected. To the mixture was added H$_2$O (20 mL) and extracted with EtOAc (20 mL×3). The combine organic layers were dried over anhydrous Na$_2$SO$_4$, filtered and concentrated to yield a residue which was purified by flash silica gel chromatography (pure PE, TLC: pure PE, R$_f$=0.75) to yield 1-methyl-2-[3-(trifluoromethyl) phenoxy]-4-vinyl-benzene (240 mg, 776.23 μmol, 36.7% yield, 90.0% purity) as colorless oil. $^1$H NMR (500 MHz, DMSO-d$_6$) δ ppm 7.59-7.56 (m, 1H), 7.43 (d, J=7.8 Hz, 1H), 7.36-7.31 (m, 2H), 7.19 (d, J=1.5 Hz, 1H), 7.16-7.11 (m, 2H), 6.69 (dd, J=11.0, 17.7 Hz, 1H), 5.80 (d, J=17.7 Hz, 1H), 5.23 (d, J=11.1 Hz, 1H), 2.13 (s, 3H).

Step 3: (5S)-3-Bromo-5-[4-methyl-3-[3-(trifluoromethyl)phenoxy]phenyl]-4,5-dihydroisoxazole and (5R)-3-bromo-5-[4-methyl-3-[3-(trifluoromethyl) phenoxy]phenyl]-4,5-dihydroisoxazole To a mixture of 1-methyl-2-[3-(trifluoromethyl)phenoxy]-4-vinyl-benzene (100 mg, 323.43 μmol, 1 eq) and dibromomethanone oxime (78.72 mg, 388.11 μmol, 1.2 eq) in EtOAc (6 mL) was added NaHCO$_3$ (271.71 mg, 3.23 mmol, 10 eq). The mixture was stirred at 25° C. for 12 h under N$_2$ atmosphere. TLC (PE/EtOAc=4/1, R$_f$=0.50) showed starting material was consumed completely, and one major new spot was detected. The mixture was diluted with H$_2$O (20 mL) and extracted with EtOAc (20 mL×3). The combine organic layers were dried over anhydrous Na$_2$SO$_4$, filtered and concentrated to yield a residue which was purified by preparative TLC (PE/EtOAc=4/1, TLC: PE/EtOAc=4/1, R$_f$=0.50) to yield a residue which was purified by preparative SFC (column: REGIS (s, s) WHELK-01 (250 mm*30 mm, 5 μm); mobile phase: [Neu-EtOH]; B %: 20%-20%, min) to yield peak 1 and peak 2. Peak 1 was concentrated under reduced pressure to yield (5S)-3-bromo-5-[4-methyl-3-[3-(trifluoromethyl)phenoxy] phenyl]-4,5-dihydroisoxazole (43.46 mg, 108.60 μmol, 33.6% yield, 100.0% purity, SFC: R$_t$=1.875, ee=100%, [α]$^{33.3}_D$=−156.346 (MeOH, c=0.053 g/100 mL)) as colorless oil. $^1$H NMR (500 MHz, CDCl$_3$) δ ppm 7.45-7.39 (m, 1H), 7.32 (d, J=8.1 Hz, 2H), 7.15 (s, 1H), 7.12 (dd, J=1.4, 7.8 Hz, 1H), 7.03 (d, J=8.2 Hz, 1H), 6.93 (d, J=1.2 Hz, 1H), 5.62 (dd, J=9.3, 10.7 Hz, 1H), 3.59 (dd, J=10.8, 17.2 Hz, 1H), 3.18 (dd, J=9.0, 17.2 Hz, 1H), 2.23 (s, 3H); ES-LCMS m/z 399.9, 401.9 [M+H]$^+$, 440.9, 442.9 [M+ACN+H]$^+$. Peak 2 was concentrated under reduced pressure to yield (5R)-3-bromo-5-[4-methyl-3-[3-(trifluoromethyl)phenoxy] phenyl]-4,5-dihydroisoxazole (33.91 mg, 84.73 μmol, 26.2% yield, 100.0% purity, SFC: R$_t$=2.356, ee=100%, [α]$^{33.2}_D$=+141.289 (MeOH, c=0.091 g/100 mL)) as colorless oil. $^1$H NMR (500 MHz, CDCl$_3$) δ ppm 7.45-7.38 (m, 1H), 7.32 (d, J=7.9 Hz, 2H), 7.15 (s, 1H), 7.12 (dd, J=1.4, 7.8 Hz, 1H), 7.03 (d, J=8.2 Hz, 1H), 6.93 (d, J=1.2 Hz, 1H), 5.62 (dd, J=9.2, 10.6 Hz, 1H), 3.59 (dd, J=11.0, 17.2 Hz, 1H), 3.18 (dd, J=8.9, 17.2 Hz, 1H), 2.23 (s, 3H); ES-LCMS m/z 399.9, 401.9 [M+H]$^+$, 440.9, 442.9 [M+ACN+H]$^+$.

I-84 & I-85

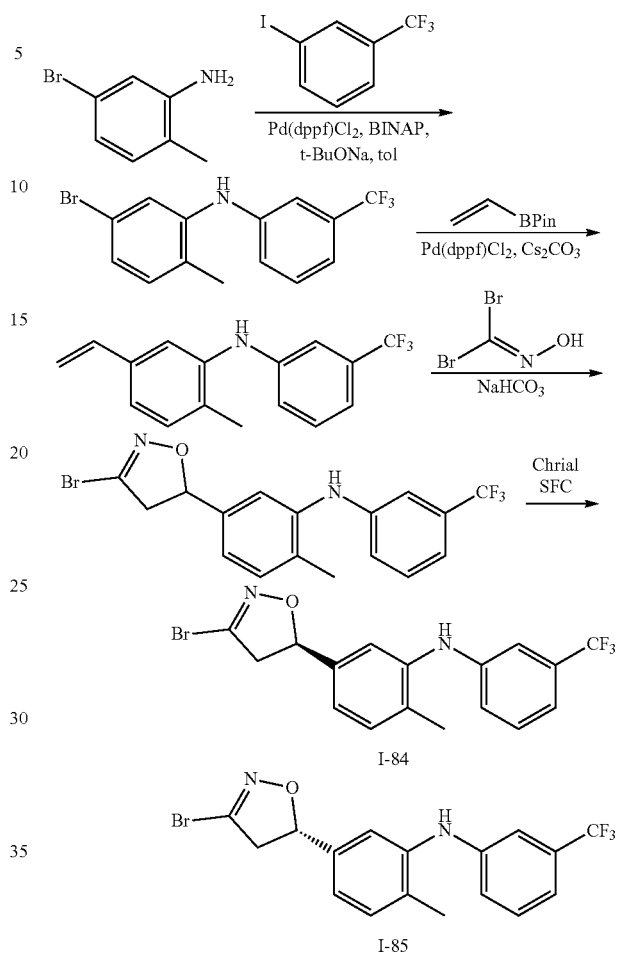

Step 1: 5-Bromo-2-methyl-N-[3-(trifluoromethyl)phenyl]aniline

To a solution of 1-iodo-3-(trifluoromethyl)benzene (3.51 g, 12.90 mmol, 1.86 mL, 1.2 eq) and 5-bromo-2-methyl-aniline (2 g, 10.75 mmol, 1 eq) in toluene (60 mL) was added Pd$_2$(dba)$_3$ (492.19 mg, 537.49 μmol, 0.05 eq), t-BuONa (1.03 g, 10.75 mmol, 1 eq) and BINAP (669.36 mg, 1.07 mmol, 0.1 eq). The mixture was stirred at 120° C. for 2 h under N$_2$ atmosphere. The reaction mixture was diluted with water (50 mL) then extracted with EtOAc (50 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=5/1, R$_f$=0.65) to yield 5-bromo-2-methyl-N-[3-(trifluoromethyl) phenyl]aniline (1.38 g, 2.80 mmol, 26.1% yield, 67.1% purity) as yellow oil. $^1$H NMR (500 MHz, DMSO-d$_6$) δ ppm 8.00 (s, 1H), 7.42 (t, J=7.8 Hz, 1H), 7.29 (d, J=1.7 Hz, 1H), 7.20-7.17 (m, 1H), 7.16-7.12 (m, 3H), 7.10 (d, J=7.6 Hz, 1H), 2.15 (s, 3H); ES-LCMS m/z 329.9, 332.0 [M+H]$^+$.

Step 2: 2-Methyl-N-[3-(trifluoromethyl)phenyl]-5-vinyl-aniline

To a solution of 5-bromo-2-methyl-N-[3-(trifluoromethyl)phenyl]aniline (1.3 g, 2.64 mmol, 1 eq), 4,4,5,5-tetramethyl-2-vinyl-1,3,2-dioxaborolane (488.32 mg, 3.17 mmol, 537.80 μL, 1.2 eq) in 1,4-dioxane (6 mL) and water (2 mL) was added Cs₂CO₃ (2.58 g, 7.93 mmol, 3 eq) and Pd(dppf)Cl₂ (193.33 mg, 264.22 μmol, 0.1 eq). The mixture was bubbled with N₂ for 2 min then stirred at 100° C. for 30 min under microwave (2 bar). The reaction mixture was diluted with water (150 mL) then extracted with EtOAc (50 mL×3). The combined organic layers were dried over Na₂SO₄, filtered and the filtrate was concentrated to yield a residue which was purified by flash silica gel chromatography (from PE/EtOAc=100/1 to 2/1, TLC: PE/EtOAc=5/1, $R_f$=0.5) to yield 2-methyl-N-[3-(trifluoromethyl)phenyl]-5-vinyl-aniline (465 mg, 1.30 mmol, 49.1% yield, 77.3% purity) as yellow oil. ¹H NMR (500 MHz, DMSO-d₆) δ ppm 7.93 (s, 1H), 7.42 (t, J=7.8 Hz, 1H), 7.29-7.28 (m, 1H), 7.10 (d, J=7.6 Hz, 1H), 7.05-7.01 (m, 4H), 6.66 (d, J=10.9, 17.6 Hz, 1H), 5.71 (d, J=17.5 Hz, 1H), 5.18 (d, J=11.0 Hz, 1H), 2.19 (s, 3H); ES-LCMS m/z 278.0 [M+H]⁺.

Step 3: 5-[(5R)-3-Bromo-4,5-dihydroisoxazol-5-yl]-2-methyl-N-[3-(trifluoromethyl)phenyl]aniline and 5-[(5S)-3-bromo-4,5-dihydroisoxazol-5-yl]-2-methyl-N-[3-(trifluoromethyl)phenyl]aniline To a solution of 2-methyl-N-[3-(trifluoromethyl)phenyl]-5-vinyl-aniline (300 mg, 836.33 μmol, 1 eq) and dibromomethanone oxime (305.34 mg, 1.51 mmol, 1.8 eq) in EtOAc (30 mL) was added NaHCO₃ (702.60 mg, 8.36 mmol, 325.28 μL, 10 eq). The mixture was stirred at 25° C. for 12 h under N₂ atmosphere. The reaction mixture was diluted with water (50 mL) then extracted with EtOAc (50 mL×3). The combined organic layers were dried over Na₂SO₄, filtered and the filtrate was concentrated to yield a residue which was purified by flash silica gel chromatography (from PE/EtOAc=100/1 to 2/1, TLC: PE/EtOAc=5/1, $R_f$=0.5) to yield the compound which was separated by SFC (column: DAICEL CHIRALPAK AD-H (250 mm*30 mm, 5 um); mobile phase: [0.1% NH₃H₂O EtOH]; B %: 25%-25%, min) to yield Peak 1 and Peak 2. Peak 1 was concentrated under reduced pressure to yield a residue which was lyophilized to yield 5-[(5R)-3-bromo-4,5-dihydroisoxazol-5-yl]-2-methyl-N-[3-(trifluoromethyl)phenyl]aniline (15.27 mg, 36.49 μmol, 4.4% yield, 95.4% purity, SFC: $R_t$=1.156 min, ee=98.3%, [α]³³·⁴_D=+92.0, MeOH, c=0.05 g/100 mL) as yellow oil. ¹H NMR (400 MHz, DMSO-d₆) δ ppm 7.96 (s, 1H), 7.38 (t, J=7.8 Hz, 1H), 7.27 (d, J=7.8 Hz, 1H), 7.19 (s, 1H), 7.10-6.96 (m, 4H), 5.68-5.59 (m, 1H), 3.74 (d, J=10.9, 17.5 Hz, 1H), 3.27-3.21 (m, 1H), 2.19 (s, 3H); ES-LCMS m/z 400.9, 403.0 [M+H]⁺. Peak 2 was concentrated under reduced pressure to yield a residue which was lyophilized to yield 5-[(5S)-3-bromo-4,5-dihydroisoxazol-5-yl]-2-methyl-N-[3-(trifluoromethyl)phenyl]aniline (24.68 mg, 59.04 μmol, 7.1% yield, 95.5% purity, SFC: $R_t$=0.987 min, ee=99.7%, [α]³³·⁴_D=−137.8, MeOH, c=0.09 g/100 mL) as yellow oil. ¹H NMR (400 MHz, DMSO-d₆) δ ppm 7.96 (s, 1H), 7.38 (t, J=7.7 Hz, 1H), 7.27 (d, J=7.6 Hz, 1H), 7.19 (s, 1H), 7.12-6.97 (m, 4H), 5.72-5.57 (m, 1H), 3.74 (d, J=11.0, 17.6 Hz, 1H), 3.27-3.21 (m, 1H), 2.19 (s, 3H); ES-LCMS m/z 400.9, 403.0 [M+H]⁺.
I-37

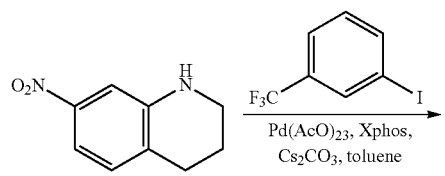

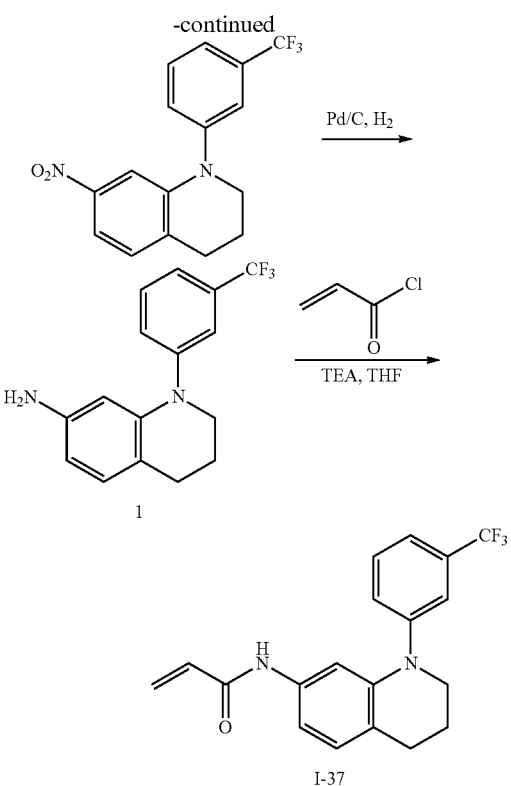

Step 1: 7-Nitro-1-[3-(trifluoromethyl)phenyl]-3,4-dihydro-2H-quinoline

To a solution of 7-nitro-1,2,3,4-tetrahydroquinoline (300 mg, 1.68 mmol, 1 eq) and 1-iodo-3-(trifluoromethyl) benzene (457.95 mg, 1.68 mmol, 242.30 μL, 1 eq) in toluene (10 mL) were added Cs₂CO₃ (1.10 g, 3.37 mmol, 2 eq), XPhos (160.52 mg, 336.72 μmol, 0.2 eq) and Pd (OAc)₂ (37.80 mg, 168.36 mol, 0.1 eq) under N₂. The mixture was stirred at 100° C. for 12 h. TLC (PE/EtOAc=5/1, $R_f$=0.44) indicated the starting material was consumed completely and one new spot formed. The mixture was concentrated and sat.aq-.NaHCO₃ (40 mL) was added. The mixture was extracted with EtOAc (40 mL×3), concentrated under reduced pressure to yield a residue which was purified by flash silica gel chromatography (From PE/EtOAc=1/0 to 5/1, $R_f$=0.44) to yield 7-nitro-1-[3-(trifluoromethyl)phenyl]-3,4-dihydro-2H-quinoline (180 mg, 558.52 μmol, 33.2% yield, 100% purity) as a light yellow solid. ES-LCMS m/z 323.0 [M+H]⁺.

Step 2: 1-[3-(Trifluoromethyl)phenyl]-3,4-dihydro-2H-quinolin-7-amine

To a solution of 7-nitro-1-[3-(trifluoromethyl)phenyl]-3,4-dihydro-2H-quinoline (180 mg, 558.52 μmol, 1 eq) in MeOH (10 mL) was added Pd/C (100 mg, 10%) under N₂. The mixture was stirred at 25° C. for 12 h under H₂ (30 psi). The reaction mixture was filtered and the filtrate was concentrated to yield 1-[3-(trifluoromethyl)phenyl]-3,4-dihydro-2H-quinolin-7-amine (150 mg, crude) which was used in the next step without further purification. ¹H NMR (400 MHz, DMSO-d₆) δ ppm 7.56-7.26 (m, 6H), 6.73 (d, J=7.4 Hz, 1H), 6.12-6.02 (m, 2H), 3.56-3.52 (m, 2H), 2.61-2.58 (m, 2H), 1.88-1.83 (m, 2H); ES-LCMS m/z 293.0 [M+H]⁺.

Step 3: N-[1-[3-(Trifluoromethyl)phenyl]-3,4-dihydro-2H-quinolin-7-yl]prop-2-enamide To a solution of 1-[3-(trifluoromethyl)phenyl]-3,4-dihydro-2H-quinolin-7-amine (150 mg, 513.17 μmol, 1 eq) in THF (5 mL) was added TEA (155.78 mg, 1.54 mmol, 214.28 μL, 3 eq) and prop-2-enoyl chloride (55.74 mg, 615.81 μmol, 50.21 μL, 1.2 eq) at 0° C. under $N_2$. The mixture was stirred at 25° C. for 1 h. The reaction mixture was concentrated under reduced pressure to yield a residue which was purified by preparative HPLC (column: Agela DuraShell C18 150*25 mm*5 μm; mobile phase: [water (0.04% $NH_3H_2O$+10 mM $NH_4HCO_3$)-ACN]; B %: 50%-80%, 10 min), followed by lyophilization to yield N-[1-[3-(trifluoromethyl)phenyl]-3,4-dihydro-2H-quinolin-7-yl]prop-2-enamide (19.23 mg, 55.52 μmol, 10.8% yield, 100% purity) as a brown solid. $^1$H NMR (400 MHz, $CD_3OD$) δ ppm 7.50-7.43 (m, 3H), 7.30 (s, 1H), 7.09 (s, 1H), 7.06-6.98 (m, 2H), 6.38-6.17 (m, 2H), 5.66 (dd, J=2.1, 9.7 Hz, 1H), 3.67-3.59 (m, 2H), 2.79 (t, J=6.5 Hz, 2H), 2.01 (q, J=6.1 Hz, 2H); ES-LCMS m/z 346.9 [M+H]$^+$.
I-38

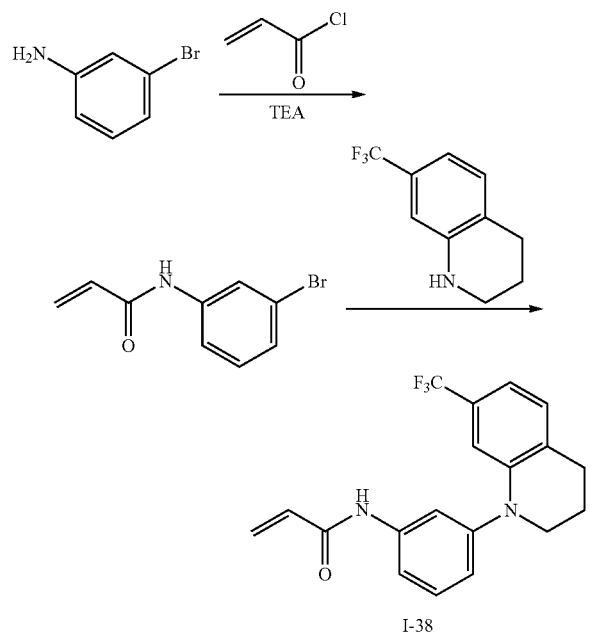

I-38

Step 1: N-(3-Bromophenyl)prop-2-enamide

To a solution of 3-bromoaniline (1 g, 5.81 mmol, 632.91 μL, 1 eq) in DCM (15 mL) was added TEA (1.18 g, 11.63 mmol, 1.62 mL, 2 eq) and prop-2-enoyl chloride (578.76 mg, 6.39 mmol, 521.40 μL, 1.1 eq) under $N_2$. The mixture was stirred at 25° C. for 1 h. TLC (PE/EtOAc=5/1, $R_f$=0.22) indicated the starting material was consumed completely and one new spot formed. The reaction mixture was concentrated under reduced pressure to yield a residue which was purified by flash silica gel chromatography (From PE/EtOAc=1/0 to 5/1, $R_f$=0.22) to yield N-(3-bromophenyl)prop-2-enamide (1.2 g, 5.20 mmol, 89.5% yield, 98.0% purity) as a white solid. $^1$H NMR (400 MHz, $CDCl_3$) δ ppm 7.85 (s, 1H), 7.48 (d, J=7.4 Hz, 1H), 7.26-7.24 (m, 1H), 7.22-7.17 (m, 1H), 6.45 (dd, J=1.2, 16.8 Hz, 1H), 6.23 (dd, J=10.4, 17.0 Hz, 1H), 5.81 (dd, J=1.2, 10.2 Hz, 1H); ES-LCMS m/z 225.9, 227.8 [M+H]$^+$.

Step 2: N-[3-[7-(Trifluoromethyl)-3,4-dihydro-2H-quinolin-1-yl]phenyl]prop-2-enamide A mixture of N-(3-bromophenyl)prop-2-enamide (200 mg, 884.68 μmol, 1 eq), 7-(trifluoromethyl)-1,2,3,4-tetrahydroquinoline (177.99 mg, 884.68 μmol, 1 eq), Ruphos (82.57 mg, 176.94 μmol, 0.2 eq), $Pd_2(dba)_3$ (81.01 mg, 88.47 μmol, 0.1 eq) and t-BuONa (170.04 mg, 1.77 mmol, 2 eq) in toluene (10 mL) was degassed and purged with $N_2$ for three times. The mixture was stirred at 100° C. for 12 h under $N_2$ atmosphere. The mixture was concentrated and sat.aq. $NaHCO_3$ (40 mL) was added. The mixture was extracted with EtOAc (40 mL×3), concentrated under reduced pressure to yield a residue which was purified by flash silica gel chromatography (From PE/EtOAc=1/0 to 5/1, $R_f$=0.58) and preparative HPLC (column: Agela DuraShell C18 150*25 mm*5 μm; mobile phase: [water (0.04% $NH_3H_2O$ 10 mM $NH_4HCO_3$)-ACN]; B %: 52%-82%, 10 min), followed by lyophilization to yield N-[3-[7-(trifluoromethyl)-3,4-dihydro-2H-quinolin-1-yl]phenyl]prop-2-enamide (12.89 mg, 37.22 μmol, 4.2% yield, 100.0% purity) as a white solid. $^1$H NMR (400 MHz, $CDCl_3$) δ ppm 7.56 (s, 1H), 7.35-7.28 (m, 2H), 7.11 (d, J=7.8 Hz, 1H), 7.02 (d, J=6.7 Hz, 1H), 6.95-6.88 (m, 2H), 6.44 (d, J=16.0 Hz, 1H), 6.29-6.19 (m, 1H), 5.79 (d, J=11.3 Hz, 1H), 3.68-3.62 (m, 2H), 2.87 (t, J=6.5 Hz, 2H), 2.08-2.01 (m, 2H); ES-LCMS m/z 347.0 [M+H]$^+$.
I-86 & I-87

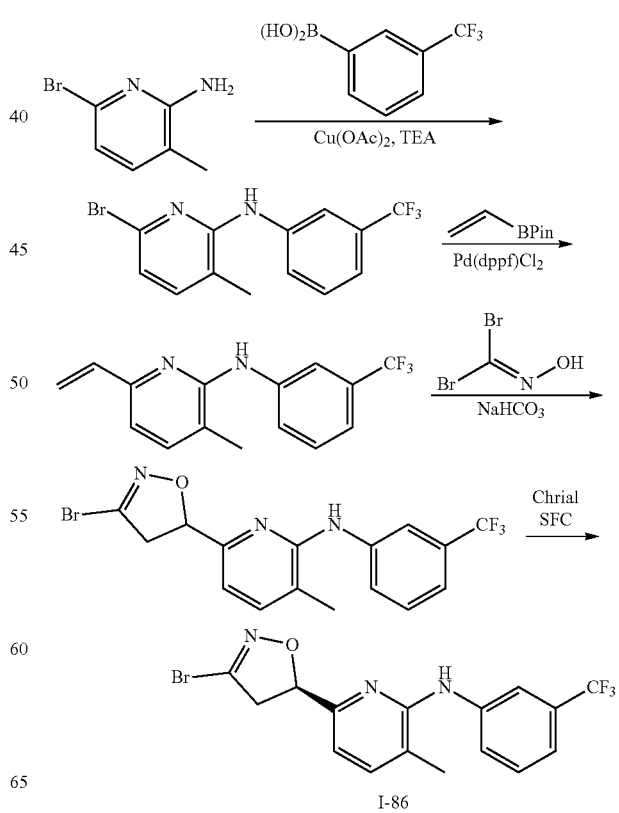

I-86

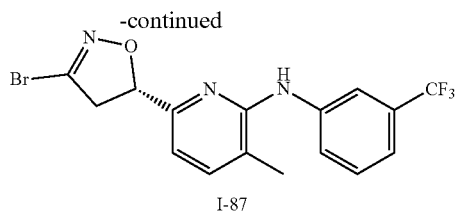

I-87

Step 1: 6-Bromo-3-methyl-N-[3-(trifluoromethyl)phenyl]pyridin-2-amine

To a solution of 6-bromo-3-methyl-pyridin-2-amine (1 g, 5.35 mmol, 1 eq) and [3-(trifluoromethyl)phenyl]boronic acid (1.52 g, 8.02 mmol, 1.5 eq) in DCM (20 mL) was added Cu(OAc)$_2$ (1.94 g, 10.69 mmol, 2 eq) and DIEA (2.07 g, 16.04 mmol, 2.79 mL, 3 eq). The mixture was stirred at 25° C. for 12 h under O$_2$ atmosphere (15 psi). The reaction mixture was filtered through a pad of celite and the filtrate was concentrated to yield a residue which was purified by flash silica gel chromatography (from PE/EtOAc=100/1 to 2/1, TLC: PE/EtOAc=3/1, R$_f$=0.65) to yield 6-bromo-3-methyl-N-[3-(trifluoromethyl)phenyl]pyridin-2-amine (861 mg, 2.60 mmol, 48.6% yield, 100.0% purity) as a yellow solid. $^1$H NMR (500 MHz, DMSO-d$_6$) δ ppm 8.47 (s, 1H), 8.12 (s, 1H), 7.97 (d, J=8.5 Hz, 1H), 7.51 (t, J=8.0 Hz, 1H), 7.43 (d, J=7.6 Hz, 1H), 7.27 (d, J=7.6 Hz, 1H), 6.99 (d, J=7.6 Hz, 1H), 2.27-2.22 (m, 3H); ES-LCMS m/z 331.0, 332.9 [M+H]$^+$.

Step 2: 3-Methyl-N-[3-(trifluoromethyl)phenyl]-6-vinyl-pyridin-2-amine

To a solution of 6-bromo-3-methyl-N-[3-(trifluoromethyl)phenyl]pyridin-2-amine (800 mg, 2.42 mmol, 1 eq), 4,4,5,5-tetramethyl-2-vinyl-1,3,2-dioxaborolane (446.51 mg, 2.90 mmol, 491.75 μL, 1.2 eq) in water (0.5 mL) and 1,4-dioxane (1.5 mL) was added Pd(dppf)Cl$_2$ (176.78 mg, 241.60 μmol, 0.1 eq) and Cs$_2$CO$_3$ (2.36 g, 7.25 mmol, 3 eq). The mixture was bubbled with N$_2$ for 2 min then stirred at 80° C. for 1 h under microwave. The reaction mixture was filtered through a pad of celite and the filtrate was concentrated to yield a residue which was purified by flash silica gel chromatography (from PE/EtOAc=100/1 to 2/1, TLC: PE/EtOAc=5/1, R$_f$=0.70) to yield 3-methyl-N-[3-(trifluoromethyl)phenyl]-6-vinyl-pyridin-2-amine (267 mg, 915.36 μmol, 37.9% yield, 95.4% purity) as yellow oil. $^1$H NMR (500 MHz, DMSO-d$_6$) δ ppm 8.50 (s, 1H), 8.27 (s, 1H), 7.98 (d, J=8.4 Hz, 1H), 7.52-7.44 (m, 2H), 7.22 (d, J=7.6 Hz, 1H), 6.82 (d, J=7.3 Hz, 1H), 6.70 (dd, J=10.6, 17.2 Hz, 1H), 6.12 (dd, J=1.9, 17.2 Hz, 1H), 5.33 (dd, J=1.8, 10.5 Hz, 1H), 2.29 (s, 3H); ES-LCMS m/z 279.0 [M+H]$^+$.

Step 3: 6-[(5R)-3-Bromo-4,5-dihydroisoxazol-5-yl]-3-methyl-N-[3-(trifluoromethyl)phenyl]pyridin-2-amine & 6-[(5S)-3-bromo-4,5-dihydroisoxazol-5-yl]-3-methyl-N-[3-(trifluoromethyl)phenyl]pyridin-2-amine To a solution of 3-methyl-N-[3-(trifluoromethyl)phenyl]-6-vinyl-pyridin-2-amine (200 mg, 684.22 μmol, 1 eq) and dibromomethanone oxime (208.17 mg, 1.03 mmol, 1.5 eq) in EtOAc (10 mL) was added NaHCO$_3$ (574.79 mg, 6.84 mmol, 10 eq). The mixture was stirred at 25° C. for 12 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=3/1, R$_f$=0.75) to yield the compound which was separated by SFC (column: DAICEL CHIRALCEL OJ-H (250 mm*30 mm, 5um); mobile phase: [0.1% NH$_3$H$_2$O/EtOH]; B %: 30%-30%) to yield Peak 1 and Peak 2. Peak 1 was concentrated under reduced pressure to yield a residue which was lyophilized to yield 6-[(5R)-3-bromo-4,5-dihydroisoxazol-5-yl]-3-methyl-N-[3-(trifluoromethyl)phenyl]pyridin-2-amine (56.51 mg, 141.21 μmol, 20.6% yield, 100.0% purity, SFC: R$_t$=3.042 min, ee=96.9%, [α]$^{30.5}_D$=+120 (MeOH, c=0.055 g/100 mL)) as a white solid; $^1$H NMR (500 MHz, DMSO-d$_6$) δ ppm 8.34 (s, 1H), 8.11 (s, 1H), 8.03 (d, J=8.1 Hz, 1H), 7.54-7.44 (m, 2H), 7.22 (d, J=7.8 Hz, 1H), 6.89 (d, J=7.3 Hz, 1H), 5.62 (dd, J=7.9, 10.8 Hz, 1H), 3.72-3.64 (m, 1H), 3.60-3.53 (m, 1H), 2.29 (s, 3H); ES-LCMS m/z 399.9, 402.0 [M+H]$^+$. Peak 2 was concentrated under reduced pressure to yield a residue which was lyophilized to yield 6-[(5S)-3-bromo-4,5-dihydroisoxazol-5-yl]-3-methyl-N-[3-(trifluoromethyl)phenyl]pyridin-2-amine (53.58 mg, 133.89 μmol, 19.6% yield, 100.0% purity, SFC: R$_t$=3.264 min, ee=94.8%, [α]$^{30.5}_D$=−118.52 (MeOH, c=0.054 g/100 mL)) as a white solid; $^1$H NMR (500 MHz, DMSO-d$_6$) δ ppm 8.34 (s, 1H), 8.12 (s, 1H), 8.03 (d, J=8.2 Hz, 1H), 7.56-7.43 (m, 2H), 7.22 (d, J=7.6 Hz, 1H), 6.90 (d, J=7.3 Hz, 1H), 5.62 (dd, J=7.9, 10.8 Hz, 1H), 3.72-3.65 (m, 1H), 3.61-3.54 (m, 1H), 2.30 (s, 3H); ES-LCMS m/z 400.0, 401.9 [M+H]$^+$.

I-39

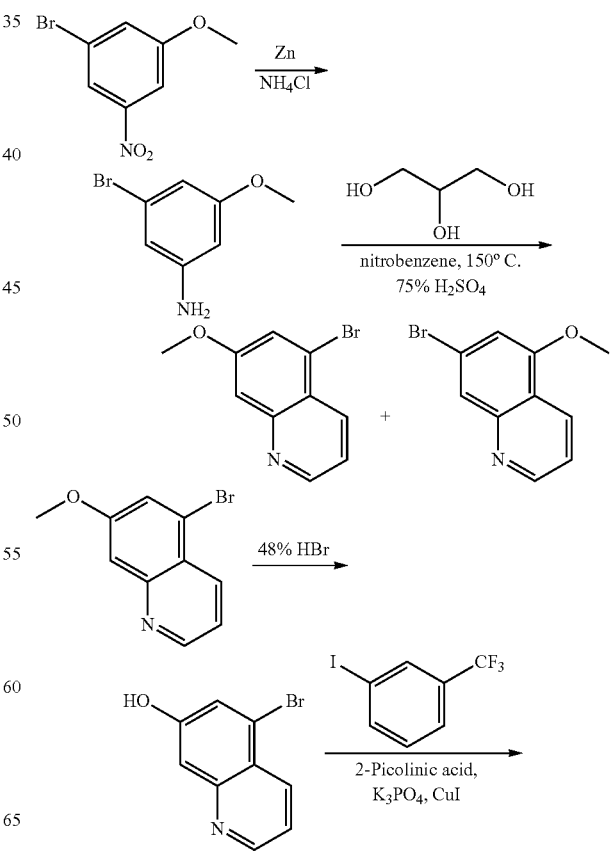

-continued

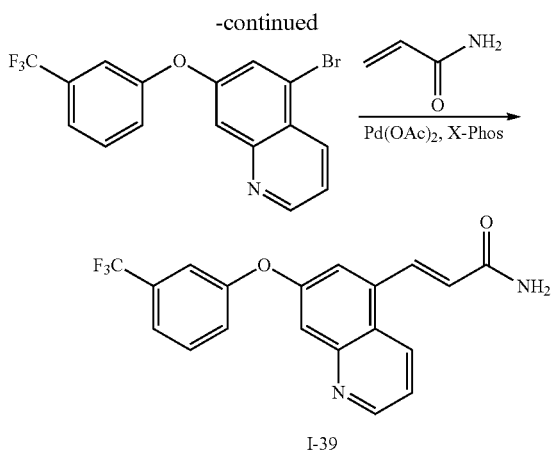

I-39

Step 1: 3-Bromo-5-methoxy-aniline

To a solution of 1-bromo-3-methoxy-5-nitro-benzene (10 g, 43.10 mmol, 1 eq) in THF (80 mL), H$_2$O (80 mL) and EtOH (80 mL) was added Fe (24.07 g, 430.98 mmol, 10 eq) and NH$_4$Cl (23.05 g, 430.98 mmol, 10 eq). The mixture was stirred at 55° C. for 12 h. TLC (PE/EtOAc=3/1, R$_f$=0.4) showed starting material was consumed completely and one major new spot was detected. The mixture was filtered and the filtrate was concentrated to yield a residue which was purified by flash silica gel chromatography (from pure PE to PE/EtOAc=2/1, TLC: PE/EtOAc=3/1, R$_f$=0.4) to yield 3-bromo-5-methoxy-aniline (6.7 g, 29.84 mmol, 69.3% yield, 90.0% purity) as a gray solid. $^1$H NMR (500 MHz, DMSO-d$_6$) δ ppm 6.33 (t, J=2.0 Hz, 1H), 6.22 (t, J=2.0 Hz, 1H), 6.09 (t, J=2.0 Hz, 1H), 5.39 (s, 2H), 3.68-3.62 (m, 3H); ES-LCMS m/z 201.9, 203.9 [M+H]$^P$, 242.9, 244.9 [M+ACN+H]$^+$.

Step 2: 7-Bromo-5-methoxy-quinoline and 5-Bromo-7-methoxy-quinoline

To a solution of 3-bromo-5-methoxy-aniline (5.7 g, 25.39 mmol, 1 eq) in H$_2$SO$_4$ (46.00 g, 351.75 mmol, 25 mL, 13.85 eq) was added glycerol (5.85 g, 63.47 mmol, 4.75 mL, 2.5 eq) and nitrobenzene (3.75 g, 30.47 mmol, 3.13 mL, 1.2 eq). The mixture was stirred at 150° C. for 3 h. TLC (PE/EtOAc=3/1, P1: R$_f$=0.60, P2: R$_f$=0.35) showed starting material was consumed completely and a lot of new spots were detected. To the mixture was added 100 g crushed ice, EtOAc (100 mL) and 15% solution of NaOH (30 mL). The mixture was stirred at 25° C. for 1 h. The mixture was filtered and the filtrate was extracted with EtOAc (60 mL×3). The combine organic layers were dried over anhydrous Na$_2$SO$_4$, filtered and concentrated under reduced pressure to yield a residue which was purified by flash silica gel chromatography (from pure PE to PE/EtOAc=4/1, TLC: PE/EtOAc=3/1, P1: R$_f$=0.60, P2: R$_f$=0.35) to yield 7-bromo-5-methoxy-quinoline (650 mg, 2.46 mmol, 9.7% yield, 90.0% purity) as a yellow solid. $^1$H NMR (500 MHz, DMSO-d$_6$) δ ppm 8.91 (dd, J=1.7, 4.1 Hz, 1H), 8.48 (dd, J=0.9, 8.4 Hz, 1H), 7.79 (d, J=0.6 Hz, 1H), 7.54 (dd, J=4.2, 8.5 Hz, 1H), 7.20 (d, J=1.5 Hz, 1H), 4.01 (s, 3H); ES-LCMS m/z 237.9, 239.9 [M+H]$^+$. And 5-bromo-7-methoxy-quinoline (1.3 g, 4.37 mmol, 17.2% yield, 80.0% purity) as a yellow solid. $^1$H NMR (500 MHz, DMSO-d$_6$) δ ppm 8.88 (dd, J=1.5, 4.5 Hz, 1H), 8.38 (d, J=8.5 Hz, 1H), 7.67 (d, J=2.5 Hz, 1H), 7.52 (dd, J=4.5, 8.4 Hz, 1H), 7.46 (d, J=2.5 Hz, 1H), 3.93 (s, 3H); ES-LCMS m/z 237.9, 239.9 [M+H]$^+$.

Step 3: 5-Bromoquinolin-7-ol

A solution of 5-bromo-7-methoxy-quinoline (1.3 g, 4.37 mmol, 1 eq) in HBr (37.25 g, 220.98 mmol, 25 mL, 48% purity, 50.59 eq) was stirred at 110° C. for 12 h. The reaction mixture was concentrated to yield a residue. To the residue was added EtOAc (50 mL) and saturated NaHCO$_3$ (60 mL, adjust pH to 8). The mixture was filtered and the filtered cake was concentrated to yield the product, the filtrate was extracted with EtOAc (60 mL×3). The combine organic layers were washed with brine (20 mL), dried over anhydrous Na$_2$SO$_4$, filtered and concentrated to dryness. The residue was purified by flash silica gel chromatography (from pure PE to EtOAc/MeOH=10/1, TLC: PE/EtOAc=1/1, R$_f$=0.40) to yield 5-bromoquinolin-7-ol (800 mg, 3.21 mmol, 73.6% yield, 90.0% purity) as a yellow solid. $^1$H NMR (500 MHz, DMSO-d$_6$) δ ppm 8.64 (dd, J=1.5, 4.1 Hz, 1H), 8.18 (d, J=8.0 Hz, 1H), 7.41 (d, J=1.5 Hz, 1H), 7.21 (dd, J=4.5, 8.5 Hz, 1H), 7.05 (s, 1H); ES-LCMS m/z 223.8, 225.8 [M+H]$^+$.

Step 4: 5-Bromo-7-[3-(trifluoromethyl)phenoxy]quinoline

To a mixture of 5-bromoquinolin-7-ol (300 mg, 1.21 mmol, 1 eq) and 1-iodo-3-(trifluoromethyl)benzene (327.79 mg, 1.21 mmol, 173.43 μL, 1 eq) in DMSO (2 mL) was added pyridine-2-carboxylic acid (14.84 mg, 120.51 μmol, 0.1 eq), K$_3$PO$_4$ (409.27 mg, 1.93 mmol, 1.6 eq) and CuI (22.95 mg, 120.51 μmol, 0.1 eq). The mixture was stirred at 120° C. for 12 h under N$_2$ atmosphere. TLC (PE/EtOAc=3/1, R$_f$=0.65) showed starting material was consumed and one major new spot was detected. The mixture was filtered and the filtrate was diluted with H$_2$O (50 mL) and extracted with EtOAc (60 mL×3). The combine organic layers were dried over anhydrous Na$_2$SO$_4$, filtered and concentrated to yield a residue which was purified by flash silica gel chromatography (from pure PE to PE/EtOAc=5/1, TLC: PE/EtOAc=3/1, R$_f$=0.65) to yield 5-bromo-7-[3-(trifluoromethyl)phenoxy]quinoline (200 mg, 488.93 μmol, 40.6% yield, 90.0% purity) as a yellow solid. $^1$H NMR (500 MHz, DMSO-d$_6$) δ ppm 8.96-8.84 (m, 1H), 8.53-8.32 (m, 1H), 8.10-7.88 (m, 1H), 7.75-7.68 (m, 1H), 7.67-7.57 (m, 3H), 7.54-7.48 (m, 1H), 7.44 (d, J=2.0 Hz, 1H).

Step 5: (E)-3-[7-[3-(Trifluoromethyl)phenoxy]-5-quinolyl]prop-2-enamide

To a mixture of 5-bromo-7-[3-(trifluoromethyl)phenoxy]quinoline (200 mg, 488.93 μmol, 1 eq) and prop-2-enamide (173.76 mg, 2.44 mmol, 168.70 μL, 5 eq) in 1,4-dioxane (10 mL) was added Cs$_2$CO$_3$ (477.91 mg, 1.47 mmol, 3 eq), Pd(OAc)$_2$ (10.98 mg, 48.89 μmol, 0.1 eq), XPhos (46.62 mg, 97.79 μmol, 0.2 eq) under N$_2$ atmosphere. The mixture was stirred under N$_2$ atmosphere at 120° C. in microwave (1 bar) for 2 h. The mixture was diluted with H$_2$O (20 mL) and extracted with EtOAc (20 mL×3). The combine organic layers were dried over anhydrous Na$_2$SO$_4$, filtered and concentrated to yield a residue which was purified by preparative HPLC (column: YMC-Actus Triart C18 150*30 mm*5 μm; mobile phase: [water (0.05% ammonia hydroxide v/v)-ACN]; B %: 46%-66%, 10 min) and lyophilized to yield (E)-3-[7-[3-(trifluoromethyl)phenoxy]-5-quinolyl]prop-2-enamide (30.13 mg, 84.09 μmol, 17.2% yield, 100.0% purity) as a white solid. $^1$H NMR (500 MHz, CDCl$_3$) δ ppm 8.94-8.88 (m, 1H), 8.53 (d, J=8.5 Hz, 1H), 8.41 (d, J=15.5 Hz, 1H), 7.60 (d, J=2.0 Hz, 1H), 7.57-7.52 (m, 2H), 7.50-7.47 (m, 1H), 7.44 (dd, J=4.5, 8.6 Hz, 1H), 7.40 (s, 1H), 7.34-7.30 (m, 1H), 6.55 (d, J=15.5 Hz, 1H), 5.61 (br s, 2H); ES-LCMS m/z 359.1 [M+H]$^+$.

I-88 & I-89

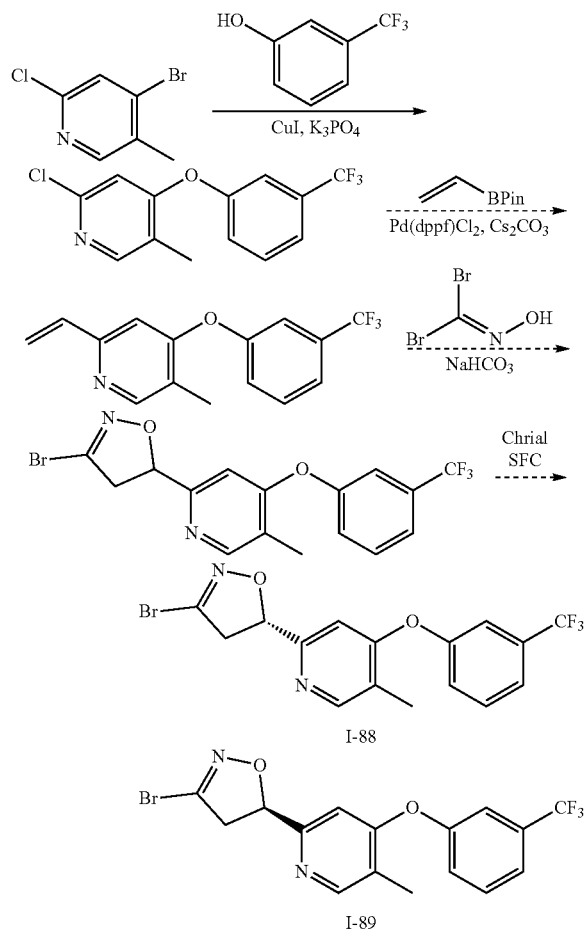

Step 1: 2-Chloro-5-methyl-4-[3-(trifluoromethyl) phenoxy] pyridine

A mixture of 4-bromo-2-chloro-5-methyl-pyridine (300 mg, 1.45 mmol, 1 eq), 3-(trifluoromethyl)phenol (235.55 mg, 1.45 mmol, 174.48 μL, 1 eq), pyridine-2-carboxylic acid (17.89 mg, 145.30 μmol, 0.1 eq), K$_3$PO$_4$ (616.85 mg, 2.91 mmol, 2 eq) and CuI (27.67 mg, 145.30 μmol, 0.1 eq) in DMSO (10 mL) was degassed and purged with N$_2$ for 3 times then the mixture was stirred at 120° C. for 12 h under N$_2$ atmosphere. The mixture was diluted with water (100 mL) then extracted with EtOAc (100 mL×3). The combined organic layers were dried over anhydrous Na$_2$SO$_4$, filtered and the filtrate was concentrated under reduced pressure to yield a residue which was purified by flash silica gel chromatography (from PE/EtOAc=100/1 to 3/1, TLC: PE/EtOAc=3/1, R$_f$=0.70) to yield 2-chloro-5-methyl-4-[3-(trifluoromethyl)phenoxy] pyridine (400 mg, 1.33 mmol, 91.4% yield, 95.5% purity) as yellow solid. $^1$H NMR (400 MHz, DMSO-d$_6$) δ ppm 8.30 (s, 1H), 7.76-7.65 (m, 2H), 7.62 (s, 1H), 7.51 (d, J=8.1 Hz, 1H), 6.71 (s, 1H), 2.24 (s, 3H); ES-LCMS m/z 287.9, 289.9 [M+H]$^+$.

Step 2: 5-Methyl-4-[3-(trifluoromethyl)phenoxy]-2-vinyl-pyridine

To a solution of 2-chloro-5-methyl-4-[3-(trifluoromethyl) phenoxy] pyridine (350 mg, 1.16 mmol, 1 eq) in 1,4-dioxane (12 mL) and water (2 mL) was added 4,4,5,5-tetramethyl-2-vinyl-1,3,2-dioxaborolane (214.75 mg, 1.39 mmol, 236.51 μL, 1.2 eq), Pd(dppf)Cl$_2$ (85.02 mg, 116.19 μmol, 0.1 eq) and Cs$_2$CO$_3$ (1.14 g, 3.49 mmol, 3 eq). The mixture was bubbled with N$_2$ for 2 min and stirred at 100° C. for 30 min under microwave. The mixture was diluted with water (100 mL) then extracted with EtOAc (100 mL×3). The combined organic layers were dried over anhydrous Na$_2$SO$_4$, filtered and the filtrate was concentrated under reduced pressure to yield a residue which was purified by flash silica gel chromatography (from PE/EtOAc=100/1 to 3/1, TLC: PE/EtOAc=3/1, R$_f$=0.70) to yield 5-methyl-4-[3-(trifluoromethyl)phenoxy]-2-vinyl-pyridine (300 mg, 1.02 mmol, 87.8% yield, 95% purity) as yellow solid. $^1$H NMR (400 MHz, DMSO-d$_6$) δ ppm 8.44 (s, 1H), 7.71-7.66 (m, 1H), 7.63-7.59 (m, 1H), 7.49 (s, 1H), 7.41 (d, J=8.1 Hz, 1H), 6.86 (s, 1H), 6.71 (dd, J=10.8, 17.4 Hz, 1H), 6.12 (dd, J=1.7, 17.4 Hz, 1H), 5.37 (dd, J=1.7, 10.8 Hz, 1H), 2.23 (s, 3H); ES-LCMS m/z 280.0 [M+H]$^+$.

Step 3: (5R)-3-Bromo-5-[5-methyl-4-[3-(trifluoromethyl)phenoxy]-2-pyridyl]-4,5-dihydroisoxazole & (5S)-3-bromo-5-[5-methyl-4-[3-(trifluoromethyl) phenoxy]-2-pyridyl]-4,5-dihydroisoxazole A mixture of 5-methyl-4-[3-(trifluoromethyl)phenoxy]-2-vinyl-pyridine (250 mg, 850.47 μmol, 1 eq), dibromomethanone oxime (345.01 mg, 1.70 mmol, 2 eq), NaHCO$_3$ (714.45 mg, 8.50 mmol, 10 eq) in EtOAc (10 mL) was degassed and purged with N$_2$ for 3 times, and then the mixture was stirred at 25° C. for 12 h under N$_2$ atmosphere. The mixture was diluted with water (100 mL) then extracted with EtOAc (100 mL×3). The combined organic layers were dried over anhydrous Na$_2$SO$_4$, filtered and the filtrate was concentrated under reduced pressure to yield a residue which was purified by flash silica gel chromatography (from PE/EtOAc=100/1 to 3/1, TLC: PE/EtOAc=3/1, R$_f$=0.65) to yield a residue which was separated by SFC (column: DAICEL CHIRAL-PAK AD-H (250 mm*30 mm, 5 μm); mobile phase: [0.1% NH$_3$·H$_2$O EtOH]; B %: 10%-10%, min) to yield Peak 1 and Peak 2. Peak 1 was concentrated under reduced pressure to yield a residue which was lyophilized to yield (5S)-3-bromo-5-[5-methyl-4-[3-(trifluoromethyl)phenoxy]-2-pyridyl]-4,5-dihydroisoxazole (31.67 mg, 77.84 μmol, 9.2% yield, 98.6% purity, SFC: R$_f$=0.511, ee=100%; [α]$_D^{30.4}$=+210.1, MeOH, c=0.159 g/100 mL) as yellow oil. $^1$H NMR (400 MHz, DMSO-d$_6$) δ ppm 8.48 (s, 1H), 7.75-7.68 (m, 1H), 7.68-7.63 (m, 1H), 7.55 (s, 1H), 7.46 (d, J=8.2 Hz, 1H), 6.79 (s, 1H), 5.65 (dd, J=7.4, 11.0 Hz, 1H), 3.73-3.65 (m, 1H), 3.60-3.50 (m, 1H), 2.27 (s, 3H); ES-LCMS m/z 400.9, 402.9 [M+H]$^+$. Peak 2 was concentrated under reduced pressure to yield a residue which was lyophilized to yield (5R)-3-bromo-5-[5-methyl-4-[3-(trifluoromethyl)phenoxy]-2-pyridyl]-4,5-dihydroisoxazole (19.39 mg, 48.33 μmol, 5.9% yield, 100% purity, SFC: R$_f$=0.417, ee=100%; [α]$_D^{30.4}$=−214.7, MeOH, c=0.109 g/100 mL) as yellow oil. $^1$H NMR (400 MHz, DMSO-d$_6$) δ ppm 8.49 (s, 1H), 7.75-7.69 (m, 1H), 7.68-7.63 (m, 1H), 7.56 (s, 1H), 7.46 (d, J=8.2 Hz, 1H), 6.80 (s, 1H), 5.66 (dd, J=7.4, 11.0 Hz, 1H), 3.74-3.65 (m, 1H), 3.59-3.51 (m, 1H), 2.27 (s, 3H); ES-LCMS m/z 400.9, 402.9 [M+H]$^+$.

I-141 & I-142

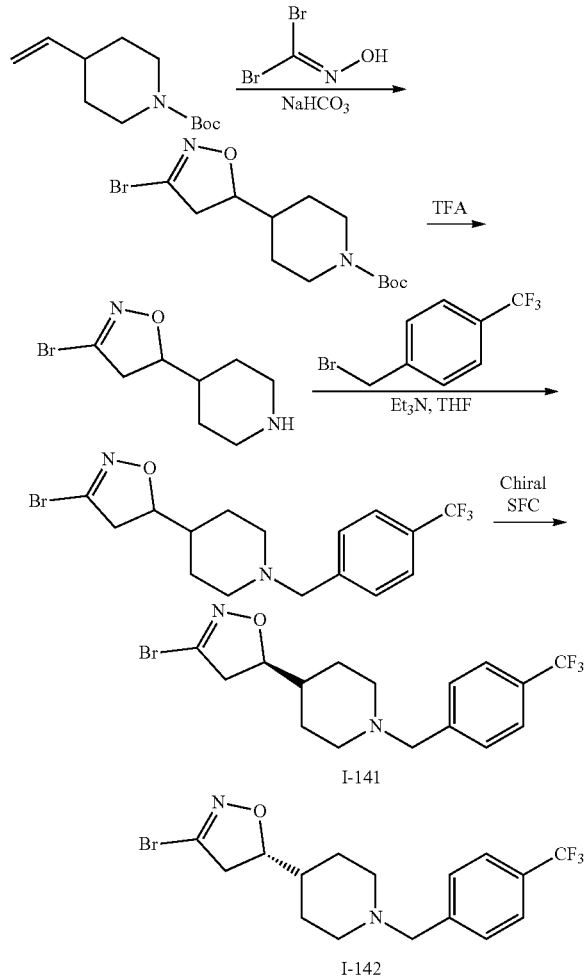

Step 1: tert-Butyl 4-(3-bromo-4,5-dihydroisoxazol-5-yl)piperidine-1-carboxylate

To a solution of tert-butyl 4-vinylpiperidine-1-carboxylate (1 g, 4.73 mmol, 1 eq) in EtOAc (20 mL) was added NaHCO$_3$ (3.98 g, 47.33 mmol, 10 eq) and dibromomethanone oxime (1.44 g, 7.10 mmol, 1.5 eq). The mixture was stirred at 25° C. for 12 h. TLC (PE/EtOAc=3/1, R$_f$=0.95) showed starting material was remained and one new spot was detected. The mixture was diluted with water (100 mL) then extracted with EtOAc (100 mL×3). The combined organic layers were dried over anhydrous Na$_2$SO$_4$, filtered and the filtrate was concentrated under reduced pressure to yield a residue which was purified by flash silica gel chromatography (from PE/EtOAc=100/1 to 3/1, TLC: PE/EtOAc=3/1, R$_f$=0.5) to yield tert-butyl 4-(3-bromo-4,5-dihydroisoxazol-5-yl)piperidine-1-carboxylate (1 g, 2.70 mmol, 57.0% yield, 90% purity) as yellow solid. $^1$H NMR (400 MHz, DMSO-d$_6$) δ ppm 4.52-4.40 (m, 1H), 4.01-3.91 (m, 2H), 3.29 (d, J=10.5 Hz, 1H), 3.10 (dd, J=8.6, 17.6 Hz, 1H), 2.67 (d, J=1.7 Hz, 2H), 1.74-1.62 (m, 2H), 1.56-1.45 (m, 1H), 1.38 (s, 9H), 1.11-0.97 (m, 2H).

Step 2: 3-Bromo-5-(4-piperidyl)-4,5-dihydroisoxazole

To a stirred solution of tert-butyl 4-(3-bromo-4,5-dihydroisoxazol-5-yl)piperidine-1-carboxylate (900 mg, 2.43 mmol, 1 eq) in TFA (9 mL) was added DCM (27 mL). The reaction mixture was stirred at 25° C. for 1 h. TLC (PE/EtOAc=3:1, R$_f$=0.00) showed starting material was remained and one new spot was detected. The filtrate was concentrated under reduced pressure to yield 3-bromo-5-(4-piperidyl)-4,5-dihydroisoxazole (930 mg, 2.41 mmol, 99.2% yield, 90% purity, TFA) as a yellow solid. $^1$H NMR (400 MHz, DMSO-d$_6$) δ ppm 8.57 (s, 1H), 4.58-4.39 (m, 1H), 3.26 (d, J=12.2 Hz, 2H), 2.86-2.74 (m, 2H), 1.86-1.71 (m, 2H), 1.66 (d, J=13.9 Hz, 1H), 1.44-1.26 (m, 3H).

Step 3: (5R)-3-Bromo-5-[1-[[4-(trifluoromethyl)phenyl]methyl]-4-piperidyl]-4,5-dihydroisoxazole & (5S)-3-bromo-5-[1-[[4-(trifluoromethyl)phenyl]methyl]-4-piperidyl]-4,5-dihydroisoxazole A mixture of 3-bromo-5-(4-piperidyl)-4,5-dihydroisoxazole (800 mg, 2.07 mmol, 1 eq, TFA), 1-(bromomethyl)-4-(trifluoromethyl)benzene (495.79 mg, 2.07 mmol, 319.87 µL, 1 eq), TEA (1.26 g, 12.44 mmol, 1.73 mL, 6 eq) in THF (12 mL) was degassed and purged with N$_2$ for 3 times, and then the mixture was stirred at 25° C. for 12 h under N$_2$ atmosphere. The filtrate was concentrated under reduced pressure to yield a residue which was purified by flash silica gel chromatography (from PE/EtOAc=100/1 to 1/1, TLC: PE/EtOAc=1/1, R$_f$=0.80) to yield the compound which was separated by SFC (column: DAICEL CHIRALPAK IG (250 mm*30 mm, 10 µm); mobile phase: [0.1% NH$_3$H$_2$O EtOH]; B %: 15%-15%, min) to yield Peak 1 and Peak 2. Peak 1 was concentrated under reduced pressure to yield a residue which was lyophilized to yield (5R)-3-bromo-5-[1-[[4-(trifluoromethyl)phenyl]methyl]-4-piperidyl]-4,5-dihydroisoxazole (66.08 mg, 168.91 µmol, 8.2% yield, 100% purity, SFC: R$_f$=2.565 min, ee=100%; [α]$^{30.4}_D$=+97.9, MeOH, c=0.049 g/100 mL) as yellow solid. $^1$H NMR (400 MHz, DMSO-d$_6$) δ ppm 7.64 (d, J=8.1 Hz, 2H), 7.48 (d, J=8.1 Hz, 2H), 4.49-4.36 (m, 1H), 3.54-3.45 (m, 2H), 3.29-3.22 (m, 2H), 3.04 (dd, J=8.8, 17.6 Hz, 1H), 2.77 (d, J=11.2 Hz, 2H), 1.93-1.80 (m, 2H), 1.65 (d, J=12.7 Hz, 1H), 1.53-1.39 (m, 2H), 1.20 (dd, J=3.5, 12.1 Hz, 1H); ES-LCMS m/z 390.9, 392.9 [M+H]$^+$. Peak 1 was concentrated under reduced pressure to yield a residue which was lyophilized to yield (5S)-3-bromo-5-[1-[[4-(trifluoromethyl)phenyl]methyl]-4-piperidyl]-4,5-dihydroisoxazole (67.11 mg, 171.54 µmol, 8.3% yield, 100% purity, SFC: R$_f$=2.666 min, ee=99.88%; [α]$^{30.3}_D$=-102.0, MeOH, c=0.049 g/100 mL) as yellow solid. $^1$H NMR (400 MHz, DMSO-d$_6$) δ ppm 7.67 (d, J=8.2 Hz, 2H), 7.52 (d, J=7.8 Hz, 2H), 4.50-4.41 (m, 1H), 3.53 (s, 2H), 3.32-3.27 (m, 2H), 3.07 (dd, J=8.6, 17.6 Hz, 1H), 2.81 (d, J=10.6 Hz, 1H), 1.96-1.87 (m, 2H), 1.68 (d, J=12.1 Hz, 1H), 1.50 (d, J=12.9 Hz, 2H), 1.31-1.23 (m, 1H); ES-LCMS m/z 390.9, 392.9 [M+H]$^+$.

I-40

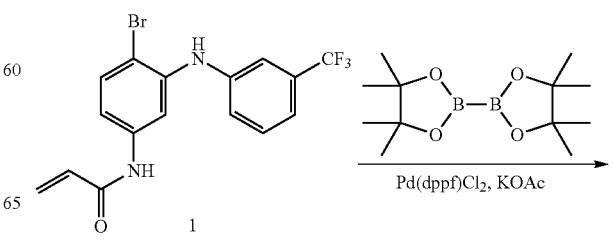

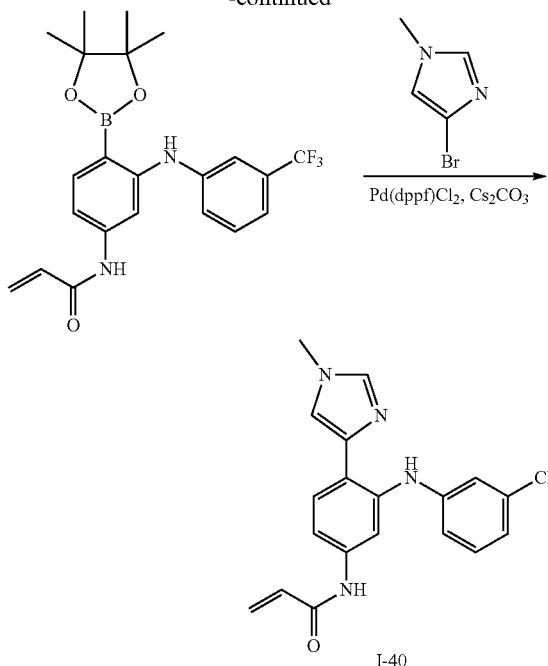

Step 1: N-[4-(4,4,5,5-Tetramethyl-1,3,2-dioxaborolan-2-yl)-3-[3-(trifluoromethyl)anilino]phenyl]prop-2-enamide A mixture of N-[4-bromo-3-[3-(trifluoromethyl)anilino]phenyl]prop-2-enamide (500 mg, 1.17 mmol, 1 eq), 4,4,5,5-tetramethyl-2-(4,4,5,5-tetramethyl-1,3,2-dioxaborolan-2-yl)-1,3,2-dioxaborolane (450.00 mg, 1.77 mmol, 1.52 eq), KOAc (450.00 mg, 4.59 mmol, 3.92 eq) and Pd(dppf)Cl$_2$ (45.00 mg, 61.50 μmol, 5.26e-2 eq) in 1,4-dioxane (10 mL) was stirred under N$_2$ atmosphere at 90° C. for 12 h. TLC (PE/EtOAc=1/1, R$_f$=0.49) showed the starting material was consumed completely. The reaction mixture was concentrated under reduced pressure to yield a residue which was purified by flash silica gel chromatography (from PE/EtOAc=100/1 to 10/1, TLC: PE/EtOAc=1/1, R$_f$=0.49) to yield N-[4-(4,4,5,5-tetramethyl-1,3,2-dioxaborolan-2-yl)-3-[3-(trifluoromethyl)anilino]phenyl]prop-2-enamide (160 mg, 333.15 μmol, 28.5% yield, 90.0% purity) as a colorless gum. $^1$H NMR (500 MHz, CDCl$_3$) δ ppm 7.89 (s, 1H), 7.72 (d, J=8.2 Hz, 1H), 7.60 (br s, 1H), 7.47-7.42 (m, 2H), 7.38 (s, 1H), 7.23 (br d, J=7.3 Hz, 1H), 7.17 (br s, 1H), 7.02 (d, J=8.2 Hz, 1H), 6.43 (d, J=17.5 Hz, 1H), 6.22 (dd, J=10.6, 16.7 Hz, 1H), 5.78 (d, J=10.1 Hz, 1H), 1.37 (s, 12H); ES-LCMS m/z 433.1 [M+H]$^+$.

Step 2: N-[4-(1-Methylimidazol-4-yl)-3-[3-(trifluoromethyl)anilino]phenyl]prop-2-enamide A mixture of N-[4-(4,4,5,5-tetramethyl-1,3,2-dioxaborolan-2-yl)-3-[3-(trifluoromethyl)anilino]phenyl]prop-2-enamide (50 mg, 104.11 μmol, 1 eq), 4-iodo-1-methylimidazole (25 mg, 120.19 μmol, 1.15 eq), Cs$_2$CO$_3$ (115 mg, 352.96 μmol, 3.39 eq) and Pd(dppf)Cl$_2$ (15 mg, 20.50 μmol, 1.97e-1 eq) in 1,4-dioxane (1.5 mL) and H$_2$O (0.5 mL) was bubbled with N$_2$ for 2 minutes and sealed. The reaction mixture was irradiated under microwave (1 bar) at 100° C. for 0.5 h. The reaction was carried out 3 times in parallel. The reaction mixture was concentrated under reduced pressure to yield a residue which was purified by flash silica gel chromatography (from PE/EtOAc=20/1 to 1/1, TLC: PE/EtOAc=1/1, R$_f$=0.25). The desired fraction was concentrated under reduced pressure to yield a residue which was purified by preparative HPLC (column: Agela DuraShell C18 150*25 mm*5 um; mobile phase: [water (0.04% NH$_3$·H$_2$O+10 mM NH$_4$HCO$_3$)-ACN]; B %: 41%-71%, 10 min). The desired fraction was lyophilized to yield N-[4-(1-methylimidazol-4-yl)-3-[3-(trifluoromethyl)anilino]phenyl]prop-2-enamide (10.29 mg, 26.63 μmol, 8.5% yield, 100.0% purity) as a white solid. $^1$H NMR (500 MHz, DMSO-d$_6$) δ ppm 10.22 (s, 1H), 10.12 (s, 1H), 7.83 (d, J=1.8 Hz, 1H), 7.79 (s, 1H), 7.64 (d, J=8.5 Hz, 1H), 7.56 (d, J=1.1 Hz, 1H), 7.50-7.46 (m, 1H), 7.40 (d, J=8.9 Hz, 1H), 7.35 (s, 1H), 7.24 (dd, J=2.1, 8.5 Hz, 1H), 7.17 (d, J=7.6 Hz, 1H), 6.48-6.35 (m, 1H), 6.24 (dd, J=2.0, 16.9 Hz, 1H), 5.75 (dd, J=1.9, 10.1 Hz, 1H), 3.71 (s, 3H); ES-LCMS m/z 387.0 [M+H]$^+$.

I-143

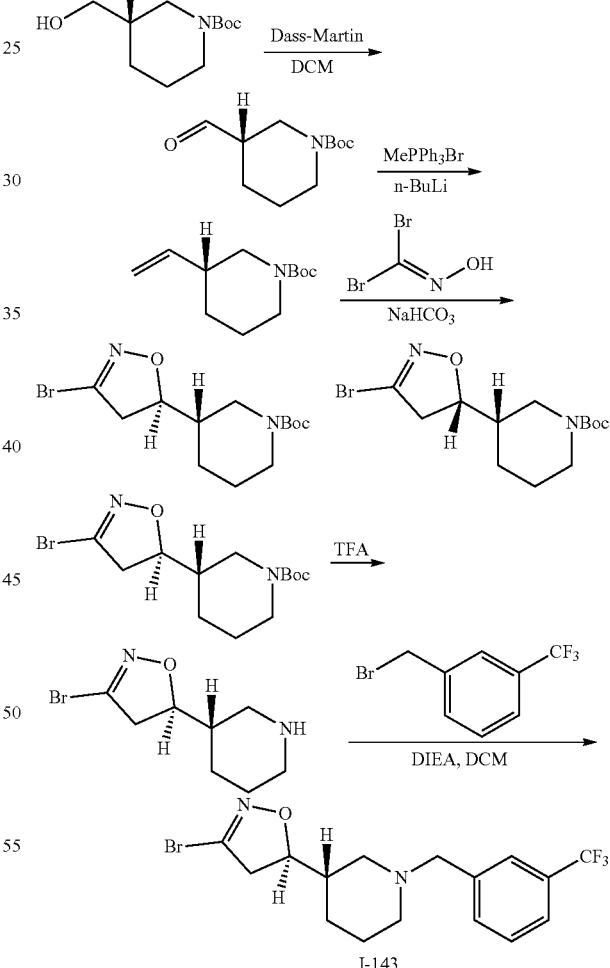

Step 1: tert-Butyl (3S)-3-formylpiperidine-1-carboxylate

To a solution of tert-butyl (3S)-3-(hydroxymethyl)piperidine-1-carboxylate (1.00 g, 4.64 mmol, 1 eq) in DCM (10 mL) was added DESS-MARTIN PERIODINANE (2.17 g, 5.11 mmol, 1.1 eq). The mixture was stirred at 25° C. for 4 h. TLC (PE/EtOAc=2/1, $R_f$=0.70) showed the starting material was consumed completely. The reaction mixture was diluted with $H_2O$ (50 mL) and filtered. The filtrate was extracted with DCM (50 mL×3). The organic layer was dried over $Na_2SO_4$, filtered and concentrated under reduced pressure to yield a residue which was purified by flash silica gel chromatography (from PE/EtOAc=100/1 to 5/1, TLC: PE/EtOAc=2/1, $R_f$=0.70) to yield tert-butyl (3S)-3-formylpiperidine-1-carboxylate (400 mg, 1.78 mmol, 38.4% yield, 95.0% purity) as colorless oil. $^1H$ NMR (500 MHz, $CDCl_3$) δ ppm 9.71 (s, 1H), 4.00-3.90 (m, 1H), 3.70-3.60 (m, 1H), 3.33 (dd, J=8.2, 13.6 Hz, 1H), 3.09 (ddd, J=3.3, 9.5, 13.1 Hz, 1H), 2.50-2.40 (m, 1H), 2.00-1.90 (m, 1H), 1.72-1.65 (m, 2H), 1.56-1.50 (m, 1H), 1.47 (s, 9H).

Step 2: tert-Butyl (3R)-3-vinylpiperidine-1-carboxylate

To a solution of methyl(triphenyl)phosphonium;bromide (800 mg, 2.24 mmol, 1.26 eq) in THF (10 mL) was added n-BuLi (2.5 M, 0.9 mL, 1.26 eq) dropwise under $N_2$ atmosphere at −78° C. The mixture was warmed to 0° C. and stirred under $N_2$ atmosphere at 0° C. for 0.5 h. The mixture was cooled to −78° C. and a solution of tert-butyl (3S)-3-formylpiperidine-1-carboxylate (400 mg, 1.78 mmol, 1 eq) in THF (5 mL) was added. The mixture was warmed to 25° C. and stirred under $N_2$ atmosphere at 25° C. for 4 h. TLC (PE/EtOAc=5/1, $R_f$=0.50) showed the starting material was consumed completely. The reaction mixture was diluted with $H_2O$ (50 mL) and extracted with EtOAc (50 mL×3). The organic layer was dried over $Na_2SO_4$, filtered and concentrated under reduced pressure to yield a residue which was purified by flash silica gel chromatography (from PE/EtOAc=100/1 to 8/1, TLC: PE/EtOAc=5/1, $R_f$=0.50) to yield tert-butyl (3R)-3-vinylpiperidine-1-carboxylate (350 mg, 1.66 mmol, 93.0% yield, N/A purity) as colorless oil. $^1H$ NMR (400 MHz, $CDCl_3$) δ ppm 5.72 (ddd, J=6.5, 10.7, 17.3 Hz, 1H), 5.14-4.96 (m, 2H), 3.96 (d, J=13.3 Hz, 2H), 2.73 (ddd, J=3.1, 11.5, 13.1 Hz, 1H), 2.60-2.50 (m, 1H), 2.23-2.11 (m, 1H), 1.91-1.82 (m, 1H), 1.72-1.63 (m, 2H), 1.54-1.50 (m, 1H), 1.46 (s, 9H).

Step 3: tert-Butyl (3S)-3-[(5R)-3-bromo-4,5-dihydroisoxazol-5-yl]piperidine-1-carboxylate and tert-butyl (3S)-3-[(5S)-3-bromo-4,5-dihydroisoxazol-5-yl]piperidine-1-carboxylate A mixture of tert-butyl (3R)-3-vinylpiperidine-1-carboxylate (200 mg, 946.52 μmol, 1 eq), dibromomethanone oxime (230.00 mg, 1.13 mmol, 1.2 eq) and $NaHCO_3$ (795.17 mg, 9.47 mmol, 10 eq) in EtOAc (10 mL) was stirred under $N_2$ atmosphere at 25° C. for 12 h. TLC (PE/EtOAc=4/1, $R_f$=0.35, 0.30) showed the starting material was consumed completely. The reaction mixture was diluted with $H_2O$ (50 mL) and extracted with EtOAc (50 mL×3). The organic layer was dried over $Na_2SO_4$, filtered and concentrated under reduced pressure to yield a residue which was purified by flash silica gel chromatography (from PE/EtOAc=100/1 to 5/1, TLC: PE/EtOAc=4/1, $R_f$=0.35, 0.30) to yield tert-butyl (3S)-3-[(5R)-3-bromo-4,5-dihydroisoxazol-5-yl]piperidine-1-carboxylate (130 mg, 388.18 μmol, 41.0% yield, 99.5% purity, SFC: $R_t$=2.246, Dr=99.84%) as a white solid and tert-butyl (3S)-3-[(5S)-3-bromo-4,5-dihydroisoxazol-5-yl]piperidine-1-carboxylate (160 mg, 478.24 μmol, 50.5% yield, 99.6% purity, SFC: $R_t$=2.346, Dr=94.44%) as a colorless gum.

tert-butyl (3S)-3-[(5R)-3-bromo-4,5-dihydroisoxazol-5-yl]piperidine-1-carboxylate: $^1H$ NMR (400 MHz, $CDCl_3$) δ ppm 4.51 (d, J=7.8 Hz, 1H), 3.84 (d, J=8.6 Hz, 2H), 3.27 (dd, J=10.6, 17.2 Hz, 1H), 3.00 (dd, J=9.2, 17.0 Hz, 1H), 2.95-2.86 (m, 1H), 2.80-2.70 (m, 1H), 2.00-1.90 (m, 1H), 1.78-1.66 (m, 2H), 1.46 (s, 9H), 1.45-1.37 (m, 2H); ES-LCMS m/z 276.9, 278.9 [M-t-Bu+H]$^+$.

tert-butyl (3S)-3-[(5S)-3-bromo-4,5-dihydroisoxazol-5-yl]piperidine-1-carboxylate: NMR (400 MHz, $CDCl_3$) δ ppm 4.56-4.38 (m, 1H), 4.23-4.11 (m, 1H), 3.98 (d, J=13.3 Hz, 1H), 3.22 (dd, J=10.6, 17.2 Hz, 1H), 2.99 (dd, J=9.4, 16.8 Hz, 1H), 2.85-2.47 (m, 2H), 1.80-1.64 (m, 4H), 1.46 (s, 9H), 1.33-1.26 (m, 1H); 276.9, 278.9 [M-t-Bu+H]$^+$.

Step 4: (5R)-3-Bromo-5-[(3S)-3-piperidyl]-4,5-dihydroisoxazole

To a solution of tert-butyl (3S)-3-[(5R)-3-bromo-4,5-dihydroisoxazol-5-yl]piperidine-1-carboxylate (130.00 mg, 388.18 μmol, 1 eq) in DCM (6 mL) was added TFA (3.06 g, 26.88 mmol, 1.99 mL, 69.24 eq) dropwise. The mixture was stirred at 25° C. for 0.5 h. TLC (PE/EtOAc=4/1, $R_f$=0.06) showed the starting material was consumed completely. The mixture was concentrated under reduced pressure to yield (5R)-3-bromo-5-[(3S)-3-piperidyl]-4,5-dihydroisoxazole (130 mg, 374.50 μmol, 96.5% yield, TFA) as a colorless gum, which was used in the next step without further purification. $^1H$ NMR (400 MHz, $CDCl_3$) δ ppm 9.15 (s, 1H), 4.61 (d, J=11.7 Hz, 1H), 3.46-3.31 (m, 3H), 3.00 (dd, J=7.8, 17.2 Hz, 1H), 2.90-2.80 (m, 2H), 2.20-2.10 (m, 1H), 2.08-2.00 (m, 2H), 1.92-1.81 (m, 2H).

Step 5: (5R)-3-Bromo-5-[(3S)-1-[[3-(trifluoromethyl)phenyl]methyl]-3-piperidyl]-4,5-dihydroisoxazole To a mixture of (5R)-3-bromo-5-[(3S)-3-piperidyl]-4,5-dihydroisoxazole (130 mg, 374.50 μmol, 1 eq, TFA) and DIEA (200.00 mg, 1.55 mmol, 269.54 μL, 4.13 eq) in DCM (5 mL) was added 1-(bromomethyl)-3-(trifluoromethyl)benzene (90 mg, 376.52 μmol, 57.32 μL, 1.01 eq). The mixture was stirred at 25° C. for 12 h. The mixture was concentrated under reduced pressure to yield a residue which was purified by preparative HPLC (column: Welch Xtimate C18 150*25 mm*5 um; mobile phase: [water (10 mM $NH_4HCO_3$)-ACN]; B %: 49%-79%, 10 min). The desired fraction was lyophilized to yield a residue which was separated by chiral SFC (column: DAICEL CHIRALCEL OJ-H (250 mm*30 mm, 5um); mobile phase: [0.1% $NH_3·H_2O$/EtOH]; B %: 15%-15%). The desired fraction was concentrated under reduced pressure to yield (5R)-3-bromo-5-[(3S)-1-[[3-(trifluoromethyl)phenyl]methyl]-3-piperidyl]-4,5-dihydroisoxazole (56.21 mg, 143.68 μmol, 38.4% yield, 100.0% purity, SFC: $R_t$=2.439, Dr.=97.990%, $[α]^{30.5}_D$=+77.97 ($CHCl_3$, c=0.118 g/100 mL)) as colorless oil. $^1H$ NMR (500 MHz, $CDCl_3$) δ ppm 7.57 (s, 1H), 7.51 (dd, J=7.6, 12.5 Hz, 2H), 7.46-7.41 (m, 1H), 4.66-4.53 (m, 1H), 3.60-3.46 (m, 2H), 3.15 (dd, J=10.5, 17.1 Hz, 1H), 2.91 (dd, J=9.2, 17.1 Hz, 1H), 2.70 (d, J=10.8 Hz, 1H), 2.64 (d, J=9.5 Hz, 1H), 2.10 (t, J=10.1 Hz, 1H), 2.01-1.94 (m, 1H), 1.88 (ttd, J=3.3, 6.5, 9.8 Hz, 1H), 1.83-1.72 (m, 2H), 1.63-1.58 (m, 1H), 1.25 (d, J=12.4 Hz, 1H); ES-LCMS m/z 390.9, 392.9 [M+H]$^+$.

I-144

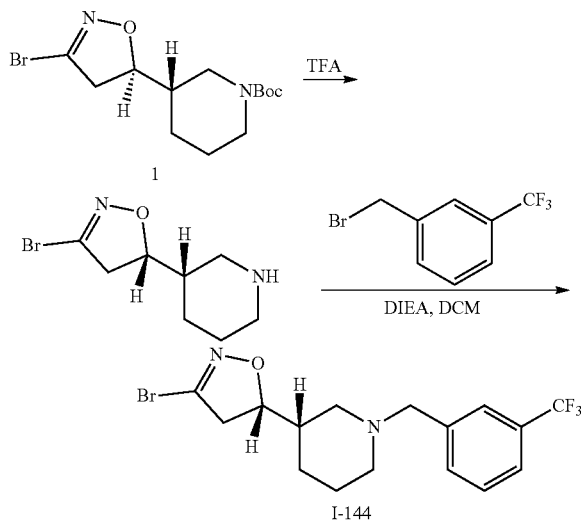

Step 1: (5S)-3-Bromo-5-[(3S)-3-piperidyl]-4,5-dihydroisoxazole

To a solution of tert-butyl (3S)-3-[(5S)-3-bromo-4,5-dihydroisoxazol-5-yl]piperidine-1-carboxylate (160.00 mg, 478.24 μmol, 1 eq) in DCM (6 mL) was added TFA (3.08 g, 27.01 mmol, 2.00 mL, 56.48 eq) dropwise. The mixture was stirred at 25° C. for 0.5 h. TLC (PE/EtOAc=4/1, $R_f$=0.06) showed the starting material was consumed completely. The mixture was concentrated under reduced pressure to yield (5S)-3-bromo-5-[(3S)-3-piperidyl]-4,5-dihydroisoxazole (160 mg, 460.92 μmol, 96.4% yield, N/A purity, TFA) as a colorless gum, which was used in the next step without further purification. $^1$H NMR (400 MHz, CDCl$_3$) δ ppm 8.99 ((br s, 1H), 8.75 (br s, 1H), 4.63-4.46 (m, 1H), 3.60 (d, J=11.3 Hz, 1H), 3.46 (d, J=10.6 Hz, 1H), 3.33 (dd, J=10.4, 17.4 Hz, 1H), 3.03 (dd, J=8.6, 17.2 Hz, 1H), 2.96-2.86 (m, 1H), 2.84-2.74 (m, 1H), 2.24-2.14 (m, 1H), 2.02-1.81 (m, 3H).

Step 2: (5S)-3-Bromo-5-[(3S)-1-[[3-(trifluoromethyl)phenyl]methyl]-3-piperidyl]-4,5-dihydroisoxazole To a mixture of (5S)-3-bromo-5-[(3S)-3-piperidyl]-4,5-dihydroisoxazole (160 mg, 686.39 μmol, 1 eq, TFA) and DIEA (355 mg, 2.75 mmol, 478.44 μL, 4 eq) in DCM (5 mL) was added 1-(bromomethyl)-3-(trifluoromethyl)benzene (167 mg, 698.65 μmol, 106.37 μL, 1.02 eq). The mixture was stirred at 25° C. for 12 h. The mixture was concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 49%-79%, 10 min). The desired fraction was lyophilized to yield a residue which was purified by preparative TLC (PE/EtOAc=3/1, $R_f$=0.30). The crude product was separated by chiral SFC (column: DAICEL CHIRALCEL OJ-H (250 mm*30 mm, 5um); mobile phase: [0.1% NH$_3$·H$_2$O EtOH]; B %: 10%-10%). The desired fraction was concentrated under reduced pressure to yield (5S)-3-bromo-5-[(3S)-1-[[3-(trifluoromethyl)phenyl]methyl]-3-piperidyl]-4,5-dihydroisoxazole (19.81 mg, 50.64 μmol, 7.4% yield, 100.0% purity, SFC: $R_f$=2.089, Dr.=100.000%, $[α]^{30.6}_D$=−88.37 (CHCl$_3$, c=0.043 g/100 mL)) as a white solid. $^1$H NMR (500 MHz, CDCl$_3$) δ ppm 7.57 (s, 1H), 7.51 (d, J=7.6 Hz, 2H), 7.46-7.40 (m, 1H), 4.57-4.46 (m, 1H), 3.62-3.49 (m, 2H), 3.19 (dd, J=10.4, 17.1 Hz, 1H), 3.04-2.91 (m, 2H), 2.73 (d, J=11.7 Hz, 1H), 2.04-1.90 (m, 3H), 1.74-1.59 (m, 3H), 1.06 (d, J=7.5 Hz, 1H); ES-LCMS m/z 390.9, 392.9 [M+H]$^+$.

I-90 & I-91

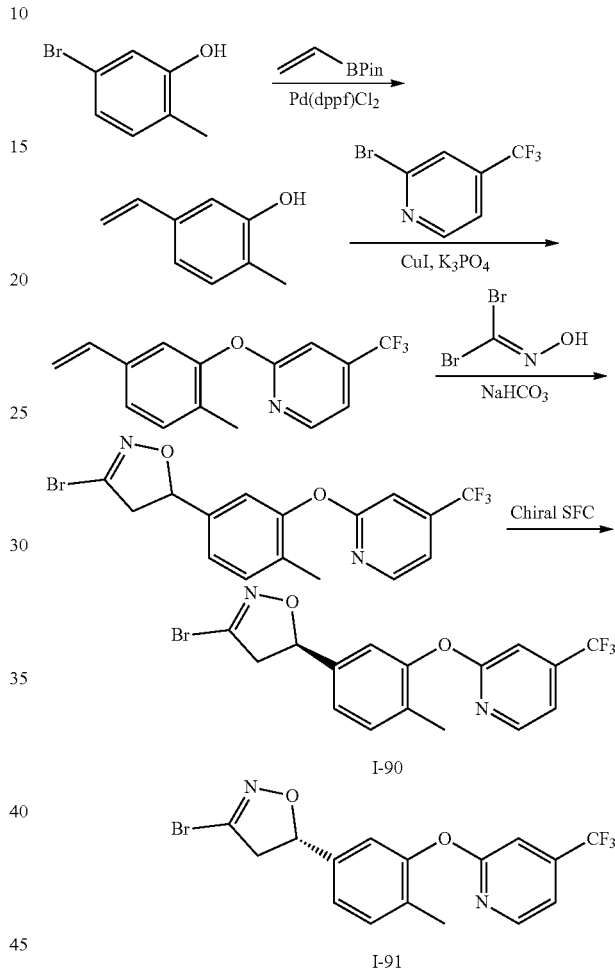

Step 1: 2-Methyl-5-vinyl-phenol

To a solution of 5-bromo-2-methyl-phenol (5 g, 26.73 mmol, 1 eq) in 1,4-dioxane (6 mL) and H$_2$O (2 mL) was added 4,4,5,5-tetramethyl-2-vinyl-1,3,2-dioxaborolane (6.18 g, 40.10 mmol, 6.80 mL, 1.5 eq), Pd(dppf)Cl$_2$ (1.96 g, 2.67 mmol, 0.1 eq) and Cs$_2$CO$_3$ (26.13 g, 80.20 mmol, 3 eq). The mixture was bubbled with N$_2$ for 3 min and stirred at 80° C. for 30 min under microwave. To the mixture was added water (30 mL) and extracted with ethyl acetate (30 mL×3). The combined organic phase was washed with brine (20 mL), dried with anhydrous Na$_2$SO$_4$, filtered and concentrated in vacuum to yield a residue which was purified by flash silica gel chromatography (from PE/EtOAc=200/1 to 5/1, TLC: PE/EtOAc=5/1, $R_f$=0.48) to yield 2-methyl-5-vinyl-phenol (1.7 g, 11.91 mmol, 44.6% yield, 94% purity) as yellow oil.

$^1$H NMR (500 MHz, CD$_3$OD) δ ppm 6.99 (d, J=7.6 Hz, 1H), 6.82 (s, 1H), 6.78 (d, J=7.6 Hz, 1H), 6.60 (dd, J=10.9, 17.6 Hz, 1H), 5.63 (d, J=17.7 Hz, 1H), 5.10 (d, J=10.8 Hz, 1H), 2.16 (s, 3H); ES-LCMS m/z 135.0 [M+H]⁺.

Step 2: 2-(2-Methyl-5-vinyl-phenoxy)-4-(trifluoromethyl)pyridine

To a solution of 2-methyl-5-vinyl-phenol (700 mg, 4.90 mmol, 1 eq) and 2-bromo-4-(trifluoromethyl)pyridine (919.88 mg, 4.07 mmol, 0.83 eq) in DMSO (20 mL) was added CuI (43.90 mg, 230.49 μmol, 0.047 eq), pyridine-2-carboxylic acid (48.30 mg, 392.32 umol, 0.08 eq) and K₃PO₄ (1.74 g, 8.19 mmol, 1.67 eq). The mixture was stirred at 120° C. for 12 h. To the mixture was added water (30 mL) and extracted with ethyl acetate (30 mL×3). The combined organic phase was washed with brine (20 mL), dried with anhydrous Na₂SO₄, filtered and concentrated in vacuum to yield a residue which was purified by flash silica gel chromatography (from PE/EtOAc=200/1 to 10/1, TLC: PE/EtOAc=10/1, R$_f$=0.35) to yield 2-(2-methyl-5-vinyl-phenoxy)-4-(trifluoromethyl)pyridine (400 mg, 1.15 mmol, 23.4% yield, 80% purity) as a yellow oil. ¹H NMR (500 MHz, CD₃OD) δ ppm 7.34 (s, 1H), 7.32 (s, 1H), 7.27 (s, 1H), 7.26 (d, J=1.8 Hz, 1H), 7.24 (s, 1H), 7.14 (s, 1H), 6.73-6.67 (m, 1H), 5.73 (d, J=17.5 Hz, 1H), 5.21 (d, J=11.0 Hz, 1H), 2.11 (s, 3H); ES-LCMS m/z 280.0 [M+H]⁺.

Step 3: (5R)-3-Bromo-5-[4-methyl-3-[[4-(trifluoromethyl)-2-pyridyl]oxy]phenyl]-4,5-dihydroisoxazole (5S)-3-Bromo-5-[4-methyl-3-[[4-(trifluoromethyl)-2-pyridyl]oxy]phenyl]-4,5-dihydroisoxazole To a solution of 2-(2-methyl-5-vinyl-phenoxy)-4-(trifluoromethyl)pyridine (400 mg, 1.15 mmol, 1 eq) and dibromomethanone oxime (464.85 mg, 2.29 mmol, 2 eq) in EtOAc (5 mL) was added NaHCO₃ (962.67 mg, 11.46 mmol, 10 eq). The mixture was stirred at 25° C. for 12 h under N₂ atmosphere. To the mixture was added water (30 mL) and extracted with ethyl acetate (30 mL×3). The combined organic phase was washed with brine (20 mL), dried with anhydrous Na₂SO₄, filtered and concentrated in vacuum to yield a residue which was purified by preparative TLC (PE/EtOAc=3/1, R$_f$=0.40) to yield the product. The product was separated by SFC (column: DAICEL CHIRALPAK AD (250 mm*30 mm, 10 μm); mobile phase: [0.1% NH₃H₂O ETOH]; B %: 30%-30%, min) to yield peak 1 and peak 2. Peak 1 was concentrated under reduced pressure to yield a residue which was dissolved in MeCN (10 mL) and H₂O (20 mL) and lyophilized to yield (5R)-3-bromo-5-[4-methyl-3-[[4-(trifluoromethyl)-2-pyridyl]oxy]phenyl]-4,5-dihydroisoxazole (16.27 mg, 40.56 μmol, 3.5% yield, 100% purity, SFC: R$_f$=2.368 min, ee=100%, [α]$^{30.3}_D$=+13.423 (MeOH, c=0.0536 g/100 mL)) as a white solid. ¹H NMR (400 MHz, CD₃OD) δ ppm 8.29 (d, J=5.5 Hz, 1H), 7.39-7.32 (m, 2H), 7.29 (s, 1H), 7.20 (dd, J=1.6, 7.8 Hz, 1H), 7.09 (d, J=1.6 Hz, 1H), 5.68 (dd, J=9.2, 10.8 Hz, 1H), 3.71 (dd, J=10.8, 17.4 Hz, 1H), 3.25 (dd, J=8.8, 17.4 Hz, 1H), 2.14 (s, 3H); ES-LCMS m/z 400.8, 402.8[M+H]⁺. Peak 2 was concentrated under reduced pressure to yield a residue which was dissolved in MeCN (10 mL) and H₂O (20 mL) and lyophilized to yield (5S)-3-bromo-5-[4-methyl-3-[[4-(trifluoromethyl)-2-pyridyl]oxy]phenyl]-4,5-dihydroisoxazole (15.43 mg, 38.46 μmol, 3.4% yield, 100% purity, R$_f$=4.567 min, ee=100%, [α]$^{30.2}_D$=-13.805 (MeOH, c=0.0565 g/100 mL)) as a white solid. ¹H NMR (400 MHz, CD₃OD) δ ppm 8.29 (d, J=5.5 Hz, 1H), 7.38-7.33 (m, 2H), 7.29 (s, 1H), 7.20 (dd, J=1.6, 7.8 Hz, 1H), 7.09 (d, J=1.6 Hz, 1H), 5.69 (dd, J=9.2, 10.8 Hz, 1H), 3.71 (dd, J=10.8, 17.4 Hz, 1H), 3.25 (dd, J=9.0, 17.6 Hz, 1H), 2.14 (s, 3H); ES-LCMS m/z 400.8, 402.8 [M+H]⁺.

I-49

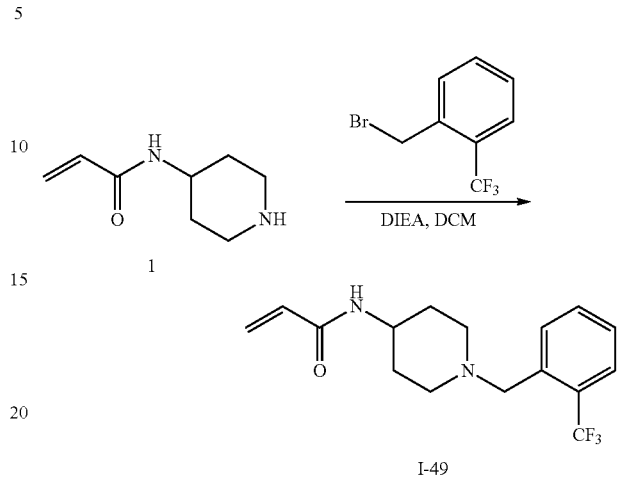

Step 1: N-[1-[[2-(Trifluoromethyl)phenyl]methyl]-4-piperidyl]prop-2-enamide

A mixture of N-(4-piperidyl)prop-2-enamide (150 mg, 924.07 μmol, 1 eq), 1-(bromomethyl)-2-(trifluoromethyl)benzene (220.88 mg, 924.07 μmol, 140.69 μL, 1 eq), DIEA (238.86 mg, 1.85 mmol, 321.91 μL, 2 eq) in DCM (3 mL) was stirred at 25° C. for 30 min under N₂ atmosphere. The solvent was removed to yield a residue which was purified by preparative HPLC (column: Agela DuraShell C18 150*25 mm*5 μm; mobile phase: [water (0.04% NH₃H₂O⁺ 10 mM NH₄HCO₃)-ACN]; B %: 37%-67%, 10 min). The desired fraction was lyophilized to yield N-[1-[[2-(trifluoromethyl)phenyl]methyl]-4-piperidyl]prop-2-enamide (74 mg, 236.93 μmol, 25.6% yield, 100% purity) as a white solid. ¹H NMR (400 MHz, DMSO-d₆) δ ppm 8.00 (d, J=7.8 Hz, 1H), 7.76 (d, J=7.8 Hz, 1H), 7.71-7.62 (m, 2H), 7.49-7.42 (m, 1H), 6.25-6.16 (m, 1H), 6.10-6.02 (m, 1H), 5.55 (dd, J=2.4, 10.0 Hz, 1H), 3.69-3.58 (m, 3H), 2.73 (d, J=11.5 Hz, 2H), 2.10 (t, J=10.8 Hz, 2H), 1.75 (d, J=10.3 Hz, 2H), 1.49-1.37 (m, 2H); ES-LCMS m/z 313.0 [M+H]⁺.

I-50

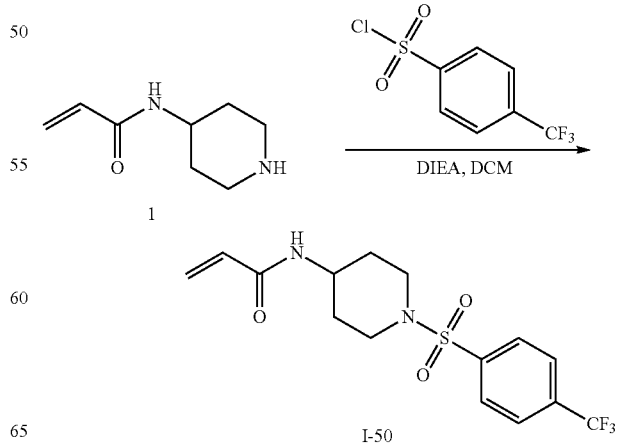

Step 1: N-[1-[4-(Trifluoromethyl)phenyl]sulfonyl-4-piperidyl]prop-2-enamide

To a solution of N-(4-piperidyl)prop-2-enamide (100 mg, 616.05 μmol, 1 eq) in DCM (5 mL) was added DIEA (159.24 mg, 1.23 mmol, 214.60 μL, 2 eq) and 4-(trifluoromethyl)benzenesulfonyl chloride (452.09 mg, 1.85 mmol, 3 eq). The mixture was stirred at 30° C. for 12 h. The reaction mixture was concentrated to yield a residue which was purified by preparative HPLC (column: Phenomenex Synergi C18 150*30 mm*4 μm; mobile phase: [water (0.05% HCl)-ACN]; B %: 41%-61%, 10 min) and lyophilized to yield N-[1-[4-(trifluoromethyl)phenyl]sulfonyl-4-piperidyl]prop-2-enamide (51.67 mg, 137.67 μmol, 22.4% yield, 96.6% purity) as a white solid. $^1$H NMR (500 MHz, DMSO-$d_6$) δ ppm 8.09-8.00 (m, 3H), 7.99-7.94 (m, 2H), 6.20-6.11 (m, 1H), 6.09-6.00 (m, 1H), 5.56 (dd, J=2.3, 10.1 Hz, 1H), 3.70-3.60 (m, 1H), 3.54 (d, J=12.1 Hz, 2H), 2.62-2.56 (m, 2H), 1.83 (d, J=10.4 Hz, 2H), 1.49-1.36 (m, 2H); ES-LCMS m/z 363.0 [M+H]$^+$, 385.0 [M+Na]$^+$.

I-51

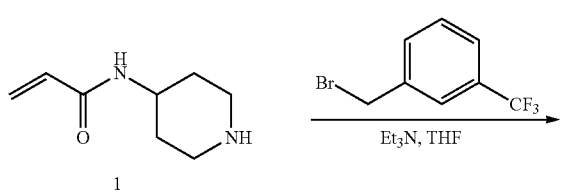

Step 1: N-[1-[[3-(Trifluoromethyl)phenyl]methyl]-4-piperidyl]prop-2-enamide

To a solution of N-(4-piperidyl)prop-2-enamide (150 mg, 924.06 μmol, 1 eq) and 1-(bromomethyl)-3-(trifluoromethyl)benzene (220.88 mg, 924.06 μmol, 140.69 μL, 1 eq) in DCM (10 mL) was added DIEA (238.86 mg, 1.85 mmol, 321.91 μL, 2 eq). The mixture was stirred at 30° C. for 30 min under N$_2$ atmosphere. The reaction mixture was concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 30%-60%, 10 min). The desired fraction was lyophilized to yield N-[1-[[3-(trifluoromethyl)phenyl]methyl]-4-piperidyl]prop-2-enamide (60 mg, 189.42 μmol, 20.5% yield, 98.6% purity) as a white solid. $^1$H NMR (400 MHz, DMSO-$d_6$) δ ppm 7.99 (d, J=7.6 Hz, 1H), 7.64-7.54 (m, 4H), 6.24-6.16 (m, 1H), 6.09-6.02 (m, 1H), 5.58-5.53 (m, 1H), 3.66-3.57 (m, 1H), 3.55 (s, 2H), 2.74 (d, J=11.7 Hz, 2H), 2.06 (t, J=10.6 Hz, 2H), 1.74 (d, J=10.0 Hz, 2H), 1.47-1.35 (m, 2H); ES-LCMS m/z 313.0 [M+H]$^+$.

P-8

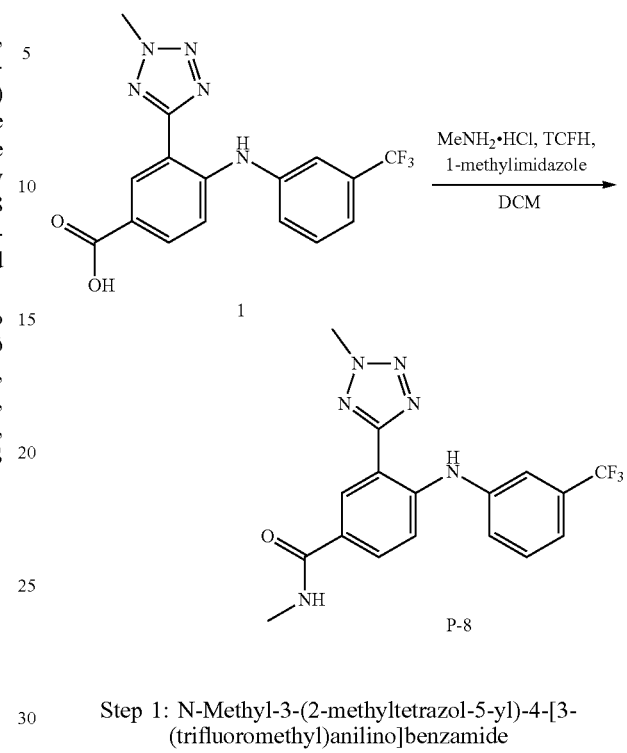

Step 1: N-Methyl-3-(2-methyltetrazol-5-yl)-4-[3-(trifluoromethyl)anilino]benzamide To a stirred solution of 3-(2-methyltetrazol-5-yl)-4-[3-(trifluoromethyl)anilino]benzoic acid (100 mg, 247.73 μmol, 1 eq) in DCM (10 mL) was added methanamine; hydrochloride (25.09 mg, 371.60 μmol, 1.5 eq), [chloro(dimethylamino)methylene]-dimethyl-ammonium; hexafluorophosphate (104.26 mg, 371.60 μmol, 1.5 eq) and 1-methylimidazole (61.02 mg, 743.20 μmol, 59.24 μL, 3 eq). The reaction mixture was stirred at 29° C. for 6 h. The reaction mixture was concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 40%-70%, 10 min). The desired fraction was lyophilized to yield N-methyl-3-(2-methyltetrazol-5-yl)-4-[3-(trifluoromethyl)anilino]benzamide (18.78 mg, 49.90 μL, 20.1% yield, 100.0% purity) as white solid. $^1$H NMR (500 MHz, CD$_3$OD) δ ppm 8.74-8.67 (m, 1H), 7.81 (dd, J=2.1, 8.9 Hz, 1H), 7.59-7.51 (m, 3H), 7.42-7.35 (m, 1H), 7.39 (d, J=8.9 Hz, 1H), 4.51-4.45 (m, 3H), 2.96-2.90 (m, 3H); ES-LCMS m/z 377.0 [M+H]$^+$.

P-7

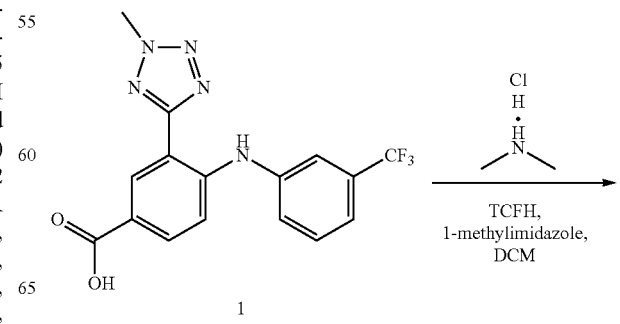

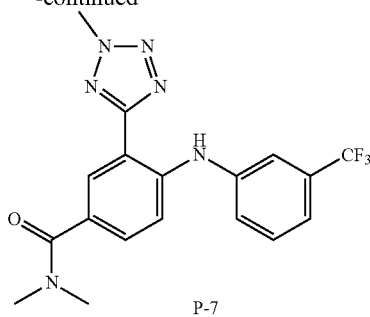

P-7

Step 1: N,N-Dimethyl-3-(2-methyltetrazol-5-yl)-4-[3-(trifluoromethyl)anilino]benzamide To a stirred solution of 3-(2-methyltetrazol-5-yl)-4-[3-(trifluoromethyl)anilino]benzoic acid (100 mg, 247.73 μmol, 1 eq) in DCM (10 mL) was added [chloro(dimethylamino)methylene]-dimethyl-ammonium;hexafluorophosphate (104.26 mg, 371.60 μmol, 1.5 eq), 1-methylimidazole (61.02 mg, 743.20 μmol, 3 eq) and N-methylmethanamine;hydrochloride (30.30 mg, 371.60 μmol, 1.5 eq). The reaction mixture was stirred at 29° C. for 6 h. The reaction mixture was concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 43%-73%, 10 min). The desired fraction was lyophilized to yield N,N-dimethyl-3-(2-methyltetrazol-5-yl)-4-[3-(trifluoromethyl)anilino]benzamide (21.49 mg, 55.05 μmol, 22.2% yield, 100.0% purity) as white solid. $^1$H NMR (500 MHz, CD$_3$OD) δ ppm 8.31 (d, J=2.0 Hz, 1H), 7.57-7.52 (m, 3H), 7.51-7.47 (m, 1H), 7.45-7.41 (m, 1H), 7.38-7.33 (m, 1H), 4.47 (s, 3H), 3.13 (s, 6H); ES-LCMS m/z 391.0 [M+H]$^+$.

I-41

Step 1: N-(3-Hydroxy-4-methyl-phenyl)prop-2-enamide

To a solution of 5-amino-2-methyl-phenol (1 g, 8.12 mmol, 1 eq) in THF (20 mL) was added DIEA (2.10 g, 16.24 mmol, 2.83 mL, 2.0 eq), prop-2-enoyl chloride (734.93 mg, 8.12 mmol, 662.10 μL, 1.0 eq). The mixture was stirred under N$_2$ at 0° C. for 1 hour. TLC (PE/EtOAc=1/1, R$_f$=0.52) showed the reaction was completed. Water (20 mL) was added and the mixture extracted with EtOAc (30 mL×3). The combine organic layers were dried over anhydrous Na$_2$SO$_4$, filtered and concentrated to yield N-(3-hydroxy-4-methyl-phenyl)prop-2-enamide (1.3 g, 6.53 mmol, 80.4% yield, 89.0% purity) as a white solid which was used for the next step directly without further purification. $^1$H NMR (500 MHz, CDCl$_3$) δ ppm 7.78 (s, 1H), 7.04 (d, J=7.9 Hz, 1H), 6.69-6.56 (m, 1H), 6.46 (d, J=16.9 Hz, 1H), 6.28-6.17 (m, 2H), 5.81 (d, J=10.4 Hz, 1H), 2.22 (s, 3H); ES-LCMS m/z 178.0 [M+H]$^+$.

Step 2: N-[3-[2-Bromo-5-(trifluoromethyl)phenoxy]-4-methyl-phenyl]prop-2-enamide A mixture of N-(3-hydroxy-4-methyl-phenyl)prop-2-enamide (200 mg, 1.00 mmol, 1 eq), 1-bromo-2-iodo-4-(trifluoromethyl)benzene (387.74 mg, 1.10 mmol, 1.1 eq), CuI (9.57 mg, 50.23 μmol, 0.05 eq), K$_3$PO$_4$ (426.45 mg, 2.01 mmol, 2.0 eq) and 2-Picolinic acid (12.37 mg, 100.45 μmol, 0.1 eq) in DMSO (3 mL) was degassed and purged with N$_2$ for three times and the mixture was stirred at 120° C. for 16 h under N$_2$ atmosphere. The mixture was concentrated and water (80 mL) was added. The mixture was extracted with EtOAc (50 mL×3). The combined organic layers were washed with brine (50 mL), dried over Na$_2$SO$_4$, filtered and concentrated. The residue was purified by preparative TLC (PE/EtOAc=5/1, R$_f$=0.14). and HPLC (column: Phenomenex Synergi C18 150*30 mm*4 um; mobile phase: [water (0.05% HCl)-ACN]; B %: 60%-80%, 10 min) to yield N-[3-[2-bromo-5-(trifluoromethyl)phenoxy]-4-methyl-phenyl]prop-2-enamide (5.64 mg, 14.09 μmol, 1.4% yield, 100.0% purity) as a white solid. $^1$H NMR (400 MHz, CDCl$_3$) δ ppm 7.75 (d, J=7.8 Hz, 1H), 7.30 (s, 1H), 7.21 (dd, J=6.1, 15.5 Hz, 3H), 6.94 (s, 1H), 6.46-6.36 (m, 1H), 6.27-6.12 (m, 1H), 5.77 (d, J=10.2 Hz, 1H), 2.20 (s, 3H). ES-LCMS m/z 399.9, 401.9 [M+H]$^+$.

I-92 & I-93

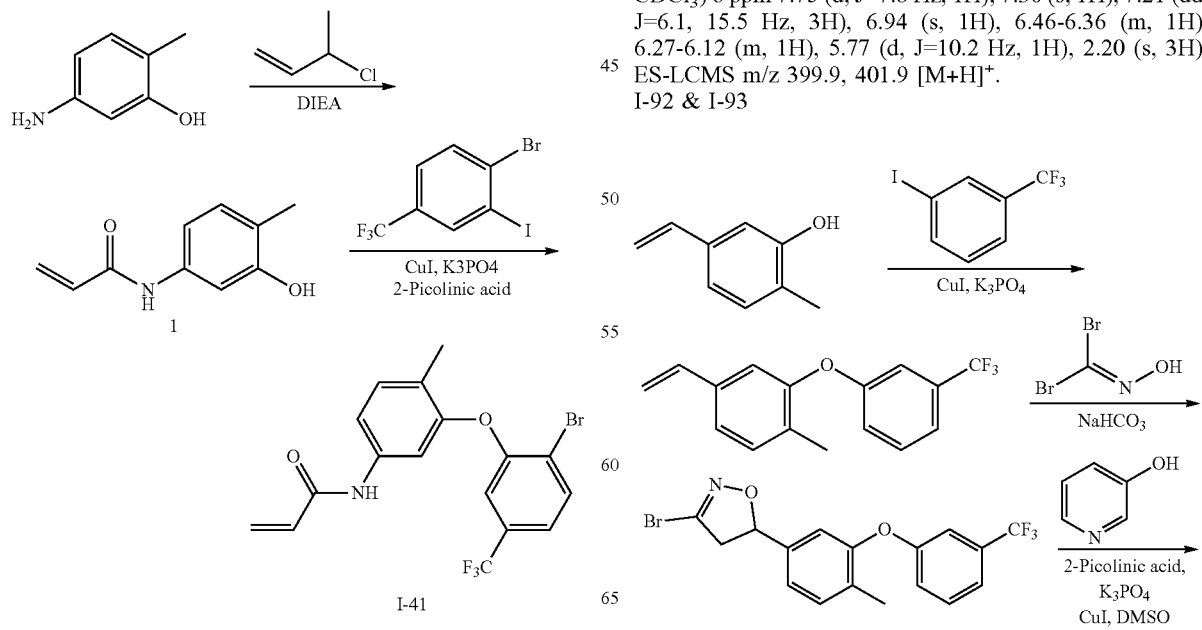

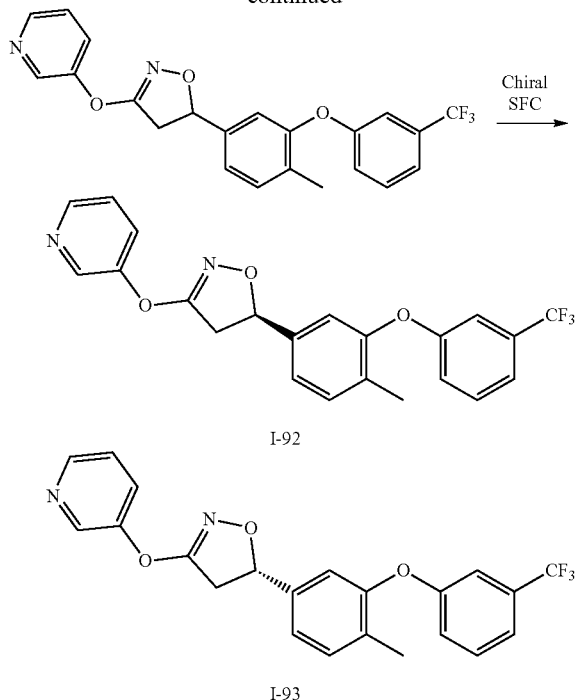

I-92

I-93

Step 1: 1-Methyl-2-[3-(trifluoromethyl)phenoxy]-4-vinyl-benzene

To a solution of 2-methyl-5-vinyl-phenol (9 g, 57.02 mmol, 1 eq) and 1-iodo-3-(trifluoromethyl)benzene (13.96 g, 51.31 mmol, 7.38 mL, 0.9 eq) in DMSO (180 mL) was added pyridine-2-carboxylic acid (561.53 mg, 4.56 mmol, 0.08 eq), $K_3PO_4$ (20.57 g, 96.93 mmol, 1.7 eq) and CuI (510.35 mg, 2.68 mmol, 0.047 eq). The mixture was stirred at 120° C. for 12 h under $N_2$ atmosphere. The reaction mixture was added $H_2O$ (150 mL) and extracted with EtOAc (150 mL×3). The combined organic layers were washed with sat. aq. NaCl (100 mL), dried over $Na_2SO_4$, filtered and concentrated under reduced pressure to yield a residue which was purified by flash silica gel chromatography (from PE/EtOAc=200/1 to 10/1, TLC: PE/EtOAc=10/1, $R_f$=0.60) to yield 1-methyl-2-[3-(trifluoromethyl)phenoxy]-4-vinyl-benzene (7 g, 21.38 mmol, 37.5% yield, 85.0% purity) as yellow liquid. $^1H$ NMR (400 MHz, $CDCl_3$) δ ppm 7.42-7.36 (m, 1H), 7.29 (d, J=7.8 Hz, 1H), 7.25-7.21 (m, 1H), 7.18 (dd, J=2.0, 10.2 Hz, 2H), 7.06-6.98 (m, 2H), 6.64 (dd, J=11.0, 17.6 Hz, 1H), 5.67 (d, J=17.2 Hz, 1H), 5.22 (d, J=11.0 Hz, 1H), 2.19 (s, 3H); ES-LCMS no desired m/z was detected.

Step 2: 3-Bromo-5-[4-methyl-3-[3-(trifluoromethyl)phenoxy]phenyl]-4,5-dihydroisoxazole To a stirred solution of 1-methyl-2-[3-(trifluoromethyl)phenoxy]-4-vinyl-benzene (1 g, 3.05 mmol, 1 eq) and dibromomethanone oxime (929.36 mg, 4.58 mmol, 1.5 eq) in EtOAc (15 mL) was added $NaHCO_3$ (2.57 g, 30.55 mmol, 10 eq). The reaction mixture was stirred at 25° C. for 12 h. The reaction mixture was diluted with $H_2O$ (20 mL) and extracted with EtOAc (30 mL×3). The combined organic layers were washed with brine (30 mL), dried over $Na_2SO_4$, filtered and concentrated under reduced pressure to yield a residue which was purified by flash silica gel chromatography (from PE/EtOAc=100/1 to 10/1, TLC: PE/EtOAc=10:1, $R_f$=0.44) to yield 3-bromo-5-[4-methyl-3-[3-(trifluoromethyl)phenoxy]phenyl]-4,5-dihydroisoxazole (870 mg, 2.15 mmol, 70.5% yield, 99.0% purity) as light yellow liquid. $^1H$ NMR (500 MHz, $CDCl_3$) δ ppm 7.43-7.39 (m, 1H), 7.31 (d, J=7.9 Hz, 2H), 7.15-7.09 (m, 2H), 7.02 (dd, J=2.3, 8.2 Hz, 1H), 6.92 (d, J=1.5 Hz, 1H), 5.61 (dd, J=9.2, 10.8 Hz, 1H), 3.58 (dd, J=11.0, 17.2 Hz, 1H), 3.17 (dd, J=9.0, 17.2 Hz, 1H), 2.22 (s, 3H); ES-LCMS m/z 399.9, 401.9 [M+H]$^+$.

Step 3: (5R)-5-[4-Methyl-3-[3-(trifluoromethyl)phenoxy]phenyl]-3-(3-pyridyloxy)-4,5-dihydroisoxazole & (5S)-5-[4-Methyl-3-[3-(trifluoromethyl)phenoxy]phenyl]-3-(3-pyridyloxy)-4,5-dihydroisoxazole To a stirred solution of 3-bromo-5-[4-methyl-3-[3-(trifluoromethyl)phenoxy]phenyl]-4,5-dihydroisoxazole (500 mg, 1.24 mmol, 0.9 eq) and pyridin-3-ol (130.70 mg, 1.37 mmol, 1 eq) in DMSO (8 mL) was added $K_3PO_4$ (495.95 mg, 2.34 mmol, 1.7 eq), 2-Picolinic acid (13.54 mg, 109.95 μmol, 0.08 eq) and CuI (13.09 mg, 68.72 μmol, 0.05 eq). The reaction mixture was stirred at 120° C. for 12 h under $N_2$ atmosphere. The reaction mixture was diluted with $H_2O$ (10 mL) and extracted with EtOAc (25 mL×3). The combined organic layers were washed with brine (20 mL), dried over $Na_2SO_4$, filtered and concentrated under reduced pressure to yield a residue which was purified by flash silica gel chromatography (from PE/EtOAc=100/1 to 2/1, TLC: PE/EtOAc=2/1, $R_f$=0.45) to yield crude product which was separated by chiral SFC (column: DAICEL CHIRALPAK AD (column: DAICEL CHIRALPAK AD-H (250 mm*30 mm, 5 μm); mobile phase: [0.1% $NH_3 \cdot H_2O$ ETOH]; B %: 30%-30%, min) to yield Peak 1 and Peak 2. Peak 1 was concentrated under reduced pressure to yield a residue which was dissolved in MeCN (20 mL) and $H_2O$ (40 mL) and lyophilized to yield (5R)-5-[4-methyl-3-[3-(trifluoromethyl)phenoxy]phenyl]-3-(3-pyridyloxy)-4,5-dihydroisoxazole (40.02 mg, 96.58 μmol, 7.0% yield, 100% purity, SFC: $R_t$=1.090 min, ee=100%, $[\alpha]^{30.1}_D$=+20.408 (MeOH, c=0.049 g/100 mL)) as red oil. $^1H$ NMR (500 MHz, $CD_3OD$) δ ppm 8.55 (d, J=2.7 Hz, 1H), 8.42 (dd, J=1.1, 4.8 Hz, 1H), 7.88-7.81 (m, 1H), 7.54-7.46 (m, 2H), 7.41-7.33 (m, 2H), 7.25 (dd, J=1.4, 7.9 Hz, 1H), 7.16-7.09 (m, 2H), 7.06 (d, J=1.4 Hz, 1H), 5.72 (t, J=9.7 Hz, 1H), 3.66 (dd, J=10.2, 16.8 Hz, 1H), 3.25 (dd, J=9.2, 16.7 Hz, 1H), 2.21 (s, 3H); ES-LCMS m/z 415.0 [M+H]$^+$. Peak 2 was concentrated under reduced pressure to yield a residue which was dissolved in MeCN (20 mL) and $H_2O$ (40 mL) and lyophilized to yield (5S)-5-[4-methyl-3-[3-(trifluoromethyl)phenoxy]phenyl]-3-(3-pyridyloxy)-4,5-dihydroisoxazole (15.24 mg, 36.78 μmol, 2.7% yield, 100% purity, SFC: $R_t$=1.249 min, ee=99.66%, $[\alpha]^{30.1}_D$=−16.667 (MeOH, c=0.048 g/100 mL)) as red oil. $^1H$ NMR (500 MHz, $CD_3OD$) ppm 8.55 (d, J=2.7 Hz, 1H), 8.42 (dd, J=1.1, 4.7 Hz, 1H), 7.84 (dd, J=1.5, 8.4 Hz, 1H), 7.54-7.46 (m, 2H), 7.41-7.33 (m, 2H), 7.25 (dd, J=1.4, 7.9 Hz, 1H), 7.15-7.09 (m, 2H), 7.06 (d, J=1.5 Hz, 1H), 5.72 (t, J=9.7 Hz, 1H), 3.66 (dd, J=10.2, 16.8 Hz, 1H), 3.25 (dd, J=9.2, 16.8 Hz, 1H), 2.21 (s, 3H); ES-LCMS m/z 415.0 [M+H]$^+$.

I-52

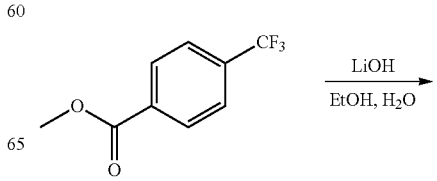

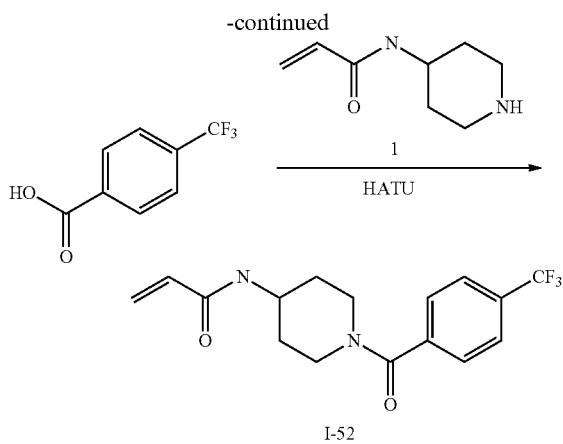

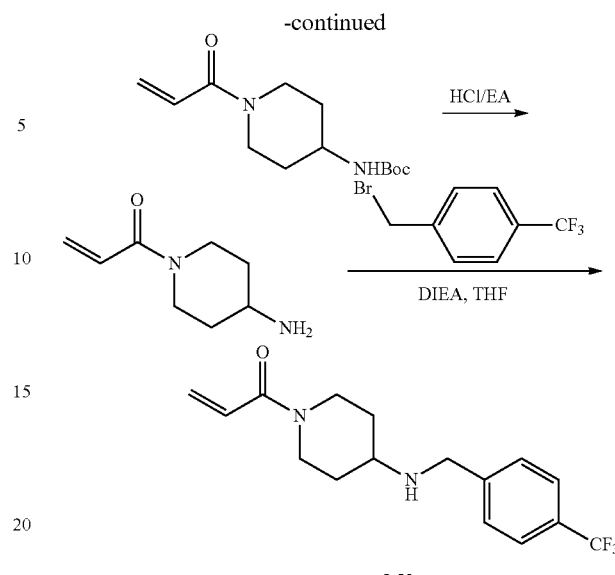

Step 1: 4-(Trifluoromethyl)benzoic Acid

To a stirred solution of methyl 4-(trifluoromethyl)benzoate (2 g, 9.80 mmol, 1.57 mL, 1 eq) in EtOH (10 mL) and H$_2$O (10 mL) was added LiOH·H$_2$O (2.47 g, 58.80 mmol, 6 eq). The reaction mixture was stirred at 25° C. for 12 h. TLC (PE/EtOAc=5/1, R$_f$=0.05) indicated Reactant 1 was consumed completely and one new spot formed. The reaction mixture was concentrated under reduced pressure to remove EtOH. The residue was adjust pH to 5 with 1 N HCl, filtered and concentrated the filter cake under reduced pressure to yield a residue which was used in the next step without further purification to yield 4-(trifluoromethyl)benzoic acid (1.86 g, 9.29 mmol, 94.8% yield, 95.0% purity) as a white solid. $^1$H NMR (400 MHz, DMSO-d$_6$) δ ppm 8.13 (d, J=8.1 Hz, 2H), 7.87 (d, J=7.6 Hz, 2H); ES-LCMS no desired m/z was detected.

Step 2: N-[1-[4-(Trifluoromethyl)benzoyl]-4-piperidyl]prop-2-enamide

To a stirred solution of 4-(trifluoromethyl)benzoic acid (200 mg, 999.37 μmol, 1 eq), DIEA (387.48 mg, 3.00 mmol, 522.21 μL, 3 eq) and HATU (683.99 mg, 1.80 mmol, 1.8 eq) in DMF (5 mL) was added N-(4-piperidyl)prop-2-enamide (194.67 mg, 1.20 mmol, 1.2 eq). The reaction mixture was stirred at 25° C. for 3 h. The reaction mixture was diluted with H$_2$O (5 mL) and extracted with EtOAc (20 mL×3). The combined organic layers were washed with brine (15 mL), dried over Na$_2$SO$_4$, filtered and concentrated under reduced pressure to yield a residue which was purified by preparative HPLC (column: Agela DuraShell C18 150*25 mm*5 μm; mobile phase: [water (0.04% NH$_3$·H$_2$O+10 mM NH$_4$HCO$_3$)-ACN]; B %: 27%-57%, 10 min) to yield N-[1-[4-(trifluoromethyl)benzoyl]-4-piperidyl]prop-2-enamide (96.69 mg, 296.31 μmol, 29.7% yield, 100% purity) as a white solid. $^1$H NMR (400 MHz, DMSO-d$_6$) δ ppm 8.10 (d, J=7.6 Hz, 1H), 7.82 (d, J=8.1 Hz, 2H), 7.59 (d, J=8.1 Hz, 2H), 6.25-6.16 (m, 1H), 6.13-6.04 (m, 1H), 5.58 (dd, J=2.2, 10.0 Hz, 1H), 4.33 (d, J=11.2 Hz, 1H), 3.99-3.82 (m, 1H), 3.45 (d, J=11.5 Hz, 1H), 3.22-2.97 (m, 2H), 1.95-1.68 (m, 2H), 1.52-1.19 (m, 2H); ES-LCMS m/z 327.0 [M+H]$^+$.

I-53

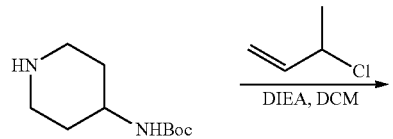

Step 1: tert-Butyl N-(1-prop-2-enoyl-4-piperidyl)

A mixture of tert-butyl N-(4-piperidyl)carbamate (3 g, 14.98 mmol, 1 eq) and DIEA (5.79 g, 44.78 mmol, 7.8 mL, 2.99 eq) in DCM (10 mL) was stirred at 28° C. The mixture was cooled to 0° C. and then prop-2-enoyl chloride (1.67 g, 18.40 mmol, 1.5 mL, 1.23 eq) was added dropwise at 0° C. The resulting mixture was stirred at 28° C. for 6 h. TLC (PE/EtOAc=1/1, R$_f$=0.50) indicated Reactant 1 was consumed completely and one new spot formed. The mixture was diluted with water (20 mL) and extracted with EtOAc (25 mL×3). The combined organic layers were dried over Na$_2$SO$_4$, filtered and concentrated under reduced pressure to yield a residue which was purified by flash silica gel chromatography (from PE/EtOAc=100/1 to 1/1, TLC: PE/EtOAc=1/1, R$_f$=0.50) to yield tert-butyl N-(1-prop-2-enoyl-4-piperidyl)carbamate (1.5 g, 5.31 mmol, 35.4% yield, 90.0% purity) as a light yellow solid. $^1$H NMR (400 MHz, DMSO-d$_6$) δ ppm 6.90-6.68 (m, 2H), 6.04 (dd, J=2.4, 16.6 Hz, 1H), 5.62 (dd, J=2.3, 10.4 Hz, 1H), 4.22 (d, J=12.7 Hz, 1H), 4.01-3.85 (m, 1H), 3.50-3.40 (m, 1H), 3.12-3.00 (m, 1H), 2.80-2.66 (m, 1H), 1.76-1.66 (m, 2H), 1.35 (s, 9H), 1.19 (t, J=11.1 Hz, 2H); ES-LCMS m/z 198.9 [M-t-Bu+H]$^+$.

Step 2: 1-(4-Amino-1-piperidyl)prop-2-en-1-one

A solution of tert-butyl N-(1-prop-2-enoyl-4-piperidyl)carbamate (1.5 g, 5.31 mmol, 1 eq) in HCl/MeOH (20 mL) was stirred at 28° C. for 1 h. TLC (PE/EtOAc=1/1) indicated Reactant 1 was consumed completely. The reaction mixture was concentrated under reduced pressure to yield 1-(4-amino-1-piperidyl)prop-2-en-1-one (1.4 g, 3.67 mmol, 69.2% yield, 50.0% purity, HCl) as light yellow oil, which was used in the next step without further purification. $^1$H NMR (400 MHz, DMSO-d$_6$) δ ppm 8.25 (br s, 2H), 6.78 (dd, J=10.4, 16.8 Hz, 1H), 6.06 (dd, J=2.3, 16.8 Hz, 1H), 5.65 (dd, J=2.4, 10.5 Hz, 1H), 4.40-4.30 (m, 1H), 4.05 (d, J=13.7 Hz, 1H), 3.22 (dd, J=5.1, 10.3 Hz, 1H), 3.11-3.01 (m, 1H), 2.73-2.62 (m, 1H), 1.92 (d, J=7.3 Hz, 2H), 1.44-1.33 (m, 2H).

Step 3: 1-[4-[[4-(Trifluoromethyl)phenyl]methylamino]-1-piperidyl]prop-2-en-1-one To a solution of 1-(4-amino-1-piperidyl)prop-2-en-1-one (100 mg, 324.24 μmol, 1 eq) and 1-(bromomethyl)-4-(trifluoromethyl)benzene (93.00 mg, 389.07 μmol, 60.00 μL, 1.2 eq) in DCM (5 mL) was added DIEA (207.76 mg, 1.61 mmol, 280.00 μL, 4.96 eq). The mixture was stirred at 28° C. for 12 h. The reaction mixture was filtered and concentrated under reduced pressure to yield a residue which was purified by preparative HPLC (column: Agela DuraShell C18 150*25 mm*5 um; mobile phase: [water (0.04% $NH_3 \cdot H_2O$+10 mM $NH_4HCO_3$)-ACN]; B %: 32%-62%, 10 min) to yield 1-[4-[[4-(trifluoromethyl)phenyl]methylamino]-1-piperidyl]prop-2-en-1-one (29.78 mg, 95.35 μmol, 29.4% yield, 100.0% purity) as a colorless oil. $^1$H NMR (400 MHz, $CD_3OD$) δ ppm 7.64-7.58 (m, 2H), 7.56-7.51 (m, 2H), 6.74 (dd, J=10.8, 16.9 Hz, 1H), 6.15 (dd, J=1.8, 16.8 Hz, 1H), 5.70 (dd, J=2.0, 10.5 Hz, 1H), 4.47 (d, J=13.2 Hz, 1H), 4.07 (d, J=13.2 Hz, 1H), 3.87 (s, 2H), 3.13 (t, J=12.1 Hz, 1H), 2.86-2.71 (m, 2H), 1.99 (d, J=11.7 Hz, 2H), 1.38-1.24 (m, 2H); ES-LCMS m/z 313.0 [M+H]$^+$.

I-54

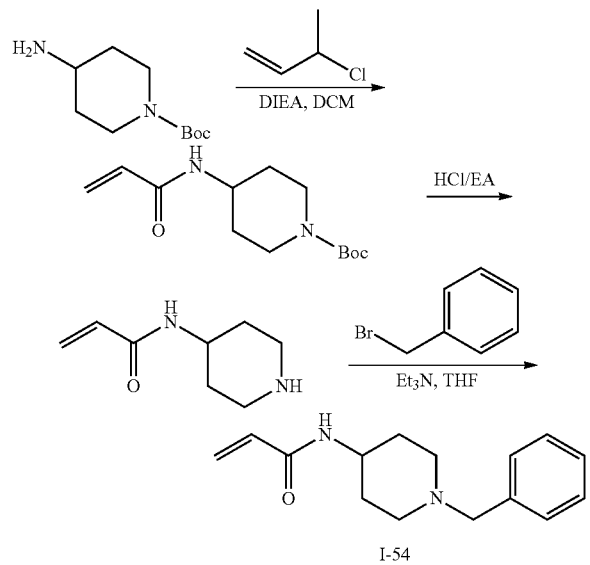

Step 1: tert-Butyl 4-(prop-2-enoylamino)piperidine-1-carboxylate

To a solution of tert-butyl 4-aminopiperidine-1-carboxylate (5 g, 24.97 mmol, 1 eq) in DCM (60 mL) was added DIEA (4.84 g, 37.45 mmol, 6.52 mL, 1.5 eq) at 0° C. then added prop-2-enoyl chloride (2.71 g, 29.96 mmol, 2.44 mL, 1.2 eq). The mixture was stirred at 0-30° C. for 1 h under $N_2$ atmosphere. The reaction mixture was diluted with water (50 mL) then extracted with EtOAc (30 mL×3). The combined organic layers were dried over $Na_2SO_4$, filtered and the filtrate was concentrated to yield a residue which was purified by flash silica gel chromatography (from PE/EtOAc=100/1 to 2/1, TLC: PE/EtOAc=1/1, $R_f$=0.75) to yield tert-butyl 4-(prop-2-enoylamino)piperidine-1-carboxylate (5.3 g, 20.84 mmol, 83.5% yield, 100.0% purity) as a white solid. $^1$H NMR (400 MHz, DMSO-$d_6$) δ ppm 8.04 (d, J=7.6 Hz, 1H), 6.24-6.14 (m, 1H), 6.12-6.03 (m, 1H), 5.57 (dd, J=2.3, 9.9 Hz, 1H), 3.95-3.69 (m, 3H), 2.85 (s, 2H), 1.73 (dd, J=2.8, 12.6 Hz, 2H), 1.39 (s, 9H), 1.32-1.14 (m, 2H); ES-LCMS m/z 255.1 [M+H]$^+$, 199.0 [M-t-Bu+H]$^+$.

Step 2: N-(4-Piperidyl)prop-2-enamide

To a solution of tert-butyl 4-(prop-2-enoylamino)piperidine-1-carboxylate (1.3 g, 5.11 mmol, 1 eq) in MeOH (10 mL) and HCl/EtOAc (4 M, 1.28 mL, 1 eq). The mixture was stirred at 25° C. for 1 h under $N_2$ atmosphere. The reaction mixture was concentrated to yield N-(4-piperidyl)prop-2-enamide (970 mg, 4.83 mmol, 94.6% yield, 95% purity, HCl) as yellow oil which was used in the next step without further purification. $^1$H NMR (400 MHz, DMSO-$d_6$) δ ppm 9.15 (s, 2H), 6.33-6.21 (m, 1H), 6.14-6.03 (m, 1H), 5.57 (dd, J=2.1, 10.1 Hz, 1H), 3.94-3.83 (m, 1H), 3.23 (d, J=12.7 Hz, 2H), 2.98-2.89 (m, 2H), 1.90 (dd, J=3.1, 13.6 Hz, 2H), 1.66 (q, J=10.3 Hz, 2H).

Step 3: N-(1-Benzyl-4-piperidyl)prop-2-enamide

To a solution of N-(4-piperidyl)prop-2-enamide (250 mg, 1.54 mmol, 1 eq) and bromomethylbenzene (263.41 mg, 1.54 mmol, 182.93 μL, 1 eq) in DCM (10 mL) was added DIEA (398.10 mg, 3.08 mmol, 536.52 μL, 2 eq). The mixture was stirred at 30° C. for 30 min under $N_2$ atmosphere. The reaction mixture was concentrated to yield a residue which was purified by preparative HPLC (column: Welch Xtimate C18 150*25 mm*5 um; mobile phase: [water (10 mM $NH_4HCO_3$)-ACN]; B %: 20%-50%, 10 min). The desired fraction was lyophilized to yield N-(1-benzyl-4-piperidyl)prop-2-enamide (110 mg, 449.31 μmol, 29.2% yield, 99.8% purity) as a white solid. $^1$H NMR (400 MHz, DMSO-$d_6$) δ ppm 7.99 (d, J=7.6 Hz, 1H), 7.36-7.20 (m, 5H), 6.26-6.15 (m, 1H), 6.10-6.01 (m, 1H), 5.55 (dd, J=2.3, 10.1 Hz, 1H), 3.65-3.55 (m, 1H), 3.44 (s, 2H), 2.74 (d, J=11.7 Hz, 2H), 2.00 (t, J=10.5 Hz, 2H), 1.73 (d, J=10.8 Hz, 2H), 1.46-1.34 (m, 2H); ES-LCMS m/z 245.0 [M+H]$^+$.

I-94 & I-95

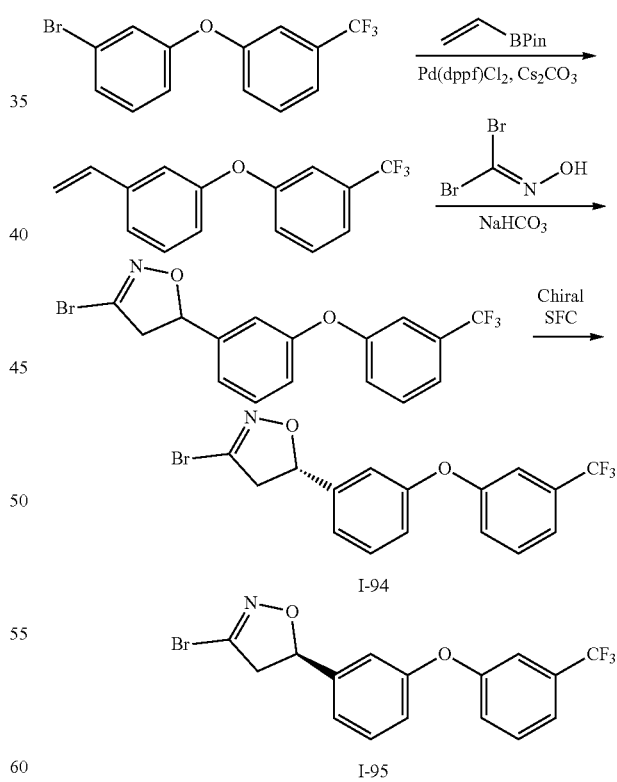

Step 1: 1-(Trifluoromethyl)-3-(3-vinylphenoxy)benzene

To a stirred solution of 1-bromo-3-[3-(trifluoromethyl) phenoxy]benzene (1.1 g, 2.08 mmol, 1 eq) and 4,4,5,5- tetramethyl-2-vinyl-1,3,2-dioxaborolane (384.67 mg, 2.50 mmol, 423.64 μL, 1.2 eq) in 1,4-dioxane (15 mL) and water (5 mL) was added Pd(dppf)Cl$_2$ (152.29 mg, 208.14 μmol, 0.1 eq) and Cs$_2$CO$_3$ (2.03 g, 6.24 mmol, 3 eq). The reaction mixture bubbled with N$_2$ for 1 min then stirred at 100° C. for 30 min under microwave. TLC (PE/EtOAc=3:1, R$_f$=0.70) showed starting material was remained and one new spot was detected. The mixture was filtered through a celite pad, and the filtrate was concentrated to yield a residue which was purified by flash silica gel chromatography (from PE/EtOAc=100/1 to 3/1, TLC: PE/EtOAc=3/1, R$_f$=0.65) to yield 1-(trifluoromethyl)-3-(3-vinylphenoxy)benzene (461 mg, 1.66 mmol, 79.6% yield, 95.0% purity) as yellow solid. $^1$H NMR (400 MHz, DMSO-d$_6$) δ ppm 7.69-7.54 (m, 2H), 7.48 (d, J=7.6 Hz, 1H), 7.43-7.39 (m, 1H), 7.34 (d, J=7.8 Hz, 1H), 7.30 (s, 1H), 7.24 (s, 1H), 6.99 (dd, J=1.5, 7.8 Hz, 1H), 6.74 (dd, J=10.9, 17.7 Hz, 1H), 5.87 (d, J=17.6 Hz, 1H), 5.30 (d, J=11.0 Hz, 1H).

Step 2: (5S)-3-Bromo-5-[3-[3-(trifluoromethyl)phenoxy]phenyl]-4,5-dihydroisoxazole & (5R)-3-bromo-5-[3-[3-(trifluoromethyl)phenoxy]phenyl]-4,5-dihydroisoxazole To a stirred solution of 1-(trifluoromethyl)-3-(3-vinylphenoxy)benzene (230 mg, 826.89 μL, 1 eq) and dibromomethanone oxime (335.44 mg, 1.65 mmol, 2 eq) in EtOAc (10 mL) was added NaHCO$_3$ (694.65 mg, 8.27 mmol, 10 eq). The reaction mixture was stirred at 25° C. for 12 h. The mixture was filtered through a celite pad and the filtrate was concentrated to yield a residue which was purified by flash silica gel chromatography (from PE/EtOAc=100/1 to 3/1, TLC: PE/EtOAc=3/1, R$_f$=0.60) to yield a residue which was separated by SFC (column: REGIS (s, s) WHELK-01 (250 mm*30 mm, 5 μm); mobile phase: [0.1% NH$_3$H$_2$O IPA]; B %: 25%-25%, min) to yield Peak 1 and Peak 2. Peak 1 was concentrated under reduced pressure to yield a residue which was lyophilized to yield (5S)-3-bromo-5-[3-[3-(trifluoromethyl)phenoxy]phenyl]-4,5-dihydroisoxazole (31.26 mg, 80.95 μmol, 9.8% yield, 100% purity, SFC: R$_t$=2.074 min, ee=100%, [α]$^{30.5}_D$=−123.4, MeOH, c=0.047 g/100 mL) as yellow oil. $^1$H NMR (400 MHz, DMSO-d$_6$) δ ppm 7.65-7.60 (m, 1H), 7.52-7.44 (m, 2H), 7.33 (s, 1H), 7.32-7.28 (m, 1H), 7.22 (d, J=7.6 Hz, 1H), 7.12 (s, 1H), 7.07 (dd, J=1.7, 8.1 Hz, 1H), 5.73 (dd, J=9.2, 10.6 Hz, 1H), 3.77 (dd, J=10.8, 17.6 Hz, 1H), 3.37-3.33 (m, 1H); ES-LCMS m/z 385.9, 387.9 [M+H]$^+$. Peak 2 was concentrated under reduced pressure to yield a residue which was lyophilized to yield (5R)-3-bromo-5-[3-[3-(trifluoromethyl)phenoxy]phenyl]-4,5-dihydroisoxazole (44.06 mg, 110.67 μmol, 13.4% yield, 97% purity, SFC: R$_t$=2.525 min, ee=100%, [α]$^{30.5}_D$=+169.5, MeOH, c=0.039 g/100 mL) as yellow oil. $^1$H NMR (400 MHz, DMSO-d$_6$) δ ppm 7.66-7.59 (m, 1H), 7.51 (d, J=8.1 Hz, 1H), 7.47 (t, J=8.1 Hz, 1H), 7.35-7.28 (m, 2H), 7.22 (d, J=8.0 Hz, 1H), 7.12 (s, 1H), 7.07 (dd, J=1.6, 8.2 Hz, 1H), 5.73 (dd, J=9.3, 10.5 Hz, 1H), 3.77 (dd, J=10.9, 17.5 Hz, 1H), 3.38-3.33 (m, 1H); ES-LCMS m/z 385.8, 387.8 [M+H]$^+$.
I-96 & I-97

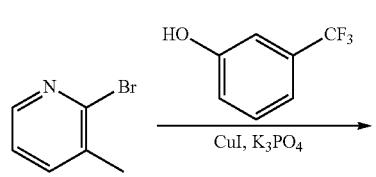

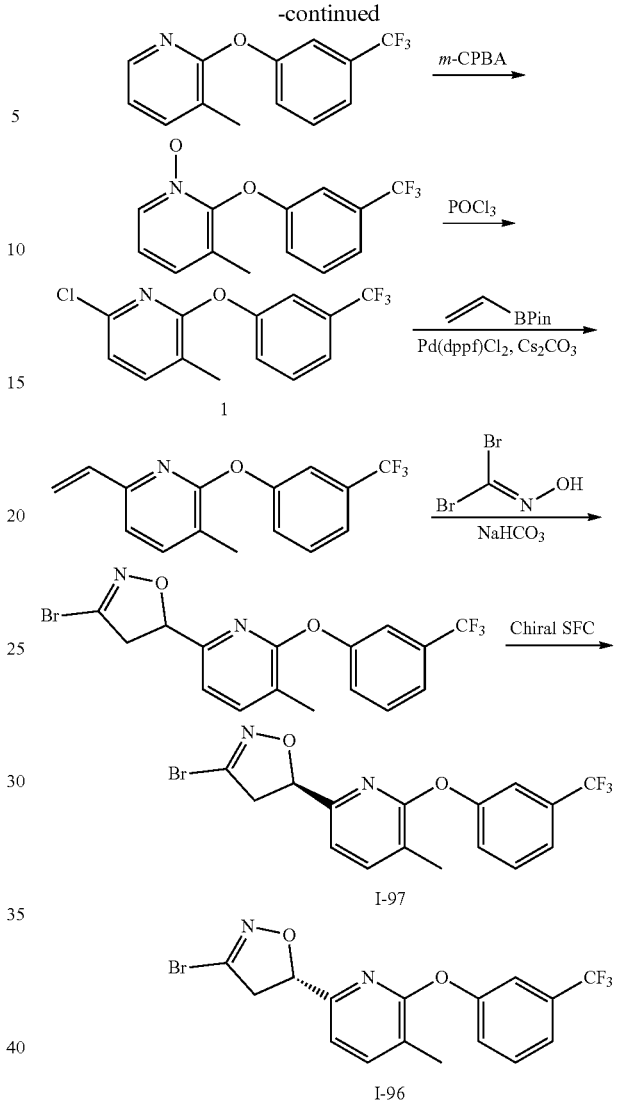

Step 1: 3-Methyl-2-[3-(trifluoromethyl)phenoxy]pyridine

A mixture of 3-(trifluoromethyl)phenol (2.0 g, 12.34 mmol, 1.48 mL, 1 eq), 2-bromo-3-methyl-pyridine (1.70 g, 9.87 mmol, 1.10 mL, 0.8 eq), CuI (117.48 mg, 616.87 μmol, 0.05 eq), K$_3$PO$_4$ (5.24 g, 24.67 mmol, 2 eq) and 2-Picolinic acid (151.89 mg, 1.23 mmol, 0.1 eq) in DMSO (40 mL) was degassed and purged with N$_2$ for three times and the mixture was stirred at 120° C. for 12 h under N$_2$ atmosphere. The mixture was added water (40 mL), extracted with EtOAc (50 mL×3). The combined organic layers were washed with brine (50 mL), dried over Na$_2$SO$_4$, filtered and concentrated to yield a residue which was purified by flash silica gel chromatography (From PE/EtOAc=1/0 to 5/1, R$_f$=0.52) to yield 3-methyl-2-[3-(trifluoromethyl)phenoxy]pyridine (900 mg, 3.53 mmol, 28.6% yield, 99.4% purity) as colorless liquid. $^1$H NMR (400 MHz, CDCl$_3$) δ ppm 8.00 (dd, J=1.2, 5.1 Hz, 1H), 7.60-7.38 (m, 4H), 7.33 (d, J=8.2 Hz, 1H), 6.97 (dd, J=4.9, 7.2 Hz, 1H), 2.37 (s, 3H); ES-LCMS m/z 254.0 [M+H]$^+$.

Step 2: 3-Methyl-1-oxido-2-[3-(trifluoromethyl) phenoxy]pyridine

To a solution of 3-methyl-2-[3-(trifluoromethyl)phenoxy] pyridine (900 mg, 3.54 mmol, 1 eq) in DCM (30 mL) was added m-CPBA (3.60 g, 17.71 mmol, 85% purity, 5 eq). The mixture was stirred at 25° C. for 12 h. sat.aq.Na$_2$S$_2$O$_3$ (30 mL) and aq. NaHCO$_3$ (4 M, 30 mL) were added. The mixture was extracted with DCM (50 mL×3). The combined organic layers were washed with brine (50 mL), dried over Na$_2$SO$_4$, filtered and concentrated to yield 3-methyl-1-oxido-2-[3-(trifluoromethyl)phenoxy]pyridine (953 mg, 2.76 mmol, 78.0% yield, 78.0% purity) as light yellow solid which was used in next step directly without further purification. 41 NMR (400 MHz, CDCl$_3$) δ ppm 2.31-2.37 (m, 3H), 7.04 (d, J=8.22 Hz, 1H), 7.15-7.24 (m, 2H), 7.36-7.41 (m, 3H), 8.36 (d, J=6.26 Hz, 1H); ES-LCMS m/z 270.0 [M+H]$^+$.

Step 3: 6-Chloro-3-methyl-2-[3-(trifluoromethyl) phenoxy]pyridine

A mixture of 3-methyl-1-oxido-2-[3-(trifluoromethyl) phenoxy]pyridin-1-ium (900 mg, 2.61 mmol, 1 eq) and POCl$_3$ (32.68 g, 213.14 mmol, 19.81 mL, 81.74 eq) was stirred at 100° C. for 12 h under N$_2$. The reaction mixture was concentrated to give a residue which was cooled to 0° C., quenched by sat. aq NaHCO$_3$ (50 mL), extracted with EtOAc (50 mL×3). The combined organic layers were washed with brine (20 mL), dried over Na$_2$SO$_4$, filtered and concentrated under reduced pressure to give a residue which was purified by flash silica gel chromatography (from PE/EtOAc=1/0 to 10/1, TLC: PE/EtOAc=10/1, R$_f$=0.70) to yield 6-chloro-3-methyl-2-[3-(trifluoromethyl)phenoxy] pyridine (700 mg, 1.50 mmol, 57.6% yield, 61.8% purity) as a yellow solid. $^1$H NMR (400 MHz, CDCl$_3$) δ ppm 7.51 (s, 2H), 7.46 (s, 1H), 7.42 (s, 1H), 7.33 (s, 1H), 7.01 (d, J=7.4 Hz, 1H), 2.33 (s, 3H); ES-LCMS m/z 287.9, 289.9 [M+H]$^+$.

Step 4: 3-Methyl-2-[3-(trifluoromethyl)phenoxy]-6-vinyl-pyridine

To a solution of 6-chloro-3-methyl-2-[3-(trifluoromethyl) phenoxy]pyridine (700 mg, 1.50 mmol, 1 eq) in 1,4-dioxane (15 mL) were added 4,4,5,5-tetramethyl-2-vinyl-1,3,2-dioxaborolane (347.42 mg, 2.26 mmol, 382.62 μL, 1.5 eq), Cs$_2$CO$_3$ (979.96 mg, 3.01 mmol, 2 eq), Pd(dppf)Cl$_2$ (110.04 mg, 150.38 μmol, 0.1 eq) and H$_2$O (5 mL). The mixture was stirred at 100° C. for 2 h under N$_2$. The mixture was concentrated and H$_2$O (40 mL) was added. The mixture was extracted with EtOAc (50 mL×3). The combined organic layers were washed with brine (50 mL), dried over Na$_2$SO$_4$, filtered and concentrated. The residue was purified by flash silica gel chromatography (From PE/EtOAc=1/0 to 5/1, R$_f$=0.55) to yield 3-methyl-2-[3-(trifluoromethyl)phenoxy]-6-vinyl-pyridine (380 mg, 1.02 mmol, 67.9% yield, 75% purity) as red liquid. $^1$H NMR (400 MHz, CDCl$_3$) δ ppm 7.44-7.36 (m, 5H), 6.93 (d, J=7.0 Hz, 1H), 6.59 (dd, J=10.6, 17.2 Hz, 1H), 5.95 (dd, J=1.6, 17.2 Hz, 1H), 5.29-5.26 (m, 1H), 2.33 (s, 3H); ES-LCMS m/z 280.0 [M+H]$^+$.

Step 5: (5R)-3-Bromo-5-[5-methyl-6-[3-(trifluoromethyl)phenoxy]-2-pyridyl]-4,5-dihydroisoxazole & (5S)-3-Bromo-5-[5-methyl-6-[3-(trifluoromethyl) phenoxy]-2-pyridyl]-4,5-dihydroisoxazole To a solution of 3-methyl-2-[3-(trifluoromethyl)phenoxy]-6-vinyl-pyridine (350.0 mg, 940.0 0 μmol, 1 eq) in EtOAc (10 mL) was added NaHCO$_3$ (789.69 mg, 9.40 mmol, 10.0 eq) and dibromomethanone oxime (381.3 mg, 1.89 mmol, 2.0 eq). The mixture was stirred at 25° C. for 12 h. TLC (PE/EtOAc=5:1, R$_f$=0.47) showed the reaction was completed. The mixture was concentrated and H$_2$O (30 mL) was added. The mixture was extracted with EtOAc (50 mL×3). The combined organic layers were washed with brine (50 mL), dried over Na$_2$SO$_4$, filtered and concentrated. The residue was purified by flash silica gel chromatography (From PE/EtOAc=I/O to 5/1, R$_f$=0.47) to yield the product which was separated by SFC (column: DAICEL CHIRALCEL OJ-H (250 mm*30 mm, 5 um); mobile phase: [0.1% NH$_3$H$_2$O ETOH]; B %: 15%-15%, min) to yield (5R)-3-bromo-5-[5-methyl-6-[3-(trifluoromethyl)phenoxy]-2-pyridyl]-4,5-dihydroisoxazole (42.61 mg, 106.21 μmol, 11.3% yield, 100.0% purity, SFC: R$_t$=2.251 min, ee=99.48%, [α]$^{29.7}_D$=+136 (MeOH, c=0.050 g/100 mL)) as a white solid. $^1$H NMR (400 MHz, CDCl$_3$) δ ppm 7.59 (dd, J=0.8, 7.4 Hz, 1H), 7.53-7.38 (m, 3H), 7.31 (d, J=7.8 Hz, 1H), 7.14 (d, J=7.4 Hz, 1H), 5.51 (dd, J=6.8, 10.4 Hz, 1H), 3.47-3.30 (m, 2H), 2.36 (s, 3H); ES-LCMS m/z 400.9, 402.9 [M+H]$^+$ and (5S)-3-bromo-5-[5-methyl-6-[3-(trifluoromethyl)phenoxy]-2-pyridyl]-4,5-dihydroisoxazole (45.53 mg, 113.5 μmol, 12.1% yield, 100.0% purity, SFC: R$_t$=1.853 min, ee=100%, [α]$^{29.8}_D$=−126 (MeOH, c=0.050 g/100 mL)) as a white solid. $^1$H NMR (400 MHz, CDCl$_3$) δ ppm 7.59 (d, J=7.4 Hz, 1H), 7.54-7.38 (m, 3H), 7.31 (d, J=8.2 Hz, 1H), 7.14 (d, J=7.4 Hz, 1H), 5.51 (dd, J=7.0, 10.6 Hz, 1H), 3.47-3.30 (m, 2H), 2.36 (s, 3H); ES-LCMS m/z 400.9, 402.9 [M+H]$^+$.

I-98 & I-99

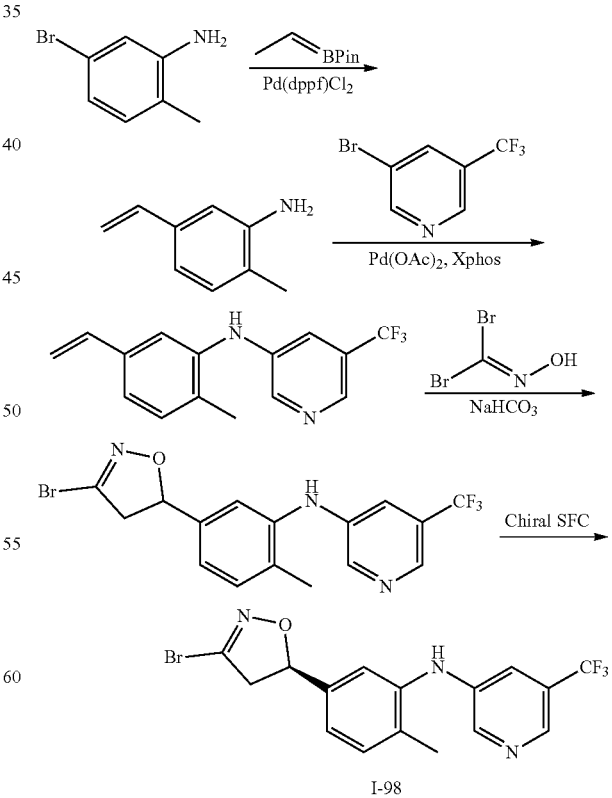

I-98

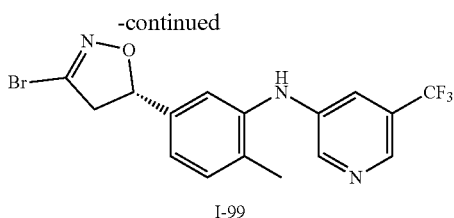

I-99

Step 1: 2-Methyl-5-vinyl-aniline

A mixture of 5-bromo-2-methyl-aniline (1.5 g, 8.06 mmol, 1 eq), 4,4,5,5-tetramethyl-2-vinyl-1,3,2-dioxaborolane (1.49 g, 9.67 mmol, 1.64 mL, 1.2 eq) and $Cs_2CO_3$ (7.88 g, 24.19 mmol, 3 eq) in 1,4-dioxane (15 mL) and $H_2O$ (5 mL) was added $Pd(dppf)Cl_2$ (589.93 mg, 806.24 µmol, 0.1 eq). The mixture was degassed and purged with $N_2$ for three times and stirred at 110° C. for 3 h under $N_2$ atmosphere. The mixture was concentrated and then water (40 mL) was added. The mixture was extracted with EtOAc (50 mL×3). The combined organic layers were washed with NaCl (50 mL), dried over $Na_2SO_4$, filtered and concentrated. The residue was purified by flash silica gel chromatography (From PE/EtOAc=1/0 to 5/1, $R_f$=0.44) to yield 2-methyl-5-vinyl-aniline (604 mg, 4.17 mmol, 51.8% yield, 92% purity) as a red liquid. $^1H$ NMR (400 MHz, $CDCl_3$) δ ppm 7.07-6.98 (m, 1H), 6.81-6.73 (m, 2H), 6.68-6.57 (m, 1H), 5.66 (dd, J=0.8, 17.6 Hz, 1H), 5.16 (dd, J=0.8, 11.0 Hz, 1H), 3.60 (s, 2H), 2.20-2.15 (m, 3H); ES-LCMS m/z 134.0 $[M+H]^+$.

Step 2: N-(2-Methyl-5-vinyl-phenyl)-5-(trifluoromethyl)pyridin-3-amine

A mixture of 2-methyl-5-vinyl-aniline (300.0 mg, 2.07 mmol, 1 eq), 3-bromo-5-(trifluoromethyl)pyridine (468.31 mg, 2.07 mmol, 1 eq), t-BuONa (398.30 mg, 4.14 mmol, 2.0 eq), RuPhos (193.39 mg, 414.45 µmol, 0.2 eq) and $Pd_2(dba)_3$ (189.76 mg, 207.22 µmol, 0.1 eq in toluene (20.0 mL) was stirred at 100° C. for 12 h under $N_2$ atmosphere. The mixture was concentrated and then sat. aq.$NaHCO_3$ (80 mL) was added. The mixture was extracted with EtOAc (50 mL×3). The combined organic layers were washed with brine (50 mL), dried over $Na_2SO_4$, filtered and concentrated. The residue was purified by flash silica gel chromatography (From PE/EtOAc=1/0 to 5/1, $R_f$=0.41) to yield N-(2-methyl-5-vinyl-phenyl)-5-(trifluoromethyl)pyridin-3-amine (420 mg, 1.39 mmol, 67.0% yield, 92% purity) as a red solid. $^1H$ NMR (400 MHz, $CDCl_3$) δ ppm 8.42-8.31 (m, 2H), 7.22 (s, 2H), 7.19-7.15 (m, 1H), 6.65 (dd, J=11.0, 17.6 Hz, 1H), 5.68 (d, J=17.6 Hz, 2H), 5.23 (d, J=11.0 Hz, 1H), 2.27-2.20 (m, 3H); ES-LCMS m/z 279.0 $[M+H]^+$.

Step 3: N-[5-[(5R)-3-Bromo-4,5-dihydroisoxazol-5-yl]-2-methyl-phenyl]-5-(trifluoromethyl)pyridin-3-amine & N-[5-[(5S)-3-Bromo-4,5-dihydroisoxazol-5-yl]-2-methyl-phenyl]-5-(trifluoromethyl)pyridin-3-amine To a solution of N-(2-methyl-5-vinyl-phenyl)-5-(trifluoromethyl)pyridin-3-amine (400.0 mg, 1.32 mmol, 1.0 eq) in EtOAc (10.0 mL) was added $NaHCO_3$ (1.11 g, 13.22 mmol, 10.0 eq) and dibromomethanone oxime (536.47 mg, 2.64 mmol, 2.0 eq) under $N_2$. The mixture was stirred at 25° C. for 12 h. The mixture was concentrated and water (80 mL) was added. The mixture was extracted with EtOAc (50 mL×3). The combined organic layers were washed with brine (50 mL), dried over $Na_2SO_4$, filtered and concentrated. The residue was purified by flash silica gel chromatography (From PE/EtOAc=1/0 to 5/1, $R_f$=0.20) to yield the product which was separated by SFC (column: Phenomenex-Cellulose-2 (250 mm*30 mm, 10 um); mobile phase: [0.1% $NH_3H_2O$ ETOH]; B %: 50%-50%, min) to yield N-[5-[(5R)-3-bromo-4,5-dihydroisoxazol-5-yl]-2-methyl-phenyl]-5-(trifluoromethyl)pyridin-3-amine (17.52 mg, 43.78 µmol, 3.3% yield, 100% purity, SFC: $R_t$=1.155 min, ee=99.66%, $[α]^{29.8}_D$=+153.333 (MeOH, c=0.030 g/100 mL)) as a yellow oil. $^1H$ NMR (400 MHz, $CDCl_3$) δ ppm 8.38 (d, J=8.2 Hz, 2H), 7.30 (d, J=7.8 Hz, 1H), 7.19 (s, 1H), 7.10-7.04 (m, 1H), 5.68-5.57 (m, 2H), 3.61 (dd, J=10.8, 17.4 Hz, 1H), 3.18 (dd, J=9.0, 17.2 Hz, 1H), 2.26 (s, 3H); ES-LCMS m/z 399.9, 401.9 $[M+H]^+$ and N-[5-[(5S)-3-bromo-4,5-dihydroisoxazol-5-yl]-2-methyl-phenyl]-5-(trifluoromethyl)pyridin-3-amine (35.84 mg, 89.11 µmol, 6.7% yield, 99.5% purity, SFC: $R_t$=0.666 min, ee=100%, $[α]^{29.7}_D$=−140 (MeOH, c=0.020 g/100 mL)) as a yellow oil. $^1H$ NMR (400 MHz, $CDCl_3$) δ ppm 8.38 (d, J=9.0 Hz, 1H), 8.42-8.33 (m, 1H), 7.30 (d, J=7.8 Hz, 1H), 7.19 (s, 1H), 7.08 (d, J=7.4 Hz, 1H), 5.68-5.56 (m, 2H), 3.61 (dd, J=11.0, 17.2 Hz, 1H), 3.18 (dd, J=8.8, 17.4 Hz, 1H), 2.26 (s, 3H); ES-LCMS m/z 399.9, 401.9 $[M+H]^+$.

I-42

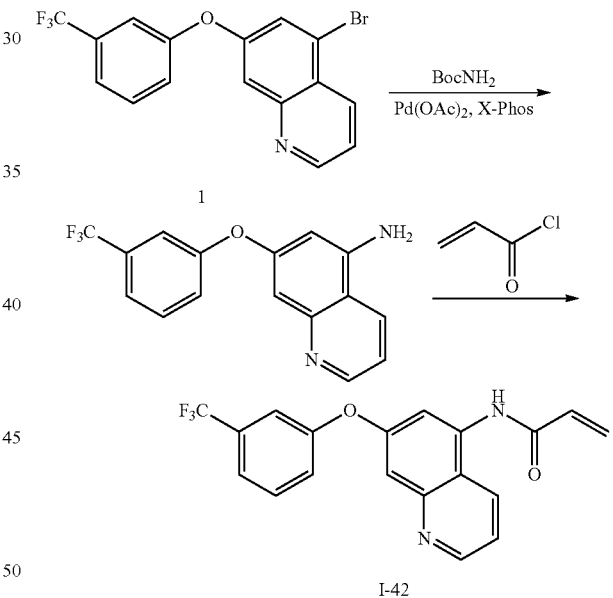

I-42

Step 1: 7-[3-(Trifluoromethyl)phenoxy]quinolin-5-amine

To a mixture of 5-bromo-7-[3-(trifluoromethyl)phenoxy]quinoline (500 mg, 1.22 mmol, 1 eq) and tert-butyl carbamate (715.96 mg, 6.11 mmol, 5 eq) in 1,4-dioxane (2 mL) was added $Cs_2CO_3$ (1.19 g, 3.67 mmol, 3 eq) $Pd(OAc)_2$ (27.44 mg, 122.23 µmol, 0.1 eq) and XPhos (58.27 mg, 122.23 µmol, 0.1 eq) under $N_2$ atmosphere. The mixture was stirred under $N_2$ atmosphere at 120° C. for 12 h. The mixture was filtered and the filtrate was diluted with $H_2O$ (50 mL) and extracted with EtOAc (40 mL×3). The combine organic layers were dried over anhydrous $Na_2SO_4$, filtered and concentrated to yield a residue which was purified by flash silica gel chromatography (from pure PE to PE/EtOAc=9/1, TLC: PE/EtOAc=1/1, R$_f$=0.6) to yield 7-[3-(trifluoromethyl)phenoxy]quinolin-5-amine (200 mg, 525.86 μmol, 43.0% yield, 80.0% purity) as yellow oil. $^1$H NMR (500 MHz, DMSO-d$_6$) δ ppm 8.73 (dd, J=1.5, 4.1 Hz, 1H), 8.49 (d, J=8.4 Hz, 1H), 7.68-7.64 (m, 1H), 7.57-7.54 (m, 1H), 7.47-7.39 (m, 2H), 7.30 (dd, J=4.3, 8.4 Hz, 1H), 6.62 (d, J=2.0 Hz, 1H), 6.44 (d, J=2.4 Hz, 1H), 6.29 (s, 2H); ES-LCMS m/z 305.1 [M+H]$^+$.

Step 2: N-[7-[3-(Trifluoromethyl)phenoxy]-5-quinolyl]prop-2-enamide

To a solution of 7-[3-(trifluoromethyl)phenoxy]quinolin-5-amine (200 mg, 525.86 μmol, 1 eq) in DCM (5 mL) was added DIEA (135.93 mg, 1.05 mmol, 183.19 μL, 2 eq) and prop-2-enoyl chloride (71.39 mg, 788.78 μmol, 64.32 μL, 1.5 eq). The mixture was stirred at 25° C. for 12 h. The mixture was diluted with H$_2$O (20 mL) and extracted with EtOAc (20 mL×3). The combine organic layers were dried over anhydrous Na$_2$SO$_4$, filtered and concentrated to yield a residue which was purified by preparative HPLC (column: YMC-Actus Triart C18 150*30 mm*5 μm; mobile phase: [water (0.05% ammonia hydroxide v/v)-ACN]; B %: 49%-69%, 10 min) and lyophilized to yield N-[7-[3-(trifluoromethyl)phenoxy]-5-quinolyl]prop-2-enamide (47.42 mg, 132.34 μmol, 25.2% yield, 100.0% purity) as a yellow solid. $^1$H NMR (500 MHz, CD$_3$OD) δ ppm 8.82 (dd, J=2.0, 4.5 Hz, 1H), 8.51 (d, J=8.0 Hz, 1H), 7.83 (d, J=2.0 Hz, 1H), 7.69-7.63 (m, 1H), 7.56 (d, J=8.0 Hz, 1H), 7.52 (dd, J=4.5, 9.0 Hz, 1H), 7.48 (s, 1H), 7.45 (d, J=8.5 Hz, 1H), 7.29 (d, J=2.0 Hz, 1H), 6.65 (dd, J=10.5, 16.9 Hz, 1H), 6.46 (dd, J=1.5, 16.9 Hz, 1H), 5.89 (dd, J=1.5, 10.5 Hz, 1H); ES-LCMS m/z 359.0 [M+H]$^+$.

I-100 & I-101

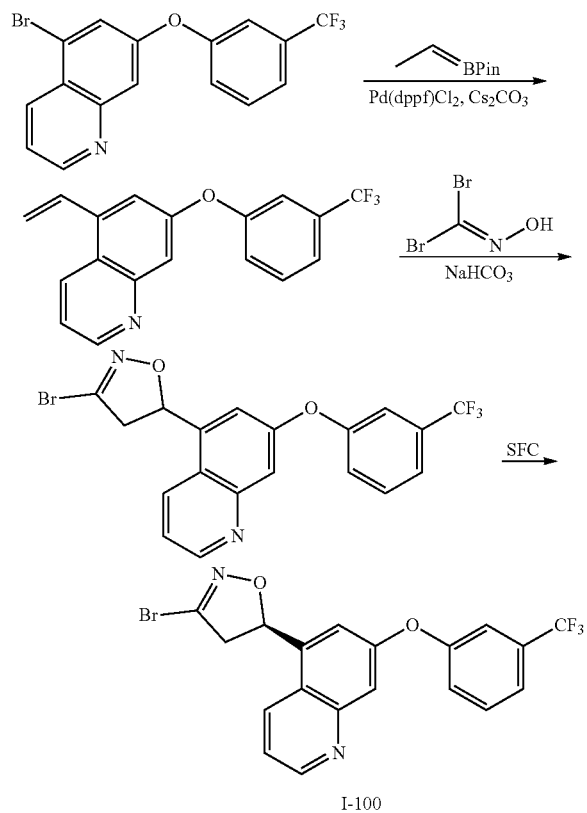

I-100

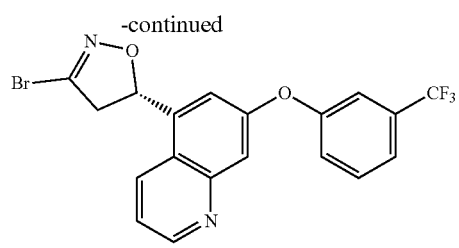

I-101

Step 1: 7-[3-(Trifluoromethyl)phenoxy]-5-vinylquinoline

To a mixture of 5-bromo-7-[3-(trifluoromethyl)phenoxy]quinoline (320 mg, 782.29 μmol, 1 eq) and 4,4,5,5-tetramethyl-2-vinyl-1,3,2-dioxaborolane (722.91 mg, 4.69 mmol, 796.15 μL, 6 eq) in 1,4-dioxane (8 mL) was added Cs$_2$CO$_3$ (2 M, 1.17 mL, 3 eq) and Pd(dppf)Cl$_2$ (57.24 mg, 78.23 μmol, 0.1 eq) under N$_2$ atmosphere. The mixture was stirred at 80° C. in microwave (0 bar) for 1 h under N$_2$ atmosphere. TLC (PE/EtOAc=4/1, R$_f$=0.40) showed starting material was consumed and one major new spot was detected. The mixture was diluted with H$_2$O (5 mL) and extracted with EtOAc (10 mL×3). The combine organic layers were dried over anhydrous Na$_2$SO$_4$, filtered and concentrated to yield a residue which was purified by preparative TLC (PE/EtOAc=4/1, TLC: PE/EtOAc=4/1, R$_f$=0.40) to yield 7-[3-(trifluoromethyl)phenoxy]-5-vinyl-quinoline (150 mg, 428.18 μmol, 54.7% yield, 90.0% purity) as yellow oil. $^1$H NMR (500 MHz, DMSO-d$_6$) δ ppm 8.89 (dd, J=1.5, 4.0 Hz, 1H), 8.66 (d, J=8.5 Hz, 1H), 7.74-7.66 (m, 2H), 7.64-7.47 (m, 5H), 7.36 (d, J=2.5 Hz, 1H), 6.01 (d, J=17.5 Hz, 1H), 5.61 (d, J=11.0 Hz, 1H); ES-LCMS m/z 316.0 [M+H]$^+$ Step 2: (5R)-3-Bromo-5-[7-[3-(trifluoromethyl)phenoxy]-5-quinolyl]-4,5-dihydroisoxazole and (5S)-3-bromo-5-[7-[3-(trifluoromethyl)phenoxy]-5-quinolyl]-4,5-dihydroisoxazole To a solution of 7-[3-(trifluoromethyl)phenoxy]-5-vinyl-quinoline (150 mg, 428.18 μmol, 1 eq) in EtOAc (10 mL) was added NaHCO$_3$ (359.71 mg, 4.28 mmol, 10 eq) and dibromomethanone oxime (173.70 mg, 856.36 μmol, 2 eq). The mixture was stirred at 30° C. for 12 h. TLC (PE/EtOAc=2/1, R$_f$=0.40) showed starting material was consumed completely and one major new spot was detected. The mixture was filtered and the filtrate was concentrated to yield a residue which was purified by preparative TLC (PE/EtOAc=2/1, TLC: PE/EtOAc=2/1, R$_f$=0.40) and then by preparative SFC (column: DAICEL CHIRALPAK IC (250 mm*30 mm, 10 μm); mobile phase: [0.1% NH$_3$H$_2$O EtOH]; B %: 40%-40%) to yield Peak 1 and Peak 2. Peak 1 was concentrated under reduced pressure to yield a residue which was dissolved in MeCN (20 mL) and H$_2$O (40 mL) and lyophilized to yield (5R)-3-bromo-5-[7-[3-(trifluoromethyl)phenoxy]-5-quinolyl]-4,5-dihydroisoxazole (30.42 mg, 69.58 μmol, 16.3% yield, 100.0% purity, R$_f$=1.617, ee=100%, [α]$^{30.4}_D$=+24.488 (MeOH, c=0.109 g/100 mL)) as a white solid. $^1$H NMR (500 MHz, CDCl$_3$) δ ppm 8.96-8.87 (m, 1H), 8.13 (d, J=8.5 Hz, 1H), 7.58-7.52 (m, 2H), 7.51-7.46 (m, 1H), 7.46-7.37 (m, 3H), 7.32 (d, J=8.0 Hz, 1H), 6.30 (dd, J=9.0, 11.1 Hz, 1H), 3.87 (dd, J=11.0, 17.0 Hz, 1H), 3.28 (dd, J=8.5, 17.0 Hz, 1H); ES-LCMS m/z 436.9, 438.9. [M+H]$^+$. Peak 2 was concentrated under reduced pressure to yield a residue which was dissolved in MeCN (20 mL) and H$_2$O (40 mL) and lyophilized to yield (5S)-3-bromo-5-[7-[3-(trifluoromethyl)phenoxy]-5-quinolyl]-4,5-dihydroisoxazole (29.00 mg, 66.33 μmol, 15.49% yield, 100% purity, R$_f$=2.635, ee=99.86%, [α]$^{30.4}_D$=−9.992 (MeOH, c=0.088 g/100 mL)) as a white solid. $^1$H NMR (500 MHz, CDCl$_3$) δ ppm 8.91 (dd, J=1.5, 4.2 Hz, 1H), 8.13 (d, J=8.5 Hz, 1H), 7.59-7.51 (m, 2H), 7.50-7.47 (m, 1H), 7.44 (d, J=2.5 Hz, 1H), 7.43-7.38 (m, 2H), 7.32 (d, J=8.0 Hz, 1H), 6.30 (dd, J=9.0, 11.0 Hz, 1H), 3.87 (dd, J=11.0, 17.0 Hz, 1H), 3.28 (dd, J=8.5, 17.0 Hz, 1H); ES-LCMS m/z 436.9, 438.9, [M+H]$^+$.

I-102 & I-104

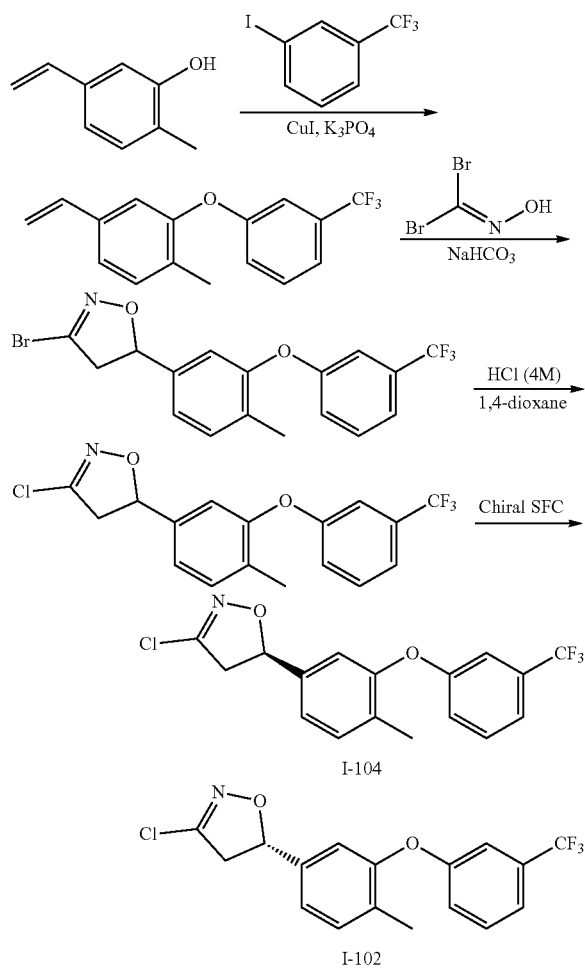

Step 1: 1-Methyl-2-(3-(trifluoromethyl)phenoxy)-4-vinylbenzene

To a solution of 2-methyl-5-vinyl-phenol (981.31 mg, 6.87 mmol, 1.1 eq) in DMSO (30 mL) was added 1-iodo-3-(trifluoromethyl)benzene (1.7 g, 6.25 mmol, 899.47 μL, 1 eq), CuI (59.51 mg, 312.49 μmol, 0.05 eq), K$_3$PO$_4$ (2.65 g, 12.50 mmol, 2.0 eq) and 2-picolinic acid (76.94 mg, 624.99 μmol, 0.1 eq). The mixture was stirred under N$_2$ atmosphere at 120° C. for 16 h. TLC (PE/EtOAc=100/1, R$_f$=0.6) showed the reaction was completed. The mixture was diluted with water (30 mL) and extracted with EtOAc (30 mL×3). The combine organic layers were dried over anhydrous Na$_2$SO$_4$, filtered and concentrated to yield a residue which was purified by flash silica gel chromatography (from pure PE to PE/EtOAc=100/1, TLC: PE/EtOAc=100/1, R$_f$=0.6) to yield 1-methyl-2-[3-(trifluoromethyl)phenoxy]-4-vinyl-benzene (1.3 g, 3.74 mmol, 59.8% yield, 80.0% purity) as yellow oil. $^1$H NMR (400 MHz, CD$_3$OD) δ ppm 7.52-7.50 (m, 1H), 7.30-7.26 (m, 3H), 7.14-7.10 (m, 3H), 6.68 (d, J=10.8, 17.6 Hz, 1H), 5.70 (d, J=17.4 Hz, 1H), 5.20 (d, J=11.0 Hz, 1H), 2.17 (s, 3H).

Step 2: 3-Bromo-5-(4-methyl-3-(3-(trifluoromethyl)phenoxy)phenyl)-4,5-dihydroisoxazole To a solution of dibromomethanone oxime (1.02 g, 5.05 mmol, 1.2 eq) in EtOAc (20 mL) was added NaHCO$_3$ (3.53 g, 42.05 mmol, 10 eq) and 1-methyl-2-[3-(trifluoromethyl)phenoxy]-4-vinyl-benzene (1.3 g, 4.20 mmol, 1 eq). The mixture was stirred at 30° C. for 16 h. After filtration, the filtrate was concentrated to yield a residue which was purified by flash silica gel chromatography (from PE/EtOAc=100/1 to 5/1, TLC: PE/EtOAc=5/1, R$_f$=0.56) to yield 3-bromo-5-[4-methyl-3-[3-(trifluoromethyl)phenoxy]phenyl]-4,5-dihydroisoxazole (270 mg, 665.24 μmol, 15.8% yield, 98.6% purity) as yellow oil. $^1$H NMR (400 MHz, CDCl$_3$) δ ppm 7.45-7.38 (m, 1H), 7.31 (d, J=7.8 Hz, 2H), 7.15-7.10 (m, 2H), 7.02 (dd, J=2.3, 8.2 Hz, 1H), 6.92 (d, J=1.6 Hz, 1H), 5.61 (dd, J=9.4, 10.6 Hz, 1H), 3.59 (dd, J=11.0, 17.2 Hz, 1H), 3.17 (dd, J=9.0, 17.2 Hz, 1H), 2.22 (s, 3H); ES-LCMS m/z 399.9, 401.9 [M+H]$^+$.

Step 3: (S)-3-Chloro-5-(4-methyl-3-(3-(trifluoromethyl)phenoxy)phenyl)-4,5-dihydroisoxazole and (R)-3-chloro-5-(4-methyl-3-(3-(trifluoromethyl)phenoxy)phenyl)-4,5-dihydroisoxazole To a solution of 3-bromo-5-[4-methyl-3-[3-(trifluoromethyl)phenoxy]phenyl]-4,5-dihydroisoxazole (150 mg, 369.58 μmol, 1 eq) in 1,4-dioxane (2 mL) was added hydrogen chloride (1.02 g, 27.98 mmol, 1 mL, 75.70 eq) (4 M in water). The mixture was stirred at 40° C. for 16 h. The reaction mixture was diluted with water (10 mL) and extracted with EtOAc (10 mL×3). The combined organic layers were washed with brine (20 mL), dried over Na$_2$SO$_4$, filtered and concentrated under reduced pressure to yield a residue which was separated by chiral SFC (column: REGIS (s,s) WHELK-O1 (250 mm*30 mm, 5 um); mobile phase: [0.1% NH$_3$H$_2$O EtOH]; B %: 20%-20%) to yield peak 1 and peak 2. Peak 1 was concentrated under reduced pressure to yield a residue which was dissolved in MeCN (100 mL) and H$_2$O (100 mL) and lyophilized to yield (5S)-3-chloro-5-[4-methyl-3-(trifluoromethyl)phenoxy]phenyl]-4,5-dihydroisoxazole (14.22 mg, 38.43 μmol, 10.4% yield, 96.1% purity, SFC: R$_f$=1.71, ee=100%, [α]$^{24.2}_D$=−70 (MeOH, c=0.020 g/100 mL)) as yellow oil. $^1$H NMR (400 MHz, CD$_3$OD) δ ppm 7.55-7.49 (m, 1H), 7.41-7.33 (m, 2H), 7.19 (dd, J=1.5, 7.8 Hz, 1H), 7.15-7.07 (m, 2H), 6.99 (d, J=1.2 Hz, 1H), 5.77-5.70 (m, 1H), 3.65 (dd, J=10.8, 17.4 Hz, 1H), 3.18 (dd, J=9.3, 17.4 Hz, 1H), 2.20 (s, 3H); ES-LCMS m/z 356.0, 358.0 [M+H]$^+$. Peak 2 was concentrated under reduced pressure to yield a residue which was dissolved in MeCN (10 mL) and H$_2$O (10 mL) and lyophilized to yield (5R)-3-chloro-5-[4-methyl-3-[3-(trifluoromethyl)phenoxy]phenyl]-4,5-dihydroisoxazole (21.42 mg, 60.21 μmol, 16.3% yield, 100.0% purity, SFC: R$_f$=2.876, ee=100.0%, [α]$^{24.2}_D$=+10 (MeOH, c=0.020 g/100 mL)) as yellow oil. $^1$H NMR (400 MHz, CD$_3$OD) δ ppm 7.52 (t, J=8.4 Hz, 1H), 7.41-7.34 (m, 2H), 7.19 (d, J=6.3 Hz, 1H), 7.15-7.08 (m, 2H), 6.99 (s, 1H), 5.74 (t, J=10.2 Hz, 1H), 3.65 (dd, J=10.8, 17.4 Hz, 1H), 3.24-3.13 (m, 1H), 2.20 (s, 3H); ES-LCMS m/z 355.9, 357.9 [M+H]$^+$.

I-105 & I-106

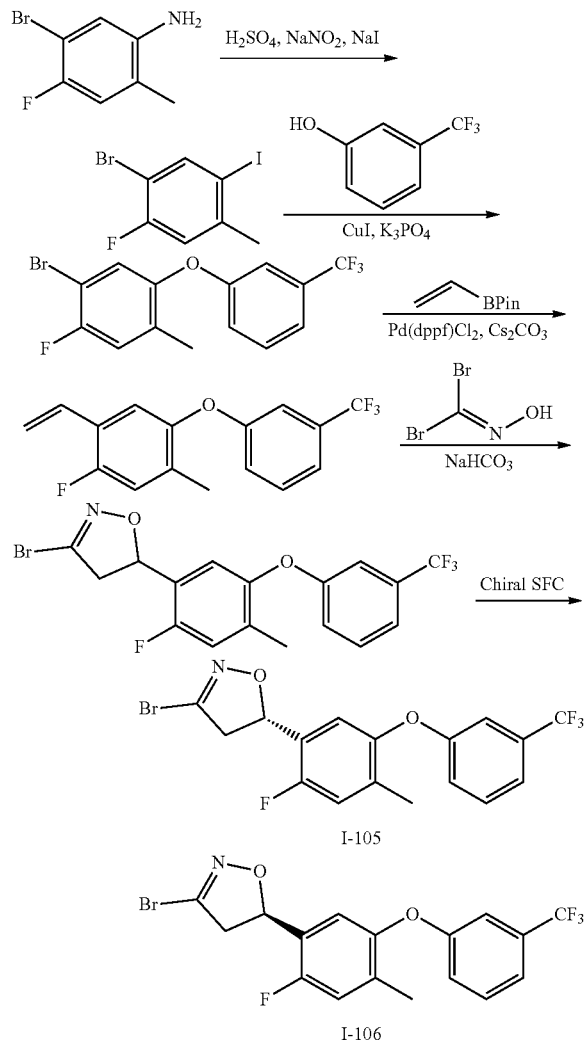

Step 1: 1-Bromo-2-fluoro-5-iodo-4-methyl-benzene

To a solution of 5-bromo-4-fluoro-2-methyl-aniline (3 g, 14.70 mmol, 1 eq) in MeCN (30 mL) cooled to 0° C. was added H$_2$SO$_4$ (3.56 g, 36.32 mmol, 1.94 mL, 2.47 eq) dissolved in H$_2$O (5 mL). After stirring for 5 min, a solution of NaNO$_2$ (2.03 g, 29.41 mmol, 2 eq) in H$_2$O (5 mL) was added dropwise and the reaction mixture was stirred for an additional 15 min at 0° C. Then a solution of NaI (8.82 g, 58.81 mmol, 4 eq) in H$_2$O (5 mL) was added. The reaction was stirred for an additional 20 min at 25° C. To the mixture was added water (100 mL) and extracted with ethyl acetate (100 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=200/1 to 100/1, TLC: PE/EtOAc=100/1, R$_f$=0.52) to yield 1-bromo-2-fluoro-5-iodo-4-methyl-benzene (4.6 g, 13.15 mmol, 89.4% yield, 90% purity) was obtained as red liquid. $^1$H NMR (400 MHz, DMSO-d$_6$) δ ppm 8.10 (d, J=7.4 Hz, 1H), 7.42 (d, J=10.6 Hz, 1H), 2.33 (s, 3H).

Step 2: 1-Bromo-2-fluoro-4-methyl-5-[3-(trifluoromethyl)phenoxy]benzene

To a solution of 1-bromo-2-fluoro-5-iodo-4-methyl-benzene (1.5 g, 4.29 mmol, 1 eq) and 3-(trifluoromethyl)phenol (590.69 mg, 3.64 mmol, 437.55 µL, 0.85 eq) in DMSO (15 mL) was added CuI (40.82 mg, 214.34 µmol, 0.05 eq), pyridine-2-carboxylic acid (42.22 mg, 342.94 µmol, 0.08 eq) and K$_3$PO$_4$ (1.52 g, 7.16 mmol, 1.67 eq). The mixture was stirred at 120° C. for 12 h. To the mixture was added water (50 mL) and extracted with ethyl acetate (50 mL×3). The combined organic phase was washed with brine (20 mL), dried with anhydrous Na$_2$SO$_4$, filtered and concentrated in vacuum to yield a residue which was purified by flash silica gel chromatography (from PE/EtOAc=200/1 to 10/1, TLC: PE/EtOAc=10/1, R$_f$=0.40) to yield 1-bromo-2-fluoro-4-methyl-5-[3-(trifluoromethyl)phenoxy]benzene (1 g, 2.01 mmol, 46.8% yield, 70% purity) as red oil. $^1$H NMR (400 MHz, CD$_3$OD) δ ppm 7.54-7.51 (m, 1H), 7.39 (d, J=4.6 Hz, 1H), 7.21 (d, J=5.4 Hz, 1H), 7.18-7.14 (m, 2H), 7.10 (d, J=6.1 Hz, 1H), 2.19-2.14 (m, 3H).

Step 3: 1-Fluoro-5-methyl-4-[3-(trifluoromethyl)phenoxy]-2-vinyl-benzene

To a solution of 1-bromo-2-fluoro-4-methyl-5-[3-(trifluoromethyl)phenoxy]benzene (1 g, 2.01 mmol, 1 eq) and 4,4,5,5-tetramethyl-2-vinyl-1,3,2-dioxaborolane (463.21 mg, 3.01 mmol, 510.14 µL, 1.5 eq) in 1,4-dioxane (10 mL) and H$_2$O (2 mL) was added Pd(dppf)Cl$_2$ (146.71 mg, 200.51 µmol, 0.1 eq) and Cs$_2$CO$_3$ (1.96 g, 6.02 mmol, 3 eq). The mixture was stirred at 100° C. for 2 h under N$_2$ atmosphere. To the mixture was added water (30 mL) and extracted with ethyl acetate (30 mL×3). The combined organic phase was washed with brine (20 mL), dried with anhydrous Na$_2$SO$_4$, filtered and concentrated in vacuum to yield a residue which was purified by flash silica gel chromatography (from PE/EtOAc=200/1 to 10/1, TLC: PE/EtOAc=10/1, R$_f$=0.39) to yield 1-fluoro-5-methyl-4-[3-(trifluoromethyl)phenoxy]-2-vinyl-benzene (350 mg, 945.12 µmol, 47.1% yield, 80% purity) colorless oil. $^1$H NMR (500 MHz, CD$_3$OD) δ ppm 7.50 (t, J=7.9 Hz, 1H), 7.34 (d, J=8.1 Hz, 1H), 7.18 (d, J=6.6 Hz, 1H), 7.11 (s, 1H), 7.08 (dd, J=4.8, 9.2 Hz, 2H), 6.84-6.78 (m, 1H), 5.76 (d, J=17.9 Hz, 1H), 5.36-5.32 (m, 1H), 2.15 (s, 3H).

Step 4: (5S)-3-Bromo-5-[2-fluoro-4-methyl-5-[3-(trifluoromethyl)phenoxy]phenyl]-4,5-dihydroisoxazole (5R)-3-Bromo-5-[2-fluoro-4-methyl-5-[3-(trifluoromethyl)phenoxy]phenyl]-4,5-dihydroisoxazole To a solution of 1-fluoro-5-methyl-4-[3-(trifluoromethyl)phenoxy]-2-vinyl-benzene (350 mg, 945.12 µmol, 1 eq) in EtOAc (10 mL) was added NaHCO$_3$ (793.99 mg, 9.45 mmol, 367.59 µL, 10 eq) and dibromomethanone oxime (287.55 mg, 1.42 mmol, 1.5 eq). The mixture was stirred at 25° C. for 12 h. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=200/1 to 3/1, TLC: PE/EtOAc=3/1, R$_f$=0.38) to yield a product. The product was separated by SFC (column: REGIS (s,s) WHELK-01 (250 mm*30 mm, 5 μm); mobile phase: [0.1% NH₃H₂O IPA]; B %: 20%-20%, min) to yield peak 1 ($R_t$=1.679 min, ee=100%) and peak 2 ($R_t$=2.064 min, ee=100%). Peak 1 was concentrated under reduced pressure to yield a residue which was dissolved in MeCN (20 mL) and H₂O (40 mL) and lyophilized to yield (5S)-3-bromo-5-[2-fluoro-4-methyl-5-[3-(trifluoromethyl)phenoxy]phenyl]-4,5-dihydroisoxazole (77.64 mg, 185.66 μmol, 19.6% yield, 100% purity, SFC: $R_t$=1.679, ee=100%, $[\alpha]^{28.3}_D$=−198.068 (MeOH, c=0.0414 g/100 mL)) as colorless oil. ¹H NMR (500 MHz, CD₃OD) δ ppm 7.54-7.48 (m, 1H), 7.36 (d, J=7.8 Hz, 1H), 7.17 (d, J=10.8 Hz, 1H), 7.12 (s, 1H), 7.08 (dd, J=2.2, 8.3 Hz, 1H), 7.02 (d, J=6.6 Hz, 1H), 5.82 (dd, J=8.5, 11.1 Hz, 1H), 3.75 (dd, J=11.2, 17.5 Hz, 1H), 3.30-3.22 (m, 1H), 2.19 (s, 3H); ES-LCMS m/z 418.1, 420.1 [M+H]⁺. Peak 2 was concentrated under reduced pressure to yield a residue which was dissolved in MeCN (20 mL) and H₂O (40 mL) and lyophilized to yield (5R)-3-bromo-5-[2-fluoro-4-methyl-5-[3-(trifluoromethyl)phenoxy]phenyl]-4,5-dihydroisoxazole (74.74 mg, 176.76 μmol, 18.7% yield, 98.9% purity, SFC: $R_t$=2.064, ee=100%, $[\alpha]^{28.3}_D$=+185.941 (MeOH, c=0.0441 g/100 mL)) as colorless oil. ¹H NMR (500 MHz, CD₃OD) δ ppm 7.51 (t, J=8.0 Hz, 1H), 7.36 (d, J=7.8 Hz, 1H), 7.17 (d, J=10.8 Hz, 1H), 7.13 (s, 1H), 7.08 (dd, J=2.2, 8.3 Hz, 1H), 7.02 (d, J=6.4 Hz, 1H), 5.82 (dd, J=8.4, 11.1 Hz, 1H), 3.75 (dd, J=11.1, 17.4 Hz, 1H), 3.29-3.23 (m, 1H), 2.19 (s, 3H); ES-LCMS m/z 418.1, 420.1 [M+H]⁺.

I-107 & I-108

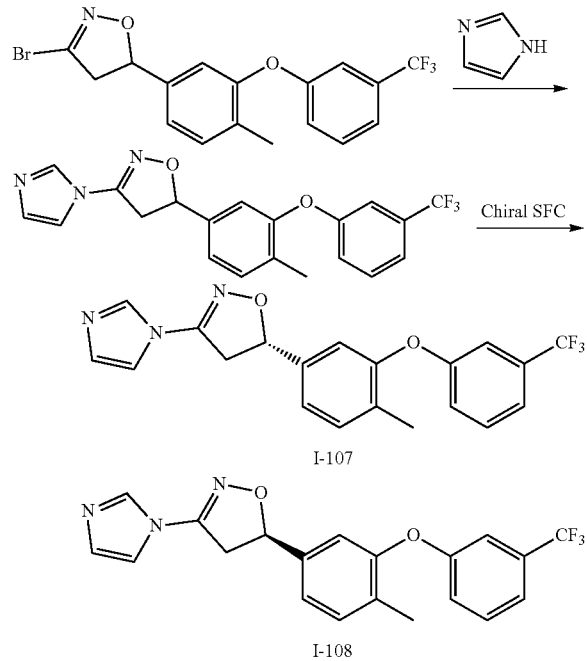

I-107

I-108

Step 1: 3-Imidazol-1-yl-5-[4-methyl-3-[3-(trifluoromethyl)phenoxy]phenyl]-4,5-dihydroisoxazole A mixture of 3-bromo-5-[4-methyl-3-[3-(trifluoromethyl)phenoxy]phenyl]-4,5-dihydroisoxazole (300 mg, 584.72 μmol, 1 eq), imidazole (199.03 mg, 2.92 mmol, 26.48 μL, 5 eq) and Cs₂CO₃ (571.54 mg, 1.75 mmol, 3 eq) in MeCN (12 mL) was stirred at 80° C. for 3 h. TLC (PE/EtOAc=1/1, $R_f$=0.28) indicated the starting material was consumed, and one major new spot was detected. The reaction mixture was quenched by addition of water (50 mL), then extracted with EtOAc (50 mL×3). The organic layer was washed with brine (20 mL), dried over Na₂SO₄, filtered, then concentrated. The residue was purified by flash silica gel chromatography (from PE/EtOAc=1/0 to 1/1, TLC: PE/EtOAc=1/1, $R_f$=0.28) to yield a 3-imidazol-1-yl-5-[4-methyl-3-[3-(trifluoromethyl)phenoxy]phenyl]-4,5-dihydroisoxazole (150 mg, 386.47 μmol, 66.0% yield, 99.8% purity) as yellow oil. ¹H NMR (400 MHz, CDCl₃) δ ppm 7.82 (s, 1H), 7.42-7.40 (m, 2H), 7.35-7.33 (m, 2H), 7.32-7.31 (m, 3H), 7.19-7.14 (m, 1H), 6.99 (d, J=1.2 Hz, 1H), 5.82-5.77 (m, 1H), 3.85-3.79 (m, 1H), 3.43-3.37 (m, 1H), 2.23 (s, 3H); ES-LCMS m/z 388.2 [M+H]⁺.

Step 2: (5S)-3-Imidazol-1-yl-5-[4-methyl-3-[3-(trifluoromethyl)phenoxy]phenyl]-4,5-dihydroisoxazole & (5R)-3-Imidazol-1-yl-5-[4-methyl-3-[3-(trifluoromethyl)phenoxy]phenyl]-4,5-dihydroisoxazole 3-Imidazol-1-yl-5-[4-methyl-3-[3-(trifluoromethyl)phenoxy]phenyl]-4,5-dihydroisoxazole (150 mg, 386.47 μmol, 1 eq) was separated by SFC (column: DAICEL CHIRALCEL OD-H (250 mm*30 mm, 5 μm); mobile phase: [0.1% NH₃H₂O ETOH]; B %: 25%-25%, min) to yield peak 1 (3.357) and peak 2 (3.507). Peak 2 was further separated by SFC (column: DAICEL CHIRALCEL OD-H (250 mm*30 mm, 5 μm); mobile phase: [0.1% NH₃H₂O ETOH]; B %: 30%-30%, min) to yield peak 2 (3.507). Peak 1 was concentrated under reduced pressure to yield a residue which was dissolved in MeCN (20 mL) and H₂O (10 mL) and lyophilized to yield (5S)-3-imidazol-1-yl-5-[4-methyl-3-[3-(trifluoromethyl)phenoxy]phenyl]-4,5-dihydroisoxazole (22.94 mg, 59.22 μmol, 15.3% yield, 100% purity) (SFC: $R_t$=3.348, ee=99.78%, $[\alpha]^{27.3}_D$=−254.901 (MeOH, c=0.051 g/100 mL)) as a white solid. ¹H NMR (500 MHz, CD₃OD) δ ppm 8.10 (s, 1H), 7.59 (s, 1H), 7.50 (t, J=8.0 Hz, 1H), 7.39 (d, J=7.8 Hz, 1H), 7.35 (d, J=7.8 Hz, 1H), 7.27 (dd, J=1.4, 7.9 Hz, 1H), 7.15-7.05 (m, 4H), 5.83 (t, J=10.0 Hz, 1H), 3.97 (dd, J=10.7, 16.8 Hz, 1H), 3.55 (dd, J=9.2, 16.9 Hz, 1H), 2.21 (s, 3H); ES-LCMS m/z 281.1 [M+H]⁺. Peak 2 was concentrated under reduced pressure to yield a residue which was dissolved in MeCN (20 mL) and H₂O (10 mL) and lyophilized to yield (5R)-3-imidazol-1-yl-5-[4-methyl-3-[3-(trifluoromethyl)phenoxy]phenyl]-4,5-dihydroisoxazole (24.17 mg, 61.40 μmol, 15.8% yield, 98.4% purity) (SFC: $R_t$=3.507, ee=94.76%, $[\alpha]^{27.1}_D$=+164.417 (MeOH, c=0.1002 g/100 mL)) as a white solid. ¹H NMR (500 MHz, CDCl₃) δ ppm 8.10 (s, 1H), 7.59 (t, J=1.4 Hz, 1H), 7.54-7.47 (m, 1H), 7.39 (d, J=7.9 Hz, 1H), 7.35 (d, J=7.8 Hz, 1H), 7.27 (dd, J=1.7, 7.8 Hz, 1H), 7.16-7.06 (m, 4H), 5.83 (t, J=9.9 Hz, 1H), 3.97 (dd, J=10.7, 16.9 Hz, 1H), 3.55 (dd, J=9.3, 16.9 Hz, 1H), 2.21 (s, 3H); ES-LCMS m/z 281.1 [M+H]⁺.

I-109 & I-110

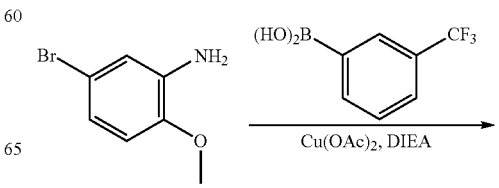

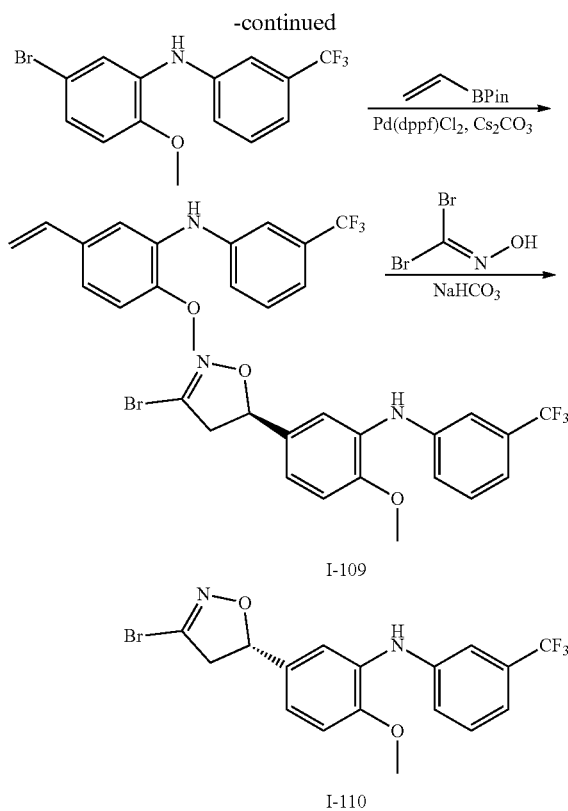

Step 1: 5-Bromo-2-methoxy-N-[3-(trifluoromethyl) phenyl]aniline

A mixture of 5-bromo-2-methoxy-aniline (500 mg, 2.47 mmol, 1 eq), [3-(trifluoromethyl)phenyl]boronic acid (470.00 mg, 2.47 mmol, 1 eq), DIEA (639.65 mg, 4.95 mmol, 862.06 μL, 2 eq) and Cu(OAc)$_2$ (539.38 mg, 2.97 mmol, 1.2 eq) in DCM (10 mL) was stirred at 25° C. for 12 h under N$_2$. The reaction mixture was quenched by addition of water (100 mL), then extracted with DCM (100 mL×3). The organic layer was washed with brine (20 mL), dried over Na$_2$SO$_4$, filtered, concentrated to yield a residue which was purified by flash silica gel chromatography (from PE/EtOAc=1/0 to 10/1, TLC: PE/EtOAc=10/1, R$_f$=0.26) to yield 5-bromo-2-methoxy-N-[3-(trifluoromethyl)phenyl] aniline (650 mg, 1.82 mmol, 73.6% yield, 97.0% purity) as yellow oil. $^1$H NMR (400 MHz, CDCl$_3$) δ ppm 7.43-7.41 (m, 1H), 7.36-7.32 (m, 3H), 7.25-7.21 (m, 1H), 7.00 (dd, J=2.0, 8.4 Hz, 1H), 6.76 (d, J=8.8 Hz, 1H), 6.25 (s, 1H), 3.88 (s, 3H); ES-LCMS m/z 345.9, 347.9 [M+H]$^+$.

Step 2: 2-Methoxy-N-[3-(trifluoromethyl)phenyl]-5-vinyl-aniline

A mixture of 5-bromo-2-methoxy-N-[3-(trifluoromethyl) phenyl]aniline (600 mg, 1.68 mmol, 1 eq), 4,4,5,5-tetramethyl-2-vinyl-1,3,2-dioxaborolane (388.12 mg, 2.52 mmol, 427.44 μL, 1.5 eq), and Cs$_2$CO$_3$ (1.10 g, 3.36 mmol, 2 eq) in 1,4-dioxane (12 mL) and H$_2$O (3 mL) was degassed with N$_2$, Pd(dppf)Cl$_2$ (61.51 mg, 84.00 μmol, 0.05 eq) was added and then heated to 100° C. for 2 h under N$_2$. The reaction mixture was quenched by addition of water (50 mL), extracted with EtOAc (50 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 10/1, TLC: PE/EtOAc=10/1, R$_f$=0.36) to yield 2-methoxy-N-[3-(trifluoromethyl)phenyl]-5-vinyl-aniline (270 mg, 828.55 μmol, 49.3% yield, 90.0% purity) as yellow oil. $^1$H NMR (500 MHz, CDCl$_3$) δ ppm 7.43-7.34 (m, 3H), 7.31 (d, J=8.1 Hz, 1H), 7.17 (d, J=7.6 Hz, 1H), 6.98 (dd, J=2.1, 8.3 Hz, 1H), 6.87 (d, J=8.4 Hz, 1H), 6.64 (dd, J=10.9, 17.5 Hz, 1H), 6.21 (br s, 1H), 5.58 (dd, J=0.6, 17.5 Hz, 1H), 5.14 (dd, J=0.6, 10.8 Hz, 1H), 3.90 (s, 3H); ES-LCMS m/z 294.0 [M+H]$^+$.

Step 3: 5-[(5S)-3-Bromo-4,5-dihydroisoxazol-5-yl]-2-methoxy-N-[3-(trifluoromethyl)phenyl]aniline & 5-[(5R)-3-Bromo-4,5-dihydroisoxazol-5-yl]-2-methoxy-N-[3-(trifluoromethyl)phenyl]aniline To a solution of 2-methoxy-N-[3-(trifluoromethyl)phenyl]-5-vinyl-aniline (270 mg, 828.55 μmol, 1 eq) in EtOAc (10 mL) was added NaHCO$_3$ (696.07 mg, 8.29 mmol, 10 eq) and dibromomethanone oxime (252.09 mg, 1.24 mmol, 1.5 eq). The mixture was stirred at 30° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.44) to yield product. The product was separated by SFC (column: DAICEL CHIRALPAK AD-H (250 mm*30 mm, 5 μm); mobile phase: [0.1% NH$_3$H$_2$O ETOH]; B %: 40%-40%, min) to yield Peak 1 and Peak 2. Peak 1 was concentrated under reduced pressure to yield a residue which was dissolved in MeCN (20 mL) and H$_2$O (10 mL) and lyophilized to yield 5-[(5R)-3-bromo-4,5-dihydroisoxazol-5-yl]-2-methoxy-N-[3-(trifluoromethyl)phenyl]aniline (66.73 mg, 154.77 μmol, 18.6% yield, 96.3% purity) (SFC: R$_t$=1.178, ee=100%, [α]$^{28.3}_D$=+191.78 (MeOH, c=0.073 g/100 mL)) as a white solid. $^1$H NMR (500 MHz, CDCl$_3$) δ ppm 7.42-7.37 (m, 1H), 7.35-7.29 (m, 2H), 7.26 (s, 1H), 7.19 (d, J=7.6 Hz, 1H), 6.93-6.90 (m, 2H), 6.28 (s, 1H), 5.59 (dd, J=9.3, 10.7 Hz, 1H), 3.98-3.86 (m, 3H), 3.57 (dd, J=10.8, 17.2 Hz, 1H), 3.20 (dd, J=9.2, 17.3 Hz, 1H); ES-LCMS m/z 415.1, 417.1 [M+H]$^+$. Peak 2 was concentrated under reduced pressure to yield a residue which was dissolved in MeCN (20 mL) and H$_2$O (10 mL) and lyophilized to yield 5-[(5R)-3-bromo-4,5-dihydroisoxazol-5-yl]-2-methoxy-N-[3-(trifluoromethyl)phenyl]aniline (66.73 mg, 154.77 μmol, 18.6% yield, 96.3% purity) (SFC: R$_t$=1.712, ee=99.88%, [α]$^{28.3}_D$=−209.52 (MeOH, c=0.063 g/100 mL)) as a white solid. $^1$H NMR (500 MHz, CDCl$_3$) δ ppm 7.42-7.37 (m, 1H), 7.34-7.29 (m, 2H), 7.26 (s, 1H), 7.19 (d, J=7.6 Hz, 1H), 6.91 (s, 2H), 6.28 (s, 1H), 5.59 (dd, J=9.3, 10.7 Hz, 1H), 3.91 (s, 3H), 3.57 (dd, J=10.8, 17.3 Hz, 1H), 3.20 (dd, J=9.2, 17.3 Hz, 1H); ES-LCMS m/z 415.1, 417.1 [M+H]$^+$.

I-145 & I-146

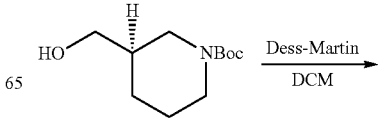

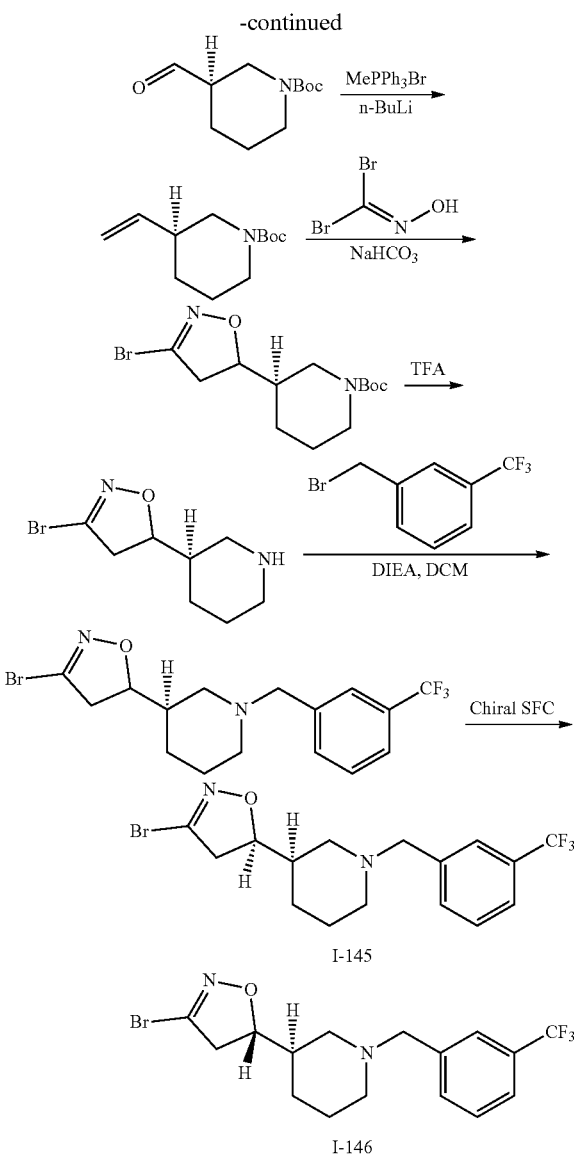

Step 1: tert-Butyl (3R)-3-formylpiperidine-1-carboxylate

To a solution of tert-butyl (3R)-3-(hydroxymethyl)piperidine-1-carboxylate (4 g, 18.58 mmol, 1 eq) in DCM (40 mL) was added Dess-Martin (11.03 g, 26.01 mmol, 8.05 mL, 1.4 eq). The mixture was stirred at 25° C. for 2 h. The reaction mixture was filtered through a pad of celite and the filtrate was concentrated to yield a residue which was purified by flash silica gel chromatography (from PE/EtOAc=100/1 to 2/1, TLC: PE/EtOAc=3/1, $R_f$=0.45) to yield tert-butyl (3R)-3-formylpiperidine-1-carboxylate (2.8 g, 9.72 mmol, 52.3% yield, 74.0% purity) as a colorless oil. $^1$H NMR (500 MHz, DMSO-d$_6$) δ ppm 9.62-9.55 (m, 1H), 3.82-3.61 (m, 1H), 3.42 (s, 2H), 3.07 (t, J=9.5 Hz, 1H), 2.45 (tt, J=4.2, 8.1 Hz, 1H), 1.89-1.81 (m, 1H), 1.65-1.57 (m, 1H), 1.56-1.50 (m, 1H), 1.38 (s, 9H), 1.36 (br s, 1H).

Step 2: tert-Butyl (3S)-3-vinylpiperidine-1-carboxylate

To a solution of methyl(triphenyl)phosphonium;bromide (2.66 g, 7.46 mmol, 1.3 eq) in THF (10 mL) was cooled to −78° C. then added n-BuLi (2.5 M, 2.98 mL, 1.3 eq) dropwise under N$_2$ atmosphere. The mixture was stirred at 0° C. for 0.5 h under N$_2$ atmosphere. The mixture was cooled to −78° C. and a solution of tert-butyl (3R)-3-formylpiperidine-1-carboxylate (1.4 g, 5.74 mmol, 1 eq) in THF (5 mL) was added slowly. The mixture was stirred at 27° C. for 4 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=5/1, $R_f$=0.65) to yield tert-butyl (3S)-3-vinylpiperidine-1-carboxylate (400 mg, 1.70 mmol, 29.7% yield, 90.0% purity) as a colorless gum. $^1$H NMR (400 MHz, DMSO-d$_6$) δ ppm 5.72 (d, J=6.5, 10.6, 17.4 Hz, 1H), 5.11-4.95 (m, 2H), 3.77 (d, J=13.2 Hz, 2H), 2.81-2.64 (m, 1H), 2.05 (d, J=5.9 Hz, 1H), 1.75 (d, J=11.7 Hz, 1H), 1.65-1.53 (m, 2H), 1.39 (s, 9H), 0.87-0.82 (m, 2H).

Step 3: tert-Butyl (3R)-3-(3-bromo-4,5-dihydroisoxazol-5-yl)piperidine-1-carboxylate To a solution of tert-butyl (3S)-3-vinylpiperidine-1-carboxylate (360 mg, 1.70 mmol, 1 eq) and dibromomethanone oxime (380.13 mg, 1.87 mmol, 1.1 eq) in EtOAc (15 mL) was added NaHCO$_3$ (1.43 g, 17.04 mmol, 10 eq). The mixture was stirred at 25° C. for 12 h under N$_2$ atmosphere. The reaction mixture was diluted with water (150 mL), extracted with EtOAc (50 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=3/1, $R_f$=0.40) to yield tert-butyl (3R)-3-(3-bromo-4,5-dihydroisoxazol-5-yl)piperidine-1-carboxylate (360 mg, 1.03 mmol, 60.2% yield, 95.0% purity) as a yellow oil. $^1$H NMR (400 MHz, CDCl$_3$) δ ppm 4.50 (s, 1H), 3.83 (s, 1H), 3.25 (dt, J=10.6, 17.9 Hz, 1H), 3.00 (dd, J=8.4, 16.5 Hz, 1H), 2.75 (s, 1H), 1.57 (s, 6H), 1.46 (s, 10H), 1.27 (t, J=7.1 Hz, 1H).

Step 4: 3-Bromo-5-[(3R)-3-piperidyl]-4,5-dihydroisoxazole

To a solution of tert-butyl (3R)-3-(3-bromo-4,5-dihydroisoxazol-5-yl)piperidine-1-carboxylate (320 mg, 960.32 μmol, 1 eq) in DCM (9 mL) was added TFA (4.62 g, 40.52 mmol, 3 mL, 42.19 eq) at 30° C. The mixture was stirred at 30° C. for 1 h. TLC (PE/EtOAc=2/1, $R_f$=0.05) showed the starting material was consumed completely. The reaction mixture was concentrated under reduced pressure to yield 3-bromo-5-[(3R)-3-piperidyl]-4,5-dihydroisoxazole (330 mg, 950.66 μmol, 99.0% yield, N/A purity, TFA) as a colorless gum, which was used in the next step without further purification. $^1$H NMR (400 MHz, CDCl$_3$) δ ppm 8.49 (br s, 1H), 4.69-4.60 (m, 1H), 4.59-4.49 (m, 1H), 3.62 (d, J=10.5 Hz, 1H), 3.36 (td, J=10.1, 17.5 Hz, 2H), 3.02 (td, J=7.4, 17.4 Hz, 2H), 2.88-2.72 (m, 2H), 2.18 (d, J=10.3 Hz, 2H), 1.94 (dd, J=3.2, 6.6 Hz, 1H).

Step 5: (5S)-3-Bromo-5-[(3R)-1-[[3-(trifluoromethyl)phenyl]methyl]-3-piperidyl]-4,5-dihydroisoxazole and (5R)-3-bromo-5-[(3R)-1-[[3-(trifluoromethyl)phenyl]methyl]-3-piperidyl]-4,5-dihydroisoxazole To a solution 3-bromo-5-[(3R)-3-piperidyl]-4,5-dihydroisoxazole (330 mg, 950.66 μmol, 1 eq, TFA) and DIEA (614.33 mg, 4.75 mmol, 827.94 μL, 5 eq) in DCM (10 mL) was added 1-(bromomethyl)-3-(trifluoromethyl)benzene (275 mg, 1.15 mmol, 175.16 μL, 1.21 eq) at 30° C. for 12 h. The reaction mixture was diluted with H₂O (50 mL) and extracted with EtOAc (50 mL×3). The organic layer was dried over Na₂SO₄, filtered and concentrated under reduced pressure to yield a residue which was purified by flash silica gel chromatography (from PE/EtOAc=100/1 to 5/1, TLC: PE/EtOAc=3/1, R$_f$=0.40). The desired compound was concentrated under reduced pressure to yield a residue (120 mg with 90% purity) which was separated by chiral SFC (column: DAICEL CHIRALPAK AD-H (250 mm*30 mm, 5 um); mobile phase: [0.1% NH₃·H₂O/EtOH]; B %: 10%-10%) to yield peak 1 and peak 2. Peak 1 was concentrated under reduced pressure to yield a residue which was dissolved in MeCN (15 mL) and water (15 mL) and lyophilized to yield (5S)-3-bromo-5-[(3R)-1-[[3-(trifluoromethyl)phenyl]methyl]-3-piperidyl]-4,5-dihydroisoxazole (55.30 mg, 140.08 μmol, 14.7% yield, 99.1% purity, SFC: R$_t$=1.849, Dr=97.02%, [α]$^{28.4}_D$=−81.48 (CHCl₃, c=0.054 g/100 mL)) as colorless oil. ¹H NMR (500 MHz, CDCl₃) δ ppm 7.58 (s, 1H), 7.55-7.48 (m, 2H), 7.46-7.42 (m, 1H), 4.66-4.55 (m, 1H), 3.60-3.46 (m, 2H), 3.15 (dd, J=10.7, 17.1 Hz, 1H), 2.91 (dd, J=9.0, 17.1 Hz, 1H), 2.75-2.60 (m, 2H), 2.15-2.05 (m, 1H), 2.02-1.94 (m, 1H), 1.95-1.85 (m, 1H), 1.84-1.72 (m, 2H), 1.63-1.59 (m, 1H), 1.28-1.20 (m, 1H); ES-LCMS m/z 391.1, 393.1 [M+H]⁺. Peak 2 was concentrated under reduced pressure to yield a residue which was dissolved in MeCN (15 mL) and water (15 mL) and lyophilized to yield (5R)-3-bromo-5-[(3R)-1-[[3-(trifluoromethyl)phenyl]methyl]-3-piperidyl]-4,5-dihydroisoxazole (33.70 mg, 83.99 μmol, 8.8% yield, 97.5% purity, SFC: R$_t$=2.141, Dr=97.22%, [α]$^{28.5}_D$=+76.19 (CHCl₃, c=0.021 g/100 mL)) as a white solid. ¹H NMR (500 MHz, CDCl₃) δ ppm 7.57 (s, 1H), 7.52 (d, J=7.5 Hz, 2H), 7.46-7.41 (m, 1H), 4.57-4.46 (m, 1H), 3.65-3.47 (m, 2H), 3.20 (dd, J=10.5, 17.2 Hz, 1H), 3.05-2.91 (m, 2H), 2.80-2.70 (m, 1H), 2.05-1.88 (m, 3H), 1.74-1.60 (m, 3H), 1.57 (s, 9H), 1.06 (d, J=9.3 Hz, 1H); ES-LCMS m/z 391.1, 393.1 [M+H]⁺.

I-111 & I-112

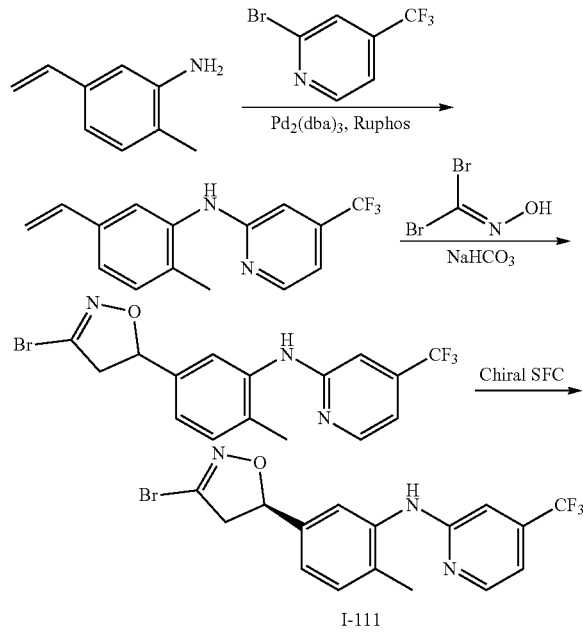

I-111

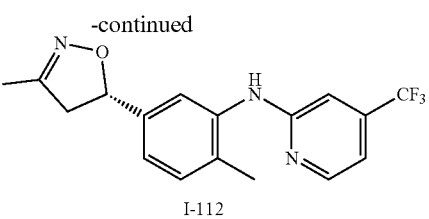

I-112

Step 1: N-(2-Methyl-5-vinyl-phenyl)-4-(trifluoromethyl)pyridin-2-amine

To a stirred solution of 2-methyl-5-vinyl-aniline (300 mg, 2.07 mmol, 1 eq) and 2-bromo-4-(trifluoromethyl)pyridine (468.31 mg, 2.07 mmol, 1 eq) in toluene (9 mL) was added Pd₂(dba)₃ (189.76 mg, 207.22 μmol, 0.1 eq), RuPhos (193.39 mg, 414.45 μmol, 0.2 eq), t-BuONa (398.30 mg, 4.14 mmol, 2 eq). The reaction mixture was stirred at 100° C. for 12 h. The mixture was filtered through a celite pad and the filtrate was concentrated to yield a residue which was purified by flash silica gel chromatography (from PE/EtOAc=100/1 to 3/1, TLC: PE/EtOAc=3/1, R$_f$=0.65) to yield N-(2-methyl-5-vinyl-phenyl)-4-(trifluoromethyl)pyridin-2-amine (470 mg, 871.52 μmol, 42.0% yield, 51.6% purity) as yellow oil. ¹H NMR (400 MHz, DMSO-d₆) δ ppm 8.26 (d, J=5.1 Hz, 1H), 7.63 (s, 1H), 7.27 (s, 1H), 7.21-7.15 (m, 2H), 6.99 (s, 1H), 6.93 (d, J=4.9 Hz, 1H), 6.69-6.63 (m, 1H), 5.79-5.71 (m, 1H), 5.26-5.20 (m, 1H), 2.19 (s, 3H); ES-LCMS m/z 279.0 [M+H]⁺.

Step 2: N-[5R-(3-Bromo-4,5-dihydroisoxazol-5-yl)-2-methyl-phenyl]-4-(trifluoromethyl)pyridin-2-amine & N-[5S-(3-bromo-4,5-dihydroisoxazol-5-yl)-2-methyl-phenyl]-4-(trifluoromethyl)pyridin-2-amine To a solution of N-(2-methyl-5-vinyl-phenyl)-4-(trifluoromethyl)pyridin-2-amine (240 mg, 445.03 μmol, 1 eq) in EtOAc (6 mL) was added dibromomethanone oxime (180.53 mg, 890.07 μmol, 2 eq) and NaHCO₃ (373.87 mg, 4.45 mmol, 10 eq). The mixture was bubbled with N₂ for 2 min and stirred at 25° C. for 12 h under microwave. The mixture was filtered through a celite pad, and the filtrate was concentrated to yield a residue which was purified by preparative HPLC (column: Agela DuraShell C18 150*25 mm*5 μm; mobile phase: [water (0.05% NH₃H₂O+10 mM NH₄HCO₃)-ACN]; B %: 49%-79%, 10 min). The desired fraction was lyophilized to yield the compound which was separated by SFC (column: DAICEL CHIRALPAK AD-H (250 mm*30 mm, 5 μm); mobile phase: [0.1% NH₃H₂O EtOH]; B %: 25%-25%, min) to yield Peak 1 and Peak 2. Peak 1 was concentrated under reduced pressure to yield a residue which was lyophilized to yield N-[5R-(3-bromo-4,5-dihydroisoxazol-5-yl)-2-methyl-phenyl]-4-(trifluoromethyl)pyridin-2-amine (27.01 mg, 67.49 μmol, 15.1% yield, 100% purity, SFC: R$_t$=1.113 min, ee=97.88%, [α]$^{28.3}_D$=+156.25, MeOH, c=0.032 g/100 mL) as yellow oil. ¹H NMR (400 MHz, DMSO-d₆) δ ppm 8.73 (s, 1H), 8.26 (d, J=5.1 Hz, 1H), 7.59 (d, J=1.2 Hz, 1H), 7.26 (d, J=7.8 Hz, 1H), 7.08-7.02 (m, 2H), 6.95 (d, J=5.1 Hz, 1H), 5.65 (dd, J=9.3, 10.5 Hz, 1H), 3.75 (dd, J=10.8, 17.6 Hz, 1H), 3.27 (dd, J=9.0, 17.4 Hz, 1H), 2.21 (s, 3H); ES-LCMS m/z 400.0, 402.1 [M+H]⁺. Peak 1 was concentrated under reduced pressure to yield a residue which was lyophilized to yield N-[5S-(3-bromo-4,5-dihydroisoxazol-5-yl)-2-methyl-phenyl]-4-(trifluoromethyl)pyridin-2-amine (18.97 mg, 47.40 µmol, 10.6% yield, 100% purity, SFC: $R_f$=1.290 min, ee=100%, $[α]^{28.0}{}_D$=−133.33, MeOH, c=0.033 g/100 mL) as yellow oil. $^1$H NMR (400 MHz, DMSO-$d_6$) δ ppm 8.74 (s, 1H), 8.27 (d, J=5.1 Hz, 1H), 7.60 (d, J=1.5 Hz, 1H), 7.27 (d, J=8.1 Hz, 1H), 7.09-7.03 (m, 2H), 6.96 (d, J=5.1 Hz, 1H), 5.66 (dd, J=9.3, 10.5 Hz, 1H), 3.76 (dd, J=10.9, 17.5 Hz, 1H), 3.28 (dd, J=9.2, 17.5 Hz, 1H), 2.22 (s, 3H); ES-LCMS m/z 400.0, 402.1 [M+H]$^+$.

I-113 & I-114

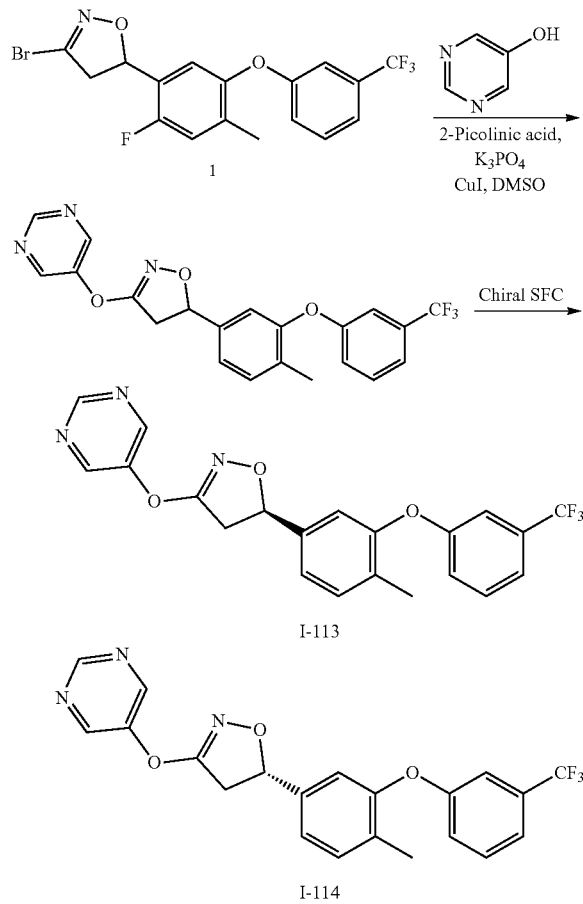

Step 1: (5R)-5-[4-Methyl-3-[3-(trifluoromethyl)phenoxy]phenyl]-3-pyrimidin-5-yloxy-4,5-dihydroisoxazole & & (5S)-5-[4-Methyl-3-[3-(trifluoromethyl)phenoxy]phenyl]-3-pyrimidin-5-yloxy-4,5-dihydroisoxazole To a stirred solution of 3-bromo-5-[4-methyl-3-[3-(trifluoromethyl)phenoxy]phenyl]-4,5-dihydroisoxazole (250 mg, 487.27 µmol, 1 eq) and pyrimidin-5-ol (51.50 mg, 536.00 µmol, 1.1 eq) in DMSO (5 mL) was added 2-Picolinic acid (4.80 mg, 38.98 µmol, 0.08 eq), $K_3PO_4$ (175.84 mg, 828.36 µmol, 1.7 eq) and CuI (4.64 mg, 24.36 µmol, 0.05 eq). The reaction mixture was stirred at 120° C. for 12 h under $N_2$ atmosphere. The reaction mixture was diluted with $H_2O$ (10 mL) and extracted with EtOAc (20 mL×3). The combined organic layers were washed with brine (15 mL), dried over $Na_2SO_4$, filtered and concentrated under reduced pressure to yield a residue which was purified by flash silica gel chromatography (from PE/EtOAc=100/1 to 2/1, TLC: PE/EtOAc=2/1, $R_f$=0.45) to yield crude product which was separated by SFC (column: DAICEL CHIRALPAK AD-H (250 mm*30 mm, 5 µm); mobile phase: [0.1% $NH_3·H_2O$ IPA]; B %: 25%-25%, min) to yield Peak 1 and Peak 2. Peak 1 was concentrated under reduced pressure to yield a residue which was dissolved in MeCN (20 mL) and $H_2O$ (40 mL) and lyophilized to yield (5R)-5-[4-methyl-3-[3-(trifluoromethyl)phenoxy]phenyl]-3-pyrimidin-5-yloxy-4,5-dihydroisoxazole (17.98 mg, 43.29 µmol, 8.9% yield, 100% purity, SFC: $R_f$=0.924 min, ee=99.92%, $[α]^{27.4}{}_D$=+28.571 (MeOH, c=0.035 g/100 mL)) as red oil. $^1$H NMR (500 MHz, MeOD) δ ppm 9.02 (s, 1H), 8.91-8.85 (m, 2H), 7.55-7.48 (m, 1H), 7.39 (d, J=7.8 Hz, 1H), 7.36 (d, J=7.8 Hz, 1H), 7.26 (dd, J=1.2, 7.9 Hz, 1H), 7.15-7.09 (m, 2H), 7.07 (s, 1H), 5.75 (t, J=9.8 Hz, 1H), 3.69 (dd, J=10.4, 16.8 Hz, 1H), 3.28 (d, J=9.5 Hz, 1H), 2.21 (s, 3H); ES-LCMS m/z 416.0 [M+H]$^+$. Peak 2 was concentrated under reduced pressure to yield a residue which was dissolved in MeCN (20 mL) and $H_2O$ (40 mL) and lyophilized to yield (5S)-5-[4-methyl-3-[3-(trifluoromethyl)phenoxy]phenyl]-3-pyrimidin-5-yloxy-4,5-dihydroisoxazole (24.36 mg, 58.65 µmol, 12.0% yield, 100% purity, SFC: $R_f$=1.117 min, ee=94.82%, $[α]^{27.4}{}_D$=−16.667 (MeOH, c=0.024 g/100 mL)) as red oil. $^1$H NMR (500 MHz, MeOD) δ ppm 9.02 (s, 1H), 8.88 (s, 2H), 7.54-7.49 (m, 1H), 7.39 (d, J=7.9 Hz, 1H), 7.36 (d, J=7.8 Hz, 1H), 7.26 (dd, J=1.5, 7.8 Hz, 1H), 7.15-7.09 (m, 2H), 7.07 (d, J=1.4 Hz, 1H), 5.75 (t, J=9.8 Hz, 1H), 3.69 (dd, J=10.3, 16.9 Hz, 1H), 3.30-3.26 (m, 1H), 2.21 (s, 3H); ES-LCMS m/z 416.0 [M+H]$^+$.

I-55

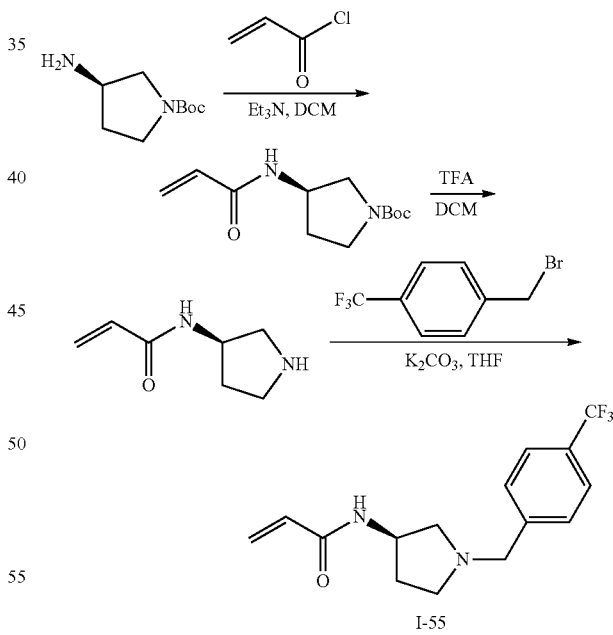

Step 1: tert-Butyl (3R)-3-(prop-2-enoylamino)pyrrolidine-1-carboxylate

To a solution of tert-butyl (3R)-3-aminopyrrolidine-1-carboxylate (500.00 mg, 2.68 mmol, 455.37 µL, 1 eq) and $Et_3N$ (543.30 mg, 5.37 mmol, 747.32 µL, 2.0 eq) in DCM (5 mL) was added prop-2-enoyl chloride (267.27 mg, 2.95 mmol, 240.78 µL, 1.1 eq). The mixture was stirred under $N_2$ atmosphere at 0° C. for 30 min. TLC (PE/EtOAc=3/1, R$_f$=0.60) showed one main spot formed. The mixture was quenched with H$_2$O (20 mL) and extracted with EtOAc (30 mL×3). The combined organic layer was dried over Na$_2$SO$_4$, filtrated and concentrated to give a residue which was purified by flash silica gel chromatography (from PE/EtOAc=100/1 to 3/1, TLC: PE/EtOAc=3/1, R$_f$=0.60) to yield tert-butyl (3R)-3-(prop-2-enoylamino)pyrrolidine-1-carboxylate (200 mg, 790.68 μmol, 29.5% yield, 95.0% purity) as a faint yellow solid. $^1$H NMR (400 MHz, DMSO-d$_6$) δ ppm 8.32 (d, J=5.1 Hz, 1H), 6.27-6.17 (m, 1H), 6.13-6.05 (m, 1H), 5.59 (dd, J=2.2, 10.0 Hz, 1H), 4.29-4.20 (m, 1H), 3.53-3.40 (m, 1H), 3.32-3.22 (m, 2H), 3.10-3.01 (m, 1H), 2.03 (td, J=6.8, 13.1 Hz, 1H), 1.74 (d, J=5.1 Hz, 1H), 1.39 (s, 9H); ES-LCMS m/z no desired MS found.

Step 2: N-[(3R)-Pyrrolidin-3-yl]prop-2-enamide

To a solution of tert-butyl (3R)-3-(prop-2-enoylamino)pyrrolidine-1-carboxylate (200 mg, 749.07 μmol, 1 eq) in DCM (5 mL) was added TFA (450 mg, 3.95 mmol, 1 mL, 5.27 eq). The mixture was stirred at 25° C. for 1 h. The reaction mixture was concentrated under reduced pressure to yield N-[(3R)-pyrrolidin-3-yl]prop-2-enamide (100 mg, 355.22 μmol, 47.4% yield, 90.3% purity, TFA) as a yellow solid, which was used in the next step without further purification. $^1$H NMR (400 MHz, DMSO-d$_6$) δ ppm 6.27-6.07 (m, 2H), 5.64 (dd, J=2.6, 9.7 Hz, 1H), 4.42-4.27 (m, 1H), 3.46-3.37 (m, 1H), 3.35-3.16 (m, 2H), 3.11-2.97 (m, 1H), 2.21-2.08 (m, 1H), 1.86 (qd, J=6.6, 13.1 Hz, 1H); ES-LCMS m/z no desired MS found.

Step 3: N-[(3R)-1-[[14-(trifluoromethyl)phenyl]methyl]pyrrolidin-3-yl]prop-2-enamide To a solution of N-[(3R)-pyrrolidin-3-yl]prop-2-enamide (100 mg, 644.16 μmol, 1 eq, TFA) and 1-(bromomethyl)-4-(trifluoromethyl)benzene (180 mg, 753.04 μmol, 116.13 μL, 1.17 eq) in THF (3 mL) was added K$_2$CO$_3$ (90.09 mg, 651.83 μmol, 1.01 eq). The mixture was stirred at 60° C. for 12 h. TLC (PE/EtOAc=3/1, R$_f$=0.47) showed one main spot formed. The reaction mixture was quenched with H$_2$O (10 mL) and extracted with EtOAc (10 mL×3). The combined organic layers dried over Na$_2$SO$_4$, filtered and concentrated under reduced pressure to yield a residue which was purified by preparative HPLC (column: Welch Xtimate C18 150×25 mm×5 μm; mobile phase: [water (10 mm NH$_4$HCO$_3$)-ACN]; B %: 35%-65%, 10 min) and then lyophilized to yield N-[(3R)-1-[[4-(trifluoromethyl)phenyl]methyl]pyrrolidin-3-yl]prop-2-enamide (17.18 mg, 56.52 μmol, 8.8% yield, 98.1% purity) as a yellow solid. $^1$H NMR (400 MHz, CDCl$_3$) δ ppm 7.58 (d, J=8.2 Hz, 2H), 7.43 (d, J=7.8 Hz, 2H), 6.27 (dd, J=1.6, 16.8 Hz, 1H), 6.10-6.01 (m, 1H), 5.64 (dd, J=1.4, 10.4 Hz, 1H), 4.64-4.51 (m, 1H), 3.73-3.61 (m, 2H), 2.93-2.84 (m, 1H), 2.68-2.55 (m, 2H), 2.40-2.24 (m, 2H), 1.73-1.67 (m, 1H); ES-LCMS m/z 299.2 [M+H]$^+$.

I-56

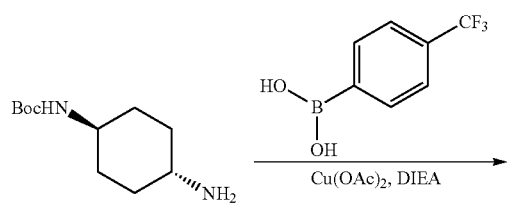

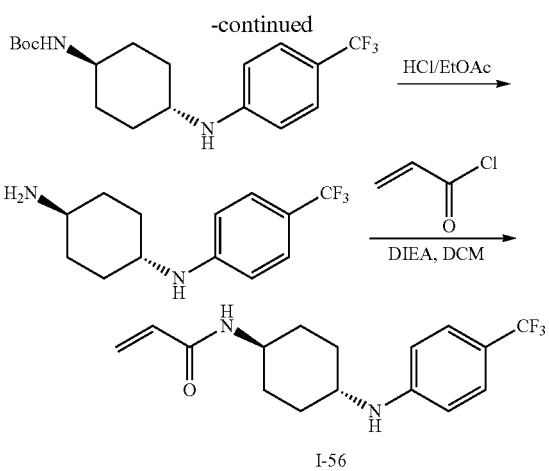

I-56

Step 1: tert-Butyl N-[4-[4-(trifluoromethyl)anilino]cyclohexyl]carbamate

To a stirred solution of tert-butyl N-(4-aminocyclohexyl)carbamate (200 mg, 933.26 μmol, 1 eq) in DCM (10 mL) was added DIEA (361.84 mg, 2.80 mmol, 487.66 μL, 3 eq), Cu(OAc)$_2$ (339.01 mg, 1.87 mmol, 2 eq) and [4-(trifluoromethyl)phenyl]boronic acid (186.11 mg, 979.92 μmol, 1.05 eq). The reaction mixture was at 29° C. for 48 h under oxygen atmosphere (15 psi). TLC (PE/EtOAc=3/1, R$_f$=0.50) showed one new spot was detected. The reaction mixture was concentrated to yield a residue which was purified by preparative TLC (PE/EtOAc=3/1, TLC: PE/EtOAc=3/1, R$_f$=0.50) to yield tert-butyl N-[4-[4-(trifluoromethyl)anilino]cyclohexyl]carbamate (100 mg, 251.12 μmol, 26.9% yield, 90.0% purity) as yellow oil. $^1$H NMR (400 MHz, DMSO-d$_6$) δ ppm 7.32 (d, J=8.3 Hz, 2H), 6.79 (d, J=7.1 Hz, 1H), 6.63 (d, J=8.3 Hz, 2H), 6.18 (d, J=7.3 Hz, 1H), 3.19 (d, J=10.5 Hz, 2H), 1.95 (d, J=10.8 Hz, 2H), 1.79 (d, J=10.5 Hz, 2H), 1.38 (s, 9H), 1.30-1.16 (m, 4H); ES-LCMS m/z 359.2 [M+H]$^+$.

Step 2: N4-[4-(Trifluoromethyl)phenyl]cyclohexane-1,4-diamine

To a stirred solution of tert-butyl N-[4-[4-(trifluoromethyl)anilino]cyclohexyl]carbamate (100 mg, 251.12 μmol, 1 eq) in DCM (10 mL) was added TFA (4.62 g, 40.52 mmol, 3 mL, 161.35 eq). The reaction mixture was at 29° C. for 1 h. TLC (PE/EtOAc=3/1) showed the starting material was consumed completely. The reaction mixture was concentrated to yield N$_4$-[4-(trifluoromethyl)phenyl]cyclohexane-1,4-diamine (100 mg, 185.06 μmol, 73.7% yield, 90.0% purity, 2TFA) as yellow oil which was used in the next step without further purification. $^1$H NMR (400 MHz, DMSO-d$_6$) δ ppm 7.79 (s, 3H), 7.35 (d, J=8.6 Hz, 2H), 6.67 (d, J=8.6 Hz, 2H), 3.28-3.16 (m, 1H), 3.02 (s, 1H), 2.03 (s, 2H), 1.95 (d, J=11.0 Hz, 2H), 1.43 (q, J=11.8 Hz, 2H), 1.28-1.19 (m, 2H).

Step 3: N-[4-[4-(Trifluoromethyl)anilino]cyclohexyl]prop-2-enamide

To a stirred solution of N4-[4-(trifluoromethyl)phenyl]cyclohexane-1,4-diamine (100 mg, 185.06 μmol, 1 eq, 2TFA) in DCM (10 mL) was added DIEA (143.51 mg, 1.11 mmol, 193.40 μL, 6 eq) and prop-2-enoyl chloride (15.07 mg, 166.55 µmol, 13.58 µL, 0.9 eq). The reaction mixture was stirred at 29° C. for 20 min. The reaction mixture was concentrated to yield a residue which was purified by preparative HPLC (column: Agela DuraShell C18 150*25 mm*5um; mobile phase: [water (0.05% NH$_3$H$_2$O+10 mM NH$_4$HCO$_3$)-ACN]; B %: 38%-68%, 10 min). The desired fraction was lyophilized to yield N-[4-[4-(trifluoromethyl) anilino]cyclohexyl]prop-2-enamide (26.14 mg, 81.18 µmol, 43.9% yield, 97.0% purity) as white solid. $^1$H NMR (400 MHz, DMSO-d$_6$) δ ppm 8.02 (d, J=7.6 Hz, 1H), 7.34 (d, J=8.6 Hz, 2H), 6.66 (d, J=8.8 Hz, 2H), 6.26-6.17 (m, 2H), 6.10-6.02 (m, 1H), 5.59-5.53 (m, 1H), 3.68-3.54 (m, 1H), 3.28-3.19 (m, 1H), 1.98 (d, J=12.2 Hz, 2H), 1.85 (d, J=11.5 Hz, 2H), 1.38-1.18 (m, 4H); ES-LCMS m/z 313.2 [M+H]$^+$.
I-57

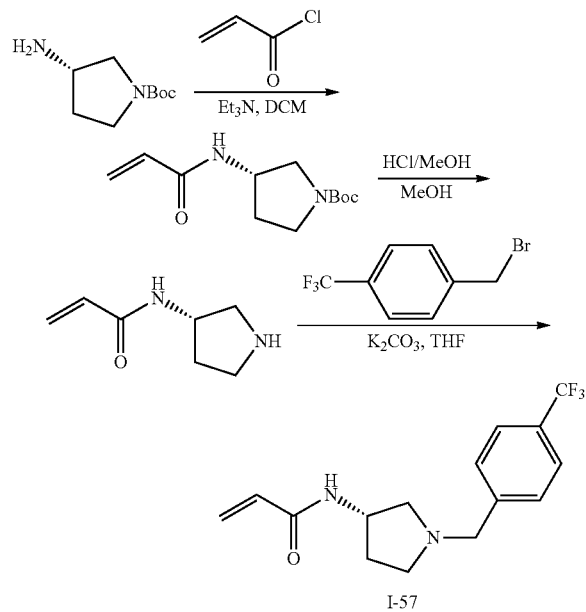

I-57

Step 1: tert-Butyl (3S)-3-(prop-2-enoylamino)pyrrolidine-1-carboxylate

A solution of tert-butyl (3S)-3-aminopyrrolidine-1-carboxylate (500.00 mg, 2.68 mmol, 1 eq) and Et$_3$N (545.25 mg, 5.39 mmol, 750 µL, 2.01 eq) in DCM (5 mL) was stirred at 28° C. The mixture was cooled to 0° C. and then prop-2-enoyl chloride (290 mg, 3.20 mmol, 261.26 µL, 1.19 eq) was added dropwise at 0° C. The resulting mixture was stirred at 28° C. for 12 h. The mixture was diluted with water (20 mL) and extracted with EtOAc (25 mL×3). The combined organic layers were dried over Na$_2$SO$_4$, filtered and concentrated under reduced pressure to yield tert-butyl (3S)-3-(prop-2-enoylamino)pyrrolidine-1-carboxylate (560 mg, 2.10 mmol, 78.1% yield, 90.0% purity) as a yellow solid, which was used in the next step without further purification. $^1$H NMR (400 MHz, DMSO-d$_6$) δ ppm 6.23-6.13 (m, 1H), 6.11-6.02 (m, 1H), 5.56 (dd, J=2.2, 10.0 Hz, 1H), 4.26-4.16 (m, 1H), 3.50-3.35 (m, 2H), 3.29-3.25 (m, 2H), 3.10-2.97 (m, 1H), 2.07-1.97 (m, 1H), 1.76-1.66 (m, 1H), 1.36 (s, 9H); ES-LCMS m/z 241.2 [M+H]$^+$.

Step 2: N-[(3S)-Pyrrolidin-3-yl]prop-2-enamide

A solution of tert-butyl (3S)-3-(prop-2-enoylamino)pyrrolidine-1-carboxylate (560 mg, 2.10 mmol, 1 eq) in DCM (6 mL) and TFA (2 mL) was stirred at 28° C. for 12 h. The reaction mixture was diluted with water (20 mL), neutralized with NaHCO$_3$ until pH=7 and extracted with EtOAc (20 mL×3). The combined organic layers were dried over Na$_2$SO$_4$, filtered and concentrated under reduced pressure to yield N-[(3S)-pyrrolidin-3-yl]prop-2-enamide (600 mg, 1.89 mmol, 90.0% yield, 80.0% purity, TFA) as a yellow oil, which was used in the next step without further purification. $^1$H NMR (400 MHz, DMSO-d$_6$) δ ppm 8.99-8.85 (m, 1H), 8.44 (d, J=4.7 Hz, 1H), 6.23-6.14 (m, 1H), 6.13 (d, J=2.7 Hz, 1H), 5.63 (dd, J=2.5, 9.6 Hz, 1H), 4.33 (td, J=6.1, 12.1 Hz, 1H), 3.42-3.33 (m, 1H), 3.30-3.20 (m, 2H), 3.06-2.97 (m, 1H), 2.23-2.04 (m, 1H), 1.85 (td, J=6.5, 13.2 Hz, 1H).

Step 3: N-[(3S)-1-[[4-(Trifluoromethyl)phenyl]methyl]pyrrolidin-3-yl]prop-2-enamide To a solution of N-[(3S)-pyrrolidin-3-yl]prop-2-enamide (300 mg, 944.12 µmol, 1 eq, TFA) in DCM (5 mL) was added DIEA (600 mg, 4.64 mmol, 808.63 µL, 4.92 eq) and 1-(bromomethyl)-4-(trifluoromethyl)benzene (180 mg, 753.04 µmol, 116.13 µL, 7.98e-1 eq). The mixture was stirred at 28° C. for 12 h. The mixture was diluted with water (20 mL) and extracted with EtOAc (25 mL×3). The combined organic layers were dried over Na$_2$SO$_4$, filtered and concentrated under reduced pressure to yield the residue which was purified by preparative HPLC (column: Agela DuraShell C18 150*25 mm*5 um; mobile phase: [water (0.05% NH$_3$·H$_2$O+10 mM/NH$_4$HCO$_3$)-ACN]; B %: 34%-49%, 14 min) to yield N-[(3S)-1-[[4-(trifluoromethyl)phenyl]methyl]pyrrolidin-3-yl]prop-2-enamide (26.17 mg, 85.08 µmol, 9.0% yield, 97.0% purity) as a white solid. $^1$H NMR (400 MHz, CDCl$_3$) δ ppm 7.59 (d, J=8.1 Hz, 2H), 7.44 (d, J=7.8 Hz, 2H), 6.28 (dd, J=1.5, 16.9 Hz, 1H), 6.13-6.00 (m, 1H), 5.89 (br s, 1H), 5.65 (dd, J=1.2, 10.3 Hz, 1H), 4.65-4.47 (m, 1H), 3.74-3.60 (m, 2H), 2.96-2.83 (m, 1H), 2.70-2.55 (m, 2H), 2.43-2.21 (m, 2H), 1.73-1.64 (m, 1H); ES-LCMS m/z 299.2 [M+H]$^+$.
I-115 & I-116

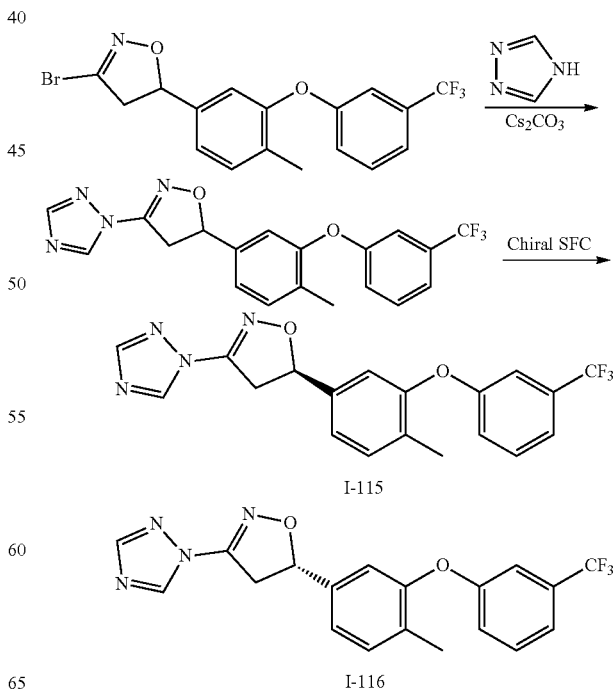

I-115

I-116

Step 1: 5-[4-Methyl-3-[3-(trifluoromethyl)phenoxy]
phenyl]-3-(1,2,4-triazol-1-yl)-4,5-dihydroisoxazole To a solution of 3-bromo-5-[4-methyl-3-[3-(trifluoromethyl)phenoxy]phenyl]-4,5-dihydroisoxazole (300 mg, 584.72 μmol, 1 eq) in DMF (10 mL) was added $Cs_2CO_3$ (571.54 mg, 1.75 mmol, 3 eq) and 4H-1,2,4-triazole (121.15 mg, 1.75 mmol, 3 eq). The mixture was stirred at 80° C. for 2 h. The reaction mixture was quenched by addition of water (50 mL), extracted with EtOAc (30 mL×3). The organic layer was washed with brine (20 mL), dried over $Na_2SO_4$, filtered, concentrated to yield a residue which was purified by preparative HPLC (column: Phenomenex Synergi C18 150*30 mm*4 μm; mobile phase: [water (0.05% HCl)-ACN]; B %: 58%-78%, 10 min), followed by lyophilization to yield 5-[4-methyl-3-[3-(trifluoromethyl)phenoxy]phenyl]-3-(1,2,4-triazol-1-yl)-4,5-dihydroisoxazole (150 mg, 384.33 μmol, 65.7% yield, 99.5% purity) as colorless oil. $^1$H NMR (400 MHz, $CD_3OD$) δ ppm 9.04 (s, 1H), 8.19 (s, 1H), 7.52 (t, J=7.9 Hz, 1H), 7.46-7.23 (m, 3H), 7.18-7.05 (m, 2H), 5.94-5.82 (m, 1H), 4.06 (dd, J=10.9, 17.2 Hz, 2H), 3.58 (dd, J=9.3, 17.4 Hz, 1H), 2.22 (s, 3H); ES-LCMS m/z 389.0 $[M+H]^+$.

Step 2: (5R)-5-[4-Methyl-3-[3-(trifluoromethyl)
phenoxy]phenyl]-3-(1,2,4-triazol-1-yl)-4,5-dihydroisoxazole & (5S)-5-[4-Methyl-3-[3-(trifluoromethyl)phenoxy]phenyl]-3-(1,2,4-triazol-1-yl)-4,5-
dihydroisoxazole 5-[4-Methyl-3-[3-(trifluoromethyl)phenoxy]phenyl]-3-(1,2,4-triazol-1-yl)-4,5-dihydroisoxazole (150.00 mg, 384.33 μmol, 1 eq) was separated by SFC (column: Phenomenex-Cellulose-2 (250 mm*30 mm, 5 μm); mobile phase: [0.1% $NH_3·H_2O$ MEOH]; B %: 40%-40%, min, Peak1, 0.805, Peak2, 0.912). Peak 1 was concentrated under reduced pressure to yield a residue which was dissolved in MeCN (10 mL) and $H_2O$ (5 mL) and lyophilized to yield (5R)-5-[4-methyl-3-[3-(trifluoromethyl)phenoxy]phenyl]-3-(1,2,4-triazol-1-yl)-4,5-dihydroisoxazole (18.04 mg, 45.66 μmol, 11.9% yield, 98.3% purity, SFC: $R_t$=0.806, ee=100%, $[α]^{29.0}_D$=+139.753 (MeOH, c=0.05 g/100 mL)) as colorless oil. $^1$H NMR (400 MHz, $CDCl_3$) δ ppm 8.81 (s, 1H), 8.07 (s, 1H), 7.45-7.39 (m, 1H), 7.37-7.30 (m, 2H), 7.21-7.14 (m, 2H), 7.06-6.98 (m, 2H), 5.82 (t, J=10.0 Hz, 1H), 3.98 (dd, J=10.9, 17.5 Hz, 1H), 3.57 (dd, J=9.0, 17.6 Hz, 1H), 2.24 (s, 3H); ES-LCMS m/z 389.0 $[M+H]^+$. Peak 2 was concentrated under reduced pressure to yield a residue which was dissolved in MeCN (10 mL) and $H_2O$ (5 mL) and lyophilized to yield (5S)-5-[4-methyl-3-[3-(trifluoromethyl)phenoxy]phenyl]-3-(1,2,4-triazol-1-yl)-4,5-dihydroisoxazole (23.13 mg, 57.89 μmol, 15.0% yield, 97.2% purity, SFC: $R_t$=0.912, ee=97.06%, $[α]^{28.9}_D$=−197.229 (MeOH, c=0.0575 g/100 mL)) as colorless oil. $^1$H NMR (400 MHz, $CDCl_3$) δ=8.81 (s, 1H), 8.07 (s, 1H), 7.46-7.39 (m, 1H), 7.36-7.30 (m, 2H), 7.21-7.13 (m, 2H), 7.06-6.98 (m, 2H), 5.82 (dd, J=9.3, 10.5 Hz, 1H), 3.98 (dd, J=11.0, 17.6 Hz, 1H), 3.57 (dd, J=9.0, 17.6 Hz, 1H), 2.24 (s, 3H); ES-LCMS m/z 389.0 $[M+H]^+$.

I-117 & I-118

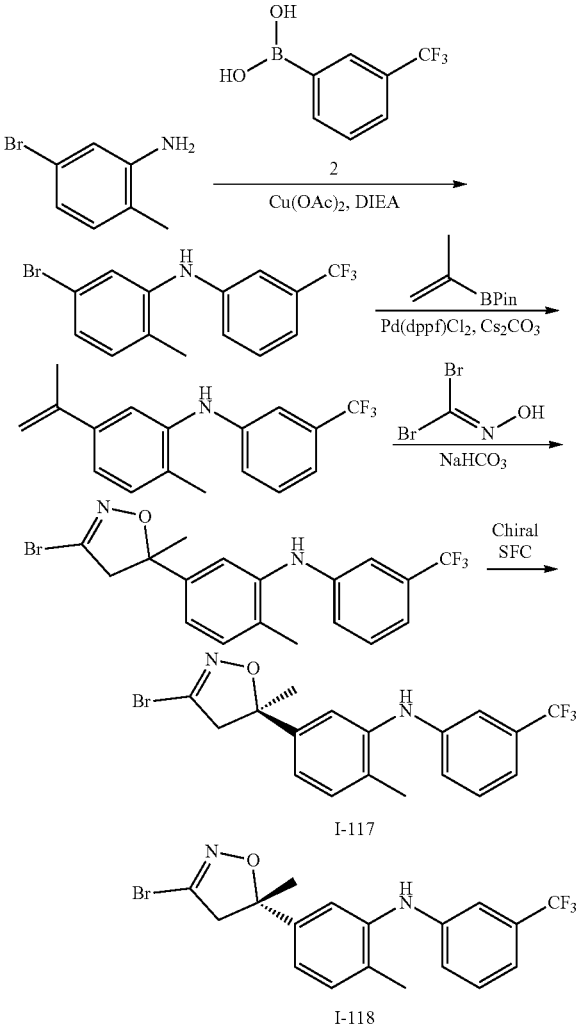

I-117

I-118

Step 1: 5-Bromo-2-methyl-N-[3-(trifluoromethyl)
phenyl]aniline

To a solution of 5-bromo-2-methyl-aniline (1 g, 5.37 mmol, 1 eq) and [3-(trifluoromethyl)phenyl]boronic acid (2.04 g, 10.75 mmol, 2 eq) in DCM (20 mL) was added $Cu(OAc)_2$ (1.95 g, 10.75 mmol, 2 eq) and DIEA (2.78 g, 21.50 mmol, 3.74 mL, 4 eq). The mixture was stirred at 28° C. for 12 h under $O_2$ (15 psi) atmosphere which was filtered through a pad of celite and the filtrate was concentrated to yield a residue which was purified by flash silica gel chromatography (from PE/EtOAc=100/1 to 2/1, TLC: PE/EtOAc=5/1, $R_f$=0.40) to yield 5-bromo-2-methyl-N-[3-(trifluoromethyl)phenyl]aniline (1.2 g, 3.33 mmol, 61.9% yield, 91.5% purity) as yellow oil. $^1$H NMR (400 MHz, DMSO-$d_6$) δ ppm 8.00 (s, 1H), 7.42 (t, J=7.7 Hz, 1H), 7.29 (d, J=1.7 Hz, 1H), 7.21-7.08 (m, 5H), 2.15 (s, 3H); ES-LCMS m/z 329.9, 331.9 $[M+H]^+$.

Step 2: 5-Isopropenyl-2-methyl-N-[3-(trifluoromethyl)phenyl]aniline

To a solution of 5-bromo-2-methyl-N-[3-(trifluoromethyl)phenyl]aniline (1 g, 2.03 mmol, 1 eq), 2-isopropenyl- 4,4,5,5-tetramethyl-1,3,2-dioxaborolane (409.84 mg, 2.44 mmol, 1.2 eq) in 1,4-dioxane (6 mL) and water (2 mL) was added Cs$_2$CO$_3$ (1.99 g, 6.10 mmol, 3 eq) and Pd(dppf)Cl$_2$ (148.72 mg, 203.25 μmol, 0.1 eq). The mixture was bubbled with N$_2$ for 2 min then stirred at 100° C. for 30 min under microwave (2 bar). The reaction mixture was diluted with water (150 mL) then extracted with EtOAc (50 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=5/1, R$_f$=0.65) to yield 5-isopropenyl-2-methyl-N-[3-(trifluoromethyl)phenyl]aniline (590 mg, 1.36 mmol, 67.0% yield, 67.2% purity) as yellow oil. $^1$H NMR (500 MHz, DMSO-d$_6$) δ ppm 7.95 (s, 1H), 7.38-7.35 (m, 1H), 7.30 (d, J=1.7 Hz, 1H), 7.24-7.22 (m, 1H), 7.18-7.16 (m, 1H), 7.05 (d, J=5.8 Hz, 2H), 7.03-6.98 (m, 2H), 5.04 (s, 1H), 2.17 (s, 3H), 2.05 (s, 3H); ES-LCMS m/z 347.0, 292.2 [M+H]$^+$.

Step 3: 5-[(5R)-3-Bromo-5-methyl-4H-isoxazol-5-yl]-2-methyl-N-[3-(trifluoromethyl)phenyl]aniline & 5-[(5S)-3-Bromo-5-methyl-4H-isoxazol-5-yl]-2-methyl-N-[3-(trifluoromethyl)phenyl]aniline To a solution of 5-isopropenyl-2-methyl-N-[3-(trifluoromethyl)phenyl]aniline (350 mg, 1.20 mmol, 1 eq) and dibromomethanone oxime (365.55 mg, 1.80 mmol, 1.5 eq) in EtOAc (10 mL) was added NaHCO$_3$ (1.01 g, 12.01 mmol, 10 eq). The mixture was stirred at 25° C. for 12 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=5/1, R$_f$=0.65) to yield the compound which was separated by SFC (column: DAICEL CHIRALCEL OJ-H (250 mm*30 mm, 5 μm); mobile phase: [0.1% NH$_3$H$_2$O EtOH]; B %: 30%-30%, min) to yield Peak 1 and Peak 2. Peak 1 was concentrated under reduced pressure to yield a residue which was lyophilized to yield 5-[(5R)-3-bromo-5-methyl-4H-isoxazol-5-yl]-2-methyl-N-[3-(trifluoromethyl)phenyl]aniline (80 mg, 193.60 μmol, 16.1% yield, 100% purity, SFC: R$_t$=4.340 min, ee=99.2%, [α]$^{29.3}_D$=+66.67, MeOH, c=0.069 g/100 mL) as yellow oil. $^1$H NMR (400 MHz, CDCl$_3$) δ ppm 7.38-7.32 (m, 1H), 7.30-7.27 (m, 1H), 7.25 (d, J=7.8 Hz, 1H), 7.15-7.10 (m, 2H), 7.07-7.02 (m, 2H), 5.56 (s, 1H), 3.38-3.26 (m, 2H), 2.25 (s, 3H), 1.75 (s, 3H); ES-LCMS m/z 413.1, 415.1 [M+H]$^+$. Peak 2 was concentrated under reduced pressure to yield a residue which was lyophilized to yield 5-[(5S)-3-bromo-5-methyl-4H-isoxazol-5-yl]-2-methyl-N-[3-(trifluoromethyl)phenyl]aniline (62 mg, 147.04 μmol, 12.2% yield, 98.0% purity SFC: R$_t$=5.143 min, ee=98.1% [α]$^{29.3}_D$=−69.10, MeOH, c=0.055 g/100 mL) as yellow oil. $^1$H NMR (400 MHz, CDCl$_3$) δ ppm 7.38-7.32 (m, 1H), 7.30 (s, 1H), 7.25 (d, J=8.1 Hz, 1H), 7.15-7.10 (m, 2H), 7.05 (dd, J=2.1, 7.7 Hz, 2H), 5.57 (s, 1H), 3.39-3.23 (m, 2H), 2.25 (s, 3H), 1.75 (s, 3H); ES-LCMS m/z 413.1, 415.1 [M+H]$^+$
I-58

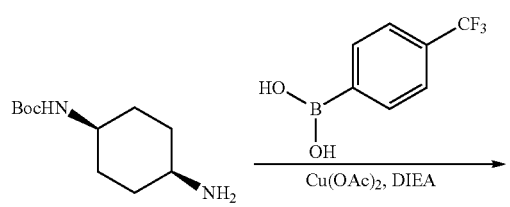

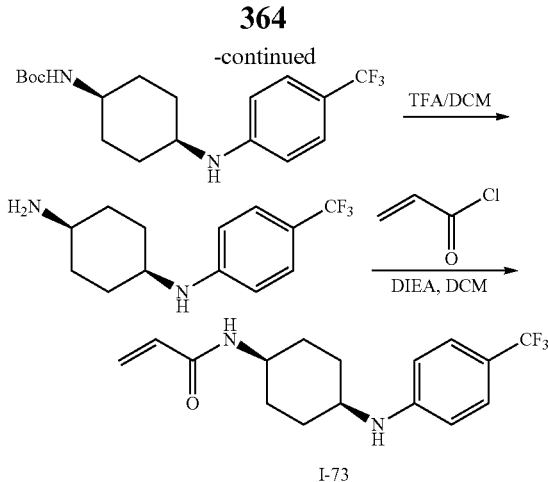

I-73

Step 1: tert-Butyl N-[4-[4-(trifluoromethyl)anilino]cyclohexyl]carbamate

To a stirred solution of tert-butyl N-(4-aminocyclohexyl)carbamate (300 mg, 1.40 mmol, 1 eq) in DCM (10 mL) was added DIEA (542.76 mg, 4.20 mmol, 731.48 μL, 3 eq), Cu(OAc)$_2$ (508.52 mg, 2.80 mmol, 2 eq) and [4-(trifluoromethyl)phenyl]boronic acid (319.05 mg, 1.68 mmol, 1.2 eq). The reaction mixture was at 29° C. for 48 h under oxygen atmosphere (15 psi). The reaction mixture was filtered and the filtrate was concentrated to yield a residue which was purified by preparative TLC (PE/EtOAc=3/1, TLC: PE/EtOAc=3/1, R$_f$=0.40) to yield tert-butyl N-[4-[4-(trifluoromethyl)anilino]cyclohexyl]carbamate (200 mg, 502.24 μmol, 35.9% yield, 90.0% purity) as a yellow solid. $^1$H NMR (400 MHz, DMSO-d$_6$) δ ppm 7.33 (d, J=8.6 Hz, 2H), 6.74 (s, 1H), 6.67 (d, J=8.6 Hz, 2H), 6.15 (d, J=6.6 Hz, 1H), 3.48-3.36 (m, 2H), 1.70-1.49 (m, 8H), 1.38 (s, 9H); ES-LCMS m/z 359.2 [M+H]$^+$.

Step 2: N4-[4-(Trifluoromethyl)phenyl]cyclohexane-1,4-diamine

To a stirred solution of tert-butyl N-[4-[4-(trifluoromethyl)anilino]cyclohexyl]carbamate (200 mg, 502.23 μmol, 1 eq) in DCM (10 mL) was added TFA (4.62 g, 40.52 mmol, 3 mL, 80.68 eq). The reaction mixture was at 29° C. for 1 h. TLC (PE/EtOAc=3/1) showed the starting material was consumed completely. The reaction mixture was concentrated to yield N$_4$-[4-(trifluoromethyl)phenyl]cyclohexane-1,4-diamine (160 mg, 296.10 μmol, 59.0% yield, 90.0% purity, 2TFA) as yellow oil which was used in the next step without further purification. $^1$H NMR (400 MHz, DMSO-d$_6$) δ ppm 7.76 (s, 3H), 7.37 (d, J=8.6 Hz, 2H), 6.70 (d, J=8.6 Hz, 2H), 3.14 (s, 2H), 1.88-1.56 (m, 8H).

Step 3: N-[4-[4-(Trifluoromethyl)anilino]cyclohexyl]prop-2-enamide

To a stirred solution of N4-[4-(trifluoromethyl)phenyl]cyclohexane-1,4-diamine (160 mg, 296.10 μmol, 1 eq, 2TFA) in DCM (10 mL) was added DIEA (229.61 mg, 1.78 mmol, 309.45 μL, 6 eq) and prop-2-enoyl chloride (24.12 mg, 266.49 μmol, 21.73 μL, 0.9 eq). The reaction mixture was stirred at 29° C. for 1 h. The reaction mixture was concentrated to yield a residue which was purified by preparative HPLC (column: Agela DuraShell C18 150*25 mm*5um; mobile phase: [water (0.05% NH$_3$H$_2$O+10 mM NH$_4$HCO$_3$)-ACN]; B %: 50%-80%, 10 min). The desired fraction was lyophilized to yield N-[4-[4-(trifluoromethyl)anilino]cyclohexyl]prop-2-enamide (22.3 mg, 71.40 μmol, 24.1% yield, 100.0% purity) as white solid. $^1$H NMR (500 MHz, DMSO-d$_6$) δ ppm 7.97 (d, J=7.0 Hz, 1H), 7.35 (d, J=8.7 Hz, 2H), 6.69 (d, J=8.7 Hz, 2H), 6.30 (dd, J=10.2, 17.1 Hz, 1H), 6.24 (d, J=6.4 Hz, 1H), 6.07 (dd, J=2.1, 17.1 Hz, 1H), 5.55 (dd, J=2.3, 10.1 Hz, 1H), 3.77 (s, 1H), 3.40 (s, 1H), 1.72-1.58 (m, 8H); ES-LCMS m/z 313.2 [M+H]$^+$.

I-147 & I-148

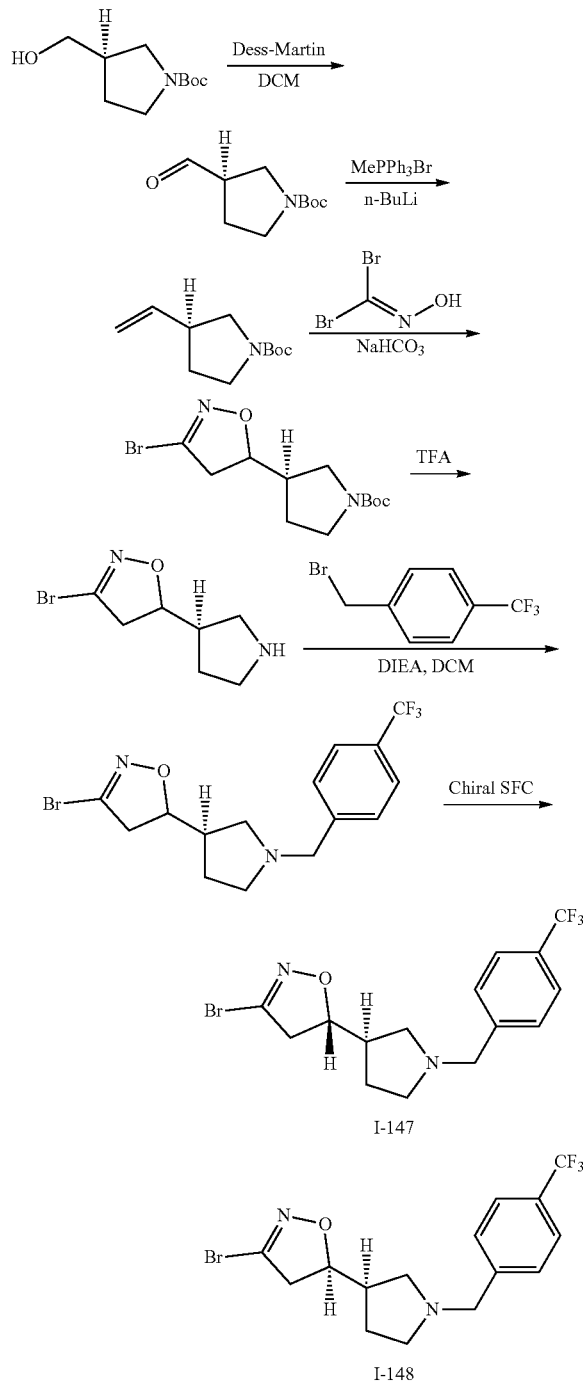

I-147

I-148

Step 1: tert-Butyl (3R)-3-formylpyrrolidine-1-carboxylate

To a solution of tert-butyl (3R)-3-(hydroxymethyl)pyrrolidine-1-carboxylate (1.5 g, 7.45 mmol, 1 eq) in DCM (50 mL) was added Dess-Martin periodinane (4.11 g, 9.69 mmol, 3.00 mL, 1.3 eq) at 30° C. The mixture was stirred at 30° C. for 12 h. TLC (PE/EtOAc=1/1, R$_f$=0.70) showed about 50% of the starting material was consumed. The mixture was filtered. The filtrate was concentrated under reduced pressure to yield a residue which was purified by flash silica gel chromatography (from PE/EtOAc=100/1 to 1/1, TLC: PE/EtOAc=1/1, R$_f$=0.70) to yield tert-butyl (3R)-3-formylpyrrolidine-1-carboxylate (800 mg, 4.02 mmol, 53.9% yield, N/A purity) as a colorless gum. $^1$H NMR (400 MHz, CDCl$_3$) δ ppm 9.70 (d, J=1.6 Hz, 1H), 3.70-3.60 (m, 1H), 3.60-3.50 (m, 1H), 3.48-3.40 (m, 2H), 3.10-3.00 (m, 1H), 2.26-2.16 (m, 2H), 1.47 (s, 9H).

Step 2: tert-Butyl (3S)-3-vinylpyrrolidine-1-carboxylate

To a solution of methyl(triphenyl)phosphonium;bromide (1.72 g, 4.82 mmol, 1.2 eq) in THF (20 mL) was added n-BuLi (2.5 M, 2.25 mL, 1.4 eq) under N$_2$ atmosphere at −70° C. The mixture was stirred under N$_2$ atmosphere at 0° C. for 0.5 h. The mixture was cooled to −70° C. A solution of tert-butyl (3R)-3-formylpyrrolidine-1-carboxylate (800 mg, 4.02 mmol, 1 eq) in THF (5 mL) was added. The mixture was warmed to 25° C. slowly and stirred under N$_2$ atmosphere at 25° C. for 2 h. TLC (PE/EtOAc=10/1, R$_f$=0.60) showed the starting material was consumed completely. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by flash silica gel chromatography (from PE/EtOAc=100/1 to 10/1, TLC: PE/EtOAc=10/1, R$_f$=0.60) to yield tert-butyl (3S)-3-vinylpyrrolidine-1-carboxylate (220 mg, 1.12 mmol, 27.8% yield, N/A purity) as colorless oil. $^1$H NMR (400 MHz, CDCl$_3$) δ ppm 5.78 (ddd, J=7.6, 10.3, 17.3 Hz, 1H), 5.16-5.08 (m, 1H), 5.04 (d, J=10.6 Hz, 1H), 3.55-3.45 (m, 2H), 3.35-3.25 (m, 1H), 3.10-3.00 (m, 1H), 2.79 (d, J=7.8 Hz, 1H), 2.01 (tdd, J=3.4, 6.5, 12.6 Hz, 1H), 1.77-1.66 (m, 1H), 1.47 (s, 9H).

Step 3: tert-Butyl (3R)-3-(3-bromo-4,5-dihydroisoxazol-5-yl)pyrrolidine-1-carboxylate A mixture of tert-butyl (3S)-3-vinylpyrrolidine-1-carboxylate (200 mg, 1.01 mmol, 1 eq), dibromomethanone oxime (250 mg, 1.23 mmol, 1.22 eq) and NaHCO$_3$ (850 mg, 10.12 mmol, 9.98 eq) in EtOAc (15 mL) was stirred at 25° C. for 2 h. TLC (PE/EtOAc=2/1, R$_f$=0.33) showed the starting material was consumed completely. The reaction mixture was diluted with H$_2$O (30 mL) and extracted with EtOAc (30 mL×3). The organic layer was dried over Na$_2$SO$_4$, filtered and concentrated under reduced pressure to yield a residue which was purified by flash silica gel chromatography (from PE/EtOAc=100/1 to 2/1, TLC: PE/EtOAc=2/1, R$_f$=0.33) to yield tert-butyl (3R)-3-(3-bromo-4,5-dihydroisoxazol-5-yl)pyrrolidine-1-carboxylate (210 mg, 636.20 μmol, 62.8% yield, 96.7% purity) as a colorless gum. $^1$H NMR (400 MHz, CDCl$_3$) δ ppm 4.66-4.56 (m, 1H), 3.63-3.44 (m, 2H), 3.31 (dd, J=10.6, 17.2 Hz, 2H), 3.24-3.03 (m, 1H), 2.94 (dd, J=8.4, 17.0 Hz, 1H), 2.46

(dd, J=7.8, 16.4 Hz, 1H), 2.10-1.94 (m, 1H), 1.88-1.78 (m, 1H), 1.46 (s, 9H); ES-LCMS m/z 263.0, 265.0 [M-t-Bu+H]$^+$.

Step 4: 3-Bromo-5-[(3R)-pyrrolidin-3-yl]-4,5-dihydroisoxazole

To a mixture of tert-butyl (3R)-3-(3-bromo-4,5-dihydroisoxazol-5-yl)pyrrolidine-1-carboxylate (210 mg, 636.20 µmol, 1 eq) in DCM (6 mL) was added TFA (3.08 g, 27.01 mmol, 2 mL, 42.46 eq) at 25° C. The mixture was stirred at 25° C. for 0.5 h. TLC (PE/EtOAc=2/1, R$_f$=0.05) showed the starting material was consumed completely. The reaction mixture was concentrated under reduced pressure to yield 3-bromo-5-[(3R)-pyrrolidin-3-yl]-4,5-dihydroisoxazole (210 mg, 630.44 µmol, 99.1% yield, N/A purity, TFA) as a colorless gum, which was used in the next step without further purification. $^1$H NMR (400 MHz, CDCl$_3$) δ ppm 4.77 (s, 1H), 3.56-3.38 (m, 4H), 3.30-3.20 (s, 1H), 23.00-2.90 (m, 1H), 2.80-2.70 (m, 1H), 2.05-1.95 (s, 2H).

Step 5: (5S)-3-Bromo-5-[(3R)-1-[[4-(trifluoromethyl)phenyl]methyl]pyrrolidin-3-yl]-4,5-dihydroisoxazole and (5R)-3-bromo-5-[(3R)-1-[[4-(trifluoromethyl)phenyl]methyl]pyrrolidin-3-yl]-4,5-dihydroisoxazole A mixture of 3-bromo-5-[(3R)-pyrrolidin-3-yl]-4,5-dihydroisoxazole (210 mg, 630.44 µmol, 1 eq, TFA), 1-(bromomethyl)-4-(trifluoromethyl)benzene (155 mg, 648.45 µmol, 1.03 eq) and DIEA (407.40 mg, 3.15 mmol, 549.05 µL, 5 eq) in DCM (15 mL) was stirred at 25° C. for 12 h. The mixture was concentrated under reduced pressure to yield a residue which was purified by flash silica gel chromatography (from PE/EtOAc=100/1 to 1/1, TLC: PE/EtOAc=1/1, R$_f$=0.25). The desired compound was concentrated under reduced pressure to yield a residue (98 mg) which was separated by chiral SFC (column: DAICEL CHIRALPAK AD (250 mm*30 mm, 10 um); mobile phase: [0.1% NH$_3$·H$_2$O/EtOH]; B %: 15%-15%) to yield peak 1 and peak 2. Peak 1 was concentrated under reduced pressure to yield a residue which was dissolved in MeCN (10 mL) and water (10 mL) and lyophilized to yield (5S)-3-bromo-5-[(3R)-1-[[4-(trifluoromethyl)phenyl]methyl]pyrrolidin-3-yl]-4,5-dihydroisoxazole (44.31 mg, 117.47 µmol, 18.6% yield, 100.0% purity, SFC: R$_t$=2.488, Dr=96.54%, [α]$^{29.3}_D$=-63.16 (CHCl$_3$, c=0.057 g/100 mL)) as a white solid. $^1$H NMR (500 MHz, CDCl$_3$) δ ppm 7.58 (d, J=7.9 Hz, 2H), 7.45 (d, J=7.9 Hz, 2H), 4.68 (ddd, J=6.5, 8.9, 10.5 Hz, 1H), 3.77-3.60 (m, 2H), 3.29-3.16 (m, 1H), 3.13-3.03 (m, 1H), 2.75-2.66 (m, 1H), 2.65-2.50 (m, 3H), 2.40 (dd, J=5.0, 8.8 Hz, 1H), 2.12-2.01 (m, 1H), 1.68 (dd, J=6.4, 13.4 Hz, 1H); ES-LCMS m/z 377.0, 379.0 [M+H]$^+$. Peak 2 was concentrated under reduced pressure to yield a residue which was dissolved in MeCN (10 mL) and water (10 mL) and lyophilized to yield (5R)-3-bromo-5-[(3R)-1-[[4-(trifluoromethyl)phenyl]methyl]pyrrolidin-3-yl]-4,5-dihydroisoxazole (39.56 mg, 102.47 µmol, 16.3% yield, 97.7% purity, SFC: R$_t$=2.631, Dr=99.62%, [α]$^{29.2}_D$=+53.85 (CHCl$_3$, c=0.052 g/100 mL)) as a white solid. $^1$H NMR (500 MHz, CDCl$_3$) δ ppm 7.59 (d, J=8.1 Hz, 2H), 7.46 (d, J=7.5 Hz, 2H), 4.72-4.64 (m, 1H), 3.75-3.65 (m, 2H), 3.27 (dd, J=10.4, 17.2 Hz, 1H), 2.94 (dd, J=8.4, 17.2 Hz, 1H), 2.76-2.48 (m, 5H), 2.09-1.98 (m, 1H), 1.60-1.50 (m, 1H); ES-LCMS m/z 377.1, 379.1 [M+H]$^+$.

I-59

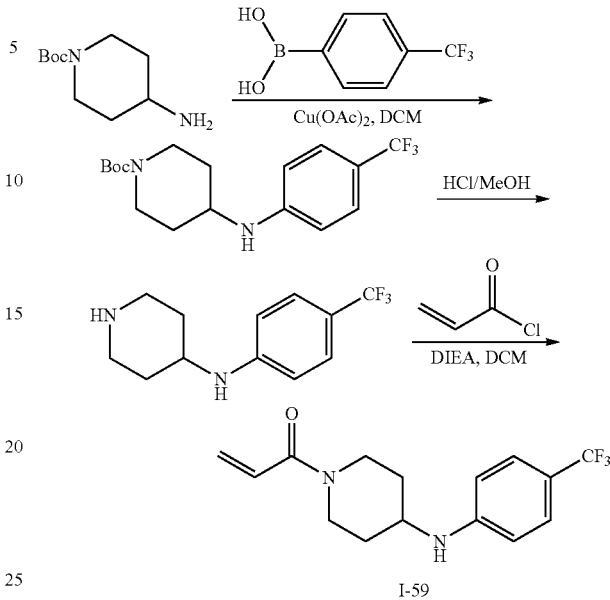

I-59

Step 1: tert-Butyl 4-[4-(trifluoromethyl)anilino]piperidine-1-carboxylate

A mixture of tert-butyl 4-aminopiperidine-1-carboxylate (500 mg, 2.50 mmol, 1 eq), [4-(trifluoromethyl)phenyl] boronic acid (950 mg, 5.00 mmol, 2 eq), Cu(OAc)$_2$ (900 mg, 4.96 mmol, 1.98 eq) and DIEA (1.6 g, 12.38 mmol, 2.16 mL, 4.96 eq) in DCM (5 mL) was degassed and purged with O2 for 3 times and then the mixture was stirred under O$_2$ atmosphere at 28° C. for 12 h. TLC (PE/EtOAc=5/1, R$_f$=0.50) indicated Reactant 1 was consumed and two new spots formed. The reaction mixture was filtered and the filtrate was concentrated under reduced pressure. The residue was diluted with water (20 mL) and extracted with EtOAc (25 mL×3). The combined organic layers were dried over Na$_2$SO$_4$, filtered and concentrated under reduced pressure to yield the residue which was purified by flash silica gel chromatography (from PE/EtOAc=100/1 to 1/1, TLC: PE/EtOAc=5/1, R$_f$=0.50) to yield tert-butyl 4-[4-(trifluoromethyl)anilino]piperidine-1-carboxylate (300 mg, 609.81 µmol, 24.4% yield, 70.0% purity) as a light yellow solid. $^1$H NMR (400 MHz, DMSO-d$_6$) δ ppm 7.32 (d, J=8.6 Hz, 2H), 6.65 (d, J=8.6 Hz, 2H), 6.23 (d, J=7.8 Hz, 1H), 3.84 (d, J=13.2 Hz, 2H), 3.51-3.39 (m, 1H), 2.88 (br s, 2H), 1.89-1.79 (m, 2H), 1.37 (s, 9H), 1.20 (d, J=7.8 Hz, 2H); ES-LCMS m/z 345.2 [M+H]$^+$.

Step 2: N-[4-(Trifluoromethyl)phenyl]piperidin-4-amine

A solution of tert-butyl 4-[4-(trifluoromethyl)anilino]piperidine-1-carboxylate (300 mg, 609.81 µmol, 1 eq) in DCM (3 mL) and TFA (1 mL) was stirred at 28° C. for 1 h. The reaction mixture was diluted with water (10 mL), neutralized with NaHCO$_3$ until pH=7, and extracted with EtOAc (10 mL×3). The combined organic layers were dried over Na$_2$SO$_4$, filtered and concentrated under reduced pressure to yield N-[4-(trifluoromethyl)phenyl]piperidin-4-amine (190 mg, 591.18 µmol, 97.0% yield, 76.0% purity) as a light yellow oil, which was used in the next step without further purification. $^1$H NMR (400 MHz, DMSO-d$_6$) δ 8.34 (br s, 1H), 7.35 (d, J=8.6 Hz, 2H), 6.68 (d, J=8.6 Hz, 2H), 6.40 (d, J=7.8 Hz, 1H), 3.69-3.45 (m, 1H), 2.97 (t, J=11.0 Hz, 2H), 2.00 (d, J=11.2 Hz, 2H), 1.61-1.42 (m, 2H), 1.18 (d, J=17.1 Hz, 2H); ES-LCMS m/z 245.2 [M+H]$^+$.

Step 3: 1-[4-[4-(Trifluoromethyl)anilino]-1-piperidyl]prop-2-en-1-one

To a solution of N-[4-(trifluoromethyl)phenyl]piperidin-4-amine (190 mg, 591.18 μmol, 1 eq) and DIEA (230 mg, 1.78 mmol, 309.97 μL, 3.01 eq) in DCM (5 mL) was added dropwise prop-2-enoyl chloride (60 mg, 662.92 μmol, 54.05 μL, 1.12 eq) at 0° C. The mixture was stirred at 28° C. for 12 h. The mixture was diluted with water (20 mL) and extracted with EtOAc (20 mL×3). The combined organic layers were dried over Na$_2$SO$_4$, filtered and concentrated under reduced pressure to yield the residue which was purified by preparative HPLC (column: Welch Xtimate C18 150*25 mm*5 um; mobile phase: [water (10 mM NH4HCO3)-ACN]; B %: 33%-63%, 10 min) to yield 1-[4-[4-(trifluoromethyl)anilino]-1-piperidyl]prop-2-en-1-one (15.98 mg, 52.60 μmol, 8.9% yield, 98.2% purity) as a white solid. $^1$H NMR (400 MHz, DMSO-d$_6$) δ ppm 7.37 (d, J=8.5 Hz, 2H), 6.84 (dd, J=10.5, 16.6 Hz, 1H), 6.71 (d, J=8.4 Hz, 2H), 6.31 (d, J=8.1 Hz, 1H), 6.11 (dd, J=1.9, 16.7 Hz, 1H), 5.68 (dd, J=1.9, 10.5 Hz, 1H), 4.30 (d, J=13.7 Hz, 1H), 4.02 (d, J=13.1 Hz, 1H), 3.70-3.51 (m, 1H), 3.25 (t, J=12.0 Hz, 1H), 2.92 (t, J=11.8 Hz, 1H), 1.89-2.00 (m, 2H), 1.37-1.18 (m, 2H); ES-LCMS m/z 299.2 [M+H]$^+$.
I-149

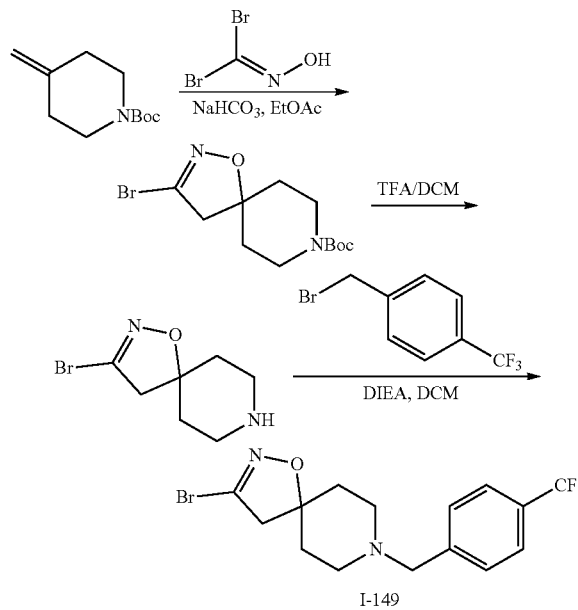

I-149

Step 1: tert-Butyl 3-bromo-1-oxa-2,8-diazaspiro[4.5]dec-2-ene-8-carboxylate

A mixture of tert-butyl 4-methylenepiperidine-1-carboxylate (500 mg, 2.53 mmol, 1 eq), dibromomethanone oxime (616.91 mg, 3.04 mmol, 1.2 eq), NaHCO$_3$ (212.92 mg, 2.53 mmol, 1 eq) in EtOAc (10 mL) was degassed and purged with N$_2$ for 3 times and then the mixture was stirred under N$_2$ atmosphere at 25° C. for 16 h. The mixture was diluted with water (20 mL) and extracted with EtOAc (20 mL×3). The combined organic layers were washed with brine (20 mL), dried over Na$_2$SO$_4$, filtered and concentrated to yield tert-butyl 3-bromo-1-oxa-2,8-diazaspiro[4.5]dec-2-ene-8-carboxylate (530 mg, 1.58 mmol, 62.2% yield, 95.0% purity) as yellow oil, which was used in the next step without further purification. $^1$H NMR (400 MHz, DMSO-d$_6$) δ ppm 3.43-3.39 (m, 4H), 3.14 (s, 2H), 1.69-1.66 (m, 4H), 1.38 (s, 9H); ES-LCMS m/z: 262.9, 264.9 [M-t-Bu+H]$^+$.

Step 2: 3-Bromo-1-oxa-2,8-diazaspiro[4.5]dec-2-ene

A mixture of tert-butyl 3-bromo-1-oxa-2,8-diazaspiro[4.5]dec-2-ene-8-carboxylate (530 mg, 1.58 mmol, 1 eq), TFA (179.86 mg, 1.58 mmol, 116.79 μL, 1 eq) in DCM (5 mL) was degassed and purged with N$_2$ for 3 times and then the mixture was stirred under N$_2$ atmosphere at 25° C. for 2 h. The reaction mixture was concentrated to yield 3-bromo-1-oxa-2, 8-diazaspiro[4.5]dec-2-ene (300 mg, 1.10 mmol, 69.5% yield, 80.0% purity) as yellow oil which was used in the next step without further purification. ES-LCMS m/z: 219.1, 221.1[M+H]$^+$.

Step 3: 3-Bromo-8-[[4-(trifluoromethyl)phenyl]methyl]-1-oxa-2,8-diazaspiro[4.5]dec-2-ene A mixture of 3-bromo-1-oxa-2,8-diazaspiro[4.5]dec-2-ene (150 mg, 547.75 μmol, 1 eq), 1-(bromomethyl)-4-(trifluoromethyl)benzene (130.93 mg, 547.75 μmol, 10.56 μL, 1 eq) and DIEA (283.17 mg, 2.19 mmol, 381.63 μL, 4 eq) in DCM (5 mL) was degassed and purged with N$_2$ for 3 times and then the mixture was stirred under N$_2$ atmosphere at 25° C. for 12 h. TLC (PE/EtOAc=1/1, R$_f$=0.52) showed the staring material was consumed completely and one new spot was formed. The reaction mixture was concentrated to give a residue which was purified by preparative HPLC (column: Agela DuraShell C18 150*25 mm*5 um; mobile phase: [water 0.05% NH$_3$·H$_2$O+10 mM NH$_4$HCO$_3$)-CAN]; B %: 52%-67%, 14 min) and then by preparative TLC (SiO$_2$, PE/EtOAc=1/1, R$_f$=0.52) to yield 3-bromo-8-[[4-(trifluoromethyl)phenyl]methyl]-1-oxa-2,8-diazaspiro[4.5]dec-2-ene (24.99 mg, 66.25 μmol, 12.1% yield, 100.0% purity) as a white solid. $^1$H NMR (400 MHz, CDCl$_3$) δ ppm 7.57 (d, J=8.4 Hz, 2H), 7.44 (d, J=8.4 Hz, 2H), 3.57 (s, 2H), 2.95 (s, 2H), 2.57-2.48 (m, 4H), 1.98-1.95 (m, 2H), 1.83-1.79 (m, 2H); ES-LCMS m/z: 377.1, 379.1 [M+H]$^+$.
I-60

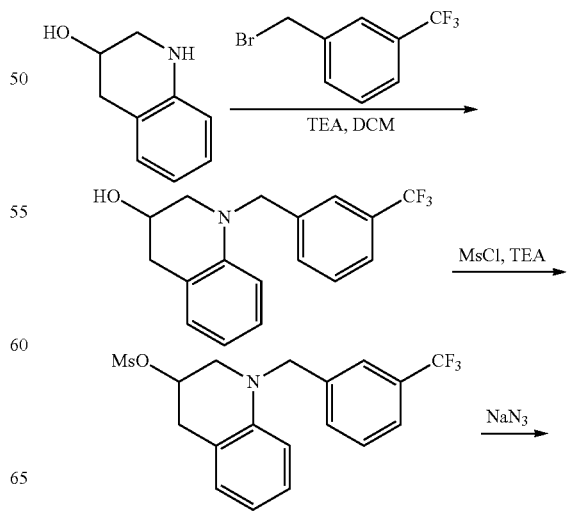

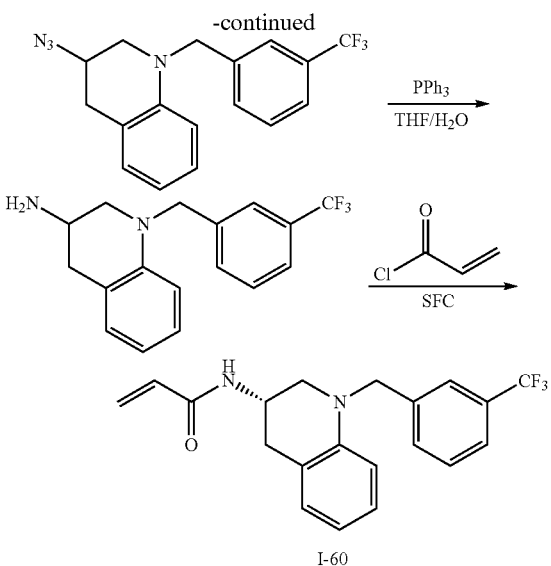

I-60

Step 1: 1-[[3-(Trifluoromethyl)phenyl]methyl]-3,4-dihydro-2H-quinolin-3-ol

To a solution of 1,2,3,4-tetrahydroquinolin-3-ol (500 mg, 3.35 mmol, 1 eq) and 1-(bromomethyl)-3-(trifluoromethyl)benzene (3.20 g, 13.41 mmol, 2.04 mL, 4 eq) in THF (20 mL) was added TEA (3.39 g, 33.51 mmol, 4.66 mL, 10 eq). The mixture was stirred at 25° C. for 12 h. TLC (PE/EtOAc=3/1, $R_f$=0.65) indicated about half of the starting material was remained and one new spot formed. The reaction mixture was concentrated to yield a residue which was purified by flash silica gel chromatography (from PE/EtOAc=1/0 to 3/1, TLC: PE/EtOAc=3/1, $R_f$=0.65) to yield 1-[[3-(trifluoromethyl)phenyl]methyl]-3,4-dihydro-2H-quinolin-3-ol (200 mg, 618.27 μmol, 18.4% yield, 95.0% purity) as yellow oil. $^1$H NMR (500 MHz, CDCl$_3$) δ ppm 7.83-7.64 (m, 4H), 7.33-7.27 (m, 2H), 6.94 (dt, J=0.6, 7.3 Hz, 1H), 6.78 (d, J=8.1 Hz, 1H), 4.88-4.74 (m, 2H), 4.64-4.51 (m, 1H), 3.80-3.70 (m, 1H), 3.55 (ddd, J=1.8, 5.4, 11.5 Hz, 1H), 3.38 (dd, J=3.8, 16.0 Hz, 1H), 3.12 (dd, J=4.4, 16.0 Hz, 1H).

Step 2: [1-[[3-(Trifluoromethyl)phenyl]methyl]-3,4-dihydro-2H-quinolin-3-yl]methanesulfonate To a solution of 1-[[3-(trifluoromethyl)phenyl]methyl]-3,4-dihydro-2H-quinolin-3-ol (200 mg, 618.27 μmol, 1 eq) and TEA (312.81 mg, 3.09 mmol, 430.28 μL, 5 eq) in THF (6 mL) was added MsCl (170 mg, 1.48 mmol, 114.86 μL, 2.40 eq) under N$_2$. The mixture was stirred at 30° C. for 2 h. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield [1-[[3-(trifluoromethyl)phenyl]methyl]-3,4-dihydro-2H-quinolin-3-yl] methanesulfonate (170 mg, crude) as a yellow solid, which was used in the next step without further purification. $^1$H NMR (500 MHz, CDCl$_3$) δ ppm 7.60-7.42 (m, 4H), 7.09-7.00 (m, 2H), 6.71 (t, J=7.3 Hz, 1H), 6.52 (d, J=8.2 Hz, 1H), 5.40-5.23 (m, 1H), 4.71-4.43 (m, 2H), 3.69-3.63 (m, 1H), 3.61-3.55 (m, 1H), 3.31-3.24 (m, 1H), 3.19-3.12 (m, 1H), 3.03 (s, 3H); ES-LCMS m/z 386.0 [M+H]$^+$.

Step 3: 3-Azido-1-[[3-(trifluoromethyl)phenyl]methyl]-3,4-dihydro-2H-quinoline To a solution of [1-[[3-(trifluoromethyl)phenyl]methyl]-3,4-dihydro-2H-quinolin-3-yl] methanesulfonate (170 mg, 441.10 μmol, 1 eq) in DMF (3 mL) was added NaN$_3$ (86.03 mg, 1.32 mmol, 3 eq) under N$_2$. The mixture was stirred at 80° C. for 1 h. The reaction mixture was quenched by addition of sat. aq. NaHCO$_3$ (20 mL), extracted with DCM (30 mL×3). The combined organic layers were dried over Na$_2$SO$_4$, filtered and concentrated under reduced pressure to remove about 80 mL DCM, and then THF (30 mL) was added to the above solution. The solution was concentrated (until about 3 mL THF remained) to yield 3-azido-1-[[3-(trifluoromethyl)phenyl]methyl]-3,4-dihydro-2H-quinoline (146 mg, 439.33 μmol, 99.6% yield, N/A purity) in THF (3 mL) as a brown liquid, which was used in next step directly without further purification. ES-LCMS m/z 333.0 [M+H]$^+$.

Step 4: 1-[[3-(Trifluoromethyl)phenyl]methyl]-3,4-dihydro-2H-quinolin-3-amine To a solution of 3-azido-1-[[3-(trifluoromethyl)phenyl]methyl]-3,4-dihydro-2H-quinoline (146 mg, 439.33 μmol, 1 eq) in THF (3 mL) and H$_2$O (0.3 mL) was added PPh$_3$ (230.46 mg, 878.66 μmol, 2 eq). The mixture was stirred at 25° C. for 12 h. The reaction mixture was concentrated. The residue was purified by flash silica gel chromatography (from DCM/MeOH=1/0 to 10/1, TLC: DCM/MeOH=10/1, $R_f$=0.27) to yield 1-[[3-(trifluoromethyl)phenyl]methyl]-3,4-dihydro-2H-quinolin-3-amine (80 mg, 247.58 μmol, 56.3% yield, 94.8% purity) as yellow oil. $^1$H NMR (400 MHz, CDCl$_3$) δ ppm 7.53-7.42 (m, 4H), 7.03 (d, J=7.0 Hz, 2H), 6.69-6.62 (m, 1H), 6.51 (d, J=7.8 Hz, 1H), 4.63-4.46 (m, 2H), 3.75 (t, J=6.7 Hz, 1H), 3.51-3.40 (m, 2H), 3.09 (d, J=17.2 Hz, 1H), 2.69 (dd, J=7.2, 15.5 Hz, 1H); ES-LCMS m/z 307.1 [M+H]$^+$.

Step 5: N-[(3S)-1-[[3-(Trifluoromethyl)phenyl]methyl]-3,4-dihydro-2H-quinolin-3-yl]prop-2-enamide To a solution of 1-[[3-(trifluoromethyl)phenyl]methyl]-3,4-dihydro-2H-quinolin-3-amine (80 mg, 247.58 μmol, 1 eq) in THF (5 mL) was added TEA (75.16 mg, 742.74 μmol, 103.38 μL, 3 eq) and prop-2-enoyl chloride (44.82 mg, 495.16 μmol, 40.37 μL, 2 eq). The mixture was stirred at 25° C. for 1 h. The reaction mixture was concentrated. The residue was purified by flash silica gel chromatography (from PE/EtOAc=1/0 to 3/1, TLC: PE/EtOAc=1/1, $R_f$=0.52) to yield a product, which was separated by SFC (column: DAICEL CHIRALPAK AD (250 mm*30 mm, 10 μm); mobile phase: [0.1% NH$_3$H$_2$O ETOH]; B %: 20%-20%, min) to yield peak 1 (2.919) and peak 2 (3.182). Peak 2 was concentrated under reduced pressure to yield a residue which was dissolved in MeCN (20 mL) and H$_2$O (10 mL) and lyophilized to yield N-[(3S)-1-[[3-(trifluoromethyl)phenyl]methyl]-3,4-dihydro-2H-quinolin-3-yl]prop-2-enamide (19.79 mg, 54.53 μmol, 22.0% yield, 99.3% purity) (SFC: $R_t$=3.260, ee=100%, $[α]^{28.3}_D$=−80.702 (MeOH, c=0.057 g/100 mL)) as a white solid. $^1$H NMR (400 MHz, CDCl$_3$) δ ppm 7.59-7.46 (m, 2H), 7.43 (d, J=5.1 Hz, 2H), 7.12-7.00 (m, 2H), 6.71 (t, J=7.0 Hz, 1H), 6.57 (d, J=8.2 Hz, 1H), 6.28 (dd, J=1.2, 16.8 Hz, 1H), 6.12-5.97 (m, 1H), 5.84 (d, J=8.2 Hz, 1H), 5.64 (dd, J=1.2, 10.2 Hz, 1H), 4.70-4.60 (m, 1H), 4.59-4.46 (m, 2H), 3.59 (d, J=11.3 Hz, 1H), 3.43-3.32 (m, 1H), 3.22 (dd, J=4.5, 16.2 Hz, 1H), 2.82 (d, J=16.4 Hz, 1H); ES-LCMS m/z 361.2 [M+H]⁺.

I-119 & I-120

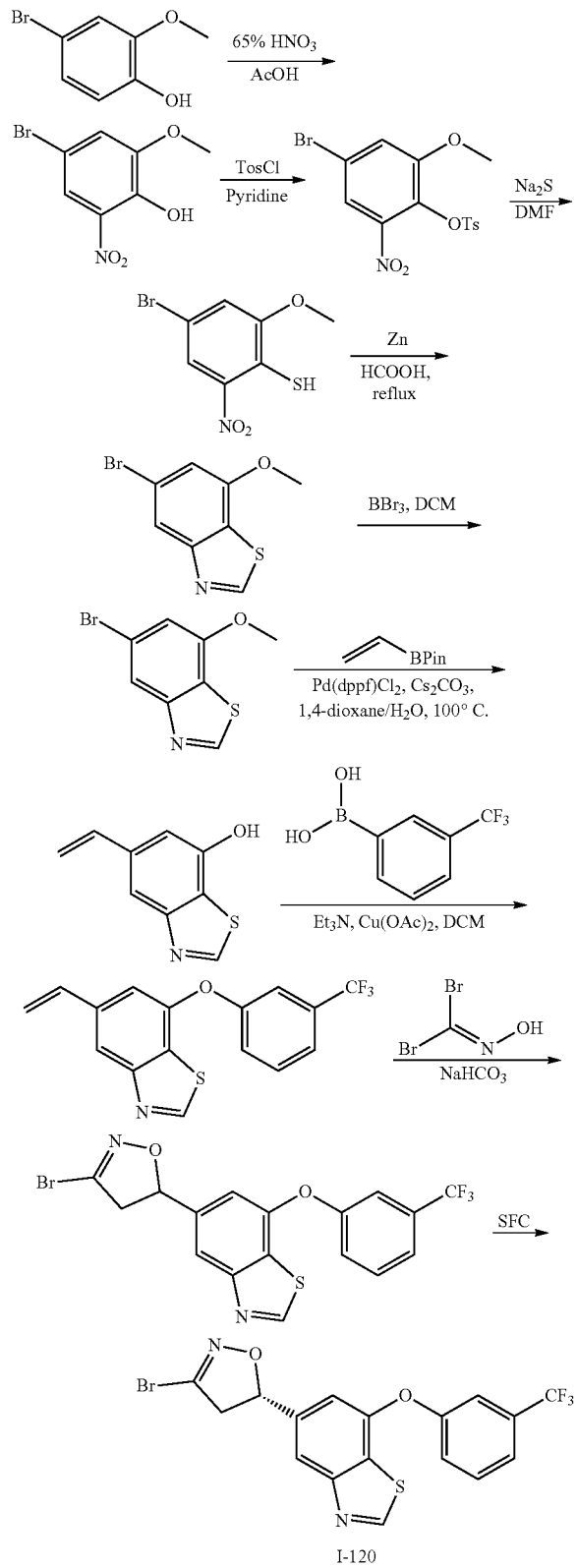

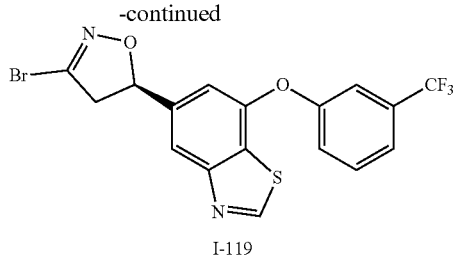

Step 1: 4-Bromo-2-methoxy-6-nitro-phenol

To a solution of 4-bromo-2-methoxy-phenol (5 g, 24.63 mmol, 1 eq) in AcOH (75 mL) was added HNO₃ (2.74 g, 29.55 mmol, 68% purity, 1.2 eq) with stirred at 0° C. under N₂. The mixture was allowed to warm to room temperature (25° C.) with stirred for 1 h under N₂. TLC (PE/EtOAc=4/1, R_f=0.6) showed that new point was formed and start material was consumed completely. The mixture was poured into ice water (150 mL) with stirred at 0° C. for 15 min. The mixture was extracted with EtOAc (150 mL×3). The combined organic layer was dried over Na₂SO₄, filtrated and concentrated to yield 4-bromo-2-methoxy-6-nitro-phenol (6.1 g, 22.13 mmol, 89.9% yield, 90.0% purity) as a white solid, which was used in the next step without further purification. ES-LCMS m/z no desired MS found.

Step 2: (4-Bromo-2-methoxy-6-nitro-phenyl) 4-methylbenzenesulfonate

To a solution of 4-bromo-2-methoxy-6-nitro-phenol (6.1 g, 22.13 mmol, 1 eq) in DCM (10 mL) was added pyridine (35.87 g, 453.45 mmol, 36.60 mL, 20.49 eq) and 4-methylbenzenesulfonyl chloride (10.55 g, 44.27 mmol, 2.0 eq). The mixture was stirred at 25° C. for 15 h. TLC (PE/EtOAc=4/1, R_f=0.4) indicated start material was consumed completely and one new spot formed. The reaction mixture was quenched by addition of H₂O (20 mL) at 25° C. and extracted with EtOAc (30 mL×3). The combined organic layers were washed with brine (30 mL), dried over Na₂SO₄, filtered and concentrated under reduced pressure to yield a residue which was purified by flash silica gel chromatography (from PE/EtOAc=10/1, TLC: PE/EtOAc=4/1, R_f=0.4) to yield (4-bromo-2-methoxy-6-nitro-phenyl) 4-methylbenzenesulfonate (1.48 g, 3.50 mmol, 15.8% yield, 95.0% purity) as a white solid.

Step 3: 4-Bromo-2-methoxy-6-nitro-benzenethiol

To a solution of (4-bromo-2-methoxy-6-nitro-phenyl) 4-methylbenzenesulfonate (1.48 g, 3.50 mmol, 1 eq) in DMF (15 mL) was added Na₂S.9H₂O (1.26 g, 5.24 mmol, 880.68 µL, 1.5 eq) with stirred under N₂·atmosphere. The mixture was stirred under N₂ atmosphere at 28° C. for 15 h. TLC (PE/EtOAc=3/1, R_f=0.72) showed that new point was formed and start material was consumed completely. The reaction mixture was quenched by addition of H₂O (20 mL) and extracted with EtOAc (20 mL×3). The combined organic layers were washed with brine (20 mL), dried over Na₂SO₄, filtered and concentrated under reduced pressure to yield 4-bromo-2-methoxy-6-nitro-benzenethiol (1.08 g, 3.48 mmol, 99.4% yield, 85.0% purity) as a yellow solid, which was used in the next step without further purification.

Step 4: 5-Bromo-7-methoxy-1,3-benzothiazole

To a solution of 4-bromo-2-methoxy-6-nitro-benzenethiol (1.08 g, 3.48 mmol, 1 eq) in HCOOH (20 mL) was added Zn (1.14 g, 17.38 mmol, 5 eq) with stirred under $N_2$ atmosphere. The mixture was stirred under $N_2$ atmosphere at 110° C. for 15 h. TLC (PE/EtOAc=3/1, $R_f$=0.72) showed that new point was formed and start material was consumed completely. The reaction mixture was quenched by addition of $H_2O$ (20 mL) and extracted with EtOAc (20 mL×3). The combined organic layers were washed with brine (20 mL), dried over $Na_2SO_4$, filtered and concentrated under reduced pressure to yield 5-bromo-7-methoxy-1,3-benzothiazole (820 mg, 3.19 mmol, 91.8% yield, 95.0% purity) as a black oil, which was used in the next step without further purification.

Step 5: 5-Bromo-1,3-benzothiazol-7-ol

To a solution of 5-bromo-7-methoxy-1, 3-benzothiazole (820 mg, 3.19 mmol, 1 eq) in DCM (15 mL) was added $BBr_3$ (799.46 mg, 3.19 mmol, 307.49 μL, 1 eq) with stirred at −60° C. under $N_2$ atmosphere. The mixture was stirred under $N_2$ atmosphere at 28° C. for 15 h. TLC (PE/EtOAc=3/1, $R_f$=0.47) showed that new point was formed and start material was consumed completely. The reaction mixture was poured into ice water (20 mL) and extracted with EtOAc (30 mL×3). The combined organic layers were washed with brine (30 mL), dried over $Na_2SO_4$ and concentrated under reduced pressure to give a residue which was purified by preparative TLC (PE/EtOAc=2/1, TLC: PE/EtOAc=3/1, $R_f$=0.47) to yield 5-bromo-1,3-benzothiazol-7-ol (258 mg, 1.12 mmol, 35.1% yield, 100.0% purity) as a black solid. $^1H$ NMR (400 MHz, DMSO-$d_6$) δ ppm 9.35 (s, 1H), 7.69 (d, J=1.6 Hz, 1H), 6.96 (d, J=1.6 Hz, 1H); ES-LCMS m/z 231.7 $[M+H]^+$.

Step 6: 5-Vinyl-1,3-benzothiazol-7-ol

To a solution of 5-bromo-1,3-benzothiazol-7-ol (258 mg, 1.12 mmol, 1 eq) and 4,4,5,5-tetramethyl-2-vinyl-1,3,2-dioxaborolane (259.05 mg, 1.68 mmol, 285.30 μL, 1.5 eq) in 1,4-dioxane (2 mL) and $H_2O$ (0.5 mL) was added Pd(dppf)$Cl_2$ (82.05 mg, 112.13 μmol, 0.1 eq) and $Cs_2CO_3$ (548.03 mg, 1.68 mmol, 1.5 eq) with stirred at 35° C. under $N_2$ atmosphere. The mixture was stirred under $N_2$ atmosphere at 110° C. for 10 h. TLC (PE/EtOAc=3/1, $R_f$=0.5) showed that new point was formed and start material was consumed completely. The reaction mixture was quenched by addition of $H_2O$ (20 mL) and extracted with EtOAc (30 mL×3). The combined organic layers were washed with brine (30 mL), dried over $Na_2SO_4$, filtered and concentrated under reduced pressure to give a residue which was purified by preparative TLC (PE/EtOAc=3/1, TLC (PE/EtOAc=3/1, $R_f$=0.5)) to yield 5-vinyl-1, 3-benzothiazol-7-ol (180 mg, 812.54 μmol, 72.5% yield, 80.0% purity) as a white solid. $^1H$ NMR (500 MHz, DMSO-$d_6$) δ ppm 10.64 (s, 1H), 9.36-9.28 (m, 1H), 7.66 (s, 1H), 7.01 (s, 1H), 6.83 (dd, J=11.5, 17.5 Hz, 1H), 5.84 (d, J=17.5 Hz, 1H), 5.31 (d, J=11.0 Hz, 1H).

Step 7: 7-[3-(Trifluoromethyl)phenoxy]-5-vinyl-1,3-benzothiazole

To a solution of 5-vinyl-1,3-benzothiazol-7-ol (170 mg, 767.40 μmol, 1 eq) and [3-(trifluoromethyl)phenyl]boronic acid (437.25 mg, 2.30 mmol, 3.0 eq) in DCM (110 mL) was added Cu(OAc)$_2$ (278.77 mg, 1.53 mmol, 2 eq) and $Et_3N$ (388.26 mg, 3.84 mmol, 534.06 μL, 5 eq). The mixture was stirred under $O_2$ (15 Psi) at 35° C. for 10 h. TLC (PE/EtOAc=3/1, $R_f$=0.6) showed that new point was formed and start material was consumed completely. The reaction mixture was quenched by addition of $H_2O$ (20 mL) and extracted with EtOAc (30 mL×3). The combined organic layers were washed with brine (30 mL), dried over $Na_2SO_4$, filtered and concentrated under reduced pressure to give a residue which was purified by preparative TLC (PE/EtOAc=1/1, TLC: PE/EtOAc=3/1, $R_f$=0.6) to yield 7-[3-(trifluoromethyl)phenoxy]-5-vinyl-1,3-benzothiazole (65 mg, 149.70 μmol, 19.5% yield, 74.0% purity) as a white solid. $^1H$ NMR (500 MHz, CDCl$_3$) δ ppm 9.05 (s, 1H), 7.98 (s, 1H), 7.53-7.48 (m, 1H), 7.36 (s, 1H), 7.20 (d, J=7.5 Hz, 1H), 7.11 (s, 1H), 7.01 (d, J=8.0 Hz, 1H), 6.82 (dd, J=11.0, 17.0 Hz, 1H), 5.79 (d, J=17.5 Hz, 1H), 5.36 (d, J=11.0 Hz, 1H); ES-LCMS m/z 321.9 $[M+H]^+$.

Step 8: 3-Bromo-5-[7-[3-(trifluoromethyl)phenoxy]-1,3-benzothiazol-5-yl]-4,5-dihydroisoxazole To a solution of 7-[3-(trifluoromethyl)phenoxy]-5-vinyl-1,3-benzothiazole (55 mg, 126.67 μmol, 1 eq) in EtOAc (10 mL) was added NaHCO$_3$ (106.41 mg, 1.27 mmol, 49.27 μL, 10 eq) and dibromomethanone oxime (28.26 mg, 139.33 μmol, 1.1 eq). The mixture was stirred at 30° C. for 10 h. TLC (PE/EtOAc=3/1, $R_f$=0.7) showed that new point was formed and start material was consumed completely. The reaction mixture was quenched by addition of $H_2O$ (5 mL) and extracted with EtOAc (10 mL×3). The combined organic layers were washed with brine (10 mL), dried over $Na_2SO_4$, filtered and concentrated under reduced pressure to give a residue which was purified by preparative TLC (PE/EtOAc=3/1, TLC: PE/EtOAc=3/1, $R_f$=0.70) to yield 3-bromo-5-[7-[3-(trifluoromethyl)phenoxy]-1,3-benzothiazol-5-yl]-4,5-dihydroisoxazole (58 mg, 123.00 μmol, 97.1% yield, 94.0% purity) as a white solid. $^1H$ NMR (500 MHz, CDCl$_3$) δ ppm 9.04 (s, 1H), 7.93 (s, 1H), 7.56-7.43 (m, 2H), 7.24-7.18 (m, 1H), 7.00 (s, 1H), 5.80 (dd, J=8.5, 10.5 Hz, 1H), 3.74-3.64 (m, 1H), 3.26-3.19 (m, 1H); ES-LCMS m/z 443.0 [M+H]

Step 9: (5R)-3-Bromo-5-[7-[3-(trifluoromethyl)phenoxy]-1,3-benzothiazol-5-yl]-4,5-dihydroisoxazole and (5S)-3-bromo-5-[7-[3-(trifluoromethyl)phenoxy]-1,3-benzothiazol-5-yl]-4,5-dihydroisoxazole 3-Bromo-5-[7-[3-(trifluoromethyl)phenoxy]-1,3-benzothiazol-5-yl]-4,5-dihydroisoxazole (58 mg, 123.00 μmol, 1 eq) was separated by SFC (column: REGIS (s,s) WHELK-01 (250 mm*30 mm, 5 μm); mobile phase: [0.1% NH$_3$H$_2$O/EtOH]; B %: 35%-35%, min) to yield peak 1 and peak 2. Peak 1 was concentrated under reduced pressure to yield a residue which was dissolved in MeCN (15 mL) and water (15 mL) and lyophilized to yield (5R)-3-bromo-5-[7-[3-(trifluoromethyl)phenoxy]-1,3-benzothiazol-5-yl]-4,5-dihydroisoxazole (17.89 mg, 38.74 μmol, 31.5% yield, 95.9% purity, SFC: $R_t$=3.100, ee=100%, $[α]^{28.4}_D$=−92.857 (MeOH, c=0.028 g/100 mL)) as colorless oil. $^1H$ NMR (400 MHz, CD$_3$OD) δ ppm 9.30 (s, 1H), 7.94 (s, 1H), 7.66-7.58 (m, 1H), 7.55-7.49 (m, 1H), 7.40 (s, 1H), 7.33 (d, J=8.0 Hz, 1H), 7.09 (s, 1H), 5.89-5.84 (m, 1H), 3.84-3.77 (m, 1H), 3.27-3.28 (m, 1H); ES-LCMS m/z 444.8 $[M+H]^+$. Peak 2 was concentrated under reduced pressure to yield a residue which was dissolved in MeCN (15 mL) and water (15 mL) and lyophilized to yield (5S)-3-bromo-5-[7-[3-(trifluoromethyl)phenoxy]-1,3-benzothiazol-5-yl]-4,5-dihydroisoxazole (14.54 mg, 32.47 μmol, 26.4% yield, 98.9% purity, SFC: $R_t$=3.547, ee=100%, $[\alpha]^{28.4}_D$=+92.308 (MeOH, c=0.026 g/100 mL)) as colorless oil. $^1$H NMR (400 MHz, CD$_3$OD) δ ppm 9.30 (s, 1H), 7.94 (s, 1H), 7.66-7.58 (m, 1H), 7.56-7.50 (m, 1H), 7.40 (s, 1H), 7.33 (d, J=8.0 Hz, 1H), 7.09 (s, 1H), 5.89-5.84 (m, 1H), 3.84-3.76 (m, 1H), 3.28-3.25 (m, 1H); ES-LCMS m/z 442.9 [M+H]$^+$.

I-61

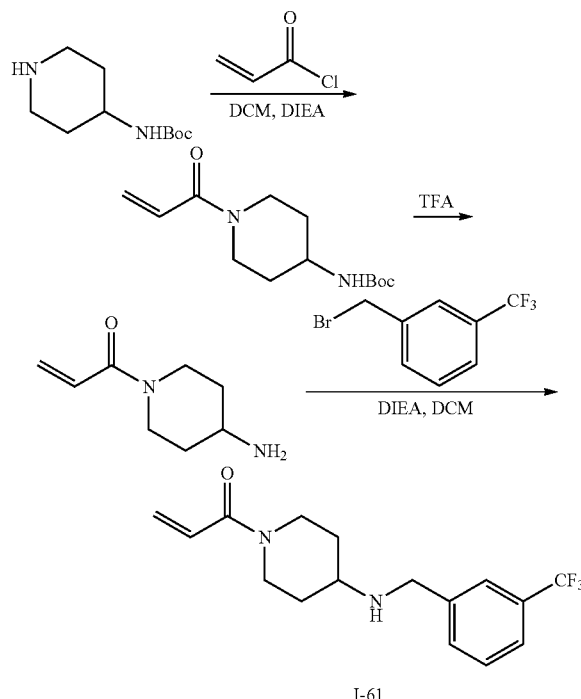

I-61

Step 1: tert-Butyl N-(1-prop-2-enoyl-4-piperidyl)carbamate

To a solution of tert-butyl N-(4-piperidyl)carbamate (2 g, 9.99 mmol, 1 eq) in DCM (25 mL) was added DIEA (1.29 g, 9.99 mmol, 1.74 mL, 1 eq) and prop-2-enoyl chloride (1.08 g, 11.98 mmol, 977.11 μL, 1.2 eq). The mixture was stirred at 25° C. for 1 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=1/1, $R_f$=0.30) to yield tert-butyl N-(1-prop-2-enoyl-4-piperidyl)carbamate (1.65 g, 6.40 mmol, 64.1% yield, 98.7% purity) as a light yellow solid. $^1$H NMR (500 MHz, DMSO-d$_6$) δ ppm 6.86 d, J=7.8 Hz, 1H), 6.79 (dd, J=10.5, 16.6 Hz, 1H), 6.07 (dd, J=2.4, 16.6 Hz, 1H), 5.64 (dd, J=2.4, 10.5 Hz, 1H), 4.25 (d, J=12.8 Hz, 1H), 3.95 (d, J=13.4 Hz, 1H), 3.49 (d, J=7.5 Hz, 1H), 3.17-3.02 (m, 1H), 2.75 (t, J=11.7 Hz, 1H), 1.75-1.73 (m, 2H), 1.38 (s, 9H), 1.27-1.17 (m, 2H); ES-LCMS m/z 255.2 [M+H]$^+$.

Step 2: 1-(4-Amino-1-piperidyl)prop-2-en-1-one

To a solution of tert-butyl N-(1-prop-2-enoyl-4-piperidyl)carbamate (300 mg, 1.16 mmol, 1 eq) in DCM (6 mL) was added TFA (3.08 g, 27.01 mmol, 2 mL, 23.20 eq). The mixture was stirred at 25° C. for 1 h under N$_2$ atmosphere. The reaction mixture was concentrated to yield 1-(4-amino-1-piperidyl)prop-2-en-1-one (300 mg, 1.06 mmol, 91.3% yield, 95.0% purity, TFA) as yellow oil which was used in the next step without further purification. $^1$H NMR (500 MHz, DMSO-d$_6$) δ ppm 7.93 (s, 2H), 6.81 (dd, J=10.5, 16.6 Hz, 1H), 6.10 (dd, J=2.3, 16.8 Hz, 1H), 5.69 (dd, J=2.3, 10.5 Hz, 1H), 4.41 (d, J=12.1 Hz, 1H), 4.08 (d, J=13.3 Hz, 1H), 3.28 (dt, J=5.4, 10.5 Hz, 1H), 3.10 (t, J=12.8 Hz, 1H), 2.74-2.62 (m, 1H), 1.92 (d, J=11.7 Hz, 2H), 1.35 (t, J=12.5 Hz, 2H).

Step 3: Ethyl 3-[[3-(4-isopropylthiazole-2-carbonyl)-1H-indol-6-yl]oxy]propanoate To a solution of (6-hydroxy-1H-indol-3-yl)-(4-isopropylthiazol-2-yl)methanone (120 mg, 387.64 μmol, 1 eq) and ethyl 3-bromopropanoate (84.21 mg, 465.17 μmol, 1.2 eq) in DMF (5 mL) was added Cs$_2$CO$_3$ (378.90 mg, 1.16 mmol, 3 eq). The mixture was stirred at 55° C. for 6 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=1/1, $R_f$=0.55) to yield ethyl 3-[[3-(4-isopropylthiazole-2-carbonyl)-1H-indol-6-yl]oxy]propanoate (160 mg, 252.96 μmol, 65.3% yield, 61.1% purity) as brown oil. $^1$H NMR (500 MHz, DMSO-d$_6$) δ ppm 7.71 (s, 1H), 7.65 (d, J=7.2 Hz, 1H), 7.59-7.51 (m, 2H), 6.80 (dd, J=10.5, 16.6 Hz, 1H), 6.06 (dd, J=2.4, 16.7 Hz, 1H), 5.64 (dd, J=2.4, 10.5 Hz, 1H), 4.18 (d, J=12.4 Hz, 1H), 3.93 (d, J=13.9 Hz, 1H), 3.81 (s, 2H), 3.10 (t, J=11.4 Hz, 1H), 2.81 (t, J=11.0 Hz, 1H), 2.64-2.61 (m, 1H), 2.45 (s, 1H), 1.85-1.83 (m, 2H), 1.22-1.14 (m, 2H); ES-LCMS m/z 313.2 [M+H]$^+$.

I-43

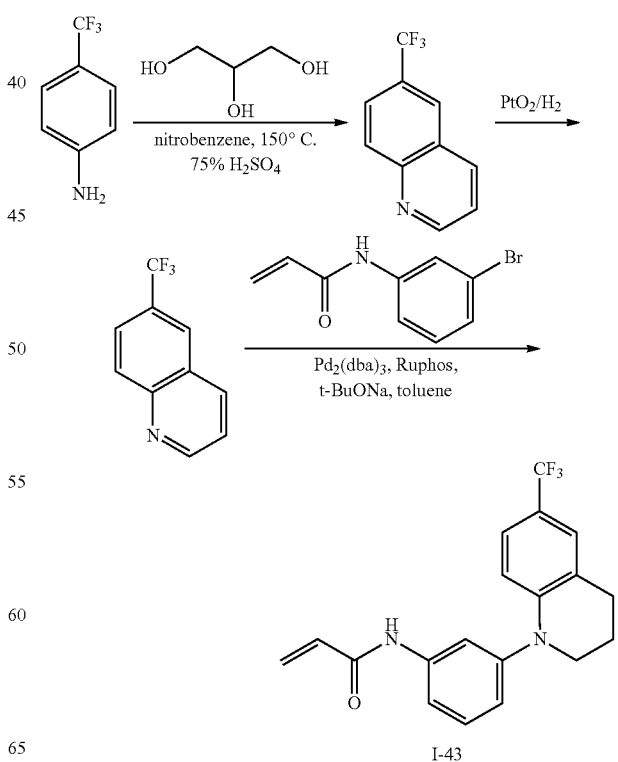

I-43

Step 1: 6-(Trifluoromethyl)quinoline

To a stirred solution of 4-(trifluoromethyl)aniline (2 g, 12.41 mmol, 1.54 mL, 1 eq) in sulfuric acid (55.20 g, 422.10 mmol, 30 mL, 75% purity, 34.01 eq) was added nitrobenzene (1.53 g, 12.41 mmol, 1.27 mL, 1 eq) and glycerol (2.86 g, 31.03 mmol, 2.32 mL, 2.5 eq). The reaction mixture was stirred at 150° C. for 3 h. The reaction mixture was poured into ice-water (200 mL) then stirred at 28° C. for 1 h. The mixture was filtered and the filtrate was extracted with EtOAc (100 mL×5). The combined organic layers were washed with saturated NaCl solution (100 mL×2), dried over $Na_2SO_4$, filtered and the filtrate was concentrated to yield a residue which was purified by flash silica gel chromatography (from PE/EtOAc=100/1 to 3/1, TLC: PE/EtOAc=3/1, $R_f$=0.25) to yield 6-(trifluoromethyl)quinoline (1.8 g, 9.13 mmol, 73.5% yield, 100.0% purity) as yellow oil. $^1$H NMR (400 MHz, $CDCl_3$) δ ppm 9.05 (dd, J=1.7, 4.2 Hz, 1H), 8.26 (dd, J=8.6, 13.7 Hz, 2H), 8.17 (s, 1H), 7.91 (dd, J=1.8, 8.9 Hz, 1H), 7.53 (dd, J=4.2, 8.3 Hz, 1H).

Step 2: 6-(Trifluoromethyl)-1,2,3,4-tetrahydroquinoline

To a stirred solution of 6-(trifluoromethyl)quinoline (1.1 g, 5.54 mmol, 1 eq) in MeOH (10 mL) was added $PtO_2$ (100 mg, 440.37 μmol) slowly. The reaction mixture was stirred at 28° C. for 12 h under $H_2$ atmosphere (50 psi). TLC (PE/EtOAc=1/1, $R_f$=0.30) showed the starting material was consumed completely and one new spot was detected. The reaction mixture was filtered through a pad of celite. The filtrate was concentrated under reduced pressure to yield 6-(trifluoromethyl)-1,2,3,4-tetrahydroquinoline (800 mg, 3.78 mmol, 68.2% yield, 95.0% purity) as yellow oil which was used in the next step without further purification. $^1$H NMR (400 MHz, $CDCl_3$) δ ppm 7.22-7.15 (m, 2H), 6.45 (d, J=9.0 Hz, 1H), 4.16 (s, 1H), 3.37-3.33 (m, 2H), 2.78 (t, J=6.4 Hz, 2H), 1.98-1.92 (m, 2H).

Step 3: N-(3-Bromophenyl)prop-2-enamide

To a stirred solution of 3-bromoaniline (2 g, 11.63 mmol, 1.27 mL, 1 eq) in DCM (20 mL) was added DIEA (4.51 g, 34.88 mmol, 6.08 mL, 3 eq) and prop-2-enoyl chloride (1.05 g, 11.63 mmol, 948.00 μL, 1 eq). The reaction mixture was stirred at 29° C. for 1 h. TLC (PE/EtOAc=3/1, $R_f$=0.30) showed the starting material was consumed completely and one new spot was detected. The reaction mixture was concentrated under reduced pressure to yield a residue which was purified by flash silica gel chromatography (from PE/EtOAc=100/1 to 3/1, TLC: PE/EtOAc=3/1, $R_f$=0.3) to yield N-(3-bromophenyl)prop-2-enamide (2.3 g, 10.17 mmol, 87.5% yield, 100.0% purity) as white solid. $^1$H NMR (500 MHz, DMSO-$d_6$) δ ppm 10.43-10.20 (m, 1H), 8.03 (t, J=1.8 Hz, 1H), 7.55 (td, J=1.6, 7.8 Hz, 1H), 7.38-7.19 (m, 2H), 6.48-6.35 (m, 1H), 6.33-6.23 (m, 1H), 5.79 (dd, J=2.0, 10.1 Hz, 1H); ES-LCMS m/z 226.0, 228.0 [M+H]$^+$.

Step 4: N-[4-[4-(Trifluoromethyl)anilino]cyclohexyl]prop-2-enamide

To a solution of 6-(trifluoromethyl)-1,2,3,4-tetrahydroquinoline (300 mg, 1.42 mmol, 1 eq) in 1,4-dioxane (9 mL) was added $Pd_2(dba)_3$ (129.72 mg, 141.66 μmol, 0.1 eq), RuPhos (66.10 mg, 141.66 μmol, 0.1 eq), t-BuONa (272.28 mg, 2.83 mmol, 2 eq) and N-(3-bromophenyl)prop-2-enamide (500 mg, 2.21 mmol, 1.56 eq). The mixture was bubbled with $N_2$ for 3 min and stirred at 120° C. for 2 h under microwave. The reaction mixture was filtered through a pad of celite. The filtrate was concentrated under reduced pressure to yield a residue which was purified by flash silica gel chromatography (from PE/EtOAc=100/1 to 1/1, TLC: PE/EtOAc=1/1, $R_f$=0.55) then re-purified by preparative HPLC (column: Phenomenex Synergi C18 150*30 mm*4 um; mobile phase: [water (0.05% HCl)-ACN]; B %: 67%-87%, 10 min). The desired fraction was lyophilized to yield the desired product (HCl salt) which was added to saturated $NaHCO_3$ solution (10 mL) then extracted with EtOAc (10 mL×3). The combined organic layers were dried over $Na_2SO_4$, filtered and the filtrate was concentrated then lyophilized to yield N-[3-[6-(trifluoromethyl)-3,4,4a,8a-tetrahydro-2H-quinolin-1-yl]phenyl]prop-2-enamide (25 mg, 71.76 μmol, 5.1% yield, 100.0% purity) as white solid. $^1$H NMR (400 MHz, DMSO-$d_6$) δ ppm 10.23 (s, 1H), 7.68 (s, 1H), 7.49 (d, J=8.1 Hz, 1H), 7.39 (t, J=8.1 Hz, 1H), 7.32 (s, 1H), 7.18 (d, J=8.8 Hz, 1H), 7.03-6.97 (m, 1H), 6.59 (d, J=8.8 Hz, 1H), 6.48-6.36 (m, 1H), 6.29-6.19 (m, 1H), 5.75 (dd, J=2.0, 10.0 Hz, 1H), 3.66-3.55 (m, 2H), 2.86 (t, J=6.2 Hz, 2H), 2.05-1.94 (m, 2H); ES-LCMS m/z 347.1 [M+H]$^+$. I-121 & I-122

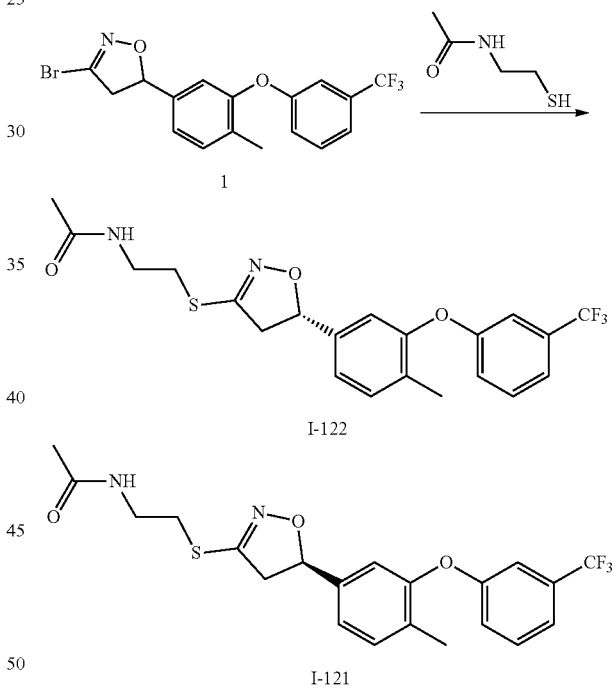

Step 1: N-[2-[[(5S)-5-[4-Methyl-3-[3-(trifluoromethyl)phenoxy]phenyl]-4,5-dihydroisoxazol-3-yl]sulfanyl]ethyl]acetamide & N-[2-[[(5R)-5-[4-Methyl-3-[3-(trifluoromethyl)phenoxy]phenyl]-4,5-dihydroisoxazol-3-yl]sulfanyl]ethyl]acetamide To a solution of 3-bromo-5-[4-methyl-3-[3-(trifluoromethyl)phenoxy]phenyl]-4,5-dihydroisoxazole (500 mg, 1.12 mmol, 1 eq), N-(2-sulfanylethyl)acetamide (266.97 mg, 2.24 mmol, 238.37 μL, 2 eq) in THF (10 mL) was added LiHMDS (1 M, 3.36 mL, 3 eq). The mixture was stirred at 25° C. for 12 h. The reaction was quenched by addition of water (50 mL), extracted with EtOAc (30 mL×3). The organic layer was washed with brine (20 mL), dried over Na₂SO₄, filtered, concentrated to yield a residue which was purified by preparative HPLC (column: Phenomenex Synergi C18 150*30 mm*4 μm; mobile phase: [water (0.05% HCl)-ACN]; B %: 58%-78%, 10 min), followed by lyophilization to yield product which was separated by SFC (column: DAICEL CHIRALPAK AD (250 mm*30 mm, 10 μm); mobile phase: [0.1% NH₃·H₂O ETOH]; B %: 20%-20%, min) to yield Peak1: Rt=3.414 and Peak 2: Rt=3.780. Peak 1 was concentrated under reduced pressure to yield a residue which was dissolved in MeCN (20 mL) and H₂O (10 mL) and lyophilized to yield N-[2-[[(5S)-5-[4-methyl-3-[3-(trifluoromethyl)phenoxy]phenyl]-4,5-dihydroisoxazol-3-yl]sulfanyl]ethyl]acetamide (15.32 mg, 34.94 μmol, 3.1% yield, 100% purity, SFC: $R_t$=3.406, ee=100%, $[\alpha]^{26.2}_D$=−56 (MeOH, c=0.05 g/100 mL)) as a white solid. ¹H NMR (500 MHz, CDCl₃) δ ppm 7.43-7.39 (m, 1H), 7.31 (t, J=7.7 Hz, 2H), 7.15 (s, 1H), 7.10 (d, J=7.8 Hz, 1H), 7.03 (d, J=8.2 Hz, 1H), 6.93 (s, 1H), 6.05 (s, 1H), 5.63-5.50 (m, 1H), 3.60 (q, J=6.1 Hz, 2H), 3.44 (dd, J=10.3, 16.4 Hz, 1H), 3.20 (t, J=6.3 Hz, 2H), 3.02 (dd, J=8.3, 16.4 Hz, 1H), 2.22 (s, 3H), 1.98 (s, 3H); ES-LCMS m/z 439.2 [M+H]⁺. Peak 2 was concentrated under reduced pressure to yield a residue which was dissolved in MeCN (20 mL) and H₂O (10 mL) and lyophilized to yield N-[2-[[(5R)-5-[4-methyl-3-[3-(trifluoromethyl)phenoxy]phenyl]-4,5-dihydroisoxazol-3-yl]sulfanyl]ethyl]acetamide (15.89 mg, 35.50 μmol, 3.1% yield, 97.9% purity SFC: Rt=3.777, ee=99.0%, $[\alpha]^{26.2}_D$=+44.9 (MeOH, c=0.049 g/100 mL)) as a white solid. ¹H NMR (400 MHz, CDCl₃) δ ppm 7.44-7.39 (m, 1H), 7.33-7.28 (m, 2H), 7.16-7.09 (m, 2H), 7.03 (d, J=8.2 Hz, 1H), 6.93 (d, J=1.6 Hz, 1H), 6.12-5.98 (m, 1H), 5.60-5.52 (m, 1H), 3.60 (q, J=6.3 Hz, 2H), 3.44 (dd, J=10.6, 16.4 Hz, 1H), 3.20 (t, J=6.3 Hz, 2H), 3.02 (dd, J=8.2, 16.4 Hz, 1H), 2.22 (s, 3H), 1.98 (s, 3H); ES-LCMS m/z 439.2 [M+H]⁺.

I-62 & I-63

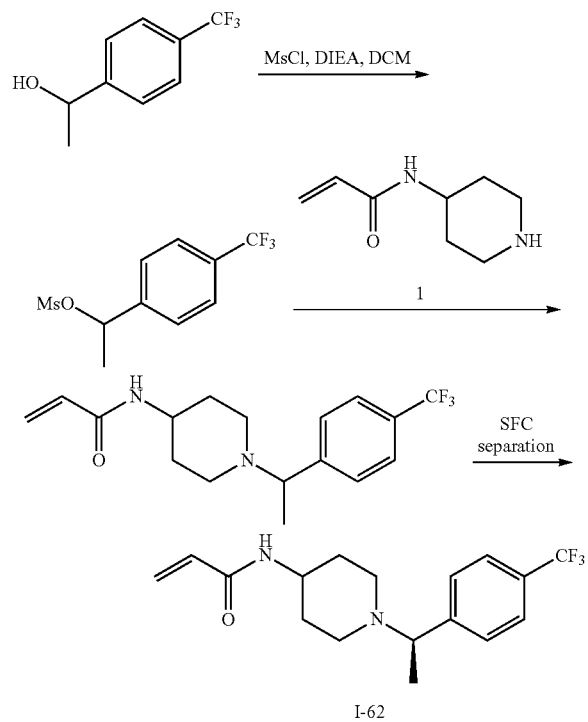

I-62

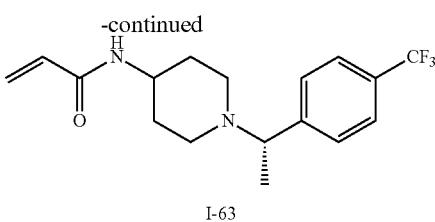

I-63

Step 1: 1-[4-(Trifluoromethyl)phenyl]ethyl methanesulfonate

To a solution of 1-[4-(trifluoromethyl)phenyl]ethanol (500 mg, 2.63 mmol, 1 eq) and DIEA (680 mg, 5.26 mmol, 916.44 μL, 2 eq) in DCM (10 mL) was added MsCl (325 mg, 2.84 mmol, 219.59 μL, 1.08 eq) at 0° C. The mixture was stirred at 0° C. for 1 h. The reaction mixture was diluted with H₂O (30 mL) and extracted with EtOAc (30 mL×3). The organic layer was dried over Na₂SO₄, filtered and concentrated under reduced pressure to yield 1-[4-(trifluoromethyl)phenyl]ethyl methanesulfonate (700 mg, 2.61 mmol, 99.2% yield, N/A purity) as a brown gum, which was used in the next step without further purification. ¹H NMR (400 MHz, CDCl₃) δ ppm 7.68 (d, J=8.2 Hz, 2H), 7.54 (d, J=8.2 Hz, 2H), 5.80 (q, J=6.7 Hz, 1H), 2.86 (s, 3H), 1.74 (d, J=6.7 Hz, 3H).

Step 2: N-[1-[(1R)-1-[4-(Trifluoromethyl)phenyl]ethyl]-4-piperidyl]prop-2-enamide and N-[1-[(1S)-1-[4-(trifluoromethyl)phenyl]ethyl]-4-piperidyl]prop-2-enamide A mixture of 1-[4-(trifluoromethyl)phenyl]ethyl methanesulfonate (400 mg, 1.49 mmol, 1 eq), N-(4-piperidyl)prop-2-enamide (450 mg, 1.65 mmol, 1.11 eq, HCl) and Cs₂CO₃ (2.43 g, 7.46 mmol, 5 eq) in DMF (20 mL) was stirred at 25° C. for 12 h. The reaction mixture was diluted with H₂O (80 mL) and extracted with EtOAc (100 mL×3). The organic layer was dried over Na₂SO₄, filtered and concentrated under reduced pressure to yield a residue which was purified by preparative HPLC (column: Phenomenex Synergi C18 150*30 mm*4 um; mobile phase: [water (0.05% HCl)-ACN]; B %: 20%-40%, 9 min). The desired fraction was basified with saturated aqueous NaHCO₃ until pH=8 and extracted with EtOAc (150 mL×3). The organic layer was dried over Na₂SO₄, filtered and concentrated under reduced pressure to yield a residue (98 mg) which was separated by chiral SFC (column: DAICEL CHIRALCEL OD-H (250 mm*30 mm, 5 um); mobile phase: [0.1% NH₃H₂O/EtOH]; B %: 15%-15%) to yield peak 1 and peak 2. Peak 1 was concentrated under reduced pressure to yield a residue which was dissolved in MeCN (20 mL) and water (20 mL) and lyophilized to yield N-[1-[(1R)-1-[4-(trifluoromethyl)phenyl]ethyl]-4-piperidyl]prop-2-enamide (30.98 mg, 94.93 μmol, 6.4% yield, 100.0% purity, SFC: $R_t$=1.728, ee=100.00%, $[\alpha]^{26.5}_D$=+22.22 (CHCl₃, c=0.054 g/100 mL)) as a white solid. ¹H NMR (500 MHz, CDCl₃) δ ppm 7.57 (d, J=8.1 Hz, 2H), 7.44 (d, J=8.1 Hz, 2H), 6.27 (d, J=16.9 Hz, 1H), 6.06 (dd, J=10.2, 16.9 Hz, 1H), 5.64 (d, J=10.2 Hz, 1H), 5.46-5.36 (m, 1H), 3.93-3.80 (m, 1H), 3.52-3.42 (m, 1H), 2.98 (d, J=10.5 Hz, 1H), 2.70 (d, J=11.1 Hz, 1H), 2.20-2.06 (m, 2H), 2.00 (d, J=14.6 Hz, 1H), 1.89 (d, J=12.4 Hz, 1H), 1.54-1.38 (m, 2H), 1.35 (d, J=6.7 Hz, 3H); ES-LCMS m/z 327.2 [M+H]⁺. Peak 2 was concentrated under reduced pressure to yield a residue which was dissolved in MeCN (20 mL) and water (20 mL) and lyophilized to yield N-[1-[(1S)-1-[4-(trifluoromethyl)phenyl]ethyl]-4-piperidyl]prop-2-enamide (34.99 mg, 107.21 µmol, 7.2% yield, 100.0% purity, SFC: $R_t$=2.038, ee=99.40%, $[\alpha]^{26.5}_D$=−32.14 (CHCl$_3$, c=0.056 g/100 mL)) as a white solid. $^1$H NMR (500 MHz, CDCl$_3$) δ ppm 7.58 (d, J=8.1 Hz, 2H), 7.44 (d, J=8.1 Hz, 2H), 6.27 (dd, J=1.1, 16.9 Hz, 1H), 6.06 (dd, J=10.2, 16.9 Hz, 1H), 5.64 (dd, J=0.8, 10.4 Hz, 1H), 5.46-5.36 (m, 1H), 3.93-3.81 (m, 1H), 3.48 (d, J=6.4 Hz, 1H), 2.99 (d, J=8.9 Hz, 1H), 2.71 (d, J=10.5 Hz, 1H), 2.19-2.06 (m, 2H), 2.00 (d, J=13.1 Hz, 1H), 1.90 (d, J=12.5 Hz, 1H), 1.55-1.41 (m, 2H), 1.36 (d, J=6.6 Hz, 3H); ES-LCMS m/z 327.2 [M+H]$^+$.

I-63

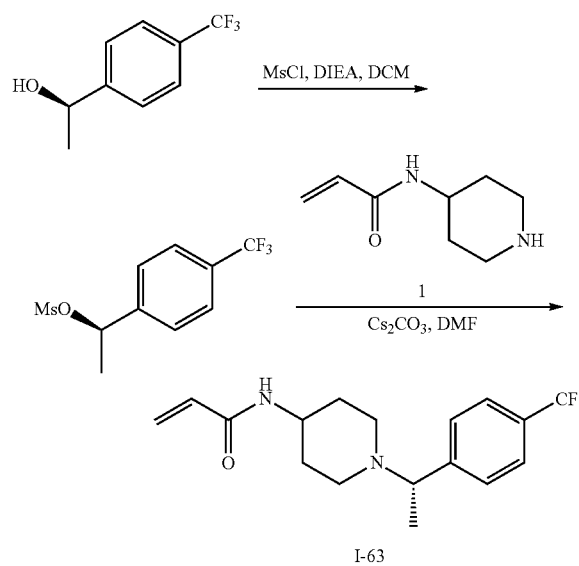

I-63

Step 1: [(1R)-1-[4-(Trifluoromethyl)phenyl]ethyl] methanesulfonate

To a solution of (1R)-1-[4-(trifluoromethyl)phenyl]ethanol (200 mg, 1.05 mmol, 1 eq) and DIEA (410 mg, 3.17 mmol, 552.56 µL, 3.02 eq) in DCM (10 mL) was added MsCl (130 mg, 1.13 mmol, 87.84 µL, 1.08 eq) at 0° C. The mixture was stirred at 25° C. for 1 h. The reaction mixture was quenched with H$_2$O (20 mL) and extracted with DCM (20 mL×3). The organic layer was dried over Na$_2$SO$_4$, filtered and concentrated under reduced pressure to yield [(1R)-1-[4-(trifluoromethyl)phenyl]ethyl] methanesulfonate (280 mg, 1.04 mmol, 99.2% yield, N/A purity) as a brown gum, which was used in the next step without further purification. $^1$H NMR (400 MHz, CDCl$_3$) δ ppm 7.67 (d, J=7.8 Hz, 2H), 7.53 (d, J=8.6 Hz, 2H), 5.78 (q, J=6.7 Hz, 1H), 2.85 (s, 3H), 1.72 (d, J=6.3 Hz, 3H).

Step 2: N-[1-[(1S)-1-[4-(Trifluoromethyl)phenyl]ethyl]-4-piperidyl]prop-2-enamide A mixture of [(1R)-1-[4-(trifluoromethyl)phenyl]ethyl] methanesulfonate (280 mg, 1.04 mmol, 1 eq), N-(4-piperidyl)prop-2-enamide (300 mg, 1.10 mmol, 1.06 eq, HCl) and Cs$_2$CO$_3$ (1.3 g, 3.99 mmol, 3.82 eq) in DMF (10 mL) was stirred at 25° C. for 48 h. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by preparative HPLC (column: Phenomenex Synergi C18 150*30 mm*4 um; mobile phase: [water (0.05% HCl)-ACN]; B %: 14%-34%, 10 min). The desired fraction was basified with saturated aqueous NaHCO$_3$ until pH=8 and extracted with EtOAc (150 mL×3). The organic layer was dried over Na$_2$SO$_4$, filtered and concentrated under reduced pressure to yield a residue (85 mg with 90.92% ee value) which was separated by chiral SFC (column: DAICEL CHIRALCEL OD (250 mm*30 mm, 10 um); mobile phase: [0.1% NH$_3$H$_2$O/EtOH]; B %: 20%-20%). The desired fraction was concentrated under reduced pressure to yield a residue which was dissolved in MeCN (20 mL) and water (20 mL) and lyophilized to yield N-[1-[(1S)-1-[4-(trifluoromethyl)phenyl]ethyl]-4-piperidyl]prop-2-enamide (44.08 mg, 132.61 µmol, 12.7% yield, 98.2% purity, SFC: $R_t$=2.050, ee=99.88%, $[\alpha]^{26.5}_D$=−32.73 (CHCl$_3$, c=0.055 g/100 mL)) as a white solid. $^1$H NMR (400 MHz, CDCl$_3$) δ ppm 7.57 (d, J=8.2 Hz, 2H), 7.44 (d, J=8.2 Hz, 2H), 6.27 (dd, J=1.4, 17.0 Hz, 1H), 6.13-6.01 (m, 1H), 5.64 (dd, J=1.4, 10.4 Hz, 1H), 5.42-5.32 (m, 1H), 3.94-3.77 (m, 1H), 3.47 (q, J=6.7 Hz, 1H), 2.97 (d, J=10.6 Hz, 1H), 2.70 (d, J=11.3 Hz, 1H), 2.21-2.06 (m, 2H), 2.00 (d, J=12.5 Hz, 1H), 1.94-1.86 (m, 1H), 1.54-1.39 (m, 2H), 1.36 (d, J=6.7 Hz, 3H); ES-LCMS m/z 327.2 [M+H]$^+$.

I-44

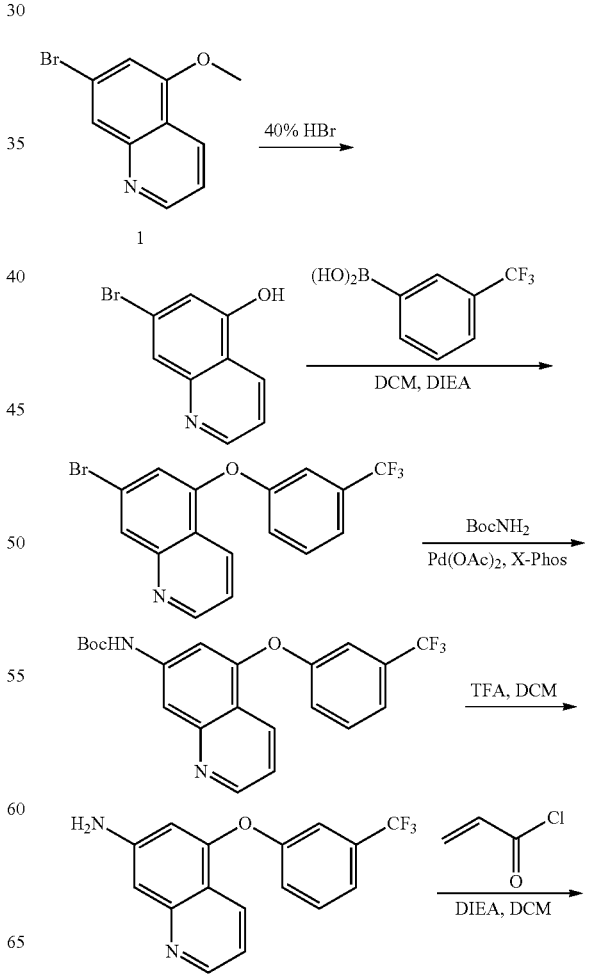

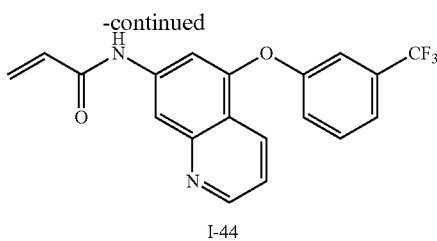

I-44

Step 1: 7-Bromoquinolin-5-ol

A solution of 7-bromo-5-methoxy-quinoline (2 g, 8.40 mmol, 1 eq) in HBr (37.25 g, 184.15 mmol, 25 mL, 40% purity, 21.92 eq) was stirred at 120° C. for 12 h. TLC (PE/EtOAc=3/1, $R_f$=0.35) showed starting material was consumed and one major new spot was detected. The reaction mixture was concentrated, diluted with $H_2O$ (100 mL) and saturated NaOH (30 mL, adjust pH to 13). The mixture was extracted with PE/EtOAc (4:1, 30 mL×2). The aqueous phase was neutralized with 2 N HCl (30 mL, adjust pH to 7) and filtered. The filtered cake was concentrated to yield 7-bromoquinolin-5-ol (1 g, 4.02 mmol, 47.8% yield, 90.0% purity) as a yellow solid. NMR (500 MHz, DMSO-$d_6$) δ ppm 11.07 (br s, 1H), 8.87 (dd, J=1.8, 4.2 Hz, 1H), 8.47 (dd, J=0.9, 8.4 Hz, 1H), 7.65 (d, J=1.1 Hz, 1H), 7.50 (dd, J=4.3, 8.4 Hz, 1H), 7.04 (d, J=1.7 Hz, 1H); ES-LCMS m/z 223.8, 225.8 [M+H]$^+$.

Step 2: 7-Bromo-5-[3-(trifluoromethyl)phenoxy]quinoline

To a solution of 7-bromoquinolin-5-ol (400 mg, 1.61 mmol, 1 eq) in DCM (40 mL) was added Cu(OAc)$_2$ (583.67 mg, 3.21 mmol, 2 eq), [3-(trifluoromethyl)phenyl]boronic acid (915.50 mg, 4.82 mmol, 96.35 μL, 3 eq) and DIEA (622.99 mg, 4.82 mmol, 839.60 μL, 3 eq). The mixture was stirred under O$_2$ (15 psi) atmosphere at 25° C. for 12 h. The mixture was filtered. The filtrate was diluted with H$_2$O (20 mL) and extracted with DCM (20 mL×3). The combine organic layers were dried over anhydrous Na$_2$SO$_4$, filtered and concentrated to yield a residue which was purified by preparative TLC (PE/EtOAc=4/1, TLC: PE/EtOAc=4/1, $R_f$=0.45) to yield 7-bromo-5-[3-(trifluoromethyl)phenoxy]quinoline (300 mg, 570.42 μmol, 35.5% yield, 70.0% purity) as yellow oil. $^1$H NMR (500 MHz, DMSO-$d_6$) δ ppm 9.01 (dd, J=1.7, 4.1 Hz, 1H), 8.53 (d, J=8.4 Hz, 1H), 8.09 (d, J=0.9 Hz, 1H), 7.71-7.66 (m, 1H), 7.64 (dd, J=4.3, 8.5 Hz, 1H), 7.45 (d, J=9.0 Hz, 1H), 7.20 (d, J=1.7 Hz, 1H), 7.05 (s, 2H); ES-LCMS m/z 367.7, 369.7 [M+H]$^+$.

Step 3: tert-Butyl N-[5-[3-(trifluoromethyl)phenoxy]-7-quinolyl]carbamate

To a mixture of 7-bromo-5-[3-(trifluoromethyl)phenoxy]quinoline (270 mg, 513.38 μmol, 1 eq) and tert-butyl carbamate (300.70 mg, 2.57 mmol, 5 eq) in 1,4-dioxane (3 mL) was added Pd(OAc)$_2$ (11.53 mg, 51.34 μmol, 0.1 eq), XPhos (24.47 mg, 51.34 μmol, 0.1 eq) and Cs$_2$CO$_3$ (501.81 mg, 1.54 mmol, 3 eq) under N$_2$ atmosphere. The mixture was stirred under N$_2$ atmosphere at 120° C. for 12 h. The mixture was filtered. The filtrate was diluted with H$_2$O (20 mL) and extracted with EtOAc (20 mL×3). The combine organic layers were dried over anhydrous Na$_2$SO$_4$, filtered and concentrated to yield a residue which was purified by flash silica gel chromatography (from pure PE to PE/EtOAc=2/3, TLC: PE/EtOAc=1/1, $R_f$=0.30) to yield tert-butyl N-[5-[3-(trifluoromethyl)phenoxy]-7-quinolyl]carbamate (200 mg, 395.67 μmol, 77.1% yield, 80.0% purity) as a yellow solid. $^1$H NMR (400 MHz, DMSO-$d_6$) δ ppm 9.74 (s, 1H), 8.86 (dd, J=1.7, 4.2 Hz, 1H), 8.38-8.31 (m, 1H), 8.04 (s, 1H), 7.70-7.63 (m, 1H), 7.61-7.55 (m, 1H), 7.52 (s, 1H), 7.39 (td, J=4.1, 8.3 Hz, 2H), 7.23 (d, J=1.7 Hz, 1H), 1.47 (s, 9H); ES-LCMS m/z 405.1 [M+H]$^+$.

Step 4: 5-[3-(Trifluoromethyl)phenoxy]quinolin-7-amine

To a solution of tert-butyl N-[5-[3-(trifluoromethyl)phenoxy]-7-quinolyl]carbamate (200 mg, 395.67 μmol, 1 eq) in DCM (5 mL) was added TFA (1.23 g, 10.80 mmol, 799.98 μL, 27.31 eq). The mixture was stirred at 25° C. for 12 h. The reaction mixture was concentrated to yield 5-[3-(trifluoromethyl)phenoxy]quinolin-7-amine (200 mg, crude, 2 TFA) as a yellow solid. $^1$H NMR (400 MHz, DMSO-$d_6$) δ ppm 8.90 (d, J=7.8 Hz, 1H), 8.82 (dd, J=1.3, 5.7 Hz, 1H), 7.81-7.74 (m, 1H), 7.72 (d, J=5.6 Hz, 2H), 7.60 (d, J=8.3 Hz, 1H), 7.45 (dd, J=5.7, 7.9 Hz, 1H), 6.71 (d, J=0.7 Hz, 1H), 6.48 (d, J=1.5 Hz, 1H); ES-LCMS m/z 305.2 [M+H]$^+$.

Step 5: N-[5-[3-(Trifluoromethyl)phenoxy]-7-quinolyl]prop-2-enamide

To a solution of 5-[3-(trifluoromethyl)phenoxy]quinolin-7-amine (200 mg, 375.72 μmol, 1 eq, 2 TFA) in DCM (2 mL) was added DIEA (242.80 mg, 1.88 mmol, 327.22 μL, 5 eq) and prop-2-enoyl chloride (68.01 mg, 751.44 μmol, 61.27 μL, 2 eq). The mixture was stirred at 25° C. for 1 h. The mixture was diluted with H$_2$O (20 mL) and extracted with DCM (20 mL×3). The combine organic layers were dried over anhydrous Na$_2$SO$_4$, filtered and concentrated to yield a residue which was purified by preparative TLC (PE/EtOAc=3/1, TLC: PE/EtOAc=3/1, $R_f$=0.45) to yield N-[5-[3-(trifluoromethyl)phenoxy]-7-quinolyl]prop-2-enamide (19.64 mg, 54.81 μmol, 14.6% yield, 100.0% purity) as a white solid. $^1$H NMR (500 MHz, DMSO-$d_6$) δ ppm 10.50 (s, 1H), 8.92 (dd, J=1.5, 4.1 Hz, 1H), 8.44 (d, J=8.2 Hz, 1H), 8.35 (s, 1H), 7.73-7.67 (m, 1H), 7.65-7.56 (m, 2H), 7.47 (dd, J=4.0, 8.3 Hz, 2H), 7.28 (d, J=1.7 Hz, 1H), 6.48-6.38 (m, 1H), 6.34-6.24 (m, 1H), 5.80 (dd, J=1.7, 10.1 Hz, 1H); ES-LCMS m/z 359.1 [M+H]$^+$.

I-123 & I-124

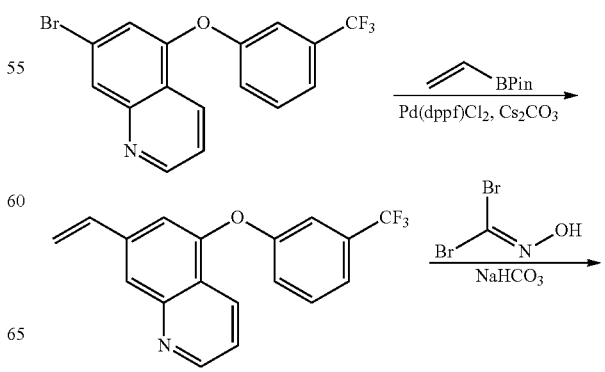

-continued

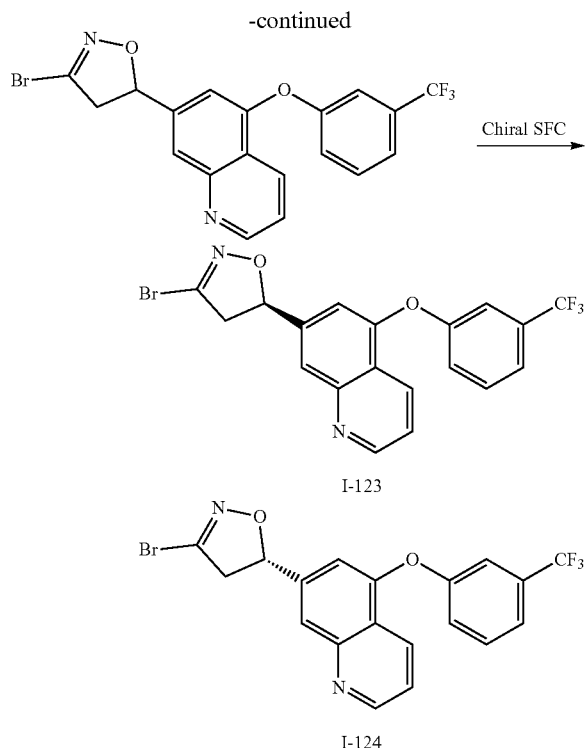

Step 1: 5-[3-(Trifluoromethyl)phenoxy]-7-vinyl-quinoline

To a mixture of 7-bromo-5-[3-(trifluoromethyl)phenoxy]quinoline (300 mg, 570.42 μmol, 1 eq) and 4,4,5,5-tetramethyl-2-vinyl-1,3,2-dioxaborolane (439.27 mg, 2.85 mmol, 483.77 μL, 5 eq) in 1,4-dioxane (5 mL) was added Pd(dppf)Cl$_2$ (41.74 mg, 57.04 μmol, 0.1 eq) and Cs$_2$CO$_3$ (2 M, 855.64 μL, 3 eq) under N$_2$ atmosphere. The mixture was stirred at 80° C. for 0.5 h in microwave (0 bar) under N$_2$ atmosphere. TLC (PE/EtOAc=3/1, R$_f$=0.45) showed starting material was consumed and one major new spot was detected. The mixture was diluted with H$_2$O (10 mL) and extracted with EtOAc (20 mL×3). The combine organic layers were dried over anhydrous Na$_2$SO$_4$, filtered and concentrated to yield a residue which was purified by preparative TLC (PE/EtOAc=4/1, TLC: PE/EtOAc=4/1, R$_f$=0.45) to yield 5-[3-(trifluoromethyl)phenoxy]-7-vinyl-quinoline (160 mg, 355.23 μmol, 62.3% yield, 70.0% purity) as yellow oil. $^1$H NMR (500 MHz, DMSO-d$_6$) δ ppm 8.96 (dd, J=1.7, 4.1 Hz, 1H), 8.37 (d, J=7.8 Hz, 1H), 7.93 (s, 1H), 7.66-7.59 (m, 1H), 7.56-7.50 (m, 2H), 7.50-7.44 (m, 2H), 7.30 (dd, J=2.1, 8.3 Hz, 1H), 6.96 (dd, J=11.0, 17.5 Hz, 1H), 6.01 (d, J=17.5 Hz, 1H), 5.44 (d, J=11.0 Hz, 1H); ES-LCMS m/z 316.0 [M+H]$^+$.

Step 2: (5R)-3-Bromo-5-[5-[3-(trifluoromethyl)phenoxy]-7-quinolyl]-4,5-dihydroisoxazole and (5S)-3-bromo-5-[5-[3-(trifluoromethyl)phenoxy]-7-quinolyl]-4,5-dihydroisoxazole To a solution of 5-[3-(trifluoromethyl)phenoxy]-7-vinyl-quinoline (150 mg, 333.03 μmol, 1 eq) in EtOAc (3 mL) was added NaHCO$_3$ (279.78 mg, 3.33 mmol, 10 eq) and dibromomethanone oxime (135.10 mg, 666.06 μmol, 2 eq). The mixture was stirred at 25° C. for 12 h. The mixture was diluted with H$_2$O (5 mL) and extracted with EtOAc (5 mL×3). The combine organic layers were dried over anhydrous Na$_2$SO$_4$, filtered and concentrated to yield a residue which was purified by preparative TLC (PE/EtOAc=3/1, TLC: PE/EtOAc=3/1, R$_f$=0.40) and then by preparative SFC (column: DAICEL CHIRALCEL OD-H (250 mm*30 mm, 5 μm); mobile phase: [0.1% NH$_3$·H$_2$O MeOH]; B %: 25%-25%, min) to yield Peak 1 and Peak 2. Peak 1 was concentrated under reduced pressure to yield a residue which was dissolved in MeCN (20 mL) and H$_2$O (40 mL) and lyophilized to yield (5R)-3-bromo-5-[5-[3-(trifluoromethyl)phenoxy]-7-quinolyl]-4,5-dihydroisoxazole (17.01 mg, 38.91 μmol, 11.7% yield, 100.0% purity, SFC: R$_t$=2.421, ee=100%, [α]$^{26.9}_D$=+138.898 (MeOH, c=0.071 g/100 mL)) as colorless oil. $^1$H NMR (500 MHz, CD$_3$OD) δ ppm 8.95 (dd, J=1.6, 4.3 Hz, 1H), 8.64 (d, J=8.5 Hz, 1H), 7.86 (s, 1H), 7.65-7.59 (m, 2H), 7.52 (d, J=7.8 Hz, 1H), 7.44 (s, 1H), 7.35 (d, J=7.8 Hz, 1H), 7.05 (d, J=1.2 Hz, 1H), 5.89 (dd, J=8.3, 11.1 Hz, 1H), 3.82 (dd, J=11.1, 17.5 Hz, 1H), 3.29-3.24 (m, 1H); ES-LCMS m/z 436.9, 438.9 [M+H]$^+$. Peak 2 was concentrated under reduced pressure to yield a residue which was dissolved in MeCN (20 mL) and H$_2$O (40 mL) and lyophilized to yield (5S)-3-bromo-5-[5-[3-(trifluoromethyl)phenoxy]-7-quinolyl]-4,5-dihydroisoxazole (18.83 mg, 42.31 μmol, 12.7% yield, 98.2% purity, SFC: R$_t$=2.911, ee=99.72%, [α]$^{26.8}_D$=−143.003 (MeOH, c=0.055 g/100 mL)) as colorless oil. $^1$H NMR (500 MHz, CD$_3$OD) δ ppm 8.95 (dd, J=1.5, 4.3 Hz, 1H), 8.63 (d, J=8.4 Hz, 1H), 7.86 (s, 1H), 7.65-7.59 (m, 2H), 7.52 (d, J=7.9 Hz, 1H), 7.44 (s, 1H), 7.34 (d, J=8.1 Hz, 1H), 7.05 (d, J=1.1 Hz, 1H), 5.88 (dd, J=8.4, 11.0 Hz, 1H), 3.82 (dd, J=11.0, 17.5 Hz, 1H), 3.29-3.25 (m, 1H); ES-LCMS m/z 436.8, 438.8 [M+H]$^+$. 1-64

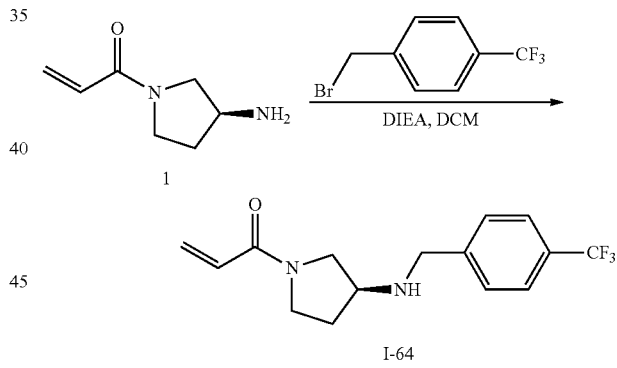

Step 1: 1-[(3S)-3-[[4-(Trifluoromethyl)phenyl]methylamino]pyrrolidin-1-yl]prop-2-en-1-one To a solution of 1-[(3S)-3-aminopyrrolidin-1-yl]prop-2-en-1-one (100 mg, 642.02 μmol, 1 eq) and 1-(bromomethyl)-4-(trifluoromethyl)benzene (170 mg, 711.20 μmol, 109.68 μL, 1.11 eq) in DCM (6 mL) as added DIEA (1.48 g, 11.48 mmol, 2 mL, 17.88 eq). The mixture was stirred at 25° C. for 2 h. TLC (PE/EtOAc=1/1, R$_f$=0.40) showed one main spot formed. The mixture was diluted with H$_2$O (20 mL) and extracted with EtOAc (20 mL×3). The combined organic layer was dried over Na$_2$SO$_4$, filtrated and concentrated under reduced pressure to yield a residue which was purified by preparative HPLC (column: Welch Xtimate C18 150×25 mm×5 μm; mobile phase: [water (10 mM NH$_4$HCO$_3$)-ACN]; B %: 26%-56%, 10 min) and then lyophilized to yield 1-[(3S)-3-[[4-(trifluoromethyl)phenyl]

methylamino]pyrrolidin-1-yl]prop-2-en-1-one (15.55 mg, 51.01 μmol, 7.9% yield, 97.9% purity) as a white oil. $^1$H NMR (500 MHz, CD$_3$OD) δ ppm 7.67-7.61 (m, 2H), 7.59-7.53 (m, 2H), 6.64-6.51 (m, 1H), 6.25 (ddd, J=1.8, 5.0, 16.8 Hz, 1H), 5.73 (ddd, J=1.8, 6.5, 10.5 Hz, 1H), 3.92-3.84 (m, 2H), 3.83-3.75 (m, 1H), 3.72-3.64 (m, 1H), 3.64-3.45 (m, 1H), 3.45-3.32 (m, 2H), 2.23-2.07 (m, 1H), 1.97-1.78 (m, 1H); ES-LCMS m/z 299.0 [M+H]$^+$.

I-65

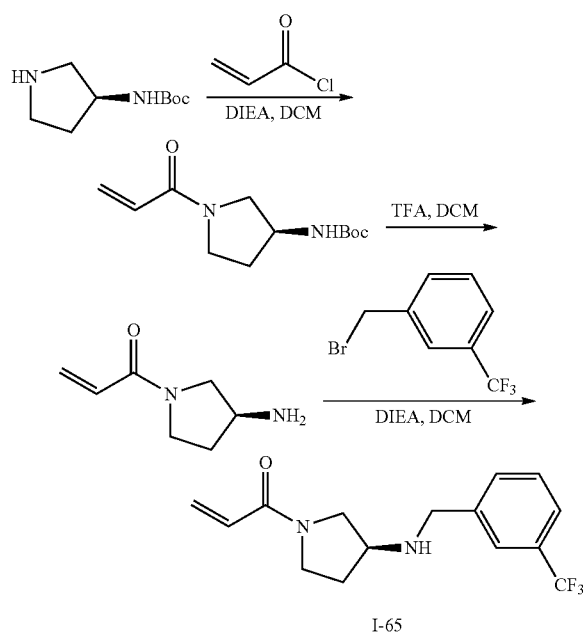

I-65

Step 1: tert-Butyl N-[(3R)-1-prop-2-enoylpyrrolidin-3-yl]carbamate

To a solution of tert-butyl N-[(3R)-pyrrolidin-3-yl]carbamate (500 mg, 2.68 mmol, 1 eq) in DCM (20 mL) was added DIEA (2.23 g, 17.22 mmol, 3 mL, 6.42 eq) and then prop-2-enoyl chloride (270 mg, 2.98 mmol, 243.24 μL, 1.11 eq) was added dropwise at 0° C. under N$_2$ atmosphere. The mixture was stirred at 0° C. for 1 h. TLC (PE/EtOAc=1/1, R$_f$=0.30) showed one main spot formed. The mixture was diluted with H$_2$O (20 mL) and extracted with EtOAc (20 mL×3). The combined organic layer was dried over Na$_2$SO$_4$, filtered and concentrated under reduced pressure to yield a residue which was purified by flash silica gel chromatography (from PE/EtOAc=100/1 to 1/1, TLC: PE/EtOAc=1/1, R$_f$=0.30) to yield tert-butyl N-[(3R)-1-prop-2-enoylpyrrolidin-3-yl]carbamate (260 mg, 1.08 mmol, 40.3% yield, 100.0% purity) as yellow oil. $^1$H NMR (500 MHz, CDCl$_3$) δ ppm 6.49-6.33 (m, 2H), 5.73-5.66 (m, 1H), 3.86-3.71 (m, 1H), 3.70-3.57 (m, 2H), 3.48-3.38 (m, 1H), 2.28-2.11 (m, 1H), 2.03-1.75 (m, 1H), 1.46 (s, 9H); ES-LCMS m/z 241.2 [M+H]$^+$.

Step 2: 1-[(3R)-3-Aminopyrrolidin-1-yl]prop-2-en-1-one

To a solution of tert-butyl N-[(3R)-1-prop-2-enoylpyrrolidin-3-yl]carbamate (254.80 mg, 1.06 mmol, 1 eq) in DCM (6 mL) was added TFA (3.02 g, 26.46 mmol, 1.96 mL, 24.96 eq). The mixture was stirred at 25° C. for 1 h. TLC (PE/EtOAc=1/1, R$_f$=0.20) showed the starting material was consumed completely. The reaction mixture was concentrated under reduced pressure to yield 1-[(3R)-3-aminopyrrolidin-1-yl]prop-2-en-1-one (150 mg, 531.07 μmol, 50.1% yield, 90.0% purity, TFA) as yellow oil, which was used in the next step without further purification. 41 NMR (400 MHz, CDCl$_3$) δ ppm 6.43 (br s, 2H), 6.04-5.89 (m, 1H), 4.37-4.06 (m, 2H), 3.99-3.76 (m, 3H), 2.62-2.32 (m, 2H); ES-LCMS m/z no desired MS found.

Step 3: 1-[(3S)-3-[[3-(trifluoromethyl)phenyl]methylamino]pyrrolidin-1-yl]prop-2-en-1-one To a solution of 1-[(3R)-3-aminopyrrolidin-1-yl]prop-2-en-1-one (150 mg, 1.05 mmol, 1 eq) and 1-(bromomethyl)-3-(trifluoromethyl)benzene (260 mg, 1.09 mmol, 165.61 μL, 1.04 eq) in DCM (3 mL) was added DIEA (727 mg, 5.63 mmol, 979.78 μL, 5.36 eq). The mixture was stirred at 25° C. for 12 h. TLC (PE/EtOAc=1/1, R$_f$=0.30) showed one main spot formed. The reaction mixture was diluted with H$_2$O (20 mL) and extracted with EtOAc (20 mL×3). The combined organic layers dried over Na$_2$SO$_4$, filtered and concentrated under reduced pressure to yield a residue which was purified by preparative HPLC (column: Welch Xtimate C18 150×25 mm×5 um; mobile phase: [water (10 mm NH$_4$HCO$_3$)-ACN]; B %: 27%-57%, 10 min); B %: 35%-65%, 10 min) and then lyophilized to yield 1-[(3S)-3-[[3-(trifluoromethyl)phenyl]methylamino]pyrrolidin-1-yl]prop-2-en-1-one (17.66 mg, 59.20 μmol, 5.6% yield, 100.0% purity) as white oil. $^1$H NMR (500 MHz, CD$_3$OD) δ ppm 7.72 (s, 1H), 7.64 (d, J=7.5 Hz, 1H), 7.59-7.50 (m, 2H), 6.58 (dt, J=10.5, 17.4 Hz, 1H), 6.29-6.23 (m, 1H), 5.73 (ddd, J=1.8, 4.4, 10.5 Hz, 1H), 3.93-3.86 (m, 2H), 3.86-3.76 (m, 1H), 3.73-3.37 (m, 4H), 2.23-2.10 (m, 1H), 1.99-1.79 (m, 1H); ES-LCMS m/z 299.1 [M+H]$^+$.

I-125, I-126, I-127, & I-148

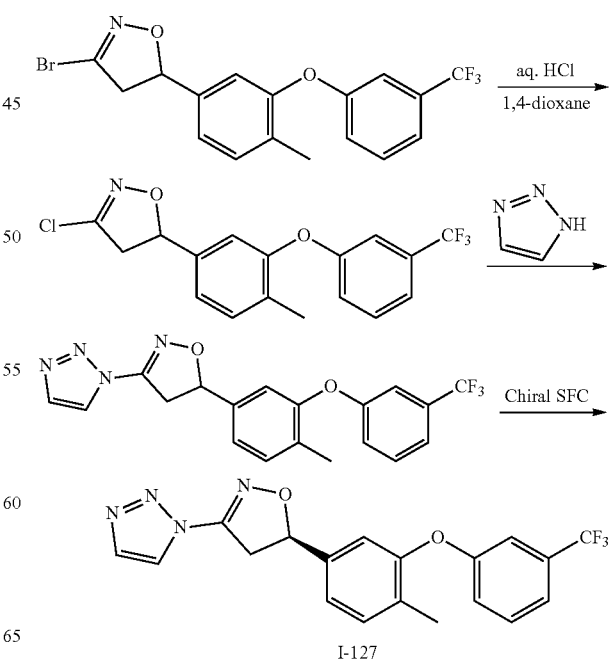

I-127

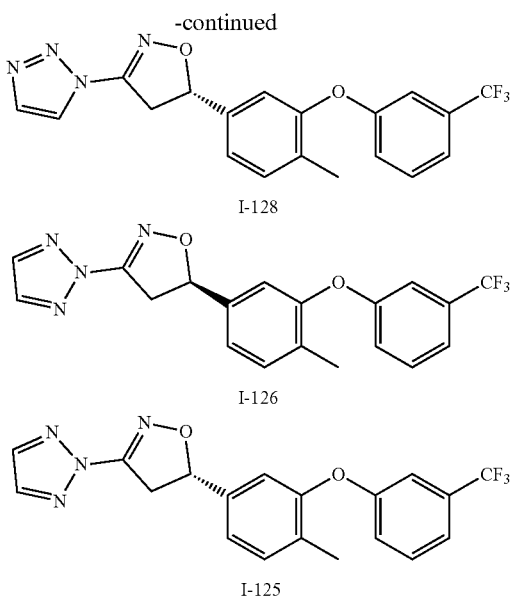

I-128

I-126

I-125

Step 1: 3-Chloro-5-[4-methyl-3-[3-(trifluoromethyl)phenoxy]phenyl]-4,5-dihydroisoxazole To a solution of 3-bromo-5-[4-methyl-3-[3-(trifluoromethyl)phenoxy]phenyl]-4,5-dihydroisoxazole (1 g, 2.25 mmol, 1 eq) in 1,4-dioxane (20 ml) was added HCl (229.50 g, 251.78 mmol, 225.00 ml, 4 N, 111.95 eq). The mixture was stirred at 40° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 3/1, TLC: PE/EtOAc=3/1, $R_f$=0.55) to yield 3-chloro-5-[4-methyl-3-[3-(trifluoromethyl)phenoxy]phenyl]-4,5-dihydroisoxazole (640 mg, 1.46 mmol, 64.8% yield, 81% purity) as white oil. $^1$H NMR (400 MHz, DMSO-$d_6$) δ ppm 7.63-7.55 (m, 1H), 7.48-7.39 (m, 2H), 7.24-7.19 (m, 2H), 7.15 (d, J=8.3 Hz, 1H), 7.07 (d, J=1.2 Hz, 1H), 5.76 (t, J=10.1 Hz, 1H), 4.02 (q, J=7.1 Hz, 1H), 3.70 (dd, J=10.8, 17.4 Hz, 1H), 2.16 (s, 3H); ES-LCMS m/z 356.1, 358.1 $[M+H]^+$.

Step 2: (5S)-5-[4-Methyl-3-[3-(trifluoromethyl)phenoxy]phenyl]-3-(triazol-2-yl)-4,5-dihydroisoxazole & (5R)-5-[4-methyl-3-[3-(trifluoromethyl)phenoxy]phenyl]-3-(triazol-1-yl)-4,5-dihydroisoxazole & (5R)-5-[4-methyl-3-[3-(trifluoromethyl)phenoxy]phenyl]-3-(triazol-2-yl)-4,5-dihydroisoxazole & (5S)-5-[4-methyl-3-[3-(trifluoromethyl)phenoxy]phenyl]-3-(triazol-1-yl)-4,5-dihydroisoxazole To a solution of 3-chloro-5-[4-methyl-3-[3-(trifluoromethyl)phenoxy]phenyl]-4,5-dihydroisoxazole (300 mg, 683.09 µmol, 1 eq) in DMF (7 mL) was added $Cs_2CO_3$ (667.69 mg, 2.05 mmol, 3 eq) and 1H-triazole (235.89 mg, 3.42 mmol, 198.22 µL, 5 eq). The mixture was stirred at 110° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 3/1, TLC: PE/EtOAc=3/1, $R_f$=0.45) to yield the compound which was separated by SFC (column: DAICEL CHIRALCEL OJ-H (250 mm*30 mm, 5 µm); mobile phase: [Neu-EtOH]; B %: 20%-20%, min) to yield (5S)-5-[4-methyl-3-[3-(trifluoromethyl)phenoxy]phenyl]-3-(triazol-2-yl)-4,5-dihydroisoxazole (57.56 mg, 148.22 µmol, 21.7% yield, 100% purity, SFC: $R_t$=2.812 min, ee=100%, $[α]^{26.1}_D$=−185.71, MeOH, c=0.042 g/100 mL)) as white oil. $^1$H NMR (500 MHz, CDCl$_3$) δ ppm 7.87 (s, 2H), 7.43-7.39 (m, 1H), 7.34-7.30 (m, 2H), 7.22 (d, J=7.6 Hz, 1H), 7.16 (s, 1H), 7.03 (s, 2H), 5.86 (t, J=9.9 Hz, 1H), 4.07 (dd, J=10.9, 17.3 Hz, 1H), 3.65 (dd, J=9.0, 17.4 Hz, 1H), 2.23 (s, 3H); ES-LCMS m/z 389.2 $[M+H]^+$ and (5R)-5-[4-methyl-3-[3-(trifluoromethyl)phenoxy]phenyl]-3-(triazol-1-yl)-4,5-dihydroisoxazole (25.55 mg, 65.79 µmol, 9.6% yield, 100% purity, SFC: $R_t$=3.103 min, ee=100%, $[α]^{26.1}_D$=+139.13, MeOH, c=0.023 g/100 ml) as white oil. $^1$H NMR (500 MHz, CDCl$_3$) δ ppm 8.29 (s, 1H), 7.83 (s, 1H), 7.45-7.40 (m, 1H), 7.37-7.31 (m, 2H), 7.21-7.16 (m, 2H), 7.05-7.00 (m, 2H), 5.90-5.84 (m, 1H), 4.15 (dd, J=10.9, 17.6 Hz, 1H), 3.74 (dd, J=9.0, 17.5 Hz, 1H), 2.24 (s, 3H); ES-LCMS m/z 389.2 $[M+H]^+$ and (5R)-5-[4-methyl-3-[3-(trifluoromethyl)phenoxy]phenyl]-3-(triazol-2-yl)-4,5-dihydroisoxazole (53.29 mg, 131.87 µmol, 19.3% yield, 96.1% purity, SFC: $R_t$=3.348 min, ee=99.84%, $[α]^{26.1}_D$=+158.14, MeOH, c=0.042 g/100 mL)) as white oil. $^1$H NMR (400 MHz, CDCl$_3$) δ ppm 7.87 (s, 2H), 7.44-7.38 (m, 1H), 7.35-7.30 (m, 2H), 7.22 (dd, J=1.5, 7.8 Hz, 1H), 7.16 (s, 1H), 7.03 (d, J=1.5 Hz, 2H), 5.85 (dd, J=9.3, 10.8 Hz, 1H), 4.07 (dd, J=10.9, 17.2 Hz, 1H), 3.65 (dd, J=9.0, 17.4 Hz, 1H), 2.23 (s, 3H); ES-LCMS m/z 389.2 $[M+H]^+$ and (5S)-5-[4-methyl-3-[3-(trifluoromethyl)phenoxy]phenyl]-3-(triazol-1-yl)-4,5-dihydroisoxazole (20.17 mg, 51.58 µmol, 7.5% yield, 99.3% purity, SFC: $R_t$=3.489 min, ee=99.66%, $[α]^{26.1}_D$=−139.13, MeOH, c=0.023 g/100 mL)) as white oil. $^1$H NMR (400 MHz, CDCl$_3$) δ ppm 8.29 (d, J=1.2 Hz, 1H), 7.82 (d, J=1.2 Hz, 1H), 7.45-7.39 (m, 1H), 7.36-7.30 (m, 2H), 7.21-7.16 (m, 2H), 7.05-7.00 (m, 2H), 5.87 (dd, J=9.2, 10.6 Hz, 1H), 4.15 (dd, J=10.9, 17.5 Hz, 1H), 3.74 (dd, J=9.0, 17.6 Hz, 1H), 2.24 (s, 3H); ES-LCMS m/z 389.2 $[M+H]^+$.

I-66

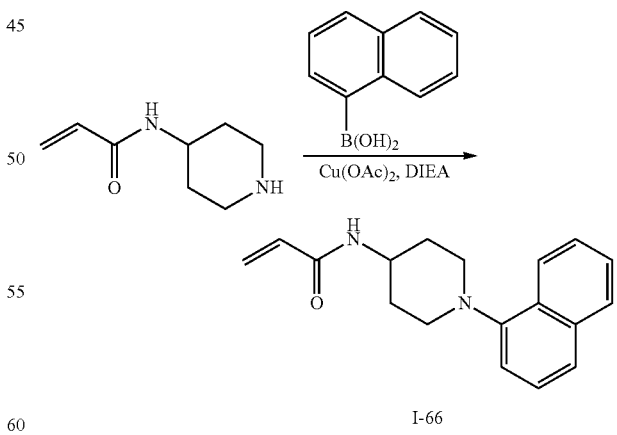

I-66

Step 1: N-[1-(1-Naphthyl)-4-piperidyl]prop-2-enamide

A mixture of N-(4-piperidyl)prop-2-enamide (500 mg, 1.84 mmol, 1 eq, HCl), 1-naphthylboronic acid (378.85 mg, 2.20 mmol, 1.2 eq), Cu(OAc)$_2$ (666.83 mg, 3.67 mmol, 2 eq) and DIEA (1.19 g, 9.18 mmol, 1.60 mL, 5 eq) in DCM (10 mL) was degassed and purged with N$_2$ for 3 times and then the mixture was stirred under N$_2$ atmosphere at 25° C. for 12 h. TLC (PE/EtOAc=1/1, R$_f$=0.42) showed one new spot was formed. The mixture was filtered and the filtrate was concentrated to give the residue which was purified by flash silica gel chromatography (from PE/EtOAc=100/1 to 1/1) to give crude product which was purified by preparative HPLC (column: Agela DuraShell C18 150*25 mm*5um; mobile phase: [water (0.05% NH$_3$·H$_2$O+10 mM NH$_4$HCO$_3$)-ACN]; B %: 37%-67%, 10 min) to yield N-[1-(1-naphthyl)-4-piperidyl]prop-2-enamide (11.50 mg, 41.02 µmol, 2.2% yield, 100.0% purity) as a red solid. $^1$H NMR (400 MHz, CDCl$_3$) δ ppm 8.17-8.14 (m, 1H), 7.85-7.82 (m, 1H), 7.56 (d, J=8.2 Hz, 1H), 7.50-7.44 (m, 2H), 7.47 (t, J=7.8 Hz, 1H), 7.10 (d, J=6.7 Hz, 1H), 6.35 (dd, J=1.4, 17.0 Hz, 1H), 6.32-6.10 (m, 1H), 5.68 (dd, J=1.2, 10.2 Hz, 1H), 5.54 (s, 1H), 4.20-4.10 (m, 1H), 3.41-3.38 (m, 2H), 2.97-2.91 (m, 2H), 2.21-2.18 (m, 2H), 1.88-1.79 (m, 2H); ES-LCMS m/z 281.1 [M+H]$^+$.

I-150 & I-151

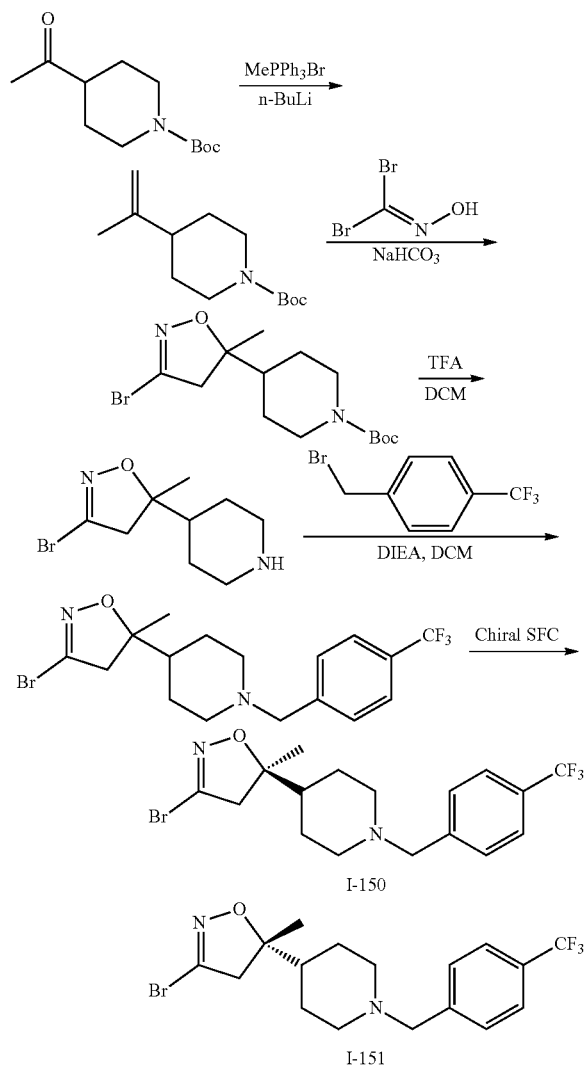

I-150

I-151

Step 1: tert-Butyl 4-isopropenylpiperidine-1-carboxylate

To a solution of methyl(triphenyl)phosphonium;bromide (1.12 g, 3.15 mmol, 1.3 eq) in THF (10 mL) was cooled to −78° C. then added n-BuLi (2.5 M, 1.45 mL, 1.5 eq) dropwise under N$_2$ atmosphere. The mixture was stirred at 0° C. for 0.5 h under N$_2$ atmosphere. The mixture was cooled to −78° C. and a solution of tert-butyl 4-acetylpiperidine-1-carboxylate (550 mg, 2.42 mmol, 1 eq) in THF (5 mL) was added slowly. The mixture was stirred at 28° C. for 4 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=5/1, R$_f$=0.65) to yield tert-butyl 4-isopropenylpiperidine-1-carboxylate (350 mg, 1.55 mmol, 64.2% yield, 100.0% purity) as colorless oil. $^1$H NMR (400 MHz, DMSO-d$_6$) δ ppm 4.72-4.65 (m, 2H), 4.07-3.90 (m, 2H), 2.67-2.50 (m, 2H), 2.0-1.95 (m, 1H), 1.68 (s, 3H), 1.67-1.63 (m, 2H), 1.38 (s, 9H), 1.23-1.13 (m, 2H)

Step 2: tert-Butyl 4-(3-bromo-5-methyl-4H-isoxazol-5-yl)piperidine-1-carboxylate To a solution of tert-butyl 4-isopropenylpiperidine-1-carboxylate (300 mg, 1.33 mmol, 1 eq) and dibromomethanone oxime (270.05 mg, 1.33 mmol, 1 eq) in EtOAc (10 mL) was added NaHCO$_3$ (1.12 g, 13.31 mmol, 10 eq). The mixture was stirred at 25° C. for 12 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=1/1, R$_f$=0.45) to yield tert-butyl 4-(3-bromo-5-methyl-4H-isoxazol-5-yl)piperidine-1-carboxylate (370 mg, 948.3 µmol, 71.2% yield, 89.0% purity) as light yellow oil. $^1$H NMR (400 MHz, CDCl$_3$) δ ppm 4.31-4.14 (m, 2H), 3.08-3.06 (m, 1H), 2.83-2.78 (m, 1H), 2.66-2.63 (m, 2H), 1.74-1.62 (m, 3H), 1.47 (s, 9H), 1.39 (s, 3H), 1.27 (t, J=7.1 Hz, 1H), 1.23-1.19 (m, 1H); ES-LCMS m/z 347.1, 348.1 [M+H]$^+$.

Step 3: 3-Bromo-5-methyl-5-(4-piperidyl)-4H-isoxazole

To a solution of tert-butyl 4-(3-bromo-5-methyl-4H-isoxazol-5-yl)piperidine-1-carboxylate (370 mg, 948.32 µmol, 1 eq) in DCM (6 mL) was added TFA (108.13 mg, 948.32 µmol, 70.21 µL, 1 eq). The mixture was stirred at 25° C. for 1 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield a residue which was 3-bromo-5-methyl-5-(4-piperidyl)-4H-isoxazole (300 mg, 805.75 µmol, 85.0% yield, 97.0% purity, TFA) as yellow oil. $^1$H NMR (400 MHz, DMSO-d$_6$) δ ppm 8.56 (s, 1H), 3.32 (d, J=12.2 Hz, 2H), 2.84 (t, J=10.5 Hz, 2H), 2.75-2.60 (m, 1H), 2.48-2.37 (m, 1H), 1.94-1.83 (m, 1H), 1.77 (t, J=13.3 Hz, 2H), 1.51-1.35 (m, 2H), 1.34-1.29 (m, 3H); ES-LCMS m/z 247.1 [M+H]$^+$.

Step 4: (5R)-3-Bromo-5-methyl-5-[1-[[4-(trifluoromethyl)phenyl]methyl]-4-piperidyl]-4H-isoxazole & (5S)-3-Bromo-5-methyl-5-[1-[[4-(trifluoromethyl)phenyl]methyl]-4-piperidyl]-4H-isoxazole To a solution of 3-bromo-5-methyl-5-(4-piperidyl)-4H-isoxazole (300 mg, 830.67 µmol, 1 eq, TFA) in DCM (15 mL) was added DIEA (536.79 mg, 4.15 mmol, 723.44 µL, 5 eq) and 1-(bromomethyl)-4-(trifluoromethyl)benzene (218.41 mg, 913.74 µmol, 140.91 µL, 1.1 eq) The mixture was stirred at 25° C. for 12 h under $N_2$ atmosphere. The reaction mixture was diluted with water (50 mL) then extracted with EtOAc (30 mL×3). The combined organic layers were dried over $Na_2SO_4$, filtered and the filtrate was concentrated to yield a residue which was purified by flash silica gel chromatography (from PE/EtOAc=100/1 to 2/1, TLC: PE/EtOAc=1/1, $R_f$=0.45) to yield which was separated by SFC (column: DAICEL CHIRALPAK AD-H (250 mm*30 mm, 5 µm); mobile phase: [0.1% $NH_3H_2O$ MeOH]; B %: 15%-15%, min) to yield Peak 1 and Peak 2. Peak 1 was concentrated under reduced pressure to yield a residue which was lyophilized to yield (5R)-3-bromo-5-methyl-5-[1-[[4-(trifluoromethyl)phenyl]methyl]-4-piperidyl]-4H-isoxazole (40 mg, 98.70 µmol, 11.9% yield, 100.0% purity, SFC: $R_t$=2.693 min, ee=99.4%, $[\alpha]^{25.9}_D$=+40.0, MeOH, c=0.025 g/100 mL) as colorless oil. $^1$H NMR (400 MHz, $CD_3OD$) δ ppm 7.65-7.60 (m, 2H), 7.53 (d, J=7.8 Hz, 2H), 3.59 (s, 2H), 3.20 (d, J=17.6 Hz, 1H), 2.97 (d, J=11.0 Hz, 2H), 2.91 (d, J=17.6 Hz, 1H), 2.03 (t, J=11.7 Hz, 2H), 1.75-1.57 (m, 3H), 1.44-1.36 (m, 2H), 1.35 (s, 3H); ES-LCMS m/z 405.1, 406.1 [M+H]$^+$. Peak 1 was concentrated under reduced pressure to yield a residue which was lyophilized to yield (5S)-3-bromo-5-methyl-5-[1-[[4-(trifluoromethyl)phenyl]methyl]-4-piperidyl]-4H-isoxazole (42 mg, 103.64 µmol, 12.5% yield, 100.0% purity, SFC: $R_t$=2.903 min, ee=93.7%, $[\alpha]^{25.9}_D$=−51.6, MeOH, c=0.031 g/100 mL) as colorless oil. $^1$H NMR (400 MHz, $CD_3OD$) δ ppm 7.65-7.61 (m, 2H), 7.55-7.51 (m, 2H), 3.59 (s, 2H), 3.20 (d, J=17.6 Hz, 1H), 2.97 (d, J=12.0 Hz, 2H), 2.91 (d, J=17.6 Hz, 1H), 2.03 (t, J=11.9 Hz, 2H), 1.74-1.57 (m, 3H), 1.45-1.36 (m, 2H), 1.35 (s, 3H); ES-LCMS m/z 405.1, 406.1 [M+H]$^+$.
I-67

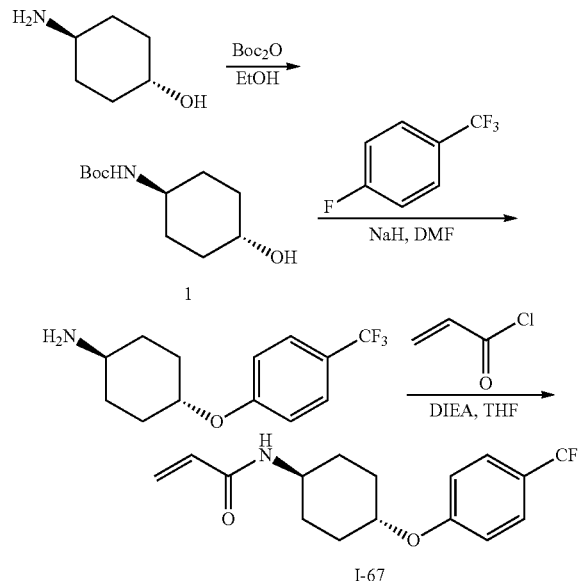

Step 1: Tert-butyl N-(4-hydroxycyclohexyl)carbamate

To a solution of 4-aminocyclohexanol (200 mg, 1.74 mmol, 1 eq) in EtOH (5 mL) was added tert-butoxycarbonyl tert-butyl carbonate (1.14 g, 5.21 mmol, 1.20 mL, 3 eq). The mixture was stirred at 29° C. for 12 h. TLC (PE/EtOAc=1/0, $R_f$=0.70) showed starting material was remained and one new spot was detected. The mixture was evaporated to yield a residue which was purified by flash silica gel chromatography (from PE/EtOAc=100/1 to 1/1, TLC: PE/EtOAc=1/1, $R_f$=0.40) to yield tert-butyl N-(4-hydroxycyclohexyl)carbamate (240 mg, 1.11 mmol, 64.2% yield, 100% purity) as a white solid. $^1$H NMR (500 MHz, DMSO-$d_6$) δ ppm 6.66 (d, J=7.9 Hz, 1H), 4.49 (d, J=4.4 Hz, 1H), 3.13 (s, 1H), 1.79-1.68 (m, 4H), 1.37 (s, 9H), 1.14 (t, J=9.5 Hz, 4H); ES-LCMS no desired m/z was detected.

Step 2: 4-[4-(Trifluoromethyl)phenoxy]cyclohexanamine

To a stirred solution of tert-butyl N-(4-hydroxycyclohexyl)carbamate (200 mg, 836.09 µmol, 1 eq) in DMF (6 mL) was added NaH (83.60 mg, 2.09 mmol, 60%, 2.5 eq) at 0° C. for 0.5 h. Then 1-fluoro-4-(trifluoromethyl)benzene (205.80 mg, 1.25 mmol, 159.54 µL, 1.5 eq) was added to the reaction mixture and stirred at 80° C. for 12 h under $N_2$ atmosphere. The reaction mixture was diluted with $H_2O$ (10 mL) and extracted with DCM and isopropanol ($V_{(DCM)}$:$V_{(isopropanol)}$=3:1; 20 mL×3). The combined organic layers were washed with brine (15 mL), dried over $Na_2SO_4$, filtered and concentrated under reduced pressure to yield a residue which was purified by flash silica gel chromatography (from DCM/MeOH=100/1 to 10/1, DCM/MeOH=100/1 to 10/1, $R_f$=0.38) to yield 4-[4-(trifluoromethyl)phenoxy]cyclohexanamine (60 mg, 196.71 µmol, 23.5% yield, 85.0% purity) as brown oil. $^1$H NMR (400 MHz, $CDCl_3$) δ ppm 7.52 (d, J=8.8 Hz, 2H), 6.93 (d, J=8.6 Hz, 2H), 4.33-4.23 (m, 1H), 2.94 (d, J=9.3 Hz, 1H), 2.17 (d, J=10.8 Hz, 2H), 2.05 (d, J=11.5 Hz, 2H), 1.60-1.49 (m, 2H), 1.47-1.36 (m, 2H); ES-LCMS m/z 260.2 [M+H]$^+$.

Step 3: N-[4-[4-(Trifluoromethyl)phenoxy]cyclohexyl]prop-2-enamide

To a stirred solution of 4-[4-(trifluoromethyl)phenoxy]cyclohexanamine (60 mg, 196.71 µmol, 1 eq) and prop-2-enoyl chloride (23.14 mg, 255.72 µmol, 20.85 uL, 1.3 eq) in THF (4 mL) was added $Et_3N$ (59.71 mg, 590.13 µmol, 82.14 µL, 3 eq). The reaction mixture was stirred at 25° C. for 12 h under $N_2$ atmosphere. The reaction mixture was diluted with $H_2O$ (10 mL) and extracted with EtOAc (20 mL×3). The combined organic layers were washed with brine (15 mL), dried over $Na_2SO_4$, filtered and concentrated under reduced pressure to yield a residue which was purified by preparative HPLC (column: Welch Xtimate C18 150*25 mm*5 µm; mobile phase: [water (10 mM $NH_4HCO_3$)-ACN]; B %: 36%-56%, 10 min) to yield N-[4-[4-(trifluoromethyl)phenoxy]cyclohexyl]prop-2-enamide (16.61 mg, 51.75 µmol, 26.3% yield, 97.6% purity) as a white solid. $^1$H NMR (500 MHz, DMSO-$d_6$) δ ppm 8.04 (d, J=6.9 Hz, 1H), 7.61 (d, J=8.7 Hz, 2H), 7.14 (d, J=8.5 Hz, 2H), 6.27-6.18 (m, 1H), 6.11-6.04 (m, 1H), 5.56 (dd, J=2.2, 10.1 Hz, 1H), 4.49-4.40 (m, 1H), 3.72-3.62 (m, 1H), 2.12-2.03 (m, 2H), 1.88 (d, J=9.8 Hz, 2H), 1.52-1.43 (m, 2H), 1.43-1.33 (m, 2H); ES-LCMS m/z 314.3 [M+H]$^+$.

I-68 & I-203

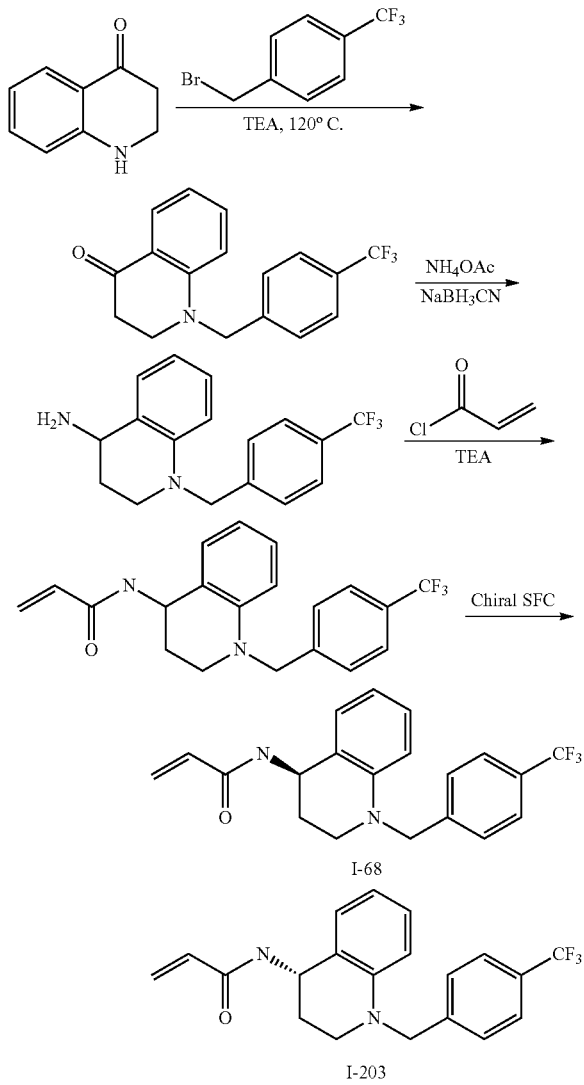

Step 1: 1-[[4-(Trifluoromethyl)phenyl]methyl]-2,3-dihydroquinolin-4-one

To a solution of 2,3-dihydro-1H-quinolin-4-one (200 mg, 1.36 mmol, 1 eq) in MeCN (5 mL) was added 1-(bromomethyl)-4-(trifluoromethyl)benzene (389.80 mg, 1.63 mmol, 251.48 μL, 1.2 eq) and DIEA (175.63 mg, 1.36 mmol, 236.70 μL, 1 eq). The mixture was stirred at 120° C. for 1.5 h under microwave. The reaction mixture was concentrated under reduced pressure to yield a residue which was purified by flash silica gel chromatography (from PE/EtOAc=100/1 to 3/1, TLC: PE/EtOAc=3/1, $R_f$=0.42) to yield 1-[[4-(trifluoromethyl)phenyl]methyl]-2,3-dihydroquinolin-4-one (370 mg, 1.19 mmol, 87.4% yield, 98.0% purity) as a yellow solid. NMR (500 MHz, CDCl$_3$) δ ppm 7.95 (dd, J=1.7, 7.9 Hz, 1H), 7.61 (d, J=8.1 Hz, 2H), 7.43 (d, J=7.9 Hz, 2H), 7.32 (ddd, J=1.7, 7.1, 8.6 Hz, 1H), 6.77 (t, J=7.4 Hz, 1H), 6.61 (d, J=8.5 Hz, 1H), 4.62 (s, 2H), 3.67-3.58 (m, 2H), 2.84-2.74 (m, 2H); ES-LCMS m/z 306.1 [M+H]$^+$.

Step 2: 1-[[4-(Trifluoromethyl)phenyl]methyl]-3,4-dihydro-2H-quinolin-4-amine

To a stirred solution of 1-[[4-(trifluoromethyl)phenyl]methyl]-2,3-dihydroquinolin-4-one (300 mg, 963.01 μmol, 1 eq) and ammonia; formic acid (850.12 mg, 13.48 mmol, 14 eq) in MeOH (6 mL) was stirred at 60° C. for 1 h. Then NaBH$_3$CN (302.58 mg, 4.82 mmol, 5 eq) was added to the reaction mixture and stirred at 60° C. for 12 h. The reaction mixture was concentrated under reduced pressure to remove MeOH. The residue was diluted with EtOAc (25 mL), then adjust pH to 2 with 6 N HCl and stirred at 25° C. for 1 h and extracted with H$_2$O (15 mL×1). The combined water layers were washed with sat. aq. NaOH to adjust pH to 9, then extracted with EtOAc (20 mL×2). The combined organic layers were washed with brine (15 mL), dried over Na$_2$SO$_4$, filtered and concentrated under reduced pressure to yield a residue which was used in the next step without further purification to yield 1-[[4-(trifluoromethyl)phenyl]methyl]-3,4-dihydro-2H-quinolin-4-amine (160 mg, 417.86 μmol, 43.4% yield, 80.0% purity) as red oil. $^1$H NMR (400 MHz, CDCl$_3$) δ ppm 7.57 (d, J=8.1 Hz, 2H), 7.38 (d, J=7.8 Hz, 2H), 7.24 (dd, J=1.2, 7.6 Hz, 1H), 7.07-7.01 (m, 1H), 6.67 (dt, J=1.0, 7.3 Hz, 1H), 6.44 (d, J=8.3 Hz, 1H), 4.55 (s, 2H), 4.08 (t, J=4.6 Hz, 1H), 3.60-3.51 (m, 1H), 3.37-3.29 (m, 1H), 2.19-2.06 (m, 1H), 1.95-1.85 (m, 1H); ES-LCMS no desired m/z was detected.

Step 3: N-[(4S)-1-[[4-(Trifluoromethyl)phenyl]methyl]-3,4-dihydro-2H-quinolin-4-yl]prop-2-enamide & N-[(4R)-1-[[4-(Trifluoromethyl)phenyl]methyl]-3,4-dihydro-2H-quinolin-4-yl]prop-2-enamide To a stirred solution of 1-[[4-(trifluoromethyl)phenyl]methyl]-3,4-dihydro-2H-quinolin-4-amine (110 mg, 287.28 μmol, 1 eq) and prop-2-enoyl chloride (39.00 mg, 430.92 μmol, 35.14 μL, 1.5 eq) in THF (5 mL) was added Et$_3$N (87.21 mg, 861.83 μmol, 119.96 μL, 3 eq). The reaction mixture was stirred at 25° C. for 12 h under N$_2$ atmosphere. The reaction mixture was concentrated under reduced pressure to remove THF. The residue was diluted with diluted with H$_2$O (15 mL) and extracted with EtOAc (20 mL×3). The combined organic layers were washed with brine (20 mL), dried over Na$_2$SO$_4$, filtered and concentrated under reduced pressure to yield a residue which was purified by preparative HPLC (column: Phenomenex Synergi C18 150*30 mm*4 μm; mobile phase: [water (0.05% HCl)-ACN]; B %: 56%-76%, 10 min) to yield crude product which was separated by chiral SFC (column: DAICEL CHIRALPAK AD-H (250 mm*30 mm, 5 μm); mobile phase: [0.1% NH$_3$H$_2$O ETOH]; B %: 20%-20%, min) to yield Peak 1 and Peak 2. Peak 1 was concentrated under reduced pressure to yield a residue which was dissolved in MeCN (20 mL) and H$_2$O (40 mL) and lyophilized to yield N-[(4S)-1-[[4-(trifluoromethyl)phenyl]methyl]-3,4-dihydro-2H-quinolin-4-yl]prop-2-enamide (27.99 mg, 77.00 μmol, 26.8% yield, 99.1% purity, SFC: $R_t$=2.763 min, ee=99.0%, $[α]^{27.8}_D$=+140 (MeOH, c=0.05 g/100 mL)) as a white solid. $^1$H NMR (400 MHz, CDCl$_3$) δ ppm 7.59 (d, J=8.1 Hz, 2H), 7.38 (d, J=8.1 Hz, 2H), 7.19 (d, J=7.6 Hz, 1H), 7.11-7.05 (m, 1H), 6.72-6.64 (m, 1H), 6.49 (d, J=8.1 Hz, 1H), 6.34 (dd, J=1.2, 17.1 Hz, 1H), 6.14-6.05 (m, 1H), 5.75 (d, J=6.8 Hz, 1H), 5.69 (dd, J=1.2, 10.3 Hz, 1H), 5.27-5.19 (m, 1H), 4.60-4.47 (m, 2H), 3.43-3.35 (m, 2H), 2.26-2.15 (m, 2H); ES-LCMS m/z 361.2 [M+H]$^+$. Peak 2 was concentrated under reduced pressure to yield a residue which was dissolved in MeCN (20 mL) and H$_2$O (40 mL) and lyophilized to yield N-[(4R)-1-[[4-(trifluoromethyl)phenyl]methyl]-3,4-dihydro-2H-quinolin-4-yl]prop-2-enamide (26.43 mg, 72.77 μmol, 25.3% yield, 99.2% purity SFC: R$_t$=3.020 min, ee=98.46%, [α]$^{27.7}_D$=−104.348 (MeOH, c=0.046 g/100 mL)) as a white solid. $^1$H NMR (400 MHz, CDCl$_3$) δ ppm 7.59 (d, J=8.1 Hz, 2H), 7.38 (d, J=8.1 Hz, 2H), 7.19 (d, J=7.6 Hz, 1H), 7.12-7.05 (m, 1H), 6.68 (t, J=7.3 Hz, 1H), 6.49 (d, J=8.3 Hz, 1H), 6.34 (dd, J=1.3, 17.0 Hz, 1H), 6.15-6.05 (m, 1H), 5.76 (d, J=6.8 Hz, 1H), 5.69 (dd, J=1.5, 10.3 Hz, 1H), 5.28-5.19 (m, 1H), 4.61-4.47 (m, 2H), 3.43-3.34 (m, 2H), 2.26-2.15 (m, 2H); ES-LCMS m/z 361.2 [M+H]$^+$.

I-129 & I-130

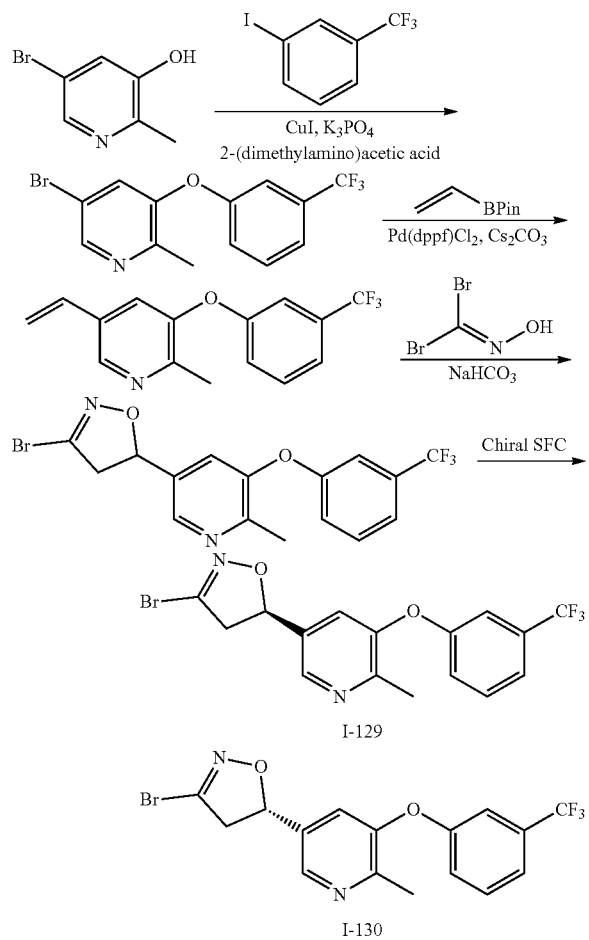

I-129

I-130

Step 1: 5-Bromo-2-methyl-3-[3-(trifluoromethyl)phenoxy]pyridine

To a stirred solution of 5-bromo-2-methyl-pyridin-3-ol (500 mg, 2.66 mmol, 1 eq) in DMSO (30 mL) was added K$_3$PO$_4$ (1.13 g, 5.32 mmol, 2 eq), CuI (50.65 mg, 265.93 μmol, 0.1 eq), pyridine-2-carboxylic acid (32.74 mg, 265.93 μmol, 0.1 eq) and 1-iodo-3-(trifluoromethyl)benzene (868.00 mg, 3.19 mmol, 459.26 μL, 1.2 eq). The reaction mixture was at 120° C. for 12 h under N$_2$ atmosphere. The reaction mixture was diluted with EtOAc (50 mL) then washed with saturated NaCl solution (30 mL×2). The aqueous phase was extracted with EtOAc (50 mL×2). The combined organic layers were dried over Na$_2$SO$_4$, filtered and the filtrate was concentrated to yield a residue which was purified by flash silica gel chromatography (from PE/EtOAc=100/1 to 3/1, TLC: PE/EtOAc=3/1, R$_f$=0.35) to yield 5-bromo-2-methyl-3-[3-(trifluoromethyl)phenoxy]pyridine (220 mg, 638.57 μmol, 24.0% yield, 96.4% purity) as yellow oil. $^1$H NMR (400 MHz, DMSO-d$_6$) δ ppm 8.61-8.43 (m, 1H), 7.80-7.69 (m, 1H), 7.67-7.60 (m, 1H), 7.58-7.51 (m, 1H), 7.41 (d, J=10.8 Hz, 1H), 7.33-7.22 (m, 1H), 2.39-2.31 (m, 3H); ES-LCMS m/z 332.0, 334.0 [M+H]$^+$.

Step 2: 2-Methyl-3-[3-(trifluoromethyl)phenoxy]-5-vinyl-pyridine

To a solution of 5-bromo-2-methyl-3-[3-(trifluoromethyl)phenoxy]pyridine (220 mg, 638.57 μmol, 1 eq) in 1,4-dioxane (3 mL) and water (1 mL) was added Pd(dppf)Cl$_2$ (46.72 mg, 63.86 μmol, 0.1 eq), Cs$_2$CO$_3$ (624.18 mg, 1.92 mmol, 3 eq) and 4,4,5,5-tetramethyl-2-vinyl-1,3,2-dioxaborolane (118.02 mg, 766.29 μmol, 129.98 μL, 1.2 eq). The mixture was bubbled with N$_2$ for 3 min and stirred at 100° C. for 30 min under microwave. The reaction mixture was diluted with EtOAc (15 mL) and filtered through a pad of celite. The filtrate was concentrated under reduced pressure to give a residue which was purified by flash silica gel chromatography (from PE/EtOAc=100/1 to 3/1, TLC: PE/EtOAc=3/1, R$_f$=0.25) to yield 2-methyl-3-[3-(trifluoromethyl)phenoxy]-5-vinyl-pyridine (150 mg, 510.28 μmol, 79.9% yield, 95.0% purity) as yellow oil. $^1$H NMR (500 MHz, DMSO-d$_6$) δ ppm 8.45 (d, J=1.4 Hz, 1H), 7.66-7.59 (m, 2H), 7.49 (d, J=7.8 Hz, 1H), 7.32 (s, 1H), 7.20 (dd, J=1.8, 8.2 Hz, 1H), 6.74 (dd, J=11.1, 17.7 Hz, 1H), 5.94 (d, J=17.7 Hz, 1H), 5.36 (d, J=11.0 Hz, 1H), 2.36 (s, 3H); ES-LCMS m/z 280.2 [M+H]$^+$.

Step 3: (5R)-3-Bromo-5-[6-methyl-5-[3-(trifluoromethyl)phenoxy]-3-pyridyl]-4,5-dihydroisoxazole & (5S)-3-bromo-5-[6-methyl-5-[3-(trifluoromethyl)phenoxy]-3-pyridyl]-4,5-dihydroisoxazole To a stirred solution of 2-methyl-3-[3-(trifluoromethyl)phenoxy]-5-vinyl-pyridine (150 mg, 483.43 μmol, 1 eq) in EtOAc (5 mL) was added NaHCO$_3$ (406.13 mg, 4.83 mmol, 188.02 μL, 10 eq) and dibromomethanone oxime (147.08 mg, 725.14 μmol, 1.5 eq). The reaction mixture was at 25° C. for 12 h under N$_2$ atmosphere. The reaction mixture was diluted with EtOAc (50 mL) then washed with saturated NaCl solution (30 mL×2). The aqueous phase was extracted with EtOAc (50 mL×2). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=2/1, R$_f$=0.30) then separated by SFC (column: DAICEL CHIRALPAK AD-H (250 mm*30 mm, 5 um); mobile phase: [0.1% NH$_3$H$_2$O EtOH]; B %: 35%-35%, min) to yield peak 1 and peak 2. Peak 1 was concentrated under reduced pressure to yield a residue which was dissolved in MeCN (20 mL) and H$_2$O (10 mL) and lyophilized to yield (5R)-3-bromo-5-[6-methyl-5-[3-(trifluoromethyl)phenoxy]-3-pyridyl]-4,5-dihydroisoxazole (25 mg, 62.32 μmol, 12.9% yield, 100.0% purity, SFC: R$_t$=2.698, ee=99.4%, [α]$^{26.1}_D$=+109.6 (MeOH, c=0.052 g/100 mL)) as yellow oil. $^1$H NMR (400 MHz, CDCl$_3$) δ ppm 8.33 (d, J=1.7 Hz, 1H), 7.51-7.45 (m, 1H), 7.43-7.38 (m, 1H), 7.23 (d, J=1.7 Hz, 1H), 7.20 (s, 1H), 7.07 (d, J=8.3 Hz, 1H), 5.69 (dd, J=9.0, 10.5 Hz, 1H), 3.66 (dd, J=10.9, 17.2 Hz, 1H), 3.18 (dd, J=8.8, 17.1 Hz, 1H), 2.52 (s, 3H), 2.54-2.50 (m, 1H); ES-LCMS m/z 401.1, 403.1 [M+H]+. Peak 2 was concentrated under reduced pressure to yield a residue which was dissolved in MeCN (20 mL) and H$_2$O (10 mL) and lyophilized to yield (5S)-3-bromo-5-[6-methyl-5-[3-(trifluoromethyl)phenoxy]-3-pyridyl]-4,5-dihydroisoxazole (25 mg, 62.32 µmol, 12.9% yield, 100.0% purity, SFC: R$_t$=4.388, ee=99.8%, $[\alpha]^{26.1}_D$=−118.5 (MeOH, c=0.054 g/100 mL)) as yellow oil. $^1$H NMR (400 MHz, CDCl$_3$) δ ppm 8.33 (d, J=1.7 Hz, 1H), 7.52-7.45 (m, 1H), 7.43-7.38 (m, 1H), 7.23 (d, J=1.7 Hz, 1H), 7.20 (s, 1H), 7.07 (d, J=8.3 Hz, 1H), 5.69 (dd, J=8.9, 10.6 Hz, 1H), 3.66 (dd, J=10.9, 17.2 Hz, 1H), 3.18 (dd, J=8.8, 17.4 Hz, 1H), 2.52 (s, 3H); ES-LCMS m/z 401.1, 403.1 [M+H]+.

I-69

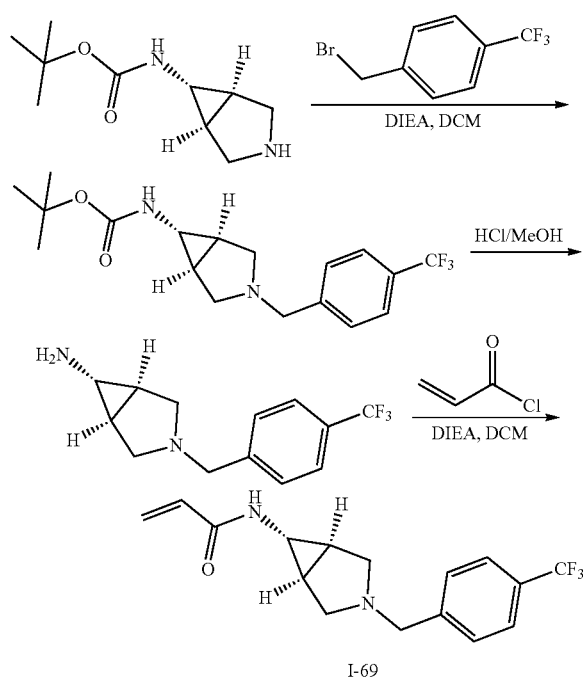

I-69

Step 1: tert-Butyl N-[(1R,5S)-3-[[4-(trifluoromethyl)phenyl]methyl]-3-azabicyclo[3.1.0]hexan-6-yl]carbamate To a solution of tert-butyl N-[(1R,5S)-3-azabicyclo[3.1.0]hexan-6-yl]carbamate (40 mg, 201.75 µmol, 1 eq) and 1-(bromomethyl)-4-(trifluoromethyl)benzene (48.23 mg, 201.75 µmol, 31.11 µL, 1 eq) in DCM (5 mL) was added DIEA (52.15 mg, 403.51 µmol, 70.28 uL, 2 eq). The mixture was stirred at 25° C. for 16 h. The solvent was removed to give a residue which was purified by preparative TLC (PE/EtOAc=3/1, R$_f$=0.45) to yield tert-butyl N-[(1R,5S)-3-[[4-(trifluoromethyl)phenyl]methyl]-3-azabicyclo[3.1.0]hexan-6-yl]carbamate (66 mg, 181.49 µmol, 89.9% yield, 98.0% purity) as a white solid. $^1$H NMR (500 MHz, CDCl$_3$) δ ppm 7.53 (d, J=8.1 Hz, 2H), 7.36 (d, J=8.1 Hz, 2H), 4.59 (br s, 1H), 3.60 (s, 2H), 3.06 (d, J=8.9 Hz, 2H), 2.90 (br s, 1H), 2.40-2.38 (m, 2H), 1.53-1.50 (m, 2H), 1.44 (s, 9H); ES-LCMS m/z 357.2 [M+H]+.

Step 2: (1R,5S)-3-[[4-(Trifluoromethyl)phenyl]methyl]-3-azabicyclo[3.1.0]hexan-6-amine A mixture of tert-butyl N-[(1R,5S)-3-[[4-(trifluoromethyl)phenyl]methyl]-3-azabicyclo[3.1.0]hexan-6-yl]carbamate (66 mg, 181.49 µmol, 1 eq) in HCl/MeOH (5 mL, 4 M) was stirred at 25° C. for 1 h. The reaction mixture was concentrated to yield (1R,5S)-3-[[4-(trifluoromethyl)phenyl]methyl]-3-azabicyclo[3.1.0]hexan-6-amine (58 mg, 178.32 µmol, 98.3% yield, 90.0% purity, HCl) as a white solid. $^1$H NMR (500 MHz, CD$_3$OD) δ ppm 7.85-7.79 (m, 4H), 4.51 (br s, 2H), 3.74-3.65 (m, 4H), 3.25-3.23 (m, 1H), 2.34-2.31 (m, 2H); ES-LCMS m/z 257.2 [M+H]+.

Step 3: N-[(1R,5S)-3-[[4-(Trifluoromethyl)phenyl]methyl]-3-azabicyclo[3.1.0]hexan-6-yl]prop-2-enamide To a solution of (1R,5S)-3-[[4-(trifluoromethyl)phenyl]methyl]-3-azabicyclo[3.1.0]hexan-6-amine (58 mg, 203.69 µmol, 1 eq) and DIEA (78.98 mg, 611.08 µmol, 106.44 µL, 3 eq) in DCM (5 mL) was added prop-2-enoyl chloride (18.44 mg, 203.69 µmol, 16.61 µL, 1 eq) at 0° C. The mixture was stirred at 0° C. for 30 min. The mixture was concentrated under reduced pressure to give a residue which was purified by preparative HPLC (column: Agela DuraShell C18 150*25 mm*5 um; mobile phase: [water (0.05% NH$_3$H$_2$O+10 mM NH$_4$HCO$_3$)-ACN]; B %: 36%-66%, 10 min), followed by lyophilization to yield N-[(1R,5S)-3-[[4-(trifluoromethyl)phenyl]methyl]-3-azabicyclo[3.1.0]hexan-6-yl]prop-2-enamide (28.3 mg, 91.20 µmol, 44.8% yield, 100% purity, SFC: R$_t$=3.013, ee=100%) as a white solid. $^1$H NMR (500 MHz, CDCl$_3$) δ ppm 7.54 (d, J=7.9 Hz, 2H), 7.37 (d, J=7.9 Hz, 2H), 6.27 (dd, J=1.1, 16.9 Hz, 1H), 6.01 (dd, J=10.4, 16.9 Hz, 1H), 5.62 (d, J=10.4 Hz, 1H), 5.52 (br s, 1H), 3.62 (s, 2H), 3.17-3.08 (m, 3H), 2.42 (d, J=8.4 Hz, 2H), 1.57-1.55 (m, 2H); ES-LCMS m/z 311.2 [M+H]+.

I-131 & I-132

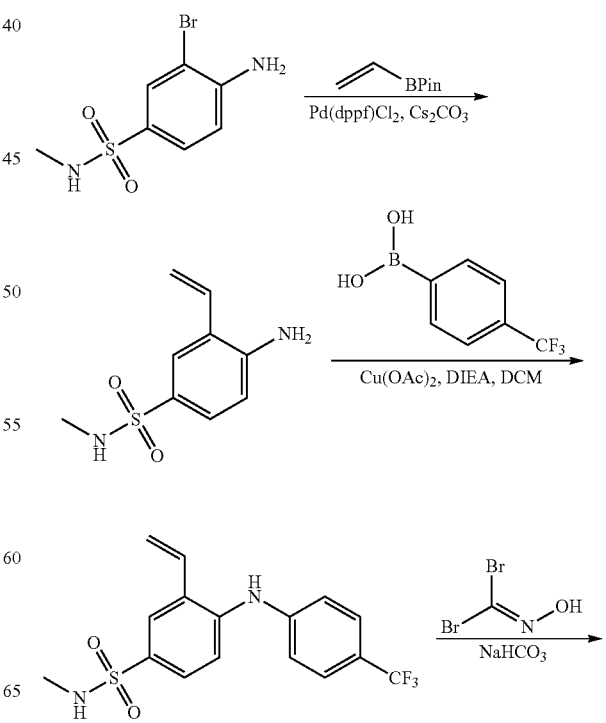

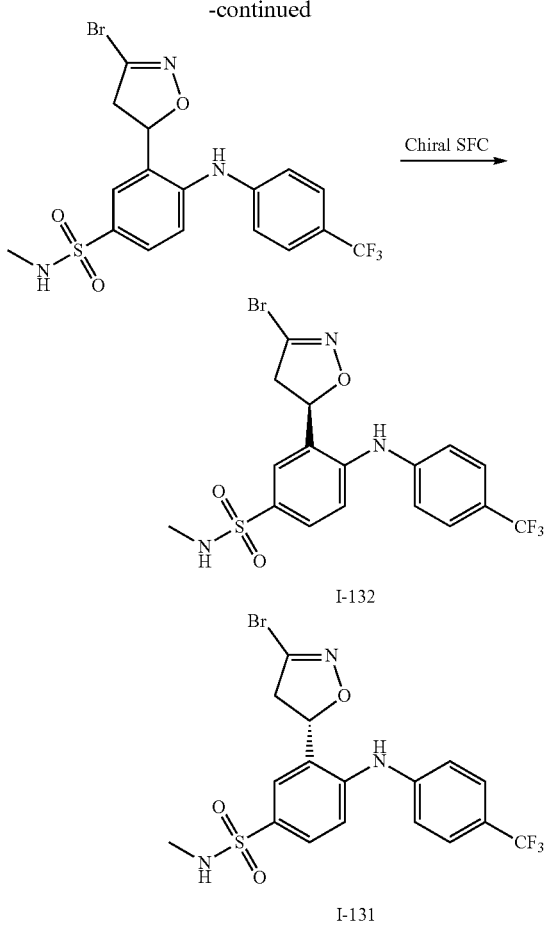

I-132

I-131

Step 1: 4-Amino-N-methyl-3-vinylbenzenesulfonamide

To a solution of 4-amino-3-bromo-N-methyl-benzenesulfonamide (1 g, 3.77 mmol, 1 eq) in 1,4-dioxane (20 mL) and H₂O (4 mL) was added Pd(dppf)Cl₂ (137.99 mg, 188.59 µmol, 0.05 eq), 4,4,5,5-tetramethyl-2-vinyl-1,3,2-dioxaborolane (668.05 mg, 4.34 mmol, 735.73 µL, 1.15 eq) and Cs₂CO₃ (2.46 g, 7.54 mmol, 2.0 eq). The mixture was stirred under N₂ atmosphere at 100° C. for 16 h. The mixture was concentrated, diluted with water (10 mL) and extracted with EtOAc (20 mL×3). The combined organic layers were washed with brine (20 mL), dried over Na₂SO₄, filtered and concentrated to yield a residue which was purified by flash silica gel chromatography (from PE/EtOAc=100/1 to 3/1, TLC: PE/EtOAc=3/1, $R_f$=0.6) to yield 4-amino-N-methyl-3-vinyl-benzenesulfonamide (700 mg, 2.97 mmol, 78.7% yield, 90.0% purity) as a yellow solid. ¹H NMR (400 MHz, CDCl₃) δ ppm 7.75 (d, J=2.20 Hz, 1H), 7.56 (dd, J=2.20, 8.56 Hz, 1H), 6.74-6.65 (m, 2H), 5.72 (dd, J=0.98, 17.36 Hz, 1H), 5.46 (dd, J=0.86, 11.13 Hz, 1H), 2.65 (d, J=5.38 Hz, 3H); ES-LCMS m/z 213.1 [M+H]⁺.

Step 2: N-Methyl-4-[4-(trifluoromethyl)anilino]-3-vinyl-benzenesulfonamide

To a solution of 4-amino-N-methyl-3-vinyl-benzenesulfonamide (400 mg, 1.70 mmol, 1 eq) in DCM (10 mL) was added Cu(OAc)₂ (462.07 mg, 2.54 mmol, 1.5 eq), [4-(trifluoromethyl)phenyl]boronic acid (644.22 mg, 3.39 mmol, 2.0 eq) and DIEA (657.58 mg, 5.09 mmol, 886.22 µL, 3.0 eq). The mixture was stirred under O₂ (15 psi) at 30° C. for 48 h. The mixture was concentrated, diluted with water (10 mL) and extracted with EtOAc (20 mL×3). The combined organic layers were washed with brine (20 mL), dried over Na₂SO₄, filtered and concentrated to yield a residue which was purified by flash silica gel chromatography (from PE/EtOAc=100/1 to 1/1, TLC: PE/EtOAc=1/1, $R_f$=0.3) to yield N-methyl-4-[4-(trifluoromethyl)anilino]-3-vinyl-benzenesulfonamide (60 mg, 151.53 µmol, 8.9% yield, 90.0% purity) as yellow oil. ¹H NMR (400 MHz, CDCl₃) δ ppm 7.92 (d, J=2.20 Hz, 1H), 7.69 (dd, J=2.20, 8.56 Hz, 1H), 7.57 (d, J=8.31 Hz, 2H), 7.39 (d, J=8.56 Hz, 1H), 7.13 (d, J=8.56 Hz, 2H), 6.86-6.79 (m, 1H), 6.02 (s, 1H), 5.80 (d, J=0.98 Hz, 1H), 5.48-5.56 (m, 1H), 2.71 (d, J=5.38 Hz, 3H); ES-LCMS m/z 357.1 [M+H]⁺.

Step 3: (S)-3-(3-Bromo-4,5-dihydroisoxazol-5-yl)-N-methyl-4-((4-(trifluoromethyl)phenyl)amino)benzenesulfonamide and (R)-3-(3-bromo-4,5-dihydroisoxazol-5-yl)-N-methyl-4-((4-(trifluoromethyl)phenyl)amino)benzenesulfonamide To a solution of dibromomethanone oxime (36.88 mg, 181.84 µmol, 1.2 eq) in EtOAc (10 mL) was added NaHCO₃ (127.30 mg, 1.52 mmol, 10 eq) and N-methyl-4-[4-(trifluoromethyl)anilino]-3-vinyl-benzenesulfonamide (60 mg, 151.53 µmol, 1 eq). The mixture was stirred at 27° C. for 16 h. The mixture was filtered, washed with EtOAc (10 mL×2). The filtrate was concentrated to give a residue which was purified by preparative TLC (PE/EtOAc=1/1, $R_f$=0.3) to yield crude product which was separated by chiral SFC (column: DAICEL CHIRALPAK IG (250 mm*30 mm, 10 um); mobile phase: [0.1% NH₃·H₂O EtOH]; B %: 25%-25%) to yield Peak 1 and Peak 2. Peak 1 was concentrated under reduced pressure to yield a residue which was dissolved in MeCN (10 mL) and H₂O (10 mL) and lyophilized to yield 3-[(5S)-3-bromo-4,5-dihydroisoxazol-5-yl]-N-methyl-4-[4-(trifluoromethyl)anilino]benzenesulfonamide (36.25 mg, 73.22 µmol, 48.3% yield, 96.6% purity, SFC: $R_t$=4.484, ee=99.5%, [α]²⁶·¹_D=−52.0 (CH₃OH, c=0.05 g/100 mL)) as a white solid. ¹H NMR (400 MHz, CDCl₃) δ ppm 7.84-7.74 (m, 2H), 7.59 (d, J=8.61 Hz, 2H), 7.51 (d, J=8.61 Hz, 1H), 7.14 (d, J=8.22 Hz, 2H), 6.69 (s, 1H), 5.78 (t, J=11.15 Hz, 1H), 4.30 (d, J=5.48 Hz, 1H), 3.52 (d, J=11.35 Hz, 2H), 2.70 (d, J=5.48 Hz, 3H); ES-LCMS m/z 478.0, 480.0 [M+H]⁺. Peak 2 was concentrated under reduced pressure to yield a residue which was dissolved in MeCN (10 mL) and H₂O (10 mL) and lyophilized to yield 3-[(5R)-3-bromo-4,5-dihydroisoxazol-5-yl]-N-methyl-4-[4-(trifluoromethyl)anilino]benzenesulfonamide (20.6 mg, 40.92 µmol, 27.0% yield, 95.0% purity, SFC: $R_t$=4.281, ee=98.1%, [α]²⁶·¹_D=+44.0 (CH₃OH, c=0.05 g/100 mL)) as a white solid. ¹H NMR (400 MHz, CDCl₃) δ ppm 7.84-7.74 (m, 2H), 7.59 (d, J=8.61 Hz, 2H), 7.51 (d, J=8.61 Hz, 1H), 7.14 (d, J=8.22 Hz, 2H), 6.69 (s, 1H), 5.78 (t, J=11.15 Hz, 1H), 4.30 (d, J=5.48 Hz, 1H), 3.52 (d, J=11.35 Hz, 2H), 2.70 (d, J=5.48 Hz, 3H); ES-LCMS m/z 478.0, 480.0 [M+H]⁺. I-152 & I-153

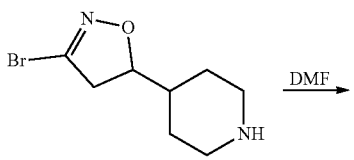

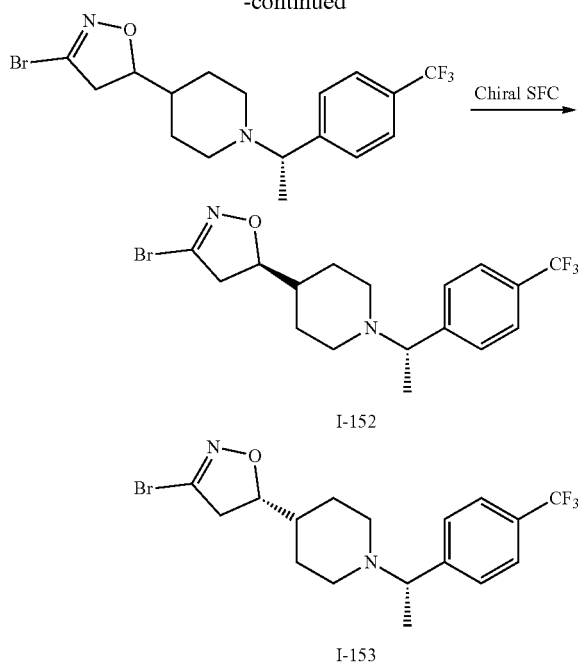

I-152

I-153

Step 1: 3-Bromo-5-[1-[(1R)-1-[4-(trifluoromethyl)phenyl]ethyl]-4-piperidyl]-4,5-dihydroisoxazole To a solution of 3-bromo-5-(4-piperidyl)-4,5-dihydroisoxazole (520 mg, 1.35 mmol, 1.06 eq, TFA) and [(1R)-1-[4-(trifluoromethyl)phenyl]ethyl] methanesulfonate (380 mg, 1.27 mmol, 1.0 eq) in DMF (3 mL) was added Cs₂CO₃ (1.25 g, 3.82 mmol, 3 eq). The mixture was stirred at 28° C. for 48 h. The reaction mixture was quenched by addition of H₂O (20 mL) and extracted with EtOAc (20 mL×3). The combined organic layers were washed with brine (30 mL), dried over Na₂SO₄, filtered and concentrated under reduced pressure to give a residue which was purified by preparative HPLC (column: Welch Xtimate C18 150*25 mm*5 um; mobile phase: [water (10 mM $NH_4HCO_3$)-ACN]; B %: 50%-80%, 10 min) to yield 3-bromo-5-[1-[(1R)-1-[4-(trifluoromethyl)phenyl]ethyl]-4-piperidyl]-4,5-dihydroisoxazole (250 mg, 616.90 μmol, 48.4% yield, 100.0% purity) as a white solid. ES-LCMS m/z 407.1 [M+H]⁺.

Step 2: (5S)-3-bromo-5-[1-[(1R)-1-[4-(trifluoromethyl)phenyl]ethyl]-4-piperidyl]-4,5-dihydroisoxazole and (5R)-3-bromo-5-[1-[(1R)-1-[4-(trifluoromethyl)phenyl]ethyl]-4-piperidyl]-4,5-dihydroisoxazole 3-bromo-5-[1-[(1R)-1-[4-(trifluoromethyl)phenyl]ethyl]-4-piperidyl]-4,5-dihydroisoxazole (250 mg, 616.90 μmol, 1 eq) was separated by SFC (column: DAICEL CHIRALPAK IG (250 mm*30 mm, 10 μm); mobile phase: [0.1% NH₃·H₂O-MeOH]; B %: 20%-20%) to yield peak 1 and peak 2. Peak 1 was concentrated under reduced pressure to yield a residue which was dissolved in MeCN (15 mL) and water (15 mL) and lyophilized to yield (5S)-3-bromo-5-[1-[(1R)-1-[4-(trifluoromethyl)phenyl]ethyl]-4-piperidyl]-4,5-dihydroisoxazole (30.1 mg, 73.68 μmol, 11.9% yield, 99.2% purity, SFC: $R_t$=2.431, Dr=99.7%, $[\alpha]^{26.9}_D$=+48.485 (MeOH, c=0.033 g/100 mL)) as colorless oil. ¹H NMR (400 MHz, CD₃OD) δ ppm 7.63 (d, J=8.0 Hz, 2H), 7.53 (d, J=8.0 Hz, 2H), 4.51-4.44 (m, 1H), 3.57 (d, J=6.4 Hz, 1H), 3.29-3.23 (m, 1H), 3.19 (d, J=10.8 Hz, 1H), 3.01 (dd, J=8.8, 17.2 Hz, 1H), 2.85 (d, J=11.2 Hz, 1H), 2.02 (t, J=11.2 Hz, 1H), 1.93 (t, J=11.2 Hz, 1H), 1.88-1.81 (m, 1H) 1.56-1.48 (m, 2H), 1.42 (d, J=6.8 Hz, 3H), 1.39-1.26 (m, 2H); ES-LCMS m/z 405.0 [M+H]⁺. Peak 2 was concentrated under reduced pressure and then separated by SFC (column: DAICEL CHIRALPAK AD-H (250 mm*30 mm, 5 um); mobile phase: [0.1% NH₃·H₂O-MeOH]; B %: 15%-15%) to yield peak 3 and peak 4. Peak 4 was concentrated under reduced pressure to yield a residue which was dissolved in MeCN (15 mL) and water (15 mL) and lyophilized to yield (5R)-3-bromo-5-[1-[(1R)-1-[4-(trifluoromethyl)phenyl]ethyl]-4-piperidyl]-4,5-dihydroisoxazole (40.05 mg, 98.8 μmol, 16.0% yield, 100.0% purity, SFC: $R_t$=2.663, Dr=99.64%, $[\alpha]^{26.8}_D$=−83.33 (MeOH, c=0.024 g/100 mL)) as colorless oil. ¹H NMR (400 MHz, CD₃OD) δ ppm 7.62 (d, J=8.0 Hz, 2H), 7.52 (d, J=8.4 Hz, 2H), 4.51-4.44 (m, 1H), 3.57-3.51 (m, 1H), 3.29-3.23 (m, 1H), 3.16 (d, J=12.0 Hz, 1H), 3.02 (dd, J=8.8, 17.2 Hz, 1H), 2.84 (d, J=9.6 Hz, 1H), 2.05-1.96 (m, 1H), 1.93-1.83 (m, 1H), 1.77-1.69 (m, 1H), 1.66-1.59 (m, 1H), 1.58-1.47 (m, 1H), 1.47-1.37 (m, 4H), 1.32-1.21 (m, 1H); ES-LCMS m/z 405.0 [M+H]⁺.

I-154 & I-155

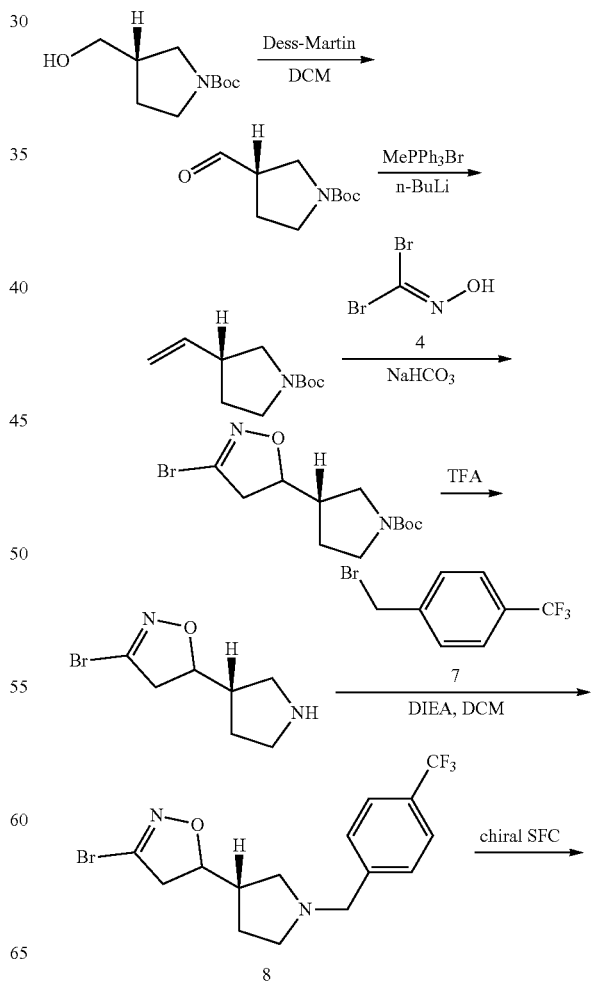

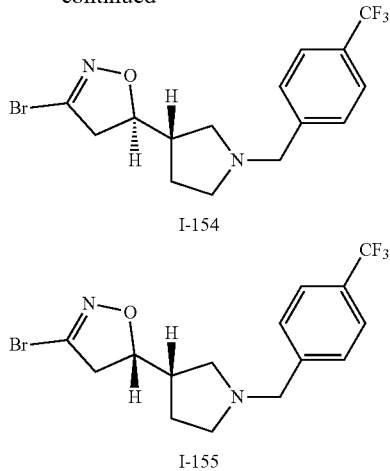

I-154

I-155

Step 1: tert-Butyl (3S)-3-formylpyrrolidine-1-carboxylate

To a mixture of tert-butyl (3S)-3-(hydroxymethyl)pyrrolidine-1-carboxylate (1.7 g, 8.45 mmol, 1 eq) in DCM (50 mL) was added Dess-Martin periodinane (4.66 g, 10.98 mmol, 1.3 eq) at 25° C. The mixture was stirred at 25° C. for 12 h. TLC (PE/EtOAc=3/1, $R_f$=0.30) showed the starting material was consumed completely. The reaction mixture was filtered. The filtrate was concentrated under reduced pressure to yield a residue which was purified by flash silica gel chromatography (from PE/EtOAc=100/1 to 4/1, TLC: PE/EtOAc=3/1, $R_f$=0.50) to yield tert-butyl (3S)-3-formylpyrrolidine-1-carboxylate (1.5 g, 7.53 mmol, 89.1% yield, N/A purity) as colorless oil. $^1$H NMR (500 MHz, CDCl$_3$) δ ppm 9.70 (d, J=1.5 Hz, 1H), 3.80-3.66 (m, 1H), 3.60-3.54 (m, 1H), 3.46-3.36 (m, 2H), 3.12-3.03 (m, 1H), 2.20-2.14 (m, 2H), 1.47 (s, 9H).

Step 2: tert-Butyl (3R)-3-vinylpyrrolidine-1-carboxylate

To a solution of methyl(triphenyl)phosphonium;bromide (4.03 g, 11.29 mmol, 1.5 eq) in THF (40 mL) was added n-BuLi (2.5 M, 5.42 mL, 1.8 eq) dropwise under N$_2$ atmosphere at −70° C. The mixture was stirred at −70~0° C. for 0.5 h. The mixture was cooled to −70° C. A solution of tert-butyl (3S)-3-formylpyrrolidine-1-carboxylate (1.5 g, 7.53 mmol, 1 eq) in THF (10 mL) was added dropwise under N$_2$ atmosphere at −70° C. The mixture was stirred at 25° C. for 11.5 h. TLC (PE/EtOAc=3/1, $R_f$=0.60) showed the starting material was consumed completely. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by flash silica gel chromatography (from PE/EtOAc=100/1 to 10/1, TLC: PE/EtOAc=3/1, $R_f$=0.60) to yield tert-butyl (3R)-3-vinylpyrrolidine-1-carboxylate (530 mg, 2.69 mmol, 35.7% yield, N/A purity) as colorless oil. $^1$H NMR (400 MHz, CDCl$_3$) δ ppm 5.77 (td, J=8.5, 17.1 Hz, 1H), 5.14-5.08 (m, 1H), 5.06-5.01 (m, 1H), 3.63-3.40 (m, 2H), 3.35-3.23 (m, 1H), 3.13-2.98 (m, 1H), 2.87-2.73 (m, 1H), 2.04-1.96 (m, 1H), 1.79-1.68 (m, 1H), 1.46 (s, 9H).

Step 3: tert-Butyl (3S)-3-(3-bromo-4,5-dihydroisoxazol-5-yl)pyrrolidine-1-carboxylate A mixture of tert-butyl (3R)-3-vinylpyrrolidine-1-carboxylate (530 mg, 2.69 mmol, 1 eq), dibromomethanone oxime (600 mg, 2.96 mmol, 1.1 eq) and NaHCO$_3$ (2.26 g, 26.87 mmol, 10 eq) in EtOAc (20 mL) was stirred at 25° C. for 12 h. TLC (PE/EtOAc=3/1, $R_f$=0.32, 0.27) showed the starting material was consumed completely. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by flash silica gel chromatography (from PE/EtOAc=100/1 to 1/1, TLC: PE/EtOAc=3/1, $R_f$=0.32, 027) to yield tert-butyl (3S)-3-(3-bromo-4,5-dihydroisoxazol-5-yl)pyrrolidine-1-carboxylate (630 mg, 1.97 mmol, 73.5% yield, 100.0% purity) as colorless oil. $^1$H NMR (400 MHz, CDCl$_3$) δ ppm 4.73-4.48 (m, 1H), 3.70-3.42 (m, 2H), 3.31 (dd, J=10.5, 17.1 Hz, 2H), 3.24-3.02 (m, 1H), 2.95 (dd, J=8.3, 16.9 Hz, 1H), 2.46 (qd, J=7.9, 16.0 Hz, 1H), 2.12-2.02 (m, 1H) 2.00-1.74 (m, 1H), 1.47 (s, 9H); ES-LCMS m/z 263.1, 2651 [M-t-Bu+H]$^+$.

Step 4: 3-Bromo-5-[(3S)-pyrrolidin-3-yl]-4,5-dihydroisoxazole

To a solution of tert-butyl (3S)-3-(3-bromo-4,5-dihydroisoxazol-5-yl)pyrrolidine-1-carboxylate (300 mg, 939.87 μmol, 1 eq) in DCM (6 mL) was added TFA (3.08 g, 27.01 mmol, 2 mL, 28.74 eq) at 25° C. The mixture was stirred at 25° C. for 1 h. The reaction mixture was concentrated under reduced pressure to yield 3-bromo-5-[(3S)-pyrrolidin-3-yl]-4,5-dihydroisoxazole (310 mg, 930.65 μmol, 99.0% yield, N/A purity, TFA) as colorless oil, which was used in the next step without further purification. $^1$H NMR (400 MHz, CDCl$_3$) δ ppm 4.90-4.69 (m, 1H), 3.62-3.52 (m, 2H), 3.44 (dd, J=10.6, 16.4 Hz, 2H), 3.34-3.24 (m, 1H), 2.99 (dd, J=7.6, 17.4 Hz, 1H), 2.80-2.70 (m, 1H), 2.34-2.24 (m, 1H), 1.96 (d, J=5.9 Hz, 1H).

Step 5: (5R)-3-Bromo-5-[(3S)-1-[[4-(trifluoromethyl)phenyl]methyl]pyrrolidin-3-yl]-4,5-dihydroisoxazole and (5S)-3-bromo-5-[(3S)-1-[[4-(trifluoromethyl)phenyl]methyl]pyrrolidin-3-yl]-4,5-dihydroisoxazole A mixture of 3-bromo-5-[(3S)-pyrrolidin-3-yl]-4,5-dihydroisoxazole (310 mg, 930.65 μmol, 1 eq, TFA), 1-(bromomethyl)-4-(trifluoromethyl)benzene (225 mg, 941.30 μmol, 1.01 eq) and DIEA (600 mg, 4.64 mmol, 808.63 μL, 4.99 eq) in DCM (20 mL) was stirred at 25° C. for 12 h. The reaction mixture was concentrated under reduced pressure to yield a residue which was purified by flash silica gel chromatography (from PE/EtOAc=100/1 to 1/1, TLC: PE/EtOAc=1/1, $R_f$=0.40). The desired fraction was concentrated under reduced pressure to yield a residue (98 mg) which was separated by chiral SFC (column: DAICEL CHIRALPAK AD (250 mm*30 mm, 10 um); mobile phase: [0.1% NH$_3$·H$_2$O/EtOH]; B %: 20%-20%) to yield peak 1 and peak 2. Peak 1 was concentrated under reduced pressure to yield a residue which was dissolved in MeCN (15 mL) and water (15 mL) and lyophilized to yield (5R)-3-bromo-5-[(3S)-1-[[4-(trifluoromethyl)phenyl]methyl]pyrrolidin-3-yl]-4,5-dihydroisoxazole (29.45 mg, 77.84 μmol, 8.4% yield, 99.7% purity, SFC: $R_t$=0.682, Dr=100%, $[\alpha]^{27.3}_D$=+64.41 (CHCl$_3$, c=0.059 g/100 mL)) as a white solid. $^1$H NMR (400 MHz, CDCl$_3$) δ ppm 7.58 (d, J=7.8 Hz, 2H), 7.44

(d, J=7.8 Hz, 2H), 4.68 (ddd, J=6.5, 8.9, 10.5 Hz, 1H), 3.72-3.61 (m, 2H), 3.27-3.18 (m, 1H), 3.13-3.04 (m, 1H), 2.69 (dt, J=5.3, 8.5 Hz, 1H), 2.57 (d, J=7.4 Hz, 3H), 2.43-2.36 (m, 1H), 2.11-1.99 (m, 1H), 1.73-1.63 (m, 1H); ES-LCMS m/z 377.1, 379.1 [M+H]+. Peak 2 was concentrated under reduced pressure to yield a residue which was dissolved in MeCN (15 mL) and water (15 mL) and lyophilized to yield (5S)-3-bromo-5-[(3S)-1-[[4-(trifluoromethyl)phenyl]methyl]pyrrolidin-3-yl]-4,5-dihydroisoxazole (40.43 mg, 105.80 μmol, 11.4% yield, 98.7% purity, SFC: $R_t$=1.338, Dr=100%, $[α]^{27.4}_D$=-61.29 (CHCl$_3$, c=0.062 g/100 mL)) as a white solid. $^1$H NMR (400 MHz, CDCl$_3$) δ ppm 7.58 (d, J=7.8 Hz, 2H), 7.44 (d, J=8.2 Hz, 2H), 4.67 (td, J=8.4, 10.2 Hz, 1H), 3.72-3.60 (m, 2H), 3.26 (dd, J=10.2, 17.2 Hz, 1H), 2.95 (dd, J=8.2, 17.2 Hz, 1H), 2.73-2.61 (m, 2H), 2.60-2.43 (m, 3H), 2.06-1.95 (m, 1H), 1.49 (qd, J=6.7, 13.5 Hz, 1H); ES-LCMS m/z 377.1, 379.1 [M+H]+.

I-70

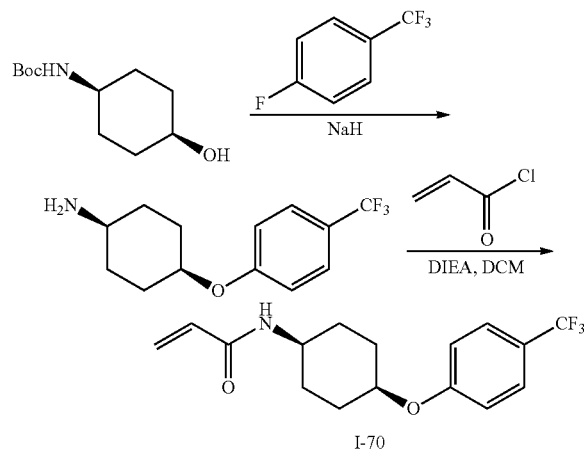

Step 1: 4-[4-(Trifluoromethyl)phenoxy]cyclohexanamine

To a stirred solution of tert-butyl N-(4-hydroxycyclohexyl)carbamate (500 mg, 2.32 mmol, 1 eq) in DMF (6 mL) was added NaH (139.33 mg, 3.48 mmol, 60% purity, 1.5 eq). The reaction mixture was stirred at 30° C. for 30 min. 1-Fluoro-4-(trifluoromethyl)benzene (381.12 mg, 2.32 mmol, 295.44 μL, 1 eq) was added to the above reaction mixture then stirred at 80° C. for 12 h. TLC (DCM/MeOH=10:1, $R_f$=0.96) showed starting material was remained and one new spot was detected. The mixture was evaporated to yield a residue which was purified by flash silica gel chromatography (from DCM/MeOH=1/0 to 10/1, TLC: DCM/MeOH=10/1, $R_f$=0.1) to yield 4-[4-(trifluoromethyl)phenoxy]cyclohexanamine (180 mg, 451.27 μmol, 19.4% yield, 65% purity) as yellow oil. $^1$H NMR (400 MHz, DMSO-d$_6$) δ ppm 7.93 (d, J=17.4 Hz, 2H), 7.68-7.61 (m, 2H), 7.13 (d, J=8.6 Hz, 2H), 3.72 (s, 1H), 3.06-2.95 (m, 1H), 1.75-1.72 (m, 1H), 1.68 (d, J=8.8 Hz, 2H), 1.61 (d, J=10.0 Hz, 3H), 1.42-1.35 (m, 2H); ES-LCMS m/z 260.3 [M+H]+.

Step 2: N-[4-[4-(Trifluoromethyl)phenoxy]cyclohexyl]prop-2-enamide

To a solution of 4-[4-(trifluoromethyl)phenoxy]cyclohexanamine (180 mg, 451.27 μmol, 1 eq) in THF (8 mL) was added Et$_3$N (136.99 mg, 1.35 mmol, 188.43 μL, 3 eq) and prop-2-enoyl chloride (61.27 mg, 676.91 μmol, 55.19 μL, 1.5 eq). The mixture was stirred at 25° C. for 1 h. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by preparative HPLC (column: Welch Xtimate C18 150*25 mm*5 μm; mobile phase: [water (10 mM NH$_4$HCO$_3$)-ACN]; B %: 38%-68%, 10 min). The desired fraction was lyophilized to yield N-[4-[4-(trifluoromethyl)phenoxy]cyclohexyl]prop-2-enamide (20 mg, 63.1 μmol, 14.0% yield, 98.8% purity) as a white solid. $^1$H NMR (400 MHz, DMSO-d$_6$) δ ppm 8.05 (d, J=7.6 Hz, 1H), 7.63 (d, J=8.6 Hz, 2H), 7.12 (d, J=8.6 Hz, 2H), 6.29-6.19 (m, 1H), 6.11-6.03 (m, 1H), 5.60-5.52 (m, 1H), 4.65 (s, 1H), 3.85-3.73 (m, 1H), 1.90 (dd, J=4.4, 13.4 Hz, 2H), 1.76-1.68 (m, 2H), 1.63 (d, J=4.6 Hz, 2H), 1.61-1.52 (m, 2H); ES-LCMS m/z 314.1 [M+H]+.

I-133 & I-134

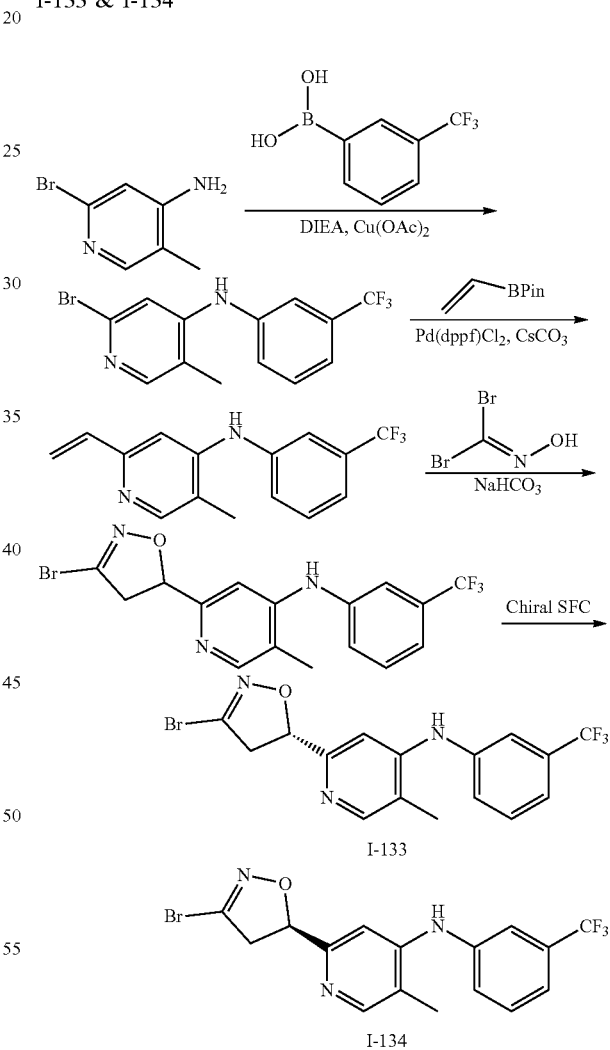

Step 1: 2-Bromo-5-methyl-N-[3-(trifluoromethyl)phenyl]pyridin-4-amine

To a solution of 2-bromo-5-methyl-pyridin-4-amine (450 mg, 2.41 mmol, 1 eq) in DCM (15 mL) was added DIEA (932.85 mg, 7.22 mmol, 1.26 mL, 3 eq), [3-(trifluoromethyl)

phenyl]boronic acid (1.14 g, 6.01 mmol, 2.5 eq), Cu(OAc)$_2$ (874.00 mg, 4.81 mmol, 2 eq). The mixture was stirred at 25° C. for 72 h under oxygen atmosphere. The reaction mixture was quenched by addition of water (50 mL), extracted with EtOAc (30 mL×3). The combined organic layers were washed with brine (10 mL), dried over Na$_2$SO$_4$, filtered and the filtrate was concentrated under reduced pressure to yield a residue which was purified by flash silica gel chromatography (from PE/EtOAc=1/0 to 3/1, TLC: PE/EtOAc=3/1, R$_f$=0.45) to yield 2-bromo-5-methyl-N-[3-(trifluoromethyl)phenyl]pyridin-4-amine (200 mg, 600.97 μmol, 25.0% yield, 99.5% purity) as a white solid. $^1$H NMR (400 MHz, DMSO-d$_6$) δ ppm 8.36 (s, 1H), 7.97 (s, 1H), 7.65-7.60 (m, 1H), 7.60-7.56 (m, 1H), 7.55 (s, 1H), 7.45 (d, J=7.1 Hz, 1H), 6.99 (s, 1H), 2.17 (s, 3H); ES-LCMS m/z 331.0, 333.0 [M+H]$^+$.

Step 2: 5-Methyl-N-[3-(trifluoromethyl)phenyl]-2-vinyl-pyridin-4-amine

To a solution of 2-bromo-5-methyl-N-[3-(trifluoromethyl)phenyl]pyridin-4-amine (100 mg, 302.00 μmol, 1 eq) in 1,4-dioxane (3 mL) and water (1 mL) was added Cs$_2$CO$_3$ (295.19 mg, 905.99 μmol, 3 eq), 4,4,5,5-tetramethyl-2-vinyl-1,3,2-dioxaborolane (55.81 mg, 362.39 μmol, 61.47 μL, 1.2 eq) and Pd(dppf)Cl$_2$ (22.10 mg, 30.20 μmol, 0.1 eq). The mixture was bubbled with N$_2$ for 2 min and stirred at 100° C. for 30 h under microwave. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.49) to yield 5-methyl-N-[3-(trifluoromethyl)phenyl]-2-vinyl-pyridin-4-amine (84 mg, 301.86 μmol, 99.9% yield, 100% purity) as yellow oil. $^1$H NMR (400 MHz, CDCl$_3$) δ ppm 8.26 (s, 1H), 7.53-7.47 (m, 1H), 7.43 (s, 1H), 7.38 (d, J=7.8 Hz, 2H), 7.05 (s, 1H), 6.68 (dd, J=10.8, 17.4 Hz, 1H), 6.06 (dd, J=1.1, 17.5 Hz, 1H), 5.81 (s, 1H), 5.39 (dd, J=1.0, 10.8 Hz, 1H), 2.25 (s, 3H); ES-LCMS m/z 279.1 [M+H]+.

Step 3: 2-[(5S)-3-Bromo-4,5-dihydroisoxazol-5-yl]-5-methyl-N-[3-(trifluoromethyl)phenyl]pyridin-4-amine & 2-[(5R)-3-bromo-4,5-dihydroisoxazol-5-yl]-5-methyl-N-[3-(trifluoromethyl)phenyl]pyridin-4-amine To a solution of 5-methyl-N-[3-(trifluoromethyl)phenyl]-2-vinyl-pyridin-4-amine (84 mg, 301.86 μmol, 1 eq) in EtOAc (4 mL) was added NaHCO$_3$ (253.58 mg, 3.02 mmol, 10 eq) and dibromomethanone oxime (73.47 mg, 362.24 μmol, 1.2 eq). The mixture was stirred at 25° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 1/1, TLC: PE/EtOAc=1/1, R$_f$=0.55) to yield the compound which was separated by SFC (column: DAICEL CHIRALPAK AD-H (250 mm*30 mm, 5 μm); mobile phase: [0.1% NH$_3$H$_2$O IPA]; B %: 20%-20%, min) to yield Peak 1 and Peak 2. Peak 1 was concentrated under reduced pressure to yield a residue which was lyophilized to yield 2-[(5S)-3-bromo-4,5-dihydroisoxazol-5-yl]-5-methyl-N-[3-(trifluoromethyl)phenyl]pyridin-4-amine (15.22 mg, 36.74 μmol, 12.2% yield, 96.6% purity, SFC: R$_t$=3.287 min, ee=99.32%, [α]$^{24.8}_D$=−243.14, MeOH, c=0.051 g/100 mL) as a green solid. $^1$H NMR (400 MHz, DMSO-d$_6$) δ ppm 8.26 (s, 1H), 8.21 (s, 1H), 7.60-7.55 (m, 1H), 7.54-7.48 (m, 2H), 7.37 (d, J=7.3 Hz, 1H), 7.10 (s, 1H), 5.63-5.56 (m, 1H), 3.73-3.63 (m, 1H), 3.59-3.51 (m, 1H), 3.59-3.50 (m, 1H), 2.22 (s, 3H); ES-LCMS m/z 399.9, 401.8 [M+H]$^+$. Peak 2 was concentrated under reduced pressure to yield a residue which was lyophilized to yield 2-[(5R)-3-bromo-4,5-dihydroisoxazol-5-yl]-5-methyl-N-[3-(trifluoromethyl)phenyl]pyridin-4-amine (17.75 mg, 43.02 μmol, 14.3% yield, 97% purity, SFC: R$_t$=3.645 min, ee=98.52%, [α]$^{24.8}_D$=+240.68, MeOH, c=0.059 g/100 mL) as a green solid. $^1$H NMR (400 MHz, DMSO-d$_6$) δ ppm 8.26 (s, 1H), 8.21 (s, 1H), 7.60-7.55 (m, 1H), 7.54-7.48 (m, 2H), 7.37 (d, J=7.3 Hz, 1H), 7.10 (s, 1H), 5.60 (dd, J=7.8, 10.8 Hz, 1H), 3.72-3.63 (m, 1H), 3.59-3.50 (m, 1H), 2.22 (s, 3H); ES-LCMS m/z 399.9, 401.8 [M+H]$^+$.

I-71

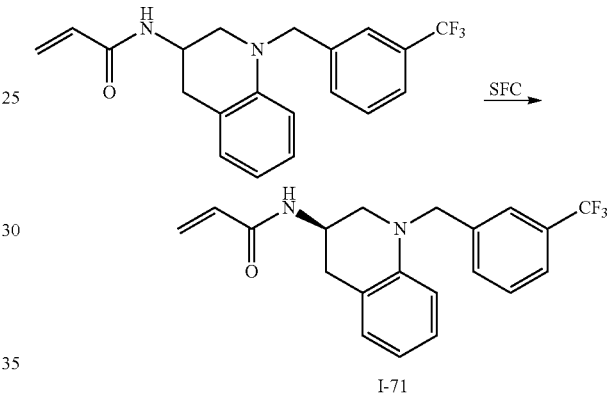

I-71

Step 1: N-[(3R)-1-[[3-(Trifluoromethyl)phenyl]methyl]-3,4-dihydro-2H-quinolin-3-yl]prop-2-enamide The starting material was separated by SFC (column: DAICEL CHIRALPAK AD-H (250 mm*30 mm, 5 μm); mobile phase: [0.1% NH$_3$·H$_2$O EtOH]; B %: 15%-15%, min) to yield peak 1 (R$_t$=2.697) and peak 2 (R$_t$=3.182). Peak 1 was second separated by SFC (column: DAICEL CHIRALCEL OD-H (250 mm*30 mm, 5 μm); mobile phase: [0.1% NH$_3$·H$_2$O EtOH]; B %: 20%-20%, min) to yield peak 1. Peak 1 was concentrated under reduced pressure to yield a residue which was dissolved in MeCN (15 mL) and H$_2$O (10 mL) and lyophilized to yield N-[(3R)-1-[[3-(trifluoromethyl)phenyl]methyl]-3,4-dihydro-2H-quinolin-3-yl]prop-2-enamide (19.41 mg, 53.38 μmol, 10.3% yield, 99.1% purity) (SFC: R$_t$=2.697, ee=100%, [α]$^{27.6}_D$=+65.384 (MeOH, c=0.052 g/100 mL)) as a white solid. $^1$H NMR (400 MHz, CDCl$_3$) δ ppm 7.56-7.48 (m, 2H), 7.46-7.41 (m, 2H), 7.11-7.02 (m, 2H), 6.74-6.68 (m, 1H), 6.57 (d, J=8.6 Hz, 1H), 6.28 (dd, J=1.2, 16.8 Hz, 1H), 6.08-5.99 (m, 1H), 5.84 (d, J=7.8 Hz, 1H), 5.65 (dd, J=1.6, 10.2 Hz, 1H), 4.67-4.60 (m, 1H), 4.59-4.48 (m, 2H), 3.59 (dd, J=2.3, 11.7 Hz, 1H), 3.41-3.34 (m, 1H), 3.22 (dd, J=4.7, 16.4 Hz, 1H), 2.82 (d, J=16.0 Hz, 1H); ES-LCMS m/z 361.2 [M+H]$^+$.

I-156 & I-157

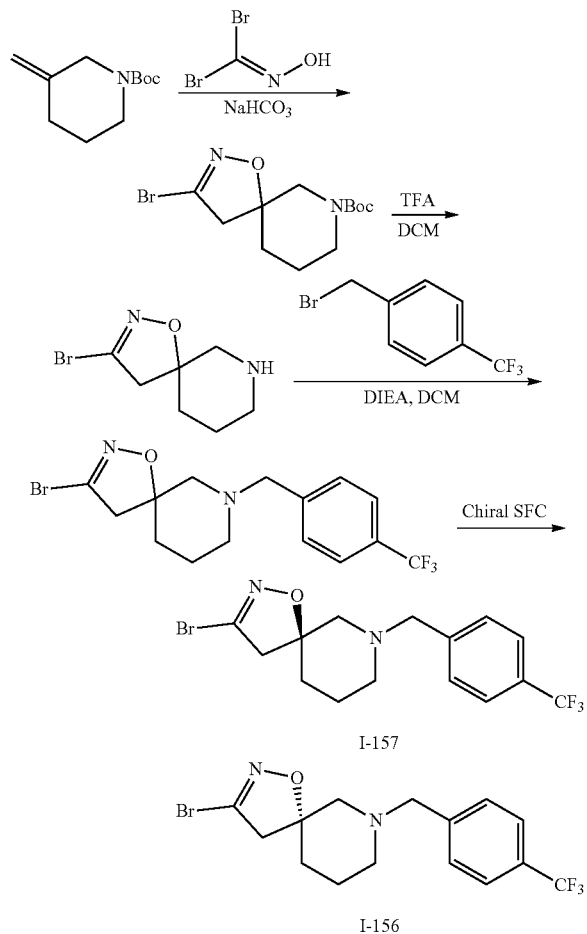

Step 1: tert-Butyl 3-bromo-1-oxa-2,9-diazaspiro[4.5]dec-2-ene-9-carboxylate

A mixture of tert-butyl 3-methylenepiperidine-1-carboxylate (1 g, 5.07 mmol, 1 eq), dibromomethanone oxime (1.54 g, 7.60 mmol, 1.5 eq), NaHCO$_3$ (4.26 g, 50.69 mmol, 10 eq) in EtOAc (10 mL) was degassed and purged with N$_2$ for 3 times. The mixture was stirred under N$_2$ atmosphere at 25° C. for 16 h. The mixture was concentrated, diluted with water (80 mL) and extracted with DCM (50 mL×3). The combined organic layers were washed with brine (50 mL), dried over Na$_2$SO$_4$, filtered and concentrated to yield a residue which was purified by flash silica gel chromatography (from PE/EtOAc=100/1 to 1/1, TLC: PE/EtOAc=3/1, R$_f$=0.44) to yield tert-butyl 3-bromo-1-oxa-2,9-diazaspiro[4.5]dec-2-ene-9-carboxylate (940 mg, 2.06 mmol, 40.7% yield, 70.0% purity) as yellow oil. $^1$H NMR (400 MHz, CDCl$_3$) δ ppm 3.72-3.59 (m, 2H), 3.23-2.94 (m, 4H), 1.97-1.78 (m, 4H), 1.46 (s, 9H); ES-LCMS m/z 319.1, 321.1 [M+H]$^+$.

Step 2: 3-Bromo-1-oxa-2,9-diazaspiro[4.5]dec-2-ene

A mixture of tert-butyl 3-bromo-1-oxa-2,9-diazaspiro[4.5]dec-2-ene-9-carboxylate (940 mg, 2.06 mmol, 1 eq), TFA (4.62 g, 40.52 mmol, 3 mL, 19.66 eq) in DCM (15 mL) was degassed and purged with N$_2$ for 3 times. The mixture was stirred under N$_2$ atmosphere at 25° C. for 2 h. The reaction mixture was concentrated to yield 3-bromo-1-oxa-2,9-diazaspiro[4.5]dec-2-ene (1.37 g, 1.32 mmol, 63.8% yield, 32.0% purity, TFA) as yellow oil, which used in the next step without further purification. $^1$H NMR (400 MHz, CD$_3$OD) δ ppm 3.27-3.11 (m, 4H), 3.08-2.96 (m, 2H), 1.97-1.81 (m, 4H); ES-LCMS m/z No mass found.

Step 3: (S) 3-Bromo-9-[[4-(trifluoromethyl)phenyl]methyl]-1-oxa-2,9-diazaspiro[4.5]dec-2-ene and (R) 3-bromo-9-[[4-(trifluoromethyl)phenyl]methyl]-1-oxa-2,9-diazaspiro[4.5]dec-2-ene A mixture of 3-bromo-1-oxa-2,9-diazaspiro[4.5]dec-2-ene (500 mg, 480.33 μmol, 1 eq), 1-(bromomethyl)-4-(trifluoromethyl)benzene (114.82 mg, 480.33 μmol, 74.07 μL, 1 eq) and DIEA (248.32 mg, 1.92 mmol, 334.66 μL, 4 eq) in DCM (5 mL) was degassed and purged with N$_2$ for 3 times. The mixture was stirred under N$_2$ atmosphere at 25° C. for 12 h. The reaction mixture was concentrated to yield a residue which was purified by preparative TLC (PE/EtOAc=5/1, R$_f$=0.45) and then separated by SFC (column: DAICEL CHIRALCEL OJ-H (250 mm*30 mm, 5 um); mobile phase: [0.1% NH$_3$H$_2$O EtOH]; B %: 10%-10%) to yield peak 1 and peak 2. Peak 1 was concentrated under reduced pressure to yield a residue which was dissolved in CH$_3$CN (10 mL) and water (20 mL), followed by lyophilization to yield (R) 3-bromo-9-[[4-(trifluoromethyl)phenyl]methyl]-1-oxa-2,9-diazaspiro[4.5]dec-2-ene (9.27 mg, 24.38 μmol, 5.1% yield, 99.2% purity, R$_t$=2.163, ee=96.8%, [α]$^{24.0}_D$=+22.857 (MeOH, c=0.035 g/100 mL)) as a white solid. $^1$H NMR (500 MHz, CD$_3$OD) δ ppm 7.63 (d, J=8.2 Hz, 2H), 7.54 (d, J=7.9 Hz, 2H), 3.69-3.58 (m, 2H), 3.25-3.16 (m, 1H), 3.12-3.01 (m, 1H), 2.55 (d, J=10.8 Hz, 2H), 2.43-2.18 (m, 2H), 1.86-1.68 (m, 3H), 1.63-1.54 (m, 1H); ES-LCMS m/z 377.1, 379.1 [M+H]$^+$. Peak 2 was concentrated under reduced pressure to yield a residue which was purified by preparative HPLC (column: YMC-Actus Triart C18 150*30 mm*5 um; mobile phase: [water (0.225% FA)-ACN]; B %: 23%-48%, 11 min) and lyophilized. The residue was dissolved in water (20 mL), adjusted to pH=10 with saturated NaHCO$_3$ solution and extracted with DCM (20 mL×2). The organic layer was dried over Na$_2$SO$_4$, concentrated to yield a residue which was dissolved in CH$_3$CN (10 mL) and water (20 mL), followed by lyophilization to yield (S) 3-bromo-9-[[4-(trifluoromethyl)phenyl]methyl]-1-oxa-2,9-diazaspiro[4.5]dec-2-ene (7.32 mg, 19.41 μmol, 4.0% yield, 100.0% purity, R$_t$=2.313, ee=91.4%, [α]$^{24.0}_D$=−56 (MeOH, c=0.05 g/100 mL)) as a white solid. $^1$H NMR (400 MHz, CD$_3$OD) δ ppm 7.58 (d, J=8.2 Hz, 2H), 7.42 (d, J=8.2 Hz, 2H), 3.59 (s, 2H), 3.19 (d, J=17.2 Hz, 1H), 2.96 (d, J=17.2 Hz, 1H), 2.71-2.55 (m, 2H), 2.30 (d, J=11.3 Hz, 1H), 2.14 (t, J=10.2 Hz, 1H), 1.88-1.68 (m, 3H), 1.55-1.49 (m, 1H); ES-LCMS m/z 376.8, 378.8 [M+H]$^+$.

I-135 & I-136

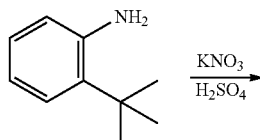

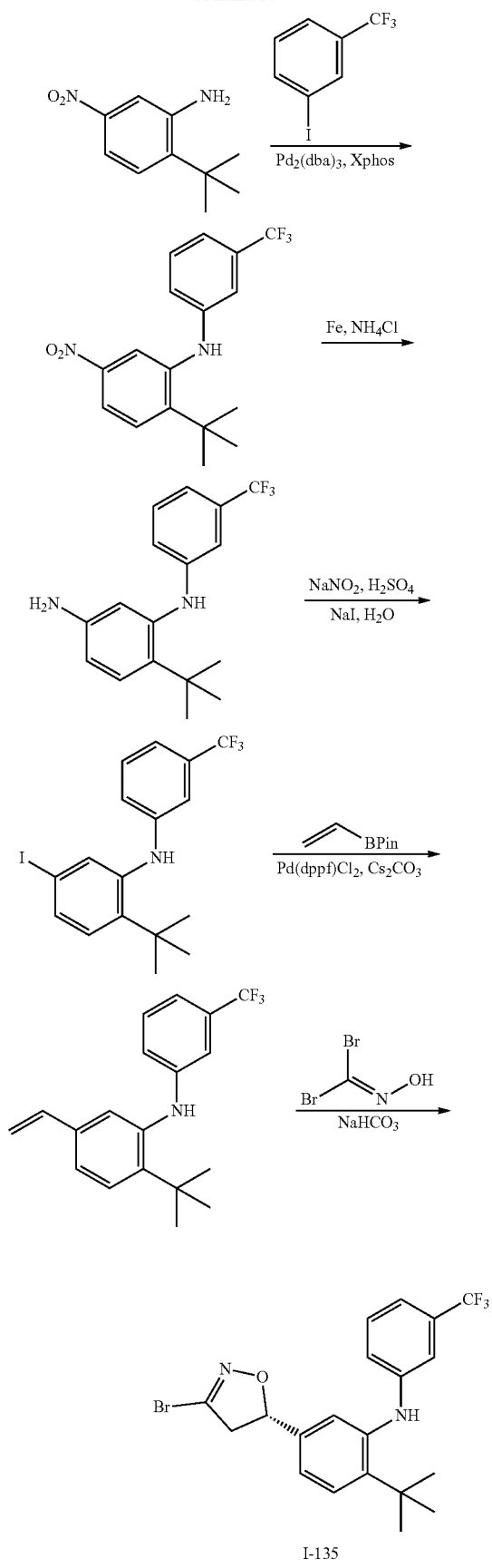

I-135

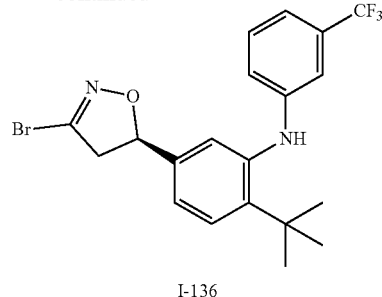

I-136

Step 1: 2-tert-Butyl-5-nitro-aniline

To a solution of 2-tert-butylaniline (2 g, 13.40 mmol, 2.09 mL, 1 eq) in $H_2SO_4$ (20 mL) was added $KNO_3$ (2.03 g, 20.10 mmol, 1.5 eq) at 0° C. The mixture was stirred at 0° C. for 5 min. TLC (PE/EtOAc=5/1, $R_f$=0.29) indicated most of the starting material was consumed and one new spot formed. The reaction mixture was quenched by addition of water (50 mL), extracted with EtOAc (50 mL×3). The organic layer was washed with brine (20 mL), dried over $Na_2SO_4$, filtered, concentrated to yield a residue which was purified by flash silica gel chromatography (from PE/EtOAc=1/0 to 5/1, TLC: PE/EtOAc=5/1, $R_f$=0.29) to yield 2-tert-butyl-5-nitro-aniline (2.15 g, 10.76 mmol, 80.2% yield, 97.2% purity) as yellow oil. $^1$H NMR (500 MHz, $CDCl_3$) δ ppm 1.22-1.27 (m, 9H) 3.91-3.99 (m, 2H) 7.14 (d, J=8.70 Hz, 1H) 7.33 (d, J=2.44 Hz, 1H) 7.34 (d, J=2.44 Hz, 1H); ES-LCMS m/z 195.0 $[M+H]^+$.

Step 2: 2-tert-Butyl-5-nitro-N-[3-(trifluoromethyl)phenyl]aniline

A mixture of 2-tert-butyl-5-nitro-aniline (2.15 g, 10.01 mmol, 1 eq), 1-iodo-3-(trifluoromethyl)benzene (4.08 g, 15.01 mmol, 2.16 mL, 1.5 eq) and t-BuONa (2.89 g, 30.03 mmol, 3 eq) in toluene (40 mL) was added $Pd_2(dba)_3$ (916.52 mg, 1.00 mmol, 0.1 eq) and XPhos (1.43 g, 3.00 mmol, 0.3 eq), degassed and purged with $N_2$ for 3 times, and then the mixture was stirred at 110° C. for 12 h under $N_2$ atmosphere. The reaction mixture was quenched by addition of water (50 mL), extracted with EtOAc (30 mL×3). The combined organic layers were washed with brine (10 mL), dried over $Na_2SO_4$, filtered, concentrated to yield a residue which was purified by flash silica gel chromatography (from PE/EtOAc=1/0 to 5/1, TLC: PE/EtOAc=5/1, $R_f$=0.53) to yield 2-tert-butyl-5-nitro-N-[3-(trifluoromethyl)phenyl]aniline (3.88 g, 8.65 mmol, 86.4% yield, 75.4% purity) as yellow oil. $^1$H NMR (400 MHz, $CDCl_3$) δ ppm 1.49 (s, 9H) 7.05 (d, J=7.83 Hz, 1H) 7.10 (s, 1H) 7.19 (d, J=7.83 Hz, 1H) 7.36-7.42 (m, 1H) 7.59 (d, J=9.00 Hz, 1H) 7.89 (dd, J=8.61, 2.35 Hz, 1H) 8.08 (d, J=2.74 Hz, 1H); ES-LCMS m/z 339.2 $[M+H]^+$.

Step 3: 4-tert-Butyl-$N_3$-[3-(trifluoromethyl)phenyl]benzene-1,3-diamine

To a solution of 2-tert-butyl-5-nitro-N-[3-(trifluoromethyl)phenyl]aniline (3.88 g, 8.60 mmol, 1 eq) in EtOH (15 mL), $H_2O$ (10 mL) and THF (15 mL), was added Fe (2.40 g, 43.01 mmol, 5 eq) and $NH_4Cl$ (4.60 g, 86.01 mmol, 10 eq). The mixture was stirred at 70° C. for 3 h under $N_2$ atmosphere. TLC (PE/EtOAc=5/1 $R_f$=0.55) indicated most of the starting material was consumed and one new spot formed. The mixture was filtered, and the filter cake was rinsed with PE (10 mL×2), dried. Then the reaction mixture was quenched by addition of water (50 mL), extracted with EtOAc (30 mL×3). The combined organic layers were washed with brine (10 mL), dried over $Na_2SO_4$, filtered, concentrated to yield a residue which was purified by flash silica gel chromatography (from PE/EtOAc=1/0 to 5/1, TLC: PE/EtOAc=5/1, $R_f$=0.55) to yield 4-tert-butyl-$N_3$-[3-(trifluoromethyl)phenyl]benzene-1,3-diamine (2.7 g, 7.01 mmol, 81.4% yield, 80.0% purity) as yellow oil. $^1$H NMR (500 MHz, $CDCl_3$) δ ppm 1.59-1.68 (m, 9H) 3.83 (s, 1H) 3.74-3.91 (m, 1H) 5.76 (s, 1H) 6.75 (dd, J=8.54, 2.29 Hz, 1H) 6.85 (d, J=2.14 Hz, 1H) 7.18 (d, J=8.39 Hz, 1H) 7.29 (s, 1H) 7.47-7.55 (m, 2H); ES-LCMS m/z 309.3 [M+H]$^+$.

Step 4: 2-tert-Butyl-5-iodo-N-[3-(trifluoromethyl)phenyl]aniline

To a solution of 4-tert-butyl-N3-[3-(trifluoromethyl)phenyl]benzene-1,3-diamine (1.2 g, 3.11 mmol, 1 eq) in MeCN (15 mL) cooled to 0° C. was added $H_2SO_4$ (763.40 mg, 7.78 mmol, 414.89 μL, 2.5 eq) dissolved in $H_2O$ (5 mL). After stirring for 5 min, a solution of $NaNO_2$ (429.63 mg, 6.23 mmol, 2 eq) in $H_2O$ (5 mL) was added dropwise and the reaction mixture was stirred for an additional 15 min at 0° C. Then a solution of NaI (1.87 g, 12.45 mmol, 4 eq) in $H_2O$ (5 mL) was added. The mixture was stirred at 60° C. for 1 h. The reaction mixture was quenched by addition of water (50 mL), extracted with EtOAc (30 mL×3). The combined organic layers were washed with brine (10 mL), dried over $Na_2SO_4$, filtered. Then The residue was purified by flash silica gel chromatography (from PE/EtOAc=1/0 to 5/1, TLC: PE/EtOAc=5/1, $R_f$=0.63) to yield 2-tert-butyl-5-iodo-N-[3-(trifluoromethyl)phenyl]aniline (460 mg, 877.82 μmol, 28.1% yield, 80% purity) as yellow oil. $^1$H NMR (400 MHz, $CDCl_3$) δ ppm 1.40 (s, 9H) 5.48 (s, 1H) 6.90-6.94 (m, 1H) 7.00 (s, 1H) 7.09 (d, J=7.43 Hz, 1H) 7.16 (d, J=8.22 Hz, 1H) 7.31 (t, J=7.83 Hz, 1H) 7.44 (dd, J=8.61, 1.96 Hz, 1H) 7.54-7.58 (m, 1H); ES-LCMS m/z 420.1 [M+H]$^+$.

Step 5: 2-tert-Butyl-N-[3-(trifluoromethyl)phenyl]-5-vinyl-aniline

To a solution of 2-tert-butyl-5-iodo-N-[3-(trifluoromethyl)phenyl]aniline (410 mg, 782.40 μmol, 1 eq), 4,4,5,5-tetramethyl-2-vinyl-1,3,2-dioxaborolane (156.65 mg, 1.02 mmol, 172.52 μL, 1.3 eq) in 1,4-dioxane (2.5 mL) and $H_2O$ (0.5 mL) was added $Pd(dppf)Cl_2$ (28.62 mg, 39.12 μmol, 0.05 eq) and $Cs_2CO_3$ (509.84 mg, 1.56 mmol, 2 eq). The mixture was stirred at 80° C. for 2 h under $N_2$ atmosphere. The reaction mixture was quenched by addition of water (50 mL), extracted with EtOAc (30 mL×3). The combined organic layers were washed with brine (10 mL), dried over $Na_2SO_4$, filtered. Then the residue was purified by flash silica gel chromatography (from PE/EtOAc=1/0 to 10/1, TLC: PE/EtOAc=10/1, $R_f$=0.61) to yield 2-tert-butyl-N-[3-(trifluoromethyl)phenyl]-5-vinyl-aniline (310 mg, 776.55 μmol, 99.2% yield, 80.0% purity) as yellow oil. $^1$H NMR (400 MHz, $CDCl_3$) δ ppm 1.35-1.43 (m, 9H) 5.12-5.29 (m, 1H) 5.44-5.53 (m, 1H) 5.64 (dd, J=17.61, 0.73 Hz, 1H) 6.54-6.71 (m, 1H) 6.84-6.92 (m, 1H) 6.96-7.08 (m, 2H) 7.12-7.20 (m, 1H) 7.23-7.32 (m, 2H) 7.38-7.44 (m, 1H); ES-LCMS m/z 320.3 [M+H]$^+$.

Step 6: 5-[(5S)-3-Bromo-4,5-dihydroisoxazol-5-yl]-2-tert-butyl-N-[3-(trifluoromethyl)phenyl]aniline & 5-[(5R)-3-Bromo-4,5-dihydroisoxazol-5-yl]-2-tert-butyl-N-[3-(trifluoromethyl)phenyl]aniline To a solution of 2-tert-butyl-N-[3-(trifluoromethyl)phenyl]-5-vinyl-aniline (280 mg, 701.40 μmol, 1 eq), dibromomethanone oxime (184.95 mg, 911.81 μmol, 1.3 eq) in EtOAc (20 mL) was added $NaHCO_3$ (589.22 mg, 7.01 mmol, 10 eq). The mixture was stirred at 25° C. for 3 h under $N_2$ atmosphere. The reaction mixture was quenched by addition of water (50 mL), extracted with EtOAc (30 mL×3). The combined organic layers were washed with brine (10 mL), dried over $Na_2SO_4$, filtered and concentrated under reduced pressure to give a residue. The residue was purified by flash silica gel chromatography (from PE/EtOAc=1/0 to 5/1, TLC: PE/EtOAc=5/1, $R_f$=0.54) to yield a product. The residue was separated by SFC (column: DAICEL CHIRALCEL OJ-H (250 mm*30 mm, 5 μm); mobile phase: [0.1% $NH_3·H_2O$ ETOH]; B %: 20%-20%, min. Peak1, 1.905, Peak 2, 2.186) to yield peak 1 (1.930) and peak 2 (2.207)). Peak 1 was concentrated under reduced pressure to yield a residue which was dissolved in MeCN (20 mL) and $H_2O$ (10 mL) and lyophilized to yield 5-[(5S)-3-bromo-4,5-dihydroisoxazol-5-yl]-2-tert-butyl-N-[3-(trifluoromethyl)phenyl]aniline (45.7 mg, 101.49 μmol, 14.4% yield, 98.0% purity) (SFC: Rt=1.930, ee=100%, $[α]^{25.7}_D$=−130.9 (MeOH, c=0.050 g/100 mL)) as a white solid. $^1$H NMR (500 MHz, $CDCl_3$) δ ppm 1.42 (s, 9H) 3.18 (dd, J=17.17, 8.93 Hz, 1H) 3.58 (dd, J=17.09, 10.83 Hz, 1H) 5.55 (s, 1H) 5.60 (dd, J=10.68, 9.16 Hz, 1H) 6.89-6.93 (m, 1H) 6.99 (s, 1H) 7.07 (d, J=7.78 Hz, 1H) 7.11 (dd, J=8.32, 1.91 Hz, 1H) 7.21-7.25 (m, 1H) 7.30 (t, J=7.86 Hz, 1H) 7.48 (d, J=8.24 Hz, 1H); ES-LCMS m/z 441.0, 443.0 [M+H]$^+$. Peak 2 was concentrated under reduced pressure to yield a residue which was dissolved in MeCN (20 mL) and $H_2O$ (10 mL) and lyophilized to yield 5-[(5R)-3-bromo-4,5-dihydroisoxazol-5-yl]-2-tert-butyl-N-[3-(trifluoromethyl)phenyl]aniline (44.57 mg, 97.06 μmol, 13.8% yield, 96.1% purity) (SFC: Rt=2.207, ee=99.94%, $[α]^{25.7}_D$=+120.0 (MeOH, c=0.055 g/100 mL)) as a white solid. $^1$H NMR (500 MHz, $CDCl_3$) δ ppm 1.38-1.45 (m, 9H) 3.18 (dd, J=17.17, 8.93 Hz, 1H) 3.58 (dd, J=17.09, 10.83 Hz, 1H) 5.54 (s, 1H) 5.60 (dd, J=10.68, 9.16 Hz, 1H) 6.91 (d, J=8.09 Hz, 1H) 6.99 (s, 1H) 7.07 (d, J=7.78 Hz, 1H) 7.11 (dd, J=8.24, 1.83 Hz, 1H) 7.23 (d, J=1.68 Hz, 1H) 7.30 (t, J=8.01 Hz, 1H) 7.48 (d, J=8.24 Hz, 1H); ES-LCMS m/z 441.0, 443.0 [M+H]$^+$.

I-137 & I-138

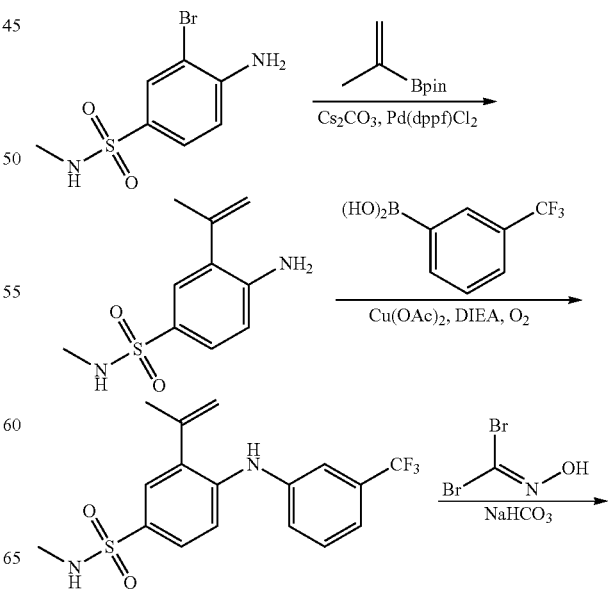

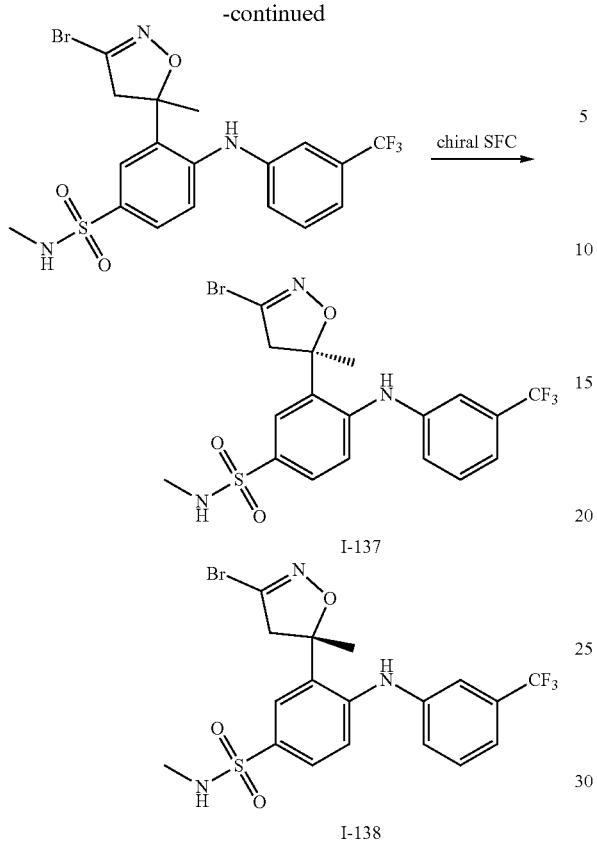

I-137

I-138

Step 1:
4-Amino-3-isopropenyl-N-methyl-benzenesulfonamide

To a solution of 4-amino-3-bromo-N-methyl-benzenesulfonamide (1 g, 2.68 mmol, 1 eq) and 2-isopropenyl-4,4,5,5-tetramethyl-1,3,2-dioxaborolane (540.01 mg, 3.21 mmol, 1.2 eq) in 1,4-dioxane (6 mL) and H$_2$O (2 mL) was added Cs$_2$CO$_3$ (2.62 g, 8.03 mmol, 3 eq) and Pd(dppf)Cl$_2$ (195.95 mg, 267.80 µmol, 0.1 eq). The mixture was stirred at 25° C. for 3 h under N$_2$ atmosphere. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=100/1 to 3/1, TLC: PE/EtOAc=3/1, R$_f$=0.28) to yield 4-amino-3-isopropenyl-N-methyl-benzenesulfonamide (550 mg, 2.21 mmol, 82.6% yield, 91% purity) as yellow oil. $^1$H NMR (500 MHz, CDCl$_3$) δ ppm 7.57-7.49 (m, 2H), 6.72 (d, J=8.1 Hz, 1H), 5.43-5.36 (m, 1H), 5.11 (d, J=0.9 Hz, 1H), 4.31 (s, 2H), 4.23 (s, 1H), 2.65 (d, J=5.5 Hz, 3H), 2.08 (s, 3H); ES-LCMS m/z 226.9 [M+H]$^+$.

Step 2: 3-Isopropenyl-N-methyl-4-[3-(trifluoromethyl)anilino]benzenesulfonamide To a solution of 4-amino-3-isopropenyl-N-methyl-benzenesulfonamide (400 mg, 1.61 mmol, 1 eq) and [3-(trifluoromethyl)phenyl]boronic acid (1.53 g, 8.04 mmol, 5 eq) in DCM (20 mL) was added Cu(OAc)$_2$ (350.59 mg, 1.93 mmol, 1.2 eq) and DIEA (415.78 mg, 3.22 mmol, 560.35 µL, 2 eq). The mixture was stirred at 25° C. for 12 h under O$_2$ (15 Psi) atmosphere. The resulting product was filtered and concentrated in vacuo to yield the residue which was purified by flash silica gel chromatography (from PE/EtOAc=100/1 to 3/1, TLC: PE/EtOAc=3/1, R$_f$=0.31) to yield 3-isopropenyl-N-methyl-4-[3-(trifluoromethyl)anilino]benzenesulfonamide (280 mg, 687.93 µmol, 42.8% yield, 91% purity) as yellow oil. $^1$H NMR (400 MHz, CDCl$_3$) δ ppm 7.65-7.62 (m, 2H), 7.49-7.44 (m, 1H), 7.39 (s, 1H), 7.36-7.31 (m, 2H), 7.31-7.28 (m, 1H), 6.36 (s, 1H), 5.48-5.44 (m, 1H), 5.17 (s, 1H), 4.29-4.22 (m, 1H), 2.70 (d, J=5.5 Hz, 3H), 2.11 (s, 3H); ES-LCMS m/z 371.2 [M+H]$^+$.

Step 3: 3-[(5R)-3-Bromo-5-methyl-4H-isoxazol-5-yl]-N-methyl-4-[3-(trifluoromethyl)anilino]benzenesulfonamide & 3-[(5S)-3-bromo-5-methyl-4H-isoxazol-5-yl]-N-methyl-4-[3-(trifluoromethyl)anilino]benzenesulfonamide To a solution of 3-isopropenyl-N-methyl-4-[3-(trifluoromethyl)anilino]benzenesulfonamide (280 mg, 687.93 µmol, 1 eq) in EtOAc (10 mL) was added NaHCO$_3$ (577.93 mg, 6.88 mmol, 10 eq) and dibromomethanone oxime (167.44 mg, 825.51 µmol, 1.2 eq). The mixture was stirred at 25° C. for 12 h. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=100/1 to 3/1, TLC: PE/EtOAc=3/1, R$_f$=0.43) to yield the product. The product was separated by SFC (column: DAICEL CHIRALCEL OJ-H (250 mm*30 mm, 5 µm); mobile phase: [0.1% NH$_3$H$_2$O ETOH]; B %: 20%-20%, min) to yield peak 1 (R$_t$=3.231 min, ee=100%) and peak 2 (R$_t$=3.403 min, ee=93.84%). Peak 1 was concentrated under reduced pressure to yield a residue which was dissolved in MeCN (20 mL) and H$_2$O (40 mL) and lyophilized to yield 3-[(5R)-3-bromo-5-methyl-4H-isoxazol-5-yl]-N-methyl-4-[3-(trifluoromethyl)anilino]benzenesulfonamide (40.65 mg, 82.57 µmol, 12.0% yield, 100% purity, SFC: R$_t$=3.231 min, ee=100%, [α]$^{25.7}_D$=−58.065 (MeOH, c=0.062 g/100 mL)) as a white solid. $^1$H NMR (400 MHz, CDCl$_3$) δ ppm 7.74-7.68 (m, 2H), 7.49-7.43 (m, 1H), 7.41-7.35 (m, 2H), 7.33 (d, J=7.0 Hz, 1H), 7.29 (s, 1H), 4.30 (s, 1H), 3.77 (d, J=17.2 Hz, 1H), 3.24 (d, J=17.2 Hz, 1H), 2.70 (d, J=5.5 Hz, 3H), 1.85 (s, 3H); ES-LCMS m/z 492.0, 494.0 [M+H]$^+$. Peak 2 was concentrated under reduced pressure to yield a residue which was dissolved in MeCN (20 mL) and H$_2$O (40 mL) and lyophilized to yield 3-[(5S)-3-bromo-5-methyl-4H-isoxazol-5-yl]-N-methyl-4-[3-(trifluoromethyl)anilino]benzenesulfonamide (59.40 mg, 120.66 µmol, 17.5% yield, 100% purity, SFC: R$_t$=3.403 min, ee=93.84%, [α]$^{25.7}_D$=+57.143 (MeOH, c=0.056 g/100 mL)) as a white solid. $^1$H NMR (400 MHz, CDCl$_3$) δ ppm 7.74-7.68 (m, 2H), 7.49-7.43 (m, 1H), 7.40-7.35 (m, 2H), 7.33 (d, J=7.8 Hz, 1H), 7.29 (s, 1H), 4.30 (s, 1H), 3.77 (d, J=17.2 Hz, 1H), 3.24 (d, J=17.2 Hz, 1H), 2.70 (d, J=5.5 Hz, 3H), 1.85 (s, 3H); ES-LCMS m/z 492.0, 494.0 [M+H]$^+$.

I-45

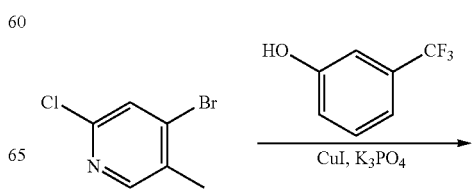

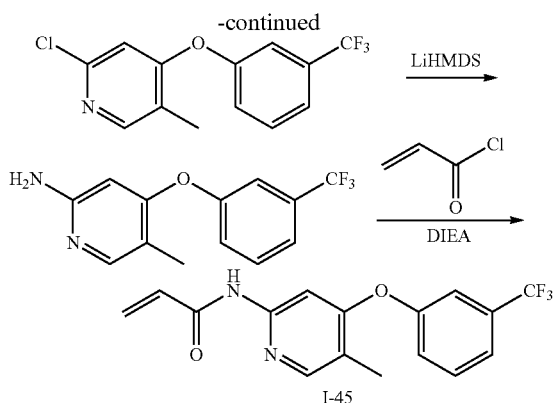

Step 1: 2-Chloro-5-methyl-4-[3-(trifluoromethyl)phenoxy]pyridine

A mixture of 4-bromo-2-chloro-5-methyl-pyridine (290 mg, 1.40 mmol, 1 eq), 3-(trifluoromethyl)phenol (239.08 mg, 1.47 mmol, 177.10 µL, 1.05 eq), CuI (26.75 mg, 140.46 µmol, 0.1 eq), K$_3$PO$_4$ (298.14 mg, 1.40 mmol, 1 eq) and pyridine-2-carboxylic acid (17.29 mg, 140.46 µmol, 0.1 eq) in DMSO (10 mL) was degassed and purged with N$_2$ for 3 times and then the mixture was stirred under N$_2$ atmosphere at 120° C. for 12 h. TLC (PE/EtOAc=5/1, R$_f$=0.60) indicated starting material was consumed completely and one new spot formed. The reaction mixture was quenched by addition of water (100 mL) and extracted with EtOAc (100 mL×3). The combined organic layers were washed with brine (40 mL), dried over Na$_2$SO$_4$, filtered and concentrated under reduced pressure to give a residue which was purified by flash silica gel chromatography (from PE/EtOAc=1/0 to 10/1, TLC: PE/EtOAc=5/1, R$_f$=0.60) to yield 2-chloro-5-methyl-4-[3-(trifluoromethyl)phenoxy]pyridine (300 mg, 907.31 µmol, 64.6% yield, 87.0% purity) as a white solid. $^1$H NMR (500 MHz, DMSO-d$_6$) δ ppm 8.31 (s, 1H), 7.75-7.71 (m, 1H), 7.70-7.67 (m, 1H), 7.63 (s, 1H), 7.52 (d, J=8.1 Hz, 1H), 6.72 (s, 1H), 2.25 (s, 3H).

Step 2: 5-Methyl-4-[3-(trifluoromethyl)phenoxy]pyridin-2-amine

A mixture of 2-chloro-5-methyl-4-[3-(trifluoromethyl)phenoxy]pyridine (300 mg, 907.31 µmol, 1 eq), Pd$_2$(dba)$_3$ (83.08 mg, 90.73 µmol, 0.1 eq), t-Bu Xphos (77.06 mg, 181.46 µmol, 0.2 eq) and LiHMDS (1 M, 4.54 mL, 5 eq) in THF (30 mL) was degassed and purged with N$_2$ for 3 times and then the mixture was stirred under N$_2$ atmosphere at 80° C. for 12 h. The reaction mixture was quenched by addition of water (50 mL) and extracted with EtOAc (50 mL×3). The combined organic layers were washed with brine (40 mL), dried over Na$_2$SO$_4$, filtered and concentrated under reduced pressure to give a residue which was purified by flash silica gel chromatography (from PE/EtOAc=3/1 to DCM/MeOH=5/1, TLC: DCM/MeOH=5/1, R$_f$=0.48) to yield 5-methyl-4-[3-(trifluoromethyl)phenoxy]pyridin-2-amine (100 mg, 298.25 µmol, 32.9% yield, 80.0% purity) as brown oil. $^1$H NMR (400 MHz, DMSO-d$_6$) δ ppm 7.76 (s, 1H), 7.70-7.66 (m, 2H), 7.59 (d, J=7.8 Hz, 1H), 7.44 (s, 1H), 7.40 (d, J=8.2 Hz, 1H), 5.73 (s, 2H), 1.97 (s, 3H); ES-LCMS: m/z 269.1 [M+H]$^+$.

Step 3: N-[5-Methyl-4-[3-(trifluoromethyl)phenoxy]-2-pyridyl]prop-2-enamide

To a solution of 5-methyl-4-[3-(trifluoromethyl)phenoxy]pyridin-2-amine (100 mg, 298.25 µmol, 1 eq) in DCM (4 mL) was added DIEA (77.09 mg, 596.49 µmol, 103.90 µL, 2 eq) and prop-2-enoyl chloride (26.99 mg, 298.25 µmol, 24.32 µL, 1 eq). The mixture was stirred at 0° C. for 20 min. The reaction mixture was quenched by addition of water (50 mL) and extracted with EtOAc (50 mL×3). The combined organic layers were washed with brine (40 mL), dried over Na$_2$SO$_4$, filtered and concentrated under reduced pressure to give a residue which was purified by flash silica gel chromatography (from PE/EtOAc=1/0 to 3/1, TLC: PE/EtOAc=3/1, R$_f$=0.40) to yield N-[5-methyl-4-[3-(trifluoromethyl)phenoxy]-2-pyridyl]prop-2-enamide (17.08 mg, 50.44 µmol, 16.9% yield, 95.2% purity) as a yellow solid. $^1$H NMR (400 MHz, CDCl$_3$) δ ppm 8.15 (s, 1H), 8.10 (s, 1H), 7.74 (s, 1H), 7.56-7.50 (m, 1H), 7.50-7.44 (m, 1H), 7.33 (s, 1H), 7.28 (s, 1H), 6.41-6.35 (m, 1H), 6.23-6.15 (m, 1H), 5.77 (d, J=10.6 Hz, 1H), 2.26 (s, 3H); ES-LCMS m/z 323.2 [M+H]$^+$.

I-139 & I-140

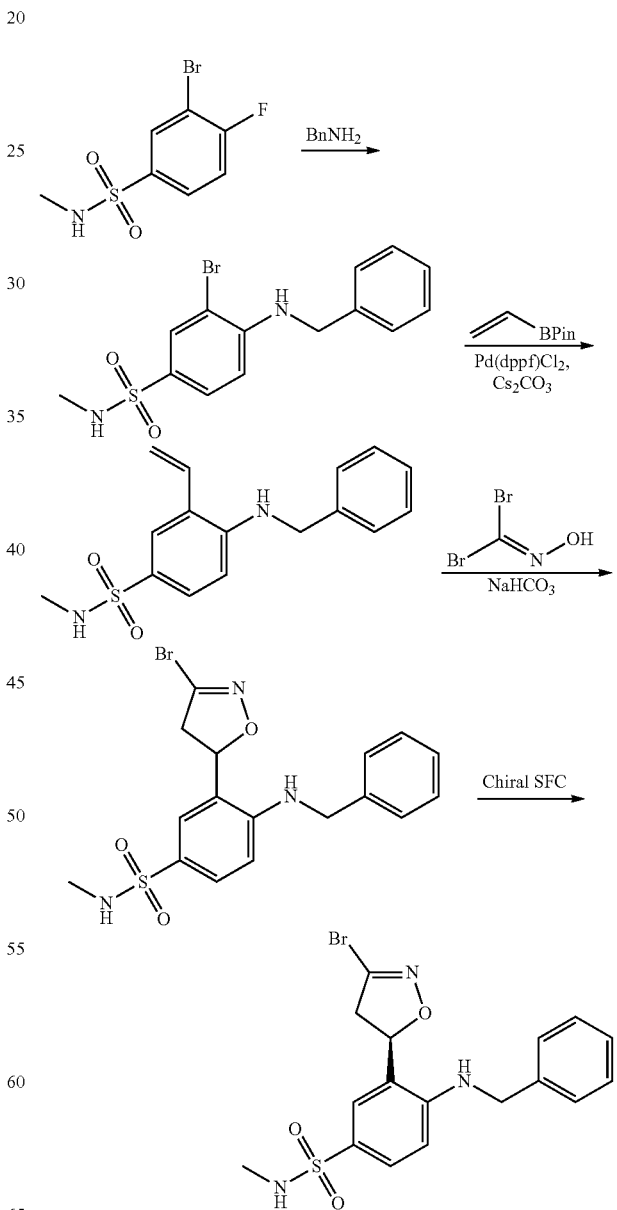

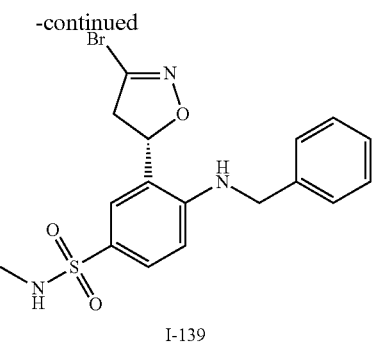

I-139

Step 1: 4-(Benzylamino)-3-bromo-N-methyl-benzenesulfonamide

A mixture of 3-bromo-4-fluoro-N-methyl-benzenesulfonamide (1 g, 3.73 mmol, 1 eq) and phenylmethanamine (800 mg, 7.47 mmol, 813.84 μL, 2 eq) in DMSO (15 mL) was stirred at 140° C. for 1 h. TLC (PE/EtOAc=1/1, $R_f$=0.40) showed the starting material was consumed completely. The reaction mixture was diluted with $H_2O$ (20 mL) and extracted with EtOAc (20 mL×3). The combined organic layers dried over $Na_2SO_4$, filtered and concentrated under reduced pressure to yield a residue which was purified by flash silica gel chromatography (from PE/EtOAc=100/1 to 1/1, TLC: PE/EtOAc=1/1, $R_f$=0.40) to yield 4-(benzylamino)-3-bromo-N-methyl-benzenesulfonamide (600 mg, 1.63 mmol, 43.7% yield, 96.5% purity) as a yellow solid. $^1$H NMR (400 MHz, $CDCl_3$) δ ppm 7.94 (d, J=2.0 Hz, 1H), 7.61 (dd, J=2.0, 8.6 Hz, 1H), 7.41-7.28 (m, 5H), 6.62 (d, J=8.6 Hz, 1H), 5.32-5.22 (m, 1H), 4.47 (d, J=5.9 Hz, 2H), 2.63 (d, J=5.5 Hz, 3H); ES-LCMS m/z 354.8, 356.8 [M+H]$^+$.

Step 2: 4-(Benzylamino)-N-methyl-3-vinyl-benzenesulfonamide

To a solution of 4-(benzylamino)-3-bromo-N-methyl-benzenesulfonamide (600 mg, 1.63 mmol, 1 eq) and 4,4,5,5-tetramethyl-2-vinyl-1,3,2-dioxaborolane (544.80 mg, 3.54 mmol, 600 μL, 2.17 eq) in 1,4-dioxane (20 mL) and $H_2O$ (4 mL) was added Pd(dppf)$Cl_2$ (120 mg, 164.00 μmol, 1.01e-1 eq) and $Cs_2CO_3$ (1.06 g, 3.26 mmol, 2 eq). The mixture was stirred under $N_2$ atmosphere at 100° C. for 2 h. TLC (PE/EtOAc=3/1, $R_f$=0.30) showed the starting material was consumed completely. The reaction mixture was quenched with $H_2O$ (30 mL) and extracted with EtOAc (30 mL×3). The combined organic layers dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.30) to yield 4-(benzylamino)-N-methyl-3-vinyl-benzenesulfonamide (400 mg, 1.19 mmol, 73.0% yield, 90.0% purity) as a yellow solid. $^1$H NMR (400 MHz, $CD_3OD$) δ ppm 7.69 (d, J=2.3 Hz, 1H), 7.43 (dd, J=2.2, 8.8 Hz, 1H), 7.36-7.29 (m, 4H), 7.24-7.18 (m, 1H), 6.95 (dd, J=11.0, 17.2 Hz, 1H), 6.55 (d, J=8.6 Hz, 1H), 5.70 (dd, J=1.6, 17.2 Hz, 1H), 5.39 (dd, J=1.6, 11.0 Hz, 1H), 4.47 (s, 2H), 2.45 (s, 3H); ES-LCMS m/z 303.1 [M+H]$^+$.

Step 3: 4-(Benzylamino)-3-[(5S)-3-bromo-4,5-dihydroisoxazol-5-yl]-N-methyl-benzenesulfonamide and 4-(benzylamino)-3-[(5R)-3-bromo-4,5-dihydroisoxazol-5-yl]-N-methyl-benzenesulfonamide To a solution of 4-(benzylamino)-N-methyl-3-vinyl-benzenesulfonamide (160 mg, 476.20 μmol, 1 eq) in EtOAc (5 mL) was added $NaHCO_3$ (200 mg, 2.38 mmol, 5 eq). The mixture was stirred at 25° C. for 12 h. TLC (PE/EtOAc=3/1, $R_f$=0.37) showed the starting material was consumed completely. The reaction mixture was diluted with $H_2O$ (30 mL) and extracted with EtOAc (30 mL×3). The organic layer was dried over $Na_2SO_4$, filtered and concentrated under reduced pressure to yield a residue which was purified by preparative HPLC (column: Welch Xtimate C18 150×25 mm×5 μm; mobile phase: [water (10 mM $NH_4HCO_3$)-ACN]; B %: 36%-66%, 10 min). The desired compound was concentrated under reduced pressure to yield a residue which was separated by chiral SFC (column: DAICEL CHIRALPAK AS (250 mm*30 mm, 10 μm); mobile phase: [0.1% $NH_3H_2O$/EtOH]; B %: 35%-35%) to yield peak 1 and peak 2. Peak 1 was concentrated under reduced pressure to yield a residue which was dissolved in MeCN (10 mL) and water (10 mL) and lyophilized to yield 4-(benzylamino)-3-[(5S)-3-bromo-4,5-dihydroisoxazol-5-yl]-N-methyl-benzenesulfonamide (24.59 mg, 57.95 μmol, 12.2% yield, 100.0% purity, SFC: $R_t$=3.649, ee=99.92%, $[α]^{28.4}_D$=−41.935 (MeOH, c=0.062 g/100 mL)) as a white solid. $^1$H NMR (400 MHz, $CDCl_3$) δ ppm 7.70 (dd, J=2.0, 8.6 Hz, 1H), 7.60 (d, J=2.3 Hz, 1H), 7.40-7.27 (m, 5H), 6.78-6.73 (m, 1H), 6.76 (d, J=8.6 Hz, 1H), 5.72 (t, J=11.3 Hz, 1H), 5.24-5.14 (m, 1H), 4.48-4.37 (m, 2H), 4.20 (d, J=5.1 Hz, 1H), 3.66-3.39 (m, 2H), 2.64 (d, J=5.5 Hz, 3H); ES-LCMS m/z 424.1, 426.1 [M+H]$^+$. Peak 2 was concentrated under reduced pressure to yield a residue which was dissolved in MeCN (10 mL) and water (10 mL) and lyophilized to yield 4-(benzylamino)-3-[(5R)-3-bromo-4,5-dihydroisoxazol-5-yl]-N-methyl-benzenesulfonamide (37.5 mg, 88.38 μmol, 18.6% yield, 100.0% purity) as a white solid, SFC: $R_t$=3.934, ee=99.30%, $[α]^{28.4}_D$=+42.86 (MeOH, c=0.028 g/100 mL)) as a white solid. $^1$H NMR (400 MHz, $CDCl_3$) δ ppm 7.70 (dd, J=2.3, 8.6 Hz, 1H), 7.62-7.62 (m, 1H), 7.60 (d, J=2.0 Hz, 1H), 7.42-7.30 (m, 5H), 6.76 (d, J=8.6 Hz, 1H), 5.72 (t, J=11.2 Hz, 1H), 5.24-5.14 (m, 1H), 4.47-4.37 (m, 2H), 4.18 (d, J=5.9 Hz, 1H), 3.65-3.42 (m, 2H), 2.64 (d, J=5.5 Hz, 3H); ES-LCMS m/z 424.1, 426.1 [M+H]$^+$.

I-72

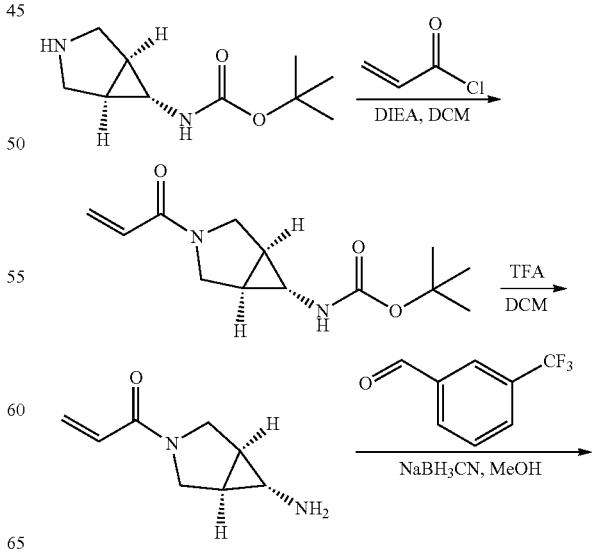

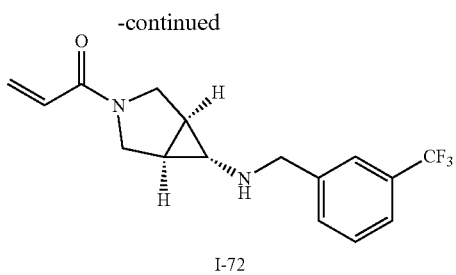

I-72

Step 1: tert-butyl N-[(1S,5R)-3-prop-2-enoyl-3-azabicyclo[3.1.0]hexan-6-yl]carbamate To a solution of tert-butyl N-[(1R,5S)-3-azabicyclo[3.1.0]hexan-6-yl]carbamate (51 mg, 257.24 μmol, 1 eq) and DIEA (99.74 mg, 771.71 μmol, 134.42 μL, 3 eq) in DCM (5 mL) was added a solution of prop-2-enoyl chloride (23.28 mg, 257.24 μmol, 20.97 μL, 1 eq) in DCM (1 mL) dropwise at 0° C. and stirred at 0° C. for 30 min. TLC (DCM/MeOH=10/1 $R_f$=0.56) showed the starting material was consumed and a new spot was formed. The solvent was removed to give a residue which was purified by preparative TLC (DCM/MeOH=10/1) to yield tert-butyl N-[(1S,5R)-3-prop-2-enoyl-3-azabicyclo[3.1.0]hexan-6-yl]carbamate (52 mg, 201.97 μmol, 78.52% yield, 98.0% purity) as colorless gum. $^1$H NMR (500 MHz, CDCl$_3$) δ ppm 6.33 (d, J=6.7 Hz, 2H), 5.71-5.61 (m, 1H), 4.72 (br s, 1H), 3.93 (d, J=12.5 Hz, 1H), 3.84 (br s, 1H), 3.67 (dd, J=4.7, 10.2 Hz, 1H), 3.53 (dd, J=4.8, 12.6 Hz, 1H), 2.30-2.27 (m, 1H), 1.86-1.82 (m, 1H), 1.78-1.70 (m, 1H), 1.44 (s, 9H); ES-LCMS m/z 253.3 [M+H]$^+$.

Step 2: 1-[(1S,5R)-6-amino-3-azabicyclo[3.1.0]hexan-3-yl]prop-2-en-1-one

To a solution of tert-butyl N-[(1S,5R)-3-prop-2-enoyl-3-azabicyclo[3.1.0]hexan-6-yl]carbamate (52 mg, 201.97 μmol, 1 eq) in DCM (1 mL) was added TFA (0.2 mL) and the mixture was stirred at 20° C. for 2 h. The solvent was removed and the residue was adjusted to pH 8 with NH$_3$·H$_2$O. The mixture was concentrated to give 1-[(1S,5R)-6-amino-3-azabicyclo[3.1.0]hexan-3-yl]prop-2-en-1-one (30 mg, crude) as colorless gum

Step 3: 1-[(1S,5R)-6-[[3-(Trifluoromethyl)phenyl]methylamino]-3-azabicyclo[3.1.0]hexan-3-yl]prop-2-en-1-one To a solution of 1-[(1R,5S)-6-amino-3-azabicyclo[3.1.0]hexan-3-yl]prop-2-en-1-one (30 mg, crude) in MeOH (5 mL) was added 3-(Trifluoromethyl)benzaldehyde (30.89 mg, 177.41 μmol, 1 eq) and the mixture was stirred at 20° C. for 1 h. NaBH$_3$CN (33.45 mg, 532.22 μmol, 3 eq) was added and the mixture was stirred at 20° C. for 16 h. The mixture was concentrated by reduced pressure to give a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 32%-62%, 10 min), followed by lyophilization to yield 1-[(1S,5R)-6-[[3-(trifluoromethyl)phenyl]methylamino]-3-azabicyclo[3.1.0]hexan-3-yl]prop-2-en-1-one (24.28 mg, 77.34 μmol, 43.60% yield, 98.85% purity) as colorless gum. $^1$H NMR (500 MHz, CDCl$_3$) δ ppm 7.56 (s, 1H), 7.52 (d, J=7.3 Hz, 1H), 7.49-7.42 (m, 2H), 6.36-6.29 (m, 2H), 5.65 (dd, J=5.3, 7.0 Hz, 1H), 3.87 (s, 2H), 3.80 (d, J=12.5 Hz, 1H), 3.65-3.62 (m, 2H), 3.49 (dd, J=4.2, 12.6 Hz, 1H), 1.93 (t, J=2.0 Hz, 1H), 1.86 (br s, 1H), 1.69-1.62 (m, 2H); ES-LCMS m/z 311.3 [M+H]$^+$.

I-73

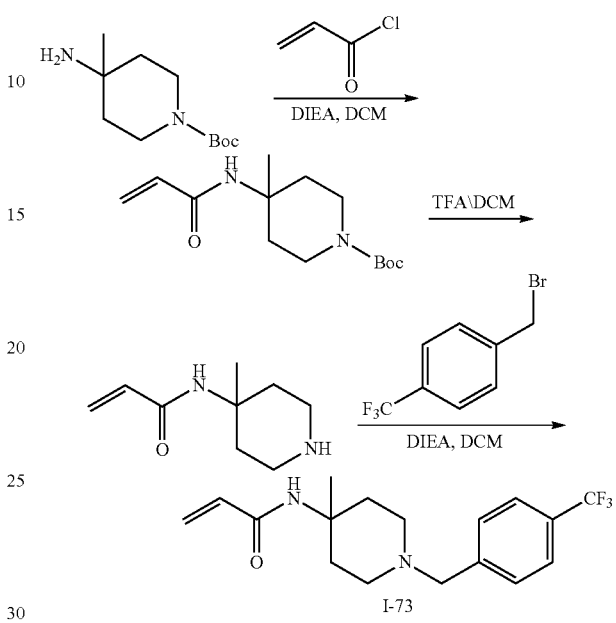

I-73

Step 1: Tert-butyl 4-methyl-4-(prop-2-enoylamino)piperidine-1-carboxylate

To a mixture of tert-butyl 4-amino-4-methyl-piperidine-1-carboxylate (200.0 mg, 933.26 μmol, 1 eq) and DIEA (241.23 mg, 1.87 mmol, 325.11 μL, 2 eq) in DCM (10 mL) cooled to 0° C. was added prop-2-enoyl chloride (84.47 mg, 933.26 μmol, 76.10 μL, 1 eq) in portion wise at 0° C. The mixture was stirred at 0° C. for 0.5 h. TLC (PE/EtOAc=1/1, $R_f$=0.29) indicated the staring material was remained and one new spot was detected. The reaction mixture was concentrated to yield a residue which was purified by flash silica gel chromatography (from PE/EtOAc=100/1 to 1/1, TLC: PE/EtOAc=1/1, $R_f$=0.29) to yield tert-butyl 4-methyl-4-(prop-2-enoylamino)piperidine-1-carboxylate (248.43 mg, 786.90 μmol, 84.3% yield, 85.0% purity) as light yellow oil. $^1$H NMR (400 MHz, CDCl$_3$) δ ppm 6.28-6.17 (m, 1H), 6.13-6.01 (m, 1H), 5.59 (dd, J=1.2, 10.2 Hz, 1H), 5.41 (s, 1H), 3.63 (s, 2H), 3.18-3.11 (m, 2H), 2.03-2.01 (m, 2H), 1.61-1.58 (m, 2H), 1.43 (s, 12H); ES-LCMS m/z 269.3 [M+H]$^+$.

Step 2: N-(4-Methyl-4-piperidyl)prop-2-enamide

To a solution of tert-butyl 4-methyl-4-(prop-2-enoylamino)piperidine-1-carboxylate (240 mg, 760.20 μmol, 1 eq) in DCM (6 mL) was added TFA (1.69 mL) under N$_2$. The mixture was stirred at 25° C. for 2 h. TLC (PE/EtOAc=5/1, $R_f$=0.01) indicated starting material was consumed completely and one new spot formed. The reaction mixture was concentrated under reduced pressure to yield N-(4-methyl-4-piperidyl)prop-2-enamide (150 mg, 713.3 μmol, 93.8% yield, 80% purity) as colorless liquid which was used in next step directly without further purification. $^1$H NMR (400 MHz, CDCl$_3$) δ ppm 8.33 (s, 1H), 7.95-7.70 (m, 1H), 6.32-6.24 (m, 1H), 6.20-6.11 (m, 1H), 5.78 (d, J=10.6 Hz, 1H), 3.33 (s, 4H), 2.59 (d, J=15.7 Hz, 2H), 1.92 (td, J=7.5, 14.4 Hz, 2H), 1.55 (s, 3H).

Step 3: N-[4-Methyl-1-[[4-(trifluoromethyl)phenyl]methyl]-4-piperidyl]prop-2-enamide To a solution of N-(4-methyl-4-piperidyl)prop-2-enamide (150 mg, 531.43 μmol, 1 eq, TFA) in DCM (8 mL) was added DIEA (274.73 mg, 2.13 mmol, 370.25 μL, 4 eq) and 1-(bromomethyl)-4-(trifluoromethyl)benzene (127.03 mg, 531.43 μmol, 81.95 μL, 1 eq) under N₂. The mixture was stirred at 25° C. for 12 h. The mixture was concentrated and water (80 mL) was added. The mixture was extracted with EtOAc (50 mL×3). The combined organic layers were washed with brine (50 mL), dried over Na₂SO₄, filtered and concentrated. The residue was purified by flash silica gel chromatography (From PE/EtOAc=1/0 to 5/1, R_f=0.08) to yield N-[4-methyl-1-[[4-(trifluoromethyl)phenyl]methyl]-4-piperidyl]prop-2-enamide (81.13 mg, 242.63 μmol, 45.6% yield, 97.6% purity) as a light yellow solid. ¹H NMR (400 MHz, CDCl₃) δ ppm 7.56 (d, J=7.8 Hz, 2H), 7.44 (d, J=7.8 Hz, 2H), 6.27-6.20 (m, 1H), 6.11-6.01 (m, 1H), 5.60 (dd, J=1.6, 10.2 Hz, 1H), 5.19 (s, 1H), 3.54 (s, 2H), 2.57 (d, J=11.0 Hz, 2H), 2.32-2.20 (m, 2H), 2.16-2.05 (m, 2H), 1.72-1.68 (m, 2H), 1.45 (s, 3H); ES-LCMS m/z 327.3 [M+H]⁺.
I-204 & I-205

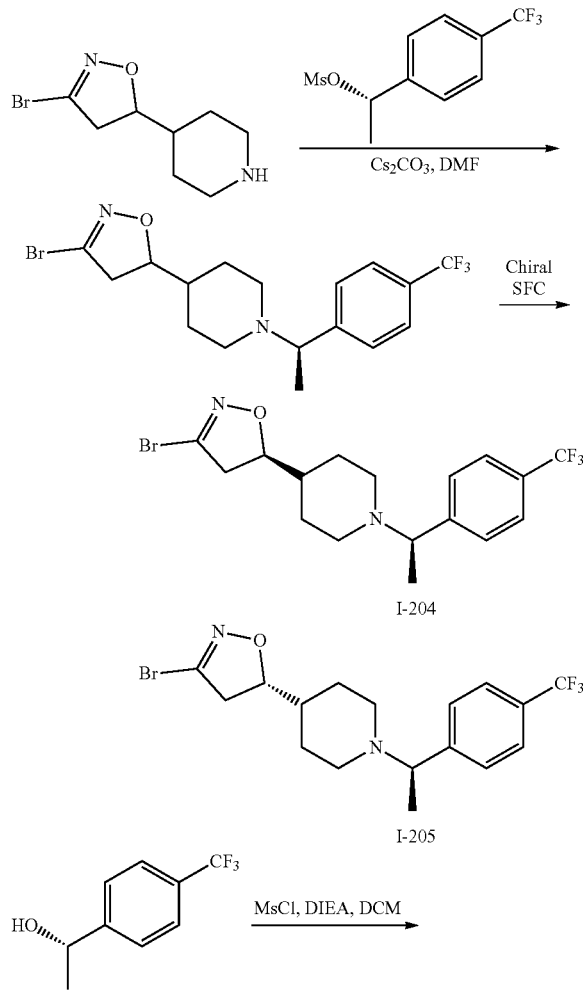

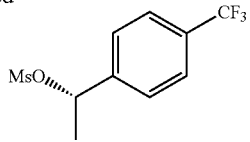

Step 1:
3-Bromo-5-(4-piperidyl)-4,5-dihydroisoxazole

To a solution of tert-butyl 4-(3-bromo-4, 5-dihydroisoxazol-5-yl)piperidine-1-carboxylate (250 mg, 675.23 μmol, 1 eq) in DCM (5 mL) was added TFA (1.54 g, 1 mL). The mixture was stirred at 25° C. for 2 h. The mixture was concentrated to yield 3-bromo-5-(4-piperidyl)-4,5-dihydroisoxazole (250 mg, 648.18 μmol, 96.0% yield, 90.0% purity, TFA) as yellow oil, which was used in the next step without further purification. ¹H NMR (400 MHz, CDCl₃) δ ppm 4.63-4.49 (m, 1H), 3.60 (d, J=11.6 Hz, 2H), 3.31 (dd, J=10.8, 17.2 Hz, 1H), 3.10-2.91 (m, 3H), 2.15-2.10 (m, 1H), 2.00-1.81 (m, 2H), 1.77-1.58 (m, 2H); ES-LCMS m/z 232.80 [M+H]⁺.

Step 2: [(1S)-1-[4-(Trifluoromethyl)phenyl]ethyl] methanesulfonate

To a solution of (1S)-1-[4-(trifluoromethyl)phenyl]ethanol (200 mg, 1.05 mmol, 1 eq) in DCM (20 mL) was added DIEA (407.78 mg, 3.16 mmol, 549.57 μL, 3.0 eq) and methanesulfonyl chloride (140 mg, 1.22 mmol, 94.59 μL, 1.16 eq) at 0° C. under N₂. The mixture was allowed to warm to room temperature (28° C.) with stirred for 1 h under N₂. TLC (PE/EtOAc=6/1, R_f=0.5) showed that new point was formed and start material was consumed completely. The reaction mixture was quenched by addition of H₂O (10 mL) and extracted with DCM (10 mL×3). The combined organic layers were dried over Na₂SO₄, filtered and concentrated under reduced pressure to yield [(1S)-1-[4-(trifluoromethyl)phenyl]ethyl] methanesulfonate (295 mg, 1.04 mmol, 99.3% yield, 95.0% purity) as yellow oil, which was used in the next step without further purification. ¹H NMR (400 MHz, CDCl₃) δ ppm 7.68 (d, J=8.4 Hz, 2H), 7.54 (d, J=8.4 Hz, 2H), 5.82-5.76 (m, 1H), 2.86 (s, 3H), 1.74 (d, J=6.8 Hz, 3H).

Step 3: 3-Bromo-5-[1-[(1R)-1-[4-(trifluoromethyl)phenyl]ethyl]-4-piperidyl]-4,5-dihydroisoxazole To a solution of 3-bromo-5-(4-piperidyl)-4, 5-dihydroisoxazole (250 mg, 965.23 μmol, 1 eq) and [(1S)-1-[4-(trifluoromethyl)phenyl]ethyl] methanesulfonate (295 mg, 1.04 mmol, 1.08 eq) in DMF (10 mL) was added Cs₂CO₃ (314.49 mg, 965.23 μmol, 1 eq). The mixture was stirred at 25° C. for 48 h. The reaction mixture was quenched by addition of H₂O (20 mL) and extracted with EtOAc (30 mL×3). The combined organic layers were washed with brine (30 mL), dried over Na₂SO₄, filtered and concentrated under reduced pressure to give a residue which was purified by preparative HPLC (column: Welch Xtimate C18 150*25 mm*5 um; mobile phase: [water (10 mM NH₄HCO₃)-ACN]; B %: 52%-82%, 10 min) to yield 3-bromo-5-[1-[(1R)-1-[4-(trifluoromethyl)phenyl]ethyl]-4-piperidyl]-4,5-dihydroisoxazole (90 mg, 210.98 μmol, 21.9% yield, 95.0% purity) as a white solid. ES-LCMS m/z 407.1 [M+H]⁺.

Step 4: (5S)-3-Bromo-5-[1-[(1R)-1-[4-(trifluoromethyl)phenyl]ethyl]-4-piperidyl]-4,5-dihydroisoxazole and (5R)-3-bromo-5-[1-[(1R)-1-[4-(trifluoromethyl)phenyl]ethyl]-4-piperidyl]-4,5-dihydroisoxazole 3-Bromo-5-[1-[(1R)-1-[4-(trifluoromethyl)phenyl]ethyl]-4-piperidyl]-4,5-dihydroisoxazole (90 mg, 210.98 mmol, 1 eq) was separated by SFC (column: DAICEL CHIRALPAK IG (250 mm*30 mm, 10 mm); mobile phase: [0.1% NH$_3$H$_2$O MeOH]; B %: 20%-20%, min) to yield peak 1 and peak 2. Peak 2 was concentrated under reduced pressure to give a residue which was dissolved in MeCN (15 mL) and water (15 mL) and lyophilized to yield (5R)-3-bromo-5-[1-[(1R)-1-[4-(trifluoromethyl)phenyl]ethyl]-4-piperidyl]-4,5-dihydroisoxazole (21.63 mg, 52.89 μmol, 25.1% yield, 99.1% purity, SFC: R$_t$=2.861, Dr=99.5%, [α]$^{26.8}_D$=−70.0 (MeOH, c=0.020 g/100 mL)) as a white solid. $^1$H NMR (400 MHz, CD$_3$OD) δ ppm 7.66 (d, J=7.6 Hz, 2H), 7.56 (d, J=7.6 Hz, 2H), 4.52-4.45 (m, 1H), 3.70 (br s, 1H), 3.30-3.16 (m, 2H), 3.02 (dd, J=8.8, 17.2 Hz, 1H), 2.92 (br s, 1H), 2.33-1.93 (m, 2H), 1.88 (d, J=12.4 Hz, 1H), 1.56 (s, 2H), 1.47 (d, J=5.6 Hz, 3H), 1.43-1.28 (m, 2H); ES-LCMS m/z 405.0 [M+H]$^+$. Peak 1 was concentrated under reduced pressure to yield a residue which was separated by SFC (column: DAICEL CHIRALPAK AD-H (250 mm*30 mm, 5 mm); mobile phase: [0.1% NH$_3$H$_2$O MeOH]; B %: 10%-10%, min) to give peak 1. Peak 1 was concentrated under reduced pressure to yield a residue which was dissolved in MeCN (15 mL) and water (15 mL) and lyophilized to yield (5S)-3-bromo-5-[1-[(1R)-1-[4-(trifluoromethyl)phenyl]ethyl]-4-piperidyl]-4,5-dihydroisoxazole (15.06 mg, 36.68 μmol, 17.4% yield, 98.7% purity, SFC: R$_t$=2.602, Dr=96.76, [α]$^{26.9}_D$=+123.81 (MeOH, c=0.021 g/100 mL)) as a white solid. $^1$H NMR (400 MHz, CD$_3$OD) δ ppm 7.62 (d, J=8.4 Hz, 2H), 7.52 (d, J=8.4 Hz, 2H), 4.52-4.44 (m, 1H), 3.55 (d, J=5.6 Hz, 1H), 3.29-3.22 (m, 1H), 3.17 (d, J=11.2 Hz, 1H), 3.02 (dd, J=8.8, 17.2 Hz, 1H), 2.84 (d, J=12.4 Hz, 1H), 2.01 (t, J=9.2 Hz, 1H), 1.89 (t, J=12.4 Hz, 1H), 1.74 (d, J=13.2 Hz, 1H), 1.63 (d, J=12.4 Hz, 1H), 1.55-1.47 (m, 1H), 1.46-1.35 (m, 4H), 1.31-1.26 (m, 1H); ES-LCMS m/z 405.0 [M+H]$^+$.

I-206 & I-207

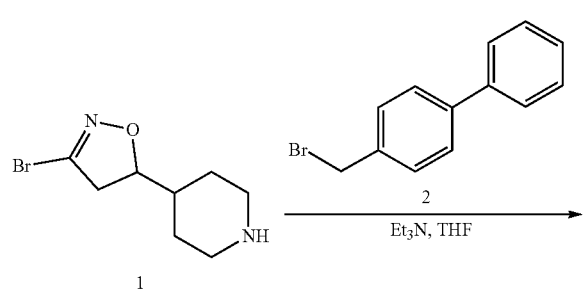

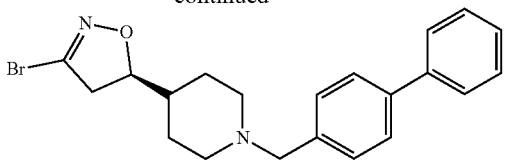

I-206

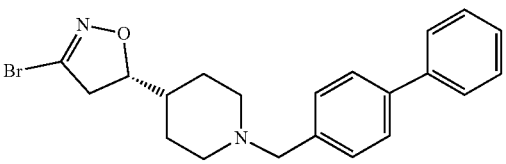

I-207

Step 1: (5R)-3-Bromo-5-[1-[(4-phenylphenyl)methyl]-4-piperidyl]-4,5-dihydroisoxazole & (5S)-3-Bromo-5-[1-[(4-phenylphenyl)methyl]-4-piperidyl]-4,5-dihydroisoxazole To a solution of 1-(bromomethyl)-4-phenyl-benzene (300 mg, 1.21 mmol, 1 eq) in THF (6 mL) was added Et$_3$N (734.64 mg, 7.26 mmol, 1.01 mL, 6 eq) and 3-bromo-5-(4-piperidyl)-4,5-dihydroisoxazole (419.56 mg, 1.09 mmol, 8.99e-1 eq, TFA) under N$_2$. The mixture was stirred at 25° C. for 4 h. TLC (PE/EtOAc=1/1, R$_f$=0.15) indicated starting material was consumed and many new spots formed. The mixture was concentrated and water (80 mL) was added. The mixture was extracted with EtOAc (50 mL×3). The combined organic layers were washed with brine (50 mL), dried over Na$_2$SO$_4$, filtered and concentrated to yield a residue which was purified by flash silica gel chromatography (From PE/EtOAc=1/0 to 1/1, R$_f$=0.15) to yield the product which was separated by SFC (column: DAICEL CHIRALPAK AD (250 mm*30 mm, 10 um); mobile phase: [0.1% NH$_3$H$_2$O EtOH]; B %: 40%-40%, min) to yield (5R)-3-bromo-5-[1-[(4-phenylphenyl)methyl]-4-piperidyl]-4,5-dihydroisoxazole (43.17 mg, 108.11 umol, 8.9% yield, 100.0% purity, SFC: R$_t$=2.874 min, ee=99.56%, [α]$^{22.4}_D$+90 (MeOH, c=0.050 g/100 mL)) as a white solid. $^1$H NMR (400 MHz, DMSO-d$_6$) δ ppm 1.15-1.26 (m, 2H), 1.49 (d, J=10.56 Hz, 2H), 1.67 (d, J=12.91 Hz, 1H), 1.88 (d, J=9.78 Hz, 2H), 2.84 (d, J=9.78 Hz, 2H), 3.06 (dd, J=17.41, 8.80 Hz, 1H), 3.27 (d, J=10.96 Hz, 1H), 3.46 (s, 2H), 4.40-4.48 (m, 1H), 7.30-7.39 (m, 3H), 7.44 (t, J=7.63 Hz, 2H), 7.61 (dd, J=16.82, 7.83 Hz, 4H); ES-LCMS m/z 399.1, 401.1 [M+H]$^+$ and (5S)-3-bromo-5-[1-[(4-phenylphenyl)methyl]-4-piperidyl]-4,5-dihydroisoxazole (46.53 mg, 116.52 umol, 9.6% yield, 100.0% purity, SFC: R$_t$=3.313 min, ee=99.50%, [α]$^{22.1}_D$=−96 (MeOH, c=0.050 g/100 mL)) as a white solid. $^1$H NMR (400 MHz, DMSO-d$_6$) δ ppm 1.16-1.25 (m, 2H), 1.48 (d, J=10.17 Hz, 2H), 1.67 (d, J=13.30 Hz, 1H), 1.83-1.94 (m, 2H) 2.84 (d, J=10.17 Hz, 2H), 3.06 (dd, J=17.41, 8.80 Hz, 1H), 3.27 (d, J=10.96 Hz, 1H), 3.46 (s, 2H), 4.35-4.52 (m, 1H), 7.30-7.38 (m, 3H), 7.44 (t, J=7.63 Hz, 2H), 7.61 (dd, J=17.41, 8.02 Hz, 4H); ES-LCMS m/z 399.1, 401.1 [M+H]$^+$.

I-208

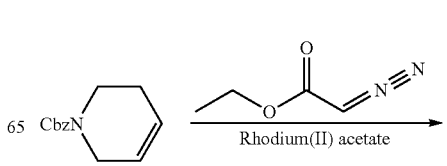

-continued

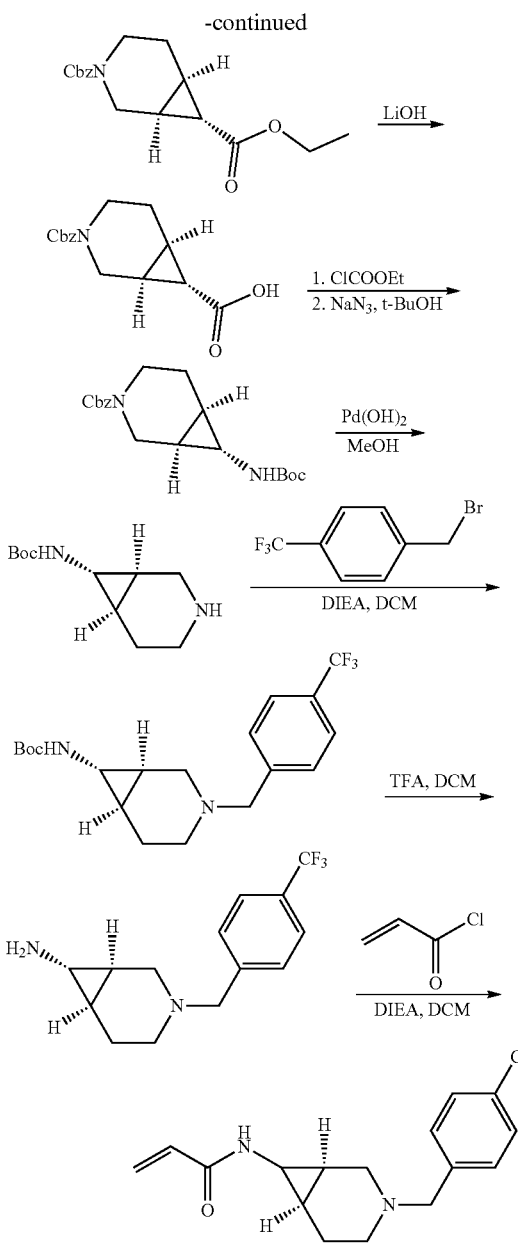

Step 1: O4-Benzyl O7-ethyl (1R,6S,7S)-4-azabicyclo[4.1.0]heptane-4,7-dicarboxylate

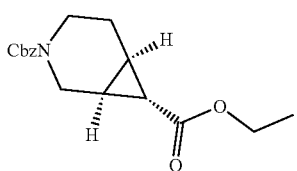 [SMILES: CCOC(=O)[C@H]1[C@@H]2CCN(C(=O)OCc3ccccc3)C[C@@H]21]

To a mixture of benzyl 3,6-dihydro-2H-pyridine-1-carboxylate (2 g, 9.21 mmol, 1 eq) and rhodium(II) acetate (40 mg, 181.00 µmol, 1.97e-2 eq) in 1,2-dichloroethane (80 mL) was added a solution of ethyl 2-diazoacetate (5.25 g, 46.03 mmol, 4.82 mL, 5 eq) in 1,2-dichloroethane (20 mL) drop-wise under $N_2$ atmosphere at 80° C. The mixture was stirred at under $N_2$ atmosphere at 80° C. for 5 h. The reaction mixture was concentrated under reduced pressure to yield a residue which was purified by flash silica gel chromatography (from PE/EtOAc=100/1 to 3/1, TLC: PE/EtOAc=3/1, $R_f$=0.41) to yield 04-benzyl 07-ethyl (1R,6S,7S)-4-azabicyclo[4.1.0]heptane-4,7-dicarboxylate (1.5 g, 4.61 mmol, 50.1% yield, 93.2% purity) as colorless oil. $^1$H NMR (400 MHz, CDCl$_3$) δ ppm 7.42-7.30 (m, 5H), 5.13 (s, 2H), 4.15-4.09 (m, 2H), 4.00 (d, J=13.7 Hz, 1H), 3.59 (d, J=13.3 Hz, 1H), 3.56-3.48 (m, 1H), 3.05 (ddd, J=5.5, 8.9, 13.8 Hz, 1H), 2.04-1.96 (m, 1H), 1.88-1.78 (m, 1H), 1.76-1.66 (m, 2H), 1.49 (t, J=4.3 Hz, 1H), 1.27 (t, J=7.2 Hz, 3H); ES-LCMS m/z 304.3 [M+H]$^+$.

Step 2: (1R,6S,7S)-4-Benzyloxycarbonyl-4-azabicyclo[4.1.0]heptane-7-carboxylic Acid

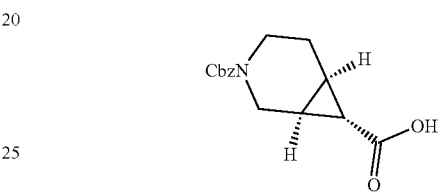

To a solution of O4-benzyl O7-ethyl (1R,6S,7S)-4-azabicyclo[4.1.0]heptane-4,7-dicarboxylate (1 g, 3.07 mmol, 1 eq) in THF (10 mL), MeOH (4 mL) and H$_2$O (4 mL) was added LiOH·H$_2$O (650 mg, 15.49 mmol, 5.04 eq). The mixture was stirred at 25° C. for 12 h. TLC (PE/EtOAc=3/1, $R_f$=0.05) showed the starting material was consumed completely. The reaction mixture was diluted with H$_2$O (50 mL) and extracted with EtOAc (50 mL×2). The organic layer was discarded. The aqueous layer was acidified with aqueous HCl (2 M) until pH=5 and extracted with EtOAc (50 mL×3). The organic layer was dried over Na$_2$SO$_4$, filtered and concentrated under reduced pressure to yield (1R,6S,7S)-4-benzyloxycarbonyl-4-azabicyclo[4.1.0]heptane-7-carboxylic acid (800 mg, 2.91 mmol, 94.6% yield, 100.0% purity) as a colorless gum, which was used in the next step without further purification. $^1$H NMR (500 MHz, CD$_3$OD) δ ppm 7.38-7.30 (m, 5H), 5.16-5.10 (m, 2H), 3.98 (d, J=14.0 Hz, 1H), 3.73 (d, J=7.9 Hz, 1H), 3.56-3.46 (m, 1H), 3.16-3.06 (m, 1H), 2.10-2.03 (m, 1H), 1.96-1.79 (m, 1H), 1.76-1.69 (m, 2H), 1.60-1.37 (m, 1H); ES-LCMS m/z 276.2 [M+H]$^+$.

Step 3: Benzyl (1R,6R,7S)-7-(tert-butoxycarbonylamino)-4-azabicyclo[4.1.0]heptane-4-carboxylate

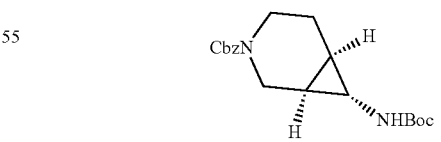

To a solution of (1R,6S,7S)-4-benzyloxycarbonyl-4-azabicyclo[4.1.0]heptane-7-carboxylic acid (750 mg, 2.72 mmol, 1 eq) and Et$_3$N (303.24 mg, 3.00 mmol, 417.11 µL, 1.1 eq) in acetone (15 mL) was added ethyl chloroformate (355 mg, 3.27 mmol, 311.40 µL, 1.2 eq) dropwise at 0° C. The mixture was stirred at 0° C. for 0.5 h. A solution of NaN$_3$ (1.01 g, 15.54 mmol, 5.70 eq) in H$_2$O (7.5 mL) was added slowly at 0° C. The mixture was stirred at 25° C. for 2 h. The mixture was diluted with water (20 mL) and extracted with EtOAc (20 mL×3). The aqueous layer was poured into NaClO (100 mL) slowly. The organic layer was dried over Na₂SO₄ and filtered and toluene (40 mL) was added. The mixture was concentrated under reduced pressure at 30° C. to remove acetone and EtOAc. The residue was added to a mixture of 4-methylbenzenesulfonic acid; pyridine (5 mg, 19.90 μmol, 7.30e-3 eq) in t-BuOH (10 mL) and toluene (30 mL) at 100° C. slowly. The mixture was stirred at 100° C. for 12 h. The reaction mixture was diluted with H₂O (50 mL) and extracted with EtOAc (50 mL×3). The organic layer was dried over Na₂SO₄, filtered and concentrated under reduced pressure to yield a residue which was purified by flash silica gel chromatography (from PE/EtOAc=100/1 to 4/1, TLC: PE/EtOAc=2/1, R$_f$=0.40) to yield benzyl (1R,6R,7S)-7-(tert-butoxycarbonylamino)-4-azabicyclo[4.1.0]heptane-4-carboxylate (780 mg, 2.22 mmol, 81.3% yield, 98.4% purity) as a colorless gum. ¹H NMR (500 MHz, CDCl₃) δ ppm 7.40-7.30 (m, 5H), 5.12 (s, 2H), 4.76-4.66 (m, 1H), 3.98-3.88 (m, 1H), 3.70-3.60 (m, 1H), 3.40-3.30 (m, 1H), 3.10-3.00 (m, 1H), 2.39-2.14 (m, 1H), 1.99 (d, J=5.8 Hz, 1H), 1.88-1.78 (m, 1H), 1.45 (s, 9H), 1.25-1.13 (m, 2H); ES-LCMS m/z 369.2 [M+Na]⁺.

Step 4: tert-Butyl N-[(1R,6R,7S)-4-azabicyclo[4.1.0]heptan-7-yl]carbamate

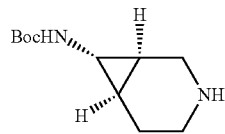 [SMILES: CC(C)(C)OC(=O)N[C@H]1[C@@H]2CCNC[C@@H]21]

A mixture of benzyl (1R,6R,7S)-7-(tert-butoxycarbonylamino)-4-azabicyclo[4.1.0]heptane-4-carboxylate (730 mg, 2.07 mmol, 1 eq) and Pd(OH)₂ (0.2 g, 20% purity) in MeOH (30 mL) was stirred under H₂ (15 psi) at 25° C. for 2 h. TLC (PE/EtOAc=2/1, R$_f$=0.05) showed the starting material was consumed completely. The mixture was filtered. The filtrate was concentrated under reduced pressure to yield tert-butyl N-[(1R,6R,7 S)-4-azabicyclo[4.1.0]heptan-7-yl]carbamate (400 mg, 1.88 mmol, 91.1% yield, N/A purity) as a pale yellow gum, which was used in the next step without further purification. ¹H NMR (500 MHz, CD₃OD) δ ppm 3.21-3.14 (m, 1H), 3.02 (d, J=13.4 Hz, 1H), 2.56-2.50 (m, 1H), 2.48-2.43 (m, 1H), 2.36 (t, J=3.4 Hz, 1H), 1.98-1.92 (m, 1H), 1.80-1.70 (m, 1H), 1.45 (s, 9H), 1.17-1.11 (m, 1H), 1.08-1.02 (m, 1H).

Step 5: tert-Butyl N-[(1R,6R,7S)-4-[[4-(trifluoromethyl)phenyl]methyl]-4-azabicyclo[4.1.0]heptan-7-yl]carbamate

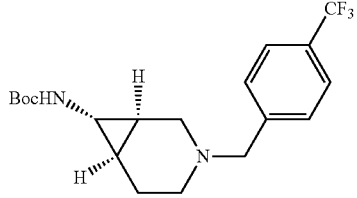 [SMILES: CC(C)(C)OC(=O)N[C@H]1[C@@H]2CCN(Cc3ccc(C(F)(F)F)cc3)C[C@@H]21]

A mixture of tert-butyl N-[(1R,6R,7S)-4-azabicyclo[4.1.0]heptan-7-yl]carbamate (50 mg, 235.53 μmol, 1 eq), 1-(bromomethyl)-4-(trifluoromethyl)benzene (50 mg, 209.18 μmol, 8.88e-1 eq) and DIEA (100 mg, 773.74 μmol, 134.77 μL, 3.29 eq) in DCM (3 mL) was stirred at 25° C. for 12 h. The reaction mixture was diluted with H₂O (20 mL) and extracted with DCM (20 mL×3). The organic layer was dried over Na₂SO₄, filtered and concentrated under reduced pressure to yield a residue which was purified by preparative TLC (PE/EtOAc=2/1, R$_f$=0.30) to yield tert-butyl N-[(1R, 6R,7S)-4-[[4-(trifluoromethyl)phenyl]methyl]-4-azabicyclo[4.1.0]heptan-7-yl]carbamate (50 mg, 132.15 μmol, 56.1% yield, 97.9% purity) as a colorless gum. ¹H NMR (500 MHz, CDCl₃) δ ppm 7.55 (d, J=7.9 Hz, 2H), 7.40 (d, J=7.9 Hz, 2H), 4.70 (br s, 1H), 3.54-3.33 (m, 2H), 2.89 (d, J=9.9 Hz, 1H), 2.62-2.52 (m, 2H), 2.26-2.16 (m, 1H), 2.03-1.91 (m, 2H), 1.73-1.58 (m, 1H), 1.45 (s, 9H), 1.22-1.04 (m, 2H); ES-LCMS m/z 371.7 [M+H]⁺.

Step 6: (1R,6R,7S)-4-[[4-(Trifluoromethyl)phenyl]methyl]-4-azabicyclo[4.1.0]heptan-7-amine

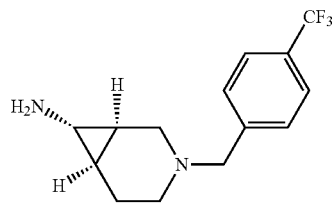 [SMILES: N[C@@H]1[C@H]2CN(Cc3ccc(C(F)(F)F)cc3)CC[C@@H]12]

To a solution of tert-butyl N-[(1R,6R,7S)-4-[[4-(trifluoromethyl)phenyl]methyl]-4-azabicyclo[4.1.0]heptan-7-yl]carbamate (50 mg, 132.15 μmol, 1 eq) in DCM (6 mL) was added TFA (3.08 g, 27.01 mmol, 2 mL, 204.40 eq). The mixture was stirred at 20° C. for 0.5 h. TLC (PE/EtOAc=1/1, R$_f$=0.05) showed the starting material was consumed completely. The reaction mixture was concentrated under reduced pressure to yield (1R,6R,7S)-4-[[4-(trifluoromethyl)phenyl]methyl]-4-azabicyclo[4.1.0]heptan-7-amine (65 mg, 130.43 μmol, 98.7% yield, N/A purity, 2TFA) as a colorless gum, which was used in the next step without further purification.

Step 7: N-[(1R,6R,7S)-4-[[4-(Trifluoromethyl)phenyl]methyl]-4-azabicyclo[4.1.0]heptan-7-yl]prop-2-enamide

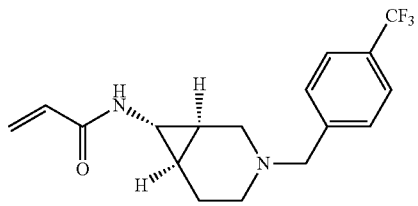 [SMILES: C=CC(=O)N[C@H]1[C@@H]2CCN(Cc3ccc(C(F)(F)F)cc3)C[C@@H]21]

To a solution of (1R,6R,7S)-4-[[4-(trifluoromethyl)phenyl]methyl]-4-azabicyclo[4.1.0]heptan-7-amine (65 mg, 130.43 μmol, 1 eq, 2TFA) and DIEA (84.29 mg, 652.17 μmol, 113.60 μL, 5 eq) in DCM (10 mL) was added prop-2-enoyl chloride (12.21 mg, 134.90 μmol, 11 μL, 1.03 eq). The mixture was stirred at 20° C. for 1 h. The reaction mixture was concentrated under reduced pressure to yield a residue which was purified by preparative HPLC (column: Phenomenex Synergi C18 150*30 mm*4 um; mobile phase: [water (0.05% HCl)-ACN]; B %: 13%-33%, 9 min). The desired fraction was basified with saturated aqueous NaHCO₃ until pH=8 and extracted with EtOAc (50 mL×3). The organic layer was dried over Na₂SO₄, filtered and concentrated under reduced pressure to yield a residue which was dissolved in MeCN (15 mL) and water (15 mL) and then lyophilized to yield N-[(1R,6R,7S)-4-[[4-(trifluoromethyl)phenyl]methyl]-4-azabicyclo[4.1.0]heptan-7-yl]prop-2-enamide (21.99 mg, 67.80 μmol, 52.0% yield, 100.0% purity) as a white solid. ¹H NMR (500 MHz, CDCl₃) δ ppm 7.56 (d, J=7.8 Hz, 2H), 7.43 (d, J=7.5 Hz, 2H), 6.28 (dd, J=1.1, 16.9 Hz, 1H), 6.03 (dd, J=10.4, 16.9 Hz, 1H), 5.68 (br s, 1H), 5.62 (dd, J=1.1, 10.2 Hz, 1H), 3.48 (d, J=12.7 Hz, 2H), 2.96 (d, J=11.3 Hz, 1H), 2.84 (q, J=3.2 Hz, 1H), 2.68-2.48 (m, 1H), 2.27 (d, J=6.3 Hz, 1H), 2.07-1.89 (m, 3H), 1.25 (d, J=12.4 Hz, 1H), 1.20-1.10 (m, 1H); ES-LCMS m/z 325.3 [M+H]⁺.

I-211

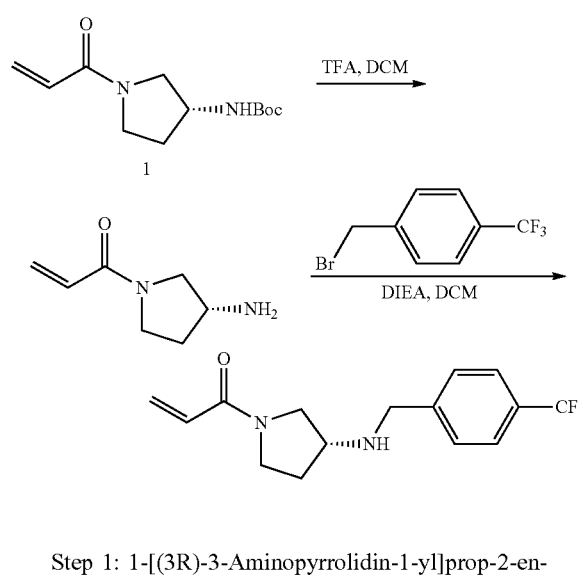

Step 1: 1-[(3R)-3-Aminopyrrolidin-1-yl]prop-2-en-1-one

A solution of tert-butyl N-[(3R)-1-prop-2-enoylpyrrolidin-3-yl]carbamate (500 mg, 1.87 mmol, 1 eq) in DCM (6 mL) and TFA (2 mL) was stirred at 28° C. for 1 h. TLC (PE/EtOAc=1/1, R_f=0.01) indicated starting material was consumed completely. The mixture was filtered and concentrated under reduced pressure to yield 1-[(3R)-3-aminopyrrolidin-1-yl]prop-2-en-1-one (450 mg, 1.77 mmol, 94.5% yield, N/A purity, TFA) as a light yellow gum, which was used in the next step without further purification. ¹H NMR (400 MHz, DMSO-d₆) δ ppm 8.05 (br s, 2H), 6.62-6.43 (m, 1H), 6.22-6.04 (m, 1H), 5.66 (dd, J=2.4, 10.3 Hz, 1H), 3.83-3.75 (m, 1H), 3.75-3.65 (m, 1H), 3.65-3.56 (m, 1H), 3.56-3.50 (m, 1H), 3.49-3.42 (m, 1H), 2.32-2.06 (m, 1H), 2.04-1.83 (m, 1H).

Step 2: 1-[(3R)-3-[[4-(Trifluoromethyl)phenyl]methylamino]pyrrolidin-1-yl]prop-2-en-1-one

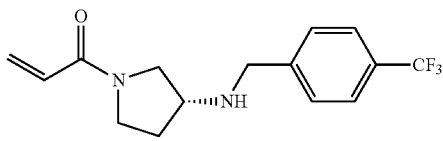 [SMILES: C=CC(=O)N1CC[C@@H](NCc2ccc(C(F)(F)F)cc2)C1]

To a solution of 1-[(3R)-3-aminopyrrolidin-1-yl]prop-2-en-1-one (450 mg, 1.77 mmol, 1 eq, TFA) and DIEA (1.14 g, 8.85 mmol, 1.54 mL, 5 eq) in DCM (10 mL) was added 1-(bromomethyl)-4-(trifluoromethyl)benzene (338.51 mg, 1.42 mmol, 218.39 μL, 0.8 eq). The mixture was stirred at 28° C. for 12 h. The mixture was diluted with water (10 mL) and extracted with EtOAc (10 mL×3). The combined organic layers were dried over Na₂SO₄, filtered and concentrated under reduced pressure to yield a residue which was purified by flash silica gel chromatography (from EtOAc/MeOH=100/1 to 20/1, TLC: EtOAc/MeOH=10/1, R_f=0.40) and preparative HPLC (column: Welch Xtimate C18 150*25 mm*5 um; mobile phase: [water (10 mM NH₄HCO₃)-ACN]; B %: 29%-59%, 10 min), followed by lyophilization to yield 1-[(3R)-3-[[4-(trifluoromethyl)phenyl]methylamino]pyrrolidin-1-yl]prop-2-en-1-one (18.47 mg, 60.36 μmol, 3.4% yield, 97.5% purity, [α]²³·⁰_D=+5.582 (MeOH, c=0.025 g/100 mL)) as colorless oil. ¹H NMR (400 MHz, CD₃OD) δ ppm 7.65-7.61 (m, 2H), 7.58-7.54 (m, 2H), 6.57 (ddd, J=10.4, 16.9, 18.1 Hz, 1H), 6.28-6.22 (m, 1H), 5.72 (ddd, J=2.0, 5.3, 10.4 Hz, 1H), 3.89-3.86 (m, 2H), 3.81-3.75 (m, 1H), 3.74-3.52 (m, 2H), 3.49-3.42 (m, 1H), 3.40-3.36 (m, 1H), 2.20-2.10 (m, 1H), 1.97-1.79 (m, 1H); ES-LCMS m/z 299.2 [M+H]⁺.

I-212

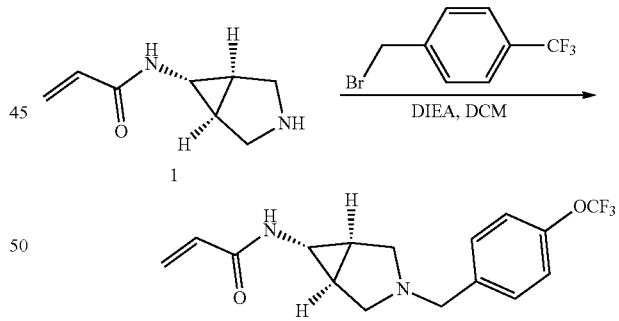

Step 1: N-[(1R,5S)-3-[[4-(Trifluoromethoxy)phenyl]methyl]-3-azabicyclo[3.1.0]hexan-6-yl]prop-2-enamide

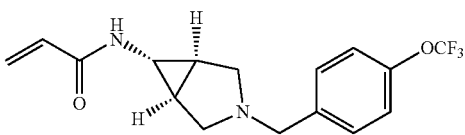 [SMILES: C=CC(=O)N[C@H]1[C@@H]2CN(Cc3ccc(OC(F)(F)F)cc3)C[C@@H]21]

To a solution of N-[(1R,5S)-3-azabicyclo[3.1.0]hexan-6-yl]prop-2-enamide (80.67 mg, 424.06 μmol, 1 eq, HCl) in DMF (30 mL) was added DIEA (328.84 mg, 2.54 mmol, 443.18 μL, 6 eq) and 1-(bromomethyl)-4-(trifluoromethoxy)benzene (108.15 mg, 424.06 μmol, 68.02 μL, 1 eq). The mixture was stirred at 20° C. for 12 h. The mixture was concentrated to yield a residue which was purified by preparative HPLC (column: Welch Xtimate C18 150*25 mm*5 μm; mobile phase: [water (10 mM NH$_4$HCO$_3$)-ACN]; B %: 35%-65%, 10 min), followed by lyophilization to yield N-[(1R,5S)-3-[[4-(trifluoromethoxy)phenyl]methyl]-3-azabicyclo[3.1.0]hexan-6-yl]prop-2-enamide (36.75 mg, 112.62 μmol, 26.6% yield, 100.0% purity) as a white solid. $^1$H NMR (400 MHz, CDCl$_3$) δ ppm 7.29 (s, 2H), 7.14 (d, J=8.1 Hz, 2H), 6.28 (dd, J=1.3, 17.0 Hz, 1H), 6.02 (dd, J=10.3, 17.1 Hz, 1H), 5.62 (dd, J=1.2, 10.3 Hz, 1H), 5.51 (br s, 1H), 3.57 (s, 2H), 3.15-3.09 (m, 3H), 2.41 (d, J=8.6 Hz, 2H), 1.66-1.56 (m, 2H); ES-LCMS m/z 327.2 [M+H]$^+$.

I-213 & I-214

Step 1: (5R)-3-Bromo-5-[1-[(4-tert-butylphenyl)methyl]-4-piperidyl]-4,5-dihydroisoxazole and (5S)-3-bromo-5-[1-[(4-tert-butylphenyl)methyl]-4-piperidyl]-4,5-dihydroisoxazole

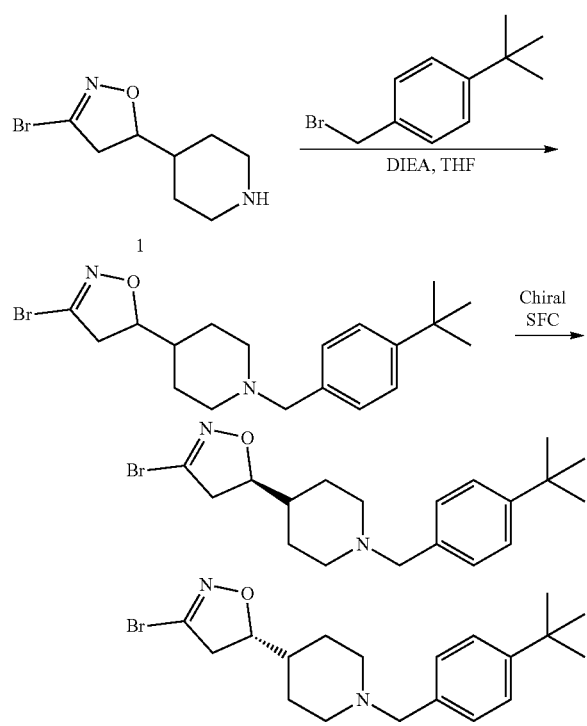

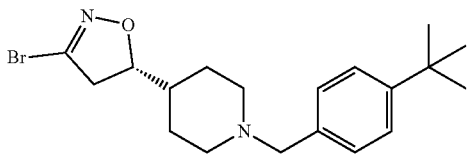

To a solution of 3-bromo-5-(4-piperidyl)-4,5-dihydroisoxazole (400 mg, 1.04 mmol, 1 eq, TFA) in THF (10 mL) was added DIEA (670.18 mg, 5.19 mmol, 903.20 μL, 5 eq) and 1-(bromomethyl)-4-tert-butyl-benzene (353.34 mg, 1.56 mmol, 284.96 μL, 1.5 eq). The mixture was stirred under N$_2$ atmosphere at 20° C. for 4 h. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=1/1, R$_f$=0.25) to yield the compound which was separated by SFC (column: DAICEL CHIRALPAK AD-H (250 mm*30 mm, 5 μm); mobile phase: [0.1% NH$_3$H$_2$O/EtOH]; B %: 20%-20%) to yield peak 1 and peak 2. Peak 1 was concentrated under reduced pressure to yield a residue which was lyophilized to yield (5R)-3-bromo-5-[1-[(4-tert-butylphenyl)methyl]-4-piperidyl]-4,5-dihydroisoxazole (63 mg, 166.08 μmol, 16.0% yield, 100.0% purity, SFC: R$_f$=3.248, ee=100.0%, [α]$^{21.7}_D$=+69.8 (MeOH, c=0.43 g/100 mL)) as yellow oil. $^1$H NMR (500 MHz, DMSO-d$_6$) δ ppm 7.32 (d, J=7.8 Hz, 2H), 7.19 (d, J=7.6 Hz, 2H), 4.48-4.41 (m, 1H), 3.38 (s, 2H), 3.30 (s, 1H), 3.07 (dd, J=8.8, 17.5 Hz, 1H), 2.80 (d, J=9.6 Hz, 2H), 1.90-1.78 (m, 2H), 1.67 (d, J=10.5 Hz, 1H), 1.48 (d, J=8.4 Hz, 2H), 1.27 (s, 9H), 1.22-1.14 (m, 2H); ES-LCMS m/z 379.2, 381.2 [M+H]$^+$. Peak 2 was concentrated under reduced pressure to yield a residue which was lyophilized to yield (5S)-3-bromo-5-[1-[(4-tert-butylphenyl)methyl]-4-piperidyl]-4,5-dihydroisoxazole (68.12 mg, 172.72 μmol, 16.7% yield, 96.2% purity, SFC: R$_f$=3.533, ee=97.3%, [α]$^{21.7}_D$=−77.7 (MeOH, c=0.43 g/100 mL)) as yellow oil. $^1$H NMR (500 MHz, DMSO-d$_6$) δ ppm 7.32 (d, J=7.9 Hz, 2H), 7.19 (d, J=7.9 Hz, 2H), 4.50-4.41 (m, 1H), 3.38 (s, 2H), 3.31-3.27 (m, 1H), 3.07 (dd, J=8.8, 17.6 Hz, 1H), 2.81 (d, J=9.0 Hz, 2H), 1.91-1.78 (m, 2H), 1.67 (d, J=12.5 Hz, 1H), 1.48 (d, J=10.4 Hz, 2H), 1.27 (s, 9H), 1.23-1.13 (m, 2H); ES-LCMS m/z 379.2, 381.2 [M+H]$^+$.

I-220

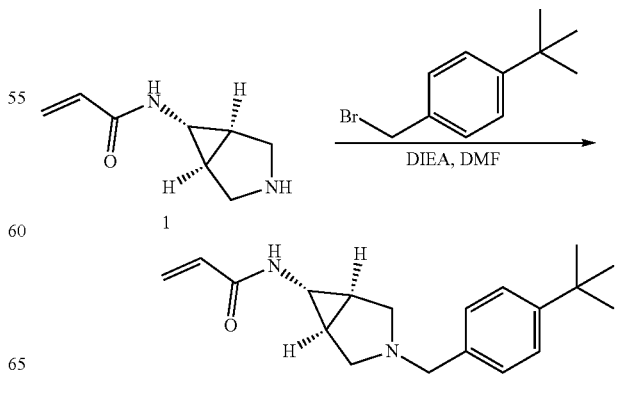

Step 1: N-[(1R,5S)-3-[(4-tert-Butylphenyl)methyl]-3-azabicyclo[3.1.0]hexan-6-yl]prop-2-enamide

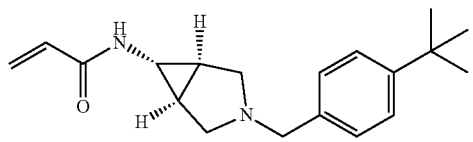 [SMILES: C=CC(=O)N[C@H]1[C@@H]2CN(Cc3ccc(C(C)(C)C)cc3)C[C@@H]21]

To a stirred solution of N-[(1R,5S)-3-azabicyclo[3.1.0]hexan-6-yl]prop-2-enamide (100 mg, 424.06 μmol, 1 eq, HCl) in DMF (3 mL) was added DIEA (219.23 mg, 1.70 mmol, 295.45 μL, 4 eq) and 1-(bromomethyl)-4-tert-butylbenzene (115.58 mg, 508.87 μmol, 93.21 μL, 1.2 eq). The reaction mixture was stirred at 28° C. for 4 h. The reaction was concentrated under reduced pressure to yield a residue which was purified by preparative HPLC (column: Agela DuraShell C18 150*25 mm*5 um; mobile phase: [water (0.05% $NH_3H_2O$+10 mM $NH_4HCO_3$)-ACN]; B %: 42%-72%, 10 min). The desired fraction was lyophilized to yield N-[(1R,5S)-3-[(4-tert-butylphenyl)methyl]-3-azabicyclo[3.1.0]hexan-6-yl]prop-2-enamide (20.77 mg, 66.71 μmol, 15.7% yield, 95.9% purity) as a white solid. $^1$H NMR (400 MHz, $CDCl_3$) δ ppm 7.31 (d, J=8.31 Hz, 2H), 7.19 (d, J=8.07 Hz, 2H), 6.27 (dd, J=17.00, 1.34 Hz, 1H), 6.06-5.97 (m, 1H), 5.61 (dd, J=10.27, 1.47 Hz, 1H), 5.50 (s, 1H), 3.55 (s, 2H), 3.18-3.07 (m, 3H), 2.41 (d, J=8.56 Hz, 2H), 1.54 (s, 2H), 1.32 (s, 9H); ES-LCMS m/z 299.3 [M+H]$^+$.
I-222

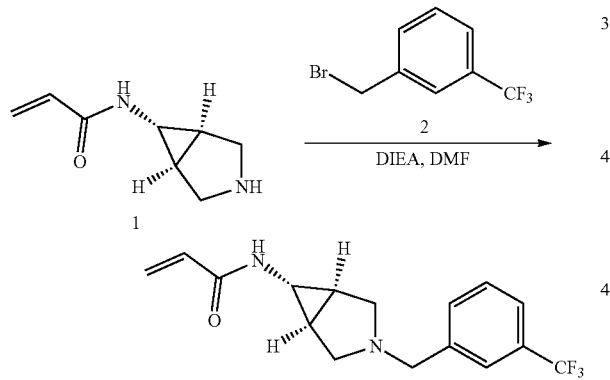

Step 1: N-[(1R,5S)-3-[[3-(Trifluoromethyl)phenyl]methyl]-3-azabicyclo[3.1.0]hexan-6-yl]prop-2-enamide

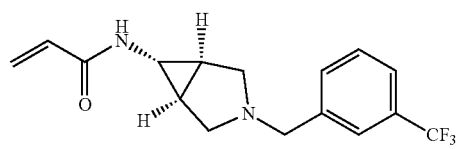 [SMILES: C=CC(=O)N[C@H]1[C@@H]2CN(Cc3cccc(C(F)(F)F)c3)C[C@@H]21]

To a solution of N-[(1R,5S)-3-azabicyclo[3.1.0]hexan-6-yl]prop-2-enamide (100 mg, 525.65 μmol, 1 eq, HCl) in DMF (5 mL) was added 1-(bromomethyl)-3-(trifluoromethyl)benzene (140 mg, 585.70 μmol, 89.17 μL, 1.11 eq) and DIEA (203.81 mg, 1.58 mmol, 274.68 μL, 3 eq). The mixture was stirred at 25° C. for 16 h. The reaction mixture was concentrated to yield a residue which was purified by preparative HPLC (column: Agela DuraShell C18 150*25 mm*5 μm; mobile phase: [water (0.05% $NH_3H_2O$+10 mM $NH_4HCO_3$)-ACN]; B %: 35%-65%, 10 min), followed by lyophilization to yield N-[(1R,5S)-3-[[3-(trifluoromethyl)phenyl]methyl]-3-azabicyclo[3.1.0]hexan-6-yl]prop-2-enamide (16.7 mg, 53.82 μmol, 10.2% yield, 100.0% purity) as a white solid. $^1$H NMR (400 MHz, $CDCl_3$) δ ppm 7.51-7.46 (m, 3H), 7.44-7.39 (m, 1H), 6.28 (dd, J=1.3, 17.0 Hz, 1H), 6.02 (dd, J=10.3, 16.9 Hz, 1H), 5.63 (dd, J=1.2, 10.3 Hz, 1H), 5.50 (s, 1H), 3.62 (s, 2H), 3.13 (d, J=8.8 Hz, 3H), 2.43 (d, J=8.8 Hz, 2H), 1.57 (s, 1H), 1.60-1.57 (m, 1H); ES-LCMS m/z 311.3 [M+H]$^+$.
I-225 & I-226

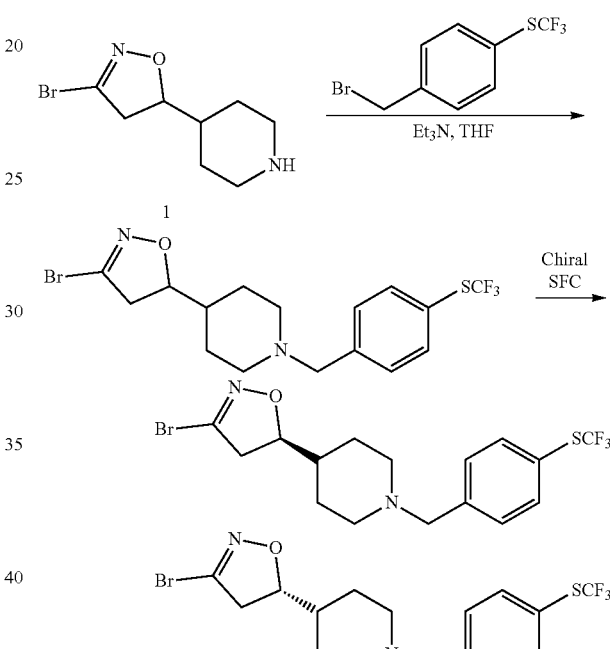

Step 1: (5R)-3-Bromo-5-[1-[[4-(trifluoromethylsulfanyl)phenyl]methyl]-4-piperidyl]-4,5-dihydroisoxazole and (5S)-3-bromo-5-[1-[[4-(trifluoromethylsulfanyl)phenyl]methyl]-4-piperidyl]-4,5-dihydroisoxazole

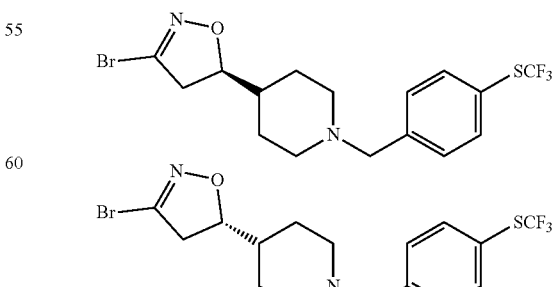

To a solution of 3-bromo-5-(4-piperidyl)-4,5-dihydroisoxazole (300 mg, 777.81 mol, 1 eq, TFA) in DCM (10 mL) was added DIEA (804.19 mg, 6.22 mmol, 1.08 mL, 8 eq) and 1-(bromomethyl)-4-(trifluoromethylsulfanyl)benzene (253.03 mg, 933.37 μmol, 117.02 μL, 1.2 eq). The mixture was stirred at 20° C. for 2 h. The reaction mixture was quenched by addition of water (50 mL) and extracted with EtOAc (50 mL×3). The combined organic layers were washed with brine (10 mL), dried over Na₂SO₄, filtered and concentrated under reduced pressure to yield a residue which was purified by preparative HPLC (column: Agela DuraShell C18 150*25 mm*5 um; mobile phase: [water (0.04% NH₃H₂O+10 mM NH₄HCO₃)-ACN]; B %: 59%-89%, 10 min) to yield the compound which was separated by SFC (column: DAICEL CHIRALPAK AD-H (250 mm*30 mm, 5 um); mobile phase: [0.1% NH₃H₂O EtOH]; B %: 20%-20%) to yield peak 1 and peak 2. Peak 1 was concentrated under reduced pressure to yield (5R)-3-bromo-5-[1-[[4-(trifluoromethylsulfanyl)phenyl]methyl]-4-piperidyl]-4,5-dihydroisoxazole (70 mg, 165.37 μmol, 21.3% yield, 100.0% purity, SFC: R$_t$=3.153, ee=98.1%; [α]$^{24.0}_D$=+71.8 (MeOH, c=0.078 g/100 mL)) as a white solid. ¹H NMR (400 MHz, DMSO-d₆) δ ppm 7.66 (d, J=7.8 Hz, 2H), 7.45 (d, J=8.2 Hz, 2H), 4.51-4.39 (m, 1H), 3.50 (s, 2H), 3.32-3.25 (m, 1H), 3.07 (dd, J=8.6, 17.6 Hz, 1H), 2.80 (d, J=10.2 Hz, 2H), 1.99-1.85 (m, 2H), 1.68 (d, J=12.9 Hz, 1H), 1.49 (d, J=12.1 Hz, 2H), 1.28-1.16 (m, 2H); ES-LCMS m/z 422.9, 424.9 [M+H]⁺. Peak 2 was concentrated under reduced pressure to yield (5S)-3-bromo-5-[1-[[4-(trifluoromethylsulfanyl)phenyl]methyl]-4-piperidyl]-4,5-dihydroisoxazole (55 mg, 129.93 μmol, 16.7% yield, 100.0% purity, SFC: R$_t$=3.307, ee=98.4%; [α]$^{24.0}_D$=−84.21 (MeOH, c=0.114 g/100 mL)) as a white solid. ¹H NMR (400 MHz, DMSO-d₆) δ ppm 7.66 (d, J=7.8 Hz, 2H), 7.46 (d, J=8.2 Hz, 2H), 4.52-4.39 (m, 1H), 3.50 (s, 2H), 3.32-3.25 (m, 1H), 3.07 (dd, J=8.6, 17.4 Hz, 1H), 2.80 (d, J=11.3 Hz, 2H), 1.97-1.84 (m, 2H), 1.68 (d, J=12.5 Hz, 1H), 1.49 (d, J=12.1 Hz, 2H), 1.30-1.11 (m, 2H); ES-LCMS m/z 422.8, 424.8 [M+H]⁺.

I-231

To a solution of N-[(1R,5S)-3-azabicyclo[3.1.0]hexan-6-yl]prop-2-enamide (50 mg, 262.82 μmol, 1 eq, HCl) in DMF (5 mL) was added 1-chloro-4-(chloromethyl)benzene (51.2 mg, 317.96 μmol, 1.21 eq) and DIEA (101.90 mg, 788.47 μmol, 137.34 μL, 3 eq). The mixture was stirred at 25° C. for 16 h. The reaction mixture was concentrated to yield a residue which was purified by preparative HPLC (column: Agela DuraShell C18 150*25 mm*5 μm; mobile phase: [water (0.05% NH₃H₂O+10 mM NH₄HCO₃)-ACN]; B %: 32%-62%, 10 min), followed by lyophilization to yield N-[(1R,5S)-3-[(4-chlorophenyl)methyl]-3-azabicyclo[3.1.0]hexan-6-yl]prop-2-enamide (12.99 mg, 46.70 μmol, 17.8% yield, 99.5% purity) as a white solid. ¹H NMR (400 MHz, CDCl₃) δ ppm 7.25 (s, 1H), 7.21-7.17 (m, 2H), 6.28 (dd, J=1.2, 16.9 Hz, 1H), 6.02 (dd, J=10.4, 17.0 Hz, 1H), 5.62 (dd, J=1.2, 10.3 Hz, 1H), 5.50 (s, 1H), 3.54 (s, 2H), 3.11 (d, J=8.8 Hz, 3H), 2.40 (d, J=8.8 Hz, 2H), 1.59 (s, 2H), 1.55 (s, 1H); ES-LCMS m/z 277.2 [M+H]⁺.

IK-232 & IK-233

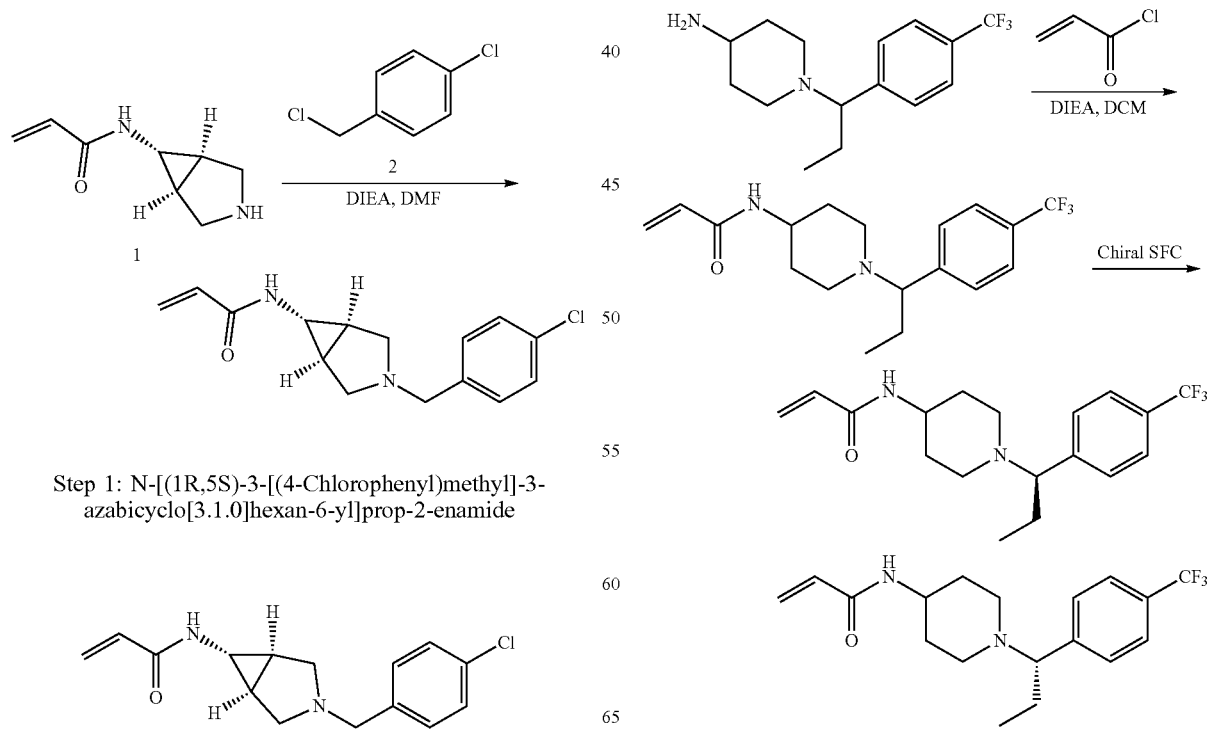

Step 1: N-[(1R,5S)-3-[(4-Chlorophenyl)methyl]-3-azabicyclo[3.1.0]hexan-6-yl]prop-2-enamide

Step 1: tert-Butyl N-[1-[1-[4-(trifluoromethyl)phenyl]propyl]-4-piperidyl]carbamate

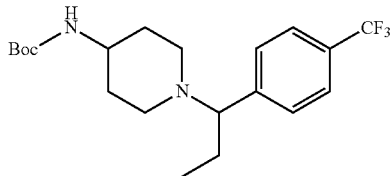 [SMILES: CCC(c1ccc(C(F)(F)F)cc1)N1CCC(NC(=O)OC(C)(C)C)CC1]

A mixture of 1-[4-(trifluoromethyl)phenyl]propan-1-one (300 mg, 1.48 mmol, 1 eq) and tert-butyl N-(4-piperidyl) carbamate (297.19 mg, 1.48 mmol, 1 eq) in Ti(i-PrO)$_4$ (1.27 g, 4.45 mmol, 1.31 mL, 3 eq) was stirred at 70° C. for 2 h. The mixture was cooled to 20° C. MeOH (10 mL) and NaBH$_3$CN (373.00 mg, 5.94 mmol, 4 eq) were added and the mixture was stirred at 40° C. for 16 h. The reaction mixture was quenched by aqueous NaOH (10 mL, 1 M), filtered by celite and washed with MeOH (15 mL×2). MeOH was evaporated under vacuo. The residue was diluted with H$_2$O (20 mL) and extracted with EtOAc (20 mL×2). The combined organic phases were washed with brine (15 mL), dried over anhydrous Na$_2$SO$_4$, filtered and concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 60%-90%, 10 min) to yield tert-butyl N-[1-[1-[4-(trifluoromethyl)phenyl]propyl]-4-piperidyl]carbamate (231 mg, 537.97 µmol, 36.3% yield, 90.0% purity) as a white solid. $^1$H NMR (400 MHz, CDCl$_3$) δ ppm 7.65 (d, J=2.6 Hz, 1H), 7.56 (d, J=8.1 Hz, 2H), 7.33 (d, J=8.1 Hz, 2H), 4.42-4.32 (m, 1H), 3.38-3.36 (m, 1H), 3.23 (dd, J=4.4, 8.5 Hz, 1H), 2.94-2.91 (m, 1H), 2.67 (d, J=11.3 Hz, 1H), 2.13-2.02 (m, 1H), 1.98-1.79 (m, 5H), 1.76-1.68 (m, 1H), 1.42 (s, 9H), 0.73-0.68 (m, 3H); ES-LCMS m/z 387.3 [M+H]$^+$.

Step 2: 1-[1-[4-(Trifluoromethyl)phenyl]propyl] piperidin-4-amine

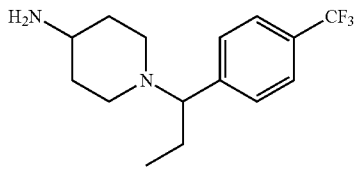 [SMILES: CCC(c1ccc(C(F)(F)F)cc1)N1CCC(N)CC1]

To a solution of tert-butyl N-[1-[1-[4-(trifluoromethyl) phenyl]propyl]-4-piperidyl]carbamate (231 mg, 537.97 µmol, 1 eq) in DCM (2.5 mL) was added TFA (0.5 mL) and the mixture was stirred at 20° C. for 2 h. The mixture was concentrated to yield 1-[1-[4-(trifluoromethyl)phenyl]propyl]piperidin-4-amine (225 mg, 393.68 µmol, 73.2% yield, 90.0% purity, 2TFA) as colorless gum, which was used in the next step without further purification. 41 NMR (400 MHz, CD$_3$OD) δ ppm 7.82 (d, J=8.3 Hz, 2H), 7.70 (d, J=8.1 Hz, 2H), 4.36 (dd, J=4.2, 11.5 Hz, 1H), 3.57-3.42 (m, 2H), 3.16-3.06 (m, 1H), 2.96 (d, J=9.8 Hz, 2H), 2.30-2.17 (m, 4H), 2.07-1.89 (m, 2H), 0.75 (t, J=7.3 Hz, 3H); ES-LCMS m/z 287.3 [M+H]$^+$.

Step 3: N-[1-[(1R)-1-[4-(Trifluoromethyl)phenyl] propyl]-4-piperidyl]prop-2-enamide and N-[1-[(1S)-1-[4-(trifluoromethyl)phenyl]propyl]-4-piperidyl] prop-2-enamide

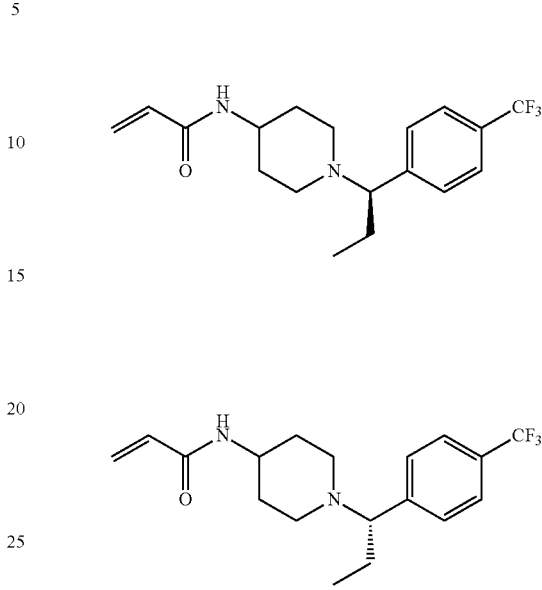

To a solution of 1-[1-[4-(trifluoromethyl)phenyl]propyl] piperidin-4-amine (225 mg, 393.68 µmol, 1 eq, 2TFA) and DIPEA (203.52 mg, 1.57 mmol, 274.28 µL, 4 eq) in DCM (10 mL) was added prop-2-enoyl chloride (35.63 mg, 393.68 µmol, 32.10 µL, 1 eq) at 0° C. The mixture was stirred at 0° C. for 1 h. The mixture was concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 40%-70%, 10 min), followed by lyophilization to yield a product which was separated by chiral SFC (column: DAICEL CHIRALCEL OD-H (250 mm*30 mm, 5 um); mobile phase: [0.1% NH$_3$H$_2$O EtOH]; B %: 10%-10%) to yield peak 1 and peak 2. Peak 1 was concentrated under reduced pressure to yield N-[1-[(1R)-1-[4-(trifluoromethyl)phenyl] propyl]-4-piperidyl]prop-2-enamide (12.89 mg, 37.29 µmol, 9.5% yield, 98.5% purity, SFC: R$_t$=2.537, ee=96.8%, [α]$^{25.8}_D$=+12.0 (MeOH, c=0.05 g/100 mL)) as a white solid. $^1$H NMR (400 MHz, CDCl$_3$) δ ppm 7.62 (d, J=7.3 Hz, 2H), 7.44 (d, J=7.3 Hz, 2H), 6.24 (dd, J=1.3, 17.0 Hz, 1H), 6.08-5.98 (m, 1H), 5.62 (dd, J=1.1, 10.4 Hz, 1H), 5.56 (br s, 1H), 3.87-3.85 (m, 1H), 3.47-3.45 (m, 1H), 3.23-3.20 (m, 1H), 2.92-2.90 (m, 1H), 2.28-2.25 (m, 1H), 2.16-1.90 (m, 4H), 1.87-1.72 (m, 1H), 1.87-1.67 (m, 1H), 1.66-1.62 (m, 1H), 1.47-1.44 (m, 1H), 0.72 (t, J=7.3 Hz, 3H); ES-LCMS m/z 341.1 [M+H]$^+$. Peak 2 was concentrated under reduced pressure to yield N-[1-[(1S)-1-[4-(trifluoromethyl)phenyl] propyl]-4-piperidyl]prop-2-enamide (15.90 mg, 46.26 µmol, 11.8% yield, 99.0% purity, SFC: R$_t$=2.657, ee=96.3%, [α]$^{25.8}_D$=−6.52 (MeOH, c=0.046 g/100 mL)) as a white solid. $^1$H NMR (400 MHz, CDCl$_3$) δ ppm 7.59 (d, J=7.8 Hz, 2H), 7.39 (d, J=7.6 Hz, 2H), 6.24 (dd, J=1.2, 16.9 Hz, 1H), 6.11-5.92 (m, 1H), 5.61 (dd, J=1.2, 10.3 Hz, 1H), 5.49 (br s, 1H), 3.90-3.75 (m, 1H), 3.39-3.34 (m, 1H), 3.12-3.09 (m, 1H), 2.83-2.79 (m, 1H), 2.21-2.18 (m, 1H), 2.13-1.89 (m, 4H), 1.85-1.82 (m, 1H), 1.69-1.63 (m, 1H), 1.59-1.41 (m, 1H), 0.71 (t, J=7.3 Hz, 3H); ES-LCMS m/z 341.1 [M+H]$^+$.

I-234

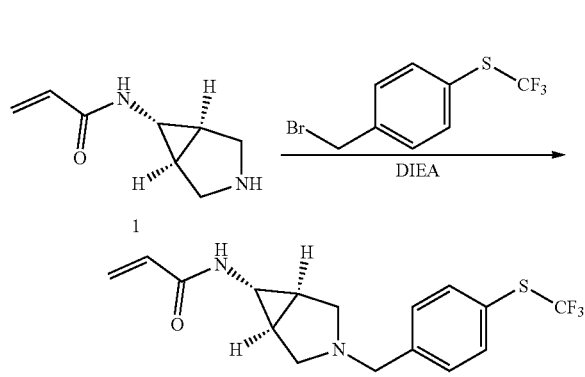

Step 1: N-[(1R,5S)-3-[[4-(Trifluoromethylsulfanyl)phenyl]methyl]-3-azabicyclo[3.1.0]hexan-6-yl]prop-2-enamide

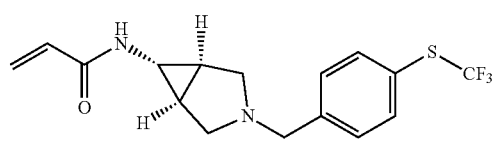 [SMILES: C=CC(=O)N[C@H]1[C@@H]2CN(Cc3ccc(SC(F)(F)F)cc3)C[C@@H]21]

To a solution of N-[(1R,5S)-3-azabicyclo[3.1.0]hexan-6-yl]prop-2-enamide (100 mg, 530.07 μmol, 1.2 eq, HCl) in DCM (5 mL) was added DIEA (171.27 mg, 1.33 mmol, 230.82 μL, 3 eq) and 1-(bromomethyl)-4-(trifluoromethylsulfanyl)benzene (119.75 mg, 441.73 μmol, 1 eq). The mixture was stirred at 25° C. for 16 h. The reaction mixture were concentrated under reduced pressure to yield a residue which was purified by preparative HPLC (column: Agela DuraShell C18 150*25 mm*5 μm; mobile phase: [water (0.05% NH$_3$H$_2$O+10 mM NH$_4$HCO$_3$)-ACN]; B %: 44%-74%, 10 min), followed by lyophilization to yield N-[(1R,5S)-3-[[4-(trifluoromethylsulfanyl)phenyl]methyl]-3-azabicyclo[3.1.0]hexan-6-yl]prop-2-enamide (40 mg, 116.83 μmol, 26.4% yield, 100.0% purity) as a white solid. $^1$H NMR (500 MHz, CD$_3$OD) δ ppm 1.58 (s, 2H) 2.45 (d, J=8.39 Hz, 2H) 3.05-3.12 (m, 3H) 3.64 (s, 2H) 5.62 (dd, J=9.61, 2.29 Hz, 1H) 6.11-6.24 (m, 2H) 7.43 (d, J=8.09 Hz, 2H) 7.62 (d, J=8.09 Hz, 2H); ES-LCMS m/z 343.1 [M+H]$^+$.

I-238 & I-239

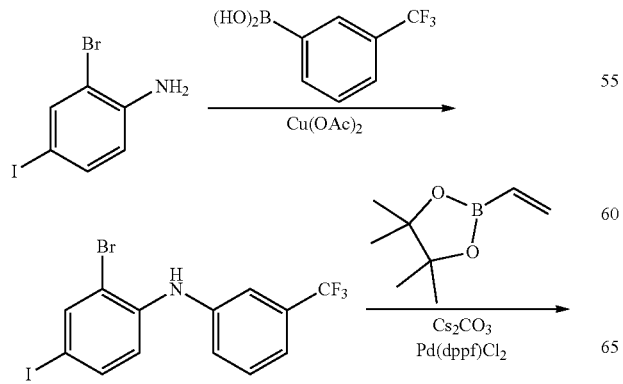

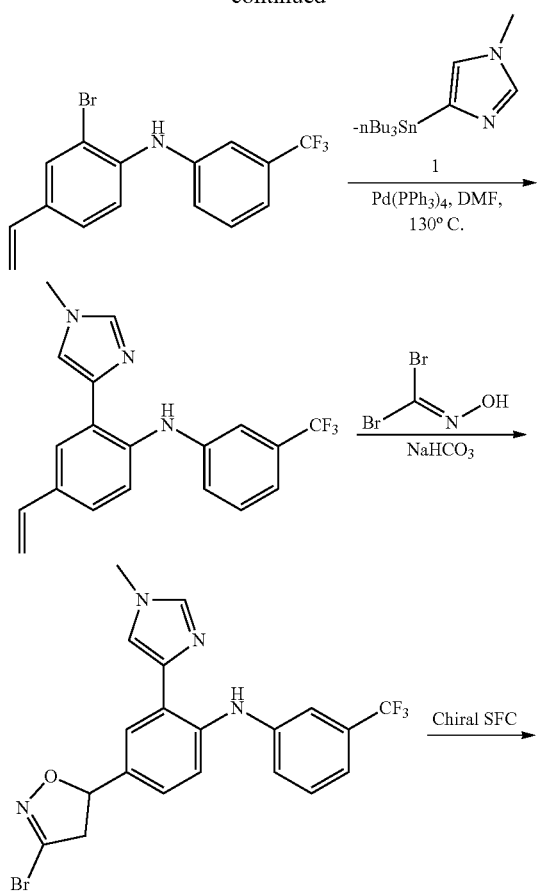

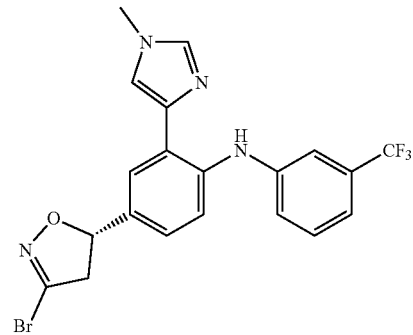

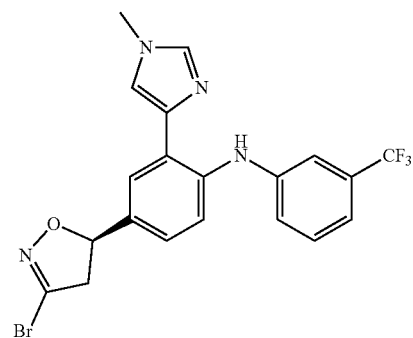 [SMILES: Cn1cnc(-c2cc([C@H]3CC(Br)=NO3)ccc2Nc2cccc(C(F)(F)F)c2)c1]

Step 1: 2-Bromo-4-iodo-N-[3-(trifluoromethyl)phenyl]aniline

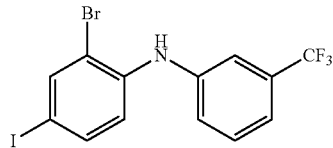 [SMILES: FC(F)(F)c1cccc(Nc2ccc(I)cc2Br)c1]

To a stirred solution of 2-bromo-4-iodo-aniline (2 g, 6.71 mmol, 1 eq) and [3-(trifluoromethyl)phenyl]boronic acid (1.28 g, 6.71 mmol, 1 eq) in DCM (40 mL) was added DIEA (2.60 g, 20.13 mmol, 3.51 mL, 3 eq) and $Cu(OAc)_2$ (2.44 g, 13.42 mmol, 2 eq). The reaction mixture was stirred at 25° C. for 24 h under $O_2$ (15 Psi). The reaction mixture was diluted with $H_2O$ (30 mL) and extracted with DCM (50 mL×3). The combined organic layers were washed with brine (50 mL), dried over $Na_2SO_4$, filtered and concentrated under reduced pressure to yield a residue which was purified by flash silica gel chromatography (from PE/EtOAc=100/1 to 10/1, TLC: PE/EtOAc=10/1, $R_f$=0.47) to yield 2-bromo-4-iodo-N-[3-(trifluoromethyl)phenyl]aniline (1.4 g, 3.07 mmol, 45.8% yield, 97.0% purity) as a red solid. $^1$H NMR (500 MHz, $CDCl_3$) δ ppm 7.86 (d, J=2.0 Hz, 1H), 7.49 (dd, J=1.9, 8.6 Hz, 1H), 7.46-7.40 (m, 1H), 7.36 (s, 1H), 7.29 (d, J=7.8 Hz, 2H), 7.01 (d, J=8.7 Hz, 1H), 6.15 (s, 1H); ES-LCMS m/z 441.9, 443.9 $[M+H]^+$.

Step 2: 2-Bromo-N-[3-(trifluoromethyl)phenyl]-4-vinyl-aniline

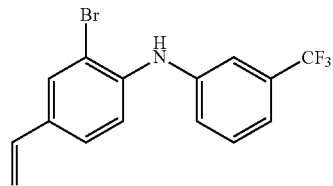 [SMILES: C=Cc1ccc(Nc2cccc(C(F)(F)F)c2)c(Br)c1]

To a stirred solution of 2-bromo-4-iodo-N-[3-(trifluoromethyl)phenyl]aniline (1.35 g, 2.96 mmol, 1 eq) and 4,4,5,5-tetramethyl-2-vinyl-1,3,2-dioxaborolane (456.28 mg, 2.96 mmol, 502.51 μL, 1 eq) in 1,4-dioxane (45 mL) and $H_2O$ (15 mL) was added $Cs_2CO_3$ (1.93 g, 5.93 mmol, 2 eq) and $Pd(dppf)Cl_2$ (216.78 mg, 296.26 μmol, 0.1 eq). The reaction mixture was bubbled with $N_2$ for 3 times and stirred under $N_2$ atmosphere at 100° C. for 3 h. The reaction mixture was diluted with $H_2O$ (30 mL) and extracted with EtOAc (60 mL×3). The combined organic layers were washed with brine (50 mL), dried over $Na_2SO_4$, filtered and concentrated under reduced pressure to yield a residue which was purified by flash silica gel chromatography (from PE/EtOAc=100/1 to 10/1, TLC: PE/EtOAc=1/1, $R_f$=0.45) to yield 2-bromo-N-[3-(trifluoromethyl)phenyl]-4-vinyl-aniline (600 mg, 1.58 mmol, 53.3% yield, 90.0% purity) as colorless oil. $^1$H NMR (500 MHz, $CDCl_3$) δ ppm 7.64 (d, J=1.8 Hz, 1H), 7.44-7.40 (m, 1H), 7.37 (s, 1H), 7.31-7.29 (m, 1H), 7.29-7.28 (m, 1H), 7.26-7.21 (m, 2H), 6.61 (dd, J=10.8, 17.5 Hz, 1H), 6.24-6.12 (m, 1H), 5.65 (d, J=17.5 Hz, 1H), 5.20 (d, J=10.8 Hz, 1H); ES-LCMS m/z 342.1, 344.1 $[M+H]^+$.

Step 3: 2-(1-Methylimidazol-4-yl)-N-[3-(trifluoromethyl)phenyl]-4-vinyl-aniline

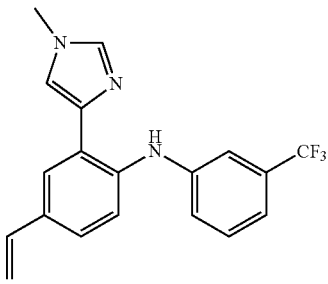 [SMILES: C=Cc1ccc(Nc2cccc(C(F)(F)F)c2)c(-c2cn(C)cn2)c1]

To a stirred solution of 2-bromo-N-[3-(trifluoromethyl)phenyl]-4-vinyl-aniline (300 mg, 789.12 μmol, 1 eq) and tributyl-(1-methylimidazol-4-yl)stannane (452.91 mg, 1.18 mmol, 1.5 eq) in DMF (8 mL) was added $Pd(PPh_3)_4$ (91.19 mg, 78.91 μmol, 0.1 eq). The reaction mixture was bubbled with $N_2$ for 3 times and stirred under $N_2$ atmosphere at 130° C. for 12 h. The reaction mixture was diluted with $H_2O$ (20 mL) and extracted with EtOAc (40 mL×3). The combined organic layers were washed with brine (40 mL), dried over $Na_2SO_4$, filtered and concentrated under reduced pressure to yield a residue which was purified by flash silica gel chromatography (from PE/EtOAc=100/1 to 2/1, TLC: PE/EtOAc=1/1, $R_f$=0.29) to yield 2-(1-methylimidazol-4-yl)-N-[3-(trifluoromethyl)phenyl]-4-vinyl-aniline (230 mg, 576.10 μmol, 73.0% yield, 86.0% purity) as red oil. $^1$H NMR (500 MHz, $CDCl_3$) δ ppm 10.09 (s, 1H), 7.53-7.50 (m, 2H), 7.44 (s, 1H), 7.40-7.37 (m, 1H), 7.37-7.32 (m, 2H), 7.29 (d, J=1.8 Hz, 1H), 7.22 (d, J=1.1 Hz, 1H), 7.12 (d, J=7.0 Hz, 1H), 6.72-6.66 (m, 1H), 5.65 (d, J=17.5 Hz, 1H), 5.14 (d, J=10.8 Hz, 1H), 3.77 (s, 3H); ES-LCMS m/z 344.3 $[M+H]^+$.

Step 4: 4-[(5S)-3-Bromo-4,5-dihydroisoxazol-5-yl]-2-(1-methylimidazol-4-yl)-N-[3-(trifluoromethyl)phenyl]aniline and 4-[(5R)-3-bromo-4,5-dihydroisoxazol-5-yl]-2-(1-methylimidazol-4-yl)-N-[3-(trifluoromethyl)phenyl]aniline

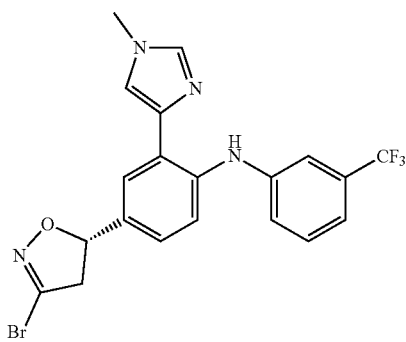

449
-continued

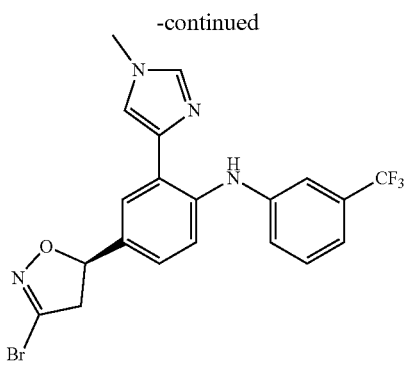

To a stirred solution of 2-(1-methylimidazol-4-yl)-N-[3-(trifluoromethyl)phenyl]-4-vinyl-aniline (190 mg, 475.91 µmol, 1 eq) in EtOAc (15 mL) was added NaHCO$_3$ (399.81 mg, 4.76 mmol, 10 eq) and dibromomethanone oxime (144.79 mg, 713.86 µmol, 1.5 eq). The reaction mixture was stirred under N$_2$ atmosphere at 25° C. for 12 h. TLC (PE/EtOAc=3/1, R$_f$=0.38) showed the starting material was consumed completely and one new spot was detected. The reaction mixture was diluted with H$_2$O (20 mL) and extracted with EtOAc (30 mL×3). The combined organic layers were washed with brine (30 mL), dried over Na$_2$SO$_4$, filtered and concentrated under reduced pressure to yield a residue which was purified by flash silica gel chromatography (from PE/EtOAc=100/1 to 3/1, TLC: PE/EtOAc=1/1, R$_f$=0.38) to yield crude product which was separated by chiral SFC (column: DAICEL CHIRALPAK AD (250 mm*30 mm, 10 µm); mobile phase: [0.1% NH$_3$H$_2$O IPA]; B %: 35%-35%) to yield peak 1 and peak 2. Peak 1 was concentrated under reduced pressure to yield a residue which was dissolved in MeCN (20 mL) and H$_2$O (40 mL) and lyophilized to yield 4-[(5S)-3-bromo-4,5-dihydroisoxazol-5-yl]-2-(1-methylimidazol-4-yl)-N-[3-(trifluoromethyl)phenyl]aniline (24.72 mg, 53.13 µmol, 11.2% yield, 100.0% purity, SFC: R$_t$=2.131, ee=100%, [α]$^{24.8}_D$=−187.755 (MeOH, c=0.049 g/100 mL)) as a white solid. $^1$H NMR (500 MHz, CDCl$_3$) δ ppm 10.16 (s, 1H), 7.52 (s, 1H), 7.47 (d, J=2.1 Hz, 1H), 7.44 (s, 1H), 7.41 (d, J=8.5 Hz, 1H), 7.39-7.33 (m, 2H), 7.24 (d, J=1.2 Hz, 1H), 7.15 (d, J=6.6 Hz, 1H), 7.12 (dd, J=2.1, 8.4 Hz, 1H), 5.68-5.62 (m, 1H), 3.81-3.74 (m, 3H), 3.59 (dd, J=10.8, 17.4 Hz, 1H), 3.27 (dd, J=9.5, 17.3 Hz, 1H); ES-LCMS m/z 465.1, 467.1 [M+H]$^+$. Peak 2 was concentrated under reduced pressure to yield a residue which was dissolved in MeCN (20 mL) and H$_2$O (40 mL) and lyophilized to yield 4-[(5R)-3-bromo-4,5-dihydroisoxazol-5-yl]-2-(1-methylimidazol-4-yl)-N-[3-(trifluoromethyl)phenyl]aniline (20.47 mg, 44.00 µmol, 9.2% yield, 100.0% purity, SFC: R$_t$=2.455, ee=98.52%, [α]$^{24.7}_D$=+152.381 (MeOH, c=0.063 g/100 mL)) as a white solid. $^1$H NMR (500 MHz, CDCl$_3$) δ ppm 10.16 (s, 1H), 7.52 (s, 1H), 7.47 (d, J=2.1 Hz, 1H), 7.44 (s, 1H), 7.41 (d, J=8.4 Hz, 1H), 7.39-7.33 (m, 2H), 7.24 (d, J=1.2 Hz, 1H), 7.15 (d, J=6.4 Hz, 1H), 7.12 (dd, J=2.2, 8.5 Hz, 1H), 5.67-5.62 (m, 1H), 3.78 (s, 3H), 3.59 (dd, J=10.8, 17.4 Hz, 1H), 3.28 (dd, J=9.5, 17.2 Hz, 1H); ES-LCMS m/z 465.1, 467.1 [M+H]$^+$.

450
I-240 & I-241

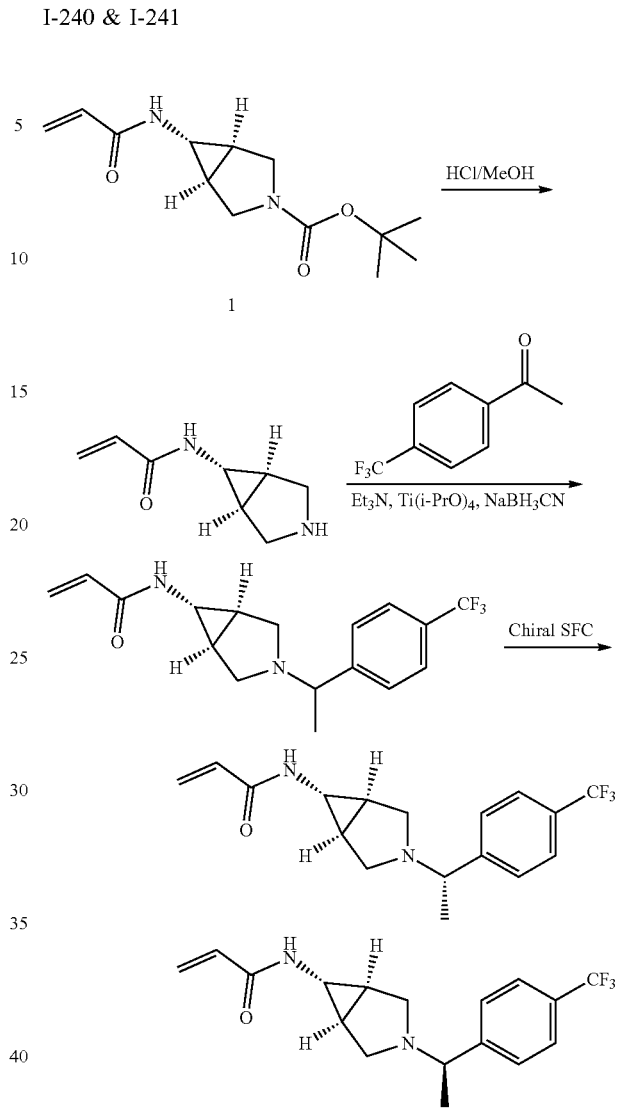

Step 1: N-[(1R,5S)-3-Azabicyclo[3.1.0]hexan-6-yl]prop-2-enamide

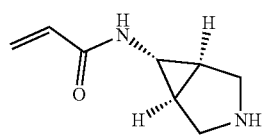

tert-Butyl (1R,5S)-6-(prop-2-enoylamino)-3-azabicyclo[3.1.0]hexane-3-carboxylate (2.7 g, 10.59 mmol, 1 eq) was added to HCl/MeOH (20 mL, 4 M) and the mixture was stirred at 20° C. for 30 min. The solvent was removed to yield N-[(1R,5S)-3-azabicyclo[3.1.0]hexan-6-yl]prop-2-enamide (2.45 g, 10.39 mmol, 98.1% yield, 80.0% purity, HCl) as brown gum, which was used in the next step without purification. $^1$H NMR (400 MHz, CD$_3$OD) δ ppm 6.27-6.12 (m, 2H), 5.66 (dd, J=2.3, 9.4 Hz, 1H), 3.53-3.49 (m, 4H), 2.73-2.70 (m, 1H), 2.02-1.98 (m, 2H).

Step 2: N-[(1R,5S)-3-[(1S)-1-[4-(Trifluoromethyl)phenyl]ethyl]-3-azabicyclo[3.1.0]hexan-6-yl]prop-2-enamide and N-[(1R,5S)-3-[(1R)-1-[4-(trifluoromethyl)phenyl]ethyl]-3-azabicyclo[3.1.0]hexan-6-yl]prop-2-enamide

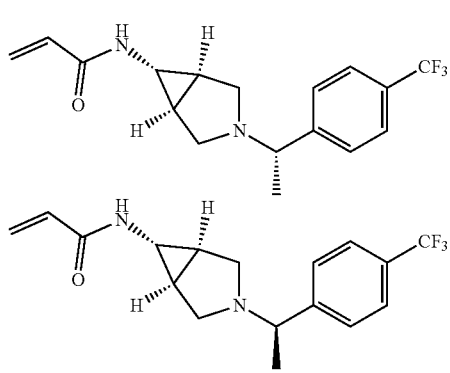

To a solution of N-[(1R,5S)-3-azabicyclo[3.1.0]hexan-6-yl]prop-2-enamide (300 mg, 1.27 mmol, 1 eq, HCl) in MeOH (10 mL) was added Et$_3$N (257.46 mg, 2.54 mmol, 354.14 µL, 2 eq) and stirred at 20° C. for 10 min. 1-[4-(Trifluoromethyl)phenyl]ethanone (287.22 mg, 1.53 mmol, 1.2 eq) and Ti(i-PrO)$_4$ (1.93 g, 6.78 mmol, 2 mL, 5.33 eq) were added and the mixture was stirred at 70° C. for 2 h. The mixture was cooled to 40° C. and NaBH$_3$CN (399.73 mg, 6.36 mmol, 5 eq) was added. The mixture was stirred at 40° C. for 16 h. TLC (MeOH/DCM=1/10, R$_f$=0.61) indicated the starting material was consumed completely and one new spot formed. The reaction mixture was quenched by aqueous NaOH (15 mL, 1M), filtered by celite and washed with MeOH (15 mL×2). The mixture was concentrated to yield a residue which was purified by preparative HPLC (column: Agela DuraShell C18 150*25 mm*5 µm; mobile phase: [water (0.05% NH$_3$H$_2$O+10 mM NH$_4$HCO$_3$)-ACN]; B %: 40%-70%, 10 min), followed by lyophilization to yield a product which was separated by SFC (column: DAICEL CHIRALPAK AD-H (250 mm*30 mm, 5 µm); mobile phase: [0.1% NH$_3$H$_2$O IPA]; B %: 15%-15%) to yield peak 1 and peak 2. Peak 1 was concentrated under reduced pressure to yield a residue which was dissolved in MeCN (10 mL) and H$_2$O (20 mL) and lyophilized to yield N-[(1R,5S)-3-[(1S)-1-[4-(trifluoromethyl)phenyl]ethyl]-3-azabicyclo[3.1.0]hexan-6-yl]prop-2-enamide (23.69 mg, 72.24 µmol, 5.7% yield, 98.9% purity, SFC: R$_t$=3.222, ee=97.88%, [α]$^{23.5}_D$=−45.16 (MeOH, c=0.031 g/100 mL)) as a white solid. $^1$H NMR (500 MHz, CDCl$_3$) δ ppm 7.53 (d, J=7.9 Hz, 2H), 7.37 (d, J=7.9 Hz, 2H), 6.27 (dd, J=1.4, 16.9 Hz, 1H), 6.01 (dd, J=10.2, 16.9 Hz, 1H), 5.61 (dd, J=1.3, 10.3 Hz, 1H), 5.50 (br s, 1H), 3.43-3.21 (m, 2H), 3.20-3.10 (m, 1H), 2.80 (d, J=9.2 Hz, 1H), 2.48 (d, J=5.3 Hz, 1H), 2.18 (d, J=6.0 Hz, 1H), 1.67-1.60 (m, 1H), 1.52-1.48 (m, 1H), 1.31-1.28 (m, 3H); ES-LCMS m/z 325.2 [M+H]$^+$. Peak 2 was concentrated under reduced pressure to yield a residue which was dissolved in MeCN (10 mL) and H$_2$O (20 mL) and lyophilized to yield N-[(1R,5S)-3-[(1R)-1-[4-(trifluoromethyl)phenyl]ethyl]-3-azabicyclo[3.1.0]hexan-6-yl]prop-2-enamide (30.04 mg, 92.62 µmol, 7.3% yield, 100.0% purity, SFC: R$_t$=3.308, ee=96.6%, [α]$^{23.5}_D$=+25.00 (MeOH, c=0.032 g/100 mL)) as a white solid. $^1$H NMR (500 MHz, CDCl$_3$) δ ppm 7.55 (d, J=6.1 Hz, 2H), 7.48-7.32 (m, 2H), 6.26 (d, J=16.6 Hz, 1H), 6.03 (dd, J=10.5, 16.7 Hz, 1H), 5.61 (d, J=10.4 Hz, 1H), 3.34-3.30 (m, 2H), 3.17-3.15 (m, 1H), 2.86-2.82 (m, 1H), 2.53-2.51 (m, 1H), 2.23-2.19 (m, 1H), 1.65-1.62 (m, 1H), 1.55-1.45 (m, 1H), 1.32-1.32 (m, 3H); ES-LCMS m/z 325.2 [M+H]$^+$.

I-249

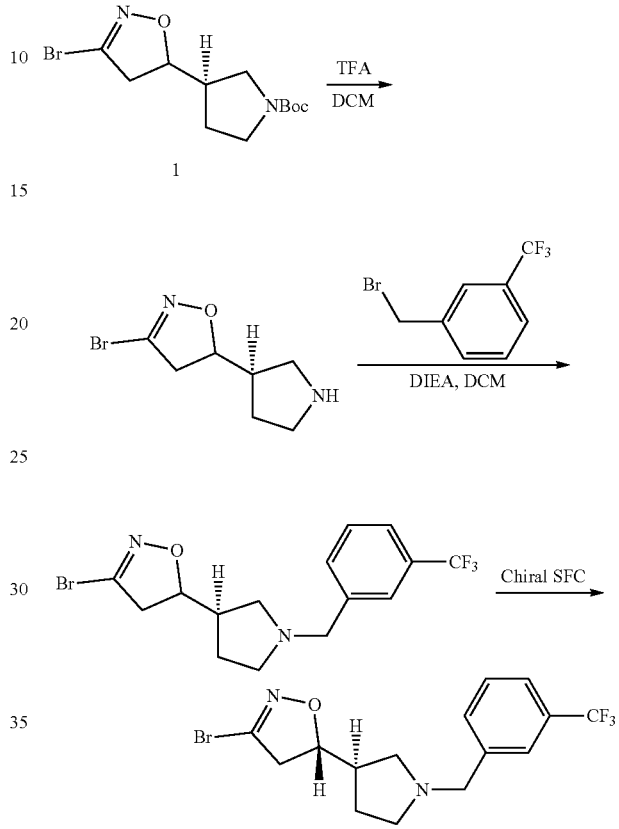

Step 1: 3-Bromo-5-[(3R)-pyrrolidin-3-yl]-4,5-dihydroisoxazole

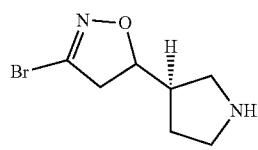 [SMILES: BrC1=NOC([C@@H]2CCNC2)C1]

To a solution of tert-butyl (3R)-3-(3-bromo-4,5-dihydroisoxazol-5-yl)pyrrolidine-1-carboxylate (600 mg, 1.69 mmol, 1 eq) in DCM (9 mL) was added TFA (3 mL). The mixture was stirred at 25° C. for 2 h. TLC (PE/EtOAc=3/1, R$_f$=0) indicated starting material was consumed completely and one new spot formed. The reaction mixture was concentrated under reduced pressure to yield 3-bromo-5-[(3R)-pyrrolidin-3-yl]-4,5-dihydroisoxazole (300 mg, 810.56 µmol, 95.8% yield, 90.0% purity, TFA) as yellow oil. $^1$H NMR (400 MHz, DMSO-d$_6$) δ ppm 4.74-4.63 (m, 1H), 3.49-3.40 (m, 1H), 3.33-3.20 (m, 2H), 3.16-3.05 (m, 2H), 2.92-2.80 (m, 1H), 2.62-2.50 (m, 1H), 2.07-1.98 (m, 1H), 1.66-1.54 (m, 1H), 1.32 (d, J=1.6 Hz, 1H).

Step 2: (5S)-3-Bromo-5-[(3R)-1-[[3-(trifluoromethyl)phenyl]methyl]pyrrolidin-3-yl]-4,5-dihydroisoxazole

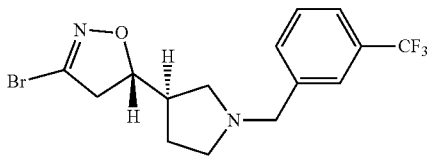 [SMILES: FC(F)(F)c1cccc(CN2CC[C@@H]([C@@H]3CC(Br)=NO3)C2)c1]

To a solution of 3-bromo-5-[(3R)-pyrrolidin-3-yl]-4,5-dihydroisoxazole (200 mg, 821.62 µmol, 1 eq) in DMF (4 mL) was added DIEA (849.49 mg, 6.57 mmol, 1.14 mL, 8 eq) and 1-(bromomethyl)-3-(trifluoromethyl)benzene (196.39 mg, 821.62 µmol, 125.09 µL, 1 eq). The mixture was stirred at 20° C. for 12 h. The reaction mixture was quenched by addition of water (50 mL) and extracted with EtOAc (50 mL×3). The combined organic layers were washed with brine (40 mL), dried over Na$_2$SO$_4$, filtered and concentrated under reduced pressure to yield a residue which was purified by preparative HPLC (Agela DuraShell C18 150*25 mm*5 um; mobile phase: [column: Agela DuraShell C18 150*25 mm*5 µm; mobile phase: [water (0.05% NH$_3$H$_2$O+10 mM NH$_4$HCO$_3$)-ACN]; B %: 48%-78%, 10 min) to yield the product which was separated by SFC (column: DAICEL CHIRALPAK IG (250 mm*30 mm, 10 um); mobile phase: [0.1% NH$_3$H$_2$O/EtOH]; B %: 15%-15%) to yield (5S)-3-bromo-5-[(3R)-1-[[3-(trifluoromethyl)phenyl]methyl]pyrrolidin-3-yl]-4,5-dihydroisoxazole (27.18 mg, 72.06 µmol, 8.8% yield, 100.0% purity, SFC: R$_t$=1.972, ee=97.5%; [α]$^{24.0}_D$+69.3 (MeOH, c=0.179 g/100 mL)) as yellow oil. $^1$H NMR (500 MHz, CDCl$_3$) δ ppm 7.58 (s, 1H), 7.55-7.48 (m, 2H), 7.47-7.41 (m, 1H), 4.67 (td, J=8.4, 10.4 Hz, 1H), 3.71-3.62 (m, 2H), 3.26 (dd, J=10.4, 17.2 Hz, 1H), 2.95 (dd, J=8.4, 17.2 Hz, 1H), 2.73-2.62 (m, 2H), 2.61-2.46 (m, 3H), 2.04-1.95 (m, 1H), 1.49 (qd, J=6.7, 13.6 Hz, 1H); ES-LCMS m/z 376.8, 378.8 [M+H]$^+$.

I-253 & I-254

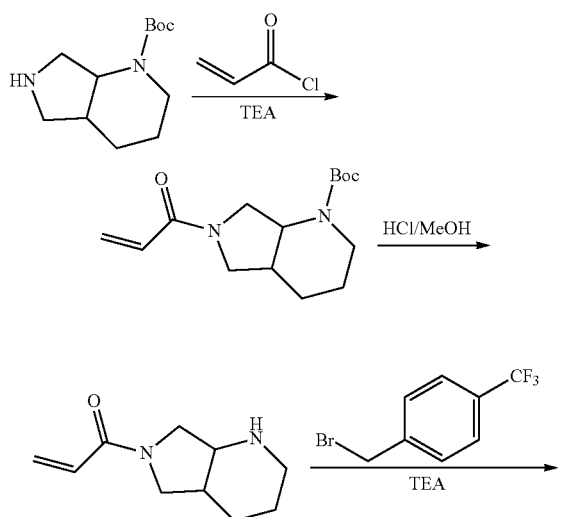

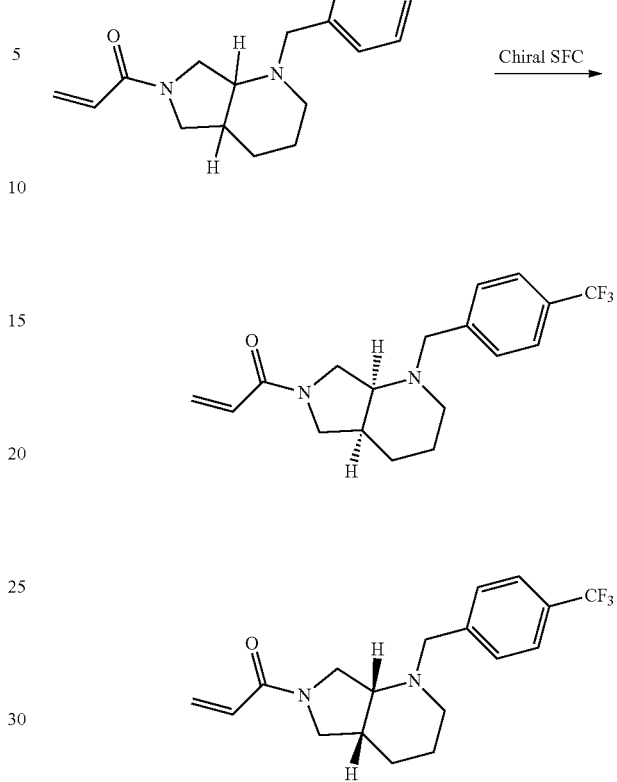

Step 1: tert-Butyl 6-prop-2-enoyl-3,4,4a,5,7,7a-hexahydro-2H-pyrrolo[3,4-b]pyridine-1-carboxylate

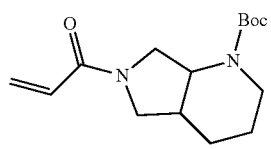 [SMILES: C=CC(=O)N1CC2CCCN(C(=O)OC(C)(C)C)C2C1]

To a solution of tert-butyl 2,3,4,4a,5,6,7,7a-octahydropyrrolo[3,4-b]pyridine-1-carboxylate (300.00 mg, 1.33 mmol, 1 eq), TEA (402.41 mg, 3.98 mmol, 553.52 µL, 3 eq) in DCM (20 mL) was added prop-2-enoyl chloride (149.97 mg, 1.66 mmol, 135.11 µL, 1.25 eq) at 0° C. under N$_2$ atmosphere. The mixture was stirred at 20° C. for 1 h. TLC (PE/EtOAc=1/1, R$_f$=0.45) indicated the starting material was consumed completely and one new spot formed. The reaction mixture was concentrated to yield a residue which was purified by flash silica gel chromatography (from PE/EtOAc=1/0 to 1/1, TLC: PE/EtOAc=1/1, R$_f$=0.45) to yield tert-butyl 6-prop-2-enoyl-3,4,4a,5,7,7a-hexahydro-2H-pyrrolo[3,4-b]pyridine-1-carboxylate (320 mg, 1.11 mmol, 83.5% yield, 97.0% purity) as colorless oil. $^1$H NMR (400 MHz, CDCl$_3$) δ ppm 6.51-6.32 (m, 2H), 5.70 (dd, J=5.1, 7.4 Hz, 1H), 4.74 (br s, 1H), 4.20-3.92 (m, 1H), 3.85-3.28 (m, 4H), 2.88-2.60 (m, 1H), 2.32-2.16 (m, 1H), 1.87-1.64 (m, 2H), 1.47 (d, J=4.3 Hz, 9H), 1.45-1.19 (m, 2H); ES-LCMS m/z 281.1 [M+H].

Step 2: 1-(1,2,3,4,4a,5,7,7a-Octahydropyrrolo[3,4-b]pyridin-6-yl)prop-2-en-1-one

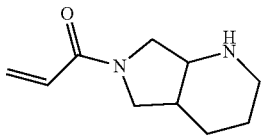

To a solution of tert-butyl 6-prop-2-enoyl-3,4,4a,5,7,7a-hexahydro-2H-pyrrolo[3,4-b]pyridine-1-carboxylate (310.00 mg, 1.07 mmol, 1 eq) in DCM (18 mL) was added HCl/MeOH (4 M, 6 mL, 22.38 eq). The mixture was stirred at 15° C. for 2 h. TLC (PE/EtOAc=3/1, $R_f$=0.00) indicated the starting material was consumed completely and one new spot formed. The reaction mixture was concentrated to yield 1-(1,2,3,4,4a,5,7,7a-octahydropyrrolo[3,4-b]pyridin-6-yl)prop-2-en-1-one (230 mg, 1.06 mmol, 98.9% yield, N/A purity, HCl) as a white solid, which was used in the next step without further purification. $^1$H NMR (500 MHz, CD$_3$OD) δ ppm 6.67-6.52 (m, 1H), 6.37-6.27 (m, 1H), 5.81 (dd, J=1.7, 10.4 Hz, 1H), 3.96-3.75 (m, 4H), 3.65-3.42 (m, 1H), 3.36-3.32 (m, 1H), 3.14-2.98 (m, 1H), 2.91-2.79 (m, 1H), 2.00-1.72 (m, 4H).

Step 3: 1-[(4aS,7aS)-1-[[4-(Trifluoromethyl)phenyl]methyl]-3,4,4a,5,7,7a-hexahydro-2H-pyrrolo[3,4-b]pyridin-6-yl]prop-2-en-1-one and 1-[(4aR,7aR)-1-[[4-(trifluoromethyl)phenyl]methyl]-3,4,4a,5,7,7a-hexahydro-2H-pyrrolo[3,4-b]pyridin-6-yl]prop-2-en-1-one

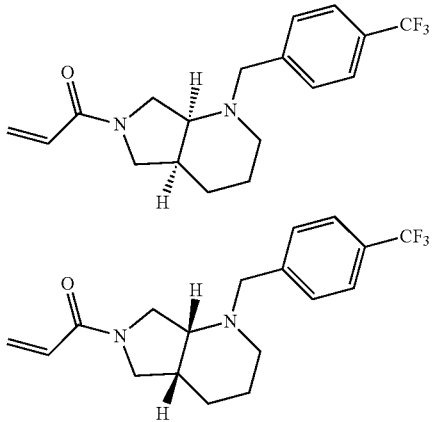

To a solution of 1-(1,2,3,4,4a,5,7,7a-octahydropyrrolo[3,4-b]pyridin-6-yl)prop-2-en-1-one (80 mg, 369.16 µmol, 1 eq, HCl) in MeCN (5 mL) was added K$_2$CO$_3$ (153.07 mg, 1.11 mmol, 3 eq) and 1-(bromomethyl)-4-(trifluoromethyl)benzene (97.07 mg, 406.08 µmol, 62.62 µL, 1.1 eq) under N$_2$ atmosphere. The mixture was stirred at 20° C. for 2 h. The reaction mixture was filtered and the filtrate was concentrated to yield a residue which was purified by flash silica gel chromatography (from PE/EtOAc=1/0 to 1/1, TLC: PE/EtOAc=1/1, $R_f$=0.46) to yield a product (100 mg). The product was further separated by chiral SFC (column: DAICEL CHIRALPAK AD-H (250 mm*30 mm, 5 µm); mobile phase: [0.1% NH$_3$·H$_2$O/EtOH]; B %: 20%-20%) to yield Peak 1 and Peak 2. Peak 1 was concentrated under reduced pressure to yield a residue which was purified by preparative HPLC (column: Welch Xtimate C18 150*25 mm*5 µm; mobile phase: [water (10 mM NH$_4$HCO$_3$)-ACN]; B %: 40%-70%, 10 min), followed by lyophilization to yield 1-[(4aS,7aS)-1-[[4-(trifluoromethyl)phenyl]methyl]-3,4,4a,5,7,7a-hexahydro-2H-pyrrolo[3,4-b]pyridin-6-yl]prop-2-en-1-one (17.26 mg, 51.01 µmol, 13.8% yield, 100.0% purity, $R_t$=2.891, ee=100%, $[α]^{18.2}_D$=−4.666 (MeOH, c=0.061 g/100 mL)) as a white solid. $^1$H NMR (500 MHz, CDCl$_3$) δ ppm 7.59-7.52 (m, 2H), 7.41 (t, J=7.3 Hz, 2H), 6.51-6.28 (m, 2H), 5.74-5.59 (m, 1H), 3.95-3.84 (m, 1H), 3.81-3.64 (m, 1H), 3.64-3.47 (m, 3H), 3.47-3.33 (m, 1H), 3.22-3.03 (m, 1H), 2.69-2.57 (m, 1H), 2.47-2.19 (m, 2H), 1.77-1.64 (m, 2H), 1.59-1.48 (m, 2H); ES-LCMS m/z 339.3 [M+H]$^+$. Peak 2 was concentrated under reduced pressure to yield a residue which was purified by preparative HPLC (column: Welch Xtimate C18 150*25 mm*5 µm; mobile phase: [water (10 mM NH$_4$HCO$_3$)-ACN]; B %: 39%-69%, 10 min), followed by lyophilization to yield 1-[(4aR,7aR)-1-[[4-(trifluoromethyl)phenyl]methyl]-3,4,4a,5,7,7a-hexahydro-2H-pyrrolo[3,4-b]pyridin-6-yl]prop-2-en-1-one (17.26 mg, 51.01 µmol, 13.8% yield, 100.0% purity, $R_t$=3.253, ee=97.58%, $[α]^{18.2}_D$=+9.152 (MeOH, c=0.055 g/100 mL)) as a white solid. $^1$H NMR (500 MHz, CDCl$_3$) δ ppm 7.59-7.51 (m, 2H), 7.41 (t, J=7.3 Hz, 2H), 6.52-6.29 (m, 2H), 5.75-5.57 (m, 1H), 3.95-3.84 (m, 1H), 3.81-3.70 (m, 1H), 3.67-3.46 (m, 3H), 3.46-3.33 (m, 1H), 3.22-3.03 (m, 1H), 2.68-2.58 (m, 1H), 2.49-2.19 (m, 2H), 1.75-1.65 (m, 2H), 1.57-1.45 (m, 2H); ES-LCMS m/z 339.3 [M+H]$^+$.

1-256

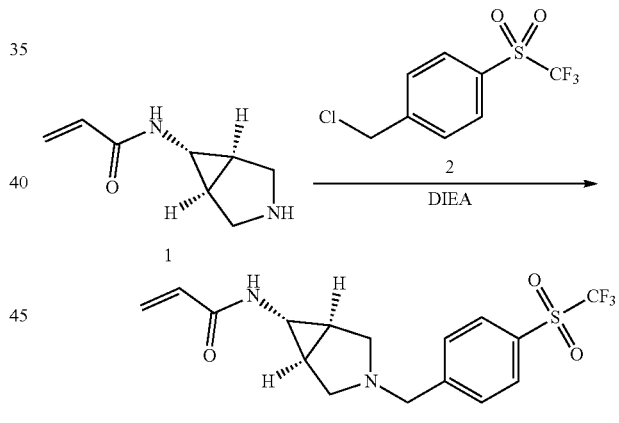

Step 1: N-[(1R,5S)-3-[[4-(Trifluoromethylsulfonyl)phenyl]methyl]-3-azabicyclo[3.1.0]hexan-6-yl]prop-2-enamide

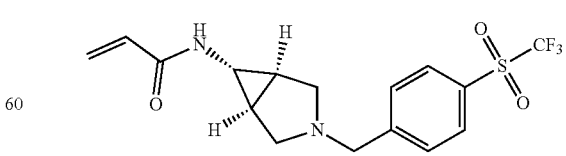

To a solution of 1-(bromomethyl)-4-(trifluoromethylsulfonyl)benzene (50 mg, 164.96 µmol, 1 eq) in DCM (5 mL) was added DIEA (63.96 mg, 494.89 mol, 86.20 µL, 3 eq) and N-[(1R,5S)-3-azabicyclo[3.1.0]hexan-6-yl]prop-2- enamide (46.68 mg, 197.96 mol, 1.2 eq, HCl). The mixture was stirred at 25° C. for 12 h. The reaction mixture were concentrated under reduced pressure to yield a residue which was purified by preparative HPLC (column: Agela DuraShell (C18 150*25 mm*5 μm; mobile phase: [water (0.04% $NH_3H_2O$+10 mM $NH_4HCO_3$)-ACN]; B %: 36%-66%, 10 min), followed by lyophilization to yield N-[(1R,5S)-3-[[4-(trifluoromethylsulfonyl)phenyl]methyl]-3-azabicyclo[3.1.0]hexan-6-yl]prop-2-enamide (25 mg, 66.78 mol, 40.4% yield, 100.0% purity) as a white solid. $^1$H NMR (500 MHz, $CD_3OD$) δ ppm 8.02 (d, J=8.2 Hz, 2H), 7.73 (d, J=8.4 Hz, 2H), 6.25-6.12 (m, 2H), 5.63 (dd, J=2.4, 9.7 Hz, 1H), 3.77 (s, 2H), 3.13 (d, J=8.9 Hz, 3H), 2.48 (d, J=8.7 Hz, 2H), 1.60 (d, J=1.1 Hz, 2H); ES-LCMS m/z 375.1 $[M+H]^+$.

I-257 & I-258

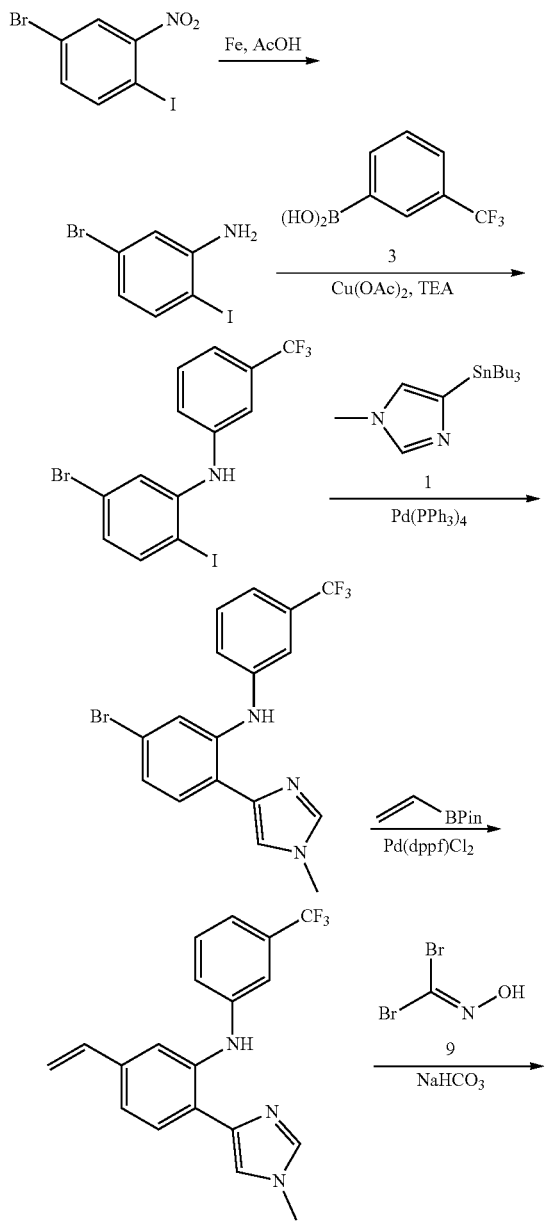

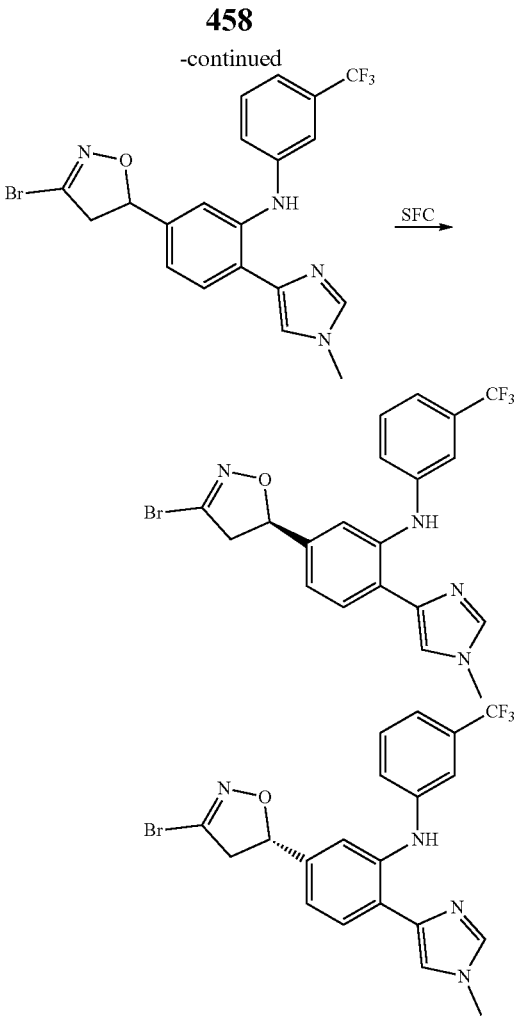

Step 1: 5-Bromo-2-iodo-aniline

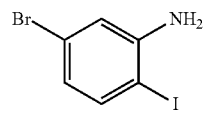

A mixture of 4-bromo-1-iodo-2-nitro-benzene (2 g, 6.10 mmol, 1 eq), $NH_4Cl$ (1.63 g, 30.50 mmol, 5 eq), Fe (1.70 g, 30.50 mmol, 5 eq) in EtOH (8 mL), THF (8 mL) and $H_2O$ (8 mL) was degassed and purged with $N_2$ for 3 times. The mixture was stirred under $N_2$ atmosphere at 70° C. for 3 h. TLC (PE/EtOAc=5/1, $R_f$=0.45) indicated starting material was consumed completely and two new spots formed. The mixture was concentrated and water (80 mL) was added. The mixture was extracted with EtOAc (50 mL×3) and the combined organic layers were washed with brine (50 mL), dried over $Na_2SO_4$, filtered and concentrated to yield a residue which was purified by flash silica gel chromatography (From PE/EtOAc=1/0 to 5/1, $R_f$=0.45) to yield 5-bromo-2-iodo-aniline (1.7 g, 5.71 mmol, 93.6% yield, 100.0% purity) as a light yellow solid. $^1$H NMR (400 MHz, DMSO-$d_6$) δ ppm 7.43 (d, J=8.2 Hz, 1H), 6.89 (d, J=2.0 Hz, 1H), 6.45 (dd, J=2.0, 8.2 Hz, 1H), 5.47 (s, 2H); ES-LCMS m/z 298.0, 300.0 $[M+H]^+$.

Step 2: 5-Bromo-2-iodo-N-[3-(trifluoromethyl)phenyl]an

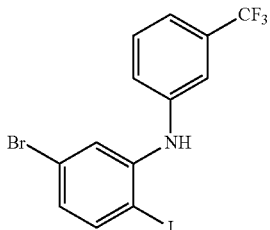

To a solution of 5-bromo-2-iodo-aniline (540 mg, 1.81 mmol, 1 eq) in DCM (8 mL) was added Cu(OAc)$_2$ (658.44 mg, 3.63 mmol, 2 eq), DIEA (702.77 mg, 5.44 mmol, 947.13 µL, 3 eq) and [3-(trifluoromethyl)phenyl]boronic acid (516.39 mg, 2.72 mmol, 1.5 eq). The mixture was stirred at 25° C. for 36 h under oxygen atmosphere (15 Psi). TLC (PE/EtOAc=5/1, R$_f$=0.71) indicated starting material was consumed completely and many new spots formed. The mixture was concentrated and water (80 mL) was added. The mixture was extracted with DCM (50 mL×3). The combined organic layers were washed with brine (50 mL), dried over Na$_2$SO$_4$, filtered and concentrated to yield a residue which was purified by flash silica gel chromatography (From PE/EtOAc=1/0 to 5/1, R$_f$=0.71) to yield 5-bromo-2-iodo-N-[3-(trifluoromethyl)phenyl]aniline (650 mg, 1.04 mmol, 57.5% yield, 70.9% purity) as red oil. $^1$H NMR (400 MHz, CDCl$_3$) δ ppm 7.64-7.61 (m, 1H), 7.48-7.42 (m, 1H), 7.35-7.29 (m, 3H), 7.27 (d, J=2.0 Hz, 1H), 6.81 (dd, J=2.2, 8.4 Hz, 1H), 5.98 (s, 1H); ES-LCMS m/z 441.7, 443.7 [M+H]$^+$.

Step 3: 5-Bromo-2-(1-methylimidazol-4-yl)-N-[3-(trifluoromethyl)phenyl]aniline

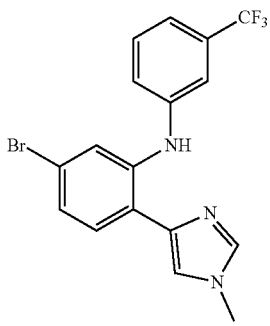 [SMILES: Cn1cnc(-c2ccc(Br)cc2Nc2cccc(C(F)(F)F)c2)c1]

To a solution of 5-bromo-2-iodo-N-[3-(trifluoromethyl)phenyl]aniline (600 mg, 962.42 µmol, 1 eq) in DMF (20 mL) were added tributyl-(1-methylimidazol-4-yl)stannane (1.07 g, 1.15 mmol, 1.2 eq) and Pd(PPh$_3$)$_4$ (111.21 mg, 96.24 µmol, 0.1 eq). The mixture was stirred under N$_2$ atmosphere at 120° C. for 12 h. The mixture was quenched by sat. aq. KF (50 mL). Water (80 mL) was added and the mixture was extracted with EtOAc (50 mL×3). The combined organic layers were washed with brine (50 mL), dried over Na$_2$SO$_4$, filtered and concentrated to yield a residue which was purified by flash silica gel chromatography (from PE/EtOAc=1/0 to 5/1, R$_f$=0.39) to yield 5-bromo-2-(1-methylimidazol-4-yl)-N-[3-(trifluoromethyl)phenyl]aniline (350 mg, 836.56 µmol, 86.9% yield, 94.7% purity) as red oil. $^1$H NMR (400 MHz, CDCl$_3$) δ ppm 10.19 (s, 1H), 8.00 (s, 1H), 7.49-7.44 (m, 2H), 7.41-7.34 (m, 3H), 7.29 (d, J=8.3 Hz, 1H), 7.18-7.13 (m, 2H), 6.94 (dd, J=2.0, 8.1 Hz, 1H), 3.73 (s, 3H); ES-LCMS m/z 396.1, 398.1 [M+H]$^+$.

Step 4: 2-(1-Methylimidazol-4-yl)-N-[3-(trifluoromethyl)phenyl]-5-vinyl-aniline

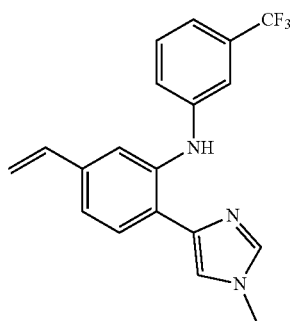 [SMILES: C=Cc1ccc(-c2cn(C)cn2)c(Nc2cccc(C(F)(F)F)c2)c1]

To a solution of 5-bromo-2-(1-methylimidazol-4-yl)-N-[3-(trifluoromethyl)phenyl]aniline (350 mg, 836.56 µmol, 1 eq) in 1,4-dioxane (12 mL) and H$_2$O (4 mL) was added 4,4,5,5-tetramethyl-2-vinyl-1,3,2-dioxaborolane (193.26 mg, 1.25 mmol, 212.85 µL, 1.5 eq) Cs$_2$CO$_3$ (545.14 mg, 1.67 mmol, 2 eq) and Pd(dppf)Cl$_2$ (48.97 mg, 66.93 µmol, 0.08 eq). The mixture was stirred under N$_2$ atmosphere at 100° C. for 12 h. The mixture was concentrated and water (80 mL) was added. The mixture was extracted with EtOAc (50 mL×3). The combined organic layers were washed with brine (50 mL), dried over Na$_2$SO$_4$, filtered and concentrated to yield a residue which was purified by flash silica gel chromatography (from PE/EtOAc=1/0 to 5/1, R$_f$=0.33) to yield 2-(1-methylimidazol-4-yl)-N-[3-(trifluoromethyl)phenyl]-5-vinyl-aniline (250 mg, 632.02 µmol, 75.6% yield, 86.8% purity) as red oil. $^1$H NMR (400 MHz, CDCl$_3$) δ ppm 10.03 (s, 1H), 7.48 (s, 1H), 7.45-7.40 (m, 3H), 7.39-7.29 (m, 2H), 7.15 (d, J=1.2 Hz, 1H), 7.10 (d, J=7.3 Hz, 1H), 6.95 (dd, J=1.5, 8.1 Hz, 1H), 6.64 (dd, J=10.8, 17.6 Hz, 1H), 5.68 (d, J=17.6 Hz, 1H), 5.20 (d, J=10.8 Hz, 1H), 3.73 (s, 3H); ES-LCMS m/z 344.6 [M+H]$^+$.

Step 5: 5-[(5R)-3-Bromo-4,5-dihydroisoxazol-5-yl]-2-(1-methylimidazol-4-yl)-N-[3-(trifluoromethyl)phenyl]aniline and 5-[(5S)-3-bromo-4,5-dihydroisoxazol-5-yl]-2-(1-methylimidazol-4-yl)-N-[3-(trifluoromethyl)phenyl]aniline

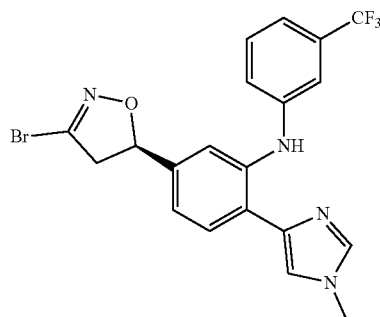

461

-continued

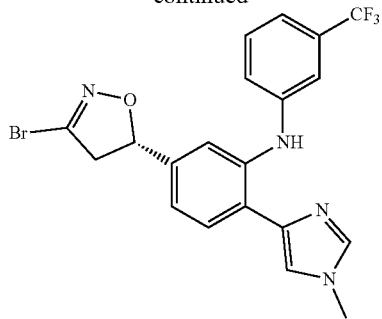

To a solution of 2-(1-methylimidazol-4-yl)-N-[3-(trifluoromethyl)phenyl]-5-vinyl-aniline (250 mg, 632.02 μmol, 1 eq) in EtOAc (15 mL) was added NaHCO$_3$ (530.96 mg, 6.32 mmol, 10 eq) and dibromomethanone oxime (166.65 mg, 821.62 μmol, 1.3 eq). The mixture was stirred under N$_2$ atmosphere at 25° C. for 14 h. The mixture was concentrated and water (80 mL) was added. The mixture was extracted with EtOAc (50 mL×3). The combined organic layers were washed with brine (50 mL), dried over Na$_2$SO$_4$, filtered and concentrated to yield a residue which was purified by flash silica gel chromatography (from PE/EtOAc=1/0 to 5/1, R$_f$=0.34) to yield peak 1 and peak 2. Peak 1 was concentrated under reduced pressure to yield a residue which was purified by preparative HPLC (column: Agela DuraShell C18 150*25 mm*5um; mobile phase: [water (0.04% NH$_3$H$_2$O+10 mM NH$_4$HCO$_3$)-ACN]; B %: 55%-85%, 10 min). The desired fraction was concentrated under reduced pressure to yield a residue which was dissolved in MeCN (20 mL) and H$_2$O (40 mL) and lyophilized to yield 5-[(5R)-3-bromo-4,5-dihydroisoxazol-5-yl]-2-(1-methylimidazol-4-yl)-N-[3-(trifluoromethyl)phenyl]aniline (40.38 mg, 86.79 μmol, 13.7% yield, 100.0% purity, SFC: R$_t$=2.420, ee=99.97%, [α]$^{24.9}_D$=+140 (MeOH, c=0.020 g/100 mL)) as a light blue solid. $^1$H NMR (400 MHz, CDCl$_3$) δ ppm 10.15 (s, 1H), 7.50-7.45 (m, 2H), 7.39 (s, 1H), 7.38-7.31 (m, 3H), 7.17 (d, J=1.2 Hz, 1H), 7.13 (d, J=6.1 Hz, 1H), 6.84 (dd, J=1.3, 7.9 Hz, 1H), 5.58 (dd, J=9.0, 10.8 Hz, 1H), 3.74 (s, 3H), 3.57 (dd, J=10.9, 17.2 Hz, 1H), 3.19 (dd, J=9.0, 17.4 Hz, 1H); ES-LCMS m/z 465, 467.0 [M+H]$^+$.

Peak 1 was concentrated under reduced pressure to yield a residue which was purified by preparative HPLC (column: Agela DuraShell C18 150*25 mm*5um; mobile phase: [water (0.04% NH$_3$H$_2$O+10 mM NH$_4$HCO$_3$)-ACN]; B %: 55%-85%, 10 min). The desired fraction was concentrated under reduced pressure to yield a residue which was dissolved in MeCN (20 mL) and H$_2$O (40 mL) and lyophilized to yield 5-[(5S)-3-bromo-4,5-dihydroisoxazol-5-yl]-2-(1-methylimidazol-4-yl)-N-[3-(trifluoromethyl)phenyl]aniline (18.82 mg, 40.45 μmol, 6.4% yield, 100.0% purity, SFC: R$_t$=3.024, ee=99.84%, [α]$^{24.9}_D$=−180 (MeOH, c=0.020 g/100 mL)) as a light blue solid. $^1$H NMR (400 MHz, CDCl$_3$) δ ppm 10.15 (s, 1H), 7.51-7.44 (m, 2H), 7.39 (s, 1H), 7.38-7.30 (m, 3H), 7.17 (d, J=1.0 Hz, 1H), 7.13 (d, J=6.1 Hz, 1H), 6.84 (dd, J=1.3, 7.9 Hz, 1H), 5.58 (dd, J=9.2, 10.6 Hz, 1H), 3.74 (s, 3H), 3.57 (dd, J=10.9, 17.2 Hz, 1H), 3.19 (dd, J=9.0, 17.4 Hz, 1H); ES-LCMS m/z 464.8, 466.8 [M+H]$^+$.

462

I-262 & I-264

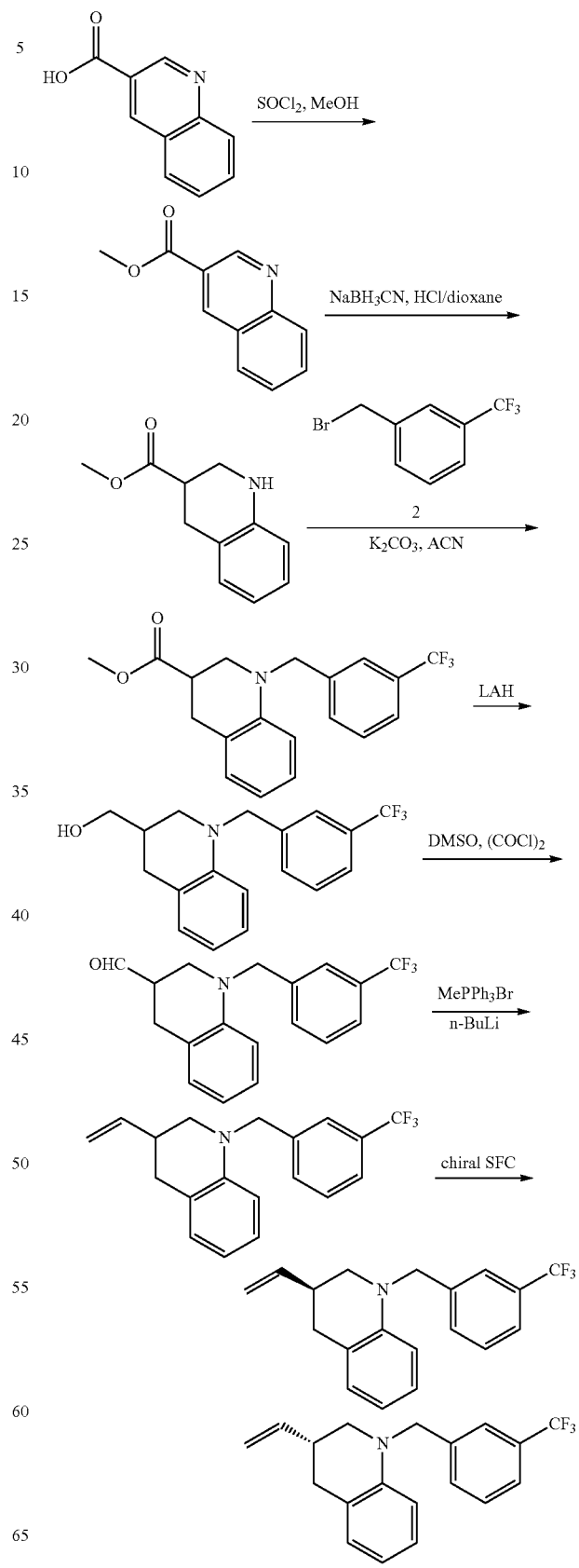

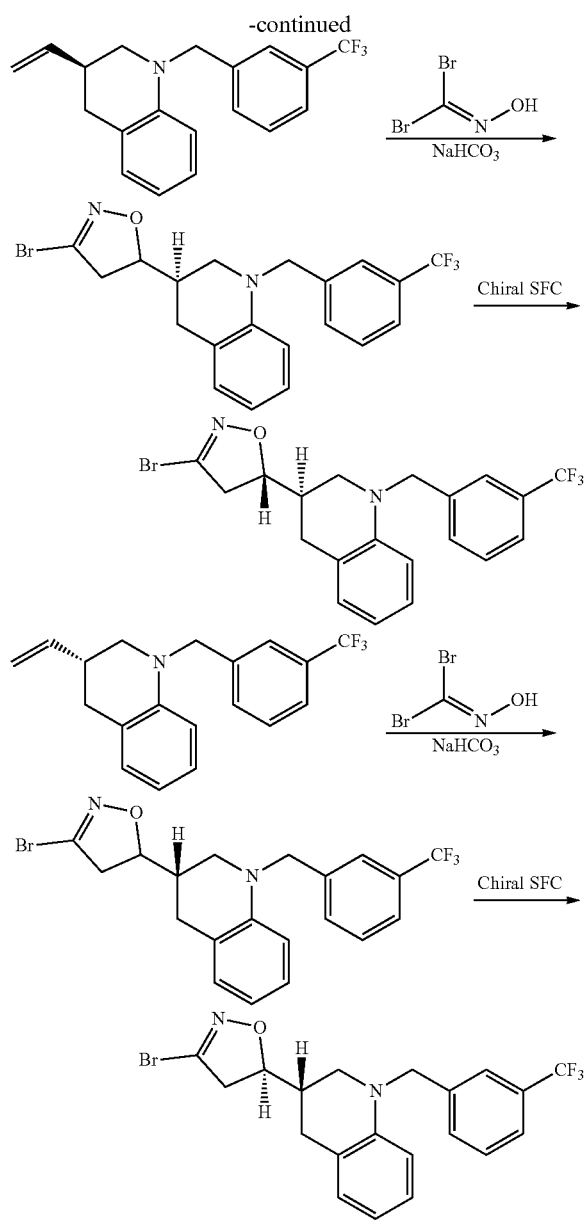

Step 1: Methyl quinoline-3-carboxylate

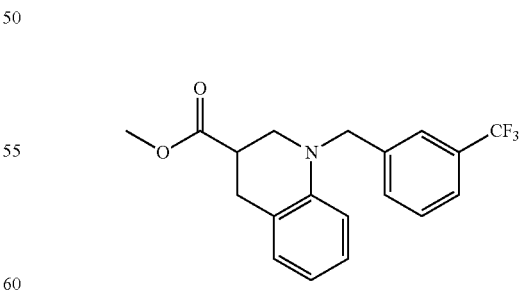

To a solution of quinoline-3-carboxylic acid (8.80 g, 50.82 mmol, 1 eq) in MeOH (150 mL) was added $SOCl_2$ (30.23 g, 254.09 mmol, 18.43 mL, 5 eq) dropwise at 0° C. The mixture was stirred at 80° C. for 2 h. TLC (PE/EtOAc=3/1, $R_f$=0.50) showed starting material was consumed and one major new spot was detected. The reaction mixture was concentrated, diluted with $H_2O$ (150 mL) and extracted with EtOAc (60 mL×3). The combine organic layers were washed with brine (80 mL), dried over anhydrous $Na_2SO_4$, filtered and concentrated to yield methyl quinoline-3-carboxylate (9.5 g, 48.21 mmol, 94.8% yield, 95.0% purity) as a yellow solid. $^1H$ NMR (400 MHz, DMSO-$d_6$) δ ppm 9.30 (d, J=2.0 Hz, 1H), 9.00 (d, J=1.5 Hz, 1H), 8.20 (d, J=8.0 Hz, 1H), 8.10 (d, J=8.5 Hz, 1H), 7.92 (ddd, J=1.5, 7.0, 8.5 Hz, 1H), 7.75-7.68 (m, 1H), 3.95 (s, 3H); ES-LCMS m/z 188.0 $[M+H]^+$.

Step 2: Methyl 1,2,3,4-tetrahydroquinoline-3-carboxylate

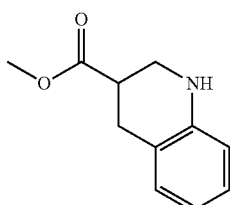

To a solution of methyl quinoline-3-carboxylate (8.8 g, 44.66 mmol, 1 eq) in THF (170 mL) and MeOH (85 mL) was added $NaBH_3CN$ (11.87 g, 188.91 mmol, 4.23 eq) and 2,6-dibromo-4-[3-(3,5-dibromo-4-hydroxy-2-methyl-phenyl)-1,1-di oxo-2,1benzoxathiol-3-yl]-3-methyl-phenol (4.92 mg, 7.05 μmol, 1.58e-4 eq). The mixture acquired a bluish color (alkaline) at 20° C. Then to the mixture was added HCl/dioxane (4 M, 300 mL, 26.87 eq) dropwise slowly to make the mixture obtained yellow color (acid). The mixture was stirred at 80° C. for 12 h. The reaction mixture was concentrated, diluted with $H_2O$ (100 mL) and extracted with EtOAc (150 mL×3). The combine organic layers were washed with brine (120 mL), dried over anhydrous $Na_2SO_4$, filtered and concentrated to yield methyl 1,2,3,4-tetrahydroquinoline-3-carboxylate (9 g, 42.36 mmol, 94.8% yield, 90.0% purity) as yellow oil. $^1H$ NMR (400 MHz, $CDCl_3$) δ ppm 7.05-6.97 (m, 2H), 6.70-6.63 (m, 1H), 6.52 (dd, J=1.0, 8.4 Hz, 1H), 4.00-3.84 (m, 1H), 3.74 (s, 3H), 3.56 (dd, J=3.5, 11.5 Hz, 1H), 3.38 (dd, J=9.5, 11.0 Hz, 1H), 3.06-3.00 (m, 2H), 2.98-2.89 (m, 1H); ES-LCMS m/z 192.0 $[M+H]^+$.

Step 3: Methyl 1-[[3-(trifluoromethyl)phenyl]methyl]-3,4-dihydro-2H-quinoline-3-carboxylate To a solution of methyl 1,2,3,4-tetrahydroquinoline-3-carboxylate (8.8 g, 41.42 mmol, 1 eq) in MeCN (150 mL) was added $K_2CO_3$ (17.17 g, 124.25 mmol, 3 eq) and 1-(bromomethyl)-3-(trifluoromethyl)benzene (19.80 g, 82.83 mmol, 12.61 mL, 2 eq). The mixture was stirred at 80° C. for 12 h. TLC (PE/EtOAc=3/1, $R_f$=0.50) showed the starting material was consumed completely and one major new spot was detected. The mixture was diluted with H₂O (150 mL) and extracted with EtOAc (150 mL×3). The combined organic layers were washed with brine (20 mL), dried over anhydrous Na₂SO₄, filtered and concentrated to yield methyl 1-[[3-(trifluoromethyl)phenyl]methyl]-3,4-dihydro-2H-quinoline-3-carboxylate (14 g, crude) as a yellow solid. ¹H NMR (400 MHz, DMSO-d₆) δ ppm 7.63-7.52 (m, 4H), 6.99 (d, J=7.5 Hz, 1H), 6.90 (t, J=7.0 Hz, 1H), 6.54 (t, J=7.5 Hz, 1H), 6.44 (d, J=8.5 Hz, 1H), 4.64-4.51 (m, 2H), 3.62 (s, 3H), 3.58-3.45 (m, 2H), 3.12-3.04 (m, 1H), 3.03-2.93 (m, 2H).

Step 4: [1-[[3-(Trifluoromethyl)phenyl]methyl]-3,4-dihydro-2H-quinolin-3-yl]methanol

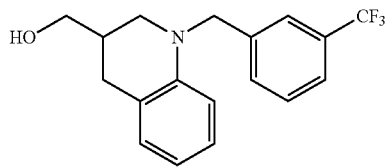 [SMILES: OCC1Cc2ccccc2N(Cc2cccc(C(F)(F)F)c2)C1]

To a solution of methyl 1-[[3-(trifluoromethyl)phenyl]methyl]-3,4-dihydro-2H-quinoline-3-carboxylate (14 g, 40.07 mmol, 1 eq) in THF (250 mL) was added LiAlH₄ (6.08 g, 160.30 mmol, 4 eq). The mixture was stirred at 20° C. for 2 h. TLC (PE/EtOAc=3/1, R_f=0.35) showed starting material was consumed completely and one major new spot was detected. H₂O (6 mL), 10% NaOH solution (6 mL) and H₂O (6 mL) were added slowly to quench the reaction. Na₂SO₄ was added and the mixture was filtered. The filtrate was concentrated to yield a residue which was purified by flash silica gel chromatography (from pure PE to PE/EtOAc=5/1, TLC: PE/EtOAc=3/1, R_f=0.45) to yield [1-[[3-(trifluoromethyl)phenyl]methyl]-3,4-dihydro-2H-quinolin-3-yl]methanol (11.5 g, 28.63 mmol, 71.5% yield, 80.0% purity) as a yellow solid. ¹H NMR (400 MHz, DMSO-d₆) δ ppm 7.67-7.48 (m, 4H), 6.92 (d, J=7.5 Hz, 1H), 6.90-6.83 (m, 1H), 6.49 (t, J=7.0 Hz, 1H), 6.43 (d, J=8.5 Hz, 1H), 4.66 (t, J=5.5 Hz, 1H), 4.61-4.52 (m, 2H), 3.51-3.34 (m, 3H), 3.13 (dd, J=9.0, 11.0 Hz, 1H), 2.75 (dd, J=3.5, 16.0 Hz, 1H), 2.08 (s, 1H); ES-LCMS m/z 322.3 [M+H]⁺.

Step 5: 1-[[3-(Trifluoromethyl)phenyl]methyl]-3,4-dihydro-2H-quinoline-3-carbaldehyde

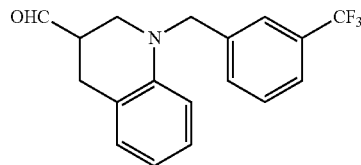 [SMILES: O=CC1Cc2ccccc2N(Cc2cccc(C(F)(F)F)c2)C1]

To a solution of oxalyl dichloride (7.90 g, 62.24 mmol, 5.45 mL, 5 eq) in DCM (150 mL) was added DMSO (9.73 g, 124.48 mmol, 9.73 mL, 10 eq) in DCM (20 mL) dropwise at −78° C. and stirred under N₂ atmosphere at −78° C. for 0.5 h. To the mixture was added [1-[[3-(trifluoromethyl)phenyl]methyl]-3,4-dihydro-2H-quinolin-3-yl]methanol (5 g, 12.45 mmol, 1 eq) in DCM (20 mL) dropwise at −78° C. The reaction mixture was stirred under N₂ atmosphere at −78° C. for 0.5 h. To the mixture was added DIEA (16.09 g, 124.48 mmol, 21.68 mL, 10 eq) in DCM (10 mL) dropwise at −78° C. The mixture was stirred under N₂ atmosphere at 20° C. for 11 h. TLC (PE/EtOAc=3/1, R_f=0.60) showed starting material was consumed and one major new spot was detected. The mixture was diluted with H₂O (150 mL) and extracted with DCM (150 mL×3). The combine organic layers were washed with brine (20 mL), dried over anhydrous Na₂SO₄, filtered and concentrated to yield 1-[[3-(trifluoromethyl)phenyl]methyl]-3,4-dihydro-2H-quinoline-3-carbaldehyde (10 g, crude) as yellow oil, which was used in the next step without further purification. ¹H NMR (500 MHz, CDCl₃) δ ppm 9.74 (s, 1H), 7.50-7.44 (m, 3H), 7.37-7.34 (m, 1H), 7.03 (d, J=7.5 Hz, 1H), 6.98-6.93 (m, 1H), 6.65-6.60 (m, 1H), 6.47-6.42 (m, 1H), 4.51-4.48 (m, 2H), 3.77-3.72 (m, 1H), 3.41 (t, J=4.0 Hz, 1H), 3.07-3.00 (m, 3H); ES-LCMS m/z 320.1 [M+H]⁺.

Step 6: (3R)-1-[[3-(Trifluoromethyl)phenyl]methyl]-3-vinyl-3,4-dihydro-2H-quinoline and (3S)-1-[[3-(trifluoromethyl)phenyl]methyl]-3-vinyl-3,4-dihydro-2H-quinoline

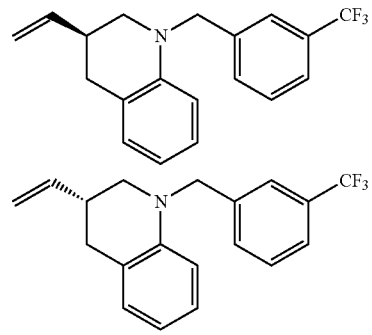

To a solution of methyl(triphenyl)phosphonium;bromide (16.7 g, 46.75 mmol, 1.49 eq) in THF (30 mL) was added n-BuLi (2.5 M, 18 mL, 1.44 eq). The mixture was stirred under N₂ atmosphere at −78° C. for 0.5 h. To the mixture was added 1-[[3-(trifluoromethyl)phenyl]methyl]-3,4-dihydro-2H-quinoline-3-carbaldehyde (10 g, 31.32 mmol, 1 eq) in THF (2 mL). The mixture was stirred under N₂ atmosphere at 20° C. for 4.5 h. TLC (PE/EtOAc=5/1, R_f=0.50) showed starting material was consumed completely and one major new spot was detected. The mixture was quenched with sat. aq. NH₄Cl (200 mL) and extracted with EtOAc (200 mL×3). The combine organic layers were washed with brine (80 mL), dried over anhydrous Na₂SO₄, filtered and concentrated to yield a residue which was purified by flash silica gel chromatography (from pure PE to PE/EtOAc=50/1, TLC: PE/EtOAc=5/1, R_f=0.50) to yield a residue which was purified by preparative HPLC (HCl condition; column: Agela ASB 150*25 mm*5 μm; mobile phase: [water (0.05% HCl)-ACN]; B %: 65%-95%, 8 min) and lyophilized to yield a residue which was separated by preparative SFC (column: DAICEL CHIRALCEL OD-H (250 mm*30 mm, 5 μm); mobile phase: [0.1% NH₃H₂O EtOH]; B %: 10%-10%, min) to yield Peak 1 and Peak 2. Peak 1 was concentrated under reduced pressure to yield a residue which was dissolved in MeCN (20 mL) and H₂O (40 mL) and lyophilized to yield (3R)-1-[[3-(trifluoromethyl)phenyl]methyl]-3-vinyl-3,4-dihydro-2H-quinoline (410 mg, 1.29 mmol, 50.6% yield, 100.0% purity, SFC: R_f=2.448, ee=77.48%, [α]²²·⁷_D=−8.810 (MeOH, c=0.048 g/100 mL)

as a white solid. $^1$H NMR (400 MHz, DMSO-$d_6$) δ ppm 7.64-7.51 (m, 4H), 6.95 (d, J=7.6 Hz, 1H), 6.89 (t, J=7.2 Hz, 1H), 6.50 (t, J=7.6 Hz, 1H), 6.43 (d, J=8.0 Hz, 1H), 5.88 (ddd, J=6.0, 10.8, 16.8 Hz, 1H), 5.22-5.03 (m, 2H), 4.69-4.51 (m, 2H), 3.41 (d, J=12.8 Hz, 1H), 3.25-3.16 (m, 1H), 2.89-2.78 (m, 1H), 2.73-2.63 (m, 2H); ES-LCMS m/z 318.4 [M+H]$^+$. Peak 2 was concentrated under reduced pressure to yield a residue which was dissolved in MeCN (20 mL) and H$_2$O (40 mL) and lyophilized to yield (3S)-1-[[3-(trifluoromethyl)phenyl]methyl]-3-vinyl-3,4-dihydro-2H-quinoline (410 mg, 1.29 mmol, 50.6% yield, 100.0% purity, SFC: R$_t$=2.560, ee=91.28%, [α]$^{22.7}_D$=+3.878 (MeOH, c=0.051 g/100 mL) as a white solid. $^1$H NMR (400 MHz, DMSO-$d_6$) δ ppm 7.64-7.52 (m, 4H), 6.95 (d, J=7.2 Hz, 1H), 6.89 (t, J=7.6 Hz, 1H), 6.50 (t, J=7.2 Hz, 1H), 6.43 (d, J=8.4 Hz, 1H), 5.88 (ddd, J=5.6, 10.8, 17.2 Hz, 1H), 5.22-5.04 (m, 2H), 4.68-4.50 (m, 2H), 3.41 (d, J=13.2 Hz, 1H), 3.26-3.17 (m, 1H), 2.89-2.79 (m, 1H), 2.74-2.63 (m, 2H); ES-LCMS m/z 318.2 [M+H]$^+$.

Step 7: (5S)-3-bromo-5-methyl-5-[(3R)-3-methyl-1-[[3-(trifluoromethyl)phenyl]methyl]-2,4-dihydroquinolin-3-yl]-4H-isoxazole

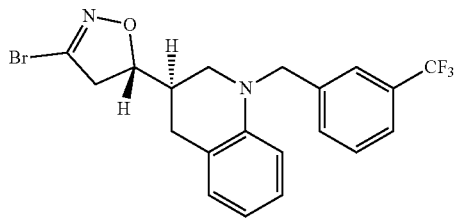 [SMILES: FC(F)(F)c1cccc(CN2C[C@H]([C@@H]3CC(Br)=NO3)Cc3ccccc32)c1]

To a solution of (3S)-1-[[3-(trifluoromethyl)phenyl]methyl]-3-vinyl-3,4-dihydro-2H-quinoline (200 mg, 630.22 μmol, 1 eq) in EtOAc (5 mL) was added NaHCO$_3$ (529.45 mg, 6.30 mmol, 10 eq) and dibromomethanone oxime (221.15 mg, 1.09 mmol, 1.73 eq). The mixture was stirred at 15° C. for 12 h. TLC (PE/EtOAc=3/1, R$_f$=0.40) showed starting material was consumed completely and one major new spot was detected. The mixture was diluted with H$_2$O (20 mL) and extracted with EtOAc (20 mL×3). The combine organic layers were dried over anhydrous Na$_2$SO$_4$, filtered and concentrated to yield a residue which was purified by flash silica gel chromatography (from pure PE to PE/EtOAc=5/1, TLC: PE/EtOAc=3/1, R$_f$=0.40) to yield a residue which was separated by preparative SFC (column: DAICEL CHIRALPAK IG (250 mm*30 mm, 10 μm); mobile phase: [0.1% NH$_3$H$_2$O EtOH]; B %: 25%-25%) to yield Peak 1 and Peak 2. Peak 2 was concentrated under reduced pressure to yield a residue which was dissolved in MeCN (20 mL) and H$_2$O (40 mL) and lyophilized to yield (5S)-3-bromo-5-methyl-5-[(3R)-3-methyl-1-[[3-(trifluoromethyl)phenyl]methyl]-2,4-dihydroquinolin-3-yl]-4H-isoxazole (37.19 mg, 79.58 μmol, 12.6% yield, 100.0% purity, SFC: R$_t$=2.808, ee=95.24%, [α]$^{25.2}_D$=+77.358 (MeOH, c=0.080 g/100 mL) as a white solid. $^1$H NMR (400 MHz, CDCl$_3$) δ ppm 7.56-7.50 (m, 2H), 7.48-7.41 (m, 2H), 7.09-7.00 (m, 2H), 6.71-6.66 (m, 1H), 6.53 (d, J=8.0 Hz, 1H), 4.77-4.68 (m, 1H), 4.57-4.47 (m, 2H), 3.35-3.28 (m, 1H), 3.28-3.19 (m, 2H), 3.06-2.93 (m, 2H), 2.90-2.80 (m, 1H), 2.42-2.32 (m, 1H); ES-LCMS m/z 439.0, 441.0 [M+H]$^+$.

Step 8: (5R)-3-Bromo-5-methyl-5-[(3S)-3-methyl-1-[[3-(trifluoromethyl)phenyl]methyl]-2,4-dihydroquinolin-3-yl]-4H-isoxazole

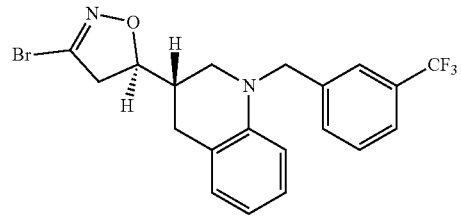 [SMILES: FC(F)(F)c1cccc(CN2C[C@@H]([C@H]3CC(Br)=NO3)Cc3ccccc32)c1]

To a solution of (3R)-1-[[3-(trifluoromethyl)phenyl]methyl]-3-vinyl-3,4-dihydro-2H-quinoline (200 mg, 630.22 μmol, 1 eq) in EtOAc (1 mL) was added NaHCO$_3$ (529.45 mg, 6.30 mmol, 10 eq) and dibromomethanone oxime (199.41 mg, 983.15 μmol, 1.56 eq). The mixture was stirred at 15° C. for 12 h. The mixture was diluted with H$_2$O (20 mL) and extracted with EtOAc (20 mL×3). The combine organic layers were dried over anhydrous Na$_2$SO$_4$, filtered and concentrated to yield a residue which was purified by flash silica gel chromatography (from pure PE to PE/EtOAc=5/1, TLC: PE/EtOAc=3/1, R$_f$=0.40). The desired fraction was concentrated under reduced pressure to yield a residue which was separated by preparative SFC (column: DAICEL CHIRALCEL OD-H (250 mm*30 mm, 5 μm); mobile phase: [0.1% NH$_3$H$_2$O EtOH]; B %: 30%-30%) to yield Peak 1 and Peak 2. Peak 2 was concentrated under reduced pressure to yield a residue which was separated by preparative SFC (column: DAICEL CHIRALPAK IG (250 mm*30 mm, 10 μm); mobile phase: [0.1% NH$_3$H$_2$O MeOH]; B %: 35%-35%) to yield Peak 3. Peak 3 was concentrated under reduced pressure to yield a residue which was dissolved in MeCN (20 mL) and H$_2$O (40 mL) and lyophilized to yield (5R)-3-bromo-5-methyl-5-[(3S)-3-methyl-1-[[3-(trifluoromethyl)phenyl]methyl]-2,4-dihydroquinolin-3-yl]-4H-isoxazole (37.95 mg, 81.21 μmol, 12.9% yield, 100.0% purity, SFC1: R$_t$=4.662, ee=100%, SFC2: R$_t$=3.802, ee=100%, [α]$^{25.1}_D$=−86.276 (MeOH, c=0.093 g/100 mL) as a white solid. $^1$H NMR (400 MHz, CDCl$_3$) δ ppm 7.57-7.49 (m, 2H), 7.49-7.41 (m, 2H), 7.09-6.99 (m, 2H), 6.72-6.65 (m, 1H), 6.53 (d, J=8.0 Hz, 1H), 4.79-4.66 (m, 1H), 4.59-4.44 (m, 2H), 3.35-3.28 (m, 1H), 3.28-3.18 (m, 2H), 3.06-2.93 (m, 2H), 2.89-2.80 (m, 1H), 2.43-2.30 (m, 1H); ES-LCMS m/z 438.8, 440.8 [M+H]$^+$.

I-265 & I-266

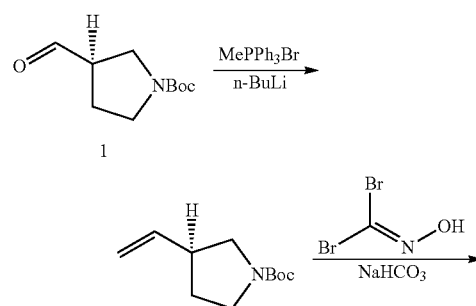

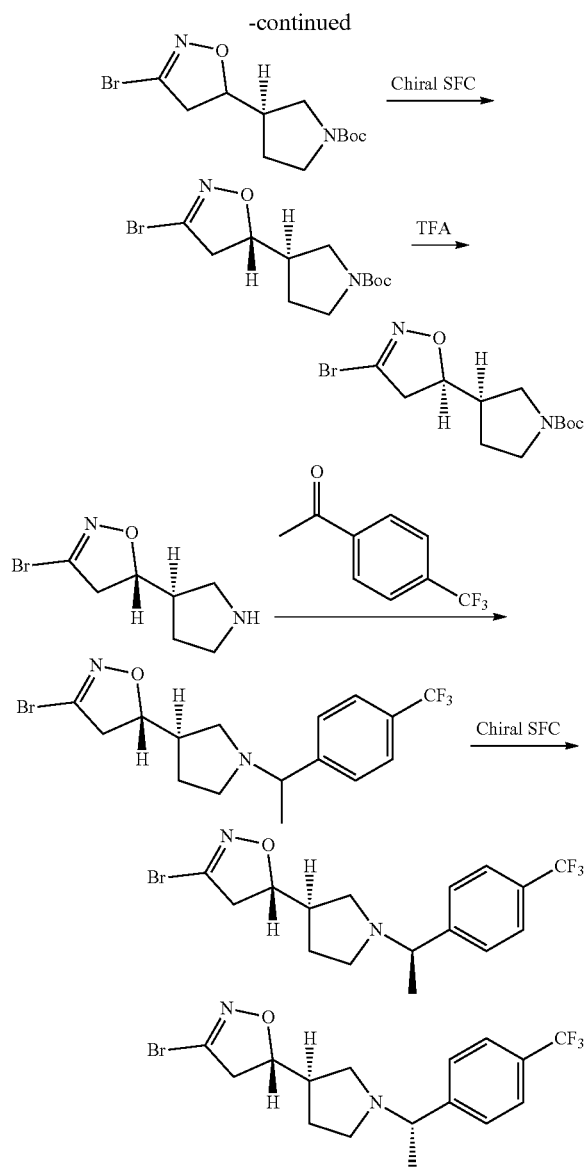

Step 1: (5R)-3-Bromo-5-[1-[[4-(trifluoromethylsulfanyl)

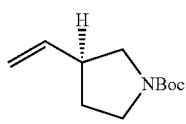

To a solution of methyl(triphenyl)phosphonium;bromide (9.96 g, 27.89 mmol, 1.3 eq) in THF (80 mL) was added n-BuLi (2.5 M, 11.16 mL, 1.3 eq) dropwise under N₂ atmosphere at −65° C. The mixture was stirred under N₂ atmosphere at 0° C. for 0.5 h. The mixture was cooled to −70° C. and a solution of tert-butyl (3R)-3-formylpyrrolidine-1-carboxylate (4.5 g, 21.46 mmol, 1 eq) in THF (20 mL) was added slowly. The mixture was stirred under N₂ atmosphere at 20° C. for 4 h. TLC (PE/EtOAc=10/1, $R_f$=0.70) indicated starting material was consumed com- pletely and one new spot formed. The reaction mixture was quenched by addition of saturated aqueous NH₄Cl (20 mL) and water (500 mL) and extracted with EtOAc (500 mL×3). The combined organic layers were washed with brine (200 mL), dried over Na₂SO₄, filtered and concentrated under reduced pressure to yield a residue which was purified by flash silica gel chromatography (from PE/EtOAc=1/0 to 20/1, TLC: PE/EtOAc=10/1, $R_f$=0.70) to yield tert-butyl (3S)-3-vinylpyrrolidine-1-carboxylate (3.5 g, 15.97 mmol, 74.4% yield, 90.0% purity) as colorless oil. ¹H NMR (500 MHz, CDCl₃) δ ppm 5.84-5.66 (m, 1H), 5.08 (d, J=17.1 Hz, 1H), 5.01 (d, J=10.4 Hz, 1H), 3.58-3.37 (m, 2H), 3.32-3.20 (m, 1H), 3.09-2.96 (m, 1H), 2.79-2.70 (m, 1H), 2.02-1.94 (m, 1H), 1.71-1.63 (m, 1H), 1.44 (s, 9H).

Step 2: tert-Butyl (3R)-3-[(5R)-3-bromo-4,5-dihydroisoxazol-5-yl]pyrrolidine-1-carboxylate and tert-butyl (3R)-3-[(5S)-3-bromo-4,5-dihydroisoxazol-5-yl]pyrrolidine-1-carboxylate

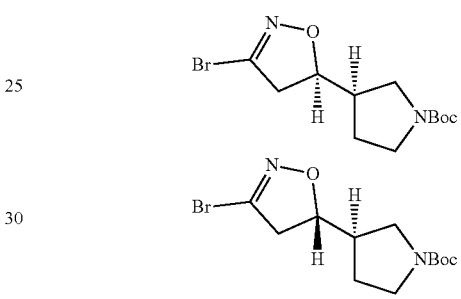

To a solution of tert-butyl (3S)-3-vinylpyrrolidine-1-carboxylate (2.9 g, 13.23 mmol, 1 eq) in EtOAc (50 mL) was added NaHCO₃ (8.89 g, 105.84 mmol, 4.12 mL, 8 eq) and dibromomethanone oxime (2.82 g, 13.89 mmol, 1.05 eq). The mixture was stirred at 20° C. for 12 h. TLC (PE/EtOAc=3/1, $R_f$=0.31, 0.29) indicated starting material was consumed completely and one new spot formed. The reaction mixture was quenched by addition of water (100 mL) and extracted with EtOAc (100 mL×3). The combined organic layers were washed with brine (400 mL), dried over Na₂SO₄, filtered and concentrated under reduced pressure to yield a residue which was purified by flash silica gel chromatography (from PE/EtOAc=1/0 to 17/3, TLC: PE/EtOAc=3/1, $R_f$=0.31, 0.29) to yield fraction 1 and fraction 2. Fraction 1 was concentrated under reduced pressure to yield tert-butyl (3R)-3-[(5R)-3-bromo-4,5-dihydroisoxazol-5-yl]pyrrolidine-1-carboxylate (1.2 g, 3.76 mmol, 28.4% yield, 100.0% purity, SFC: $R_t$=2.362, ee=94.5%; $[\alpha]^{23.7}_D$=−57.6 (MeOH, c=0.250 g/100 mL)) as a white solid. ¹H NMR (400 MHz, CDCl₃) δ ppm 4.70-4.52 (m, 1H), 3.62-3.41 (m, 2H), 3.34-3.27 (m, 2H), 3.13-2.99 (m, 1H), 2.97-2.84 (m, 1H), 2.48-2.41 (m, 1H), 2.11-2.03 (m, 1H), 1.91-1.68 (m, 1H), 1.45 (s, 9H). ES-LCMS m/z 262.9, 264.9 [M-t-Bu+H]⁺. Fraction 2 was concentrated under reduced pressure to yield tert-butyl (3R)-3-[(5S)-3-bromo-4,5-dihydroisoxazol-5-yl]pyrrolidine-1-carboxylate (1.1 g, 3.45 mmol, 26.1% yield, 100.0% purity, SFC: $R_t$=2.009, ee=95.4%; $[\alpha]^{23.7}_D$=+88.1 (MeOH, c=0.270 g/100 mL)) as a white solid. ¹H NMR (500 MHz, CDCl₃) δ ppm 4.71-4.50 (m, 1H), 3.65-3.55 (m, 1H), 3.54-3.41 (m, 1H), 3.33-3.28 (m, 2H), 3.20 (dd, J=8.5, 10.6 Hz, 1H), 2.96-2.91 (m, 1H), 2.49-2.41 (m, 1H), 1.99-1.88 (m, 1H), 1.71-1.64 (m, 1H), 1.45 (s, 9H).

Step 3: (5S)-3-Bromo-5-[(3R)-pyrrolidin-3-yl]-4,5-dihydroisoxazole

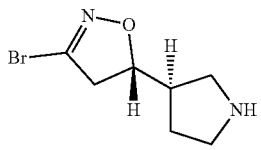 [SMILES: BrC1=NO[C@H]([C@@H]2CCNC2)C1]

To a solution of tert-butyl (3R)-3-[(5S)-3-bromo-4,5-dihydroisoxazol-5-yl]pyrrolidine-1-carboxylate (700 mg, 1.97 mmol, 1 eq) in DCM (10 mL) was added TFA (2.10 mL, 28.36 mmol, 14.37 eq). The mixture was stirred at 20° C. for 2 h. TLC (PE/EtOAc=3/1, R$_f$=0) indicated starting material was consumed completely and one new spot formed. The reaction mixture was concentrated to yield (5S)-3-bromo-5-[(3R)-pyrrolidin-3-yl]-4,5-dihydroisoxazole (700 mg, 1.89 mmol, 95.8% yield, 90.0% purity, TFA) as yellow oil. $^1$H NMR (500 MHz, DMSO-d$_6$) δ ppm 4.68 (d, J=8.1, 10.4 Hz, 1H), 3.47 (dd, J=10.5, 17.5 Hz, 1H), 3.36-3.30 (m, 1H), 3.28-3.23 (m, 1H), 3.20-3.10 (m, 2H), 3.00-2.89 (m, 1H), 2.60-2.54 (m, 1H), 2.10-2.01 (m, 1H), 1.60 (d, J=8.3, 13.0 Hz, 1H) 1.34 (s, 1H).

Step 4: (5S)-3-Bromo-5-[(3R)-1-[(1R)-1-[4-(trifluoromethyl)phenyl]ethyl]pyrrolidin-3-yl]-4,5-dihydroisoxazole and (5S)-3-bromo-5-[(3R)-1-[(1S)-1-[4-(trifluoromethyl)phenyl]ethyl]pyrrolidin-3-yl]-4,5-dihydroisoxazole

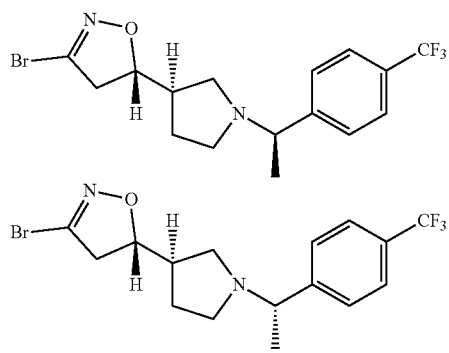

To a solution of (5S)-3-bromo-5-[(3R)-pyrrolidin-3-yl]-4,5-dihydroisoxazole (300 mg, 810.56 μmol, 1 eq, TFA) in MeOH (0.5 mL) and Ti(i-PrO)$_4$ (2 mL) was added 1-[4-(trifluoromethyl)phenyl]ethanone (198.26 mg, 1.05 mmol, 1.3 eq), DIEA (314.27 mg, 2.43 mmol, 423.55 μL, 3 eq) and the mixture was stirred at 80° C. for 2 h. The reaction mixture was cooled to 15° C. MeOH (30 mL) and NaBH$_3$CN (254.68 mg, 4.05 mmol, 5 eq) were added and the mixture was stirred at 50° C. for 12 h. The reaction mixture was quenched by addition of 15% NaOH (5 mL) and water (50 mL) and extracted with EtOAc (50 mL×3). The combined organic layers were washed with brine (40 mL), dried over Na$_2$SO$_4$, filtered and concentrated under reduced pressure to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 53%-83%, 10 min) to yield the compound which was separated by SFC (column: DAICEL CHIRALPAK IG (250 mm*30 mm, 10 um); mobile phase: [0.1% NH$_3$H$_2$O/MeOH]; B %: 30%-30%) to yield peak 1 and peak 2. Peak 1 was concentrated under reduced pressure to yield (5S)-3-bromo-5-[(3R)-1-[(1R)-1-[4-(trifluoromethyl)phenyl]ethyl]pyrrolidin-3-yl]-4,5-dihydroisoxazole (19.01 mg, 46.11 μmol, 5.7% yield, 94.9% purity, SFC: R$_t$=2.166, ee=100%, [α]$^{24.0}_D$=+99.1 (MeOH, c=0.063 g/100 mL)) as a white solid. $^1$H NMR (400 MHz, CDCl$_3$) δ ppm 7.56 (d, J=7.8 Hz, 2H), 7.42 (d, J=8.2 Hz, 2H), 4.67-4.56 (m, 1H), 3.31-3.18 (m, 2H), 2.96 (dd, J=8.6, 17.2 Hz, 1H), 2.76-2.61 (m, 2H), 2.51-2.33 (m, 3H), 2.02-1.88 (m, 1H), 1.46 (dd, J=6.7, 12.9 Hz, 1H), 1.37 (d, J=6.3 Hz, 3H); ES-LCMS m/z 391.0, 393.0 [M+H]$^+$. Peak 2 was concentrated under reduced pressure to yield (5S)-3-bromo-5-[(3R)-1-[(1S)-1-[4-(trifluoromethyl)phenyl]ethyl]pyrrolidin-3-yl]-4,5-dihydroisoxazole (24.29 mg, 59.36 μmol, 7.3% yield, 95.6% purity, SFC: R$_t$=3.155, ee=95.4%, [α]$^{24.0}_D$=+46.5 (MeOH, c=0.051 g/100 mL)) as a white solid. $^1$H NMR (400 MHz, CDCl$_3$) δ ppm 7.56 (d, J=7.8 Hz, 2H), 7.43 (d, J=7.8 Hz, 2H), 4.66 (q, J=8.9 Hz, 1H), 3.24 (dd, J=10.4, 17.0 Hz, 2H), 2.90 (dd, J=8.2, 17.2 Hz, 1H), 2.62-2.50 (m, 3H), 2.49-2.42 (m, 2H), 1.97 (s, 1H), 1.45-1.39 (m, 1H), 1.36 (d, J=6.3 Hz, 3H); ES-LCMS m/z 391.0, 393.0 [M+H]$^+$.

I-275

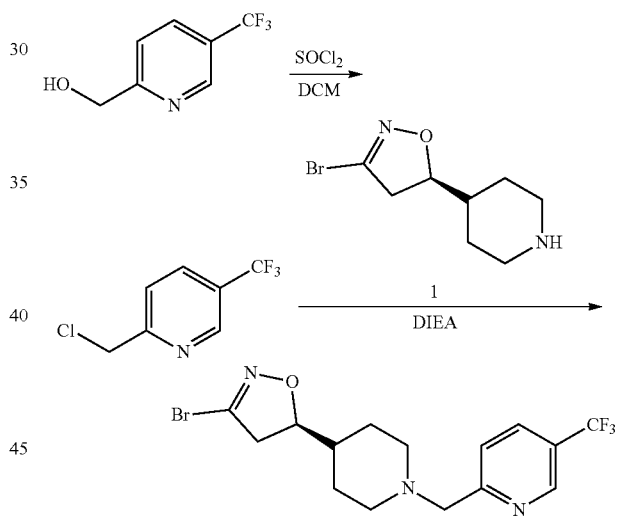

Step 1: 2-(Chloromethyl)-5-(trifluoromethyl)pyridine

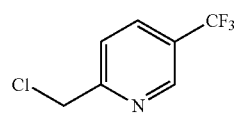 [SMILES: FC(F)(F)c1ccc(CCl)nc1]

To a solution of [5-(trifluoromethyl)-2-pyridyl]methanol (200 mg, 1.13 mmol, 155.04 μL, 1 eq) in DCM (3 mL) was added SOCl$_2$ (403.01 mg, 3.39 mmol, 245.74 μL, 3 eq). The reaction mixture was stirred at 50° C. for 2 h. The reaction mixture was concentrated under reduced pressure to yield 2-(chloromethyl)-5-(trifluoromethyl)pyridine (200 mg, 971.52 μmol, 86.0% yield, 95.0% purity) as yellow oil. $^1$H NMR (500 MHz, DMSO-$d_6$) δ ppm 8.97 (s, 1H), 8.28 (dd, J=2.1, 8.2 Hz, 1H), 7.80 (d, J=8.2 Hz, 1H), 4.90 (s, 2H).

Step 2: (5R)-3-Bromo-5-[1-[[5-(trifluoromethyl)-2-pyridyl]methyl]-4-piperidyl]-4,5-dihydroisoxazole

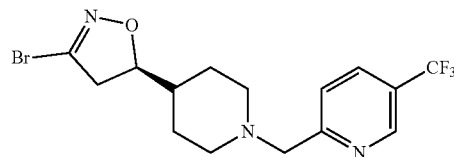 [SMILES: FC(F)(F)c1ccc(CN2CCC([C@H]3CC(Br)=NO3)CC2)nc1]

To a solution of 2-(chloromethyl)-5-(trifluoromethyl) pyridine (73.68 mg, 357.93 μmol, 95% purity, 1 eq) in DMF (2 mL) was added DIEA (138.78 mg, 1.07 mmol, 187.03 μL, 3 eq) and (5R)-3-bromo-5-(4-piperidyl)-4,5-dihydroisoxazole (87.83 mg, 357.93 μmol, 95% purity, 1 eq). The mixture was stirred under $N_2$ atmosphere at 15° C. for 2 h. The reaction mixture was quenched by addition of water (20 mL) and extracted with EtOAc (20 mL×3). The combined organic layers were washed with brine (10 mL), dried over $Na_2SO_4$, filtered and concentrated under reduced pressure to yield a residue which was purified by preparative HPLC (column: Phenomenex Synergi C18 150*30 mm*4 um; mobile phase: [water (0.05% HCl)-ACN]; B %: 20%-40%, 9 min). The desired fraction was basified with saturated $NaHCO_3$ (20 mL) and extracted with EtOAc (20 mL×3). The combined organic layers were washed with brine (10 mL), dried over $Na_2SO_4$, concentrated under reduced pressure and lyophilized to yield (5R)-3-bromo-5-[1-[[5-(trifluoromethyl)-2-pyridyl]methyl]-4-piperidyl]-4,5-dihydroisoxazole (17.48 mg, 44.03 μmol, 12.3% yield, 98.8% purity, $[\alpha]^{25.1}_D$=−89.9 (MeOH, c=0.0356 g/100 mL)) as a white solid. $^1$H NMR (400 MHz, $CDCl_3$) δ ppm 8.81 (s, 1H), 7.89 (dd, J=1.8, 8.0 Hz, 1H), 7.57 (d, J=8.2 Hz, 1H), 4.61-4.44 (m, 1H), 3.71 (s, 2H), 3.24-3.06 (m, 1H), 2.99-2.88 (m, 3H), 2.15-2.04 (m, 2H), 1.85 (d, J=13.3 Hz, 1H), 1.71-1.58 (m, 2H), 1.49-1.35 (m, 2H); ES-LCMS m/z 392.1, 394.1 [M+H]$^+$.
I-276

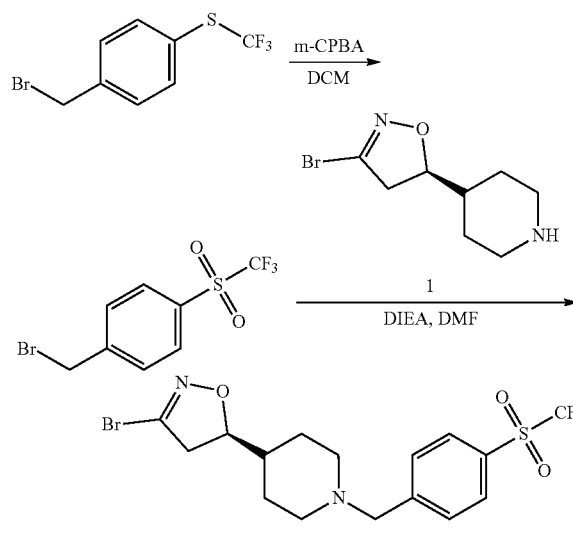

Step 1: 1-(Bromomethyl)-4-(trifluoromethylsulfonyl)benzene

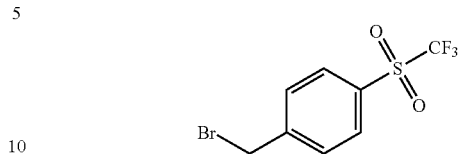

To a solution of 1-(bromomethyl)-4-(trifluoromethylsulfanyl)benzene (500 mg, 1.84 mmol, 1 eq) in DCM (15 mL) was added m-CPBA (1.87 g, 9.22 mmol, 85% purity, 5 eq). The mixture was stirred at 40° C. for 24 h. The reaction mixture was concentrated to yield a residue which was purified by flash silica gel chromatography (from PE/EtOAc=1/0 to 11/1, TLC: PE/EtOAc=3/1, $R_f$=0.65) to yield 1-(bromomethyl)-4-(trifluoromethylsulfonyl)benzene (499 mg, 1.65 mmol, 89.3% yield, 100.0% purity) as a white solid. $^1$H NMR (400 MHz, $CDCl_3$) δ ppm 8.03 (d, J=8.3 Hz, 2H), 7.70 (d, J=8.6 Hz, 2H), 4.54 (s, 2H).

Step 2: (5R)-3-Bromo-5-[1-[[4-(trifluoromethylsulfonyl)phenyl]methyl]-4-piperidyl]-4,5-dihydroisoxazole

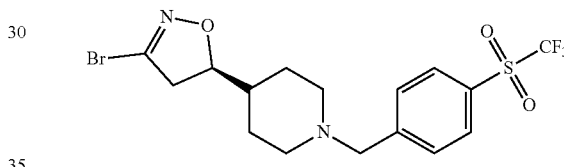

To a solution of (5R)-3-bromo-5-(4-piperidyl)-4,5-dihydroisoxazole (50 mg, 197.76 μmol, 92.2% purity, 1 eq) in DMF (2 mL) was added 1-(bromomethyl)-4-(trifluoromethylsulfonyl)benzene (59.94 mg, 197.76 μmol, 100% purity, 1 eq) and DIEA (51.12 mg, 395.53 μmol, 68.89 μL, 2 eq). The mixture was stirred at 20° C. for 16 h. The reaction mixture was concentrated to yield a residue which was purified by preparative HPLC (column: Agela DuraShell C18 150*25 mm*5 μm; mobile phase: [water (0.04% $NH_3H_2O$+10 mM $NH_4HCO_3$)-ACN]; B %: 50%-80%, 10 min), followed by lyophilization to yield (5R)-3-bromo-5-[1-[[4-(trifluoromethylsulfonyl)phenyl]methyl]-4-piperidyl]-4,5-dihydroisoxazole (8.12 mg, 17.48 μmol, 8.8% yield, 98.0% purity) as colorless oil. $^1$H NMR (400 MHz, $CDCl_3$) δ ppm 7.99 (d, J=7.8 Hz, 2H), 7.65 (d, J=8.2 Hz, 2H), 4.54-4.47 (m, 1H), 3.62 (s, 2H), 3.21 (dd, J=10.6, 17.2 Hz, 1H), 3.00-2.87 (m, 3H), 2.07-1.99 (m, 2H), 1.86 (d, J=13.3 Hz, 1H), 1.64 (s, 2H), 1.46-1.36 (m, 2H); ES-LCMS m/z 455, 457.0 [M+H]$^+$.
I-279

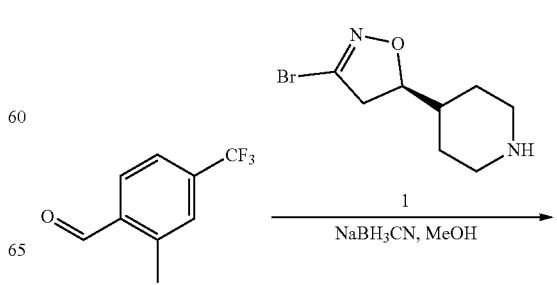

Step 1: (5R)-3-Bromo-5-[1-{[2-methyl-4-(trifluoromethyl)phenyl]methyl}-4-piperidyl]-4,5-dihydroisoxazole

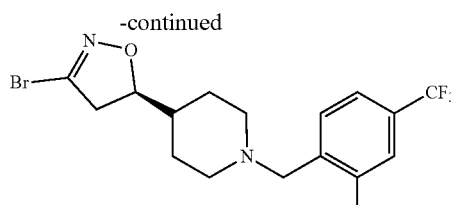

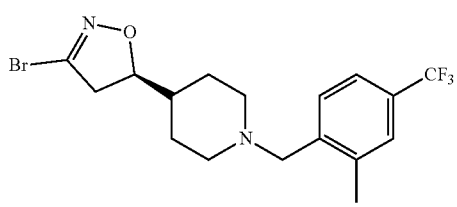 [SMILES: Cc1cc(C(F)(F)F)ccc1CN1CCC([C@H]2CC(Br)=NO2)CC1]

To a solution of (5R)-3-bromo-5-(4-piperidyl)-4,5-dihydroisoxazole (50 mg, 132.80 μmol, 92.2%, 1 eq, TFA) in MeOH (2 mL) was added 2-methyl-4-(trifluoromethyl)benzaldehyde (37.48 mg, 199.21 μmol, 1.5 eq) and DIEA (85.82 mg, 664.02 μmol, 115.66 μL, 5 eq) at 50° C. After addition, the mixture was stirred at this temperature for 2 h. NaBH$_3$CN (33.38 mg, 531.22 μmol, 4 eq) was added partwise at 15° C. The resulting mixture was stirred at 15° C. for 2 h. The solvent was removed to yield a residue which was purified by preparative HPLC (column: Agela DuraShell C18 150*25 mm*5 μm; mobile phase: [water (0.04% NH$_3$H$_2$O+10 mM NH$_4$HCO$_3$)-ACN]; B %: 63%-93%, 10 min) and lyophilized to yield (5R)-3-bromo-5-[1-[[2-methyl-4-(trifluoromethyl)phenyl]methyl]-4-piperidyl]-4,5-dihydroisoxazole (4.31 mg, 10.17 μmol, 7.7% yield, 95.6% purity, $[\alpha]^{19.5}_D$=−60.0 (MeOH, c=0.002 g/100 mL)) as a white solid. $^1$H NMR (400 MHz, CDCl$_3$) δ ppm 7.40 (s, 3H), 4.53-4.45 (m, 1H), 3.47 (s, 2H), 3.19 (dd, J=10.5, 17.1 Hz, 1H), 2.96 (dd, J=9.0, 17.1 Hz, 3H), 2.40 (s, 3H), 2.09-1.94 (m, 2H), 1.83 (d, J=11.7 Hz, 1H), 1.68-1.61 (m, 1H), 1.44-1.24 (m, 3H); ES-LCMS m/z 405.1, 407.1 [M+H]$^+$.

I-290

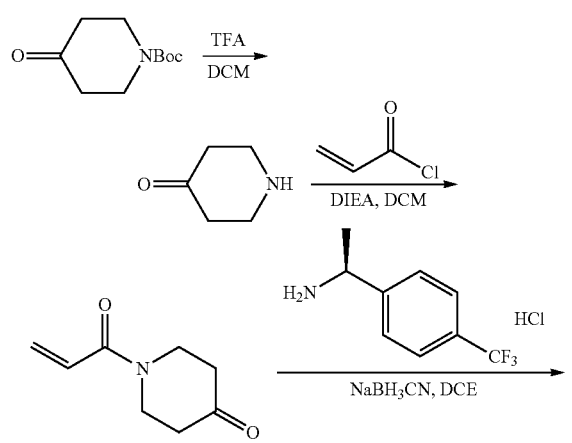

Step 1: Piperidin-4-one

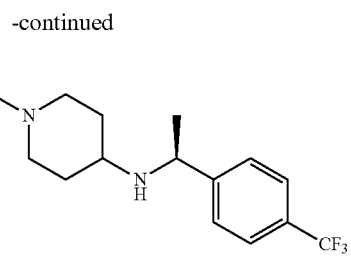

To a solution of tert-butyl 4-oxopiperidine-1-carboxylate (2 g, 10.04 mmol, 1 eq) in DCM (10 mL) was added TFA (2 mL). The mixture was stirred at 20° C. for 1 h. TLC (DCM/MeOH=10/1, R$_f$=0.6) indicated the starting material was consumed completely and one new spot formed. The reaction mixture was concentrated to yield piperidin-4-one (1.82 g, 5.98 mmol, 59.5% yield, 70.0% purity, TFA) as yellow oil which was used in the next step without further purification. $^1$H NMR (500 MHz, CD$_3$OD) δ ppm 3.25-3.20 (m, 4H), 1.99-1.90 (m, 4H).

Step 2: 1-Prop-2-enoylpiperidin-4-one

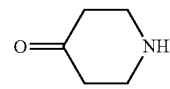

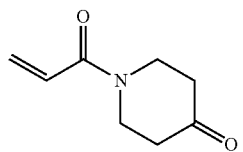

To a solution of piperidin-4-one (1 g, 3.28 mmol, 70% purity, 1 eq, TFA) and DIEA (848.85 mg, 6.57 mmol, 1.14 mL, 2 eq) in DCM (5 mL) was added a solution of prop-2-enoyl chloride (594.46 mg, 6.57 mmol, 535.55 μL, 2 eq) in DCM (2 mL). The mixture was stirred at 0° C. for 30 min. TLC (DCM/MeOH=10/1, R$_f$=0.8) indicated the starting material was consumed completely and three new spots formed. The reaction mixture was concentrated to yield a residue which was purified by flash silica gel chromatography (from PE/EtOAc=1/0 to 1/2, TLC: DCM/MeOH=10/1, R$_f$=0.8) to yield 1-prop-2-enoylpiperidin-4-one (190 mg, 1.12 mmol, 34.0% yield, 90.0% purity) as yellow oil. $^1$H NMR (400 MHz, CDCl$_3$) δ ppm 6.63 (dd, J=10.4, 16.8 Hz, 1H), 6.36 (d, J=16.8, 1H), 5.77 (dd, J=1.6, 10.4 Hz, 1H), 3.93-3.85 (m, 4H), 2.52-2.49 (m, 4H).

Step 3: 1-[4-[[(1S)-1-[4-(Trifluoromethyl)phenyl]ethyl]amino]-1-piperidyl]prop-2-en-1-one

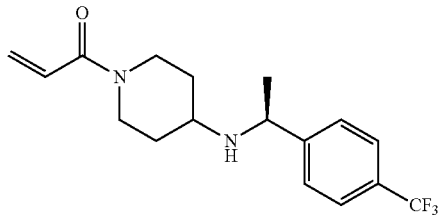 [SMILES: C=CC(=O)N1CCC(N[C@@H](C)c2ccc(C(F)(F)F)cc2)CC1]

A mixture of 1-prop-2-enoylpiperidin-4-one (80 mg, 470.04 μmol, 90% purity, 1 eq) and (1S)-1-[4-(trifluoromethyl)phenyl]ethanamine (106.06 mg, 470.04 μmol, 1 eq, HCl) in DCE (5 mL) was stirred at 40° C. for 16 h. NaBH$_3$CN (118.15 mg, 1.88 mmol, 4 eq) was added and the mixture was stirred at 40° C. for 1 h. The solvent was removed to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 33%-63%, 10 min) to yield 1-[4-[[(1S)-1-[4-(trifluoromethyl)phenyl]ethyl]amino]-1-piperidyl]prop-2-en-1-one (110.68 mg, 339.14 μmol, 72.2% yield, 100.0% purity, $[\alpha]^{2.24}_D$=−60.13 (MeOH, c=0.193 g/100 mL)) as a white solid. $^1$H NMR (500 MHz, CD$_3$OD) δ ppm 7.68-7.62 (m, 2H), 7.58 (d, J=8.1 Hz, 2H), 6.75 (ddd, J=6.3, 10.6, 16.8 Hz, 1H), 6.17 (d, J=16.8 Hz, 1H), 5.72 (dd, J=1.9, 10.6 Hz, 1H), 4.46 (t, J=15.1 Hz, 1H), 4.13-4.00 (m, 2H), 3.10-2.96 (m, 1H), 2.74-2.60 (m, 1H), 2.58-2.49 (m, 1H), 2.05 (d, J=13.0 Hz, 1H), 1.81 (d, J=12.8 Hz, 1H), 1.38 (d, J=6.7 Hz, 3H), 1.35-1.22 (m, 2H); ES-LCMS m/z 327.1 [M+H]$^+$.

I-298

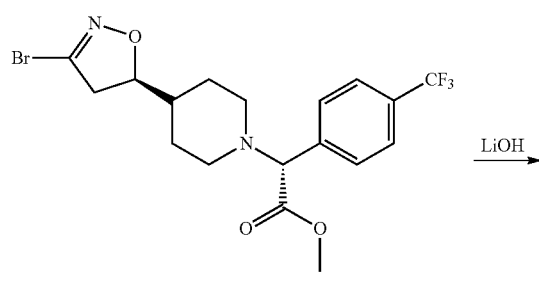

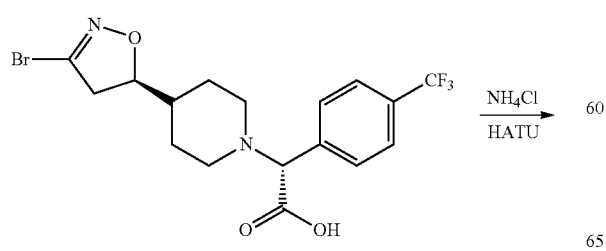

Step 1: 2-[4-[(5R)-3-Bromo-4,5-dihydroisoxazol-5-yl]-1-piperidyl]-2-[4-(trifluoromethyl)phenyl]acetic Acid

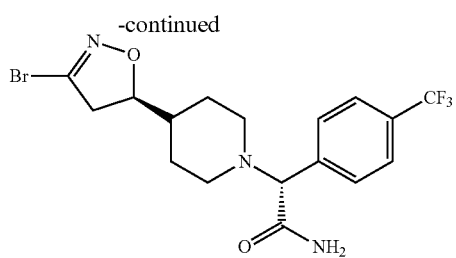

To a solution of methyl 2-[4-[(5R)-3-bromo-4,5-dihydroisoxazol-5-yl]-1-piperidyl]-2-[4-(trifluoromethyl)phenyl]acetate (150 mg, 333.88 μmol, 100% purity, 1 eq) in i-PrOH (1.5 mL), water (1.5 mL) and THF (1.5 mL) were added LiOH (23.99 mg, 1.00 mmol, 3 eq). The mixture was stirred under N$_2$ atmosphere at 70° C. for 1 h. The mixture was adjusted pH to 5-6 with 2 N HCl. The reaction mixture was concentrated under reduced pressure to yield 2-[4-[(5R)-3-bromo-4,5-dihydroisoxazol-5-yl]-1-piperidyl]-2-[4-(trifluoromethyl)phenyl]acetic acid (145 mg, 319.49 μmol, 95.7% yield, 95.9% purity) as a white solid, which was used in the next step without further purification. $^1$H NMR (400 MHz, DMSO-d$_6$) δ ppm 7.57 (s, 4H), 4.42 (d, J=8.6 Hz, 1H), 3.65 (s, 1H), 3.35-3.23 (m, 4H), 3.08-2.98 (m, 1H), 2.55 (d, J=11.3 Hz, 1H), 1.81-1.52 (m, 2H), 1.30-1.11 (m, 2H), 1.04-1.00 (m, 1H); ES-LCMS m/z 434.8, 436.8 [M+H]$^+$.

Step 2: 2-[4-[(5R)-3-Bromo-4,5-dihydroisoxazol-5-yl]-1-piperidyl]-2-[4-(trifluoromethyl)phenyl]acetamide

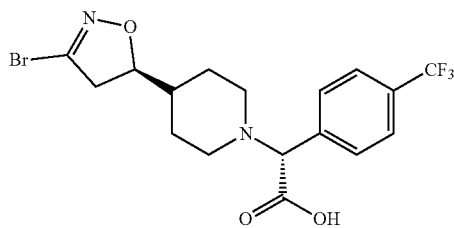 [SMILES: O=C(O)[C@@H](c1ccc(C(F)(F)F)cc1)N1CCC([C@H]2CC(Br)=NO2)CC1]

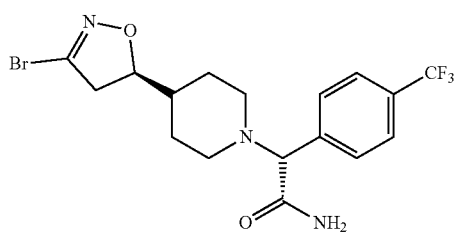

To a solution of 2-[4-[(5R)-3-bromo-4,5-dihydroisoxazol-5-yl]-1-piperidyl]-2-[4-(trifluoromethyl)phenyl]acetic acid (45 mg, 98.22 μmol, 95% purity, 1 eq) in DMF (2 mL) was added NH$_4$Cl (15.76 mg, 294.67 μmol, 3 eq), DIEA (63.47 mg, 491.11 μmol, 85.54 μL, 5 eq) and HATU (74.69 mg, 196.45 µmol, 2 eq). The mixture was stirred under N₂ atmosphere at 50° C. for 2 h. The reaction mixture was purified by preparative HPLC (column: Welch Xtimate C18 150*25 mm*5 um; mobile phase: [water (10 mM NH₄HCO₃)-ACN]; B %: 36%-66%, 10 min) to yield 2-[4-[(5R)-3-bromo-4,5-dihydroisoxazol-5-yl]-1-piperidyl]-2-[4-(trifluoromethyl)phenyl]acetamide (16.18 mg, 37.26 mol, 37.9% yield, 100.0% purity, $[\alpha]^{21.3}_D = -68$ (MeOH, c=0.1 g/100 mL)) as a white solid. ¹H NMR (400 MHz, CD₃OD) δ ppm 7.66-7.61 (m, 4H), 4.54-4.43 (m, 1H), 3.90 (s, 1H), 3.29-3.22 (m, 1H), 3.14 (d, J=11.3 Hz, 1H), 3.04 (ddd, J=4.7, 8.8, 17.4 Hz, 1H), 2.68 (d, J=11.7 Hz, 1H), 2.17-2.05 (m, 1H), 1.87-1.68 (m, 2H), 1.63-1.45 (m, 3H), 1.44-1.28 (m, 1H); ES-LCMS m/z 434.1, 436.1 [M+H]⁺.

I-299

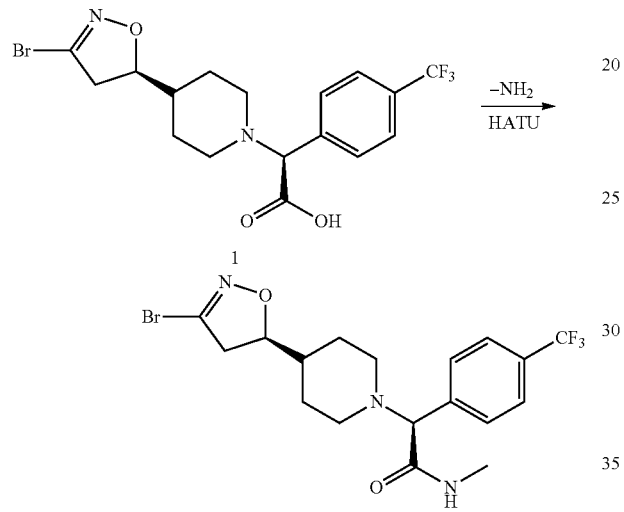

Step 1: (2S)-2-[4-[(5R)-3-Bromo-4,5-dihydroisoxazol-5-yl]-1-piperidyl]-N-methyl-2-[4-(trifluoromethyl)phenyl]acetamide To a stirred solution of (2S)-2-[4-[(5R)-3-bromo-4,5-dihydroisoxazol-5-yl]-1-piperidyl]-2-[4-(trifluoromethyl)phenyl]acetic acid (50 mg, 114.88 µmol, 1 eq) and methanamine (23.27 mg, 344.64 µmol, 3 eq, HCl) in DMF (3 mL) was added HATU (87.36 mg, 229.76 µmol, 2 eq) and DIEA (74.24 mg, 574.40 µmol, 100.05 µL, 5 eq). The reaction mixture was stirred at 70° C. for 1 h. The reaction mixture was filtered and the filtrate was purified by preparative HPLC (column: Welch Xtimate C18 150*25 mm*5 um; mobile phase: [water (10 mM NH₄HCO₃)-ACN]; B %: 35%-65%, 10 min). The desired fraction was lyophilized to yield (2S)-2-[4-[(5R)-3-bromo-4,5-dihydroisoxazol-5-yl]-1-piperidyl]-N-methyl-2-[4-(trifluoromethyl)phenyl]acetamide (23.38 mg, 52.16 µmol, 45.4% yield, 100.0% purity, $[\alpha]^{21.5}_D = -81.6$ (MeOH, c=0.125 g/100 mL)) as a white solid. ¹H NMR (400 MHz, CD₃OD) δ ppm 7.62 (q, J=8.3 Hz, 4H), 4.57-4.43 (m, 1H), 3.88 (s, 1H), 3.30-3.22 (m, 1H), 3.10-2.97 (m, 2H), 2.74 (s, 3H), 2.66 (d, J=11.0 Hz, 1H), 2.18-2.02 (m, 1H), 1.86-1.66 (m, 2H), 1.65-1.45 (m, 3H), 1.45-1.32 (m, 1H); ES-LCMS m/z 448.0, 450.0 [M+H]⁺.

I-300

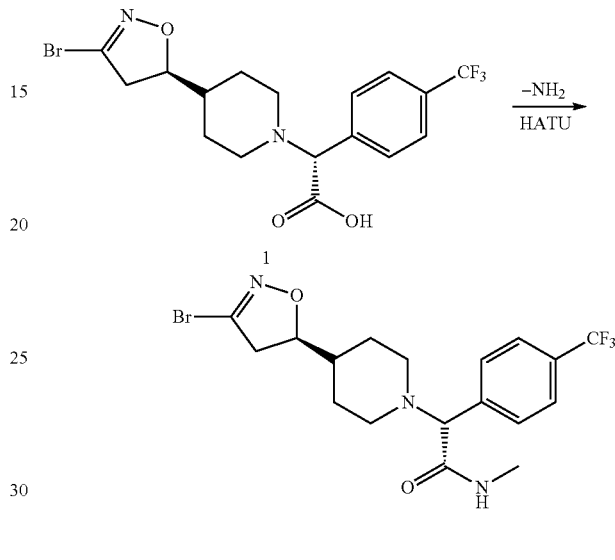

Step 1: 2-[4-[(5R)-3-Bromo-4,5-dihydroisoxazol-5-yl]-1-piperidyl]-N-methyl-2-[4-(trifluoromethyl)phenyl]acetamide

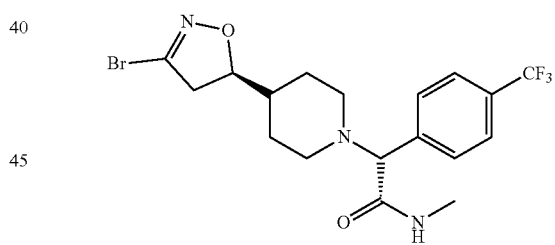

To a solution of 2-[4-[(5R)-3-bromo-4,5-dihydroisoxazol-5-yl]-1-piperidyl]-2-[4-(trifluoromethyl)phenyl]acetic acid (50 mg, 109.14 µmol, 95% purity, 1 eq) in DMF (3 mL) was added HATU (82.99 mg, 218.27 µmol, 2 eq), DIEA (70.52 mg, 545.68 µmol, 95.05 µL, 5 eq) and methanamine (22.11 mg, 327.41 µmol, 3 eq, HCl). The mixture was stirred under N₂ atmosphere at 50° C. for 2 h. The reaction mixture was purified by preparative HPLC (column: Welch Xtimate C18 150*25 mm*5 um; mobile phase: [water (10 mM NH₄HCO₃)-ACN]; B %: 37%-67%, 10 min) to yield 2-[4-[(5R)-3-bromo-4,5-dihydroisoxazol-5-yl]-1-piperidyl]-N-methyl-2-[4-(trifluoromethyl)phenyl]acetamide (15.18 mg, 33.86 mol, 31.0% yield, 100.0% purity, $[\alpha]^{23.0}_D = -100$ (MeOH, c=0.1 g/100 mL)) as a white solid. ¹H NMR (400 MHz, CD₃OD) δ ppm 7.62 (q, J=8.3 Hz, 4H), 4.55-4.45 (m, 1H), 3.88 (s, 1H), 3.30-3.23 (m, 1H), 3.10-2.97 (m, 2H), 2.73 (s, 3H), 2.66 (d, J=11.3 Hz, 1H), 2.15-2.04 (m, 1H), 1.85-1.67 (m, 2H), 1.64-1.46 (m, 3H), 1.44-1.27 (m, 1H); ES-LCMS m/z 448.1, 450.1 [M+H]⁺.

I-303 & I-304

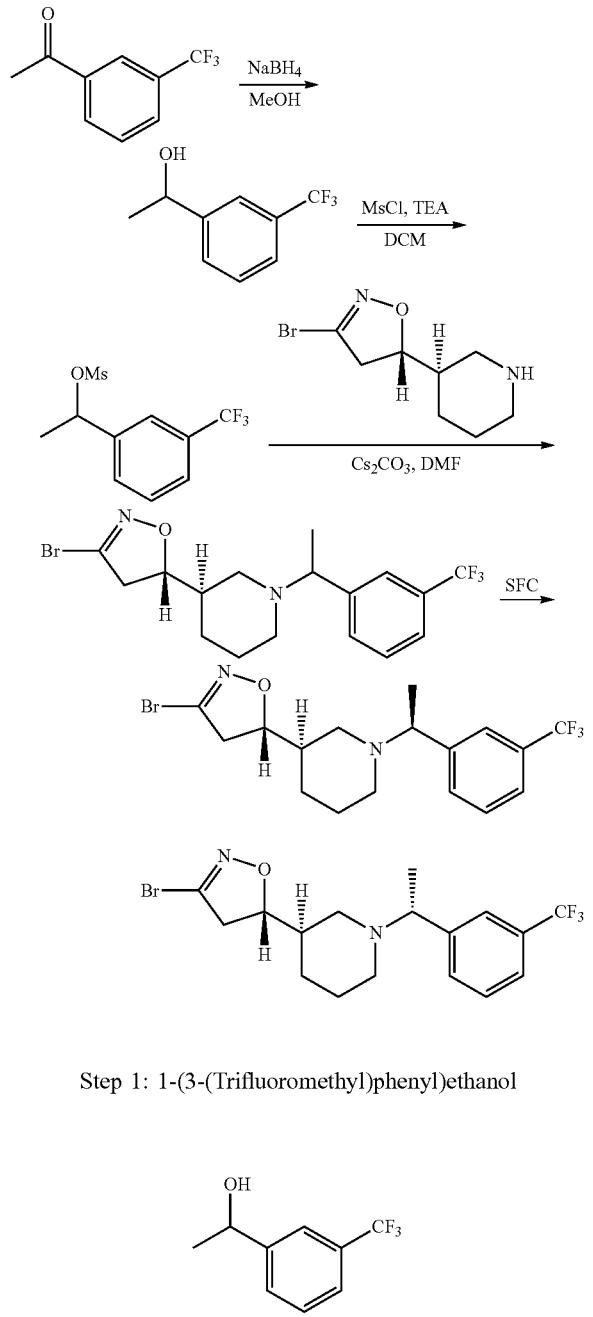

Step 1: 1-(3-(Trifluoromethyl)phenyl)ethanol

To a solution of 1-[3-(trifluoromethyl)phenyl]ethanone (2.3 g, 12.22 mmol, 1.83 mL, 1 eq) in MeOH (20 mL) was added NaBH₄ (508.70 mg, 13.45 mmol, 1.1 eq). The mixture was stirred at 18° C. for 1 h. TLC (PE/EtOAc=4/1, R_f=0.35) showed the starting material was consumed and one new spot was detected. The mixture was concentrated, diluted with water (20 mL) and extracted with EtOAc (20 mL×3). The combined organic layers were washed with brine (20 mL), dried over Na₂SO₄, filtered and concentrated to yield 1-[3-(trifluoromethyl)phenyl]ethanol (2.3 g, 12.09 mmol, 98.9% yield, 100.0% purity) as yellow oil, which was used in the next step without further purification. ¹H NMR (400 MHz, CDCl₃) δ ppm 7.66 (s, 1H), 7.61-7.52 (m, 2H), 7.51-7.44 (m, 1H), 5.06-4.86 (m, 1H), 1.91 (d, J=4.4 Hz, 1H), 1.53 (d, J=6.6 Hz, 3H); ES-LCMS m/z 214.3 [M+H]⁺.

Step 2: 1-(3-(Trifluoromethyl)phenyl)ethyl methanesulfonate

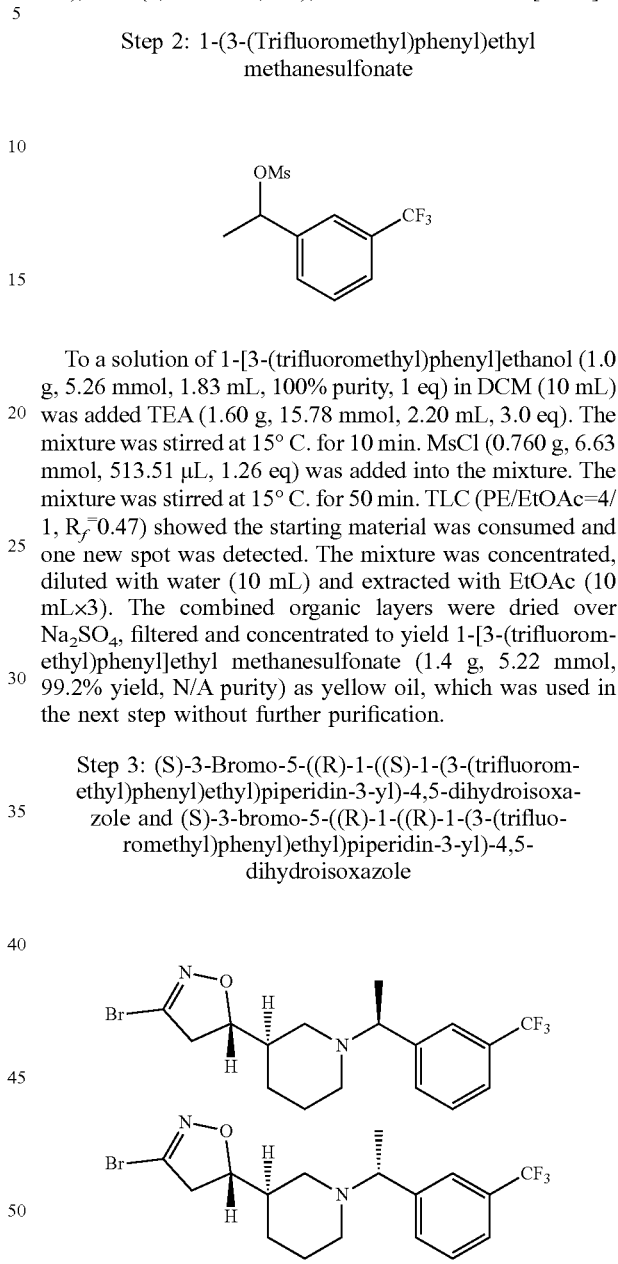

To a solution of 1-[3-(trifluoromethyl)phenyl]ethanol (1.0 g, 5.26 mmol, 1.83 mL, 100% purity, 1 eq) in DCM (10 mL) was added TEA (1.60 g, 15.78 mmol, 2.20 mL, 3.0 eq). The mixture was stirred at 15° C. for 10 min. MsCl (0.760 g, 6.63 mmol, 513.51 µL, 1.26 eq) was added into the mixture. The mixture was stirred at 15° C. for 50 min. TLC (PE/EtOAc=4/1, R_f=0.47) showed the starting material was consumed and one new spot was detected. The mixture was concentrated, diluted with water (10 mL) and extracted with EtOAc (10 mL×3). The combined organic layers were dried over Na₂SO₄, filtered and concentrated to yield 1-[3-(trifluoromethyl)phenyl]ethyl methanesulfonate (1.4 g, 5.22 mmol, 99.2% yield, N/A purity) as yellow oil, which was used in the next step without further purification.

Step 3: (S)-3-Bromo-5-((R)-1-((S)-1-(3-(trifluoromethyl)phenyl)ethyl)piperidin-3-yl)-4,5-dihydroisoxazole and (S)-3-bromo-5-((R)-1-((R)-1-(3-(trifluoromethyl)phenyl)ethyl)piperidin-3-yl)-4,5-dihydroisoxazole To a solution of 1-[3-(trifluoromethyl)phenyl]ethyl methanesulfonate (1.38 g, 5.14 mmol, N/A purity, 2.0.0 eq) in DMF (10 mL) was added (5S)-3-bromo-5-[(3R)-3-piperidyl]-4,5-dihydroisoxazole (600 mg, 2.57 mmol, N/A purity, 1 eq, TFA), Cs₂CO₃ (2.51 g, 7.72 mmol, 3 eq). The mixture was stirred at 20° C. for 72 h. The mixture was filtered, washed with DCM (50 mL×2). The filtrate was concentrated to yield a residue which was purified by preparative HPLC (column: YMC-Actus Triart C18 100*30 mm*5um; mobile phase: [water (0.1% TFA)-ACN]; B %: 25%-55%, 11 min), followed by lyophilization to yield the reside which was purified by SFC (column: DAICEL CHIRALPAK AY-H (250 mm*30 mm, 5um); mobile phase: [0.1% NH₃H₂O/IPA]; B %: 15%-15%), followed by lyophilization to yield peak 1 and peak 2. Peak 1 was concentrated under reduced pressure to yield a residue which was dissolved in MeCN (20 mL) and H₂O (40 mL) and lyophilized to yield (5S)-3-bromo-5-[(3R)-1-[(1S)-1-[3-(trifluoromethyl)phenyl]ethyl]-3-piperidyl]-4,5-dihydroisoxazole (29.98 mg, 73.98 μmol, 2.9% yield, 100.0% purity, $R_t$=1.513, ee=100.0%, $[\alpha]^{25.6}_D$=+108 (MeOH, c=0.1 g/100 mL) as a white solid. ¹H NMR (400 MHz, CDCl₃) δ ppm 7.58-7.48 (m, 3H), 7.47-7.40 (m, 1H), 4.49 (q, J=9.3 Hz, 1H), 3.55 (q, J=6.5 Hz, 1H), 3.26-3.12 (m, 2H), 3.06-2.93 (m, 1H), 2.70 (d, J=11.0 Hz, 1H), 1.98-1.83 (m, 3H), 1.6-1.52 (m, 3H), 1.40 (d, J=6.7 Hz, 3H), 1.10-0.94 (m, 1H); ES-LCMS m/z 405.1, 407.1 [M+H]⁺. Peak 2 was concentrated under reduced pressure to yield a residue which was dissolved in MeCN (20 mL) and H₂O (40 mL) and lyophilized to yield (S)-3-bromo-5-((R)-1-((R)-1-(3-(trifluoromethyl)phenyl)ethyl)piperidin-3-yl)-4,5-dihydroisoxazole (15.49 mg, 38.22 μmol, 1.5% yield, 100.0% purity, $R_t$=1.988, ee=100.0%, $[\alpha]^{25.6}_D$=+72 (MeOH, c=0.1 g/100 mL) as a white solid. ¹H NMR (400 MHz, CDCl₃) δ ppm 7.60-7.39 (m, 4H), 4.53-4.41 (m, 1H), 3.66 (s, 1H), 3.17 (dd, J=10.4, 17.0 Hz, 1H), 3.02-2.78 (m, 3H), 2.16-1.86 (m, 3H), 1.79-1.54 (m, 3H), 1.42 (d, J=5.1 Hz, 3H), 1.02 (d, J=7.8 Hz, 1H); ES-LCMS m/z 405.1, 407.1 [M+H]⁺.

I-305

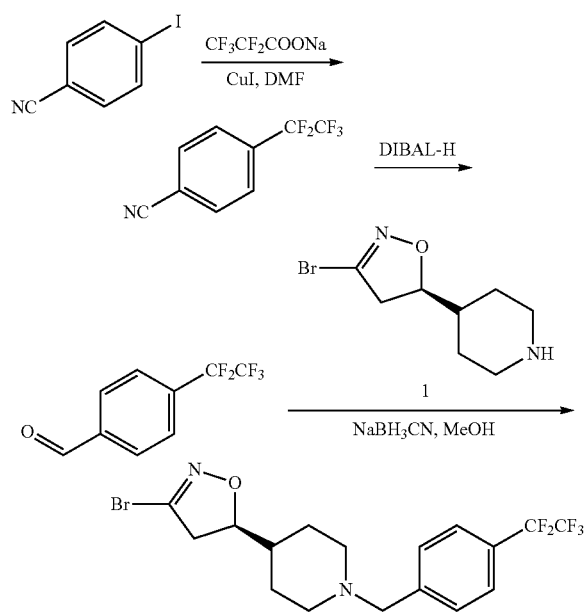

Step 1: 4-(1,1,2,2,2-Pentafluoroethyl)benzonitrile

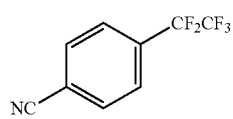

To a solution of 4-iodobenzonitrile (1 g, 4.37 mmol, 1 eq) and 2,2,3,3,3-pentafluoropropanoyloxysodium (2.11 g, 11.35 mmol, 2.6 eq) in DMF (12 mL) was added CuI (2.16 g, 11.35 mmol, 2.6 eq) under N₂ atmosphere. The mixture was stirred at 150° C. for 4 h under microwave (2 bar). TLC (PE/EtOAc=10/1, $R_f$=0.79) indicated the starting material was consumed completely and two new spots formed. The reaction mixture from another batch was combined with this batch and worked up together. The combined reaction mixture was quenched by addition of water (100 mL), NH₃·H₂O (10 mL) and extracted with EtOAc (60 mL×3). The combined organic layers were washed with brine (30 mL), dried over Na₂SO₄, filtered and concentrated under reduced pressure to yield a residue which was purified by flash silica gel chromatography (from PE/EtOAc=1/0 to 10/1, TLC: PE/EtOAc=10/1, $R_f$=0.79) to yield 4-(1,1,2,2,2-pentafluoroethyl)benzonitrile (850 mg, 3.65 mmol, 41.8% yield, 95.0% purity) as yellow oil. ¹H NMR (400 MHz, CDCl₃) δ ppm 7.87-7.80 (m, 2H), 7.79-7.72 (m, 2H); ES-LCMS no desired m/z was found.

Step 2: 4-(1,1,2,2,2-Pentafluoroethyl)benzaldehyde

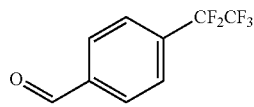

To a solution of 4-(1,1,2,2,2-pentafluoroethyl)benzonitrile (400 mg, 1.72 mmol, 95%, 1 eq) in THF (10 mL) was added DIBAL-H (1 M, 10.31 mL, 6 eq) at −70° C. under N₂ atmosphere. After being stirred for 30 min, the mixture was stirred at 20° C. for 1.5 h. TLC (PE/EtOAc=10/1, $R_f$=0.62) indicated half of the starting material was remained and one new spot formed. The reaction mixture was quenched by addition of NH₄Cl (20 mL) and extracted with EtOAc (50 mL×3). The combined organic layers were washed with brine (10 mL), dried over Na₂SO₄, filtered and concentrated under reduced pressure to yield a residue which was purified by preparative TLC (PE/EtOAc=10/0, TLC: PE/EtOAc=10/1, $R_f$=0.62) to yield 4-(1,1,2,2,2-pentafluoroethyl)benzaldehyde (200 mg, 446.18 μmol, 25.9% yield, 50.0% purity) as yellow oil. ¹H NMR (400 MHz, CDCl₃) δ ppm 10.13 (s, 1H), 8.04 (d, J=8.6 Hz, 2H), 7.81 (d, J=8.2 Hz, 2H); ES-LCMS no desired m/z was found.

Step 3: (5R)-3-Bromo-5-[1-[[4-(1,1,2,2,2-pentafluoroethyl)phenyl]methyl]-4-piperidyl]-4,5-dihydroisoxazole

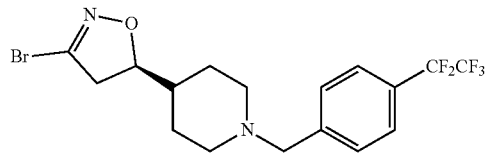

To a solution of 4-(1,1,2,2,2-pentafluoroethyl)benzaldehyde (180 mg, 401.56 μmol, 50% purity, 1 eq) in MeOH (8 mL) was added (5R)-3-bromo-5-(4-piperidyl)-4,5-dihydroisoxazole (219.51 mg, 518.54 μmol, 82% purity, 1.29 eq, TFA) and Et₃N (40.63 mg, 401.56 μmol, 55.89 μL, 1 eq) at 60° C. for 2 h under N₂ atmosphere. NaBH₃CN (126.17 mg, 2.01 mmol, 5 eq) was added. The mixture was stirred at 25° C. for 1 h. The mixture was neutralized with 2 N NaOH to pH 8. The mixture was concentrated, diluted with water (80 mL) and extracted with EtOAc (50 mL×3). The combined organic layers were washed with brine (50 mL), dried over Na₂SO₄, filtered and concentrated to yield a residue which was purified by preparative HPLC (column: Agela DuraShell C18 150*25 mm*5 um; mobile phase: [water (0.04% NH₃H₂O+10 mM NH₄HCO₃)-ACN]; B %: 70%-100%, 10 min) to yield (5R)-3-bromo-5-[1-[[4-(1,1,2,2,2-pentafluoroethyl)phenyl]methyl]-4-piperidyl]-4,5-dihydroisoxazole (22.35 mg, 49.64 μmol, 12.4% yield, 98.0% purity, [α]$^{23.4}_D$=−14.7 (MeOH, c=0.03 g/100 mL)) as white oil. ¹H NMR (400 MHz, CDCl₃) δ ppm 7.55 (d, J=7.8 Hz, 2H), 7.46 (d, J=6.8 Hz, 2H), 4.56-4.43 (m, 1H), 3.55 (s, 2H), 3.20 (dd, J=10.6, 17.2 Hz, 1H), 2.96 (dd, J=8.9, 17.2 Hz, 3H), 1.99 (s, 2H), 1.85 (d, J=13.0 Hz, 1H), 1.69 (s, 1H), 1.46-1.22 (m, 2H), 0.92-0.78 (m, 1H); ES-LCMS m/z 441.1, 443.1 [M+H]⁺.

I-306 & I-307

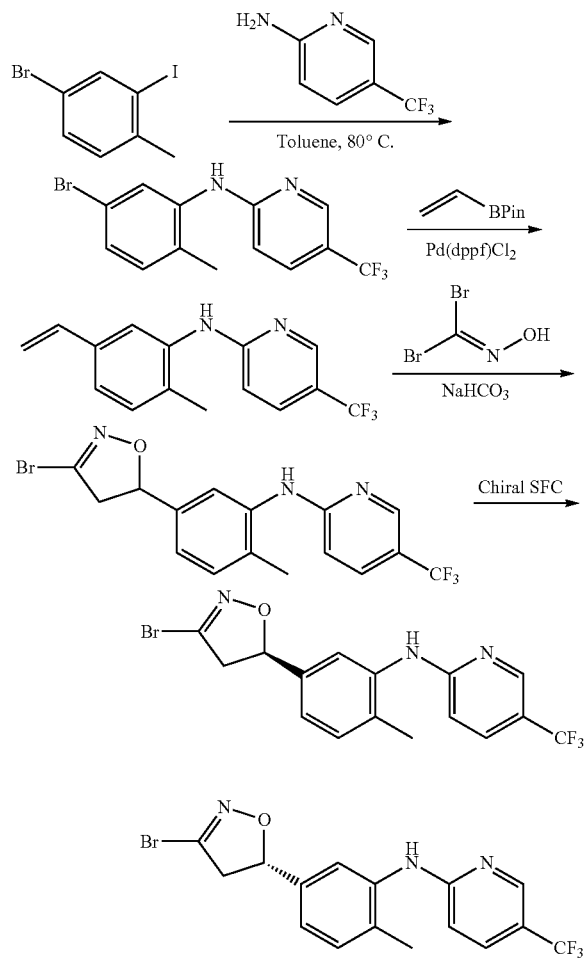

Step 1: N-(5-Bromo-2-methylphenyl)-5-(trifluoromethyl)pyridin-2-amine

To a solution of 4-bromo-2-iodo-1-methyl-benzene (1 g, 3.37 mmol, 1.3 eq) 5-(trifluoromethyl)pyridin-2-amine (419.97 mg, 2.59 mmol, 1 eq) and Cs₂CO₃ (1.69 g, 5.18 mmol, 2 eq) in toluene (25 mL) was added Ruphos (181.33 mg, 388.59 μmol, 0.15 eq) and Pd₂(dba)₃ (118.61 mg, 129.53 μmol, 0.05 eq) under N₂ atmosphere. The mixture was stirred at 80° C. for 3 h. The reaction mixture was quenched by addition of water (30 mL) and extracted with EtOAc (30 mL×3). The combined organic layers were washed with brine (40 mL), dried over Na₂SO₄, filtered and concentrated under reduced pressure to yield a residue which was purified by flash silica gel chromatography (from pure PE to PE/EtOAc=1/3, TLC: PE/EtOAc=3/1, R$_f$=0.60) to yield N-(5-bromo-2-methyl-phenyl)-5-(trifluoromethyl)pyridin-2-amine (330 mg, 627.85 μmol, 24.2% yield, 63.0% purity) as yellow oil. ¹H NMR (400 MHz, CDCl₃) δ ppm 8.45 (br s, 1H), 7.64-7.63 (m, 2H), 7.44-7.43 (m, 2H), 7.16-7.15 (m, 1H), 2.23 (s, 3H).

Step 2: N-(2-Methyl-5-vinylphenyl)-5-(trifluoromethyl)pyridin-2-amine

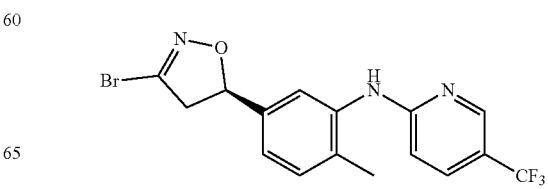

To a solution of N-(5-bromo-2-methyl-phenyl)-5-(trifluoromethyl)pyridin-2-amine (300 mg, 570.77 μmol, 63.0% purity, 1 eq) and 4,4,5,5-tetramethyl-2-vinyl-1,3,2-dioxaborolane (105.49 mg, 684.93 μmol, 116.18 μl, 1.2 eq) in 1,4-dioxane (5 mL) and H₂O (1 mL) was added K₂CO₃ (118.33 mg, 856.16 μmol, 1.5 eq) and Pd(dppf)Cl₂ (20.88 mg, 28.54 μmol, 0.05 eq) under N₂ atmosphere. The mixture was stirred at 90° C. for 2 h. The reaction mixture was quenched by addition of water (8 mL) and extracted with EtOAc (10 mL×3). The combined organic layers were washed with brine (10 mL), dried over Na₂SO₄, filtered and concentrated under reduced pressure to yield a residue which was purified by flash silica gel chromatography (from pure PE to PE/EtOAc=3/1, TLC: PE/EtOAc=3/1, R$_f$=0.65) to yield N-(2-methyl-5-vinyl-phenyl)-5-(trifluoromethyl)pyridin-2-amine (110 mg, 351.81 μmol, 61.6% yield, 89.0% purity) as a yellow oil. ¹H NMR (400 MHz, CDCl₃) δ ppm 8.41 (s, 1H), 7.65-7.56 (m, 2H), 7.42-7.38 (m, 2H), 6.56 (d, J=8.4 Hz, 2H), 5.70 (d, J=17.6 Hz, 1H), 5.23 (d, J=11.2 Hz, 1H), 2.28 (s, 3H); ES-LCMS m/z 279.2 [M+H]⁺.

Step 3: (R)—N-(5-(3-Bromo-4,5-dihydroisoxazol-5-yl)-2-methylphenyl)-5-(trifluoromethyl)pyridin-2-amine and (S)—N-(5-(3-bromo-4,5-dihydroisoxazol-5-yl)-2-methylphenyl)-5-(trifluoromethyl)pyridin-2-amine 487
-continued

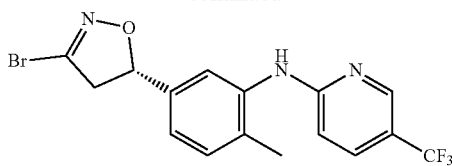

To a solution of N-(2-methyl-5-vinyl-phenyl)-5-(trifluoromethyl)pyridin-2-amine (200 mg, 574.98 µmol, 80% purity, 1 eq) in EtOAc (5 mL) was added NaHCO₃ (483.02 mg, 5.75 mmol, 10 eq) and dibromomethanone oxime (233.25 mg, 1.15 mmol, 2 eq) under N₂ atmosphere. The mixture was stirred at 30° C. for 12 h. The reaction mixture was quenched by addition of water (10 mL) and extracted with EtOAc (10 mL×3). The combined organic layers were washed with brine (10 mL), dried over Na₂SO₄, filtered and concentrated under reduced pressure to yield a residue which was purified by preparative HPLC (column: YMC-Actus Triart C18 150*30 mm*5 µm; mobile phase: [water (0.225% FA)-ACN]; B %: 54%-81%, 11 min) to yield desired product which was separated by SFC (column: DAICEL CHIRALPAK AD (250 mm*30 mm, 10 um); mobile phase: [0.1% NH₃H₂O EtOH]; B %: 35%-35%) to yield peak 1 and peak 2. Peak 1 was concentrated under reduced pressure to yield a residue which was dissolved in MeCN (2 mL) and water (15 mL) and lyophilized to yield N-[5-[(5R)-3-bromo-4,5-dihydroisoxazol-5-yl]-2-methyl-phenyl]-5-(trifluoromethyl)pyridin-2-amine (21.74 mg, 51.88 µmol, 9.0% yield, 95.5% purity, SFC: R$_f$=4.631, ee=100%, [α]$^{26.9}_D$=+156.571 (DMSO, c=0.175 g/100 mL)) as a white solid. ¹H NMR (400 MHz, CDCl₃) δ ppm 8.44 (s, 1H), 7.66 (dd, J=2.0, 8.8 Hz, 1H), 7.45 (s, 1H), 7.32 (d, J=7.6 Hz, 1H), 7.13 (dd, J=1.2, 7.6 Hz, 1H), 6.60 (d, J=8.8 Hz, 1H), 6.55 (s, 1H), 5.70-5.62 (m, 1H), 3.63 (m, 1H), 3.22 (m, 1H), 2.29 (s, 3H); ES-LCMS m/z 402.1 [M+H]⁺. Peak 2 was concentrated under reduced pressure to yield a residue which was dissolved in MeCN (2 mL) and water (15 mL) and lyophilized to yield N-[5-[(5S)-3-bromo-4,5-dihydroisoxazol-5-yl]-2-methyl-phenyl]-5-(trifluoromethyl)pyridin-2-amine (23.08 mg, 57.67 µmol, 10.0% yield, 100.0% purity, SFC: R$_f$=6.469, ee=100%, [α]$^{26.9}_D$=−3.429 (DMSO, c=0.175 g/100 mL)) as a white solid. ¹H NMR (400 MHz, CDCl₃) δ ppm 8.44 (s, 1H), 7.66 (d, J=8.8 Hz, 1H), 7.45 (d, J=1.2 Hz, 1H), 7.32 (d, J=7.6 Hz, 1H), 7.13 (dd, J=1.6, 8.0 Hz, 1H), 6.63-6.55 (m, 2H), 5.68-5.63 (m, 1H), 3.66-3.59 (m, 1H), 3.25-3.19 (m, 1H), 2.29 (s, 3H); ES-LCMS m/z 402.1 [M+H]⁺.

I-308 & I-309

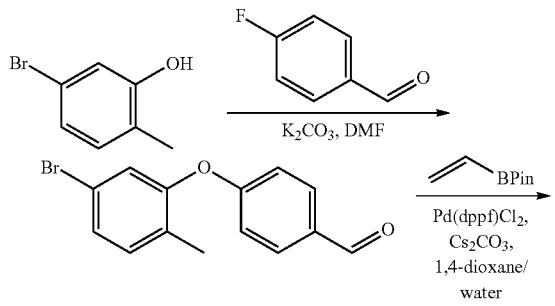

488
-continued

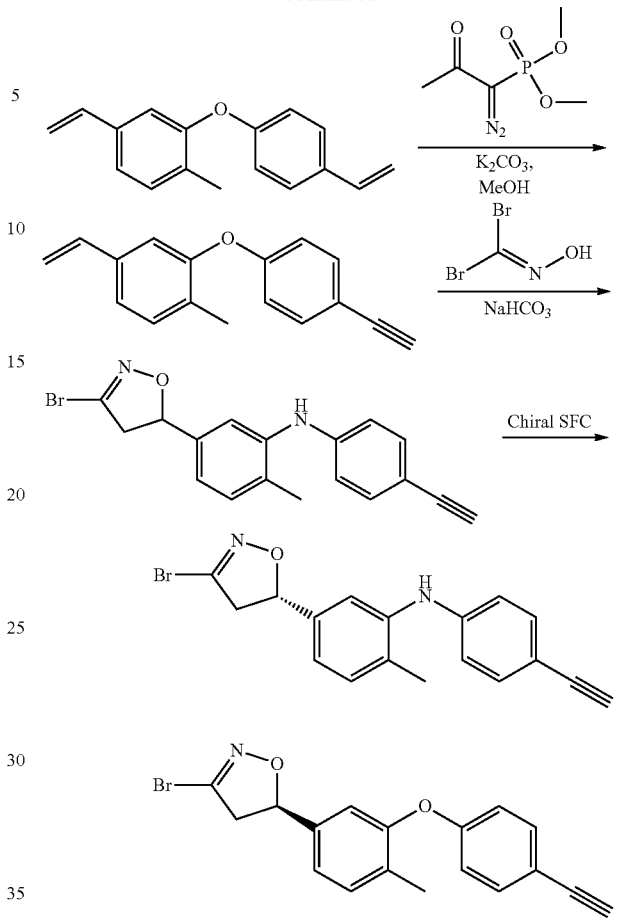

Step 1:
4-(5-Bromo-2-methyl-phenoxy)benzaldehyde

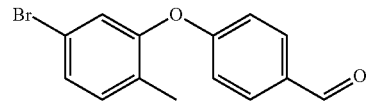 [SMILES: Cc1ccc(Br)cc1Oc1ccc(C=O)cc1]

A mixture of 5-bromo-2-methyl-phenol (1 g, 5.35 mmol, 1 eq), 4-fluorobenzaldehyde (1 g, 8.06 mmol, 1.51 eq) and K₂CO₃ (1.48 g, 10.69 mmol, 2 eq) in DMF (4 mL) was stirred at 120° C. for 12 h. TLC (PE/EtOAc=10/1, R$_f$=0.40) showed the starting material was consumed completely. The reaction mixture was diluted with H₂O (50 mL) and extracted with EtOAc (50 mL×3). The organic layer was washed with brine (50 mL×2), dried over Na₂SO₄, filtered and concentrated under reduced pressure to yield a residue which was purified by flash silica gel chromatography (from PE/EtOAc=100/1 to 10/1, TLC: PE/EtOAc=10/1, R$_f$=0.40) to yield 4-(5-bromo-2-methyl-phenoxy)benzaldehyde (1.5 g, 4.81 mmol, 90.0% yield, 93.4% purity) as colorless oil. ¹H NMR (500 MHz, CDCl₃) δ ppm 9.94 (s, 1H), 7.86 (d, J=8.7 Hz, 2H), 7.30 (dd, J=1.8, 8.1 Hz, 1H), 7.18 (d, J=8.2 Hz, 1H), 7.16 (d, J=1.7 Hz, 1H), 6.99 (d, J=8.7 Hz, 2H), 2.16 (s, 3H); ES-LCMS m/z 291.1, 293.1 [M+H]⁺.

Step 2: 4-(2-Methyl-5-vinyl-phenoxy)benzaldehyde

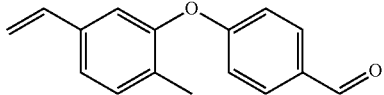 [SMILES: C=Cc1ccc(C)c(Oc2ccc(C=O)cc2)c1]

A mixture of 4-(5-bromo-2-methyl-phenoxy)benzaldehyde (1 g, 3.21 mmol, 93.4% purity, 1 eq), 4,4,5,5-tetramethyl-2-vinyl-1,3,2-dioxaborolane (1 g, 6.49 mmol, 1.10 mL, 2.02 eq), Pd(dppf)Cl$_2$ (140 mg, 191.33 µmol, 5.96e-2 eq) and Cs$_2$CO$_3$ (3.14 g, 9.62 mmol, 3 eq) in 1,4-dioxane (20 mL) and H$_2$O (10 mL) was stirred under N$_2$ atmosphere at 90° C. for 2 h. TLC (PE/EtOAc=10/1, R$_f$=0.43) showed the starting material was almost consumed. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by flash silica gel chromatography (from PE/EtOAc=100/1 to 20/1, TLC: PE/EtOAc=10/1, R$_f$=0.43) to yield 4-(2-methyl-5-vinyl-phenoxy)benzaldehyde (800 mg, 2.52 mmol, 78.5% yield, 75.0% purity) as colorless oil. $^1$H NMR (400 MHz, CDCl$_3$) δ ppm 9.92 (s, 1H), 7.86-7.83 (m, 2H), 7.25-7.15 (m, 2H), 7.08 (s, 1H), 6.98 (d, J=8.6 Hz, 2H), 6.66 (dd, J=10.8, 17.6 Hz, 1H), 5.70 (d, J=17.6 Hz, 1H), 5.25 (d, J=10.8 Hz, 1H), 2.17 (s, 3H); ES-LCMS m/z 239.2 [M+H]$^+$.

Step 3: 2-(4-Ethynylphenoxy)-1-methyl-4-vinyl-benzene

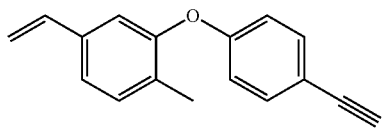 [SMILES: C#Cc1ccc(Oc2cc(C=C)ccc2C)cc1]

A mixture of 4-(2-methyl-5-vinyl-phenoxy)benzaldehyde (300 mg, 944.26 µmol, 75% purity, 1 eq), 1-diazo-1-dimethoxyphosphoryl-propan-2-one (360 mg, 1.87 mmol, 1.98 eq) and K$_2$CO$_3$ (360 mg, 2.60 mmol, 2.76 eq) in MeOH (4 mL) was stirred at 15° C. for 12 h. TLC (PE, R$_f$=0.40) showed the starting material was consumed completely. The reaction mixture was diluted with H$_2$O (20 mL) and extracted with EtOAc (20 mL×3). The organic layer was dried over Na$_2$SO$_4$, filtered and concentrated under reduced pressure to yield a residue which was purified by flash silica gel chromatography (PE, TLC: PE, R$_f$=0.40) to yield 2-(4-ethynylphenoxy)-1-methyl-4-vinyl-benzene (150 mg, 608.22 µmol, 64.4% yield, 95.0% purity) as colorless oil. $^1$H NMR (500 MHz, CDCl$_3$) δ ppm 7.44 (d, J=8.7 Hz, 2H), 7.25-7.20 (m, 1H), 7.20-7.14 (m, 1H), 7.01 (s, 1H), 6.87-6.81 (m, 2H), 6.64 (dd, J=10.9, 17.6 Hz, 1H), 5.67 (d, J=17.5 Hz, 1H), 5.22 (d, J=10.8 Hz, 1H), 3.03 (s, 1H), 2.19 (s, 3H).

Step 4: (5S)-3-Bromo-5-[3-(4-ethynylphenoxy)-4-methyl-phenyl]-4,5-dihydroisoxazole and (5R)-3-bromo-5-[3-(4-ethynylphenoxy)-4-methyl-phenyl]-4,5-dihydroisoxazole

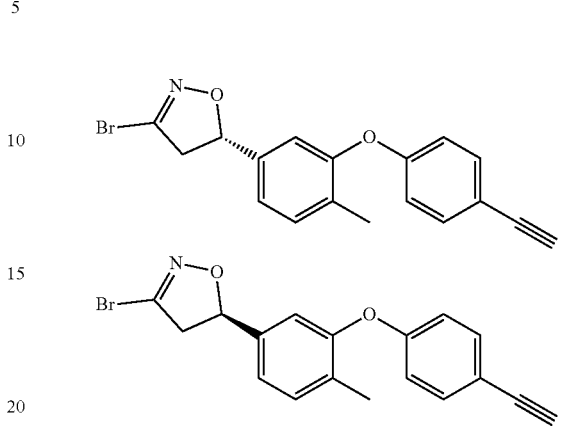

A mixture of 2-(4-ethynylphenoxy)-1-methyl-4-vinyl-benzene (150 mg, 608.22 µmol, 95% purity, 1 eq), dibromomethanone oxime (150 mg, 739.53 µmol, 1.22 eq) and NaHCO$_3$ (500 mg, 5.95 mmol, 9.79 eq) in EtOAc (4 mL) was stirred at 15° C. for 12 h. TLC (PE/EtOAc=3/1, R$_f$=0.45) showed the starting material was consumed completely. The reaction mixture was diluted with H$_2$O (20 mL) and extracted with EtOAc (20 mL×3). The organic layer was dried over Na$_2$SO$_4$, filtered and concentrated under reduced pressure to yield a residue which was purified by flash silica gel chromatography (from PE/EtOAc=100/1 to 10/1, TLC: PE/EtOAc=3/1, R$_f$=0.45). The desired fraction was concentrated under reduced pressure to yield a residue which was separated by chiral SFC (column: DAICEL CHIRALCEL OJ-H (250 mm*30 mm, 5um); mobile phase: [0.1% NH$_3$H$_2$O/EtOH]; B %: 35%-35%) to yield peak 1 and peak 2. Peak 1 was concentrated under reduced pressure to yield a residue which was dissolved in MeCN (10 mL) and water (10 mL) and lyophilized to yield (5S)-3-bromo-5-[3-(4-ethynylphenoxy)-4-methyl-phenyl]-4,5-dihydroisoxazole (42.34 mg, 118.86 µmol, 19.5% yield, 100.0% purity, SFC: R$_t$=4.321, ee=99.90%, [α]$^{22.3}_D$=−147.27 (MeOH, c=0.110 g/100 mL)) as a colorless gum. $^1$H NMR (500 MHz, CDCl$_3$) δ ppm 7.44 (d, J=8.9 Hz, 2H), 7.30 (d, J=8.1 Hz, 1H), 7.10 (dd, J=1.8, 7.9 Hz, 1H), 6.93 (d, J=1.7 Hz, 1H), 6.82 (d, J=8.9 Hz, 2H), 5.61 (dd, J=9.2, 10.8 Hz, 1H), 3.58 (dd, J=10.8, 17.2 Hz, 1H), 3.18 (dd, J=9.2, 17.2 Hz, 1H), 3.03 (s, 1H), 2.21 (s, 3H); ES-LCMS m/z 356.1, 358.1 [M+H]$^+$. Peak 2 was concentrated under reduced pressure to yield a residue which was dissolved in MeCN (10 mL) and water (10 mL) and lyophilized to yield (5R)-3-bromo-5-[3-(4-ethynylphenoxy)-4-methyl-phenyl]-4,5-dihydroisoxazole (47.98 mg, 133.14 µmol, 21.9% yield, 98.8% purity, SFC: R$_t$=4.811, ee=98.48%, [α]$^{22.1}_D$=+144.00 (MeOH, c=0.100 g/100 mL)) as a colorless gum. $^1$H NMR (500 MHz, CDCl$_3$) δ ppm 7.44 (d, J=8.9 Hz, 2H), 7.32-7.28 (m, 1H), 7.10 (dd, J=1.8, 7.9 Hz, 1H), 6.93 (d, J=1.8 Hz, 1H), 6.82 (d, J=8.9 Hz, 2H), 5.61 (dd, J=9.2, 10.7 Hz, 1H), 3.58 (dd, J=10.8, 17.2 Hz, 1H), 3.18 (dd, J=9.0, 17.2 Hz, 1H), 3.03 (s, 1H), 2.21 (s, 3H); ES-LCMS m/z 356.1, 358.1 [M+H]$^+$.

I-237

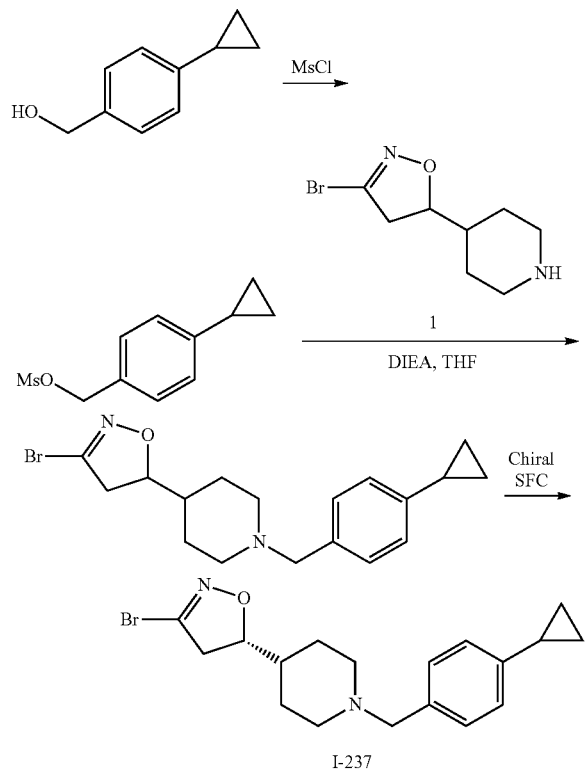

Step 1: (4-Cyclopropylphenyl)methyl methanesulfonate

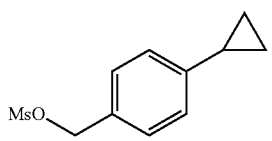 [SMILES: CS(=O)(=O)OCc1ccc(C2CC2)cc1]

To a solution of (4-cyclopropylphenyl)methanol (300 mg, 2.02 mmol, 1 eq) in DCM (5 mL) was added Et$_3$N (614.51 mg, 6.07 mmol, 845.27 μL, 3 eq) and MsCl (278.26 mg, 2.43 mmol, 188.01 μL, 1.2 eq) at 0° C. The mixture was stirred at 25° C. for 2 h. TLC (PE/EtOAc=3/1, R$_f$=0.47) indicated the starting material was consumed completely and one new spots formed. To the ice water was added the reaction mixture slowly and the mixture was adjusted pH to 7-8 by sat. aq. NaHCO$_3$. The mixture was extracted with EtOAc (30 mL×3). The combined organic layer was dried over anhydrous Na$_2$SO$_4$, filtered and concentrated in vacuum to yield (4-cyclopropylphenyl) methyl methanesulfonate (300 mg, 1.06 mmol, 52.4% yield, 80.0% purity) as yellow oil, which was used in the next step without further purification. $^1$H NMR (400 MHz, CDCl$_3$) δ ppm 7.35 (d, J=7.8 Hz, 1H), 7.29 (s, 1H), 7.13 (d, J=8.2 Hz, 1H), 7.06 (d, J=8.2 Hz, 1H), 3.37 (q, J=7.3 Hz, 3H), 3.18-3.05 (m, 2H), 1.91 (d, J=7.8 Hz, 1H), 1.09-1.01 (m, 1H), 0.98 (dd, J=1.8, 8.4 Hz, 1H), 0.76-0.68 (m, 2H).

Step 2: (S)3-Bromo-5-[1-[(4-cyclopropylphenyl)methyl]-4-piperidyl]-4,5-dihydroisoxazole

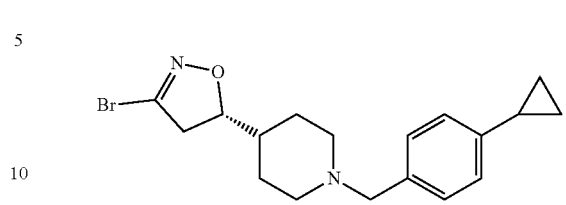

To a solution of 3-bromo-5-(4-piperidyl)-4,5-dihydroisoxazole (400 mg, 1.04 mmol, 1 eq, TFA) in THF (8 mL) was added Et$_3$N (629.65 mg, 6.22 mmol, 866.09 μL, 6.00 eq) and (4-cyclopropylphenyl)methyl methanesulfonate (293.35 mg, 1.04 mmol, 1 eq). The mixture was stirred under N$_2$ atmosphere at 28° C. for 4 h. TLC (PE/EtOAc=3/1, R$_f$=0.40) indicated the starting material was consumed completely and one new spots formed. The mixture was diluted with water (30 mL) and extracted with EtOAc (30 mL×3). The combined organic phase was washed with brine (20 mL), dried over anhydrous Na$_2$SO$_4$, filtered and concentrated in vacuum to yield a residue which was purified by preparative HPLC (column: Agela DuraShell C18 150*25 mm*5 μm; mobile phase: [water (0.05% NH$_3$·H$_2$O+10 mM NH$_4$HCO$_3$)-ACN]; B %: 55%-85%, 10 min), followed by lyophilization to yield product. The product was separated by SFC (column: DAICEL CHIRALPAK AD-H (250 mm*30 mm, 5 μm); mobile phase: [0.1% NH$_3$·H$_2$O EtOH]; B %: 25%-25%) to yield peak 1 (R$_t$=1.333 min, ee=99.06%) and peak 2 (R$_t$=1.417 min, ee=94.90%). Peak 2 was concentrated under reduced pressure to yield a residue which was dissolved in MeCN (20 mL) and H$_2$O (40 mL) and lyophilized to yield (S)3-bromo-5-[1-[(4-cyclopropylphenyl)methyl]-4-piperidyl]-4,5-dihydroisoxazole (38.52 mg, 106.03 μmol, 10.2% yield, 100.0% purity, R$_t$=1.417, ee=94.90%, $[α]^{23}_D$=−87.500 (c=0.032 g/100 mL)) as a white solid. $^1$H NMR (500 MHz, CDCl$_3$) δ ppm 7.21 (d, J=7.8 Hz, 2H), 7.03 (d, J=7.9 Hz, 2H), 4.53-4.43 (m, 1H), 3.52 (s, 2H), 3.17 (dd, J=10.6, 17.2 Hz, 1H), 3.03-2.91 (m, 3H), 2.08-1.92 (m, 2H), 1.91-1.87 (m, 1H), 1.84 (d, J=13.0 Hz, 1H), 1.62 (dd, J=3.8, 7.0 Hz, 1H), 1.54 (s, 1H), 1.47-1.38 (m, 2H), 0.99-0.91 (m, 2H), 0.71-0.67 (m, 2H); ES-LCMS m/z 363.2, 365.2 [M+H]$^+$.

I-242

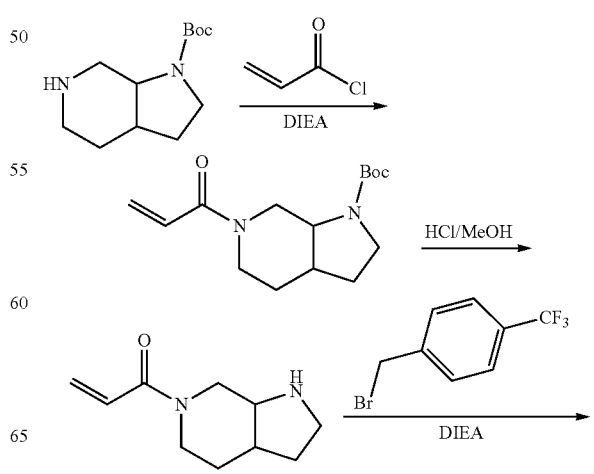

493

-continued

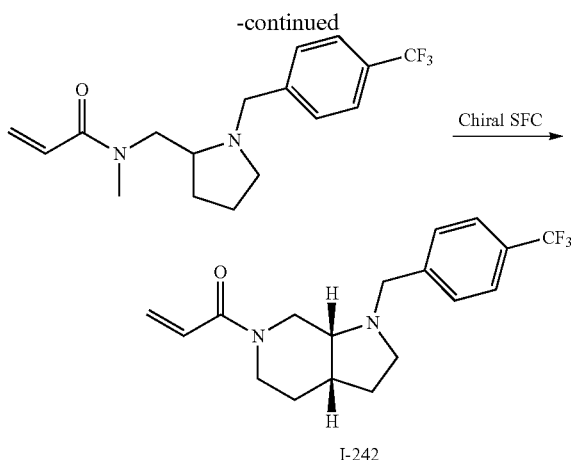

I-242

Step 1: tert-Butyl 6-prop-2-enoyl-3,3a,4,5,7,7a-hexahydro-2H-pyrrolo[2,3-c]pyridine-1-carboxylate

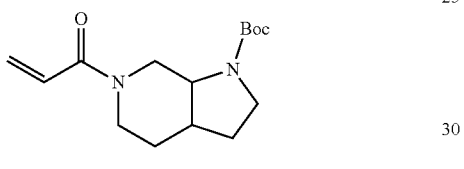

To a solution of tert-butyl 2,3,3a,4,5,6,7,7a-octahydropyrrolo[2,3-c]pyridine-1-carboxylate (1 g, 4.42 mmol, 1 eq) in DCM (10 mL) was added DIEA (1.71 g, 13.26 mmol, 2.31 mL, 3 eq) and prop-2-enoyl chloride (599.88 mg, 6.63 mmol, 540.44 μL, 1.5 eq) at 0° C. The mixture was stirred at 25° C. for 1 h. TLC (PE/EtOAc=3/1, $R_f$=0.45) indicated the starting material was consumed completely and one new spots formed. The mixture was quenched with water (30 mL) and extracted with DCM (30 mL×3). The combined organic phase was washed with brine (20 mL), dried over anhydrous $Na_2SO_4$, filtered and concentrated in vacuum to yield a residue which was purified by flash silica gel chromatography (from PE/EtOAc=100/1 to 3/1, TLC: PE/EtOAc=3/1, $R_f$=0.45) to yield tert-butyl 6-prop-2-enoyl-3,3a,4,5,7,7a-hexahydro-2H-pyrrolo[2,3-c]pyridine-1-carboxylate (1.1 g, 3.81 mmol, 86.1% yield, 97.0% purity) as yellow oil. $^1$H NMR (500 MHz, $CDCl_3$) δ ppm 6.68 (dd, J=10.5, 16.6 Hz, 1H), 6.34-6.30 (m, 1H), 5.69 (d, J=10.4 Hz, 1H), 3.98 (dd, J=5.3, 14.2 Hz, 1H), 3.76 (s, 2H), 3.38 (d, J=5.2 Hz, 2H), 3.15-3.06 (m, 1H), 2.50-2.38 (m, 2H), 1.90 (d, J=4.9 Hz, 3H), 1.58 (d, J=5.0 Hz, 1H), 1.46 (s, 9H); ES-LCMS m/z 281.3 [M+H]$^+$.

Step 2: 1-(1,2,3,3a,4,5,7,7a-Octahydropyrrolo[2,3-c]pyridin-6-yl)prop-2-en-1-one

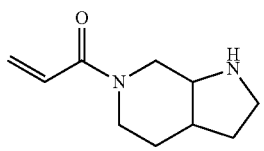

A mixture of tert-butyl 6-prop-2-enoyl-3,3a,4,5,7,7a-hexahydro-2H-pyrrolo[2,3-c]pyridine-1-carboxylate (1.1 g, 3.81 mmol, 1 eq) in TFA (4 mL) and DCM (10 mL) was stirred under $N_2$ atmosphere at 25° C. for 1 h. The reaction mixture was concentrated under reduced pressure to yield 1-(1,2,3,3a,4,5,7,7a-octahydropyrrolo[2,3-c]pyridin-6-yl)prop-2-en-1-one (1.1 g, 3.70 mmol, 97.2% yield, 99.0%, TFA) as yellow oil, which was used in the next step without further purification. $^1$H NMR (500 MHz, $CDCl_3$) δ ppm 6.70-6.45 (m, 1H), 6.20 (d, J=16.6 Hz, 1H), 5.80 (d, J=10.5 Hz, 1H), 4.81 (d, J=15.0 Hz, 1H), 3.99 (d, J=13.0 Hz, 1H), 3.88 (s, 1H), 3.63-3.41 (m, 2H), 3.32 (d, J=15.7 Hz, 1H), 3.20 (t, J=11.8 Hz, 1H), 2.60 (s, 1H), 2.66-2.55 (m, 1H), 2.34-2.22 (m, 1H), 1.93 (d, J=10.1 Hz, 2H), 1.73 (d, J=10.4 Hz, 1H); ES-LCMS m/z 181.2 [M+H]$^+$.

Step 3: 1-[(3aR,7aR)-1-[[4-(Trifluoromethyl)phenyl]methyl]-3,3a,4,5,7,7a-hexahydro-2H-pyrrolo[2,3-c]pyridin-6-yl]prop-2-en-1-one To a solution of 1-(1,2,3,3a,4,5,7,7a-octahydropyrrolo[2,3-c]pyridin-6-yl)prop-2-en-1-one (400 mg, 1.35 mmol, 1 eq, TFA) in DCM (10 mL) was added DIEA (1.04 g, 8.07 mmol, 1.41 mL, 6 eq) and 1-(bromomethyl)-4-(trifluoromethyl)benzene (321.67 mg, 1.35 mmol, 207.53 μL, 1 eq). The mixture was stirred at 25° C. for 1 h. The mixture was diluted with water (30 mL) and extracted with DCM (30 mL×3). The combined organic phase was washed with brine (20 mL), dried over anhydrous $Na_2SO_4$, filtered and concentrated in vacuum to yield a residue which was purified by flash silica gel chromatography (from PE/EtOAc=100/1 to 1/1, TLC: PE/EtOAc=1/1, $R_f$=0.35) to yield the product. The product was separated by SFC (column: DAICEL CHIRALPAK IG (250 mm*30 mm, 10 μm); mobile phase: [0.1% $NH_3 \cdot H_2O$/EtOH]; B %: 20%-20%) to yield peak 1 ($R_t$=2.662 min, ee=99.87%) and peak 2 ($R_t$=2.968 min, ee=99.72%). Peak 1 was purified by preparative HPLC (column: Agela DuraShell C18 150*25 mm*5 μm; mobile phase: [water (0.05% $NH_3 \cdot H_2O$+10 mM $NH_4HCO_3$)-ACN]; B %: 44%-74%, 10 min), followed by lyophilization to yield 1-[(3aR,7aR)-1-[[4-(trifluoromethyl)phenyl]methyl]-3,3a,4,5,7,7a-hexahydro-2H-pyrrolo[2,3-c]pyridin-6-yl]prop-2-en-1-one (14.24 mg, 42.08 μmol, 3.1% yield, 100.0% purity, SFC: $R_t$=2.662, ee=99.87%, $[α]^{23.1}_D$=+20.689 (MeOH, c=0.029 g/100 mL)) as colorless oil. $^1$H NMR (400 MHz, $CDCl_3$) δ ppm 7.60-7.47 (m, 2H), 7.39 (t, J=7.8 Hz, 2H), 6.61 (dd, J=10.6, 16.8 Hz, 1H), 6.67-6.17 (m, 1H), 5.77-5.46 (m, 1H), 4.26-4.18 (m, 1H), 4.06-3.89 (m, 1H), 3.86-3.59 (m, 1H), 3.51-3.41 (m, 1H), 3.39-3.28 (m, 1H), 3.25-3.11 (m, 1H), 3.02-2.82 (m, 1H), 2.75-2.64 (m, 1H), 2.40-2.28 (m, 1H), 2.26-2.13 (m, 1H), 1.98-1.87 (m, 1H), 1.78 (d, J=5.9 Hz, 1H), 1.70-1.64 (m, 1H), 1.56-1.42 (m, 1H); ES-LCMS m/z 339.2 [M+H]$^+$.

I-386

Step 1: tert-Butyl N-[(3R)-1-prop-2-enoylpyrrolidin-3-yl]carbamate

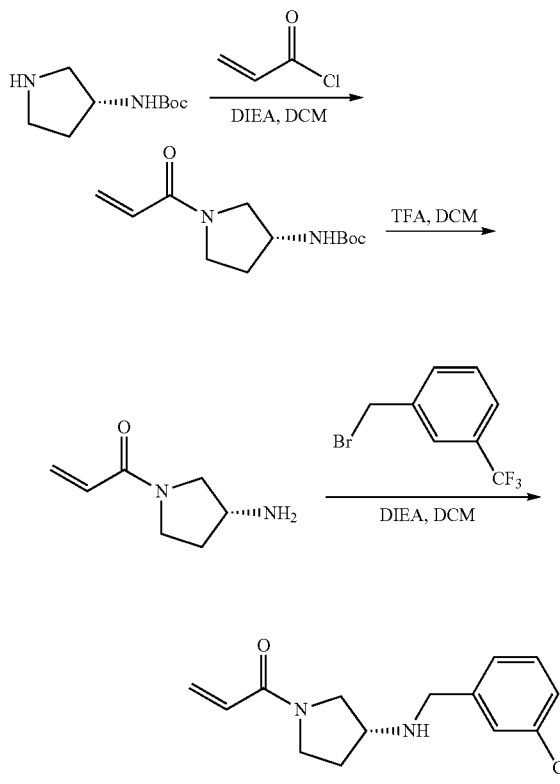

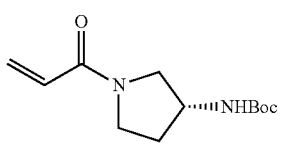 [SMILES: C=CC(=O)N1CC[C@@H](NC(=O)OC(C)(C)C)C1]

To a solution of tert-butyl N-[(3R)-pyrrolidin-3-yl]carbamate (2 g, 10.74 mmol, 1 eq) in DCM (25 mL) was added DIEA (5.94 g, 45.93 mmol, 8 mL, 4.28 eq) and prop-2-enoyl chloride (1.22 g, 13.49 mmol, 1.1 mL, 1.26 eq) dropwise at 0° C. The mixture was stirred at 0° C. for 1 h. TLC (PE/EtOAc=1/1, $R_f$=0.24) showed the starting material was consumed completely. The reaction mixture was diluted with $H_2O$ (50 mL) and extracted with EtOAc (50 mL×3). The combined organic layers dried over $Na_2SO_4$, filtered and concentrated under reduced pressure to yield a residue which was purified by flash silica gel chromatography (from PE/EtOAc=100/1 to 1/1, TLC: PE/EtOAc=1/1, $R_f$=0.24) to yield tert-butyl N-[(3R)-1-prop-2-enoylpyrrolidin-3-yl]carbamate (2 g, 7.49 mmol, 69.8% yield, 90.0% purity) as a white solid. $^1$H NMR (400 MHz, $CD_3OD$) δ ppm 6.58 (dt, J=10.4, 17.3 Hz, 1H), 6.26 (td, J=2.3, 16.8 Hz, 1H), 5.74 (td, J=2.5, 10.3 Hz, 1H), 4.20-4.08 (m, 1H), 3.88-3.54 (m, 3H), 3.47-3.33 (m, 1H), 2.24-2.08 (m, 1H), 2.00-1.84 (m, 1H), 1.45 (s, 9H); ES-LCMS m/z 241.3 [M+H]$^+$.

Step 2: 1-[(3R)-3-Aminopyrrolidin-1-yl]prop-2-en-1-one

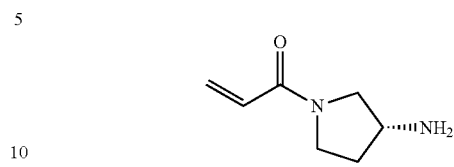

To a solution of tert-butyl N-[(3R)-1-prop-2-enoylpyrrolidin-3-yl]carbamate (200 mg, 749.07 μmol, 1 eq) in DCM (3 mL) was added TFA (2.31 g, 20.26 mmol, 1.5 mL, 27.05 eq). The mixture was stirred at 25° C. for 1 h. TLC (PE/EtOAc=1/1, $R_f$=0.05) showed the starting material was consumed completely. The reaction mixture was concentrated under reduced pressure to yield 1-[(3R)-3-aminopyrrolidin-1-yl]prop-2-en-1-one (105 mg, 413.05 μmol, 55.1% yield, N/A purity, TFA) as colorless oil which was used in the next step without further purification. $^1$H NMR (500 MHz, $CD_3OD$) δ ppm 6.67-6.53 (m, 1H), 6.35-6.26 (m, 1H), 5.79 (dd, J=1.7, 10.5 Hz, 1H), 4.02-3.69 (m, 4H), 3.68-3.62 (m, 1H), 2.50-2.33 (m, 1H), 2.22-2.04 (m, 1H).

Step 3: 1-[(3R)-3-[[3-(Trifluoromethyl)phenyl]methylamino]pyrrolidin-1-yl]prop-2-en-1-one

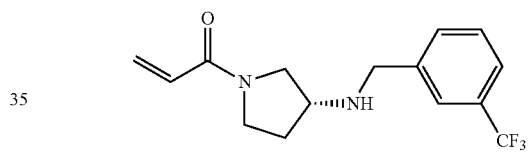

To a solution of 1-[(3R)-3-aminopyrrolidin-1-yl]prop-2-en-1-one (105 mg, 749.02 μmol, 1 eq) in DCM (3 mL) was added DIEA (742.00 mg, 5.74 mmol, 1 mL, 7.66 eq) and 1-(bromomethyl)-3-(trifluoromethyl)benzene (180 mg, 753.04 μmol, 114.65 μL, 1.01 eq). The mixture was stirred at 25° C. for 12 h. TLC (PE/EtOAc=1/1, $R_f$=0.08) showed the starting material was consumed completely. The reaction mixture was diluted with $H_2O$ (20 mL) and extracted with EtOAc (20 mL×3). The organic layer was dried over $Na_2SO_4$, filtered and concentrated under reduced pressure to yield a residue which was purified by preparative HPLC (column: Phenomenex Synergi C18 150*30 mm*4 um; mobile phase: [water (0.05% HCl)-ACN]; B %: 12%-32%, 10 min). The desired compound was basified with saturated aqueous $NaHCO_3$ until pH=8 and extracted with EtOAc (50 mL×3). The organic layer was dried over $Na_2SO_4$, filtered and concentrated under reduced pressure to yield a residue which was dissolved in MeCN (10 mL) and water (10 mL) and lyophilized to yield 1-[(3R)-3-[[3-(trifluoromethyl)phenyl]methylamino]pyrrolidin-1-yl]prop-2-en-1-one (17.41 mg, 58.36 μmol, 7.8% yield, 100.0% purity, ([α]$^{24.5}_D$=+34.783 (MeOH, c=0.023 g/100 mL)) as colorless oil. $^1$H NMR (400 MHz, $CD_3OD$) δ ppm 7.72 (s, 1H), 7.64 (d, J=7.0 Hz, 1H), 7.59-7.55 (m, 1H), 7.55-7.50 (m, 1H), 6.58 (ddd, J=10.6, 14.5, 16.8 Hz, 1H), 6.32-6.22 (m, 1H), 5.78-5.69 (m, 1H), 3.90-3.87 (m, 2H), 3.86-3.68 (m, 2H), 3.68-3.58 (m, 1H), 3.52-3.32 (m, 3H), 2.22-2.10 (m, 1H), 1.97-1.78 (m, 1H); ES-LCMS m/z 299.3 [M+H]$^+$.

I-246

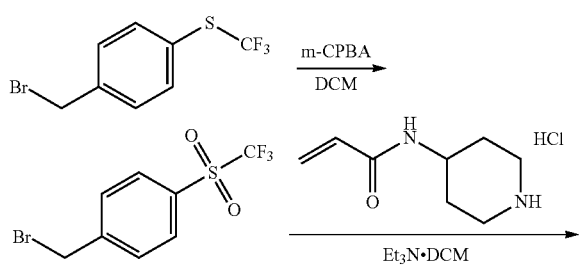

Step 1:
1-(Bromomethyl)-4-(trifluoromethylsulfonyl)benzene

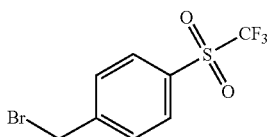

To a solution of 1-(bromomethyl)-4-(trifluoromethylsulfanyl)benzene (250 mg, 922.18 µmol, 1 eq) in DCM (5 mL) was added m-CPBA (1.09 g, 5.35 mmol, 85% purity, 5.80 eq). The mixture was stirred at 40° C. for 16 h. The reaction mixture was added sat.aq. NaHCO₃ until to pH 8 and diluted with H₂O (20 mL), extracted with EtOAc (30 mL×3). The combined organic layers were dried over Na₂SO₄, filtered and concentrated under reduced pressure to yield a residue which was purified by flash silica gel chromatography (from PE/EtOAc=1/0 to 9/1, TLC: PE/EtOAc=3/1, $R_f$=0.65) to yield 1-(bromomethyl)-4-(trifluoromethylsulfonyl)benzene (240 mg, 791.83 µmol, 85.9% yield, 100.0% purity) as colorless oil. ¹H NMR (400 MHz, CDCl₃) δ ppm 8.03 (d, J=8.3 Hz, 2H), 7.70 (d, J=8.6 Hz, 2H), 4.54 (s, 2H).

Step 2: N-[1-[[4-(Trifluoromethylsulfonyl)phenyl]methyl]-4-piperidyl]prop-2-enamide

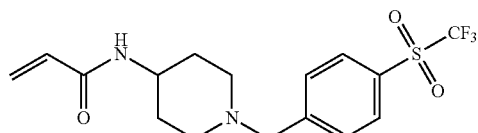

To a solution of 1-(bromomethyl)-4-(trifluoromethylsulfonyl)benzene (100 mg, 329.93 µmol, 1 eq) in DCM (15 mL) was added N-(4-piperidyl)prop-2-enamide (81.78 mg, 428.91 µmol, 1.3 eq, HCl) and Et₃N (100.16 mg, 989.79 µmol, 137.77 µL, 3 eq). The mixture was stirred at 20° C. for 16 h. The reaction mixture was concentrated to yield a residue which was purified by preparative HPLC (column: Agela DuraShell C18 150*25 mm*5 µm; mobile phase: [water (0.04% NH₃H₂O+10 mM NH₄HCO₃)-ACN]; B %: 32%-62%, 10 min). The desired fraction was lyophilization to yield N-[1-[[4-(trifluoromethylsulfonyl)phenyl]methyl]-4-piperidyl]prop-2-enamide (20.59 mg, 54.70 µmol, 16.6% yield, 100.0% purity) as a white solid. ¹H NMR (400 MHz, CDCl₃) δ ppm 7.99 (d, J=8.3 Hz, 2H), 7.65 (d, J=8.6 Hz, 2H), 6.30 (dd, J=1.2, 16.9 Hz, 1H), 6.13-6.03 (m, 1H), 5.66 (dd, J=1.5, 10.3 Hz, 1H), 5.46-5.25 (m, 1H), 3.99-3.88 (m, 1H), 3.63 (s, 2H), 2.81 (d, J=11.7 Hz, 2H), 2.22 (t, J=10.5 Hz, 2H), 1.99 (d, J=12.5 Hz, 2H), 1.56-1.46 (m, 2H); ES-LCMS m/z 377.2 [M+H]⁺.

I-248

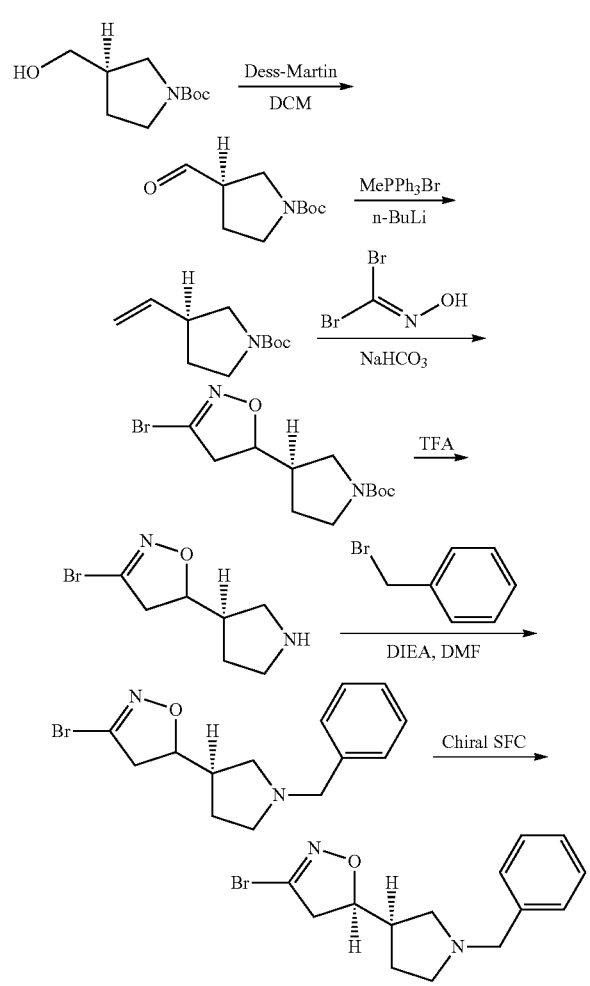

Step 1: tert-Butyl (3R)-3-formylpyrrolidine-1-carboxylate

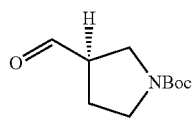

To a solution of tert-butyl (3R)-3-(hydroxymethyl)pyrrolidine-1-carboxylate (8 g, 39.75 mmol, 1 eq) in DCM (100 mL) was added Dess-Martin (20.23 g, 47.70 mmol, 1.2 eq).

The mixture was stirred at 20° C. for 4 h. TLC (PE/EtOAc=3/1, R$_f$=0.30) indicated starting material was consumed completely and one new spot formed. The reaction mixture was quenched by addition of water (500 mL), extracted with EtOAc (500 mL×3). The combined organic layers were washed with brine (400 mL), dried over Na$_2$SO$_4$, filtered and concentrated under reduced pressure to give a residue which was purified by flash silica gel chromatography (from PE/EtOAc=1/0 to 3/1, TLC:PE/EtOAc=3/1, R$_f$=0.30) to yield tert-butyl (3R)-3-formylpyrrolidine-1-carboxylate (6 g, 28.61 mmol, 72.0% yield, 95% purity) as a colorless liquid. $^1$H NMR (400 MHz, CDCl$_3$) δ ppm 9.65 (d, J=1.5 Hz, 1H), 3.66 (d, J=9.5 Hz, 1H), 3.57-3.43 (m, 1H), 3.41-3.25 (m, 2H), 2.99 (s, 1H), 2.24-2.03 (m, 2H), 1.42 (s, 9H)

Step 2: tert-Butyl (3S)-3-vinylpyrrolidine-1-carboxylate

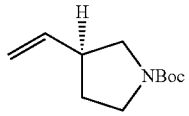

To a solution of methyl(triphenyl)phosphonium; bromide (2.45 g, 6.87 mmol, 1.2 eq) in THF (30 mL) was cooled to −65° C., added n-BuLi (2.75 mL, 2.5 M, 1.2 eq) dropwise under N$_2$ atmosphere. The mixture was stirred at 0° C. for 0.5 h under N$_2$ atmosphere. The mixture was cooled to −65° C. and a solution of tert-butyl (3R)-3-formylpyrrolidine-1-carboxylate (1.2 g, 5.72 mmol, 1 eq) in THF (4 mL) was added slowly. The mixture was stirred at 20° C. for 12 h under N$_2$ atmosphere. TLC (PE/EtOAc=10/1, R$_f$=0.59) indicated starting material was consumed completely and one new spot formed. The reaction mixture was quenched by addition of NH$_4$Cl (50 mL), extracted with EtOAc (50 mL×3). The combined organic layers were washed with brine (40 mL), dried over Na$_2$SO$_4$, filtered and concentrated under reduced pressure to give a residue which was purified by flash silica gel chromatography (from PE/EtOAc=1/0 to 10/1, TLC: PE/EtOAc=10/1, R$_f$=0.59) to yield tert-butyl (3S)-3-vinylpyrrolidine-1-carboxylate (1.05 g, 4.79 mmol, 83.7% yield, 90% purity) as colorless liquid. $^1$H NMR (500 MHz, CDCl$_3$) δ ppm 5.84-5.66 (m, 1H), 5.08 (d, J=17.1 Hz, 1H), 5.01 (d, J=10.4 Hz, 1H), 3.58-3.37 (m, 2H), 3.32-3.20 (m, 1H), 3.09-2.96 (m, 1H), 2.79-2.70 (m, 1H), 2.02-1.94 (m, 1H), 1.71-1.63 (m, 1H), 1.44 (s, 9H).

Step 3: tert-Butyl (3R)-3-(3-bromo-4,5-dihydroisoxazol-5-yl)pyrrolidine-1-carboxylate

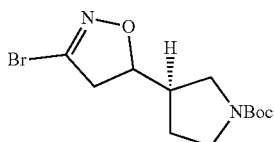

To a solution of tert-butyl (3S)-3-vinylpyrrolidine-1-carboxylate (1.05, 4.79 mmol, 1 eq) in EtOAc (20 mL) was added NaHCO$_3$ (4.02 g, 47.90 mmol, 10 eq) and dibromomethanone oxime (1.17 g, 5.75 mmol, 1.2 eq). The mixture was stirred at 20° C. for 12 h. TLC (PE/EtOAc=3/1, R$_f$=0.34) indicated starting material was consumed completely and one new spot formed. The reaction mixture was quenched by addition of water (50 mL), extracted with EtOAc (50 mL×3). The combined organic layers were washed with brine (40 mL), dried over Na$_2$SO$_4$, filtered and concentrated under reduced pressure to yield tert-butyl (3R)-3-(3-bromo-4,5-dihydroisoxazol-5-yl)pyrrolidine-1-carboxylate (1.2 g, 3.38 mmol, 70.6% yield, 90% purity) as yellow oil. $^1$H NMR (400 MHz, DMSO-d$_6$) δ ppm 4.75-4.48 (m, 1H), 3.40-3.25 (m, 3H), 3.18-3.03 (m, 2H), 2.99-2.81 (m, 1H), 2.45-2.27 (m, 1H), 1.94-1.82 (m, 1H), 1.68-1.45 (m, 1H), 1.35 (s, 9H).

Step 4: 3-Bromo-5-[(3R)-pyrrolidin-3-yl]-4,5-dihydroisoxazole

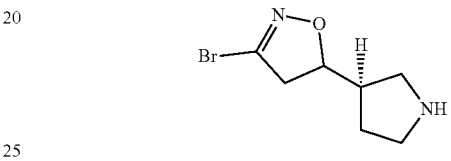

To a solution of tert-butyl (3R)-3-(3-bromo-4,5-dihydroisoxazol-5-yl)pyrrolidine-1-carboxylate (300 mg, 845.88 μmol, 1 eq) in DCM (5 mL) was added TFA (1.35 mL, 18.23 mmol) and the mixture was stirred at 25° C. for 2 h. TLC (PE/EtOAc=3/1, R$_f$=0) indicated starting material was consumed completely and one new spot formed. The reaction mixture was concentrated under reduced pressure to yield 3-bromo-5-[(3R)-pyrrolidin-3-yl]-4,5-dihydroisoxazole (300 mg, 810.56 μmol, 95.8% yield, 90% purity, TFA) as yellow oil. $^1$H NMR (400 MHz, CDCl$_3$) δ ppm 4.82-4.41 (m, 1H), 3.47-2.82 (m, 6H), 2.59-2.39 (m, 1H), 2.15-1.94 (m, 1H), 1.87-1.45 (m, 1H), 1.41-1.31 (m, 1H).

Step 5: (5R)-5-[(3R)-1-Benzylpyrrolidin-3-yl]-3-bromo-4,5-dihydroisoxazole

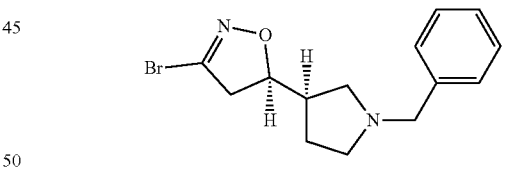

To a solution of 3-bromo-5-[(3R)-pyrrolidin-3-yl]-4,5-dihydroisoxazole (300 mg, 810.56 μmol, 1 eq, TFA) in DMF (3 mL) was added DIEA (523.79 mg, 4.05 mmol, 705.91 μL, 5 eq) and bromomethylbenzene (207.95 mg, 1.22 mmol, 144.41 μL, 1.5 eq). The mixture was stirred at 20° C. for 12 h. The reaction mixture was quenched by addition of water (40 mL), extracted with EtOAc (20 mL×3). The combined organic layers were washed with brine (10 mL), dried over Na$_2$SO$_4$, filtered and concentrated under reduced pressure to yield a residue. which was purified by preparative HPLC (column: Phenomenex Synergi C18 150*30 mm*4 μm; mobile phase: [water (0.05% HCl)-ACN]; B %: 11%-31%, 9 min]; B %: 60%-90%, 10 min) to yield a residue which was separated by SFC (column: DAICEL CHIRALPAK IG (250 mm*30 mm, 10 μm); mobile phase: [0.1% NH$_3$H$_2$O EtOH]; B %: 50%-50%, min) to yield (5R)-5-[(3R)-1- benzylpyrrolidin-3-yl]-3-bromo-4,5-dihydroisoxazole (55.80 mg, 179.02 μmol, 22.1% yield, 99.2% purity, SFC: $R_t$=3.958 min, ee=99.4%; $[\alpha]^{29.0}_D$=−78.0, MeOH, c=0.123 g/100 mL) as yellow oil. $^1$H NMR (400 MHz, CDCl$_3$) δ ppm 7.35-7.27 (m, 4H), 7.26-7.23 (m, 1H), 4.66 (t, J=6.7, 9.6 Hz, 1H), 3.64-3.54 (m, 2H), 3.24-3.15 (m, 1H), 3.13-3.02 (m, 1H), 2.65 (t, J=5.3, 8.7 Hz, 1H), 2.60-2.47 (m, 3H), 2.41-2.31 (m, 1H), 2.12-1.92 (m, 1H), 1.74-1.54 (m, 1H); ES-LCMS m/z 308.8, 310.8 [M+H]$^+$.

I-269

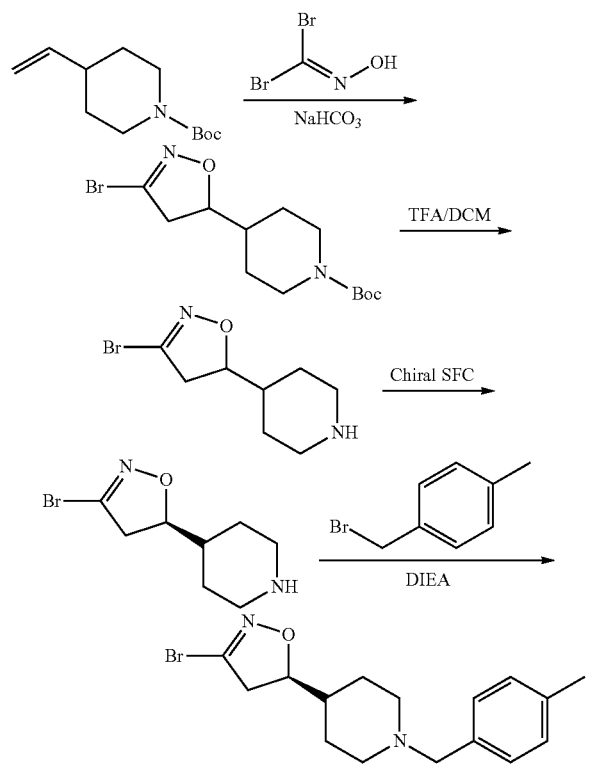

Step 1: tert-Butyl 4-(3-bromo-4,5-dihydroisoxazol-5-yl)piperidine-1-carboxylate

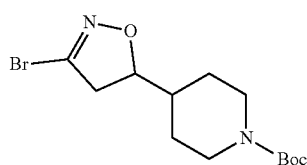 [SMILES: CC(C)(C)OC(=O)N1CCC(C2CC(Br)=NO2)CC1]

To a stirred solution of tert-butyl 4-vinylpiperidine-1-carboxylate (14.5 g, 65.19 mmol, 1 eq) in EtOAc (200 mL) was added NaHCO$_3$ (54.77 g, 651.92 mmol, 10 eq) and dibromomethanone oxime (15.87 g, 78.23 mmol, 1.2 eq). The reaction mixture was stirred at 20° C. for 12 h. TLC (PE/EtOAc=3/1, $R_f$=0.25) showed starting material was consumed completely and one new spot was detected. The reaction mixture was diluted with water (200 mL) then extracted with EtOAc (100 mL×3). The combined organic layers were dried over Na$_2$SO$_4$, filtered and the filtrate was concentrated to yield a residue which was purified by flash silica gel chromatography (from PE/EtOAc=100/1 to 3/1, TLC: PE/EtOAc=3/1, $R_f$=0.25) to yield tert-butyl 4-(3-bromo-4,5-dihydroisoxazol-5-yl)piperidine-1-carboxylate (14 g, 39.91 mmol, 61.2% yield, 95% purity) as yellow oil. $^1$H NMR (400 MHz, CDCl$_3$) δ ppm 4.54-4.41 (m, 1H), 4.26-4.10 (m, 2H), 3.20 (dd, J=10.8, 17.1 Hz, 1H), 2.94 (dd, J=8.8, 17.1 Hz, 1H), 2.67 (s, 2H), 1.82 (d, J=13.2 Hz, 1H), 1.78-1.67 (m, 1H), 1.55 (d, J=13.0 Hz, 1H), 1.45 (s, 9H), 1.25-1.14 (m, 2H).

Step 2: (5R)-3-Bromo-5-(4-piperidyl)-4,5-dihydroisoxazole

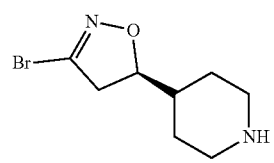 [SMILES: BrC1=NO[C@@H](C2CCNCC2)C1]

To a stirred solution of tert-butyl 4-(3-bromo-4,5-dihydroisoxazol-5-yl)piperidine-1-carboxylate (14 g, 39.91 mmol, 1 eq) in DCM (90 mL) was added TFA (46.20 g, 405.19 mmol, 30 mL, 10.15 eq). The reaction mixture was stirred at 25° C. for 2 h. TLC (PE/EtOAc=3/1, $R_f$=0.25) showed starting material was consumed completely and one new spot was detected. The reaction mixture was concentrated to yield a residue which was dissolved in DCM (100 mL), adjusted pH to 8-9 by Na$_2$CO$_3$ solid then filtered. The filtrate was concentrated to yield a residue which was separated by SFC (column: DAICEL CHIRALPAK AD (250 mm*30 mm, 10 um); mobile phase: [0.1% NH$_3$H$_2$O EtOH]; B %: 30%-30%, min) to yield peak 1 ($R_t$=4.075 min) and peak 2 ($R_t$=4.401 min). Peak 2 was concentrated under reduced pressure to yield a residue which was lyophilized to yield (5R)-3-bromo-5-(4-piperidyl)-4,5-dihydroisoxazole (2.5 g, 9.89 mmol, 24.8% yield, 92.2% purity, SFC: $R_t$=4.401 min, ee=94.50%) as yellow oil. $^1$H NMR (400 MHz, DMSO-d$_6$) δ ppm 4.50-4.34 (m, 1H), 3.32 (d, J=10.8 Hz, 1H), 3.05 (dd, J=8.8, 17.6 Hz, 1H), 2.91 (d, J=11.5 Hz, 2H), 2.38 (q, J=10.0 Hz, 2H), 1.65-1.50 (m, 2H), 1.41 (d, J=12.2 Hz, 1H), 1.13-0.96 (m, 2H); ES-LCMS m/z 233.1, 235.1 [M+H]$^+$.

Step 3: (5R)-3-Bromo-5-[1-(p-tolylmethyl)-4-piperidyl]-4,5-dihydroisoxazole

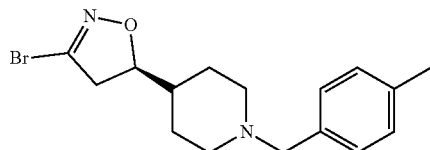

To a stirred solution of (5R)-3-bromo-5-(4-piperidyl)-4,5-dihydroisoxazole (70 mg, 276.87 μmol, 1 eq) in DMF (2 mL) was added DIEA (71.57 mg, 553.74 μmol, 96.45 μL, 2 eq) and 1-(bromomethyl)-4-methyl-benzene (53.80 mg, 290.71 μmol, 1.05 eq). The reaction mixture was stirred at 15° C. for 12 h. The reaction mixture was filtered and the filtrate was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 50%-

80%, 10 min). The desired fraction was lyophilized to yield (5R)-3-bromo-5-[1-(p-tolylmethyl)-4-piperidyl]-4,5-dihydroisoxazole (27.91 mg, 82.76 μmol, 29.9% yield, 100% purity, $[\alpha]^{18.2}_D = -164.0$ (MeOH, c=0.10 g/100 mL)) as white solid. $^1$H NMR (400 MHz, DMSO-d$_6$) δ ppm 7.22-7.04 (m, 4H), 4.51-4.37 (m, 1H), 3.37 (s, 2H), 3.28 (d, J=10.5 Hz, 1H), 3.07 (dd, J=8.8, 17.6 Hz, 1H), 2.79 (d, J=11.2 Hz, 2H), 2.27 (s, 3H), 1.92-1.76 (m, 2H), 1.66 (d, J=12.7 Hz, 1H), 1.51-1.43 (m, 2H), 1.25-1.12 (m, 2H); ES-LCMS m/z 337.2, 339.2 [M+H]$^+$.

I-297

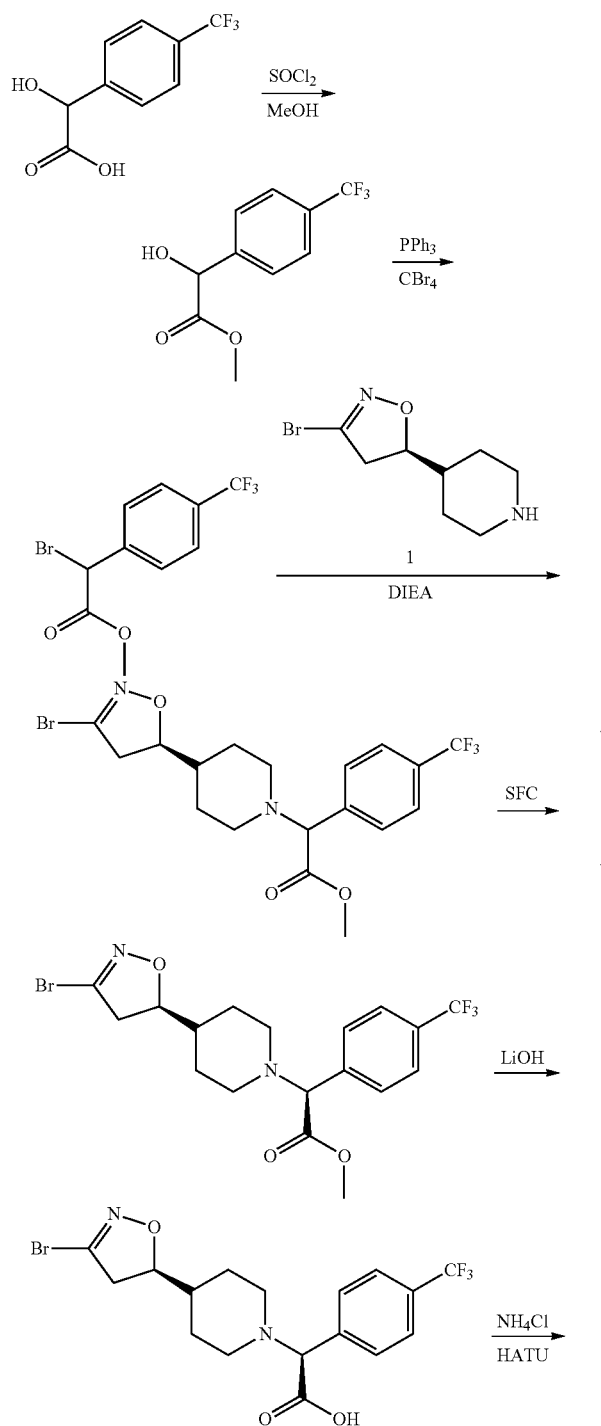

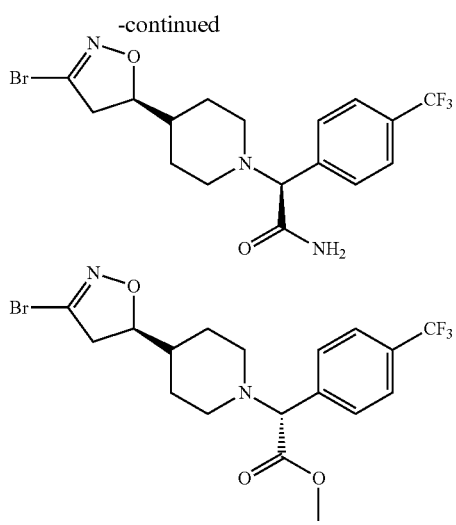

Step 1: Methyl 2-hydroxy-2-[4-(trifluoromethyl)phenyl]acetate

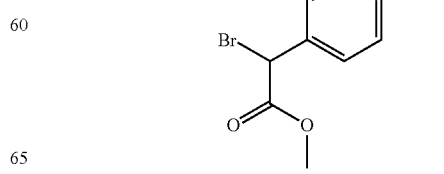

To a solution of 2-hydroxy-2-[4-(trifluoromethyl)phenyl] acetic acid (4.5 g, 20.44 mmol, 1 eq) in MeOH (30 mL) was added DMF (747.02 mg, 10.22 mmol, 786.34 μL, 0.5 eq) and SOCl$_2$ (4.86 g, 40.88 mmol, 2.97 mL, 2 eq). The mixture was stirred at 70° C. for 12 h under N$_2$. TLC (PE/EtOAc=3/1, R$_f$=0.41) indicated starting material was consumed completely and two new spots formed. The mixture was concentrated and then sat. aq NaHCO$_3$ (80 mL) was added. The mixture was extracted with EtOAc (50 mL×3). The combined organic layers were washed with brine (50 mL), dried over Na$_2$SO$_4$, filtered and concentrated to yield a residue which was purified by flash silica gel chromatography (From PE/EtOAc=1/0 to 3/1, R$_f$=0.41) to yield methyl 2-hydroxy-2-[4-(trifluoromethyl)phenyl]acetate (4.7 g, 16.06 mmol, 78.6% yield, 80.0% purity) as white liquid. $^1$H NMR (400 MHz, CDCl$_3$) δ ppm 7.65-7.62 (m, 2H), 7.58-7.56 (m, 2H), 5.25 (d, J=5.1 Hz, 1H), 3.78 (s, 3H), 3.55 (d, J=5.5 Hz, 1H).

Step 2: Methyl 2-bromo-2-[4-(trifluoromethyl)phenyl]acetate

To a solution of methyl 2-hydroxy-2-[4-(trifluoromethyl)phenyl]acetate (4.7 g, 16.06 mmol, 80% purity, 1 eq) in DCM (30 mL) was added PPh₃ (4.21 g, 16.06 mmol, 1 eq) at 0° C., then added CBr₄ (5.32 g, 16.06 mmol, 1 eq). The mixture was stirred at 25° C. for 12 h under N₂. TLC (PE/EtOAc=5/1, R$_f$=0.72) indicated starting material was consumed completely and two new spots formed. The mixture was concentrated and then water (80 mL) was added. The mixture was extracted with EtOAc (50 mL×3). The combined organic layers were washed with brine (50 mL), dried over Na₂SO₄, filtered and concentrated to yield a residue which was purified by flash silica gel chromatography (From PE/EtOAc=1/0 to 5/1, R$_f$=0.72) to yield methyl 2-bromo-2-[4-(trifluoromethyl)phenyl]acetate (4.3 g, 11.58 mmol, 72.1% yield, 80.0% purity) as light yellow liquid. ¹H NMR (400 MHz, CDCl₃) δ ppm 7.69-7.66 (m, 2H), 7.64-7.62 (m, 2H), 5.37 (s, 1H), 3.81 (s, 3H).

Step 3: Methyl (2S)-2-[4-[(5R)-3-bromo-4,5-dihydroisoxazol-5-yl]-1-piperidyl]-2-[4-(trifluoromethyl)phenyl]acetate & Methyl (2R)-2-[4-[(5R)-3-bromo-4,5-dihydroisoxazol-5-yl]-1-piperidyl]-2-[4-(trifluoromethyl)phenyl]acetate

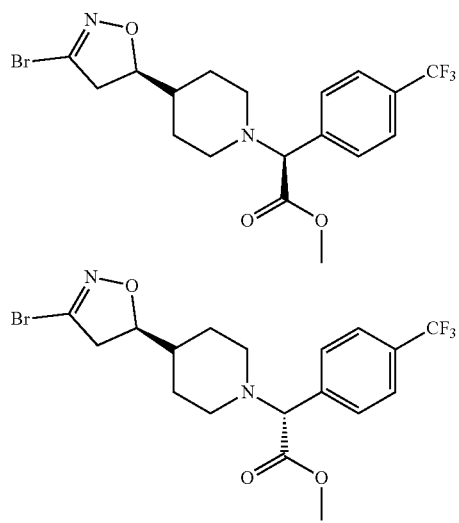

To a stirred solution of 3-bromo-5-(4-piperidyl)-4,5-dihydroisoxazole (2.5 g, 6.48 mmol, 90% purity, 1 eq, TFA) in DMF (30 mL) was added DIEA (4.19 g, 32.41 mmol, 5.65 mL, 5 eq) and methyl 2-bromo-2-[4-(trifluoromethyl)phenyl]acetate (2.53 g, 6.81 mmol, 80% purity, 1.05 eq). The reaction mixture was stirred at 15° C. for 12 h. The reaction mixture was diluted with water (100 mL) then extracted with EtOAc (50 mL×4). The combined organic layers were dried over Na₂SO₄, filtered and the filtrate was concentrated to yield a residue which was purified by flash silica gel chromatography (from PE/EtOAc=100/1 to 3/1, TLC: PE/EtOAc=3/1, R$_f$=0.50) then separated by SFC (column: DAICEL CHIRALPAK IG (250 mm*30 mm, 10 um); mobile phase: [0.1% NH₃H₂O EtOH]; B %: 20%-20%, min) to yield peak 1 (R$_t$=2.651 min) and peak 2 (R$_t$=2.911 min). Peak 1 was concentrated under reduced pressure to yield a residue which was lyophilized to yield methyl (2S)-2-[4-[(5R)-3-bromo-4,5-dihydroisoxazol-5-yl]-1-piperidyl]-2-[4-(trifluoromethyl)phenyl]acetate (250 mg, 556.47 μmol, 8.6% yield, 100% purity, SFC: R$_t$=2.651 min, ee=97.5%, [α]$^{20.8}_D$=−113.511 (MeOH, c=0.125 g/100 mL)) as yellow oil. ¹H NMR (500 MHz, DMSO-d₆) δ ppm 7.74 (d, J=8.1 Hz, 2H), 7.61 (d, J=8.2 Hz, 2H), 4.50-4.41 (m, 1H), 4.32 (s, 1H), 3.72-3.53 (m, 3H), 3.29-3.25 (m, 1H), 3.07 (dd, J=8.7, 17.5 Hz, 1H), 2.82 (d, J=11.0 Hz, 1H), 2.69 (d, J=10.2 Hz, 1H), 2.14-2.05 (m, 1H), 1.97-1.88 (m, 1H), 1.64 (d, J=12.8 Hz, 1H), 1.56-1.44 (m, 2H), 1.31-1.14 (m, 2H); ES-LCMS m/z 449.0, 451.0 [M+H]⁺. Peak 2 was concentrated under reduced pressure to yield a residue which was lyophilized to yield Methyl (2R)-2-[4-[(5R)-3-bromo-4,5-dihydroisoxazol-5-yl]-1-piperidyl]-2-[4-(trifluoromethyl)phenyl]acetate (250 mg, 556.47 μmol, 8.6% yield, 100% purity, SFC: R$_t$=2.911 min, ee=98.3%, [α]$^{20.8}_D$=−50.377 (MeOH, c=0.175 g/100 mL)) as yellow oil. ¹H NMR (500 MHz, DMSO-d₆) δ ppm 7.73 (d, J=8.1 Hz, 2H), 7.61 (d, J=8.1 Hz, 2H), 4.52-4.38 (m, 1H), 4.32 (s, 1H), 3.68-3.58 (m, 3H), 3.30-3.26 (m, 1H), 3.06 (dd, J=8.7, 17.5 Hz, 1H), 2.82 (d, J=11.1 Hz, 1H), 2.69 (d, J=11.3 Hz, 1H), 2.14-2.03 (m, 1H), 1.99-1.90 (m, 1H), 1.69 (d, J=12.8 Hz, 1H), 1.56-1.40 (m, 2H), 1.29-1.16 (m, 2H); ES-LCMS m/z 449.1, 451.1 [M+H]⁺.

Step 4: (2S)-2-[4-[(5R)-3-Bromo-4,5-dihydroisoxazol-5-yl]-1-piperidyl]-2-[4-(trifluoromethyl)phenyl]acetic Acid

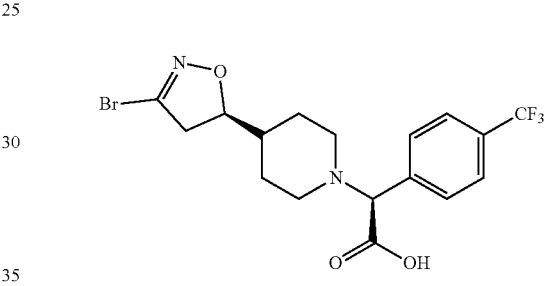

To a stirred solution of methyl (2S)-2-[4-[(5R)-3-bromo-4,5-dihydroisoxazol-5-yl]-1-piperidyl]-2-[4-(trifluoromethyl)phenyl]acetate (140.00 mg, 311.62 μmol, 100% purity, 1 eq) in i-PrOH (1.5 mL)/THF (1.5 mL)/water (1.5 mL) was added LiOH (22.39 mg, 934.87 μmol, 3 eq). The reaction mixture was stirred at 70° C. for 1 h. The reaction mixture was concentrated to yield (2S)-2-[4-[(5R)-3-bromo-4,5-dihydroisoxazol-5-yl]-1-piperidyl]-2-[4-(trifluoromethyl)phenyl]acetic acid (150 mg, crude) as yellow solid which was used in the next step without further purification. ¹H NMR (400 MHz, DMSO-d₆) δ ppm 7.63-7.47 (m, 4H), 4.50-4.36 (m, 1H), 3.49 (d, J=4.6 Hz, 1H), 3.32-3.18 (m, 3H), 3.11-2.99 (m, 1H), 1.87 (t, J=11.7 Hz, 1H), 1.73-1.52 (m, 2H), 1.50-1.32 (m, 2H), 1.30-1.22 (m, 1H), 1.18-1.09 (m, 1H); ES-LCMS m/z 435.0, 437.0 [M+H]⁺.

Step 5: (2S)-2-[4-[(5R)-3-Bromo-4,5-dihydroisoxazol-5-yl]-1-piperidyl]-2-[4-(trifluoromethyl)phenyl]acetamide

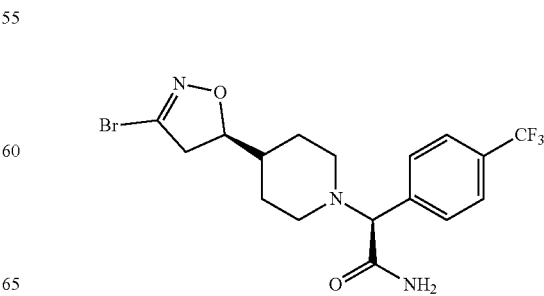

To a stirred solution of (2S)-2-[4-[(5R)-3-bromo-4,5-dihydroisoxazol-5-yl]-1-piperidyl]-2-[4-(trifluoromethyl)phenyl]acetic acid (40 mg, 91.90 μmol, 1 eq) in DMF (3 mL) was added NH$_4$Cl (14.75 mg, 275.71 μmol, 3 eq), HATU (69.89 mg, 183.81 μmol, 2 eq) and DIEA (59.39 mg, 459.52 μmol, 80.04 μL, 5 eq). The reaction mixture was stirred at 50° C. for 2 h. The reaction mixture was filtered and the filtrate was purified by preparative HPLC (column: Welch Xtimate C18 150*25 mm*5 um; mobile phase: [water (10 mM NH$_4$HCO$_3$)-ACN]; B %: 33%-53%, 15 min). The desired fraction was lyophilized to yield (2S)-2-[4-[(5R)-3-bromo-4,5-dihydroisoxazol-5-yl]-1-piperidyl]-2-[4-(trifluoromethyl)phenyl]acetamide (9.04 mg, 20.82 μmol, 22.65% yield, 100% purity, $[\alpha]^{21.2}_D=-86.0$ (MeOH, c=0.100 g/100 mL)) as white solid. $^1$H NMR (400 MHz, CD$_3$OD) δ ppm 7.69-7.60 (m, 4H), 4.50 (dt, J=6.5, 9.6 Hz, 1H), 3.91 (s, 1H), 3.30-3.23 (m, 1H), 3.14 (d, J=11.0 Hz, 1H), 3.10-2.99 (m, 1H), 2.69 (d, J=11.5 Hz, 1H), 2.19-2.06 (m, 1H), 1.87-1.68 (m, 2H), 1.66-1.46 (m, 3H), 1.45-1.31 (m, 1H); ES-LCMS m/z 434.0, 436.0 [M+H]$^+$.

Example 2. TEAD inhibition Assay

TEAD inhibition can be assayed using Hippo Pathway TEAD Reporter—MCF7 Cell Line (BPS Bioscience, Catalog #: 60618).
Background
The Hippo pathway regulates cell proliferation and cell death. It is activated by high cell density and cell stress to stop cell proliferation and induce apoptosis. The mammalian Hippo pathway comprises MST kinases and LATS kinases. When the Hippo pathway is activated, MST kinases phosphorylate LATS kinases, which phosphorylate transcriptional co-activators YAP and TAZ. Unphosphorylated YAP and TAZ remain in nucleus and interact with TEAD/TEF transcriptional factors to turn on cell cycle-promoting gene transcription. However, when phosphorylated, YAP and TAZ are recruited from the nucleus to the cytosol, so that the YAP and TAZ-dependent gene transcription is turned off. Dysfunction of the Hippo pathway is frequently detected in human cancer and its down-regulation correlates with the aggressive properties of cancer cells and poor prognosis.
Description
The TEAD Reporter—MCF7 cell line contains the firefly luciferase gene under the control of TEAD responsive elements stably integrated into the human breast cancer cell line, MCF7. Inside the cells, basal unphosphorylated YAP/TAZ remains in the nucleus and induces the constitutive expression of luciferase reporter. The cell line is validated for the inhibition of the expression of luciferase reporter by the activators of the Hippo pathway.
Application
  Monitor Hippo pathway activity.
  Screen for activators or inhibitors of the Hippo pathway.
Format
  Each vial contains ~1.5×106 cells in 1 ml of 10% DMSO.
Storage
  Immediately upon receipt, store in liquid nitrogen.
General Culture Conditions
  Thaw Medium 1 (BPS Bioscience #60187)+10 μg/ml of Insulin (Sigma-Aldrich #I0516): MEM medium (Hyclone #SH30024.01) supplemented with 10% FBS (Invitrogen #26140-079), 1% non-essential amino acids (Hyclone #SH30238.01), 1 mM Na pyruvate (Hyclone #SH30239.01), 1% Penicillin/Streptomycin (Hyclone SV30010.01), plus 10 μg/ml of insulin (Sigma-Aldrich #I0516)

Growth Medium 1B (BPS Bioscience #79531)+10 μg/ml of Insulin (Sigma-Aldrich #I0516): Thaw Medium 1 (BPS Cat. #60187)+10 μg/ml of insulin (Sigma-Aldrich #I0516), and 400 μg/ml of Geneticin (invitrogen #11811031).
  Cells should be grown at 37° C. with 5% CO$_2$ using Growth Medium 1B with 10 μg/ml of Insulin. It may be necessary to adjust the percentage of CO$_2$ in the incubator depending on the NaHCO$_3$ level in the basal medium.
  To thaw the cells, it is recommended to quickly thaw the frozen cells from liquid nitrogen in a 37° C. water-bath, transfer to a tube containing 10 ml of Thaw Medium 1+Insulin (no Geneticin), spin down cells, resuspend cells in pre-warmed Thaw Medium 1+Insulin (no Geneticin), transfer resuspended cells to a T25 flask and culture in a CO$_2$ incubator at 37° C. overnight. The next day, replace the medium with fresh Thaw Medium 1+Insulin (no Geneticin), and continue growing culture in a CO$_2$ incubator at 37° C. until the cells are ready to be split. At first passage, switch to Growth Medium 1B+10 μg/ml of Insulin (includes Thaw Medium 1, Insulin, and Geneticin). Cells should be split before they reach complete confluence.
  To passage the cells, rinse cells with phosphate buffered saline (PBS), and detach cells from the culture vessel with 0.25% Trypsin/EDTA. Add Growth Medium 1B+10 μg/ml of Insulin (Includes Thaw Medium 1, Insulin, and Geneticin) and transfer to a tube, spin down the cells, then, resuspend cells and seed appropriate aliquots of cell suspension into new culture vessels. Subcultivation ration: 1:5 to 1:10 weekly.
  To freeze down the cells, rinse cells with phosphate buffered saline (PBS), and detach cells from culture vessel with Trypsin/EDTA. Add Growth Medium 1B+10 μg/ml of Insulin (Includes Thaw Medium 1, Insulin, and Geneticin) and transfer to a tube, spin down cells, and resuspend in freezing medium (10% DMSO+90% FBS). Place at −80° C. overnight and place in liquid nitrogen the next day. Alternatively, vials may be placed directly in liquid nitrogen.
Functional Validation and Assay Performance
  The following assays are designed for 96-well format. To perform the assay in different tissue culture formats, the cell number and reagent volume should be scaled appropriately.
Materials Required but not Supplied for Cell Culture
  Thaw Medium 1 (BPS Bioscience #60187)+10 μg/ml of insulin
  Growth Medium 1B (BPS Bioscience #79531)+10 μg/ml of insulin
  Insulin Solution from Bovine Pancreas (Sigma-Aldrich #: 10516)
Materials Required but Not Supplied for Cellular Assay
  H$_2$O$_2$: activator of Hippo pathway (activate MST kinases)
  Insulin
  Assay Medium: Thaw Medium 1 (BPS Cat. #60187)+10 μg/ml of insulin
  Insulin Solution from Bovine Pancreas (Sigma-Aldrich Cat #: I0516)
  Okadaic acid (BPS bioscience #27047): activator of Hippo pathway (activate MST kinases). Prepare 10 mM stock in DMSO.
  96-well tissue culture plate or 96-well tissue culture-treated white clear-bottom assay plate
  ONE-Step™ Luciferase Assay System (BPS, Cat. #60690)
  Luminometer
*Mycoplasma* Testing
  The cell line has been screened using the PCR-based VenorGeM *Mycoplasma* Detection kit (Sigma-Aldrich) to confirm the absence of *Mycoplasma* species.

Inhibition of TEAD Reporter Activity by Activator of Hippo Pathway in TEAD Reporter—MCF7 Cells 1) Harvest TEAD Reporter—MCF7 cells from culture in growth medium and seed cells at a density of 35,000 cells per well into white clear-bottom 96-well microplate in 45 µl of assay medium.
2) Incubate cells at 37° C. in a $CO_2$ incubator for overnight.
3) Dilute the activators ($H_2O_2$ or okadaic acid) stock in assay medium. Add 5 µl of diluted activators to the wells. The final concentration of DMSO in assay medium is 0.1%.
4) Add 5 µl of assay medium with same concentration of DMSO without activator to control wells.
5) Add 50 µl of assay medium with DMSO to cell-free control wells (for determining background luminescence).
6) Set up each treatment in at least triplicate.
7) Incubate cells at 37° C. in a $CO_2$ incubator for 5-6 hours.
8) Perform luciferase assay using the ONE-Step™ Luciferase Assay System following the protocol provided: Add 100 µl of ONE-Step™ Luciferase reagent per well and rock at room temperature for ~15 minutes. Measure luminescence using a luminometer.
9) Data Analysis: Obtain the background-subtracted luminescence by subtracting the average background luminescence (cell-free control wells) from the luminescence reading of all wells.

Certain compounds were tested in TEAD reporter assay, and in H226 and H28. The data are listed in Table 2 below. A: EC50<0.1 uM; B: 0.1 uM≤EC50≤0.5 uM; C: EC50>0.5 uM.

TABLE 2

In vitro Data of Certain Exemplary Compounds.

| Compound | TEAD Reporter Assay EC50 (uM) | H226 EC50 (uM) | H28 EC50 (uM) |
|---|---|---|---|
| I-27 | A | A | C |
| I-28 | C | C | C |
| I-29 | A | B | C |
| I-30 | A | A | C |
| I-31 | A | A | C |
| I-32 | C | C | |
| I-33 | A | A | C |
| I-34 | C | | |
| I-35 | A | A | C |
| I-36 | A | A | C |
| I-37 | C | B | |
| I-38 | C | C | |
| I-39 | C | C | |
| I-40 | A | A | C |
| I-41 | C | C | |
| I-42 | A | B | |
| I-43 | C | C | |
| I-44 | A | A | |
| I-45 | A | A | |
| I-46 | B | B | C |
| I-47 | C | C | |
| I-48 | C | | |
| I-49 | C | C | C |
| I-50 | C | C | C |
| I-51 | C | C | |
| I-52 | B | B | |
| I-53 | B | B | |
| I-54 | C | C | |
| I-55 | B | B | |
| I-56 | C | C | |
| I-57 | C | C | |
| I-58 | C | C | |
| I-59 | C | C | |
| I-60 | B | A | |
| I-61 | C | C | |
| I-62 | A | A | |
| I-63 | B | C | |
| I-64 | A | A | |
| I-65 | B | C | |
| I-66 | C | C | |
| I-67 | B | B | |
| I-68 | B | C | |
| I-69 | A | A | |
| I-70 | A | A | |
| I-71 | A | A | |
| I-72 | B | A | |
| I-73 | C | C | |
| isomer 2 of I-74 | C | C | C |
| isomer 1 of I-74 | B | A | C |
| isomer 2 of I-75 | B | A | C |
| isomer 1 of I-75 | C | B | C |
| isomer 2 of I-76 | B | B | C |
| isomer 1 of I-76 | C | C | |
| isomer 2 of I-77 | C | B | C |
| isomer 1 of I-77 | A | A | C |
| isomer 2 of I-78 | A | A | C |
| isomer 1 of I-78 | C | B | C |
| isomer 2 of I-79 | C | C | |
| isomer 1 of I-79 | C | C | |
| isomer 2 of I-80 | C | B | |
| isomer 1 of I-80 | B | A | |
| isomer 2 of I-81 | C | C | |
| isomer 1 of I-81 | C | A | |
| isomer 2 of I-103 | A | A | C |
| isomer 1 of I-103 | C | C | |
| isomer 2 of I-166 | C | A | C |
| isomer 1 of I-166 | C | B | |
| isomer 2 of I-167 | B | A | |
| isomer 1 of I-167 | A | A | C |
| isomer 2 of I-168 | C | | |
| isomer 1 of I-168 | B | A | |
| isomer 2 of I-169 | C | C | |
| isomer 1 of I-169 | C | C | |
| isomer 2 of I-170 | A | A | C |
| isomer 1 of I-170 | C | B | |
| isomer 2 of I-171 | B | A | C |
| isomer 1 of I-171 | C | C | |
| isomer 2 of I-172 | C | C | |
| isomer 1 of I-172 | C | C | |
| isomer 2 of I-173 | C | C | |
| isomer 1 of I-173 | C | C | |
| isomer 2 of I-174 | C | B | |
| isomer 1 of I-174 | C | B | |
| isomer 2 of I-175 | A | A | C |
| isomer 1 of I-175 | C | B | |
| isomer 2 of I-176 | C | C | |
| isomer 1 of I-176 | C | C | |
| isomer 2 of I-177 | A | A | |
| isomer 1 of I-177 | C | B | |
| isomer 2 of I-178 | C | C | |
| isomer 1 of I-178 | C | C | |
| isomer 2 of I-179 | C | C | |
| isomer 1 of I-179 | C | C | |
| isomer 2 of I-180 | A | A | |
| isomer 1 of I-180 | C | B | |
| isomer 2 of I-181 | B | A | |
| isomer 1 of I-181 | C | B | |
| isomer 2 of I-182 | B | B | |
| isomer 1 of I-182 | A | A | |
| isomer 2 of I-183 | C | C | |
| isomer 1 of I-183 | B | B | |
| isomer 2 of I-184 | C | C | |
| isomer 1 of I-184 | C | C | |
| isomer 2 of I-185 | C | C | |
| isomer 1 of I-185 | C | C | |
| isomer 2 of I-186 | A | B | C |
| isomer 1 of I-186 | A | A | C |

TABLE 2-continued

In vitro Data of Certain Exemplary Compounds.

| Compound | TEAD Reporter Assay EC50 (uM) | H226 EC50 (uM) | H28 EC50 (uM) |
|---|---|---|---|
| isomer 2 of I-187 | B | B | C |
| isomer 1 of I-187 | C | C | |
| isomer 2 of I-188 | C | C | |
| isomer 1 of I-188 | A | A | C |
| isomer 2 of I-189 | C | B | |
| isomer 1 of I-189 | A | A | C |
| I-149 | C | B | |
| isomer 2 of I-190 | C | C | |
| isomer 1 of I-190 | A | B | |
| isomer 2 of I-191 | C | B | |
| isomer 1 of I-191 | A | A | |
| isomer 2 of I-192 | B | B | |
| isomer 1 of I-192 | B | B | |
| isomer 2 of I-193 | C | C | |
| isomer 1 of I-193 | C | C | |
| 208 | A | A | |
| isomer 1 of I-316 | C | C | |
| isomer 2 of I-316 | C | C | |
| 211 | A | A | |
| 212 | B | A | |
| isomer 1 of I-318 | B | C | |
| isomer 2 of I-318 | B | B | |
| 217 | C | C | |
| isomer 1 of I-321 | C | C | |
| isomer 2 of I-321 | C | C | |
| 220 | A | A | |
| 221 | C | C | |
| 222 | A | A | |
| 223 | C | C | |
| 224 | C | C | |
| isomer 1 of I-326 | A | B | |
| isomer 2 of I-326 | C | C | |
| isomer 1 of I-327 | C | C | |
| isomer 2 of I-327 | B | B | |
| isomer 2 of I-328 | C | C | |
| isomer 1 of I-328 | C | C | |
| 231 | A | A | |
| isomer 1 of I-330 | C | C | |
| isomer 2 of I-330 | C | C | |
| 234 | C | A | |
| isomer 1 of I-332 | C | C | |
| 236 | C | C | |
| isomer 2 of I-332 | B | C | |
| isomer 2 of I-333 | B | B | |
| isomer 1 of I-333 | B | A | |
| isomer 2 of I-334 | A | A | |
| isomer 1 of I-334 | A | A | |
| isomer 2 of I-335 | B | B | |
| isomer 1 of I-335 | B | C | |
| isomer 2 of I-336 | C | C | |
| isomer 1 of I-336 | C | C | |
| 246 | C | C | |
| isomer 2 of I-337 | C | C | |
| isomer 1 of I-337 | C | C | |
| isomer 2 of I-338 | B | A | |
| isomer 1 of I-338 | B | C | |
| 251 | C | C | |
| 252 | C | C | |
| isomer 1 of I-339 | B | B | |
| isomer 2 of I-339 | B | B | |
| 255 | C | C | |
| 256 | C | A | |
| isomer 1 of I-341 | A | A | |
| isomer 2 of I-341 | C | C | |
| 259 | C | C | |
| 260 | C | C | |
| isomer 1 of I-342 | B | C | |
| isomer 2 of I-342 | C | B | |
| isomer 3 of I-342 | C | C | |
| isomer 4 of I-342 | B | B | |
| isomer 1 of I-343 | A | A | |
| isomer 2 of I-343 | B | B | |
| isomer 3 of I-343 | C | C | |
| isomer 4 of I-343 | C | C | |
| 269 | B | C | |
| 270 | C | C | |
| 271 | C | C | |
| 272 | C | C | |
| 273 | C | C | |
| 274 | B | C | |
| 275 | B | C | |
| 276 | B | C | |
| 277 | C | C | |
| 278 | C | C | |
| 279 | C | C | |
| isomer 1 of I-344 | C | C | |
| isomer 2 of I-344 | C | C | |
| isomer 1 of I-345 | C | C | |
| isomer 2 of I-345 | C | C | |
| 284 | C | C | |
| 285 | C | C | |
| 286 | C | C | |
| 287 | C | C | |
| 288 | C | C | |
| 289 | B | C | |
| 290 | B | B | |
| isomer 1 of I-346 | C | C | |
| isomer 2 of I-346 | C | C | |
| 293 | C | C | |
| 294 | C | C | |
| 295 | C | C | |
| 296 | C | C | |
| isomer 1 of I-347 | B | C | |
| isomer 2 of I-347 | B | B | |
| isomer 1 of I-348 | B | B | |
| isomer 2 of I-348 | B | B | |
| isomer 1 of I-349 | B | C | |
| isomer 2 of I-349 | B | C | |
| isomer 1 of I-350 | C | C | |
| isomer 2 of I-350 | C | B | |
| 305 | A | C | |
| isomer 1 of I-351 | A | A | |
| isomer 2 of I-351 | B | B | |
| isomer 1 of I-352 | B | B | |
| isomer 2 of I-352 | A | A | |
| isomer 1 of I-384 | B | B | |
| isomer 2 of I-384 | A | B | |
| I-386 | B | B | |
| I-387 | C | C | |
| I-388 | C | C | |
| I-389 | C | C | |
| isomer 1 of I-402 | C | B | |
| isomer 2 of I-402 | C | C | |
| I-393 | C | C | |
| I-394 | B | B | |
| I-395 | C | C | |
| I-397 | C | B | |
| isomer 1 of I-403 | B | B | |
| isomer 2 of I-403 | B | B | |
| isomer 1 of I-404 | C | C | |
| isomer 2 of I-404 | C | C | |

Example 3: Mouse Pharmacokinetics Study

Figure 4:
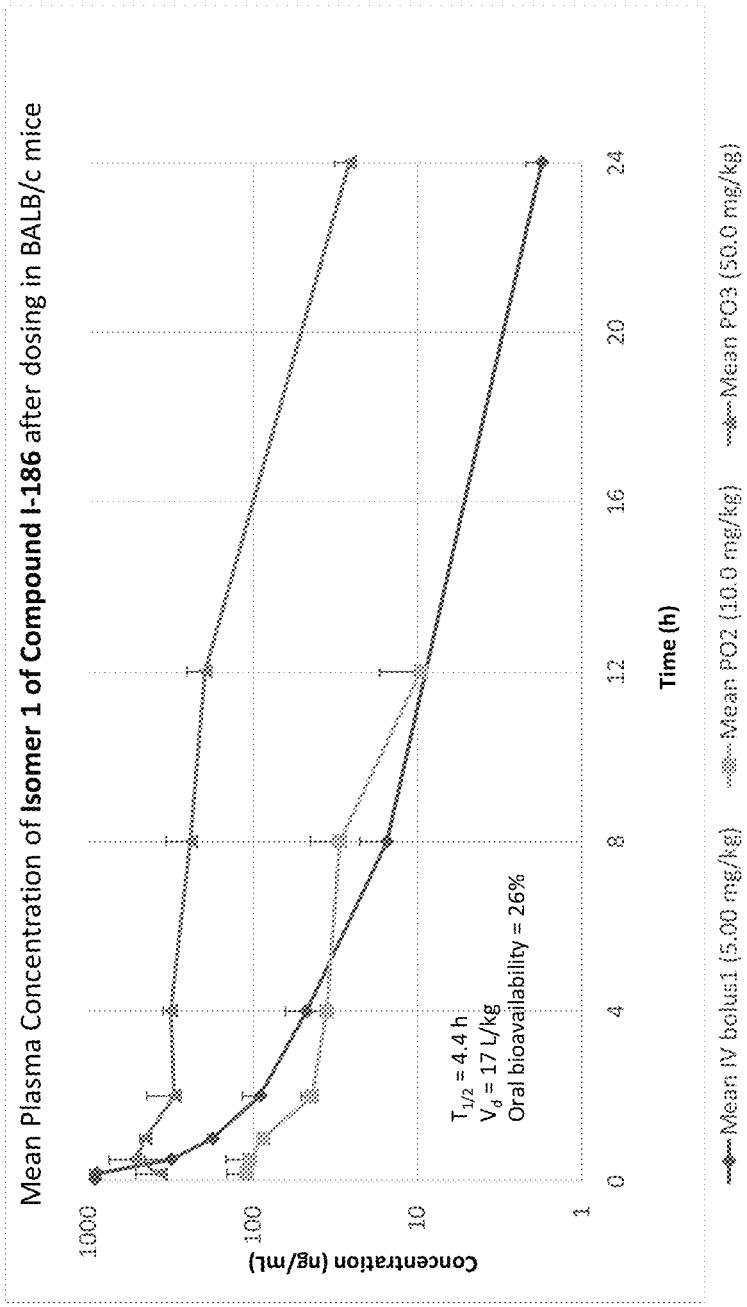
FIG. 4 depicts pharmacokinetic (PK) properties of isomer 1 of compound I-186 following dosing in BALB/c mice.

Formulated compounds were administered intravenously or orally via gavage to BALB/c mice. Typically, at 0.167, 0.5, 1, 2, 4, 6, 12, and 24 hours post-dose, blood was collected and processed to plasma by centrifugation and stored at −80° C. until analysis. Internal standard was added to each sample prior to protein precipitation with acetonitrile or TCA. The precipitates were filtered through a filter plate and the samples were analyzed by LC/MS/MS. A standard curve was prepared in plasma from typically from 1.0 ng/mL to 3000 ng/mL and processed in the same manner as the samples. Sample analysis was typically performed on a suitable LC/MS/MS system fitted with an analytical UPLC column and compounds eluted from the analytical column with a gradient from 30-95% 0.1% formic acid (v/v) in ACN: 0.1% formic acid (v/v) in water. Mass spectrometric detection of test compound and the internal standard was performed by MRM in positive mode. The pharmacokinetics of each compound were analyzed by Phoenix WinNonlin software (Pharsight, St. Louis, MO) via noncompartmental analysis. Compounds in Table 3 were dosed in 5% DMS/95% PEG400 at 10 mg/kg by oral gavage with Cmax and $AUC_{0\text{-}last}$ summarized in Table 3. FIG. 4 depicts pharmacokinetic (PK) properties of isomer 1 of compound I-186 following dosing in BALB/c mice.

TABLE 3

Summary of Cmax and $AUC_{0\text{-}last}$ Data

| Compound | Cmax (ng/mL) | $AUC_{0\text{-}last}$ (ng*h/mL) |
|---|---|---|
| P-5 | 246 | 397 |
| Isomer 2 of I-12 | 23 | 48 |
| Isomer 1 of I-1 | 71.9 | 62 |
| I-46 | 735 | 1137 |
| isomer 1 of I-77 | 38 | 77 |
| isomer 1 of I-186 | 110 | 435 |
| isomer 2 of I-187 | 11 | 20 |
| isomer 2 of I-166 | 15 | 33 |
| isomer 1 of I-188 | 17 | 14 |
| isomer 1 of I-189 | 36 | 86 |
| I-62 | 345 | 368 |
| I-203 | 63.3 | 275 |
| I-69 | 1161 | 1241 |
| isomer 1 of I-191 | 48 | 114 |
| isomer 2 of I-184 | 774 | 2519 |
| I-208 | 318 | 226 |
| I-211 | 1247 | 1260 |
| isomer 1 of I-333 | 211 | 492 |
| isomer 2 of I-334 | 528 | 489 |
| isomer 1 of I-334 | 318 | 403 |
| isomer 1 of I-341 | 55 | 119 |

Example 4. CTGF Data Analysis

NU/NU nude female mice obtained from Charles River Laboratories and were subcutaneously injected with NCI-H226 (ATCC) human mesothelioma cells. Once tumors grew to an average size of 350-400 mm³, mice were randomized into each treatment group. NCI-H226 tumor bearing mice were treated by oral gavage with Vehicle (5% DMSO/95% PEG 400) or a TEAD inhibitor for a total of 3 administrations. 4 hours post-third administration, mice were euthanized and tumors were collected for isolation of RNA for pharmacodynamic (PD) analysis.

RNA was extracted from the tumors utilizing the QIAZOL (Qiagen) lysis reagent, tissues were then homogenized for 10 minutes using TissueLyser II (Qiagen). Once sample disruption and digestion was complete, chloroform was added to each sample, the homogenate was separated into aqueous and organic phases by centrifugation.

RNA was then isolated from samples using the KingFisher Flex automated extraction system and MagMAX mirvana total RNA isolation kit. Manufacturer's recommended protocol for high-throughput isolation of RNA from tissue samples was followed for RNA extraction.

Expression of the YAP/TEAD-regulated gene, CCN2 that encodes CTFG (Connective Tissue Growth Factor), and the housekeeping gene, human glyceraldehyde 3-phosphate dehydrogenase (GAPDH), were quantified by qRT-PCR analysis using the TaqMan Gene Expression Master Mix and TaqMan probes. CTGF and GAPDH cycle threshold (Ct) values for tumor cDNA samples were determined, and CTGF expression was normalized to GAPDH as an internal control.

The relative CTGF mRNA expression levels for each treatment group from tumor tissues were normalized to the vehicle control group. For comparisons between vehicle control and TEAD inhibitor treatment groups, an independent sample t-test was used for statistical analysis.

Figure 5:
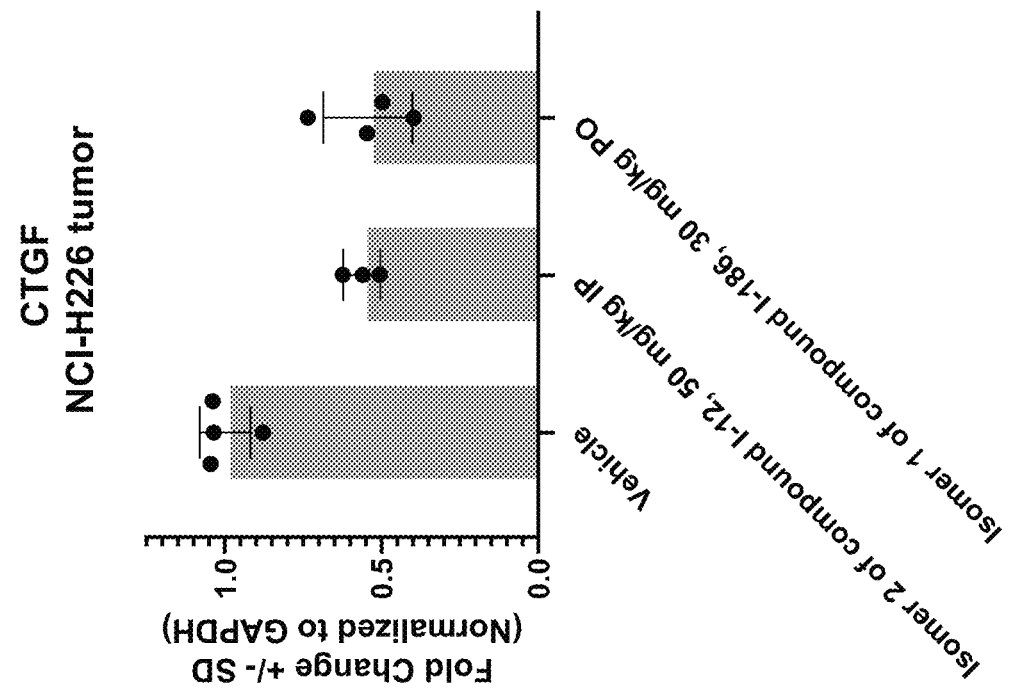
FIG. 5 depicts pharmacodynamic (PD) properties of isomer 2 of compound I-12 and isomer 1 of compound I-186 using real-time PCR.

FIG. 5 depicts pharmacodynamic (PD) properties of isomer 2 of compound I-12 and isomer 1 of compound I-186 using real-time PCR.

Example 5. Anti-Proliferation Assay

Individual cell lines were grown in medium according to supplier instructions and seeded into 96-well plates at a density that ensured logarithmic growth over 72 hours. TEAD inhibitor compounds were administered to cells at a top concentration of 10 μm and subsequently a 10 point 3-fold serial dilution was conducted. After 72 hours, proliferation was quantified using Cell TITERGLO™ (Promega, Inc.) and compared to vehicle control. IC50 and EC50 values were generated using XLFit curve fitting software.

Figure 2:
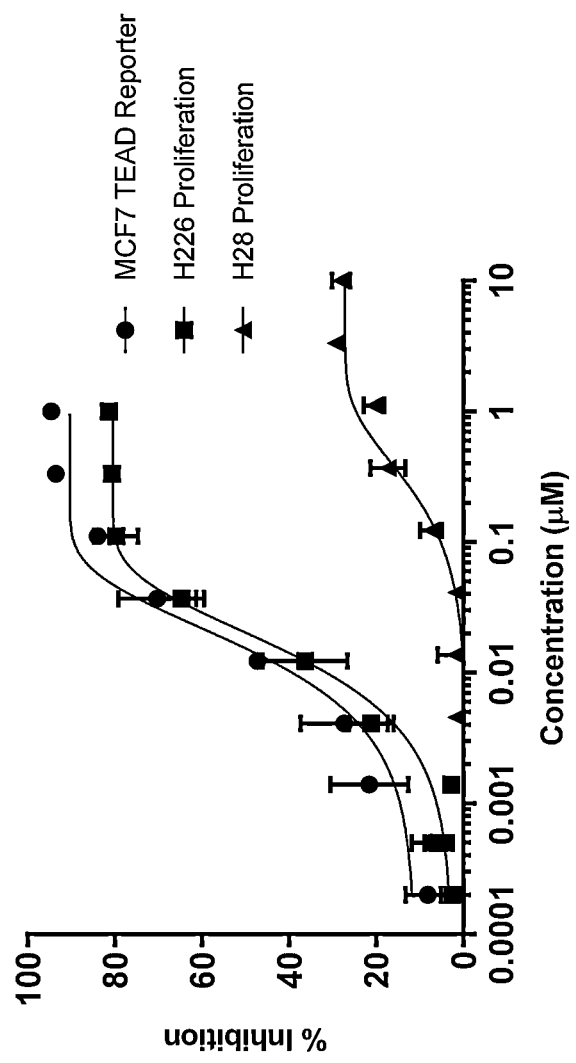
FIG. 2 demonstrates inhibition of cell growth of an NF2 mutant cell line by isomer 2 of compound I-12. The effect of isomer 2 of compound I-12 on cell proliferation is dependent on the presence of a Hippo/NF2 mutation. No effect is seen by isomer 2 of compound I-12 on the NF2 wild-type H28 cell line.

FIG. 2 demonstrates inhibition of cell growth of an NF2 mutant cell line by isomer 2 of compound I-12. The effect of isomer 2 of compound I-12 on cell proliferation is dependent on the presence of a Hippo/NF2 mutation. No effect is seen by isomer 2 of compound I-12 on the NF2 wild-type H28 cell line.

FIG. 3 shows anti-proliferative effects of isomer 2 of compound I-12 as evaluated in a 3-day Cell TITERGLO™ assay. The cell lines were chosen based on Cancer Dependency score and a sampling of known interacting oncogenes. Cell lines showing anti-proliferative effects following treatment with isomer 2 of compound I-12 and having EC50<0.2 μM or <1.0 μM are indicated by boxes. EC50 values were calculated from inflection points.

Example 6. In vivo Inhibition of Tumor Growth

NCI-11226 In Vivo Efficacy Studies 6-8 week old nu/nu nude mice (CRL) were inoculated subcutaneously with 5×106 NCI-H226 human mesothelioma tumor cells in the right flank. Tumor growth was monitored twice per week using vernier calipers and mean tumor volume (MTV) was calculated using the formula V=W2×L/2.

When the MTV reached approximately 150-200 mm³, animals were randomized into treatment groups (n=8-10/group) and dosed per os (PO) on a once everyday (QD) schedule for 27-40 days with either Vehicle (5% DMSO+ 95% PEG 400) or TEAD inhibitors, such as isomer 2 of compound I-12, and/or isomer 1 of compound I-186.

Randomization and treatments started on Day 0 and % Tumor Growth Inhibition was calculated on the last day of the study (when the control MTV reaches maximum allowable tumor volume), the following calculation was performed.

% TGI=100−[MTV treated/MTV control]×100

Tumor growth and body weight change were measured twice per week.

For comparisons between vehicle control and TEAD inhibitor treatment groups, an independent sample t-test was used for statistical analysis.

TABLE 5

Tumor Growth Inhibition (TGI) at Various Doses and Administration Routes

| Treatment | Dose (mg/kg) | Route of administration | Schedule | % TGI at the end of study | Day of calculation |
|---|---|---|---|---|---|
| Isomer 2 of Compound I-12 | 200 | PO | QD | 79.6 | 28 |
| Isomer 2 of Compound I-12 | 50 | IP | QD | 82.6 | 28 |
| Isomer 1 of Compound I-186 | 30 | PO | QD | 49.9 | 40 |
| Isomer 1 of Compound I-186 | 30 | PO | QD | 65.3 | 27 |
| Isomer 1 of Compound I-186 | 75 | PO | QD | 67.3 | 27 |
| Isomer 1 of Compound I-186 | 75 | PO | Q2D | 57.1 | 27 |

Figures 6A, 6B:
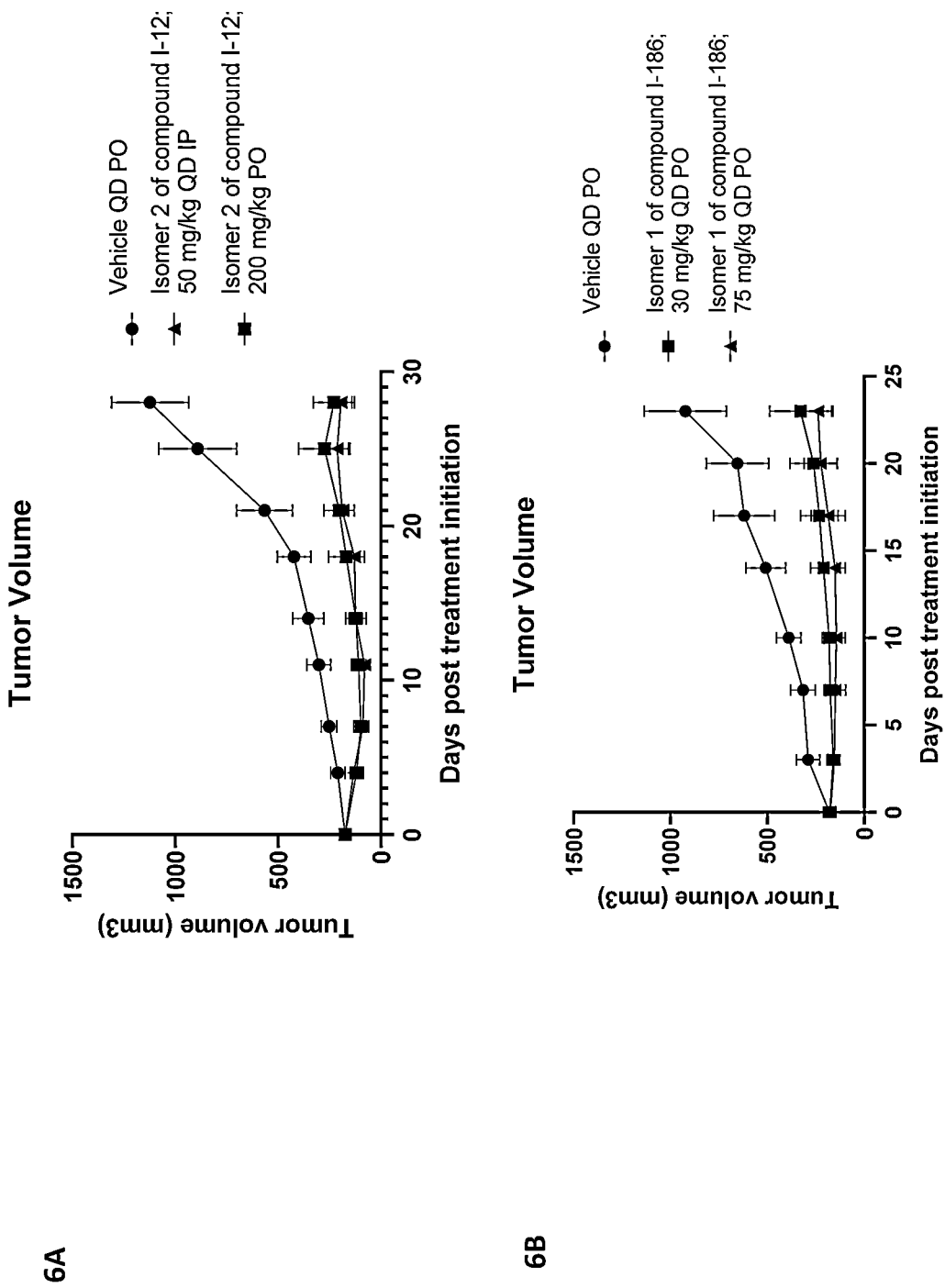
FIGS. 6A-6B demonstrate anti-tumor activities of isomer 2 of compound I-12 (6A) and isomer 1 of compound I-186 (6B) in an H226 mesothelioma xenograft model. No effects were observed on body weights throughout studies. Kidneys at end of studies showed no signs of damage by histopathology.

FIGS. 6A-6B demonstrate anti-tumor activities of isomer 2 of compound I-12 (6A) and isomer 1 of compound I-186 (6B) in an H226 mesothelioma xenograft model. No effects were observed on body weights throughout studies. Kidneys at end of studies showed no signs of damage by histopathology.

MSTO-211H In Vivo Efficacy Studies 6-8 week old SCID mice (CRL) were inoculated subcutaneously with $5 \times 10^6$ MSTO-211H human mesothelioma tumor cells in the right flank. Tumor growth was monitored twice per week using vernier calipers and mean tumor volume (MTV) was calculated using the formula $V = W2 \times L/2$.

When the MTV reached approximately 150-200 mm³, animals were randomized into treatment groups (n=6-8/group) and dosed per os (PO) on a once everyday (QD) schedule for 22-25 days with either Vehicle (5% DMSO+ 95% PEG 400) or TEAD inhibitors, such as compound I-27.

Randomization and treatments started on Day 0 and % Tumor Growth Inhibition was calculated on the last day of the study (when the control MTV reaches maximum allowable tumor volume), the following calculation was performed.

% TGI=100−[MTV treated/MTV control]×100

Tumor growth and body weight change were measured twice per week.

For comparisons between vehicle control and TEAD inhibitor treatment groups, an independent sample t-test was used for statistical analysis.

Figure 7:
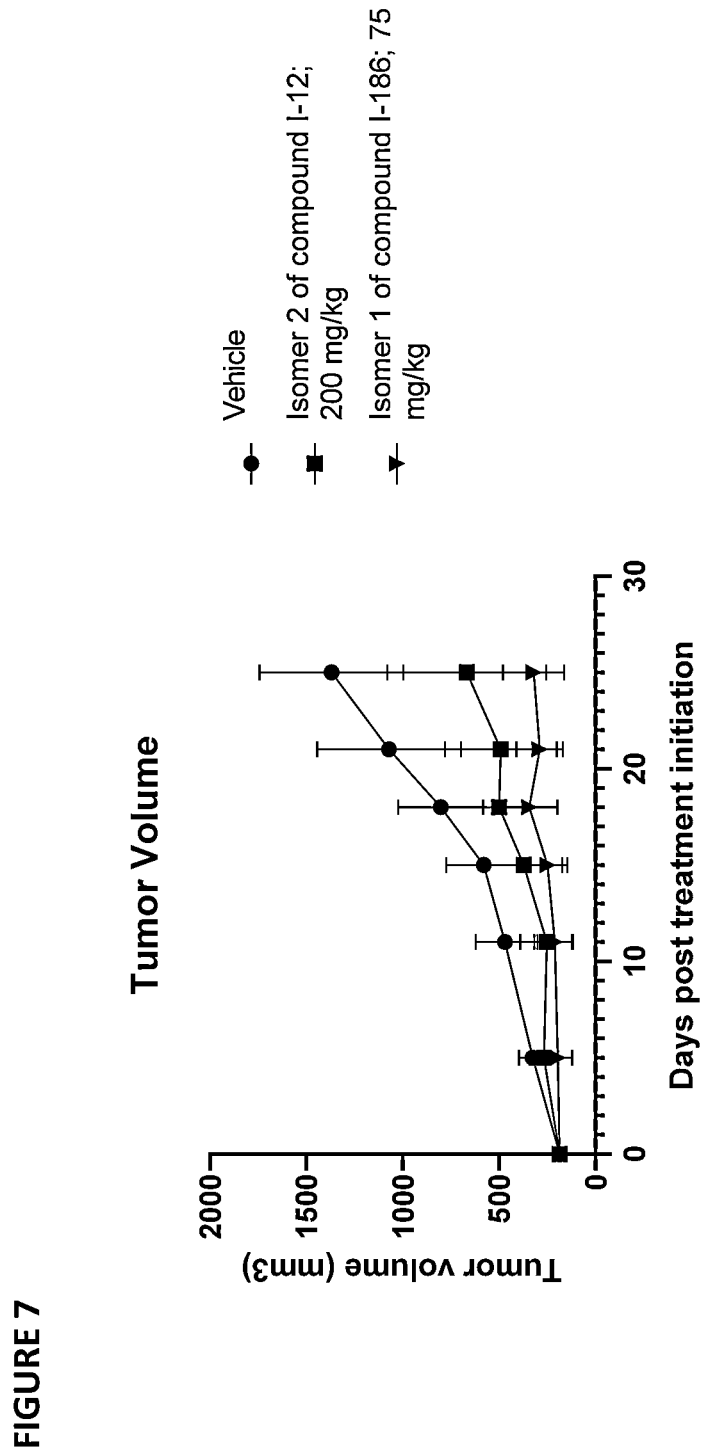
FIG. 7 demonstrates anti-tumor activities of isomer 2 of compound I-12 and isomer 1 of compound I-186 in an MSTO-211H mesothelioma xenograft model. No effects were observed on body weights throughout studies. Kidneys at end of studies showed no signs of damage by histopathology.

FIG. 7 demonstrates anti-tumor activities of isomer 2 of compound I-12 and isomer 1 of compound I-186 in an MSTO-211H mesothelioma xenograft model. No effects were observed on body weights throughout studies. Kidneys at end of studies showed no signs of damage by histopathology.

Example 7: TEAD Selectivity Assays

The TEAD targeting selectivity profiles of the TEAD inhibitor compounds described herein can be determined by either or both of two exemplary assays provided herein designed to monitor the interaction of TEAD isoforms or variants, e.g., human TEAD1 (UniProt KB ID P28347-1 (SEQ ID NO: 1)), human TEAD2 (UniProtKB ID Q15562 (SEQ ID NO: 2)), human TEAD3 (UniProtKB ID Q99594 (SEQ ID NO: 3)), and human TEAD4 (UniProtKB ID Q15561 (SEQ ID NO: 4), and YAP1 or TAZ. While co-immunoprecipitation techniques can be used to monitor protein-protein interactions, it is difficult to increase the throughput based on the basic methodology required. Accordingly, alternative but complementary assays are employed to monitor the interaction of the different TEAD isoforms or variants, e.g., human TEAD1 (UniProt KB ID P28347-1 (SEQ ID NO: 1)), human TEAD2 (UniProtKB ID Q15562 (SEQ ID NO: 2)), human TEAD3 (UniProtKB ID Q99594 (SEQ ID NO: 3)), and human TEAD4 (UniProtKB ID Q15561 (SEQ ID NO: 4), and YAP1 (or TAZ).

The first exemplary assay is an in vitro biochemical fluorescent polarization assay using recombinantly expressed and purified YAP-binding domains of individual TEAD isoforms and a fluorescently labeled peptide derived from the primary sequence of YAP1. (Bum-Erdene et al., Cell Chem Biol. 2019 Mar. 21; 26(3):378-389.e13, the contents of which are herein incorporated by reference in their entireties). Compounds are incubated with individual TEAD isoform proteins and the fluorescent peptide and potency is determined by quantifying the displacement of the peptide.

The second exemplary assay is a cell-based assay employing the split luciferase reporter system (Hall et al., ACS Chem. Biol. 2012, 7, 11, 1848-1857, the contents of which are herein incorporated by reference in their entireties). Briefly, the YAP-binding domain of each TEAD isoform is transiently co-expressed with the TEAD-binding domain or either YAP1 or TAZ in HEK293 cells and the proximity of the two chimeric gene fusion products is monitored by luciferase activity (Nouri et al. Cancers (Basel), 2019 Oct. 19; 11(10), the contents of which are herein incorporated by reference in their entireties). Compounds that interfere with the interaction of a TEAD isoform and YAP1 (or TAZ) decrease the resulting luciferase activity relative to vehicle treated controls. Similar in process to the fluorescent polarization assay, these chimeric gene fusions are recombinantly expressed in bacteria or insect cells and employed as an in vitro biochemical assay with a similar luciferase readout as the cell-based assay.

Example 8. Inhibition of Malignant Mesothelioma Tumor Cell Growth

The tumor cell growth inhibitory activity of the TEAD inhibitors described herein is evaluated in NCI-H2052 mesothelioma cell line harboring a NF2 mutation. This cell line is selected, in part, based on its mutational status and the ability of a siRNA directed against YAP, TAZ or TEAD1-TEAD4 to inhibit cell proliferation. The nuclear localization of YAP at confluence is also taken into account. 10,000 cells/well were plated in a 96-well black plate with clear flat bottom TC-Treated Imaging plate in regular medium with serum, which was replaced the day after with starvation medium containing 1% serum. After one day growth in the starvation medium, cells are incubated with TEAD inhibitor compounds. The starting concentration is 30 μM and serial dilutions in DMSO and medium are performed until 0.1 μM to achieve a final DMSO concentration of 0.5%. The cells are then allowed to grow for 3 days, and then, EdU (Invitrogen, Molecular Probe) is added in each well at a final concentration of 10 μM and the cells are returned to the incubator for an additional 24 h. The starvation medium is removed and 100 μl of PFA 4% containing Hoechst dye is added in each well to fix the cells. Plates are then incubated at room temperature for 15 min, washed twice with PBS, and the cells permeabilized by adding 100 μl per well of triton-100 containing 0.3% BSA. After 20 min, cells are washed with PBS and EdU detection is performed according to the instructions of the manufacturer. Image acquisition is performed, for example, using the ImageXpress Micro and analyzed using the MetaXpress software (Molecular Device).

While we have described a number of embodiments of this invention, it is apparent that our basic examples may be altered to provide other embodiments that utilize the compounds and methods of this invention. Therefore, it will be appreciated that the scope of this invention is to be defined by the application and appended claims rather than by the specific embodiments that have been represented by way of example.

---

What is claimed is:

1. A method for treating a cancer in a patient, comprising administering to the patient a compound of Formula I':

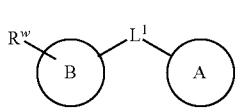

I' or a pharmaceutically acceptable salt thereof, wherein:
L$^1$ is C$_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is optionally substituted phenyl;

Ring B is optionally substituted

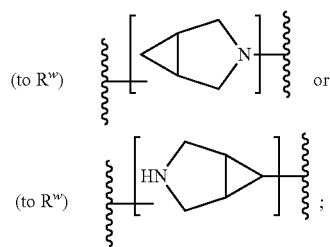

R$^w$ is -L-Y;

L is a covalent bond or a bivalent C$_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, C(=NR)—, —N=N—, or —C(=N$_2$)—;

Y is hydrogen, C$_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups;

each R$^e$ is independently selected from -Q-Z, oxo, NO$_2$, halogen, CN, or a C$_{1-6}$ aliphatic optionally substituted with oxo, halogen, NO$_2$, or CN;

Q is a covalent bond or a bivalent C$_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—;

Z is hydrogen or C$_{1-6}$ aliphatic optionally substituted with oxo, halogen, NO$_2$, or CN; and each R is independently —H or optionally substituted —C$_{1-6}$ aliphatic.

2. The method of claim 1, wherein L$^1$ is C$_{1-6}$ bivalent straight or branched hydrocarbon chain wherein 1, 2, or 3 methylene units of the chain are independently replaced with —O—, —CH(OR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, or —N(R)C(O)N(R)—.

3. The method of claim 2, wherein L$^1$ is —CH$_2$—.

4. The method of claim 1, wherein Ring A is phenyl, optionally substituted 1-2 times by halogen, —CN, —NO$_2$, or —C$_{1-6}$ aliphatic substituted 0-6 times by halogen, —CN, or —NO$_2$.

5. The method of claim 4, wherein Ring A is

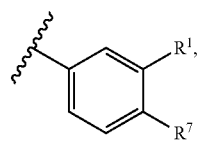

R$^1$ is hydrogen, and R$^7$ is —C$_{1-6}$ aliphatic substituted 0-6 times by halogen.

6. The method of claim 1, wherein Ring B is

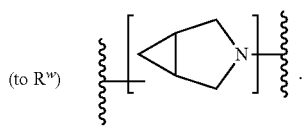

7. The method of claim 6, wherein Ring B is

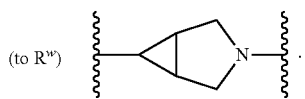

8. The method of claim 1, wherein R$^w$ is a

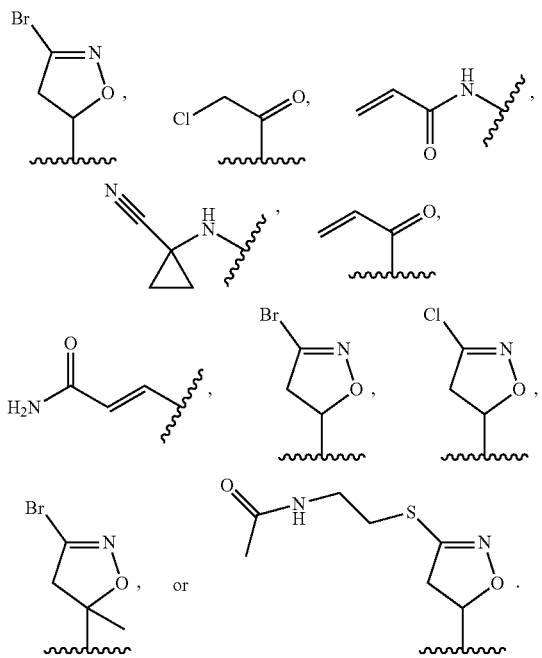

9. The method of claim 1, wherein the compound is of Formula (IX) or (X):

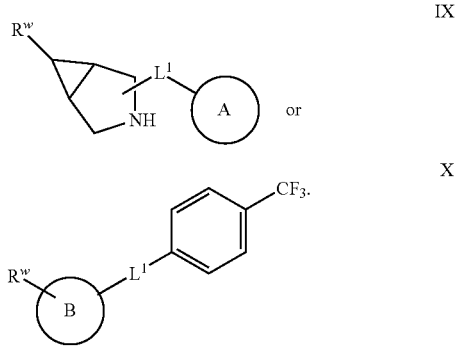

10. The method of claim 9, wherein the compound is of Formula (IXa), (IXb), or (Xa):

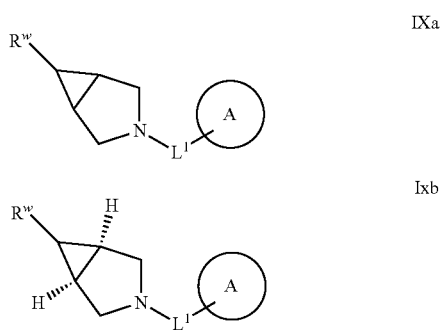

Xa

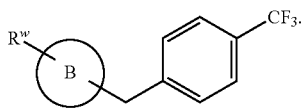

11. The method of claim 1, wherein the compound is of Formula (XII):

XII

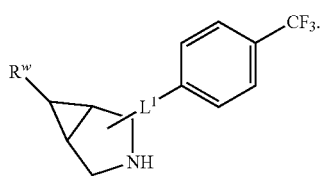

12. The method of claim 11, wherein the compound is of Formula (XIIa):

XIIa

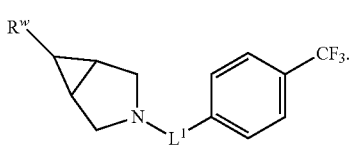

13. The method of claim 1, wherein the compound is of Formula (XIII) or (XIV):

XIII

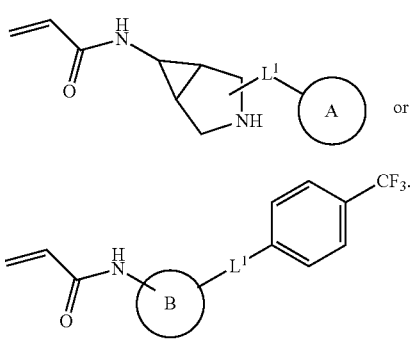

or

XIV

14. The method of claim 13, wherein the compound is of Formula (XIIIa) or (XIIIb)

XIIIa

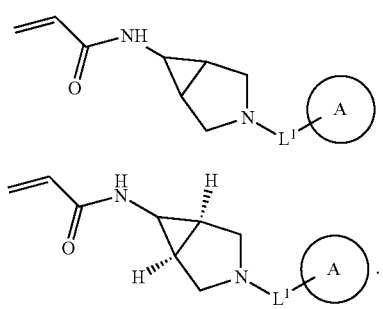

XIIIb

15. The method of claim 1, wherein the compound is of Formula (XV):

XV

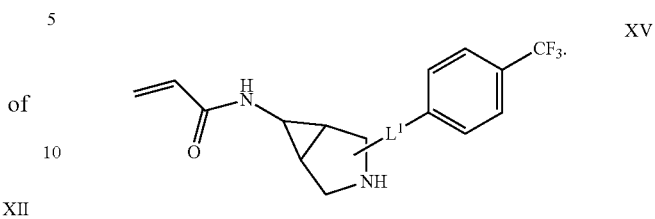

16. The method of claim 15, wherein the compound is of Formula (XVa) or (XVb):

XVa

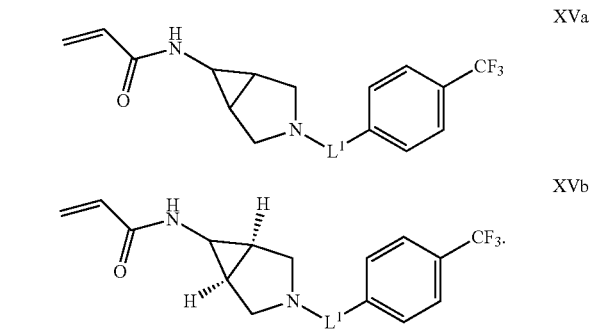

XVb

17. The method of claim 1, wherein the compound is selected from:

I-160

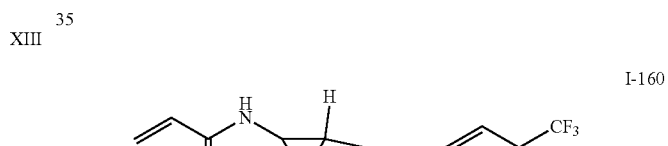

I-317

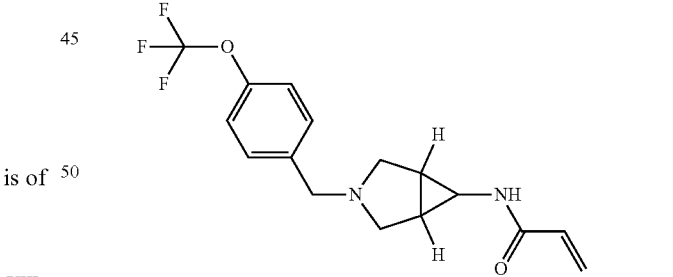

I-322

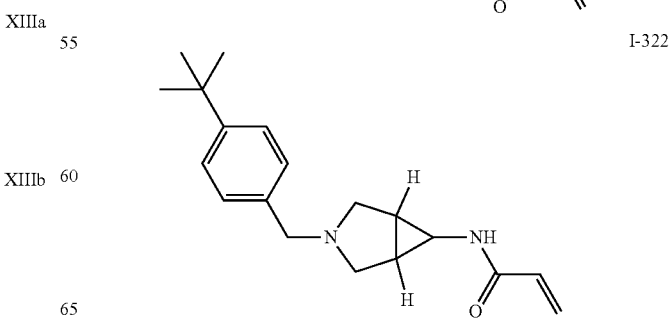

I-323
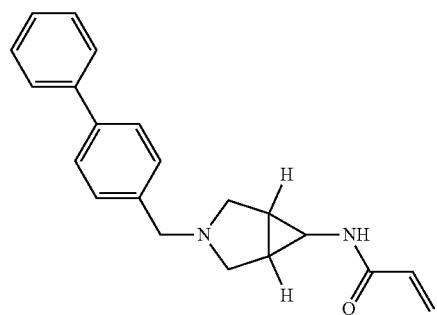
I-324
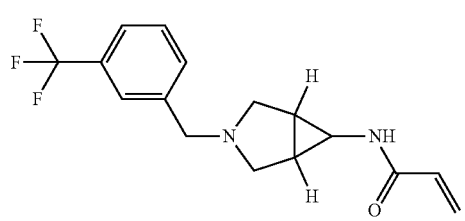
I-325
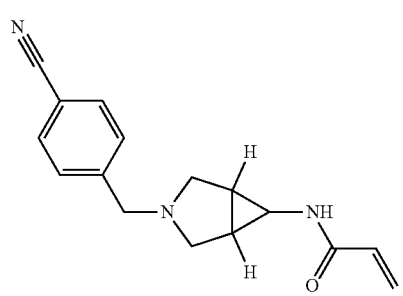
I-329
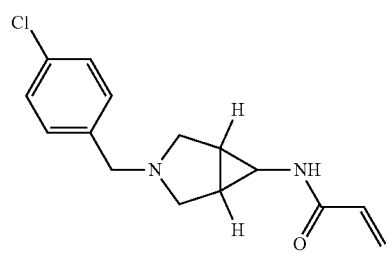
I-331
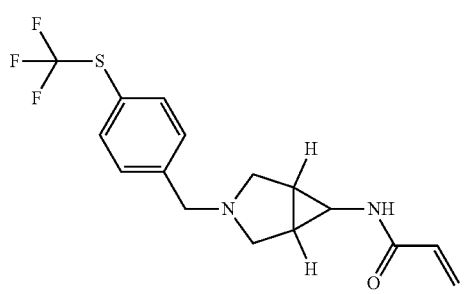
I-340
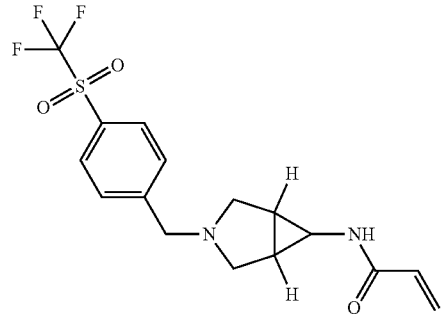
I-375
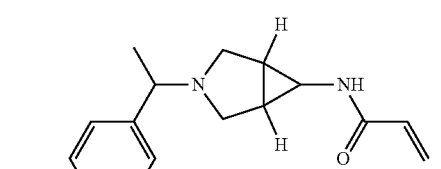
I-72
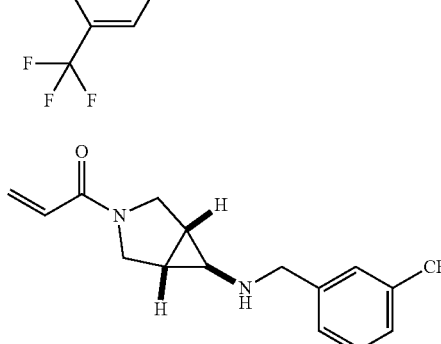
I-69
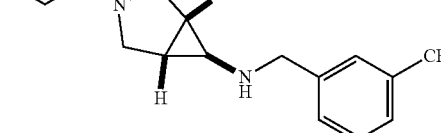
I-161
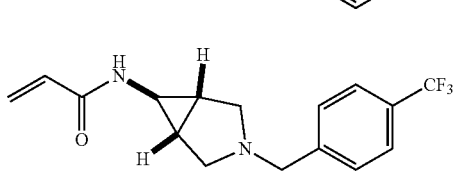
I-162
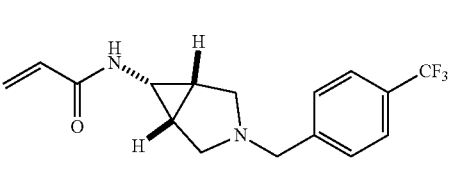
I-212
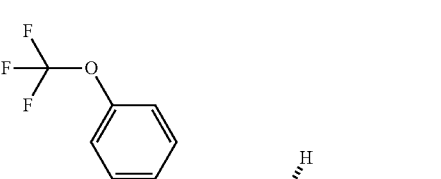

| | |
|---|---|
| I-220 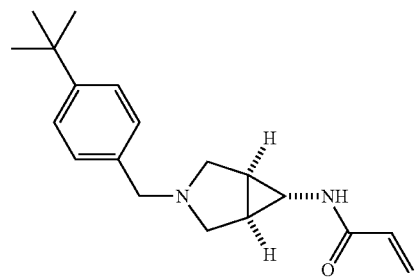 | I-240 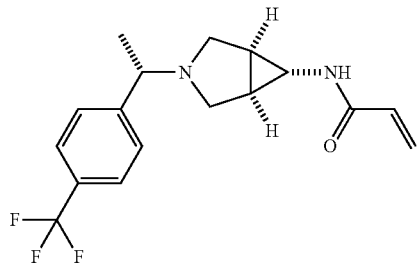 |
| I-221 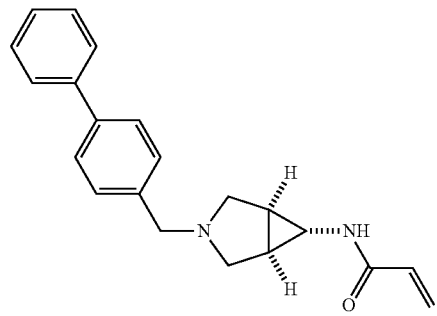 | I-241 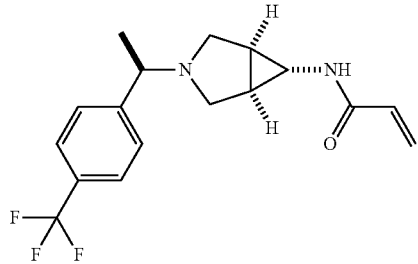 |
| I-222 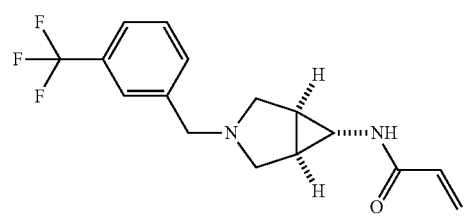 | I-256 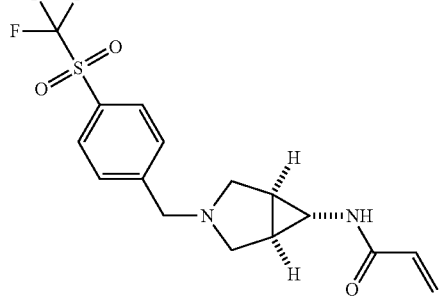 |
| I-224 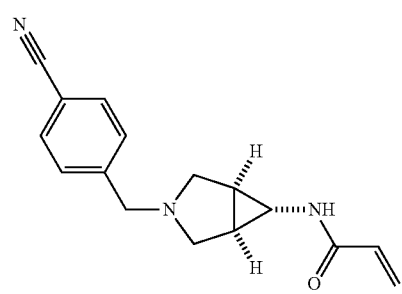 | I-334 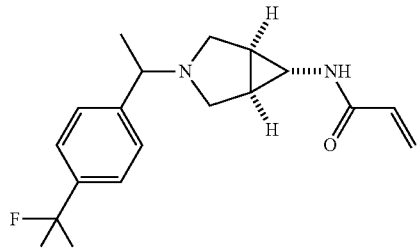 |
| I-231 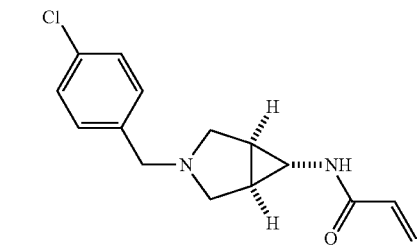 | I-163 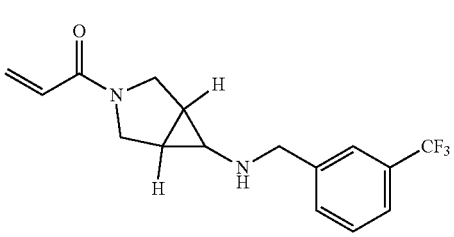 |
| I-234 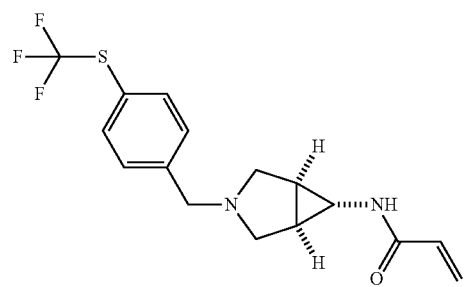 | I-164 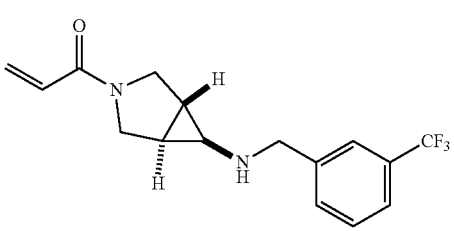 |

-continued

I-165

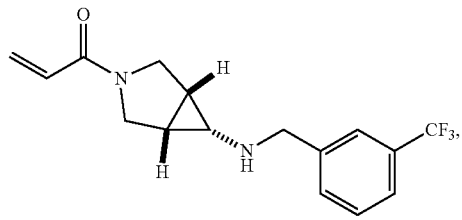

or a pharmaceutically acceptable salt thereof.

18. The method of claim 2, wherein $L^1$ is $C_{1-6}$ bivalent straight or branched hydrocarbon chain wherein 1, 2, or 3 methylene units of the chain are independently replaced with —N(R)—.

19. The method of claim 1, wherein $L^1$ is —CH$_2$—, —CH(CH$_3$)—, —NH—CH$_2$—, —NH—CH(CH$_3$)—, —C(O)—NH—, or —N(CH$_3$)—,

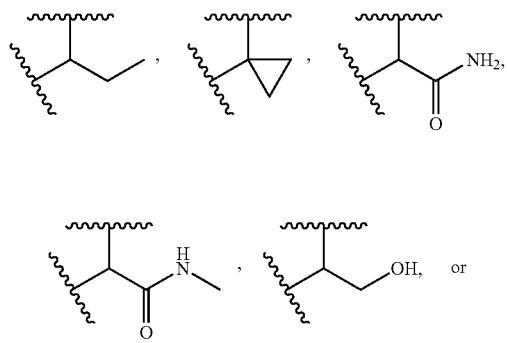

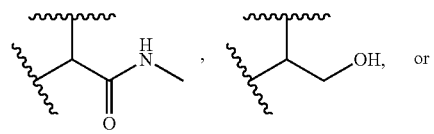

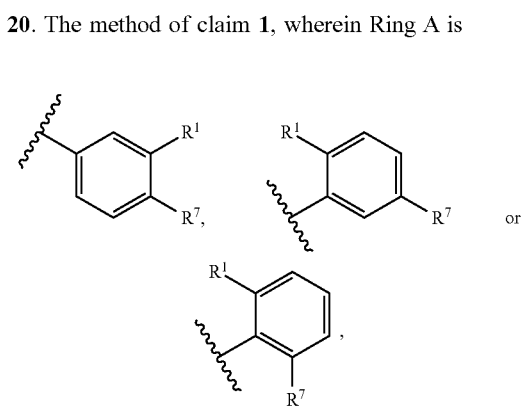

20. The method of claim 1, wherein Ring A is wherein each of $R^1$ and $R^7$ is independently —H, -halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is independently substituted 0, 1, 2, 3, 4, 5, or 6 times by -halogen, —CN, or —NO$_2$.

21. The method of claim 1, wherein Ring A is

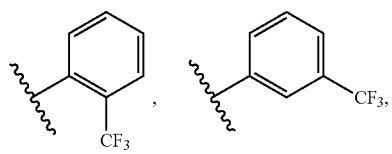

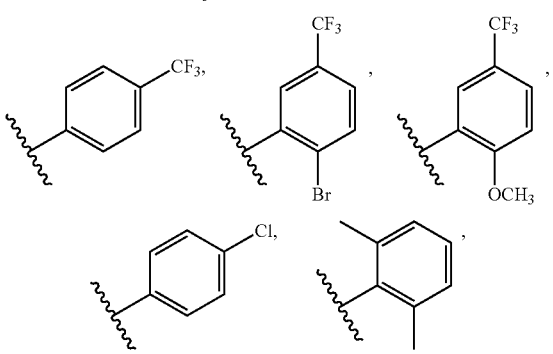

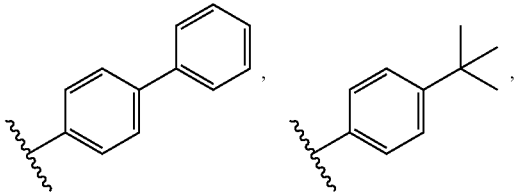

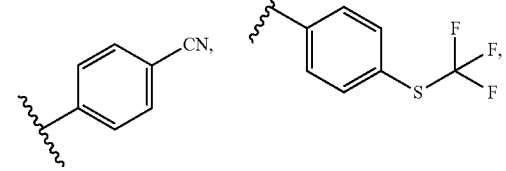

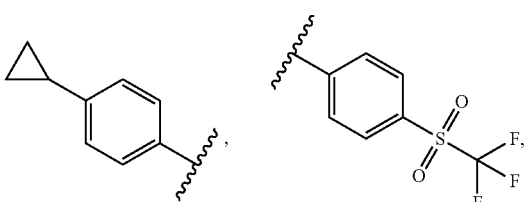

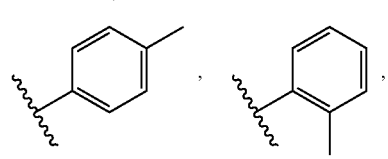

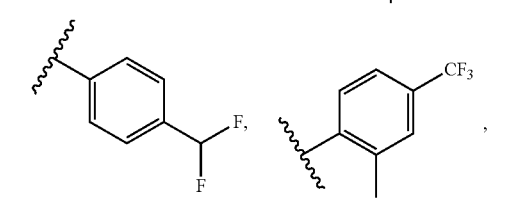

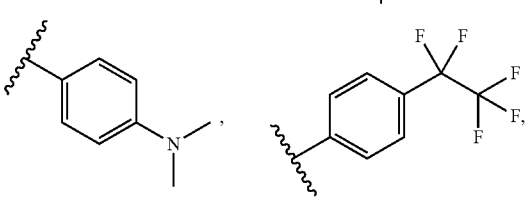

-continued

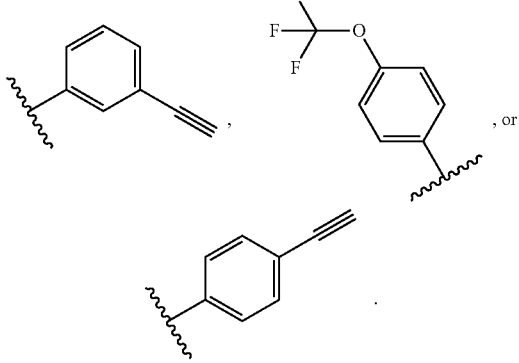

22. The method of claim 1, wherein:
L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene—; and Y is hydrogen or C$_{1-6}$ aliphatic optionally substituted with oxo, halogen, NO$_2$, or CN.

23. The method of claim 1, wherein:
L is a covalent bond;
Y is a partially unsaturated 4-6 membered heterocyclic ring having 1-2 heteroatoms independently selected from nitrogen, oxygen, or sulfur, wherein said ring is substituted with 1-4 Re groups; and
each Re is independently selected from oxo, NO$_2$, halogen, and CN.

24. The method of claim 1, wherein the cancer is associated with increased TEAD expression or increased TEAD activity.

25. The method of claim 1, wherein the cancer is associated with increased TEAD1 expression or increased TEAD1 activity; increased TEAD2 expression or increased TEAD2 activity; increased TEAD3 expression or increased TEAD3 activity; increased TEAD4 expression or increased TEAD4 activity; or any combination thereof.

26. The method of claim 1, wherein the cancer is a cancer in which YAP is localized in the nucleus of the cancer cells.

27. The method of claim 1, wherein the cancer is lung cancer, thyroid cancer, ovarian cancer, colorectal cancer, prostate cancer, cancer of the pancreas, cancer of the esophagus, liver cancer, breast cancer, skin cancer, mesothelioma or leukemia.

* * * * *

SEQUENCE LISTING

```
Sequence total quantity: 8
SEQ ID NO: 1            moltype = AA  length = 426
FEATURE                 Location/Qualifiers
source                  1..426
                        mol_type = protein
                        organism = Homo sapiens
SEQUENCE: 1
MEPSSWSGSE SPAENMERMS DSADKPIDND AEGVWSPDIE QSFQEALAIY PPCGRRKIIL    60
SDEGKMYGRN ELIARYIKLR TGKTRTRKQV SSHIQVLARR KSRDFHSKLK DQTAKDKALQ   120
HMAAMSSAQI VSATAIHNKL GLPGIPRPTF PGAPGFWPGM IQTGQPGSSQ DVKPFVQQAY   180
PIQPAVTAPI PGFEPASAPA PSVPAWQGRS IGTTKLRLVE FSAFLEQQRD PDSYNKHLFV   240
HIGHANHSYS DPLLESVDIR QIYDKFPEKK GGLKELFGKG PQNAFFLVKF WADLNCNIQD   300
DAGAFYGVTS QYESSENMTV TCSTKVCSFG KQVVEKVETE YARFENGRFV YRINRSPMCE   360
YMINFIHKLK HLPEKYMMNS VLENFTILLV VTNRDTQETL LCMACVFEVS NSEHGAQHHI   420
YRLVKD                                                              426

SEQ ID NO: 2            moltype = AA  length = 447
FEATURE                 Location/Qualifiers
source                  1..447
                        mol_type = protein
                        organism = Homo sapiens
SEQUENCE: 2
MGEPRAGAAL DDGSGWTGSE EGSEEGTGGS EGAGGDGGPD AEGVWSPDIE QSFQEALAIY    60
PPCGRRKIIL SDEGKMYGRN ELIARYIKLR TGKTRTRKQV SSHIQVLARR KSREIQSKLK   120
DQVSKDKAFQ TMATMSSAQL ISAPSLQAKL GPTGPQASEL FQFWSGGSGP PWNVPDVKPF   180
SQTPFTLSLT PPSTDLPGYE PPQALSPLPP PTPSPPAWQA RGLGTARLQL VEFSAFVEPP   240
DAVDSYQRHL FVHISQHCPS PGAPPLESVD VRQIYDKFPE KKGGLRELYD RGPPHAFFLV   300
KFWADLNWGP SGEEAGAGGS ISSGGFYGVS SQYESLEHMT LTCSSKVCSF GKQVVEKVET   360
ERAQLEDGRF VYRLLRSPMC EYLVNFLHKL RQLPERYMMN SVLENFTILQ VVTNRDTQEL   420
LLCTAYVFEV STSERGAQHH IYRLVRD                                       447

SEQ ID NO: 3            moltype = AA  length = 435
FEATURE                 Location/Qualifiers
source                  1..435
                        mol_type = protein
                        organism = Homo sapiens
SEQUENCE: 3
MASNSWNASS SPGEAREDGP EGLDKGLDND AEGVWSPDIE QSFQEALAIY PPCGRRKIIL    60
SDEGKMYGRN ELIARYIKLR TGKTRTRKQV SSHIQVLARK KVREYQVGIK AMNLDQVSKD   120
KALQSMASMS SAQIVSASVL QNKFSPPSPL PQAVFSTSSR FWSSPPLLGQ QPGPSQDIKP   180
FAQPAYPIQP PLPPTLSSYE PLAPLPSAAA SVPVWQDRTI ASSRLRLLEY SAFMEVQRDP   240
DTYSKHLFVH IGQTNPAFSD PPLEAVDVRQ IYDKFPEKKG GLKELYEKGP PNAFFLVKFW   300
ADLNSTIQEG PGAFYGVSSQ YSSADSMTIS VSTKVCSFGK QVVEKVETEY ARLENGRFVY   360
RIHRSPMCEY MINFIHKLKH LPEKYMMNSV LENFTILQVV TSRDSQETLL VIAFVFEVST   420
SEHGAQHHVY KLVKD                                                    435

SEQ ID NO: 4            moltype = AA  length = 434
FEATURE                 Location/Qualifiers
source                  1..434
                        mol_type = protein
```

```
                        organism = Homo sapiens
SEQUENCE: 4
MEGTAGTITS NEWSSPTSPE GSTASGGSQA LDKPIDNDAE GVWSPDIEQS FQEALAIYPP   60
CGRRKIILSD EGKMYGRNEL IARYIKLRTG KTRTRKQVSS HIQVLARRKA REIQAKLKDQ  120
AAKDKALQSM AAMSSAQIIS ATAPHSSMAL ARGPGRPAVS GFWQGALPGQ AGTSHDVKPF  180
SQQTYAVQPP LPLPGFESPA GPAPSPSAPP APPWQGRSVA SSKLWMLEFS AFLEQQQDPD  240
TYNKHLFVHI GQSSPSYSDP YLEAVDIRQI YDKFPEKKGG LKDLFERGPS NAFFLVKFWA  300
DLNTNIEDEG SSFYGVSSQY ESPENMIITC STKVCSFGKQ VVEKVETEYA RYENGHYSYR  360
IHRSPLCEYM INFIHKLKHL PEKYMMNSVL ENFTILQVVT NRDTQETLLC IAYVFEVSAS  420
EHGAQHHIYR LVKE                                                   434

SEQ ID NO: 5              moltype = AA  length = 221
FEATURE                   Location/Qualifiers
source                    1..221
                          mol_type = protein
                          organism = Homo sapiens
SEQUENCE: 5
WQGRSIGTTK LRLVEFSAFL EQQRDPDSYN KHLFVHIGHA NHSYSDPLLE SVDIRQIYDK   60
FPEKKGGLKE LFGKGPQNAF FLVKFWADLN CNIQDDAGAF YGVTSQYESS ENMTVTCSTK  120
VCSFGKQVVE KVETEYARFE NGRFVYRINR SPMCEYMINF IHKLKHLPEK YMMNSVLENF  180
TILLVVTNRD TQETLLCMAC VFEVSNSEHG AQHHIYRLVK D                     221

SEQ ID NO: 6              moltype = AA  length = 230
FEATURE                   Location/Qualifiers
source                    1..230
                          mol_type = protein
                          organism = Homo sapiens
SEQUENCE: 6
WQARGLGTAR LQLVEFSAFV EPPDAVDSYQ RHLFVHISQH CPSPGAPPLE SVDVRQIYDK   60
FPEKKGGLRE LYDRGPPHAF FLVKFWADLN WGPSGEEAGA GGSISSGGFY GVSSQYESLE  120
HMTLTCSSKV CSFGKQVVEK VETERAQLED GRFVYRLLRS PMCEYLVNFL HKLRQLPERY  180
MMNSVLENFT ILQVVTNRDT QELLLCTAYV FEVSTSERGA QHHIYRLVRD             230

SEQ ID NO: 7              moltype = AA  length = 221
FEATURE                   Location/Qualifiers
source                    1..221
                          mol_type = protein
                          organism = Homo sapiens
SEQUENCE: 7
WQDRTIASSR LRLLEYSAFM EVQRDPDTYS KHLFVHIGQT NPAFSDPPLE AVDVRQIYDK   60
FPEKKGGLKE LYEKGPPNAF FLVKFWADLN STIQEGPGAF YGVSSQYSSA DSMTISVSTK  120
VCSFGKQVVE KVETEYARLE NGRFVYRIHR SPMCEYMINF IHKLKHLPEK YMMNSVLENF  180
TILQVVTSRD SQETLLVIAF VFEVSTSEHG AQHHVYKLVK D                     221

SEQ ID NO: 8              moltype = AA  length = 221
FEATURE                   Location/Qualifiers
source                    1..221
                          mol_type = protein
                          organism = Homo sapiens
SEQUENCE: 8
WQGRSVASSK LWMLEFSAFL EQQQDPDTYN KHLFVHIGQS SPSYSDPYLE AVDIRQIYDK   60
FPEKKGGLKD LFERGPSNAF FLVKFWADLN TNIEDEGSSF YGVSSQYESP ENMIITCSTK  120
VCSFGKQVVE KVETEYARYE NGHYSYRIHR SPLCEYMINF IHKLKHLPEK YMMNSVLENF  180
TILQVVTNRD TQETLLCIAY VFEVSASEHG AQHHIYRLVK E                     221
```